(12) United States Patent
Beatty et al.

(10) Patent No.: US 10,640,569 B2
(45) Date of Patent: May 5, 2020

(54) HUMAN MESOTHELIN CHIMERIC ANTIGEN RECEPTORS AND USES THEREOF

(71) Applicants: Novartis AG, Basel (CH); The Trustees of the University of Pennsylvania, Philadelphia, PA (US)

(72) Inventors: Gregory Beatty, Philadelphia, PA (US); Boris Engels, Cambridge, MA (US); Neeraja Idamakanti, Cambridge, MA (US); Carl H. June, Merion Station, PA (US); Andreas Loew, Cambridge, MA (US); Huijuan Song, Shanghai (CN); Qilong Wu, Shanghai (CN)

(73) Assignees: Novartis AG, Basel (CH); The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 15/105,082

(22) PCT Filed: Dec. 19, 2014

(86) PCT No.: PCT/CN2014/094393
§ 371 (c)(1),
(2) Date: Jun. 16, 2016

(87) PCT Pub. No.: WO2015/090230
PCT Pub. Date: Jun. 25, 2015

(65) Prior Publication Data
US 2016/0311917 A1 Oct. 27, 2016

(30) Foreign Application Priority Data

Dec. 19, 2013 (WO) ................ PCT/CN2013/089979
Jul. 21, 2014 (WO) ................ PCT/CN2014/082610
Nov. 6, 2014 (WO) ................ PCT/CN2014/090509

(51) Int. Cl.
| | |
|---|---|
| *C07K 16/30* | (2006.01) |
| *C07K 14/725* | (2006.01) |
| *C12N 15/86* | (2006.01) |
| *A61K 39/00* | (2006.01) |
| *A61K 38/17* | (2006.01) |
| *A61K 39/395* | (2006.01) |
| *A61K 48/00* | (2006.01) |
| *C07K 14/705* | (2006.01) |
| *C07K 14/715* | (2006.01) |
| *C12N 5/0783* | (2010.01) |
| *C12N 15/85* | (2006.01) |
| *A61K 38/00* | (2006.01) |
| *A61K 31/436* | (2006.01) |

(52) U.S. Cl.
CPC ............ *C07K 16/30* (2013.01); *A61K 31/436* (2013.01); *A61K 38/1774* (2013.01); *A61K 38/1793* (2013.01); *A61K 39/0011* (2013.01); *A61K 39/39558* (2013.01); *A61K 48/0058* (2013.01); *C07K 14/7051* (2013.01); *C07K 14/70517* (2013.01); *C07K 14/7151* (2013.01); *C07K 16/303* (2013.01); *C07K 16/3061* (2013.01); *C07K 16/3069* (2013.01); *C12N 5/0638* (2013.01); *C12N 15/85* (2013.01); *C12N 15/86* (2013.01); *A61K 38/00* (2013.01); *A61K 2039/505* (2013.01); *A61K 2039/5158* (2013.01); *C07K 2317/565* (2013.01); *C07K 2317/622* (2013.01); *C07K 2317/73* (2013.01); *C07K 2317/92* (2013.01); *C07K 2319/00* (2013.01); *C07K 2319/02* (2013.01); *C07K 2319/03* (2013.01); *C07K 2319/74* (2013.01); *C12N 2740/15041* (2013.01)

(58) Field of Classification Search
CPC ............ A61K 51/1084; A61K 51/1087; C12N 5/0638
See application file for complete search history.

(56) References Cited

U.S. PATENT DOCUMENTS

| | | | |
|---|---|---|---|
| 5,359,046 A | 10/1994 | Capon et al. | |
| 5,686,281 A | 11/1997 | Roberts | |
| 5,712,149 A | 1/1998 | Roberts | |
| 5,874,240 A | 2/1999 | Ni et al. | |
| 5,906,936 A | 5/1999 | Eshhar et al. | |
| 6,103,521 A | 8/2000 | Capon et al. | |
| 6,319,494 B1 | 11/2001 | Capon et al. | |
| 6,355,779 B1 | 3/2002 | Goodwin et al. | |
| 6,410,319 B1 | 6/2002 | Raubitschek et al. | |

(Continued)

FOREIGN PATENT DOCUMENTS

| | | |
|---|---|---|
| CN | 102134276 A | 7/2011 |
| CN | 102775500 A | 11/2012 |

(Continued)

OTHER PUBLICATIONS

Rudikoff et al. (PNAS USA, 1982, 79: 1979-1983) (Year: 1982).*

(Continued)

*Primary Examiner* — Peter J Reddig

(74) *Attorney, Agent, or Firm* — Lando & Anastasi, LLP

(57) ABSTRACT

Provided are compositions and methods for treating diseases associated with expression of mesothelin. Also provided are a chimeric antigen receptor(CAR) specific to mesothelin, vectors encoding the same, and recombinant T cells comprising the mesothelin CAR. Further provided are methods of administering a genetically modified T cell expressing a CAR that comprises a mesothelin binding domain.

49 Claims, 53 Drawing Sheets

Specification includes a Sequence Listing.

(56) References Cited

U.S. PATENT DOCUMENTS

| | | |
|---|---|---|
| 6,569,997 B1 | 5/2003 | Kwon |
| 7,049,136 B2 | 5/2006 | Seed et al. |
| 7,052,906 B1 | 5/2006 | Lawson et al. |
| 7,070,995 B2 | 7/2006 | Jensen |
| 7,265,209 B2 | 9/2007 | Jensen |
| 7,319,143 B2 | 1/2008 | Gross et al. |
| 7,320,787 B2 | 1/2008 | Seed et al. |
| 7,446,190 B2 | 11/2008 | Sadelain et al. |
| 7,446,191 B2 | 11/2008 | Jensen |
| 7,514,537 B2 | 4/2009 | Jensen |
| 7,638,326 B2 | 12/2009 | June et al. |
| 7,741,465 B1 | 6/2010 | Eshhar et al. |
| 7,745,140 B2 | 6/2010 | June et al. |
| 7,754,482 B2 | 7/2010 | Riley et al. |
| 7,994,298 B2 | 8/2011 | Zhang et al. |
| 8,211,422 B2 | 7/2012 | Eshhar et al. |
| 8,252,914 B2 | 8/2012 | Zhang et al. |
| 8,268,970 B2 | 9/2012 | Terrett et al. |
| 8,389,282 B2 | 3/2013 | Sadelain et al. |
| 8,399,645 B2 | 3/2013 | Campana et al. |
| 8,465,743 B2 | 6/2013 | Rosenberg et al. |
| 8,637,307 B2 | 1/2014 | June et al. |
| 8,722,400 B2 | 5/2014 | Riley et al. |
| 8,906,682 B2 | 12/2014 | June et al. |
| 8,911,993 B2 | 12/2014 | June et al. |
| 8,916,381 B1 | 12/2014 | June et al. |
| 8,975,071 B1 | 3/2015 | June et al. |
| 9,101,584 B2 | 8/2015 | June et al. |
| 9,102,760 B2 | 8/2015 | June et al. |
| 9,102,761 B2 | 8/2015 | June et al. |
| 9,394,368 B2 | 7/2016 | Brogdon et al. |
| 9,573,988 B2 | 2/2017 | Brogdon et al. |
| 9,745,368 B2 | 8/2017 | Milone et al. |
| 9,777,061 B2 | 10/2017 | Ebersbach et al. |
| 9,815,901 B2 | 11/2017 | Brogdon et al. |
| 10,287,354 B2 * | 5/2019 | Brogdon ............ C07K 14/7051 |
| 2003/0060444 A1 | 3/2003 | Finney et al. |
| 2003/0077249 A1 | 4/2003 | Bebbington et al. |
| 2003/0105000 A1* | 6/2003 | Pero ................ A61K 38/06 514/19.3 |
| 2003/0148982 A1 | 8/2003 | Brenner et al. |
| 2003/0224520 A1 | 12/2003 | June et al. |
| 2004/0038886 A1 | 2/2004 | Finney et al. |
| 2004/0043401 A1 | 3/2004 | Sadelain et al. |
| 2005/0113564 A1 | 5/2005 | Campana et al. |
| 2005/0129671 A1 | 6/2005 | Cooper et al. |
| 2007/0036773 A1 | 2/2007 | Cooper et al. |
| 2008/0131415 A1 | 6/2008 | Riddell et al. |
| 2009/0257994 A1 | 10/2009 | Jensen |
| 2011/0052554 A1 | 3/2011 | Zakrzewski et al. |
| 2012/0107933 A1* | 5/2012 | Ho .................. C07K 16/30 435/375 |
| 2012/0148552 A1 | 6/2012 | Jensen |
| 2012/0321667 A1 | 12/2012 | Sentman |
| 2013/0071409 A1 | 3/2013 | Riley et al. |
| 2013/0071414 A1 | 3/2013 | Dotti et al. |
| 2013/0149337 A1 | 6/2013 | Cooper et al. |
| 2013/0155909 A1 | 6/2013 | Jackson et al. |
| 2013/0287748 A1 | 10/2013 | June et al. |
| 2014/0050708 A1 | 2/2014 | Powell et al. |
| 2014/0099309 A1 | 4/2014 | Powell, Jr. et al. |
| 2014/0099340 A1 | 4/2014 | June et al. |
| 2014/0106449 A1 | 4/2014 | June et al. |
| 2014/0186947 A1 | 7/2014 | June et al. |
| 2014/0212446 A1 | 7/2014 | Riley et al. |
| 2014/0219975 A1 | 8/2014 | June et al. |
| 2014/0227237 A1 | 8/2014 | June et al. |
| 2014/0271635 A1 | 9/2014 | Brogdon et al. |
| 2014/0322169 A1 | 10/2014 | Harper et al. |
| 2014/0322183 A1 | 10/2014 | Milone et al. |
| 2014/0322212 A1 | 10/2014 | Brogdon et al. |
| 2014/0322275 A1 | 10/2014 | Brogdon et al. |
| 2014/0370045 A1 | 12/2014 | June et al. |
| 2015/0017141 A1 | 1/2015 | June et al. |
| 2015/0140019 A1 | 5/2015 | June et al. |
| 2015/0190428 A1 | 7/2015 | June et al. |
| 2015/0202286 A1 | 7/2015 | June et al. |
| 2015/0283178 A1 | 10/2015 | June et al. |
| 2015/0290244 A1 | 10/2015 | June et al. |
| 2015/0342994 A1 | 12/2015 | Riley et al. |
| 2016/0046724 A1 | 2/2016 | Brogdon et al. |
| 2016/0051651 A1 | 2/2016 | Brogdon et al. |
| 2016/0068601 A1 | 3/2016 | Brogdon et al. |
| 2016/0096892 A1 | 4/2016 | Brogdon et al. |
| 2016/0185861 A1 | 6/2016 | Bedoya et al. |
| 2016/0311907 A1 | 10/2016 | Brogdon et al. |
| 2016/0340406 A1 | 11/2016 | Zhao et al. |
| 2016/0362472 A1 | 12/2016 | Bitter et al. |
| 2017/0008963 A1 | 1/2017 | Brogdon et al. |
| 2017/0081411 A1 | 3/2017 | Engels et al. |
| 2017/0137783 A1* | 5/2017 | Bedoya ............ C07K 14/7051 |
| 2017/0183415 A1 | 6/2017 | Brogdon et al. |
| 2017/0209492 A1 | 7/2017 | June et al. |
| 2017/0211055 A1* | 7/2017 | Brogdon ............ C12N 9/52 |
| 2017/0226495 A1 | 8/2017 | Guimaraes |
| 2017/0239294 A1 | 8/2017 | Thomas-Tikhonenko et al. |
| 2017/0260268 A1* | 9/2017 | Beatty ............ C07K 14/705 |
| 2017/0274014 A1 | 9/2017 | Brogdon et al. |
| 2017/0306416 A1 | 10/2017 | Bedoya et al. |
| 2017/0335281 A1 | 11/2017 | Loew et al. |
| 2018/0022795 A1 | 1/2018 | Milone et al. |
| 2018/0044423 A1 | 2/2018 | Ebersbach et al. |
| 2018/0044424 A1* | 2/2018 | June ............ A61K 45/06 |
| 2018/0118834 A1* | 5/2018 | Brogdon ............ C12N 15/86 |
| 2018/0125892 A1 | 5/2018 | Brannetti et al. |
| 2018/0133296 A1 | 5/2018 | Barrett et al. |
| 2018/0140602 A1 | 5/2018 | Angst et al. |
| 2018/0230193 A1 | 8/2018 | Loew et al. |
| 2018/0252727 A1 | 9/2018 | Garfall et al. |
| 2018/0258149 A1 | 9/2018 | Motz et al. |
| 2018/0298068 A1 | 10/2018 | Albelda |
| 2018/0312595 A1 | 11/2018 | Brogdon et al. |
| 2018/0334490 A1* | 11/2018 | Brogdon ............ C07K 16/2803 |
| 2019/0000880 A1 | 1/2019 | Motz et al. |
| 2019/0000944 A1* | 1/2019 | Brogdon ............ A61K 39/0011 |

FOREIGN PATENT DOCUMENTS

| | | |
|---|---|---|
| CN | 103145849 A | 6/2013 |
| CN | 103347897 A | 10/2013 |
| EP | 0574512 A1 | 12/1993 |
| EP | 0871495 A1 | 10/1998 |
| EP | 1226244 A2 | 7/2002 |
| JP | 2010-539981 A | 12/2010 |
| JP | 2013-518900 A | 5/2013 |
| WO | 1992015322 A1 | 9/1992 |
| WO | 199530014 A1 | 11/1995 |
| WO | 9623814 A1 | 8/1996 |
| WO | 9624671 A1 | 8/1996 |
| WO | 1997015669 A1 | 5/1997 |
| WO | 9723613 A2 | 7/1997 |
| WO | 9818809 A1 | 5/1998 |
| WO | 9900494 A2 | 1/1999 |
| WO | 9957268 A1 | 11/1999 |
| WO | 0014257 A1 | 3/2000 |
| WO | 2002033101 A1 | 4/2002 |
| WO | 02077029 A2 | 10/2002 |
| WO | 02088334 A1 | 11/2002 |
| WO | 2003057171 A2 | 7/2003 |
| WO | 2005019429 A2 | 3/2005 |
| WO | 2005044996 A2 | 5/2005 |
| WO | 2005/118788 A2 | 12/2005 |
| WO | 2006060878 A1 | 6/2006 |
| WO | 2008045437 A2 | 4/2008 |
| WO | 2009045957 A1 | 4/2009 |
| WO | 2010085660 A2 | 7/2010 |
| WO | 2010095031 A2 | 8/2010 |
| WO | 2010111282 A1 | 9/2010 |
| WO | 2011059836 A1 | 5/2011 |
| WO | 2011097477 A1 | 8/2011 |
| WO | 2012058460 A2 | 5/2012 |
| WO | 2012079000 A1 | 6/2012 |
| WO | 2012082841 A2 | 6/2012 |
| WO | 2012087962 A2 | 6/2012 |

(56) References Cited

FOREIGN PATENT DOCUMENTS

| WO | 2012/099973 | A2 | | 7/2012 | |
| WO | 2012127464 | A2 | | 9/2012 | |
| WO | 2012129514 | A1 | | 9/2012 | |
| WO | 2012135854 | A2 | | 10/2012 | |
| WO | 2012138858 | A1 | | 10/2012 | |
| WO | 2013019615 | A2 | | 2/2013 | |
| WO | 2013033626 | A2 | | 3/2013 | |
| WO | 2013040371 | A2 | | 3/2013 | |
| WO | 2013040557 | A2 | | 3/2013 | |
| WO | 2013059593 | A1 | | 4/2013 | |
| WO | 2013063419 | A2 | | 5/2013 | |
| WO | 2013074916 | A1 | | 5/2013 | |
| WO | WO-2013063419 | A2 | * | 5/2013 | ......... C07K 14/7051 |
| WO | 2013/126712 | A1 | | 8/2013 | |
| WO | 2013126729 | A1 | | 8/2013 | |
| WO | 2013126733 | A1 | | 8/2013 | |
| WO | 2013142034 | A1 | | 9/2013 | |
| WO | 2014/011984 | A1 | | 1/2014 | |
| WO | 2014/011987 | A1 | | 1/2014 | |
| WO | 2014/011993 | A2 | | 1/2014 | |
| WO | 2014/012001 | A2 | | 1/2014 | |
| WO | 2014011988 | A1 | | 1/2014 | |
| WO | 2014011996 | A1 | | 1/2014 | |
| WO | 2014031687 | A1 | | 2/2014 | |
| WO | 2014039513 | A2 | | 3/2014 | |
| WO | 2014/055442 | A2 | | 4/2014 | |
| WO | 2014052064 | A1 | | 4/2014 | |
| WO | 2014055657 | A1 | | 4/2014 | |
| WO | 2014130635 | A1 | | 8/2014 | |
| WO | 2014/145252 | A2 | | 9/2014 | |
| WO | 2015090229 | A1 | | 6/2015 | |
| WO | 2015090230 | A1 | | 6/2015 | |
| WO | 2015112626 | A1 | | 7/2015 | |
| WO | 2015/142661 | A1 | | 9/2015 | |
| WO | 2015142675 | A2 | | 9/2015 | |
| WO | 2015157252 | A1 | | 10/2015 | |
| WO | 2016014501 | A1 | | 1/2016 | |
| WO | 2016014530 | A1 | | 1/2016 | |
| WO | 2016014535 | A1 | | 1/2016 | |
| WO | 2016014553 | A1 | | 1/2016 | |
| WO | 2016014565 | A2 | | 1/2016 | |
| WO | 2016014576 | A1 | | 1/2016 | |
| WO | 2016019300 | A1 | | 2/2016 | |
| WO | 2016025880 | A1 | | 2/2016 | |
| WO | 2016028896 | A1 | | 2/2016 | |
| WO | 2016044605 | A1 | | 3/2016 | |
| WO | 2017/112741 | A1 | | 6/2017 | |

OTHER PUBLICATIONS

Coleman et al. (Research in Immunology, 1994; 145(1): 33-36) (Year: 1994).*
Burgess et al. (J of Cell Bio. 111:2129-2138, 1990) (Year: 1990).*
Ibragimova and wade (Biophysical Journal, Oct. 1999, vol. 77, pp. 2191-2198) (Year: 1999).*
International Search Report and Written Opinion for International Application No. PCT/US2016/067957 dated Apr. 7, 2017.
Morello et al. "Mesothelin-Targeted CARs: Driving T Cells to Solid Tumors" Cancer Discovery (2015) pp. OF1-OF15; DOI: 10.1158/2159-8290.CD-15-0583.
Supplementary European Search Report for European Application No. EP14871351.4 dated May 23, 2017.
Tanyi et al. "Abstract CT105: Safety and feasibility of chimeric antigen receptor modified T cells directed against mesothelin (CART-meso) in patients with mesothelin expressing cancers" Cancer Research; Proceedings: AACR 106th Annual Meeting 2015; Apr. 18-22, 2015; Philadelphia, PA (2015) vol. 75, No. 15.
Kochenderfer et al. "Construction and Pre-clinical Evaluation of an Anti-CD19 Chimeric Antigen Receptor", J Immunother (2009) vol. 32, No. 7, pp. 389-702.
Kochenderfer et al., "Eradication of B-lineage cells and regression of lymphoma in a patient treated with autologous T cells genetically-engineered to recognize CD19," Blood 116: 4099-4102 (2010).
Kohn et al., "CARs on Track in the Clinic—Workshop of the Blood and Marrow Transplant Clinical Trials Network Subcommittee on Cell and Gene Therapy" Meeting Report—Molecular Therapy (2011) vol. 19 No. 3.
Kraus et al., "Antigen-dependent CD28 Signaling Selectively Enhances Survival and Proliferation in Genetically Modified Activated Human Primary T Lymphocytes" J. Exp. Med. (1998) vol. 188 Np 4 pp. 619-626.
Kwon et al., "cDNA sequences of two inducible T-cell genes". Proc. Natl. Acad. Sci. U.S.A. 86(6): 1963-1967 (1989).
Lamanna et al., "Pentostatin, Cyclophosphamide, and Rutuximab Is an Active, Well-Tolerated Regimen for Patients With Previously Treated Chronic Lymphocytic Leukemia" Journal of Clinical Oncology (2008) vol. 24 No. 10 pp. 1575-1581.
Lamers et al., "Treatment of Metastatic Renal Cell Carcinoma With Autologous T-Lymphocytes Genetically Retargeted Against Carbonic Anhydrase IX: First Clinical Experience," J. Clin. Oncol. 24(13): e20-e22 (2006).
Lanitis et al., "Redirected Antitumor Activity of Primary Human Lymphocytes Transduced With a Fully Human Anti-mesothelin Chimeric Receptor" Molecular Therapy, 20(3):633-643 (2012).
Laport et al., "Adoptive transfer of costimulated T cells induces lymphocytosis in patients with relapsed/refractory non-Hodgkin lymphoma following CD34 +-selected hematopoietic cell transplantation" Blood (2003) vol. 102 No. 6 pp. 2004-2013.
Lee et al., "In vivo Inhibition of Human CD19-Targeted Effector T Cells by Natural T Regulatory Cells in a Xenotransplant Murine Model of B Cell Malignancy" Cancer Research (2011) vol. 71 No. 8 pp. 2871-2881.
Lee et al., "The Future is Now: Chimeric Antigen Receptors as New Targeted Therapies for Childhood Cancer," Clin. Cancer Res. 18: 2780-2790 (2012).
Letourneur et al., "T-cell and basophil activation through the cytoplasmic tail of T-cell-receptor zeta family proteins," Proc. Natl. Acad. Sci. U.S.A. 88: 8905-8909 (1991).
Levine et al., "Gene transfer in humans using a conditionally replicating lentiviral vector" PNAS (2006) vol. 103 No. 46 pp. 17372-17377.
MaCallan et al., "Measurement and modeling of human T cell kinetics" European Journal of Immunology (2003) vol. 33 pp. 2316-2326.
Maher et al., "Human T lymphocyte cytotoxicity and proliferation directed by a single chimeric TCRzeta/CD28 receptor," Nat. Biotechnol. 20: 70-75 (2002).
Mato et al., "Ibrutinib-induced pneumonitis in patients with chronic lymphocyticleukemia" Blood (2016) vol. 127 No. 8 pp. 1064-1067.
Maus et al., "T cells expressing chimeric antigen receptors can cause anaphylaxis in humans" Cancel Immunol Res, 1:26-31 (2013).
McGuinness et al., "Anti-tumor activity of human T cells expressing the CC49-zeta chimeric immune receptor," Hum. Gene Ther. 10: 165-173 (1999).
Milone et al., "Chimeric Receptors Containing CD137 Signal Transduction Domains Mediate Enhanced Survival of T Cells and Increased Antileukemic Efficacy In Vivo" Molecular Therapy (2009) vol. 17 No. 8 pp. 1453-1464.
Molina, "A Decade of Rituximab: Improving Survival Outcomes in Non-Hodgkin's Lymphoma" Annu. Rev. Med. (2008) vol. 59 pp. 237-250.
Morgan et al., "Case Report of a Serious Adverse Event Following the Administration of T Cells Transduced With a Chimeric Anitgen Receptor Recognizing ErbB2," Mol. Ther. 18(4): 843-851 (2010).
Moritz and Groner, "A spacer region between the single chain antibody- and the CD3 zeta-chain domain of chimeric T cell receptor components is required for efficient ligand binding and signaling activity," Gene Therapy 2(8): 539-546 (1995).
Moritz et al., "Cytotoxic T lymphocytes with a grafted recognition specificity for ERBB2-expressing tumor cells" Proc. Natl. Acad. Sci (1994) vol. 91 pp. 4318-4322.
Naldini et al., "In Vivo Gene Delivery and Stable Transduction of Nondividing Cells by a Lentiviral Vector" Science (1996) vol. 272 pp. 263-267.
NCBI accession HM_852952 accessed Sep. 29, 2015 from http://www.ncbi.nlm.nih.gov/nuccore/hm852952.

(56) References Cited

OTHER PUBLICATIONS

Nicholson et al., "Construction and Characterisation of a Function CD19 Specific Single Chain Fv Fragment for Immunotherapy of B Lineage Leukaemia and Lymphoma," Molecular Immunology 34(I6-I7): 1157-1165 (1997).
Park and Brentjens "Adoptive Immunotherapy for B-cell Malignancies with Autologous Chimeric Antigen Receptor Modified Tumor Targeted T Cells" Discovery Medicine (2010) vol. 9 No. 47 pp. 277-288.
Park et al. "Adoptive Transfer of Chimeric Antigen Receptor Re-directed Cytolytic T Lymphocyte Clones in Patients with Neuroblastoma", Molecular Therapy (2007) vol. 15 No. 4 pp. 825-833.
Patel et al., "Impact of chimeric immune receptor extracellular protein domains on T cell function" Gene Therapy (1999) vol. 6 pp. 412-419.
Porter et al. "Chimeric Antigen Receptor-Modified T Cells in Chronic Lymphoid Leukemia", The New England Journal of Medicine (2011) vol. 365 No. 8 pp. 725-733.
Porter et al., "A phase 1 trial of donor lumphocyte infusions expanded and activated ex vivo via CD3/CD28 costimulation" Blood (2006) vol. 107 No. 4 pp. 1325-1331.
Porter et al., "Chimeric Antigen Receptor Therapy for B-cell Malignancies" Journal of Cancer (2011) vol. 2 pp. 331-312.
Pule et al., "Virus-specific T cells engineered to coexpress tumor-specific receptors: persistence and antitumor activity in individuals with neuroblastoma" Nat. Med. (2008) vol. 14 No. 11 pp. 1264-1270.
Rapoport et al., "Restoration of immunity in lymphopenic individuals with cancer by vaccination and adoptive T-cell transfer" Nature Medicine (2005) vol. 11 No. 11 pp. 1230-1237.
Roederer, "T-cell dynamics of immunodeficiency" Nature Medicine (1995) vol. 1 No. 7 pp. 621-622.
Romeo et al., "Cellular immunity to HIV activated by CD4 fused to T cell or Fc receptor polypeptides," Cell 64:1037-1046 (1991).
Sabbagh et al., "TNF family ligands define niches for T cell memory" Trends in Immunology (2007) vol. 28 No. 8 pp. 333-339.
Sadelain et al. "The promise and potential pitfalls of chimeric antigen receptors." Current Opinion Immunology (2009) vol. 21 No. 2 pp. 215-223.
Sadelain et al., "Targeting Tumours with Genetically Enhanced T Lymphocytes," Nature Reviews: Cancer 3: 35-45 (2003).
Savoldo et al., "CD28 costimulation improves expansion and persistence of chimeric antigen receptor-modified T cells in lymphoma patients" The Journal of Clinical Investigation (2011) vol. 121 No. 5 pp. 1822-1826.
Sebestyen et al., "Human TCR That Incorporate CD3 Induce Highly Preferred Pairing between TCR and Chains following Gene Transfer" Journal of Immunology (2008) vol. 180 pp. 7736-7746.
Shirasu et al., "Functional Design of Chimeric T-Cell Antigen Receptors for Adoptive Immunotherapy of Cancer: Architecture and Outcomes," AntiCancer Res. 32: 2377-2384 (2012).
Sorror et al., "Outcomes after allogeneic hematopoietic cell transplantation with nonmyeloablative or myeloablative conditioning regimens for treatment of lymphoma and chronic lymphocytic leukemia" Blood (2008) vol. 111 No. 1 pp. 446-452.
Tchou et al "Mesothelin, a novel immunotherapy target for triple negative breast cancer" Breast Cancer Research and Treatment (2012) vol. 133, Iss 2, pp. 799-804.
Till et al., "Adoptive immunotherapy for indolent non-Hodgkin lymphoma and mantle cell lymphoma using genetically modified autologous CD20-specific T cells" Blood (2008) vol. 112 No. 6 pp. 2261-2271.
Uckun et al., "Detailed studies on expression and function of CD19 surface determinant by using B43 monoclonal antibody and the clinical potential of anti-CD19 immunotoxins" Blood (1988) vol. 71 pp. 13-29.
Vinay & Kwon, "Role of 4-1BB in immune responses" Immunology (1998) vol. 10 pp. 481-489.

Willemsen et al., "Genetic Engineering of T Cell Specificity for Immunotherapy of Cancer" Human Immunology (2003) vol. 64 pp. 56-68.
Zhao et al., "A Herceptin-Based Chimeric Antigen Receptor with Modified Signaling Domains Leads to Enhanced Survival of Transduced T Lymphocytes and Antitumor Activity" The Journal of Immunology (2009) vol. 183 pp. 5563-5574.
Zufferey et al., "Multiply attenuated lentiviral vector achieves efficient gene delivery in vivo" Nature Biotechnology (1997) vol. 15 pp. 871-876.
Baeksgaard & Sorensen, "Acute tumor lysis syndrome in solid tumors—a case report and review of the literature" Cancer Chemotherapy Pharmacology (2003) vol. 51 pp. 187-192.
Batzer et al. "Enhanced evolutionary PCR using oligonucleotides with inosine at the 3'-terminus" (1991) vol. 19, No. 18, pp. 5081.
Bondanza et al. "Suicide gene therapy of graft-versus-host disease induced by central memory human T lymphocytes" Blood (2006) vol. 107 No. 5 pp. 1828-1836.
Brentjens et al. "Genetically Targeted T Cells Eradicate Systemic Acute Lymphoblastic Leukemia Xenografts", Clinical Cancer Research(2007) vol. 13, No. 18, pp. 5426-5435.
Brentjens et al. "Treatment of Chronic Lymphocytic Leukemia With Genetically Targeted Autologous T Cells: Case Report of an Unforeseen Adverse Event in a Phase I Clinical Trial" The American Society of Gene Therapy (2010) vol. 18 No. 4 pp. 666-668.
Brentjens et al., "A Phase I Trial for the Treatment of chemo-Refractory Chronic Lymphocytic Leukemia with CD19—Targeted Autologous T Cells" Molecular Therapy (2008) vol. 16 Suppl 1 p. S15.
Brentjens et al., "CD19-Targeted T Cells Rapidly Induce Molecular Remissions in Adults with Chemotherapy—Refractory Acute Lymphoblastic Leukemia," Sci. Transl. Med. 5:177ra138 (2013).
Brentjens et al., "Eradication of systemic B-cell tumors by genetically targeted human T lymphocytes co-stimulated by CD80 and interleukin-15" Nature Medicine (2003) vol. 9 No. 3 pp. 279-286.
Brentjens et al., "Safety and persistence of adoptively transferred autologous CD19-targeted T cells in patients with relapsed or chemotherapy refractory B-cell leukemias" Blood (2011) vol. 118 No. 18 pp. 4817-4828.
Brocker and Karjalainen, "Signals through T Cell Receptor—Chain alone Are Insufficient to Prime Resting T Lymphocytes" J. Exp. Med. (1995) vol. 181 pp. 1653-1659.
Call & Wucherpfennig, "The T Cell Receptor: Critical Role of the Membrane Environment in Receptor Assembly and Function" Annu. Rev. Immunol. (2005) vol. 23 pp. 101-125.
Carpenito et al. "Control of large, established tumor xenografts with genetically retargeted human T cells containing CD28 and CD137 domains", Proc Natl Arad Sci USA (2009) vol. 106 pp. 3360-3365.
Davila et al. "B Cell Aplasia in a Patient with Relapsed B Cell Acute Lymphoblastic Leukemia Following Re-Induction and Consolidation with Autologous T Cells Genetically Targeted to the CD19 Antigen" 53rd ASH Annual Meeting and Exposition (2010) Oral and Poster Abstract.
Dohner et al., "p53 Gene Deletion Predicts for Poor Survival and Non-Response to Therapy With Purine Analogs in Chronic B-Cell Leukemias" Blood (1995) vol. 85 No. 6 pp. 1580-1589.
Dropulic and June, "Gene-Based Immunotherapy for Human Immunodeficiency Virus Infection and Acquired Immunodeficiency Syndrome" Human Gene Therapy (2006) vol. 17 pp. 577-588.
Dull et al, "A Third-Generation Lentivirus Vector with a Conditional Packaging System" Journal of Virology (1998) vol. 12 No. 11 pp. 8463-8471.
Eshhar et al., "Specific activation and targeting of cytotoxic lymphocytes through chimeric single chains consisting of antibody-binding domains and the gamma or zeta subunits of the immunoglobulin and T-cell receptors," PNAS USA 90: 720-724 (1993).
Finney et al., "Activation of resting human primary T cells with chimeric receptors: costimulation from CD28, inducible costimulator, CD134, and CD137 (4-1BB) in series with signals from the TCR zeta chain," J. Immunol. 172: 104-113 (2004).
Finney et al., "Chimeric receptors providing both primary and costimulatory signaling in T cells from a single gene product," J. Immunol. 161: 2791-2797 (1998).

(56) References Cited

OTHER PUBLICATIONS

Frey, N. "Genetically Engineered Lymphocyte Therapy in Treating Patients With B-Cell Leukemia or Lymphoma That is Resistant or Refractory to Chemotherapy" (2015) Clinical Trial NCT01029366.
Friedmann-Morvinski et al., "Redirected primary T cells harboring a chimeric receptor require costimulation for their antigen-specific activation," Blood 105: 3087-3093 (2005).
Geiger & Jyothi, "Development and Application of Receptor-Modified T Lymphocytes for Adoptive Immunotherapy" Transfusion Medicine Reviews (2001) vol. 15 No. 1 pp. 21-34.
Geiger et al., "Integrated src kinase and constimulatory activity enhances signal transduction through single-chain chimeric receptors in T lymphocytes," Blood 98(8): 2364-2371 (2001).
GenBank Accession No. NP_000725.1 accessed on Jan. 7, 2016 from http://www.ncbi.nlm.nih.gov/protein/NP_000725.
GenBank Accession No. NP_932170.1 accessed Jan. 7, 2016 from http://www.ncbi.nlm.nih.gov/protein/NP_932170.
Gilham et al., "Primary Polyclonal Human T Lymphocytes Targeted to Carcino-Embryonic Antigens and Neural Cell Adhesion Molecule Tumor Antigens by CD3-Based Chimeric Immune Receptors" Journal of Immunotherapy (2002) vol. 25 No. 2 pp. 139-151.
Gong et al. "Cancer Patient T Cells Genetically Targeted to Prostate-Specific Membrane Antigen Specifically Lyse Prostate Cancer Cells and Release Cytokines in Response to Prostate-Specific Membrane Antigen" Neoplasia (1999) vol. 1 No. 2 pp. 123-127.
Gribben et al., "Stem cell transplantation for indolent lymphoma and chronic lymphocytic leukemia" Biol Blood Marrow Transplant (2011) vol. 17 (1 Suppl): S63-S70.
Griffin, "Development and applications of surface-linked single chain antibodies against T-cell antigens" Journal of Immunological Methods (2001) vol. 248 pp. 77-90.
Gross et al., "Endowing T cells with antibody specificity using chimeric T cell receptors," The FASEB Journal 6: 3370-3378 (1992).
Grupp et al. "Chimeric Antigen Receptor-Modified T Cells for Acute Lymphoid Leukemia", New England Journal of Medicine (2013) vol. 368 No. 16 pp. 1509-1518.
Hallek et al., "Guidelines for the diagnosis and treatment of chronic lymphocytic leukemia: a report from the International Workshop on Chronic Lymphocytic Leukemia updating the National Cancer Institute Working Group 1996 guidelines" Blood (2008) vol. 111 No. 12 pp. 5446-5456.
Hekele et al., "Growth Retardation of Tumors by Adoptive Transfer of Cytotoxic T Lymphocytes Reprogrammed by CD44V6-Specific SCFV:—Chimera" Int J. Cancer (1996) vol. 68 pp. 232-238.
Ho et al., "Adoptive immunotherapy: Engineering T cell responses as biological weapons for tumor mass destruction" Cancer Cell (2003) vol. 3 pp. 431-437.
Hollyman et al. "Manufacturing validation of biologically functional T cells targeted to CD19 antigen for autologous adoptive cell therapy" J Immunother (2009) vol. 32 No. 2 pp. 169-180.
Homback et al., "The Recombinant T Cell Receptor Strategy: Insights into Structure and Function of Recombinant Immunoreceptors on the Way Towards an Optimal Receptor Design for Cellular Immunotherapy," Current Gene Therapy 2: 211-226 (2002).
Imai et al., "Chimeric receptors with 4-1BB signaling capacity provoke potent cytotoxicity against acute lymphoblastic leukemia," Leukemia 18: 676-684 (2004).
Imai et al., "Genetic modification of primary natural killer cells overcomes inhibitory signals and induces specific killing of leukemic cells" Blood (2005) vol. 106 No. 1 pp. 376-383.
International Search Report and Written Opinion for International application No. PCT/CN2014/094393, dated Mar. 30, 2015.
International Search Report for International Application No. PCT/CN2013/089979 dated Sep. 26, 2014.
International Search Report from PCT/US2011/064191 dated Jan. 5, 2012.
Irving et al., "The cytoplasmic domain of the T cell receptor zeta chain is sufficient to couple to receptor-associated signal transduction pathways," Cell 64: 891-901 (1991).
Jena, Bipulendu et al. "Redirecting T-cell specificity by introducing a tumor-specific chimeric antigen receptor, Blood, May 3, 2010", vol. 116, No. 7, pp. 1035-1044.
Jensen et al., "Anti-Transgene Rejection Responses Contribute to Attenuated Persistence of Adoptively Transferred CD20/CD19-Specific Chimeric Antigen Receptor Re-directed T Cells in Humans" Biol Blood Marrow Transplant (2010) vol. 16 No. 9 pp. 1245-1256.
Johnson et al., "Gene therapy with human and mouse T-cell receptors mediates cancer regression and targets normal tissues expressing cognate antigen" Blood (2009) vol. 114 No. 3 pp. 535-545.
June et al., "Engineering lymphocyte subsets: tools, trials and tribulations" Nat Rev Immunol (2009) vol. 9 No. 10 pp. 704-716.
Kalos et al. "T Cells with Chimeric Antigen Receptors Have Potent Antitumor Effects and Can Establish Memory in Patients with Advanced Leukemia", Science Translation Medicine (2011) vol. 3 No. 95 95ra73.
Kershaw et al., "A Phase I Study on Adoptive Immunotherapy Using Gene-Modified T Cells for Ovarian Cancer," Clin. Cancer Res. 12(20 Pt 1): 6106-6115 (2006).
Kim et al., "Human 4-1BB regulates CD28 co-stimulation to promote Th1 cell responses" Eur. J. Immunol. (1998) vol. 28 pp. 881-890.
Kochenderfer et al, "A Phase I Clinical Trial of Treatment of B-Cell Malignancies with Autologous Anti-Cd19-CAR-Transduced T Cells" Blood (2010) vol. 116 No. 21 pp. 1179-1180 & 52nd Annual Meeting of the American-Society-of-Hematology (ASH); Orlando, FL, USA; Dec. 4-7, 2010 abstract.
Kaneko et al. "A Binding Domain on Mesothelin for CA125/MUC16" The Journal of Biological Chemistry (2009) vol. 284, No. 6, pp. 3739-3749.
John et al. "Blockade of PD-1 immunosuppression boosts CAR T-cell therapy" OncoImmunology (2013) vol. 2, No. 10, e26286, pp. 1-3.
Singapore Search Report and Written Opinion for Singapore Application No. 11201604815R dated Jul. 26, 2018.
Chang et al. "Molecular cloning of mesothelin, a differentiation antigen present on mesothelium, mesotheliomas, and ovarian cancers" Proc Natl Acad Sci (1996) vol. 93, No. 1, pp. 136-140.
Chowdhury et al. "Isolation of a high-affinity stable single-chain Fv specific for mesothelin from DNA-immunized mice by phage display and construction of a recombinant immunotoxin with anti-tumor?activity" Proc Natl Acad Sci (1998) vol. 95, No. 2, pp. 669-674.
Kawalekar, et al. "Distinct Signaling by Chimeric Antigen Receptors (CARs) Containing CD28 Signaling Domain Versus 4-1BB in Primary Human T Cells." Blood (2013) vol. 122 pp. 2902.

\* cited by examiner

FIG. 2
A
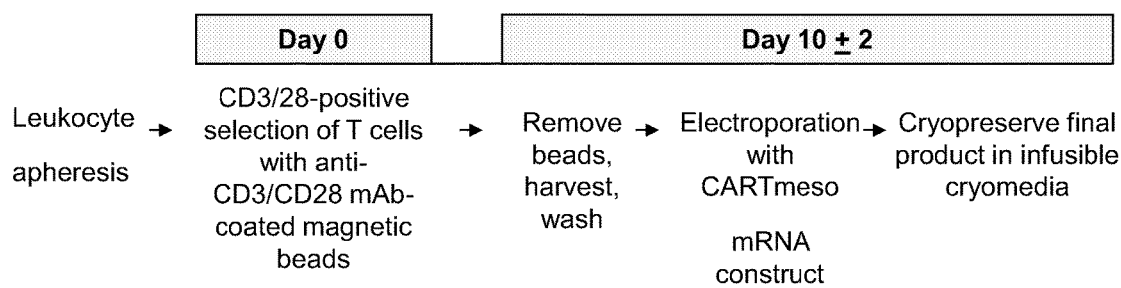
B
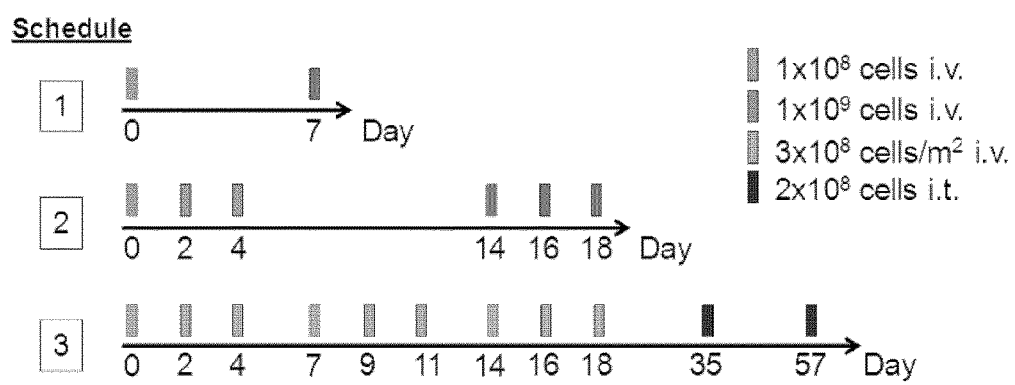

FIG. 3
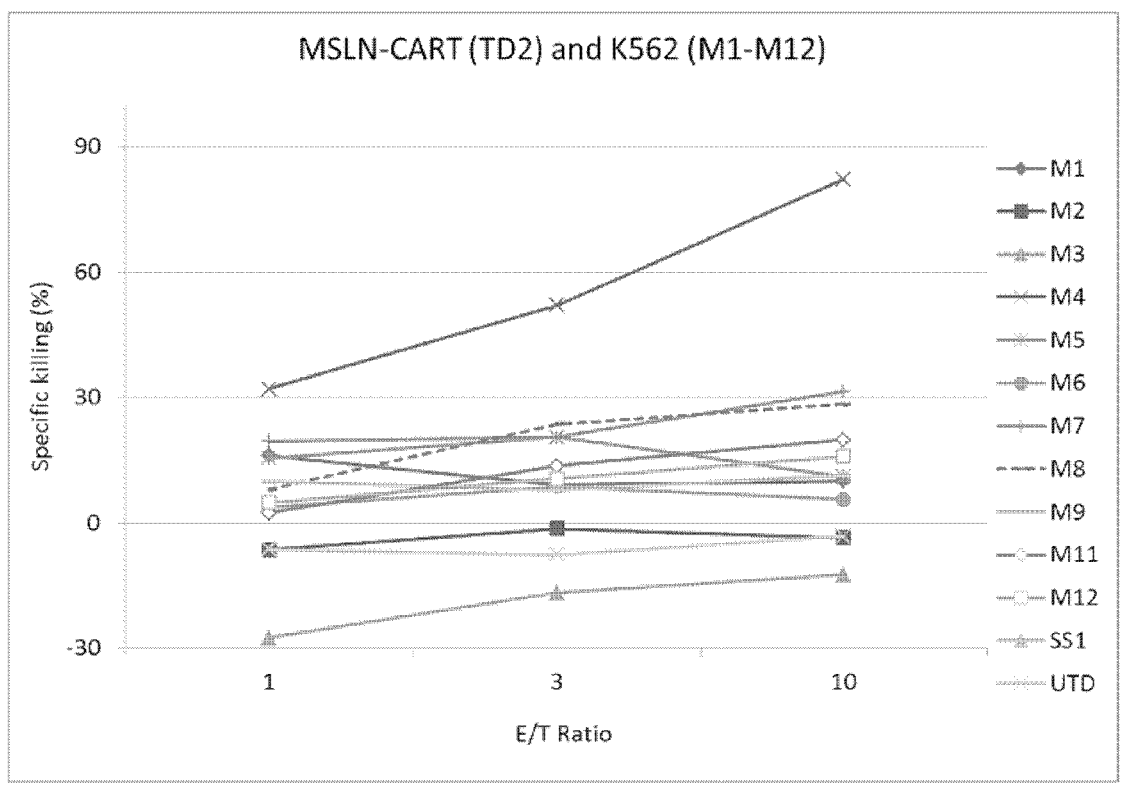
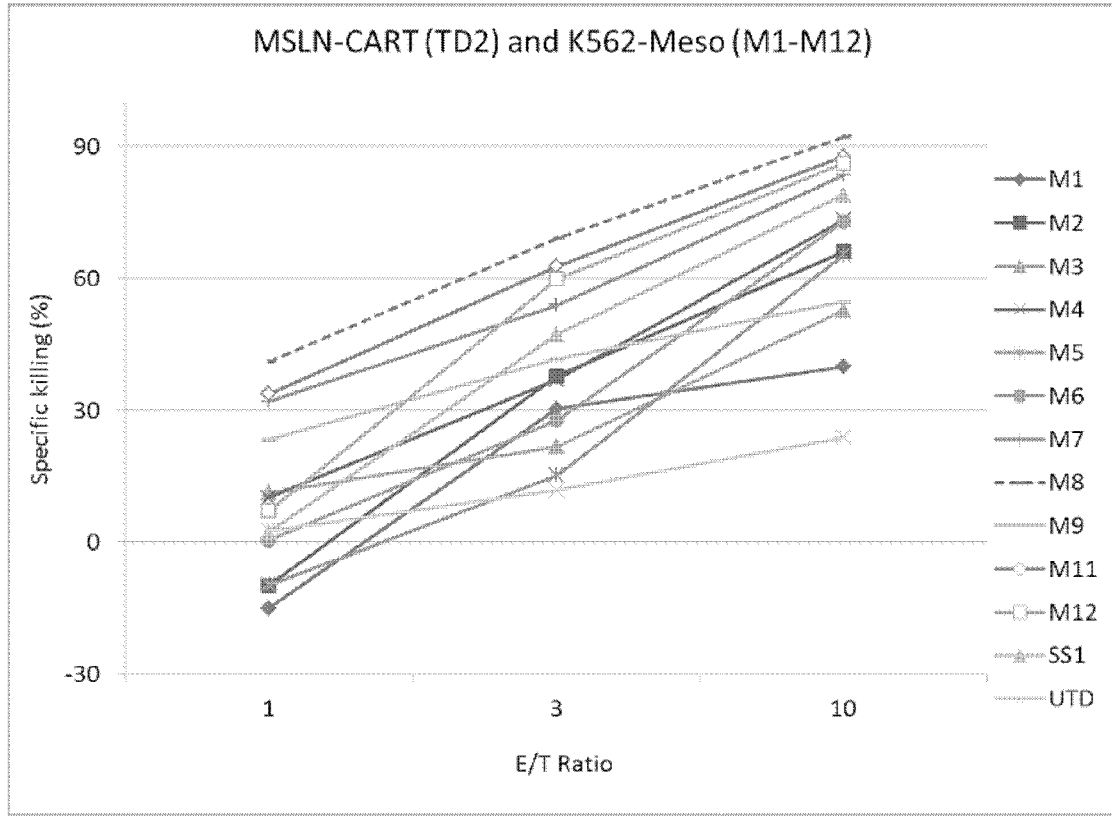

FIG. 4
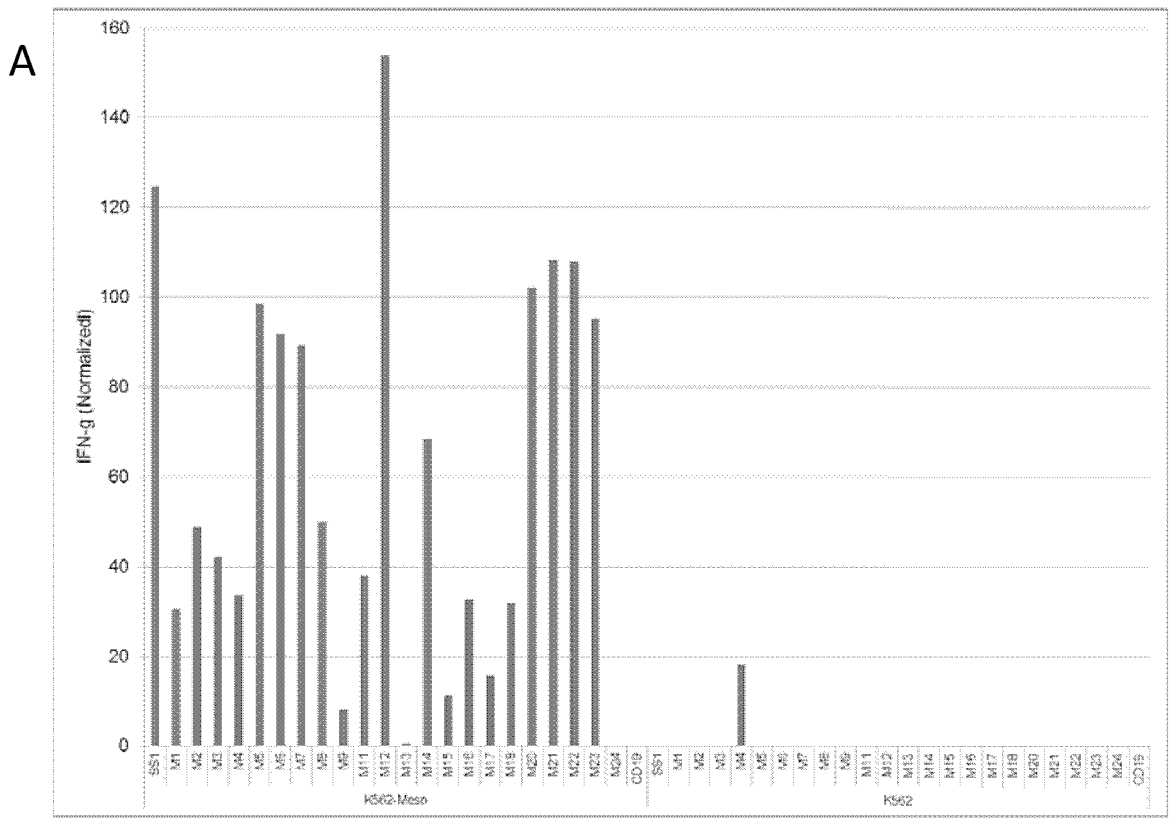
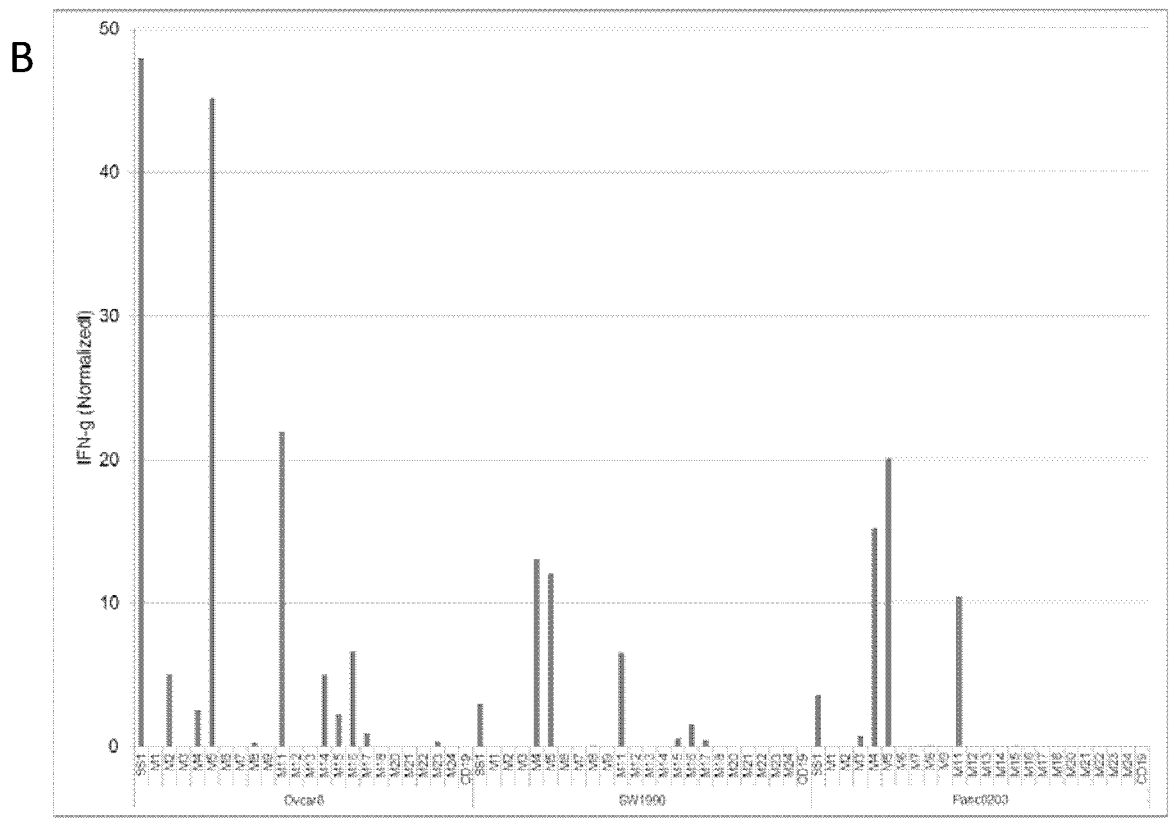

FIG. 9
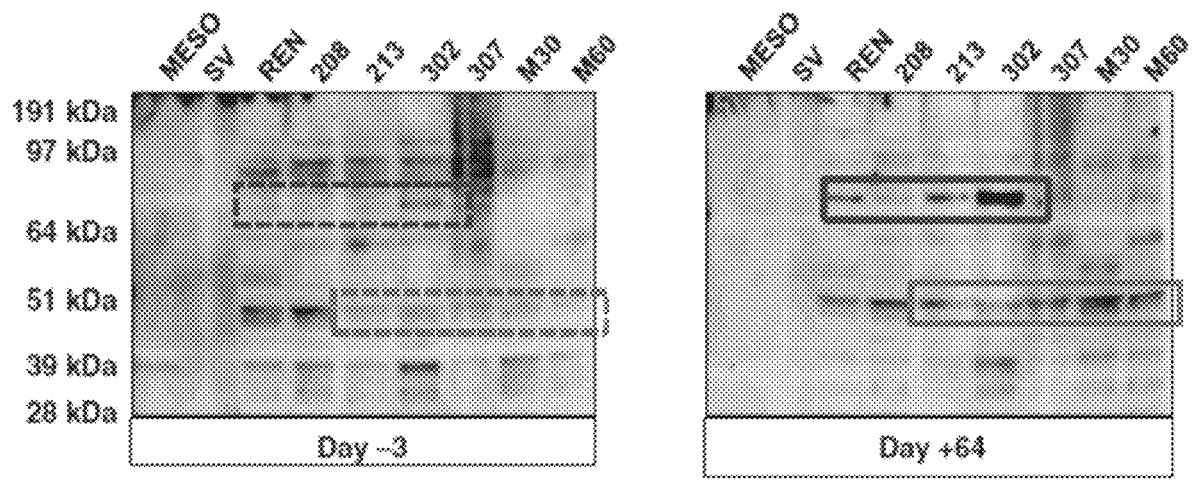
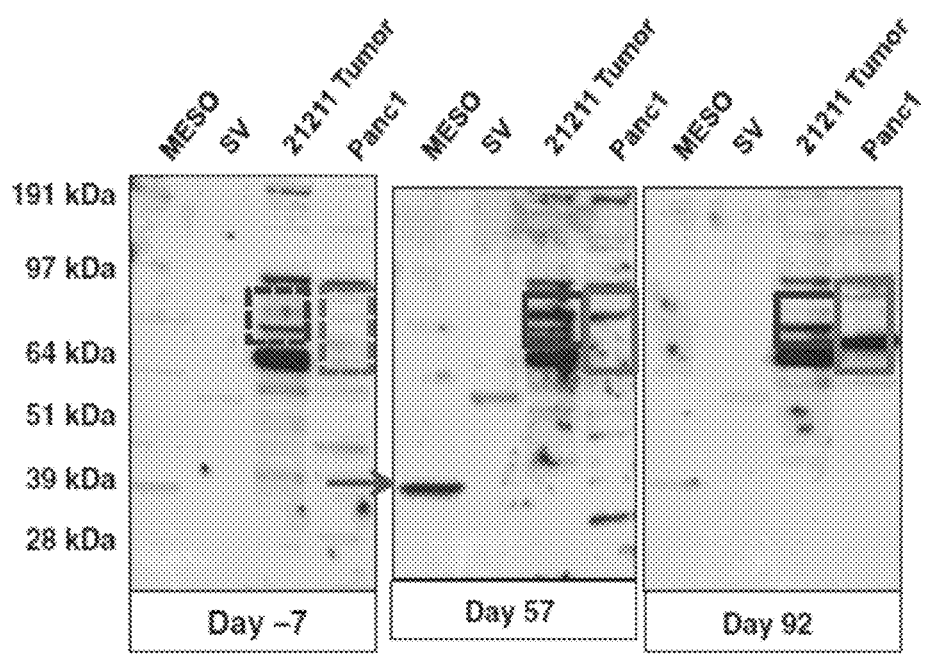

FIG. 16
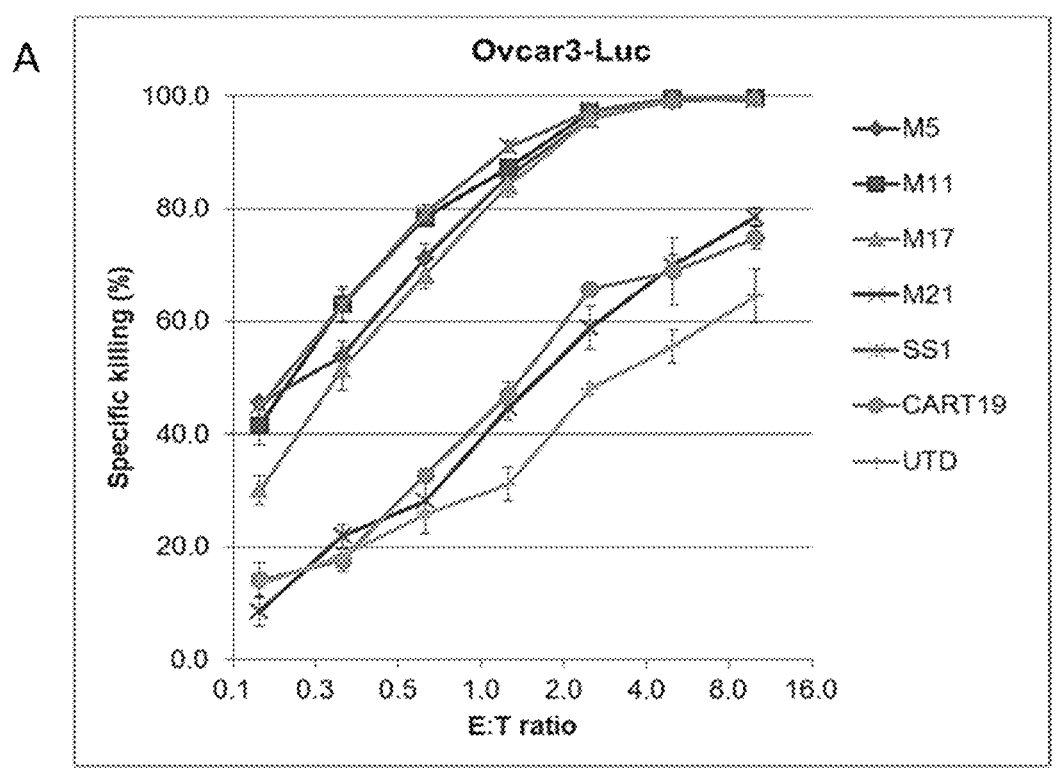
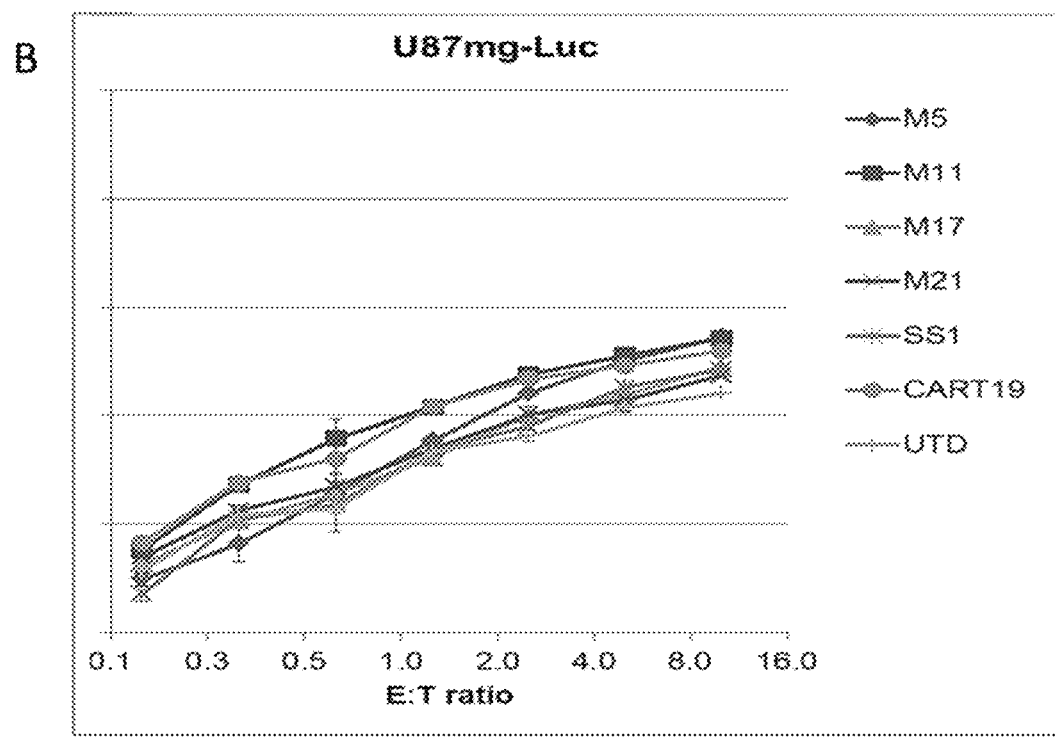

FIG. 17
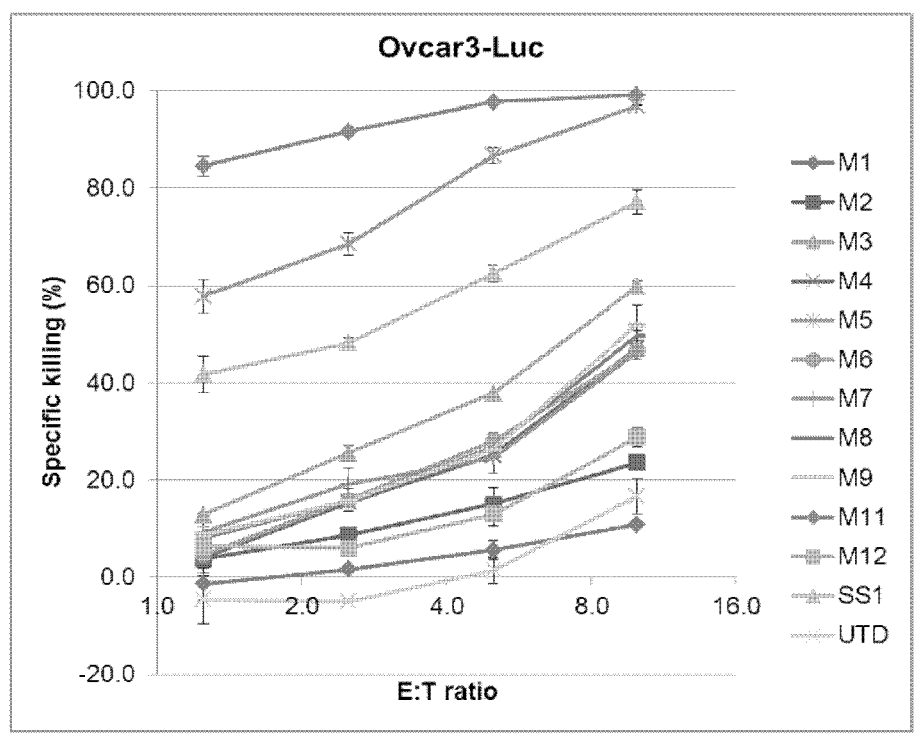
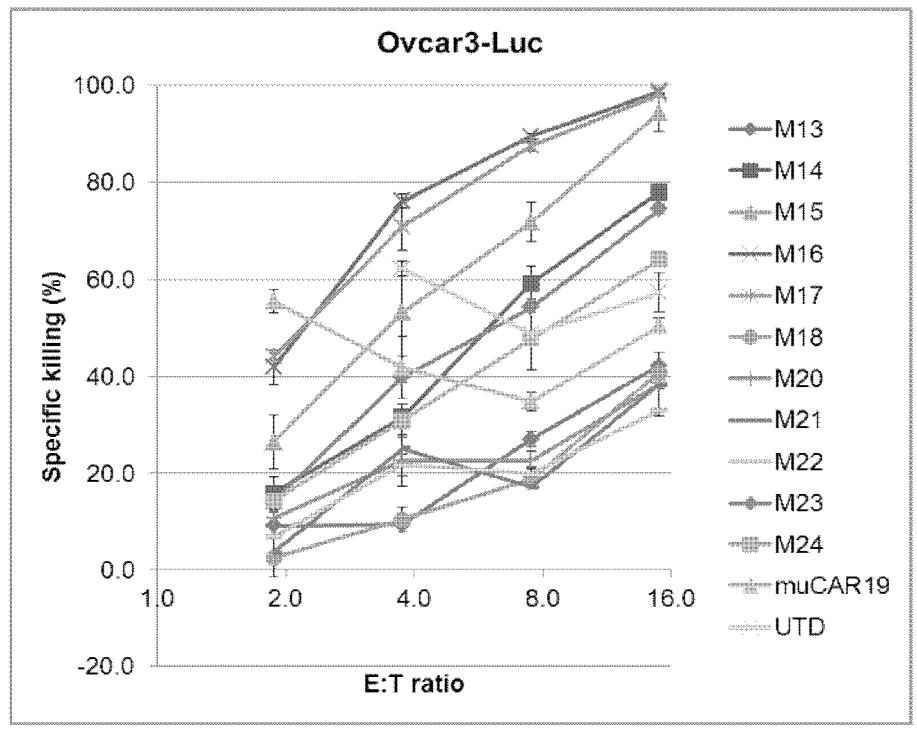

EMMESO TIL ex vivo killing assay (immediate harvest)

IFNg level after 20hr 50:1 coculture with 5K EMMESO/ffluc cells pre/post 30IU/ml IL2 overnight rest FIG. 27
A
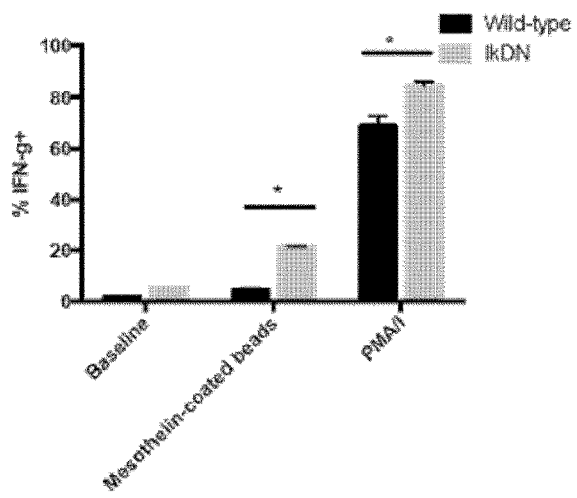
B
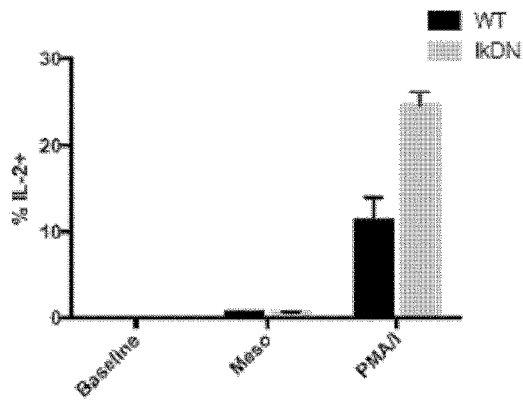
C
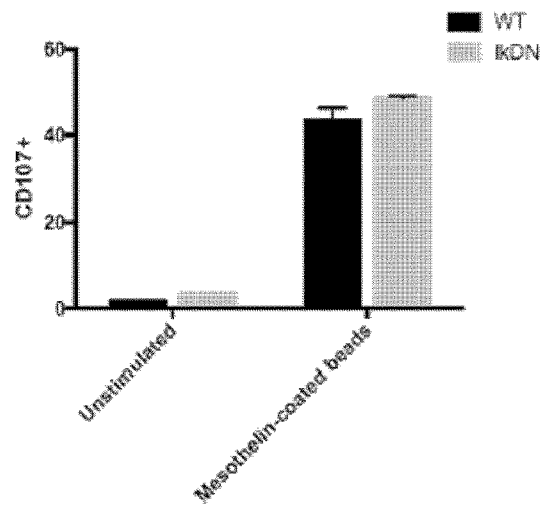

FIG. 32
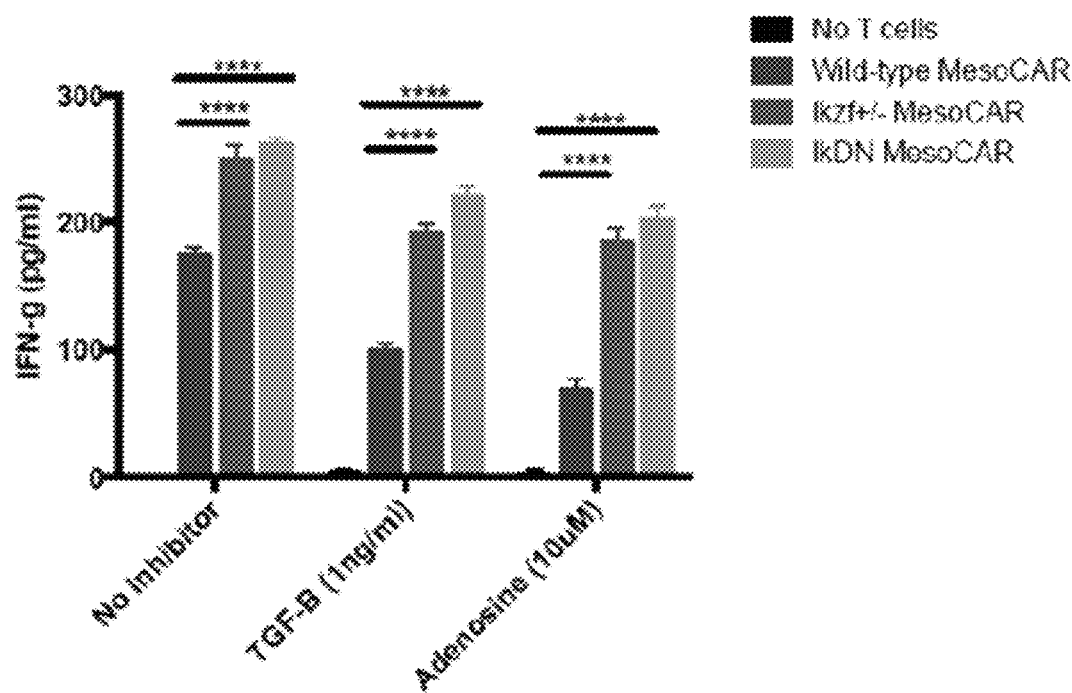
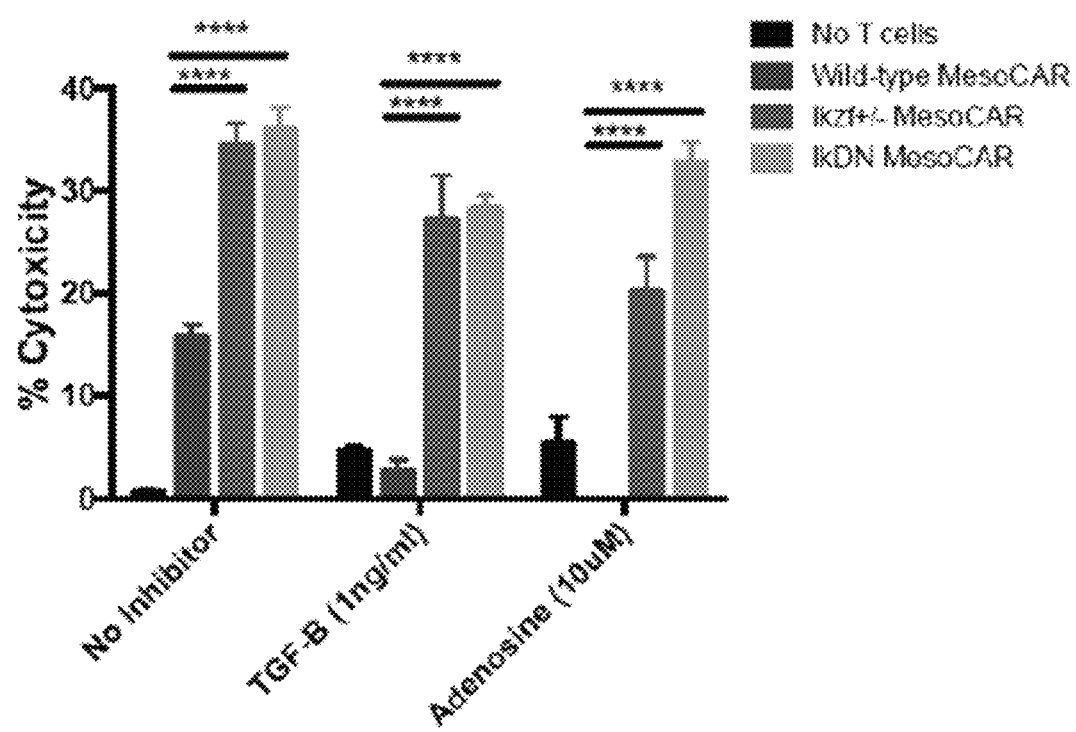

FIG. 33
A.
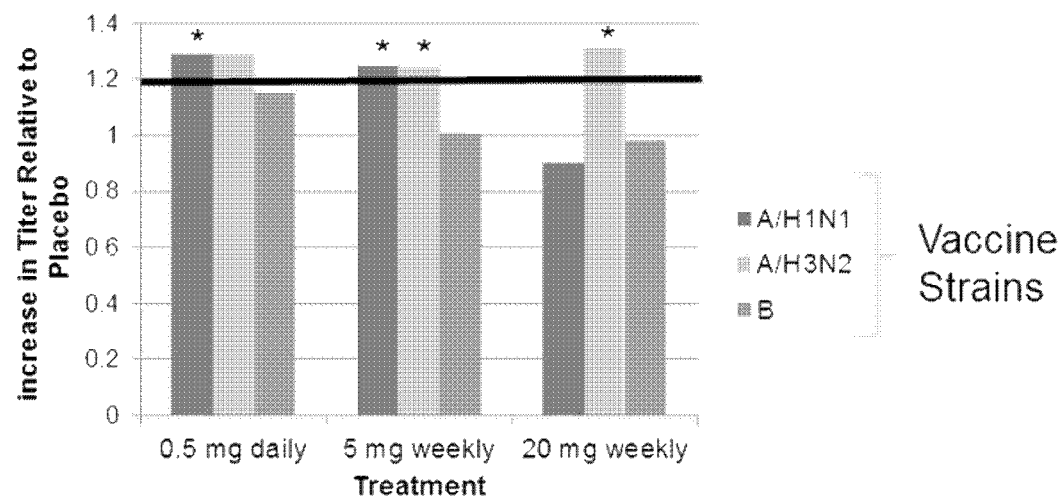
B.
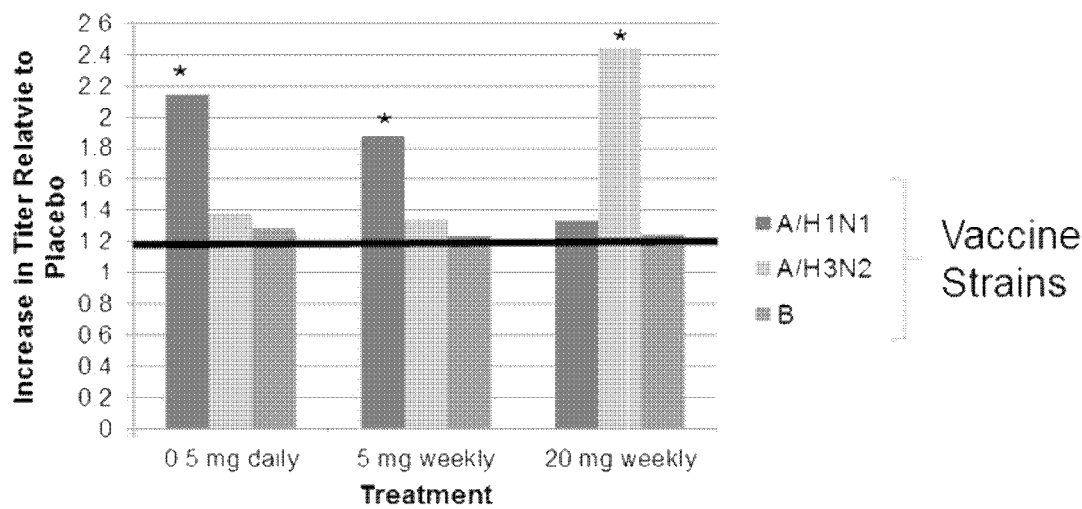

FIG. 36
A.
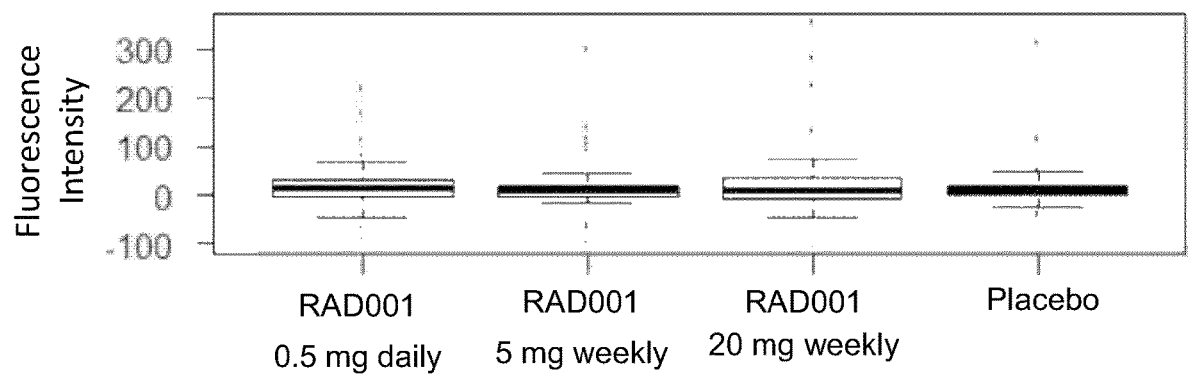
B.
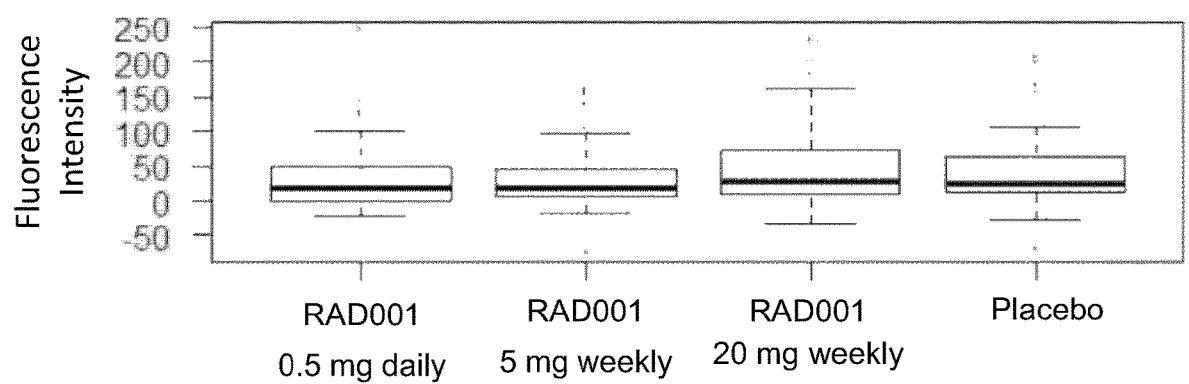

FIG. 37
A.
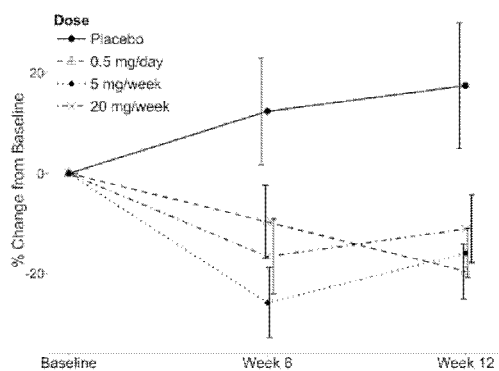
B.
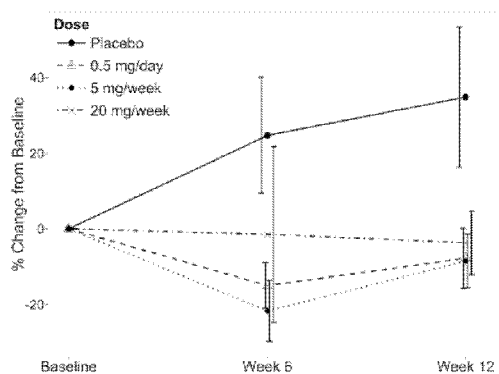
C.
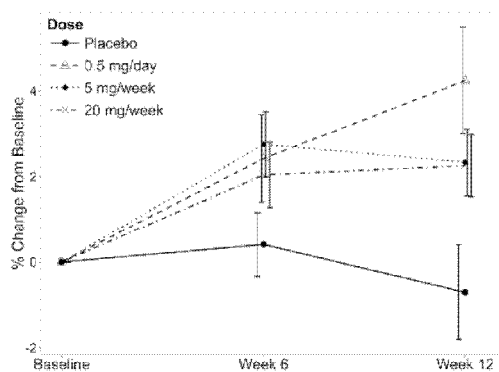

FIG. 38
A.
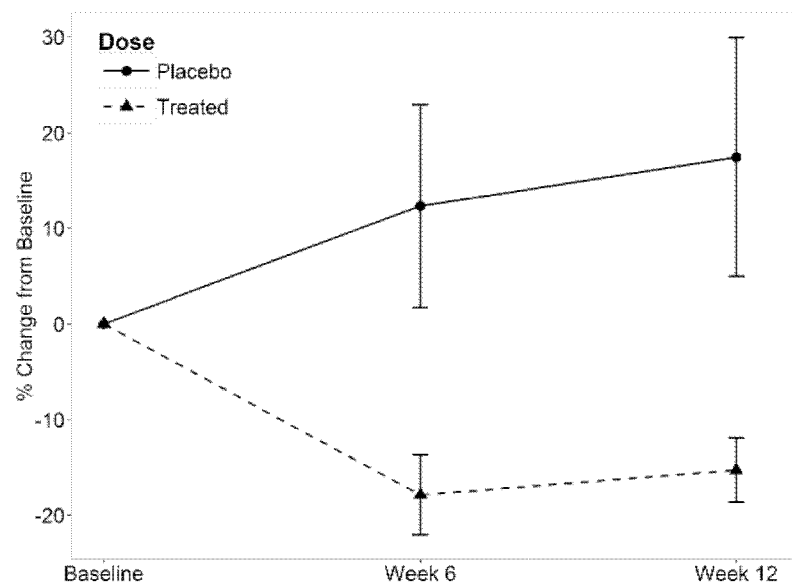
B.
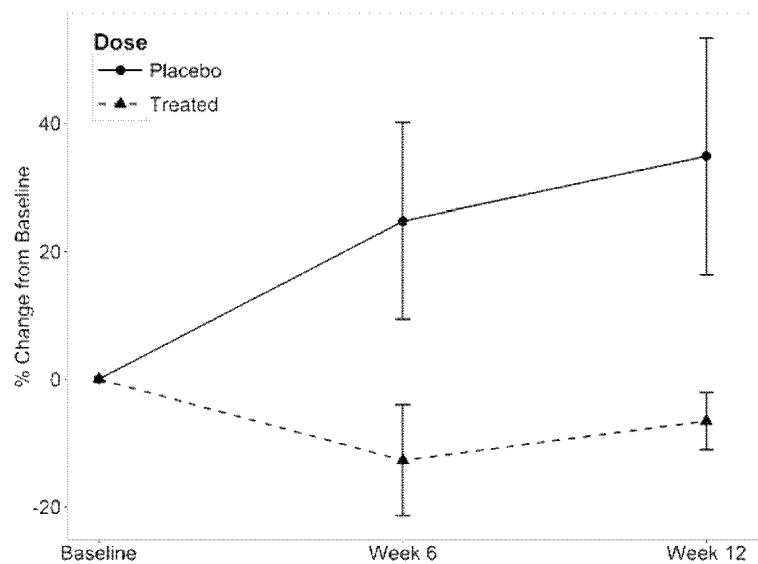

L G P H V E G L K A E E R H R P V R D W I L R Q R Q D D L D T L G L G L Q G    (SEQ ID NO: 278)
          555         560         565         570         575         580         585
```

FIG. 46

$E_{296}$VEKT$_{300}$
$A_{301}$CPSGKKAREIDESLIFYKKWELEACVDAALLATQMDRVNAIPFTYEQLD$_{350}$ $V_{351}$LKHKLDELYPQGYPESVIQHLGYLFLKMSPEDIRKWNVTSLETLKALLE$_{400}$ $V_{401}$NKGHEMSPQAPRRPLPQVATLIDRFVKGRGQLDKDTLDTLTAFYPGYLC$_{450}$ $S_{451}$LSPEELSSVPPSSIWAVRPQDLDTCDPRQLDVLYPKARLAFQNMNGSEY$_{500}$ $F_{501}$VKIQSFLGGAPTEDLKALSQQNVSMDLATFMKLRTDAVLPLTVAEVQKL$_{550}$ $L_{551}$GPHVEGLKAEERHRPVRDWILRQRQDDLDTLGLGLQG$_{588}$  (SEQ ID NO: 278)

═══ *Protected by M5*
▬▬▬ *Protected by SS1*

*Vector constructs*

… # HUMAN MESOTHELIN CHIMERIC ANTIGEN RECEPTORS AND USES THEREOF

STATEMENT REGARDING FEDERALLY SPONSORED RESEARCH OR DEVELOPMENT

This invention was made with a government support under grant numbers CA138907 and CA120409 award by the national Institute of Health. The government has certain rights in the invention.

This application is a U.S. national phase application and claims the benefit of priority under 35 U.S.C. § 371 of International Application No. PCT/CN2014/094393, filed Dec. 19, 2014, which claims priority to International Application No. PCT/CN2013/089979, filed Dec. 19, 2013, International Application No. PCT/CN2014/082610, filed Jul. 21, 2014 and International Application No. PCT/CN2014/090509, filed Nov. 6, 2014, and the entire contents of each of these applications are incorporated herein by reference.

SEQUENCE LISTING

The instant application contains a Sequence Listing which has been submitted electronically in ASCII format and is hereby incorporated by reference in its entirety. Said ASCII copy, created on Jun. 16, 2016 is named N2067-7033WO4_SL.TXT and is 375,836 bytes in size.

FIELD OF THE INVENTION

The present invention relates generally to the use of T cells engineered to express a Chimeric Antigen Receptor (CAR) to treat a disease associated with expression of mesothelin.

BACKGROUND OF THE INVENTION

Mesothelin was originally identified by Pastan and colleagues as a tumor associated antigen due to its limited expression by normal tissues and overexpression on tumors. Chang K, et al., *Cancer Res.* 1992; 52(1):181-186 and Chang K, et al. *ProcNatlAcadSciUSA*. 1996; 93(1):136-140. The mesothelin gene encodes a precursor 71-kDa protein that is processed to yield the 40-kDa protein, mesothelin, which is anchored at the cell membrane by a glycosylphosphatidyl inositol (GPI) linkage and an amino-terminal 31-kDa shed fragment, called megakaryocyte potentiating factor (MPF). Both fragments contain N-glycosylation sites. A soluble splice variant of the 40-kDa carboxyl-terminal fragment called "soluble mesothelin/MPF-related" has been found in the sera of patients with pancreatic ductal adenocarcinoma (PDA). Johnston, F, et al. *Clinical Cancer Research.* 2009; 15(21):6511. Mesothelin is currently being explored both as a therapeutic target as well as a bio-marker for disease activity and therapeutic response. Argani P, et al. *Clin Cancer Res.* 2001; 7(12):3862-3868.

Mesothelin is a differentiation antigen that is also present on normal tissues. Using the mouse anti-human mesothelin antibody K1 that was developed by the Pastan group, strong K1 reactivity has been demonstrated within mesothelial cells that line the peritoneal, pleural, and pericardial cavities, although at lower levels than usually seen for malignant tissues. Chang K, et al. *Cancer Res.* 1992; 52(1):181-186. Weak K1 reactivity has been detected within the Fallopian tube epithelium, tracheal basal epithelium and tonsils epithelium. Mesothelin has also been found on all layers of the cornea. Jirsova K, et al. *Experimental eye research.* 2010; 91(5):623-629. However, K1 reactivity has not been detected in the majority of normal tissues including the liver, kidneys, spleen, bone marrow, lymph nodes, thymus, cardiac muscle, tongue, skeletal muscle, skin, cerebral cortex, cerebellum, spinal cord, peripheral nerve, pituitary, adrenal, salivary gland, mammary gland, thyroid, parathyroid, testis, prostate, epididymis, cervical epithelium, lung parenchyma, esophagus, small-bowel epithelium, colon epithelium, bladder epithelium, gall-bladder epithelium. Chang K, et al., *Cancer Res.* 1992; 52(1):181-186.

Mesothelin is overexpressed in the vast majority of primary pancreatic adenocarcinomas with rare and weak expression seen in benign pancreatic tissue. Argani P, et al. *Clin Cancer Res.* 2001; 7(12):3862-3868. Epithelial malignant pleural mesothelioma (MPM) universally expresses mesothelin while sarcomatoid MPM does not express mesothelin. Most serous epithelial ovarian carcinomas, and the related primary peritoneal carcinomas, express mesothelin.

Mesothelin is a target of a natural immune response in ovarian cancer, and has been proposed to be a target for cancer immunotherapy. Bracci L, et al. *Clin Cancer Res.* 2007; 13(2 Pt 1):644-653; Moschella F, et al. *Cancer Res.* 2011; 71(10):3528-3539; Gross G, et al. *FASEB J.* 1992; 6(15):3370-3378; Sadelain M, et al. *NatRevCancer.* 2003; 3(1):35-45; Muul L M, et al. *Blood.* 2003; 101(7):2563-2569; Yee C, et al. *Proc Natl Acad Sci USA.* 2002; 99(25):16168-16173. The presence of mesothelin-specific CTLs in patients with pancreatic cancer correlates with overall survival. Thomas A M, et al. *J Exp Med.* 2004; 200:297-306. In addition, Pastan and coworkers have used soluble antibody fragments of an anti-mesothelin antibody conjugated to immunotoxins to treat cancer patients with mesothelin-positive tumors. This approach has demonstrated adequate safety and some clinical activity in pancreatic cancer. Hassan R, et al. *Cancer Immun.* 2007; 7:20 and Hassan R, et al. *Clin Cancer Res.* 2007; 13(17):5144-5149. In ovarian cancer, this therapeutic strategy produced one minor response by RECIST criteria and stable disease in a second patient who also had complete resolution of their ascites.

SUMMARY OF THE INVENTION

The invention features, e.g., methods of providing an immune response in patients by administering an immune effector cell that is engineered to express a Chimeric Antigen Receptor (CAR) that comprises an antibody (e.g., scFv) that specifically targets mesothelin. In particular, the invention pertains to the use of an immune effector cell such as, e.g., a T cell or NK cell, engineered to express a CAR that includes an antibody such as antigen binding fragment thereof to treat a cancer associated with expression of mesothelin (or MSLN). In particular, the invention pertains to adoptive cell transfer that may be particularly suitable for patients with mesothelin-expressing cancers, such as, e.g., mesothelioma (e.g., malignant pleural mesothelioma, lung cancer (e.g., non-small cell lung cancer, small cell lung cancer, squamous cell lung cancer, or large cell lung cancer), pancreatic cancer (e.g., pancreatic ductal adenocarcinoma, pancreatic metatstatic), ovarian cancer, colorectal cancer and bladder cancer, or any combination thereof.

Accordingly, in one aspect, the invention pertains to an isolated nucleic acid molecule encoding a chimeric antigen receptor (CAR), wherein the CAR comprises an anti-mesothelin binding domain (e.g., a human anti-mesothelin binding domain), a transmembrane domain, and an intracellular signaling domain comprising a stimulatory domain. In one embodiment, the encoded anti-mesothelin binding domain comprises one or more (e.g., all three) light chain complementary determining region 1 (LC CDR1), light chain complementary determining region 2 (LC CDR2), and light chain complementary determining region 3 (LC CDR3) of a human anti-mesothelin binding domain described herein, and one or more (e.g., all three) heavy chain complementary determining region 1 (HC CDR1), heavy chain complementary determining region 2 (HC CDR2), and heavy chain complementary determining region 3 (HC CDR3) of a human anti-mesothelin binding domain described herein. In one embodiment, the encoded human anti-mesothelin binding domain comprises, or consists of, a light chain variable region described herein (e.g., in Table 2, 4 or 5) and/or a heavy chain variable region described herein (e.g., in Table 2, 4, or 5). In one embodiment, the encoded anti-mesothelin binding domain is a scFv comprising or consisting of a light chain and a heavy chain of an amino acid sequence of Table 2. In an embodiment, the anti-mesothelin binding domain (e.g., an scFV) comprises or consists: a light chain variable region comprising an amino acid sequence having at least one, two or three modifications (e.g., substitutions) but not more than 30, 20 or 10 modifications (e.g., substitutions) of an amino acid sequence of a light chain variable region provided in Table 2, or a sequence with 95-99% identity with an amino acid sequence of Table 2; and/or a heavy chain variable region comprising, or consisting of, an amino acid sequence having at least one, two or three modifications (e.g., substitutions) but not more than 30, 20 or 10 modifications (e.g., substitutions) of an amino acid sequence of a heavy chain variable region provided in Table 2, or a sequence with 95-99% identity to an amino acid sequence of Table 2. In one embodiment, the human anti-mesothelin binding domain comprises, or consists of, a sequence selected from the group consisting of SEQ ID NO: 39; SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, and SEQ ID NO: 62, or a sequence with 95-99% identity thereof. In one embodiment, the nucleic acid sequence encoding the human anti-mesothelin binding domain comprises, or consists of, a sequence selected from the group consisting of SEQ ID NO: 87; SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, and SEQ ID NO: 110, or a sequence with 95-99% identify thereof.

In one embodiment, the isolated nucleic acid further comprises a sequence encoding a transmembrane domain, e.g., a transmembrane domain described herein. In one embodiment, the encoded transmembrane domain comprises, or consists of, a transmembrane domain of a protein selected from the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In one embodiment, the encoded transmembrane domain comprises, or consists of, a sequence of SEQ ID NO: 12. In one embodiment, the transmembrane domain comprises, or consists of, an amino acid sequence having at least one, two or three modifications (e.g., substitutions) but not more than 20, 10 or 5 modifications (e.g., substitutions) of an amino acid sequence of SEQ ID NO: 12, or a sequence with 95-99% identity to an amino acid sequence of SEQ ID NO: 12.

In one embodiment, the encoded CAR includes an anti-mesothelin binding domain, e.g., an anti-mesothelin binding domain described herein, connected to the transmembrane domain by a hinge region, e.g., a hinge region described herein. In one embodiment, the hinge region comprises, or consists of, SEQ ID NO: 6 or SEQ ID NO: 8.

In one embodiment, the isolated nucleic acid molecule further comprises a sequence encoding a costimulatory domain, e.g., a costimulatory domain described herein. In one embodiment, the costimulatory domain is a functional signaling domain obtained from a protein selected from the group consisting of OX40, CD27, CD28, CD5, ICAM-1, LFA-1 (CD11a/CD18), ICOS (CD278), and 4-1BB (CD137). In one embodiment, the encoded costimulatory domain comprises, or consists of, a sequence of SEQ ID NO:14. In one embodiment, the costimulatory domain comprises, or consists of, an amino acid sequence having at least one, two or three modifications (e.g., substitutions) but not more than 20, 10 or 5 modifications (e.g., substitutions) of an amino acid sequence of SEQ ID NO: 14, or a sequence with 95-99% identity to an amino acid sequence of SEQ ID NO: 14.

In one embodiment, the isolated nucleic acid comprises a sequence encoding an intracellular signaling domain, e.g., an intracellular signaling domain described herein. In one embodiment, the isolated nucleic acid encodes a functional signaling domain of 4-1BB and/or a functional signaling domain of CD3 zeta. In one embodiment, the encoded intracellular signaling domain comprises the sequence of SEQ ID NO: 7 and/or the sequence of SEQ ID NO: 9 or SEQ ID NO: 10. In one embodiment, the intracellular signaling domain comprises an amino acid sequence having at least one, two or three modifications (e.g., substitutions) but not more than 20, 10 or 5 modifications (e.g., substitutions) of an amino acid sequence of SEQ ID NO:7 and/or an amino acid sequence of SEQ ID NO:9 or SEQ ID NO: 10, or a sequence with 95-99% identity to an amino acid sequence of SEQ ID NO:7 and/or an amino acid sequence of SEQ ID NO:9 or SEQ ID NO: 10. In one embodiment, the encoded intracellular signaling domain comprises, or consists of, the sequence of SEQ ID NO: 7 and the sequence of SEQ ID NO: 9 or SEQ ID NO: 10, wherein the sequences comprising the intracellular signaling domain are expressed in the same frame and as a single polypeptide chain.

In another aspect, the invention pertains to an isolated nucleic acid molecule encoding a CAR construct comprising a leader sequence, e.g., of SEQ ID NO: 1; an anti-mesothelin binding domain described herein, e.g., having an amino acid sequence of Table 2, or a sequence with 95-99% identify thereof; a hinge region, e.g., of SEQ ID NO: 2; a transmembrane domain, e.g., having a sequence of SEQ ID NO: 6; a costimulatory domain, e.g., a 4-1BB costimulatory domain having a sequence of SEQ ID NO:7; and a primary signaling domain, e.g., CD3 zeta stimulatory domain having a sequence of SEQ ID NO:9 or 10. In one embodiment, the isolated nucleic acid molecule comprises (e.g., consists of) a nucleic acid sequence encoding a polypeptide having an amino acid sequence of Table 2. In one embodiment, the isolated nucleic acid molecule comprises (consists of) a nucleic acid encoding a polypeptide having an amino acid sequence having at least one, two or three modifications (e.g., substitutions) but not more than 30, 20 or 10 modifications (e.g., substitutions) of an amino acid sequence of Table 2, or a sequence with 95-99% identity to an amino acid sequence of Table 2.

In another aspect, the invention pertains to an isolated polypeptide molecule encoded by the nucleic acid sequence, e.g., a nucleic acid described herein.

In another aspect, the invention pertains to an isolated polypeptide molecule comprising, or consisting of, a sequence selected from the group consisting of Table 2, an amino acid sequence having at least one, two or three modifications (e.g., substitutions) but not more than 30, 20 or 10 modifications (e.g., substitutions) of an amino acid sequence of a heavy chain variable region provided in Table 2, or a sequence with 95-99% identity to an amino acid sequence of Table 2. In one embodiment, the isolated polypeptide comprises one or more (e.g., all three) light chain complementary determining region 1 (LC CDR1), light chain complementary determining region 2 (LC CDR2), and light chain complementary determining region 3 (LC CDR3) of a human anti-mesothelin binding domain described herein, and one or more (e.g., all three) heavy chain complementary determining region 1 (HC CDR1), heavy chain complementary determining region 2 (HC CDR2), and heavy chain complementary determining region 3 (HC CDR3) of a human anti-mesothelin binding domain described herein.

In another aspect, the invention pertains to an isolated chimeric antigen receptor (CAR) molecule comprising an anti-mesothelin binding domain described herein, e.g., a human anti-mesothelin binding domain described herein, a transmembrane domain, and an intracellular signaling domain comprising a stimulatory domain.

In one embodiment, the anti-mesothelin binding domain does not compete for binding to human mesothelin with an antigen binding domain comprising a sequence comprising SEQ ID NO: 279.

In one embodiment, the anti-mesothelin binding domain competes for binding to human mesothelin with an antigen binding domain comprising a LC CDR1, LC CDR2 and LC CDR3 of an anti-mesothelin light chain amino acid sequence selected from SEQ ID NO: 43 or SEQ ID NO: 49 and an HC CDR1, HC CDR2, and HC CDR3 of an anti-mesothelin heavy chain amino acid sequence selected from SEQ ID NO: 43 or SEQ ID NO: 49. In one embodiment, the anti-mesothelin binding domain competes for binding to human mesothelin with an antigen binding domain comprising SEQ ID NO:43 or SEQ ID NO:49.

In one embodiment, the anti-mesothelin binding domain binds to a different epitope of human mesothelin than the epitope of human mesothelin targeted by the antigen binding domain comprising a sequence comprising SEQ ID NO: 279. In an embodiment, the epitope comprises a sequence of amino acids selected from amino acids 314-315, 317-318, 346-349, and 369-375 of SEQ ID NO: 278, or any combination thereof. In an embodiment, the epitope comprises one or more amino acids selected from amino acids 314-315, 317-318, 346-349, and 369-375 of SEQ ID NO: 278, or any combination thereof.

In an embodiment, the anti-mesothelin binding domain described herein does not bind to the N-terminus of mesothelin as shown in SEQ ID NO: 278. In one embodiment, the anti-mesothelin binding domain binds to the C-terminus of human mesothelin. In one embodiment, the anti-mesothelin binding domain binds an epitope within amino acids 450-588 of SEQ ID NO: 278. In one embodiment, the epitope bound by the anti-mesothelin binding domain comprises a sequence selected from amino acids 485-490, 498-507, 532-537, and 545-572 of SEQ ID NO: 278, or a combination thereof. In one embodiment, the epitope bound by the anti-mesothelin binding domain comprises one or more amino acids selected from amino acids 485-490, 498-507, 532-537, and 545-572 of SEQ ID NO: 278, or any combination thereof. In these embodiments, SEQ ID NO: 278 represents amino acids 296-588 of human mesothelin, e.g., the first amino acid of SEQ ID NO: 278 is amino acid 296 and the last amino acid of SEQ ID NO: 278 is amino acid 588.

In one embodiment, the anti-mesothelin binding domain comprises one or more (e.g., all three) light chain complementary determining region 1 (LC CDR1), light chain complementary determining region 2 (LC CDR2), and light chain complementary determining region 3 (LC CDR3) of a human anti-mesothelin binding domain described herein, and one or more (e.g., all three) heavy chain complementary determining region 1 (HC CDR1), heavy chain complementary determining region 2 (HC CDR2), and heavy chain complementary determining region 3 (HC CDR3) of a human anti-mesothelin binding domain described herein. In one embodiment, the human anti-mesothelin binding domain comprises, or consists of, a light chain variable region described herein (e.g., in Table 2) and/or a heavy chain variable region described herein (e.g., in Table 2). In one embodiment, the anti-mesothelin binding domain is a scFv comprising, or consisting of, a light chain variable region and a heavy chain variable region of an amino acid sequence of Table 2. In an embodiment, the anti-mesothelin binding domain (e.g., an scFV) comprises, or consists of: a light chain variable region comprising an amino acid sequence having at least one, two or three modifications (e.g., substitutions) but not more than 30, 20 or 10 modifications (e.g., substitutions) of an amino acid sequence of a light chain variable region provided in Table 2, or a sequence with 95-99% identity to an amino acid sequence of Table 2; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided in Table 2, or a sequence with 95-99% identity to an amino acid sequence of Table 2. In one embodiment, the human anti-mesothelin binding domain comprises, or consists of, a sequence selected from the group consisting of SEQ ID NO: 39; SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, and SEQ ID NO: 62, or a sequence with 95-99% identity thereof.

In one embodiment, the transmembrane domain is a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In one embodiment, the transmembrane domain comprises a transmembrane domain described herein, e.g., having a sequence of SEQ ID NO:6, an amino acid sequence having at least one, two or three modifications (e.g., substitutions) but not more than 20, 10 or 5 modifications (e.g., substitutions) of an amino acid sequence of SEQ ID NO:6, or a sequence with 95-99% identity to an amino acid sequence of SEQ ID NO:6.

In one embodiment, the anti-mesothelin binding domain is connected to the transmembrane domain by a hinge region. In one embodiment, the hinge region comprises a hinge region described herein, e.g., a hinge region of SEQ ID NO:2.

In one embodiment, the isolated CAR molecule further comprises a costimulatory domain, e.g., a costimulatory domain described herein. In one embodiment, the costimulatory domain is a functional signaling domain obtained from a protein selected from the group consisting of OX40, CD27, CD28, CDS, ICAM-1, LFA-1 (CD11a/CD18), ICOS (CD278), and 4-1BB (CD137) or functional variant thereof. In one embodiment, the costimulatory domain comprises, or consists of, a sequence of SEQ ID NO:7. In one embodiment, the costimulatory domain comprises, or consists of, an amino acid sequence having at least one, two or three modifications (e.g., substitutions) but not more than 20, 10 or 5 modifications (e.g., substitutions) of an amino acid sequence of SEQ ID NO:7, or a sequence with 95-99% identity to an amino acid sequence of SEQ ID NO:7.

In one embodiment, the isolated CAR molecule comprises an intracellular signaling domain, e.g., an intracellular signaling domain described herein. In one embodiment, the intracellular signaling domain comprises a functional signaling domain of 4-1BB and/or a functional signaling domain of CD3 zeta. In one embodiment, the intracellular signaling domain comprises, or consists of, the sequence of SEQ ID NO: 7 and/or the sequence of SEQ ID NO: 9 or SEQ ID NO: 10. In one embodiment, the intracellular signaling domain comprises, or consists of, an amino acid sequence having at least one, two or three modifications (e.g., substitutions) but not more than 20, 10 or 5 modifications (e.g., substitutions) of an amino acid sequence of SEQ ID NO:7 and/or an amino acid sequence of SEQ ID NO:9 or SEQ ID NO: 10, or a sequence with 95-99% identity to an amino acid sequence of SEQ ID NO:7 and/or an amino acid sequence of SEQ ID NO:9 or SEQ ID NO: 10. In one embodiment, the intracellular signaling domain comprises, or consists of, the sequence of SEQ ID NO: 9 and the sequence of SEQ ID NO: 9 or SEQ ID NO: 10, wherein the sequences comprising the intracellular signaling domain are expressed in the same frame and as a single polypeptide chain.

In another aspect, the invention pertains to an isolated CAR molecule comprising a leader sequence, e.g., of SEQ ID NO: 1; an anti-mesothelin binding domain described herein, e.g., having an amino acid sequence of Table 2, or a sequence with 95-99% identify thereof; a hinge region, e.g., of SEQ ID NO:2; a transmembrane domain, e.g., having a sequence of SEQ ID NO: 6; a costimulatory domain, e.g., a 4-1BB costimulatory domain having a sequence of SEQ ID NO:7; and a primary signaling domain, e.g., CD3 zeta stimulatory domain having a sequence of SEQ ID NO:9 or SEQ ID NO: 10. In one embodiment, the isolated CAR molecule comprises (e.g., consists of) a polypeptide having an amino acid sequence of Table 2. In one embodiment, the isolated CAR molecule comprises (consists of) a polypeptide having an amino acid sequence having at least one, two or three modifications (e.g., substitutions) but not more than 30, 20 or 10 modifications (e.g., substitutions) of an amino acid sequence of Table 2, or a sequence with 95-99% identity to an amino acid sequence of Table 2. In one embodiment, the isolated CAR molecule comprises, or consists of, an amino acid sequence selected from the group consisting of SEQ ID NO: 63; SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, and SEQ ID NO: 86.

In another aspect, the invention pertains to a vector comprising a nucleic acid sequence described herein. In one embodiment, the nucleic acid sequence encodes a CAR molecule, e.g., a CAR molecule described herein. In one embodiment, the vector is selected from the group consisting of a DNA, a RNA, a plasmid, a lentivirus vector, adenoviral vector, or a retrovirus vector.

In one embodiment, the vector is a lentivirus vector, e.g., a lentivirus vector described herein. In one embodiment, the vector further comprises a promoter. In one embodiment, the promoter is an EF-1α promoter. In one embodiment, the EF-1α promoter comprises a sequence of SEQ ID NO: 11.

In one embodiment, the vector is an in vitro transcribed vector, e.g., a vector that transcribes RNA of a nucleic acid molecule described herein. In one embodiment, the RNA is transcribed from an in vitro transcription vector, wherein the vector is pD-A.anti-meso BD OF.2bg.150A, wherein the anti-meso BD is an anti-mesothelin binding domain described herein. In one embodiment, the nucleic acid sequence in the vector further comprises a poly(A) tail, e.g., a poly A tail described herein, e.g., comprising about 150 adenosine bases (SEQ ID NO: 271). In one embodiment, the nucleic acid sequence in the vector further comprises a 3'UTR, e.g., a 3'UTR described herein, e.g., comprising at least one repeat of a 3'UTR derived from human beta-globulin.

In another aspect, the invention pertains to a cell comprising the vector. The cell can be, e.g., a cell described herein. In one embodiment, the cell is a human T cell, e.g., a T cell described herein, or a human NK cell, e.g., a human NK cell described herein. In one embodiment, the human T cell is a CD8+ T cell. In one embodiment, the cell is an autologous T cell. In one embodiment, the cell is an allogeneic T cell. In one embodiment, the cell is a T cell and the T cell is diaglycerol kinase (DGK) deficient. In one embodiment, the cell is a T cell and the T cell is Ikaros deficient. In one embodiment, the cell is a T cell and the T cell is both DGK and Ikaros deficient.

In one aspect, the CAR-expressing cell described herein can further comprise a second CAR, e.g., a second CAR that includes a different antigen binding domain, e.g., to the same target (mesothelin) or a different target (e.g., a target other than mesothelin on stroma cells, e.g., FAP; a target other than mesothelin on prostate cancer cells, e.g., androgen receptor, OR51E2, PSMA, PSCA, PDGRF-β, TARP, GloboH, MAD-CT-1, or MAD-CT-2; a target other than mesothelin on ovararian cancer cells, e.g., Tn, PRSS21, CD171, Lewis Y, folate receptor α, claudin6, GloboH, or sperm protein 17; e.g., a target other than mesothelin on lung cancer cells, e.g., VEGF, HER3, IGF-1R, EGFR, DLL4, or Trop-2). In one embodiment, the CAR-expressing cell comprises a first CAR that targets a first antigen and includes an intracellular signaling domain having a costimulatory signaling domain but not a primary signaling domain, and a second CAR that targets a second, different, antigen and includes an intracellular signaling domain having a primary signaling domain but not a costimulatory signaling domain. In one embodiment, the CAR expressing cell comprises a first mesothelin CAR that includes a mesothelin binding domain, a transmembrane domain and a costimulatory domain and a second CAR that targets an antigen other than mesothelin (e.g., an antigen expressed on stroma cells, lung cancer cells, prostate cancer cells or ovarian cancer cells)

and includes an antigen binding domain, a transmembrane domain and a primary signaling domain. In another embodiment, the CAR expressing cell comprises a first mesothelin CAR that includes a mesothelin binding domain, a transmembrane domain and a primary signaling domain and a second CAR that targets an antigen other than mesothelin (e.g., an antigen expressed on stroma cells, lung cancer cells, prostate cancer cells or ovarian cancer cells) and includes an antigen binding domain to the antigen, a transmembrane domain and a costimulatory signaling domain.

In one embodiment, the CAR-expressing cell comprises a mesothelin CAR described herein and an inhibitory CAR. In one embodiment, the inhibitory CAR comprises an antigen binding domain that binds an antigen found on normal cells but not cancer cells, e.g., normal cells that also express mesothelin. In one embodiment, the inhibitory CAR comprises the antigen binding domain, a transmembrane domain and an intracellular domain of an inhibitory molecule. For example, the intracellular domain of the inhibitory CAR can be an intracellular domain of PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 and TGFR beta.

In another embodiment, the CAR-expressing cell described herein can further express another agent, e.g., an agent which enhances the activity or fitness of a CAR-expressing cell, e.g., an agent described herein. For example, in one embodiment, the agent can be an agent which inhibits a molecule that modulates or regulates, e.g., inhibits, T cell function. In some embodiments, the molecule that modulates or regulates T cell function is an inhibitory molecule. Examples of inhibitory molecules include PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 and TGFR beta. In embodiments, an agent, e.g., an inhibitory nucleic acid, e.g., a dsRNA, e.g., an siRNA or shRNA; or e.g., an inhibitory protein or system, e.g., a clustered regularly interspaced short palindromic repeats (CRISPR), a transcription-activator like effector nuclease (TALEN), or a zinc finger endonuclease (ZFN), e.g., as described herein, can be used to inhibit expression of a molecule that modulates or regulates, e.g., inhibits, T-cell function in the CAR-expressing cell. In an embodiment the agent is an shRNA, e.g., an shRNA described herein. In an embodiment, the agent that modulates or regulates, e.g., inhibits, T-cell function is inhibited within a CAR-expressing cell. For example, a dsRNA molecule that inhibits expression of a molecule that modulates or regulates, e.g., inhibits, T-cell function is linked to the nucleic acid that encodes a component, e.g., all of the components, of the CAR.

In one embodiment, the agent which inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, PD-L1, CEACAM (e.g., CEACAM-1, CEACAM-3 and/or CEACAM-5), LAG3, CTLA4, VISTA, CD160, BTLA, LAIR1, TIM3, 2B4, TGFR beta and TIGIT, or a fragment of any of these (e.g., at least a portion of the extracellular domain of any of these), and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein)). In one embodiment, the agent comprises a first polypeptide of PD1 or a fragment thereof (e.g., at least a portion of the extracellular domain of PD1), and a second polypeptide of an intracellular signaling domain described herein (e.g., a CD28 signaling domain described herein and/or a CD3 zeta signaling domain described herein).

In another aspect, the invention pertains to a method of making a cell comprising transducing a cell described herein, e.g., a T cell or a NK cell, with a vector of comprising a nucleic acid encoding a CAR molecule, e.g., a CAR molecule described herein. In one embodiment, the vector is a lentiviral vector described herein.

The present invention also provides a method of generating a population of RNA-engineered cells, e.g., cells described herein, e.g., T cells or NK cells, transiently expressing exogenous RNA. The method comprises introducing an in vitro transcribed RNA or synthetic RNA into a cell, where the RNA comprises a nucleic acid encoding a CAR molecule described herein.

In another aspect, the invention pertains to a method of providing anti-tumor immunity in a subject comprising administering to the subject an effective amount of a cell comprising a CAR molecule, e.g., a cell expressing a CAR molecule described herein, a cell described herein. In one embodiment, the cell is an autologous T cell or NK cell. In one embodiment, the cell is an allogeneic T cell or NK cell. In one embodiment, the subject is a human.

In another aspect, the invention pertains to a method of treating a subject having a disease associated with expression of mesothelin (e.g., a proliferative disease, a precancerous condition, and a noncancer related indication associated with the expression of mesothelin) comprising administering to the subject an effective amount of a cell comprising a CAR molecule, e.g., as described herein.

In one embodiment, the disease associated with mesothelin is cancer, e.g., a cancer described herein. In one embodiment, the disease associated with mesothelin is selected from the group consisting of: mesothelioma (e.g., malignant pleural mesothelioma), lung cancer (e.g., non-small cell lung cancer, small cell lung cancer, squamous cell lung cancer, or large cell lung cancer), pancreatic cancer (e.g., pancreatic ductal adenocarcinoma), ovarian cancer, colorectal cancer and bladder cancer or any combination thereof. In one embodiment, the disease is pancreatic cancer, e.g., metastatic pancreatic ductal adenocarcinoma (PDA), e.g., in a subject who has progressed on at least one prior standard therapy. In one embodiment, the disease is mesothelioma (e.g., malignant pleural mesothelioma), e.g., in a subject who has progressed on at least one prior standard therapy. In one embodiment, the disease is ovarian cancer, e.g., serous epithelial ovarian cancer, e.g., in a subject who has progressed after at least one prior regimen of standard therapy.

In one embodiment, the mesothelin CAR expressing cell, e.g., T cell or NK cell, is administered to a subject that has received a previous dose of melphalan.

In one embodiment, the cells expressing a CAR molecule, e.g., a CAR molecule described herein, are administered in combination with an agent that enhances the activity or fitness of a cell expressing a CAR molecule, e.g., an agent described herein.

In one embodiment, the cells expressing a CAR molecule, e.g., a CAR molecule described herein, are administered in combination with a low, immune enhancing dose of an mTOR inhibitor. While not wishing to be bound by theory, it is believed that treatment with a low, immune enhancing, dose (e.g., a dose that is insufficient to completely suppress the immune system but sufficient to improve immune function) is accompanied by a decrease in PD-1 positive T cells or an increase in PD-1 negative cells. PD-1 positive T cells, but not PD-1 negative T cells, can be exhausted by engagement with cells which express a PD-1 ligand, e.g., PD-L1 or PD-L2.

In an embodiment this approach can be used to optimize the performance of CAR cells described herein in the subject. While not wishing to be bound by theory, it is believed that, in an embodiment, the performance of endogenous, non-modified immune effector cells, e.g., T cells, is improved. While not wishing to be bound by theory, it is believed that, in an embodiment, the performance of a mesothelin CAR expressing cell is improved. In other embodiments, cells, e.g., T cells or NK cells, which have, or will be engineered to express a CAR, can be treated ex vivo by contact with an amount of an mTOR inhibitor that increases the number of PD1 negative immune effector cells, e.g., T cells or increases the ratio of PD1 negative immune effector cells, e.g., T cells/PD1 positive immune effector cells, e.g., T cells.

In an embodiment, administration of a low, immune enhancing, dose of an mTOR inhibitor, e.g., an allosteric inhibitor, e.g., RAD001, or a catalytic inhibitor, is initiated prior to administration of an CAR expressing cell described herein, e.g., T cells or NK cells. In an embodiment, the CAR cells are administered after a sufficient time, or sufficient dosing, of an mTOR inhibitor, such that the level of PD1 negative immune effector cells, e.g., T cells, or the ratio of PD1 negative immune effector cells, e.g., T cells/PD1 positive immune effector cells, e.g., T cells, has been, at least transiently, increased.

In an embodiment, the cell, e.g., T cell or NK cell, to be engineered to express a CAR, is harvested after a sufficient time, or after sufficient dosing of the low, immune enhancing, dose of an mTOR inhibitor, such that the level of PD1 negative immune effector cells, e.g., T cells, or the ratio of PD1 negative immune effector cells, e.g., T cells/PD1 positive immune effector cells, e.g., T cells, in the subject or harvested from the subject has been, at least transiently, increased.

In one embodiment, the cells expressing a CAR molecule, e.g., a CAR molecule described herein, are administered in combination with an agent that ameliorates one or more side effect associated with administration of a cell expressing a CAR molecule, e.g., an agent described herein.

In one embodiment, the cells expressing a CAR molecule, e.g., a CAR molecule described herein, are administered in combination with an agent that treats the disease associated with mesothelin expression, e.g., an agent described herein.

In one embodiment, the cells expressing a CAR molecule, e.g., a CAR molecule described herein, are administered at a dose and/or dosing schedule described herein.

In one embodiment, the cells expressing a CAR molecule, e.g., a CAR molecule described herein, are administered as a first line treatment for the disease, e.g., the cancer, e.g., the cancer described herein. In another embodiment, the cells expressing a CAR molecule, e.g., a CAR molecule described herein, are administered as a second, third, fourth line treatment for the disease, e.g., the cancer, e.g., the cancer described herein.

In one embodiment, a population of cells described herein is administered.

In one embodiment, the CAR molecule is introduced into T cells or NK cells, e.g., using in vitro transcription, and the subject (e.g., human) receives an initial administration of cells comprising a CAR molecule, and one or more subsequent administrations of cells comprising a CAR molecule, wherein the one or more subsequent administrations are administered less than 15 days, e.g., 14, 13, 12, 11, 10, 9, 8, 7, 6, 5, 4, 3, or 2 days after the previous administration. In one embodiment, more than one administration of cells comprising a CAR molecule are administered to the subject (e.g., human) per week, e.g., 2, 3, or 4 administrations of cells comprising a CAR molecule are administered per week. In one embodiment, the subject (e.g., human subject) receives more than one administration of cells comprising a CAR molecule per week (e.g., 2, 3 or 4 administrations per week) (also referred to herein as a cycle), followed by a week of no administration of cells comprising a CAR molecule, and then one or more additional administration of cells comprising a CAR molecule (e.g., more than one administration of the cells comprising a CAR molecule per week) is administered to the subject. In another embodiment, the subject (e.g., human subject) receives more than one cycle of cells comprising a CAR molecule, and the time between each cycle is less than 10, 9, 8, 7, 6, 5, 4, or 3 days. In one embodiment, the cells comprising a CAR molecule are administered every other day for 3 administrations per week. In one embodiment, the cells comprising a CAR molecule are administered for at least two, three, four, five, six, seven, eight or more weeks.

In one aspect, the invention includes a population of autologous or allogenic cells that are transfected or transduced with a vector comprising a nucleic acid molecule encoding a mesothelin-CAR molecule, e.g., as described herein. In one embodiment, the vector is a retroviral vector. In one embodiment, the vector is a self-inactivating lentiviral vector as described elsewhere herein. In one embodiment, the vector is delivered (e.g., by transfecting or electroporating) to a cell, e.g., a T cell or a NK cell, wherein the vector comprises a nucleic acid molecule encoding a mesothelin CAR molecule as described herein, which is transcribed as an mRNA molecule, and the mesothelin CAR molecule is translated from the RNA molecule and expressed on the surface of the cell.

In another aspect, the present invention provides a population of CAR-expressing cells, e.g., CART cells. In some embodiments, the population of CAR-expressing cells comprises a mixture of cells expressing different CARs. For example, in one embodiment, the population of CART cells can include a first cell expressing a CAR having an anti-mesothelin binding domain described herein, and a second cell expressing a CAR having a different anti-mesothelin binding domain, e.g., an anti-mesothelin binding domain described herein that differs from the anti-mesothelin binding domain in the CAR expressed by the first cell. As another example, the population of CAR-expressing cells can include a first cell expressing a CAR that includes an anti-mesothelin binding domain, e.g., as described herein, and a second cell expressing a CAR that includes an antigen binding domain to a target other than mesothelin (e.g., a target other than mesothelin on stroma cells, e.g., FAP; a target other than mesothelin on prostate cancer cells, e.g., androgen receptor, OR51E2, PSMA, PSCA, PDGRF-β, TARP, GloboH, MAD-CT-1, or MAD-CT-2; a target other than mesothelin on ovararian cancer cells, e.g., Tn, PRSS21, CD171, Lewis Y, folate receptor α, claudin6, GloboH, or sperm protein 17; e.g., a target other than mesothelin on lung cancer cells, e.g., VEGF, HER3, IGF-1R, EGFR, DLL4, or Trop-2). In one embodiment, the population of CAR-expressing cells includes, e.g., a first cell expressing a CAR that includes a primary intracellular signaling domain, and a second cell expressing a CAR that includes a secondary signaling domain.

In another aspect, the present invention provides a population of cells wherein at least one cell in the population expresses a CAR having an anti-mesothelin binding domain described herein, and a second cell expressing another agent, e.g., an agent which enhances the activity or function of a CAR-expressing cell. For example, in one embodiment, the agent can be an agent which inhibits a molecule that modulates or regulates, e.g., inhibits, T cell function. In some embodiments, the molecule that modulates or regulates T cell function is an inhibitory molecule, e.g., an agent described herein. Examples of inhibitory molecules include PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 and TGFR beta. In embodiments, an agent, e.g., an inhibitory nucleic acid, e.g., a dsRNA, e.g., an siRNA or shRNA; or e.g., an inhibitory protein or system, e.g., a clustered regularly interspaced short palindromic repeats (CRISPR), a transcription-activator like effector nuclease (TALEN), or a zinc finger endonuclease (ZFN), e.g., as described herein, can be used to inhibit expression of a molecule that modulates or regulates, e.g., inhibits, T-cell function in the CAR-expressing cell. In an embodiment the agent is an shRNA, e.g., an shRNA described herein. In an embodiment, the agent that modulates or regulates, e.g., inhibits, T-cell function is inhibited within a CAR-expressing cell. For example, a dsRNA molecule that inhibits expression of a molecule that modulates or regulates, e.g., inhibits, T-cell function is linked to the nucleic acid that encodes a component, e.g., all of the components, of the CAR.

In one embodiment, the agent which inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, PD-L1, CEACAM (e.g., CEACAM-1, CEACAM-3 and/or CEACAM-5), LAG3, CTLA4, VISTA, CD160, BTLA, LAIR1, TIM3, 2B4, TGFR beta and TIGIT, or a fragment of any of these (e.g., at least a portion of an extracellular domain of any of these), and a second polypeptide which is an intracellular signaling domain described herein (e.g., comprising a costimulatory domain (e.g., 41BB, CD27 or CD28, as described herein) and/or a primary signaling domain (e.g., a CD3 zeta signaling domain described herein). In one embodiment, the agent comprises a first polypeptide of PD1 or a fragment thereof (e.g., at least a portion of the extracellular domain of PD1), and a second polypeptide of an intracellular signaling domain described herein (e.g., a CD28 signaling domain described herein and/or a CD3 zeta signaling domain described herein).

In one embodiment, the nucleic acid molecule encoding a mesothelin CAR molecule, e.g., as described herein, is expressed as an mRNA molecule. In one embodiment, the genetically modified mesothelin CAR-expressing cells, e.g., T cells or NK cells, can be generated by transfecting or electroporating an RNA molecule encoding the desired CARs (e.g., without a vector sequence) into the cell. In one embodiment, a mesothelin CAR molecule is translated from the RNA molecule once it is incorporated and expressed on the surface of the recombinant cell.

In another aspect, the invention pertains to the isolated nucleic acid molecule encoding a CAR molecule, e.g., a CAR molecule described herein, a CAR molecule described herein, a vector comprising a CAR molecule described herein, and/or a cell comprising a CAR molecule described herein for use as a medicament.

In another aspect, the invention pertains to the isolated nucleic acid molecule encoding a CAR molecule described herein, a CAR molecule described herein, a vector comprising a CAR molecule described herein, and/or a cell comprising a CAR molecule described herein for use in the treatment of a disease expressing mesothelin, e.g., as described herein.

BRIEF DESCRIPTION OF THE DRAWINGS

FIG. 2 depicts cell manufacturing and treatment schedules that can be used. (A) Autologous cells are obtained by leukocyte apheresis and T cells are enriched by expansion with anti-CD3/CD28 mAb coated magnetic beads. Cells are expanded for 8 to 12 days. On the last day of culture, the beads are removed using a magnetic field and the cells are washed, electroporated with human meso CAR mRNA construct, and cryopreserved in infusible medium. (B) Three treatment infusion schedules are depicted. On Schedule 1, patients receive $1 \times 10^8$ human meso bearing CART cells by intravenous (i.v.) infusion on day 0 followed by $1 \times 10^9$ human meso bearing CART cells one week later. Safety can be monitored for a minimum of one month before patients are eligible for Schedule 2. On Schedule 2, patients receive $1 \times 10^8$ human meso bearing CART cells by i.v. infusion three times per week for one week followed by one week of rest and then $1 \times 10^9$ human meso bearing CART cells administered three times per week for one week. On Schedule 3, patients receive $3 \times 10^8/m^2$ human meso bearing CART cells by i.v. infusion three times per week for three weeks followed by intra-tumoral injection into a primary lesion of $2 \times 10^8$ human meso bearing CART cells on days+35 and +57.

FIGS. 3A and 3B are graphic representations of cytotoxicity as assayed donor 2 (healthy donor) T cell transduced with mouse SS1 CAR or the anti-MSLN CARs M1 to M12 of the invention and cultured with either control K562 cells that do not express MSLN as shown in FIG. 3A, or K562 cells transduced to express MSLN (K562-Meso) as shown in FIG. 3B.

FIGS. 4A and 4B are graphs showing the IFNγ secretion of the mouse SS1 and CD19 CART and the anti-MSLN CARTs upon stimulation by MSLN+ cells. FIG. 4A shows reactivity to the transduced cell line K562-Meso and its MSLN-negative parental line K562. FIG. 4B shows reactivity toward cancer cells naturally expressing MSLN; the ovarian cancer line Ovcar8 and the pancreatic cancer lines SW1990 and Panc0203.

FIGS. 9A and 9B show CARTmeso cell induction of anti-tumor antibodies. Sera was obtained from the MPM patient (FIG. 9A) and the pancreatic cancer patient (FIG. 9B).

After tumors grew to ~200 mm³ in size, mesoCAR T cells were injected via tail vein and measured for 39 days post injection.

Figure 11:
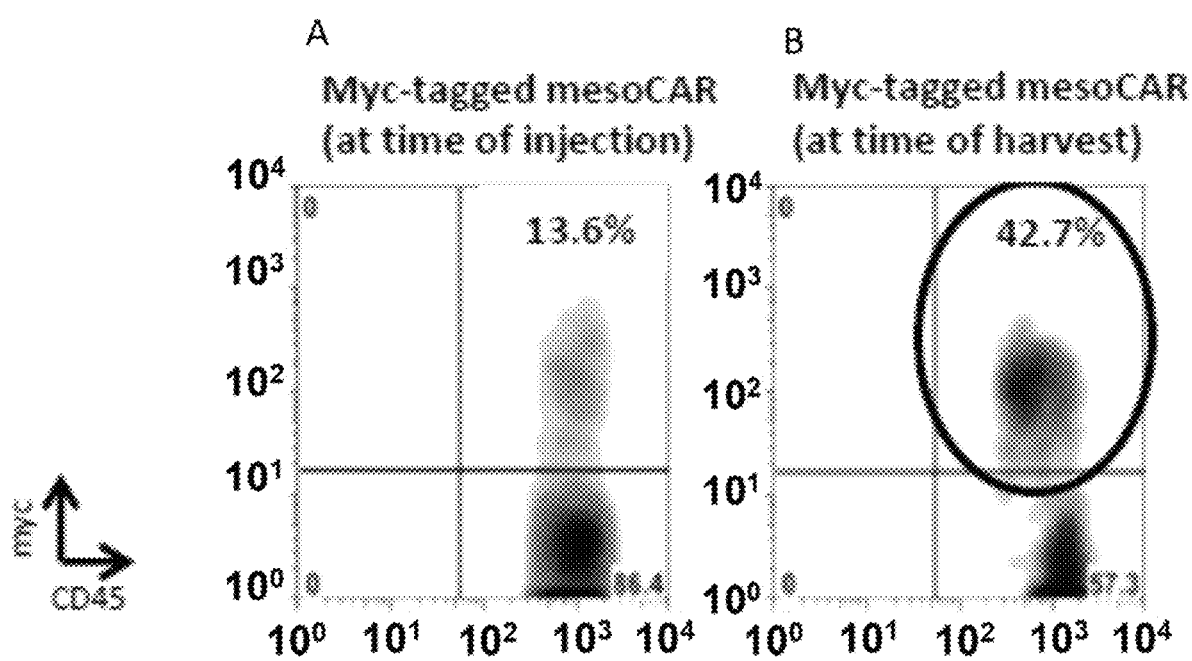

FIGS. 11A and 11B show the expression of mesoCAR by flow cytometry analysis at the time of injection (FIG. 11A) or after 40 days at the time of harvest from xenograft tumors.

Figure 12:
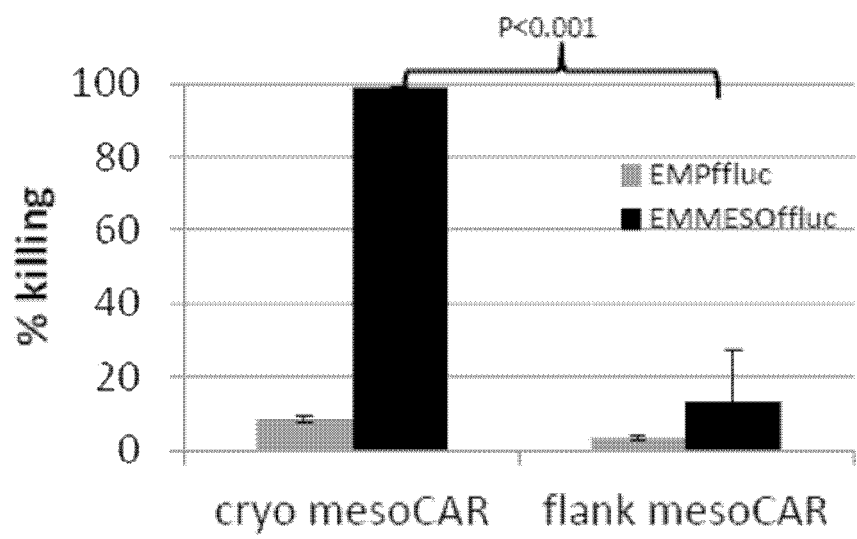

FIG. 12 shows the functional capacity of mesoCAR T cells with regard to in vitro killing when isolated from the flank of NSG mice after 39 days, or cryo preserved after transduction.

Figure 13:
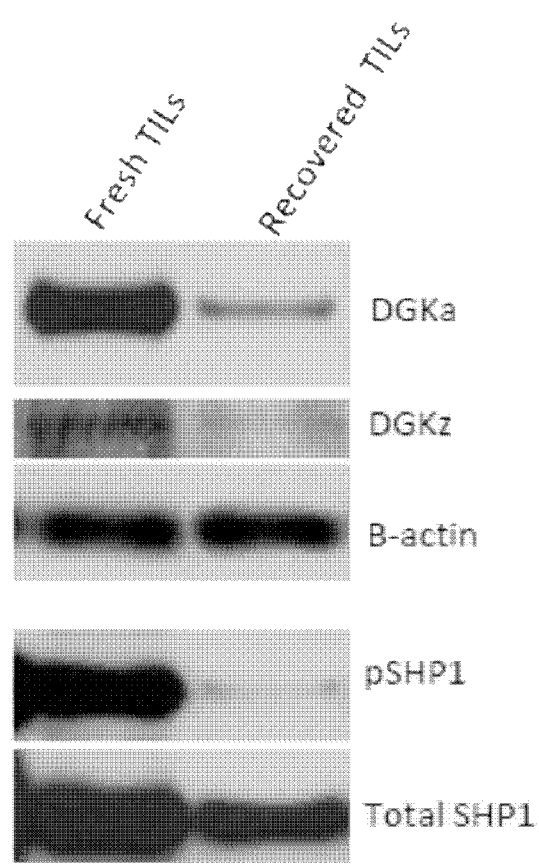

FIG. 13 shows the expression of inhibitor enzymes DGK and SHP1 in TILs isolated from EMESO flank tumor compared to overnight-rested TILs.

Figure 14:
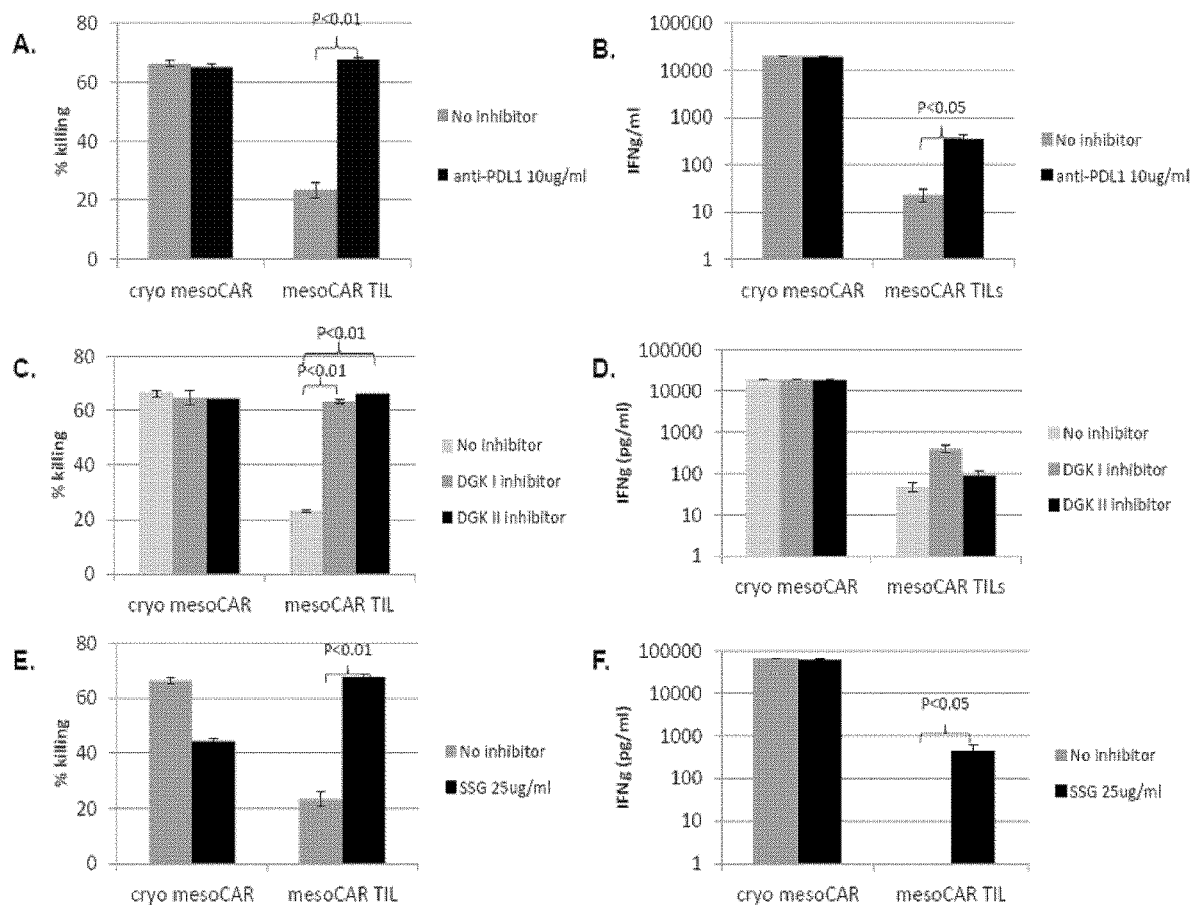

FIGS. 14A, 14B, 14C, 14D, 14E, and 14F show the effect of treatment with inhibitors (anti-PDL1, DGK inhibitor, and SSG) of inhibitory mechanisms that downregulate meso-CART function on tumor cell killing (FIGS. 14A, 14C and 14E) and IFNgamma cytokine secretion (FIGS. 14B, 14C, and 14F).

Figure 15A:
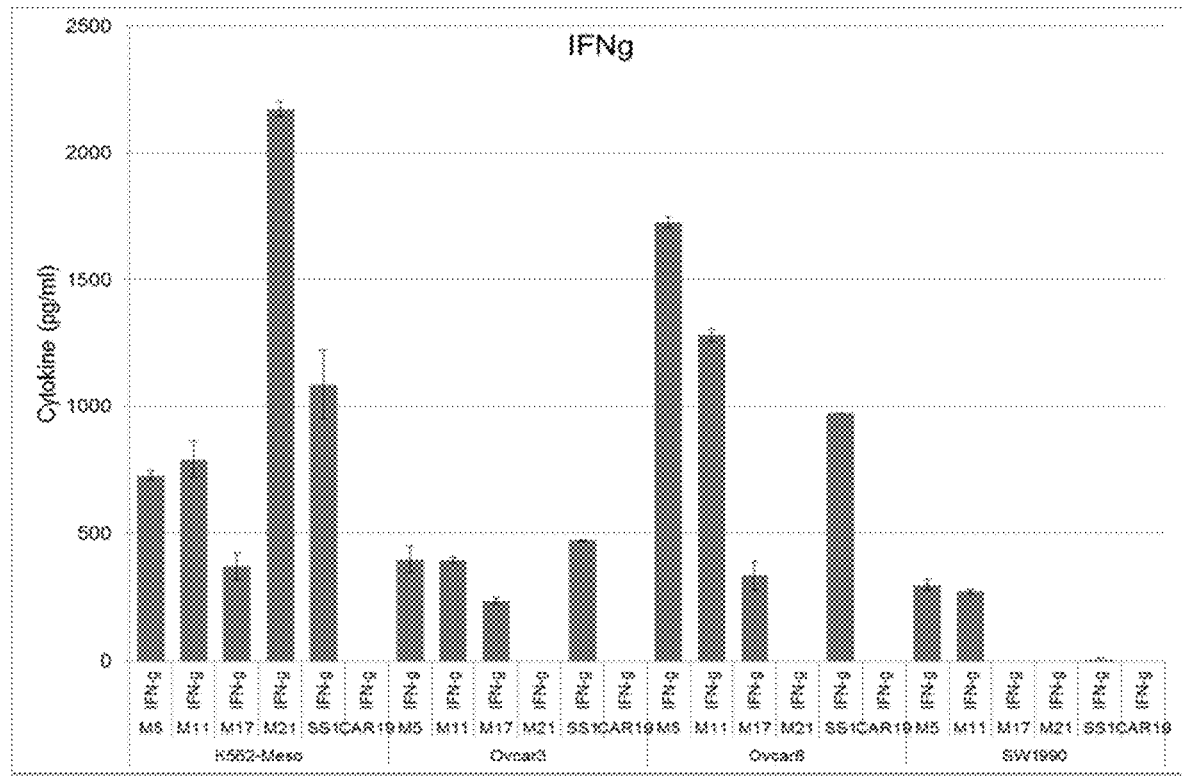
Figure 15B:
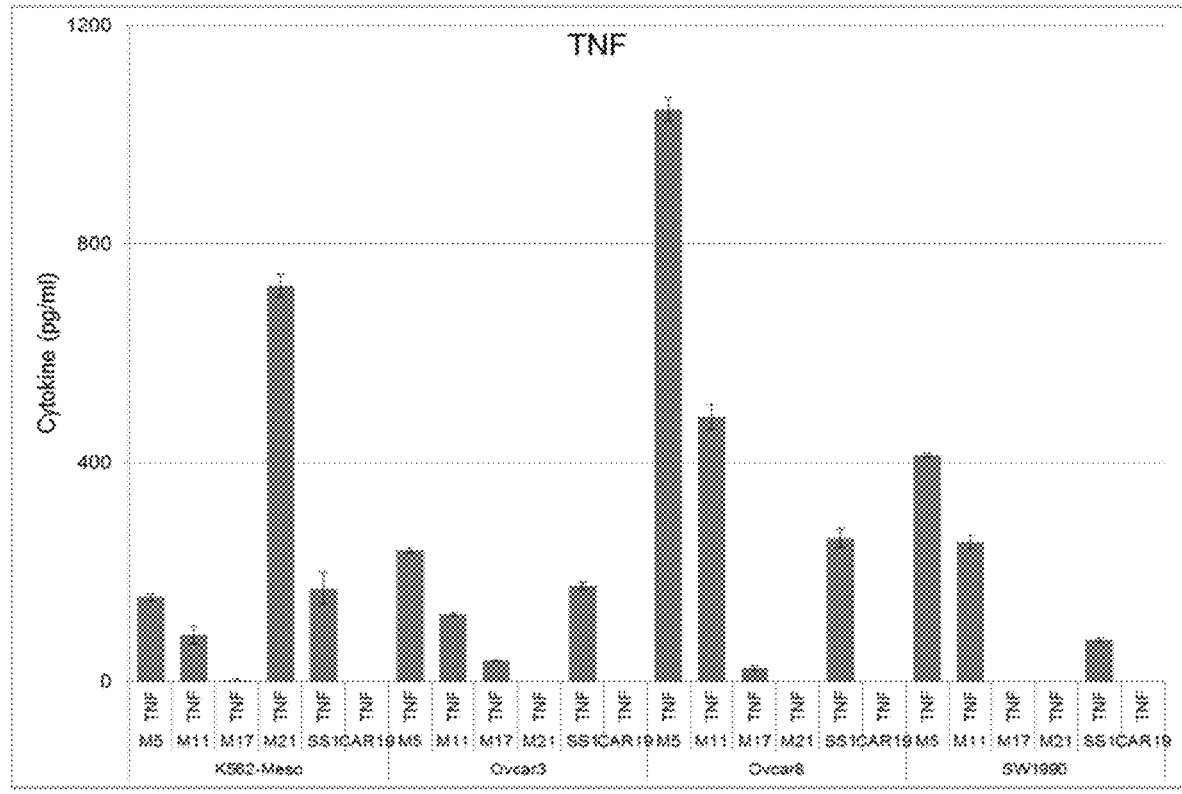
Figure 15C:
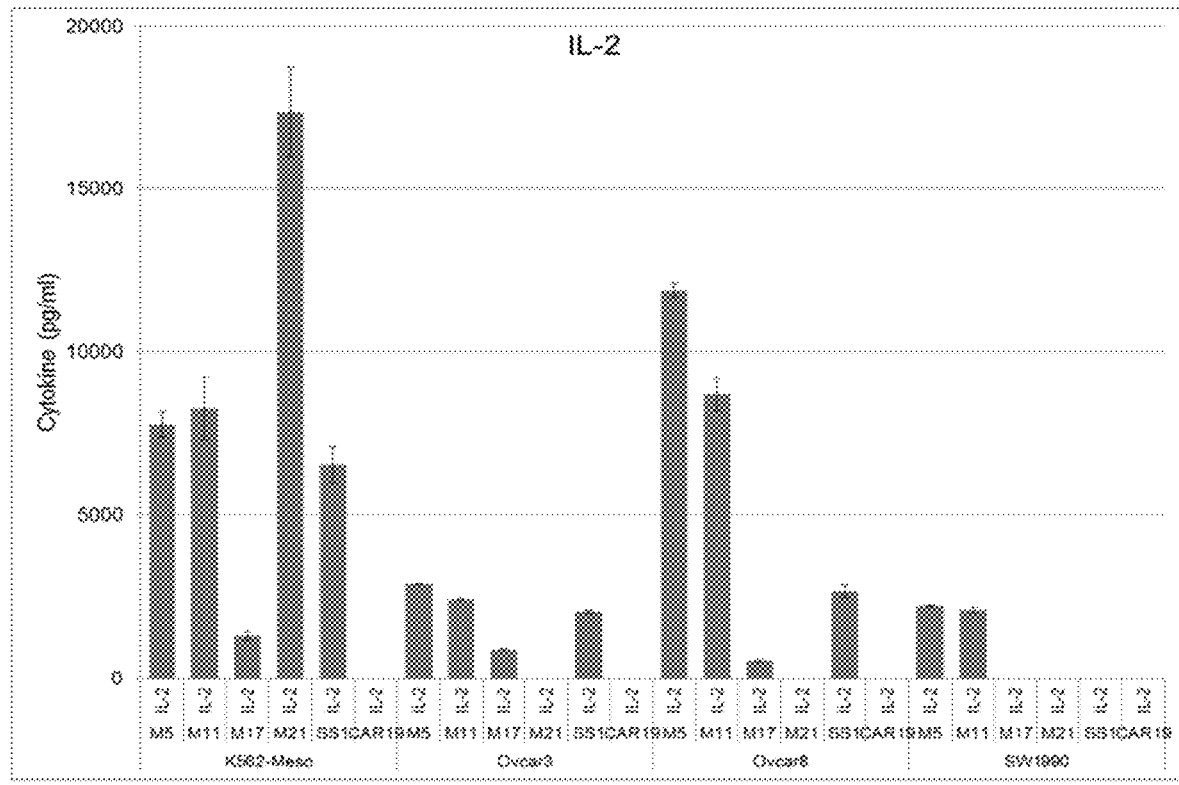
Figure 15D:
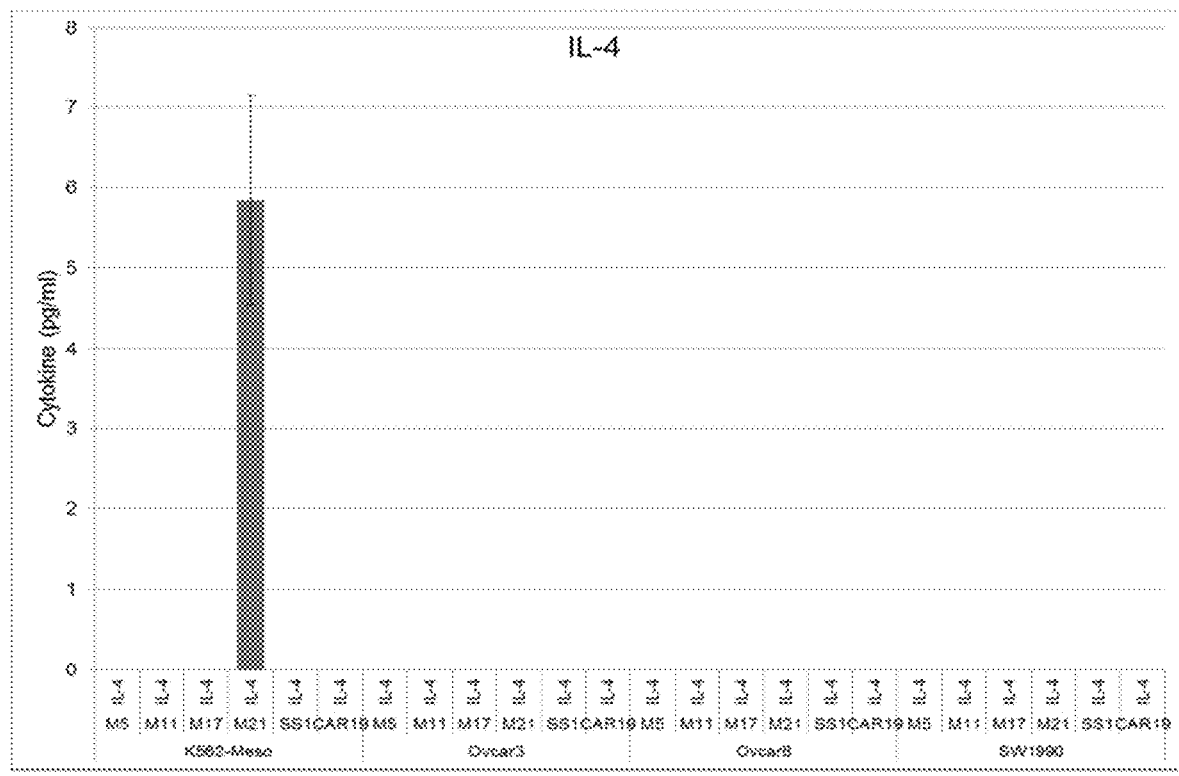

FIGS. 15A, 15B, 15C, and 15D show cytokine secretion from a small panel of human CART-MSLN after stimulation with various tumor cell lines. FIG. 15A shows IFNgamma secretion. FIG. 15B shows TNF. FIG. 15C shows IL-2. FIG. 15D shows IL-4.

FIGS. 16A and 16B show the results of the killing assay of CART-MSLN-5, CART-MSLN-11, CART-MSLN17, and murine CART-MSLN-SS1 against Ovcar3 (FIG. 16A) and U87 mg (FIG. 16B) tumor cells.

FIGS. 17A and 17B show the results of the killing assay of the panel of CART-MSLN against Ovcar3 tumor cells.

Figure 18:
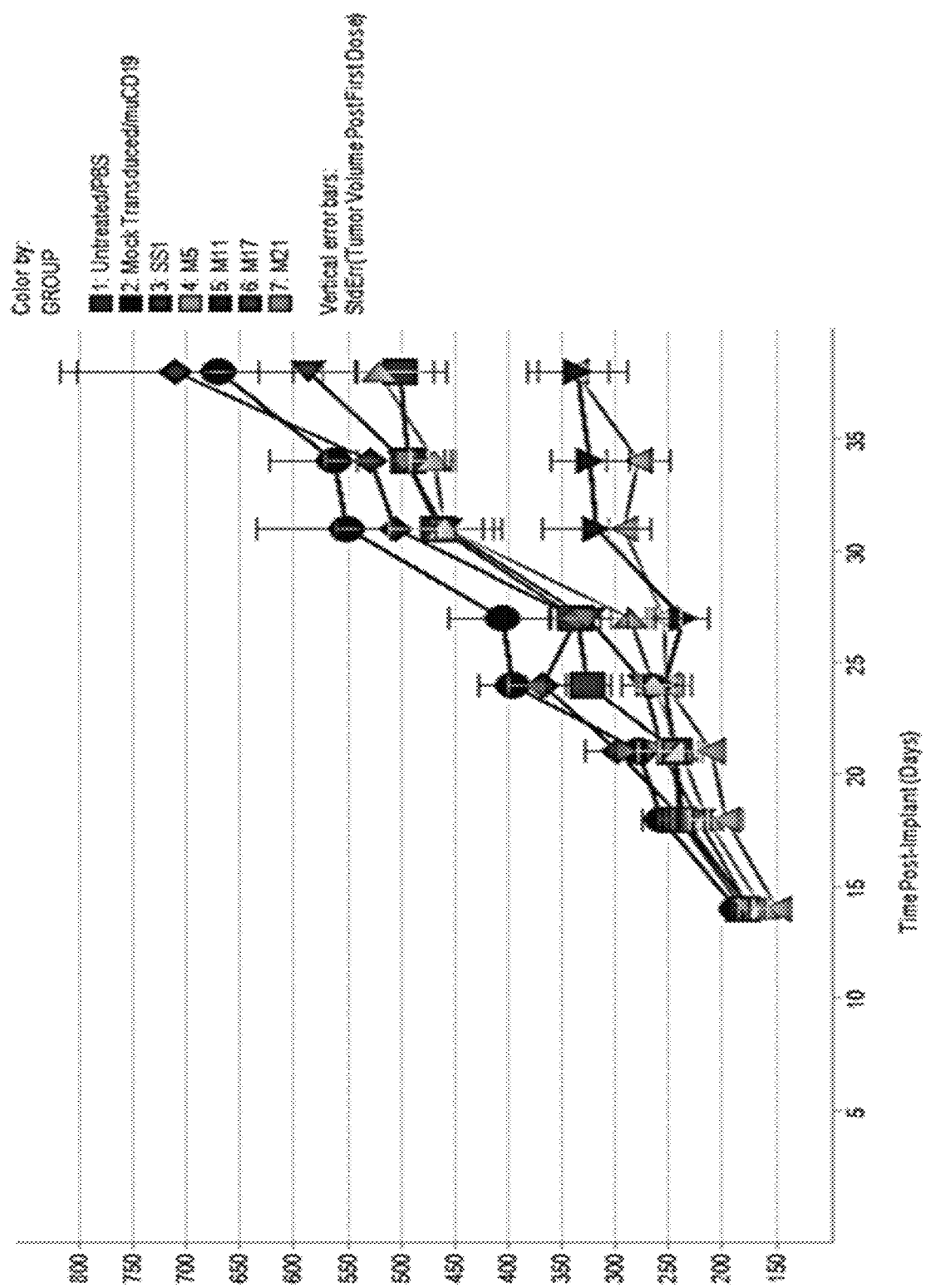

FIG. 18 shows the anti-tumor activity of a first set of CART-MSLN (including M5, M11, M17, and M21) in the Ovcar8 xenograft model.

Figure 19:
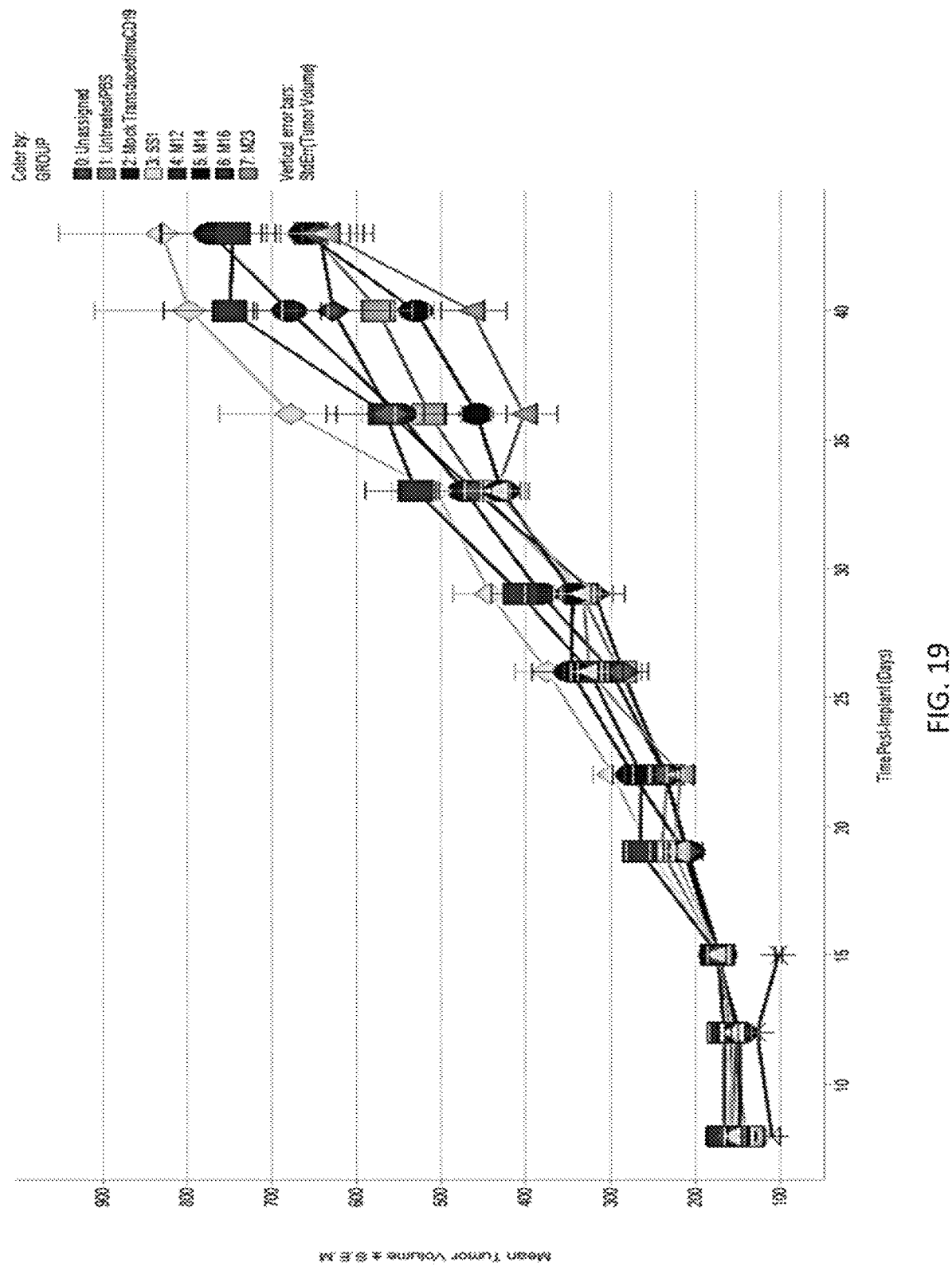

FIG. 19 shows the anti-tumor activity of a second set of CART-MSLN (including M12, M14, M16, and M23) in the Ovcar8 xenograft model.

Figure 20A:
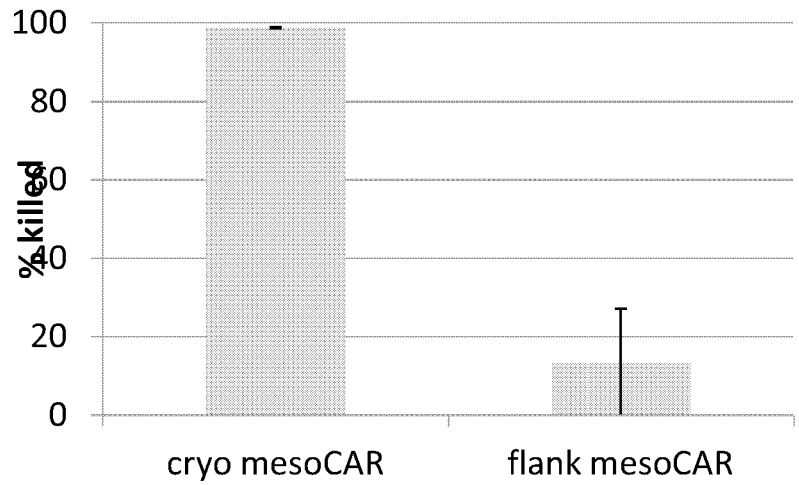
Figure 20B:
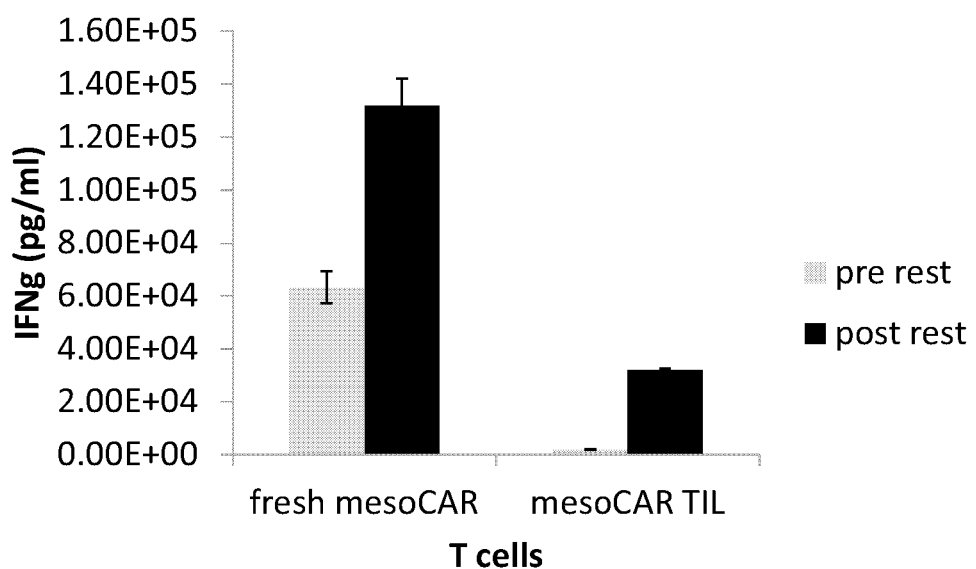
Figure 20C:
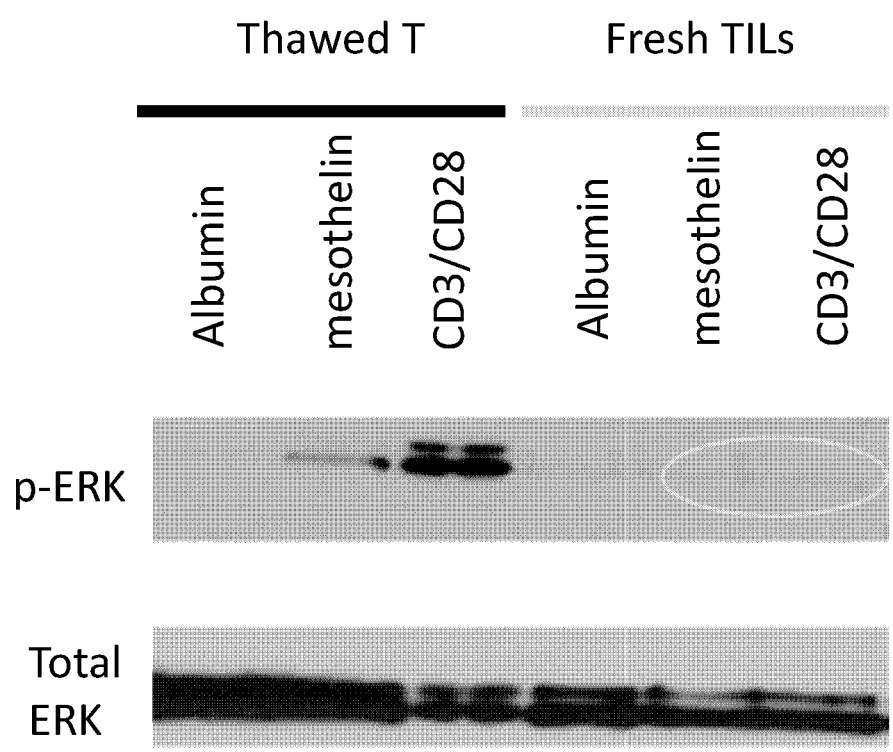

FIGS. 20A, 20B, and 20C depicts the loss of fucntionality of mesoCAR T cells in the tumor microenvironment (TILs) over time compared to fresh or thawed mesoCAR T cells. A) Cytotoxicity assay; B) IFNγ release assay; and C) western blot analysis of ERK signaling (via phosphorylation).

Figure 21:
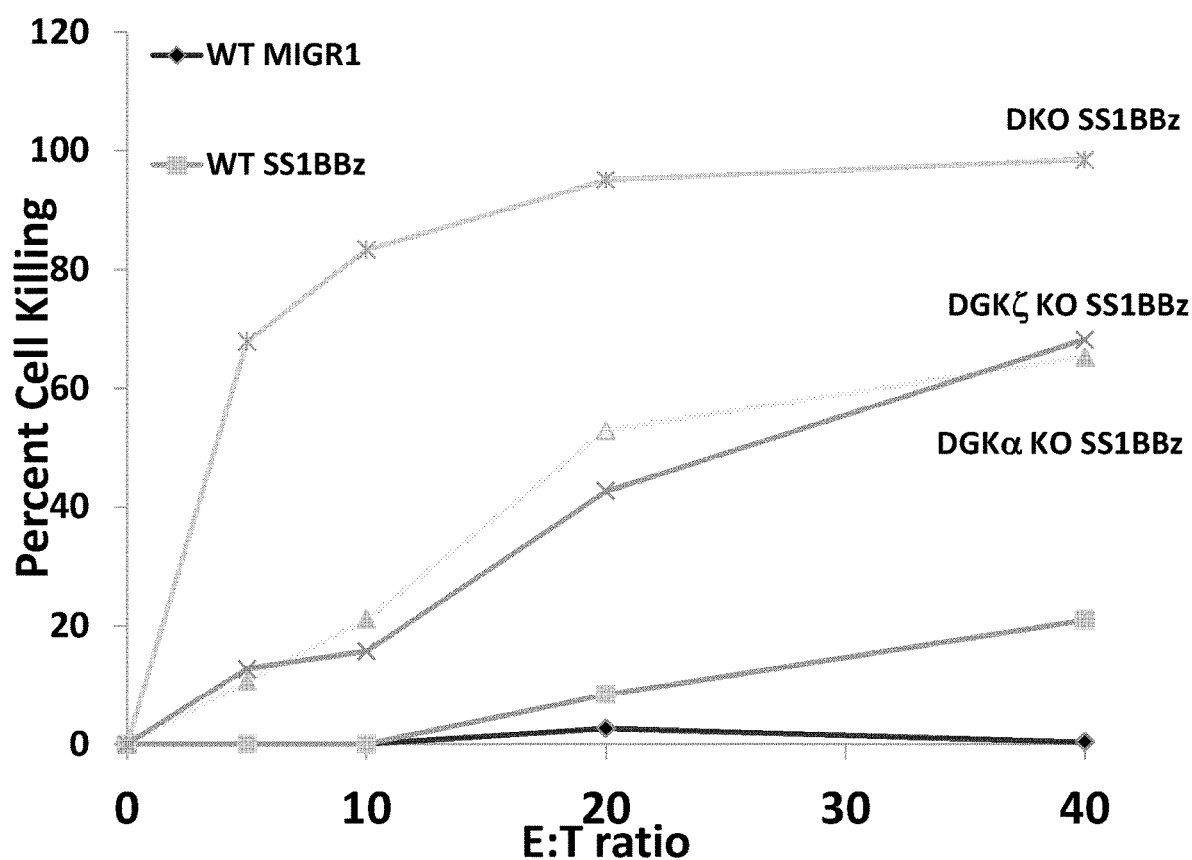

FIG. 21 depicts the effect of deletion of DGK on cytotoxicity of mesoCAR T cells. Percent target cell killing is assessed at different effector:target ratios.

Figure 22:
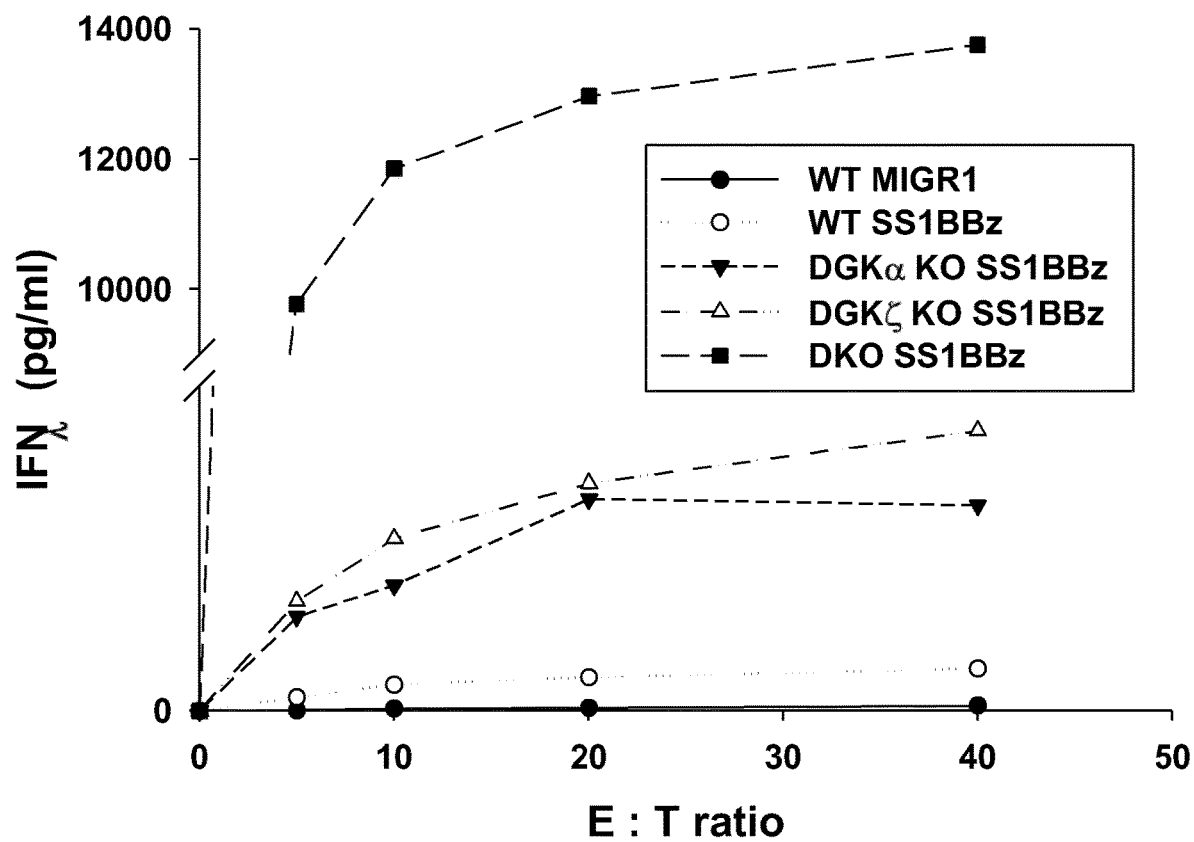

FIG. 22 depicts the effect of deletion of DGK on IFNγ production and release from mesoCAR T cells. Concentration of IFNγ is assessed at different effector:target ratios.

Figure 23:
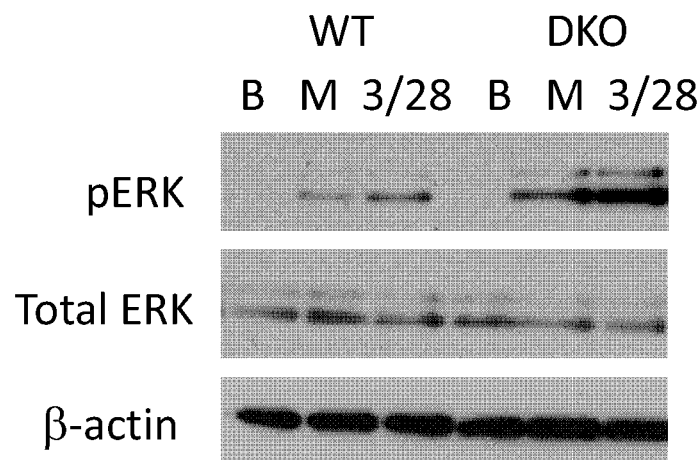

FIG. 23 depicts the effect of deletion of DGK on ERK signaling, or T cell activation, mesoCAR T cells. B: albumin, M: mesothelin, 3/28: CD3/CD28 stimulated cells.

Figure 24:
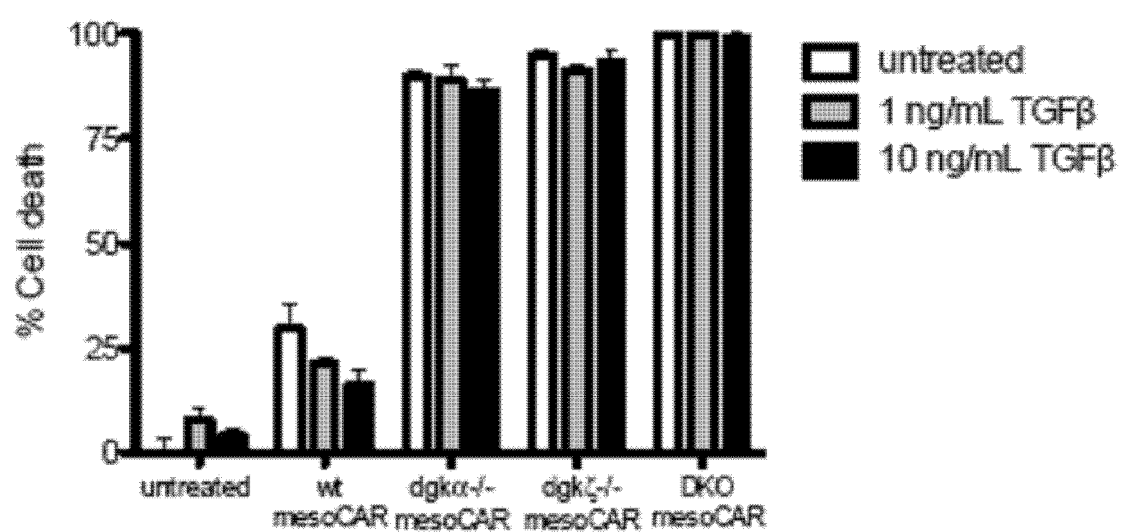

FIG. 24 depicts the effect of deletion of DGK on TGFβ sensitivity of mesoCAR T cells with regard to cytotoxic activity.

Figure 25A:
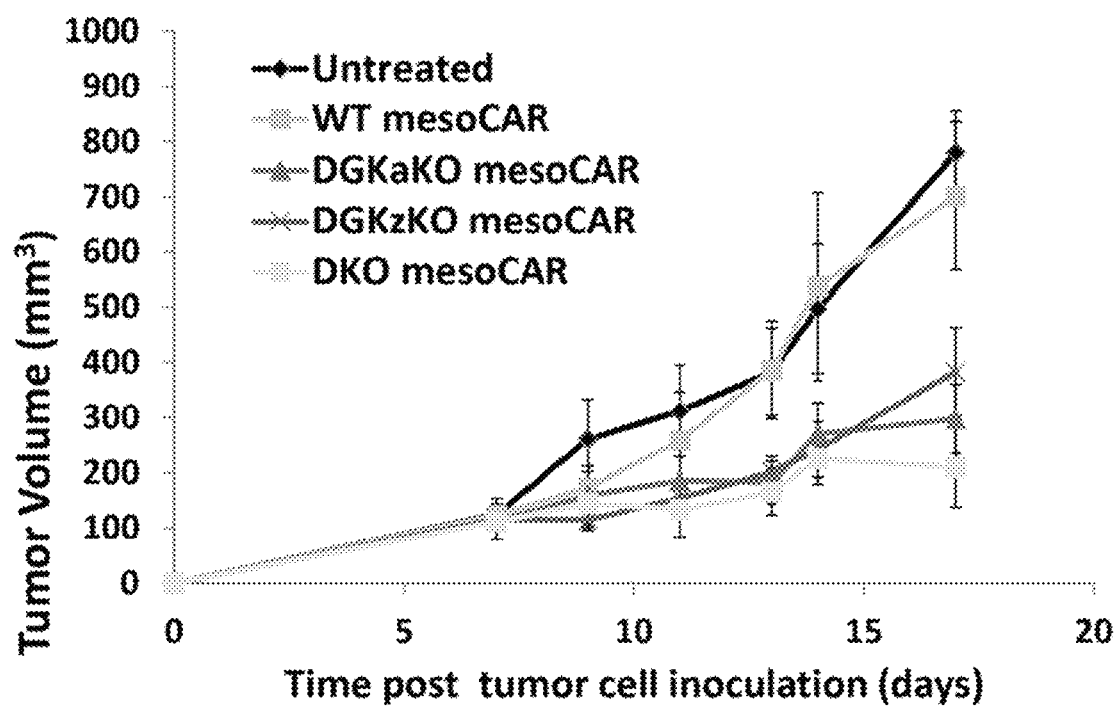
Figure 25B:
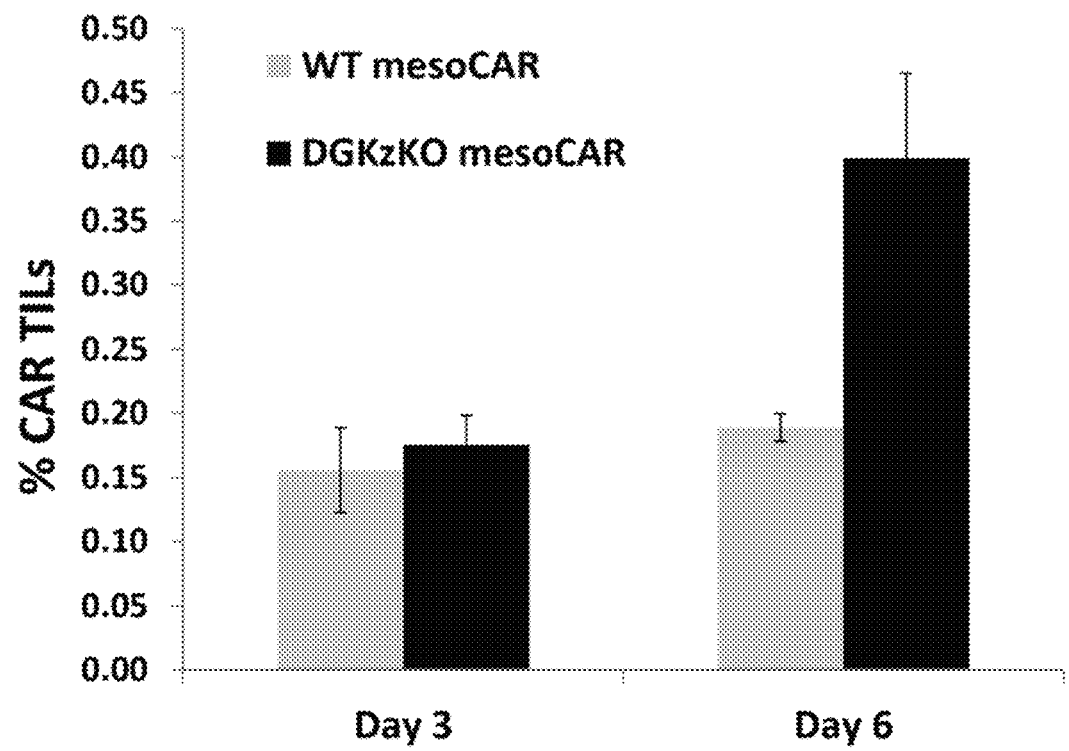

FIGS. 25A and 25B depict the effect of deletion of DGK on therapeutic efficacy of mesoCAR T cells in a tumor mouse model. A) Effect on anti-tumor activity is shown by tumor volume over time. B) Persistance and proliferation of tumor infiltrating cells.

Figure 26A:
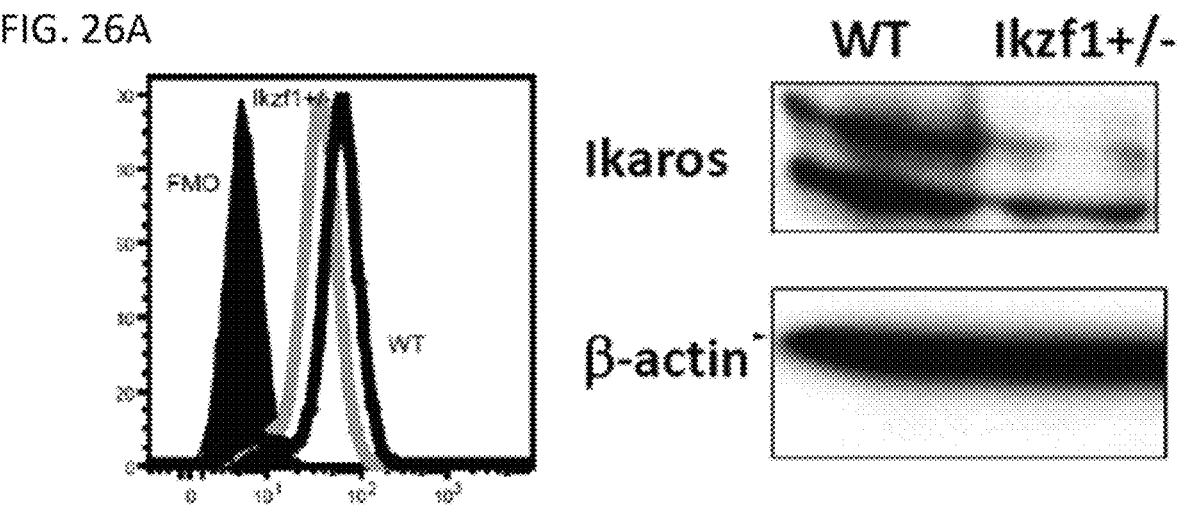

FIGS. 26A, 26B, 26C, 26D, 26E, and 26F shows the cytokine production and cytotoxic mediator release in CAR-expressing T cells with reduced levels of Ikaros. FIG. 26A shows Ikaros expression in wild-type and Ikzf1+/− CAR T cells as measured by flow cytometry (left panel) and western blot (right panel). Following stimulation with mesothelin-coated beads, PMA/Ionomycin (PMA/I), or BSA-coated beads (control), the percentage of cells producing IFN-γ (FIG. 26B), TNF-α (FIG. 26C), and IL-2 (FIG. 26D), the cytotoxic mediator granzyme B (FIG. 26E), and CD107a expression (FIG. 26F) was determined.

FIGS. 27A, 27B, and 27C shows cytokine production and cytotoxic mediator release in CAR-expressing T cells with a dominant negative allele of Ikaros (IkDN). Following stimulation with mesothelin-coated beads, PMA/Ionomycin (PMA/I), or BSA-coated beads (control), the percentage of cells producing IFN-γ (FIG. 27A), IL-2 (FIG. 27B), and CD107a expression (FIG. 27C) was determined.

Figure 28A:
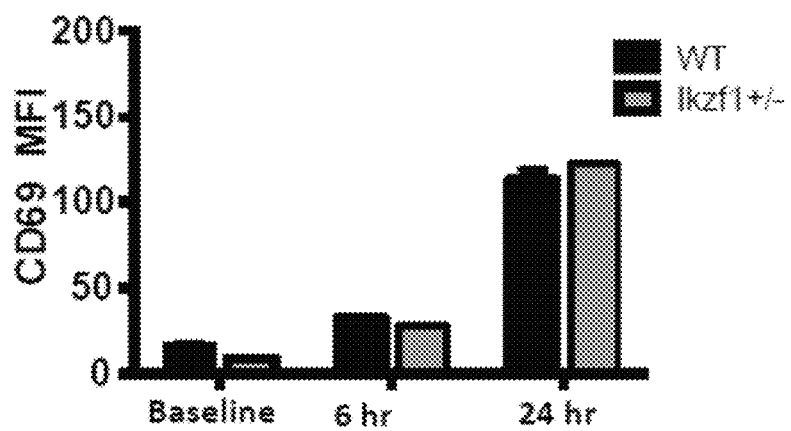
Figure 28B:
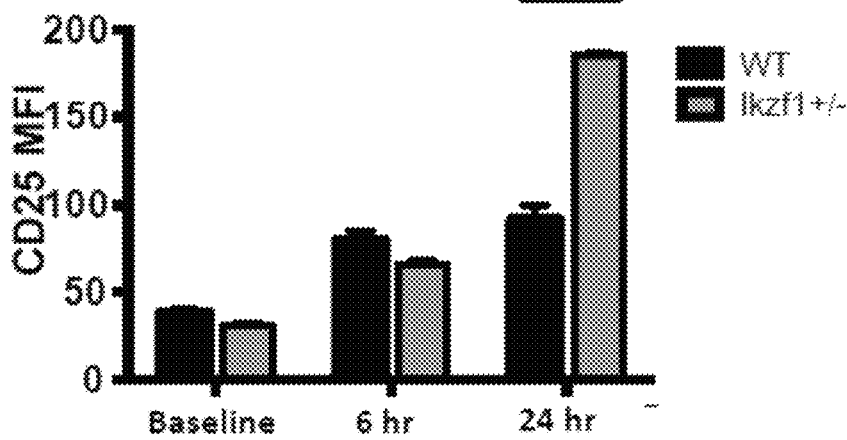
Figure 28C:
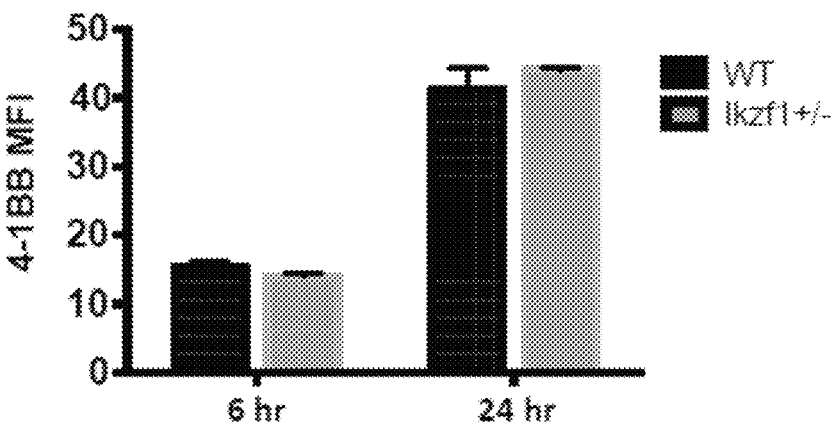
Figure 28D:
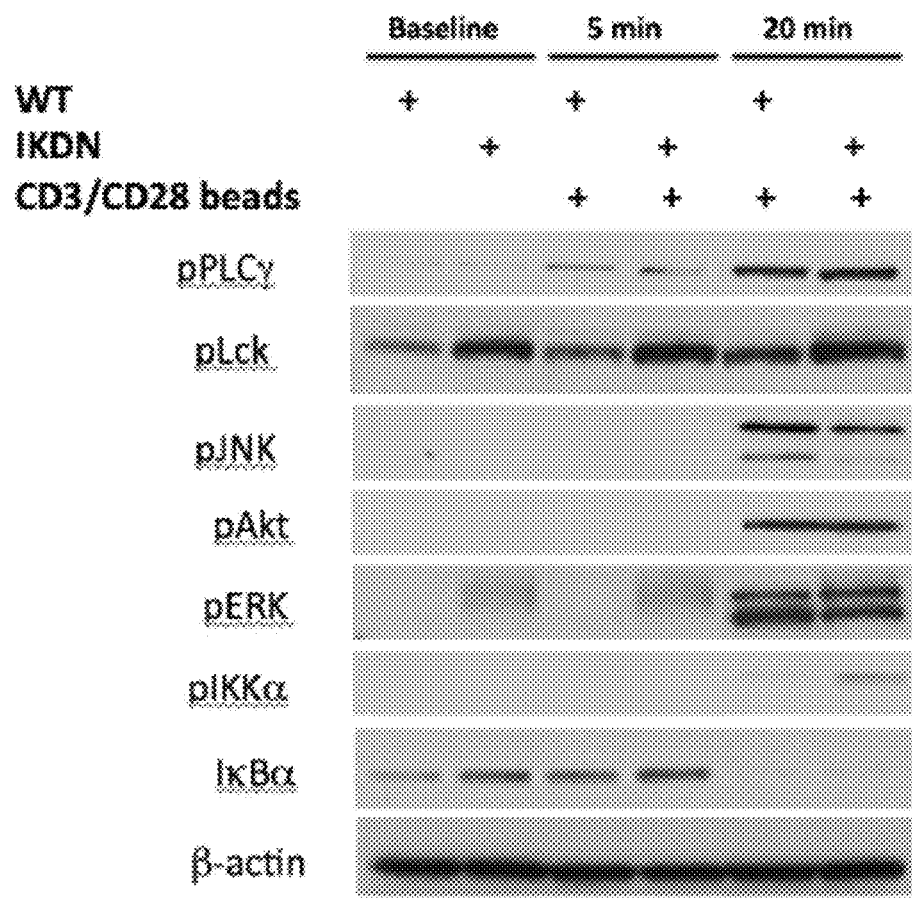
Figure 28E:
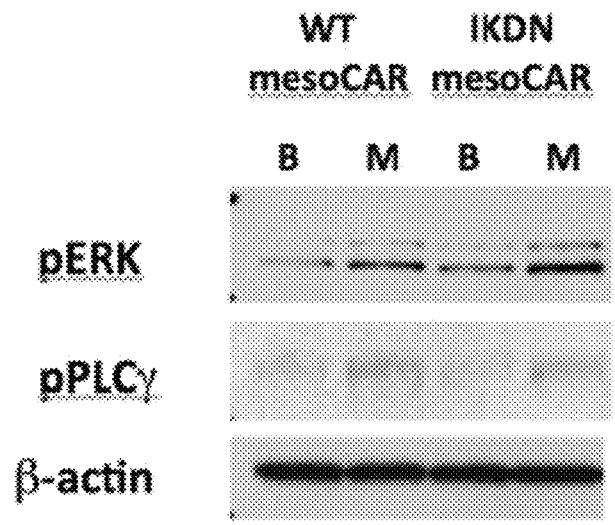

FIGS. 28A, 28B, 28C, 28D, and 28E shows that the depletion of Ikaros did not augment activation and signaling of CAR T cells following antigen stimulation. The levels of CD69 (FIG. 28A), CD25 (FIG. 28B), and 4-1BB (FIG. 28C) was determined by flow cytometry at the indicated time points in Ikzf1+/− CAR T cells. In FIG. 28D, the RAS/ERK signaling pathways were examined in wild-type (WT) and Ikaros dominant negative cells (IkDN) after TCR stimulation with CD3/CD28 antibodies. The levels of phosphorylated TCR signaling proteins such as phosphorylated PLCγ, phosphorylated Lck, phosphorylated JNK, phosphorylated Akt, phosphorylated ERK, phosphorylated IKKα, and IκBα were assessed by western blot. In FIG. 28E, WT and IkDN cells transduced with mesoCAR were stimulated with BSA or mesothelin-coated beads, and downstream signaling pathways were examined by western blot by assessing the levels of phosphorylated ERK and phosphorylated PLCγ.

Figure 29A:
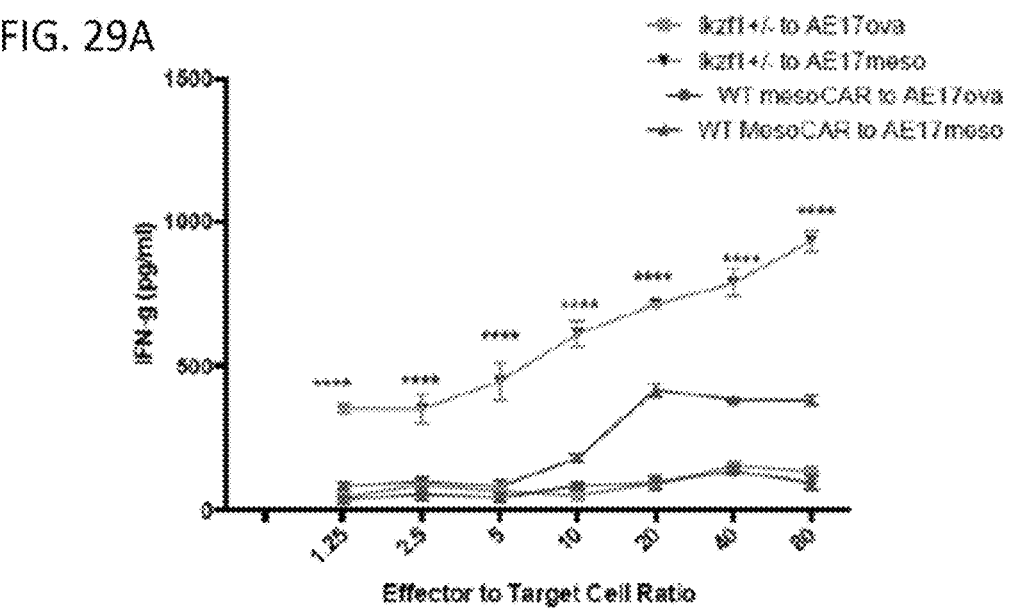

FIGS. 29A, 29B, 29C, 29D, and 29E shows that the reduction of Ikaros in CAR T cells augments the response against target cells AE17 or mesothelin-expressing AE17 (AE17 meso) in vitro. FIG. 29A depicts IFNγ production in WT and Ikzf1+/− meso CART cells at the indicated effector: target cell ratios. Cytolysis of meso CAR-expressing WT and Ikzf1+/−(FIG. 29B) and IkDN (FIG. 29C) was measured at the indicated effector:target cell ratios. IFNγ production (FIG. 29D) and cytolysis (FIG. 29E) of WT and Ikzf1+/− transduced with FAP-CAR was measured at the indicated effector:target cell ratios, where the target cells were FAP-expressing 3T3 cells.

FIGS. 30A, 30B, and 30C shows the efficacy of CAR T cells with depletion of Ikaros against established tumors in vivo. CAR T cells were administered to mice bearing established mesothelin-expressing AE17 tumors. Tumor volume was measured after administration with mesoCAR-expressing WT and Ikzf1+/−(FIG. 30A) or IkDN (FIG. 30B). Tumor volume was measured after administration of FAP-CAR-expressing WT and Ikzf1+/−(FIG. 30C).

Figure 31A:
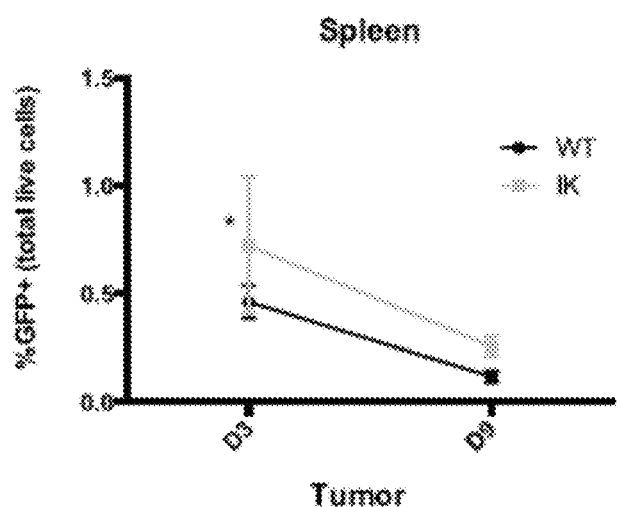
Figure 31B:
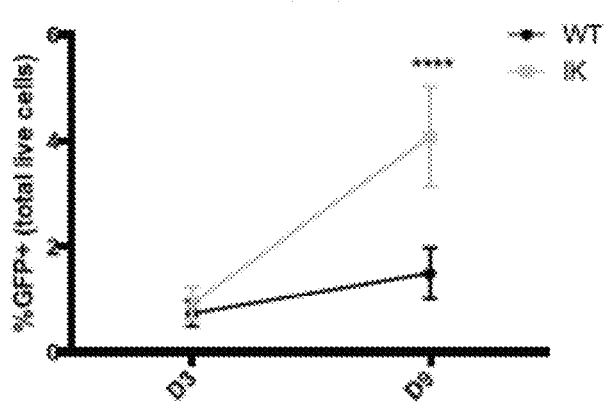
Figure 31C:
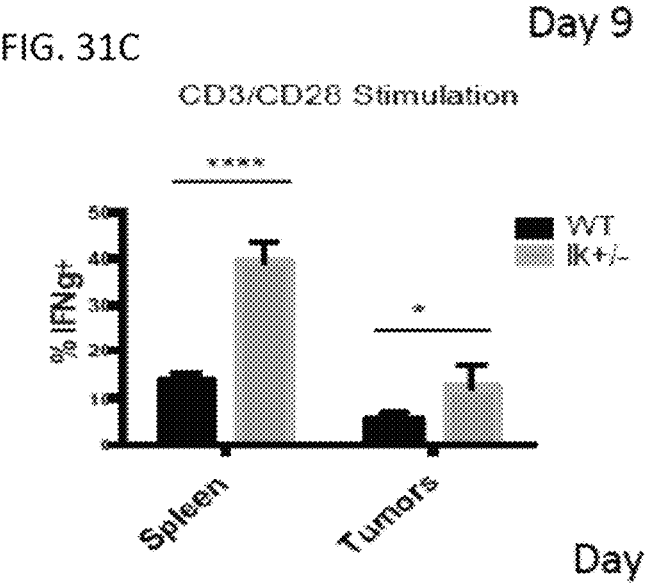
Figure 31D:
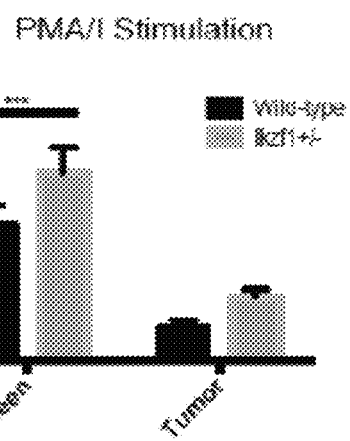

FIGS. 31A, 31B, 31C, 31D, 31E, and 31F shows the increased persistence and resistance of Ikzf1+/− CAR T cells in the immunosuppressive tumor microenvironment compared to WT CAR T cells. The percentage of CAR-expressing WT or Ikzf1+/− cells (GFP positive) were detected by flow cytometry from harvested from the spleen (FIG. 31A) and the tumors (FIG. 31B). The functional capacity of the CAR T cells harvested 3 days after infusion from the spleen or tumors was assessed by measuring IFNγ production after stimulation with CD3/CD28 antibodies (FIG. 31C) or PMA/Ionomycin (PMA/I) (FIG. 31D). Regulatory T cells (CD4+ FoxP3+ expression) and macrophages (CD206 expression) were assessed by measuring the expression of Treg or macrophage markers on CAR T cells harvested 9 days after infusion from the spleen or tumors.

FIGS. 32A and 32B shows that T cells with reduced Ikaros levels are less sensitive to soluble inhibitory factors TGFβ and adenosine. MesoCAR-expressing WT, Ikzf1+/−, and IkDN cells were tested for their ability to produce IFNγ (FIG. 32A) and cytotoxicity (FIG. 32B) in response to TGF-β or adenosine.

FIGS. 33A and 33B are graphs showing an increase in titers to influenza vaccine strains as compared to placebo. In FIG. 33A, the increase above baseline in influenza geometric mean titers to each of the 3 influenza vaccine strains (H1N1 A/California/07/2009, H3N2 A/Victoria/210/2009, B/Brisbane/60/2008) relative to the increase in the placebo cohort 4 weeks after vaccination is shown for each of the RAD001 dosing cohorts in the intention to treat population. The bold black line indicates the 1.2 fold increase in titers relative to placebo that is required to be met for 2 out of 3 influenza vaccine strains to meet the primary endpoint of the study. The star "*" indicates that the increase in GMT titer relative to placebo exceeds 1 with posterior probability of at least 80%. FIG. 33B is a graph of the same data as in FIG. 33A for the subset of subjects with baseline influenza titers <=1:40.

Figure 34:
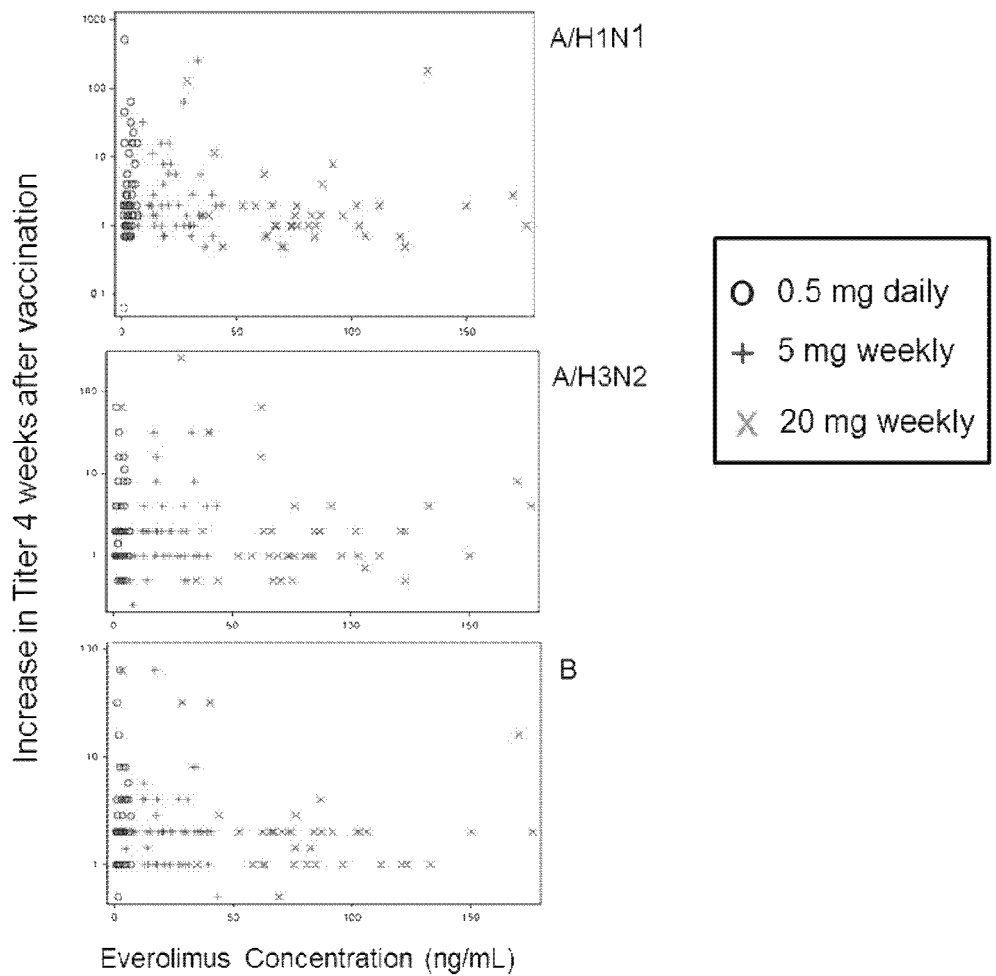

FIG. 34 shows a scatter plot of RAD001 concentration versus fold increase in geometric mean titer to each influenza vaccine strain 4 weeks after vaccination. RAD001 concentrations (1 hour post dose) were measured after subjects had been dosed for 4 weeks. All subjects who had pharmacokinetic measurements were included in the analysis set. The fold increase in geometric mean titers at 4 weeks post vaccination relative to baseline is shown on the y axis.

Figure 35:
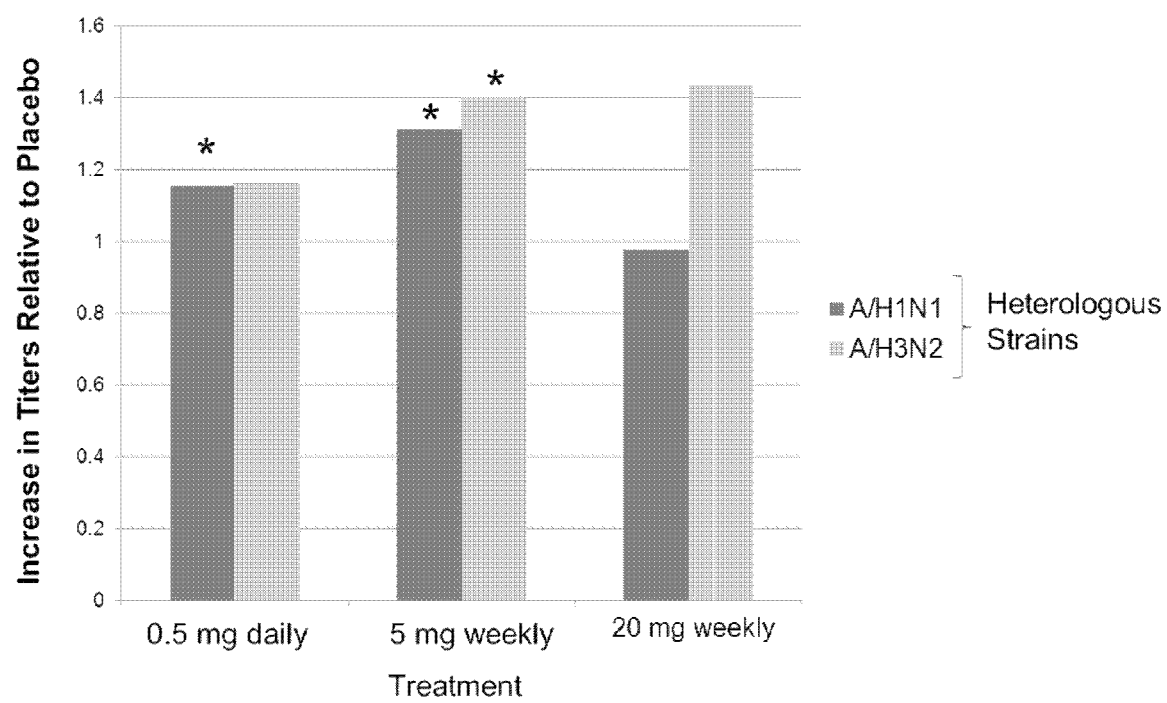

FIG. 35 is a graphic representation showing increase in titers to heterologous influenza strains as compared to placebo. The increase above baseline in influenza geometric mean titers to 2 heterologous influenza strains (A/H1N1 strain A/New Jersey/8/76 and A/H3N2 strain A/Victoria/361/11) not contained in the influenza vaccine relative to the increase in the placebo cohort 4 weeks after vaccination is shown for each of the RAD001 dosing cohorts in the intention to treat population. * indicates increase in titer relative to placebo exceeds 1 with a posterior probability of at least 80%.

FIGS. 36A and 36B are graphic representations of IgG and IgM levels before and after influenza vaccination. Levels of anti-A/H1N1/California/07/2009 influenza IgG and IgM were measured in serum obtained from subjects before and 4 weeks post influenza vaccination. No significant difference in the change from baseline to 4 weeks post vaccination in anti-H1N1 influenza IgG and IgM levels were detected between the RAD001 and placebo cohorts (all p values >0.05 by Kruskal-Wallis rank sum test).

FIGS. 37A, 37B, and 37C are graphic representations of the decrease in percent of PD-1-positive CD4 and CD8 and increase in PD-1-negative CD4 T cells after RAD001 treatment. The percent of PD-1-positive CD4, CD8 and PD-1-negative CD4 T cells was determined by FACS analysis of PBMC samples at baseline, after 6 weeks of study drug treatment (Week 6) and 6 weeks after study drug discontinuation and 4 weeks after influenza vaccination (Week 12). FIG. 37A shows there was a significant decrease (−37.1-−28.5%) in PD-1-positive CD4 T cells at week 12 in cohorts receiving RAD001 at dose levels 0.5 mg/Day (n=25), 5 mg/Week (n=29) and 20 mg/Week (n=30) as compared to the placebo cohort (n=25) with p=0.002 (0.02), p=0.003 (q=0.03), and p=0.01 (q=0.05) respectively. FIG. 37B shows there was a significant decrease (−43.3-−38.5%) in PD-1-positive CD8 T cells at week 12 in cohorts receiving RAD001 (n=109) at dose levels 0.5 mg/Day (n=25), 5 mg/Week (n=29) and 20 mg/Week (n=30) as compared to the placebo cohort (n=25) with p=0.01 (0.05), p=0.007 (q=0.04), and p=0.01 (q=0.05) respectively. FIG. 37C shows was a significant increase (3.0-4.9%) in PD-1-negative CD4 T cells at week 12 in cohorts receiving RAD001 (n=109) at dose levels 0.5 mg/Day (n=25), 5 mg/Week (n=29) and 20 mg/Week (n=30) as compared to the placebo cohort (n=25) with p=0.0007 (0.02), p=0.03 (q=0.07), and p=0.03 (q=0.08) respectively.

FIGS. 38A and 38B are graphic representations of the decrease in percent of PD-1-positive CD4 and CD8 and increase in PD-1-negative CD4 T cells after RAD001 treatment adjusted for differences in baseline PD-1 expression. The percent of PD-1-positive CD4, CD8 and PD-1-negative CD4 T cells was determined by FACS analysis of PBMC samples at baseline, after 6 weeks of study drug treatment (Week 6) and 6 weeks after study drug discontinuation and 4 weeks after influenza vaccination (Week 12). FIG. 38A shows a significant decrease of 30.2% in PD-1+CD4 T cells at week 6 in the pooled RAD cohort (n=84) compared to placebo cohort (n=25) with p=0.03 (q=0.13). The decrease in PD-1-positive CD4 T cells at week 12 in the pooled RAD as compared to the placebo cohort is 32.7% with p=0.05 (q=0.19). FIG. 38B shows a significant decrease of 37.4% in PD-1-positive CD8 T cells at week 6 in the pooled RAD001 cohort (n=84) compared to placebo cohort (n=25) with p=0.008 (q=0.07). The decrease in PD-1-positive CD8 T cells at week 12 in the pooled RAD001 as compared to the placebo cohort is 41.4% with p=0.066 (q=0.21). FIGS. 38A and 38B represent the data in FIGS. 37A, 37B, and 37C but with the different RAD001 dosage groups of FIGS. 37A, 37B, and 37C pooled into the single RAD001-treated group in FIGS. 38A and 38B.

Figure 39:
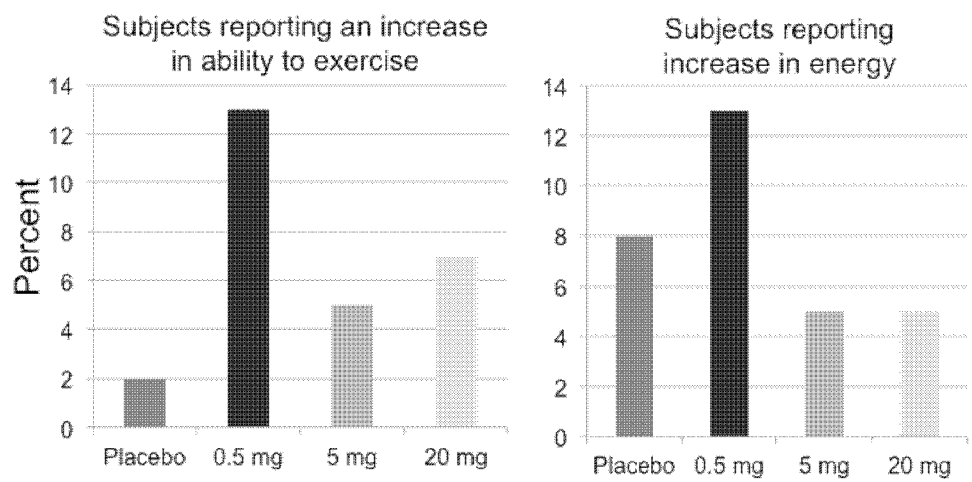

FIG. 39 depicts increases in exercise and energy in elderly subjects in response to RAD001.

FIGS. 40A and 40B depict the predicted effect of RAD001 on P70 S6K activity in cells. FIG. 40A depicts P70 S6 kinase inhibition with higher doses of weekly and daily RAD001; FIG. 40B depicts P70 S6 kinase inhibition with lower doses of weekly RAD001.

Figure 41A:
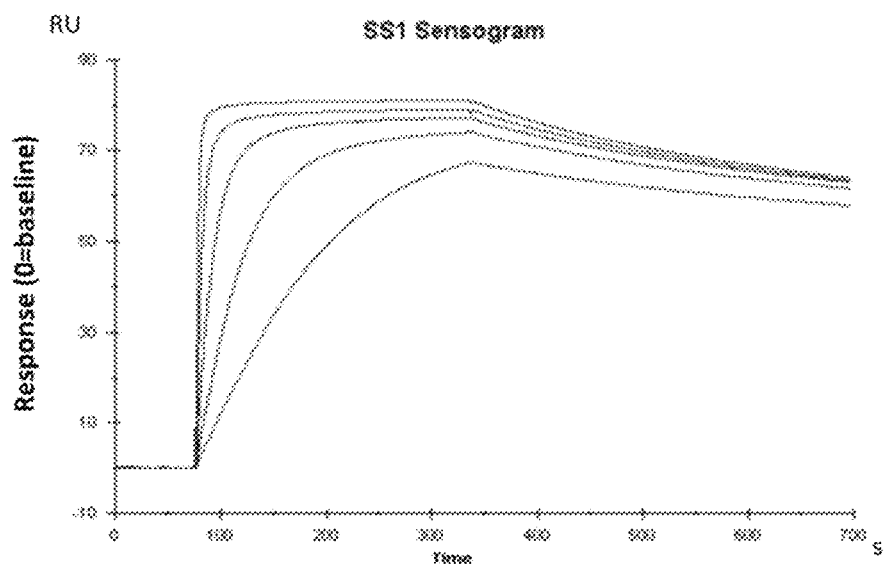
Figure 41B:
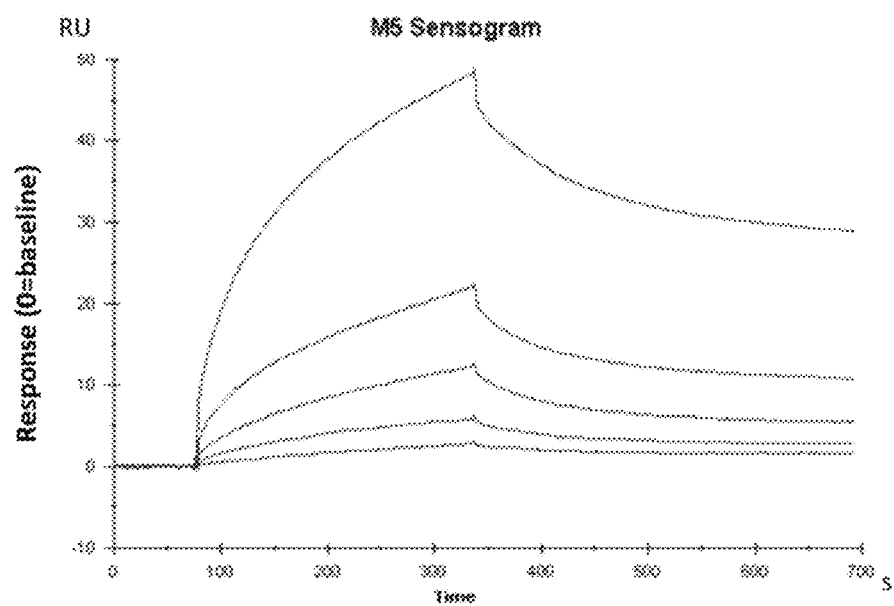
Figure 41C:
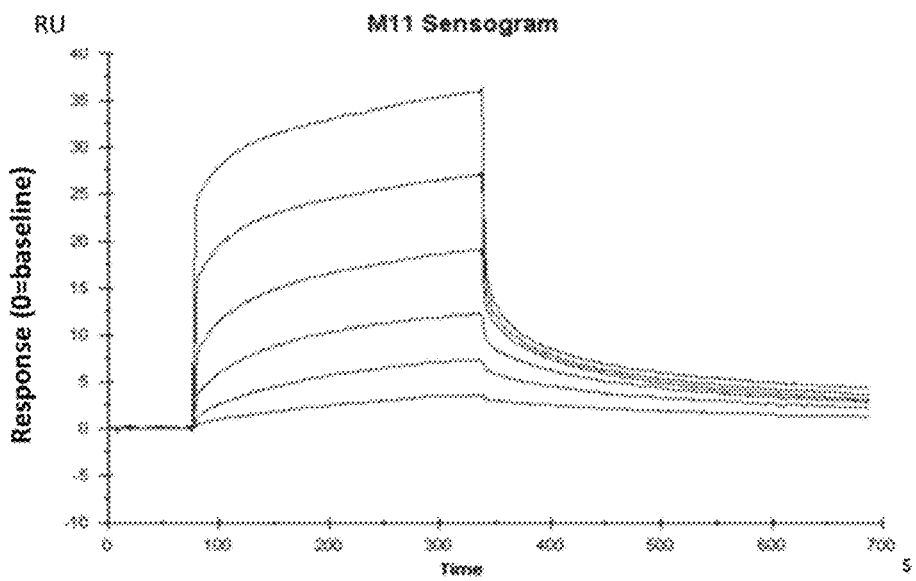

FIGS. 41A, 41B, and 41C are Biacore T200 SPR sensograms for the scFvs SS1 (FIG. 41A), M5 (FIG. 41B), and M11 (FIG. 41C).

Figure 42A:
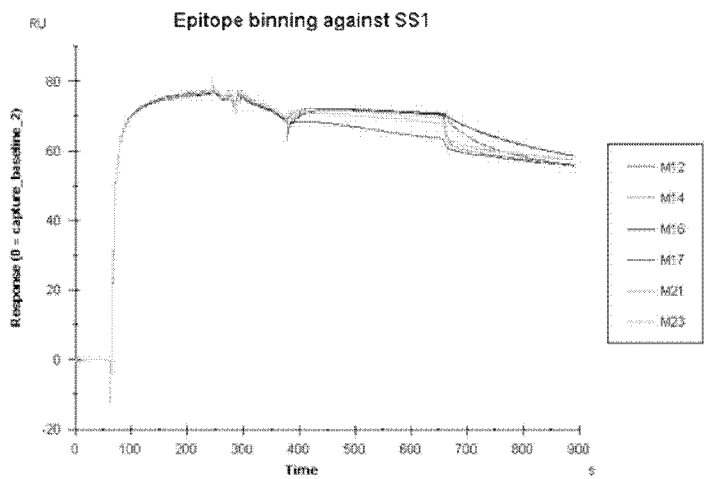
Figure 42B:
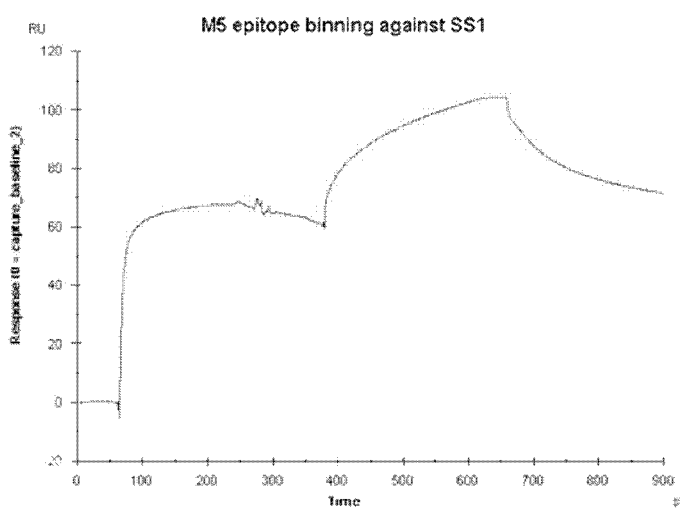
Figure 42C:
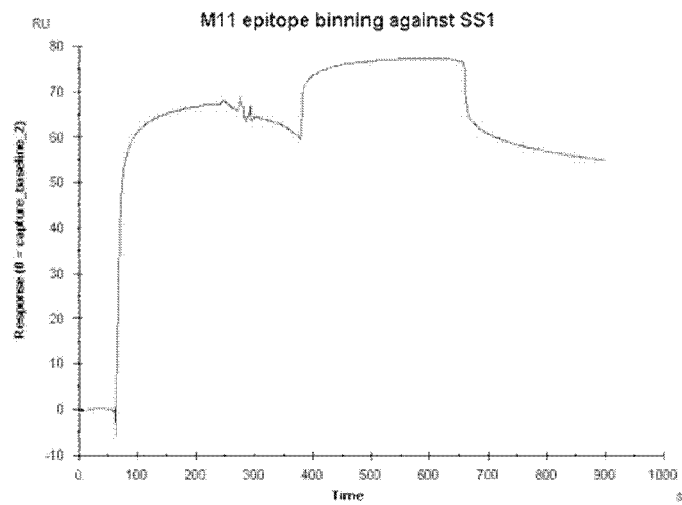

FIGS. 42A, 42B, and 42C are epitope binning SPR sensograms for the anti-human mesothelin scFvs in comparison to the murine SS1 scFv. Competitive binding was observed for scFvs M12, M14, M16, M17, M21, and M23 (FIG. 42A). ScFv M5 (FIG. 42B) and M11 (FIG. 42C) bind to a different epitope than SS1.

Figure 43:
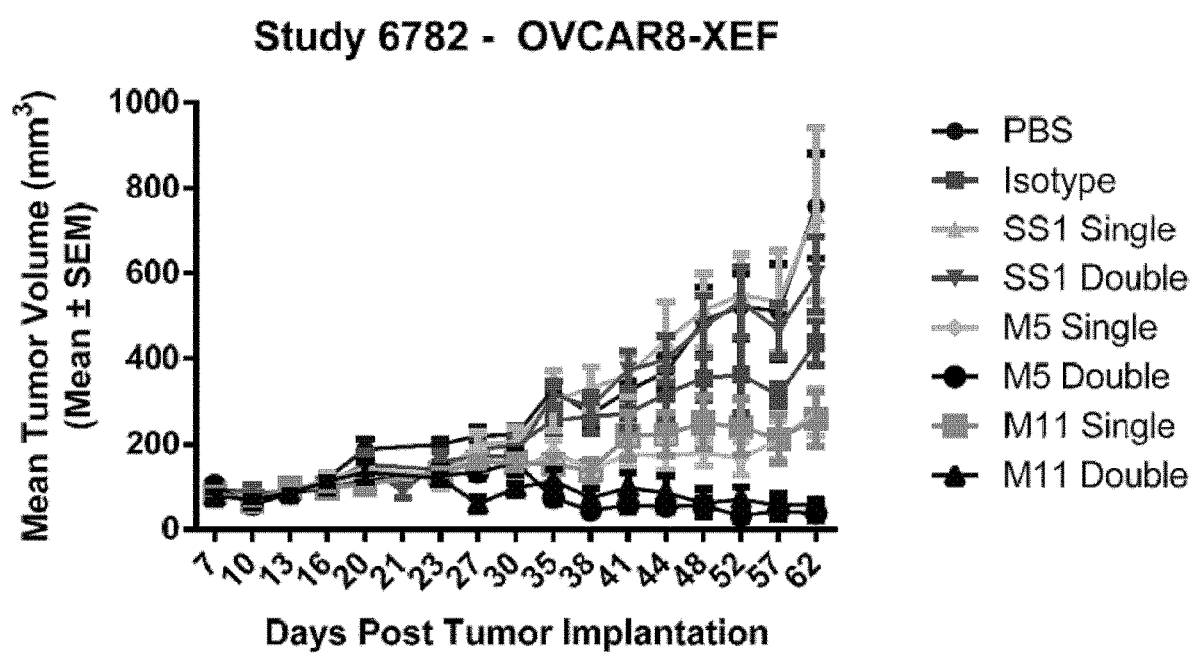

FIG. 43 is a graph depicting tumor growth after various mesothelin CAR T treatments in the OVCAR8 tumor model. Mean tumor volume +/− SEM to day 62 post tumor implantation. T cells were administered on days 14 and 19. Small circles: mice treated with 100 ul of PBS via the lateral tail vein; black squares: mice treated with Isotype control T cells; gray triangles: mice treated with one dose of SS1 CAR T cells; inverted triangles: mice treated with a double dose of SS1 CAR T cells; diamonds: mice treated with a single dose of M5 CAR T cells; large circles: mice treated with a double dose of M5 CAR T cells; gray squares: mice treated with a single dose of M11 CAR T cells; and black triangles: mice treated with a double dose of M11 CAR T cells.

FIG. 44 is a schematic representation of the human mesothelin peptide coverage in hydrogen deuterium exchange mass spectrometry analysis. Each black bar represents a peptide.

Figure 45A:
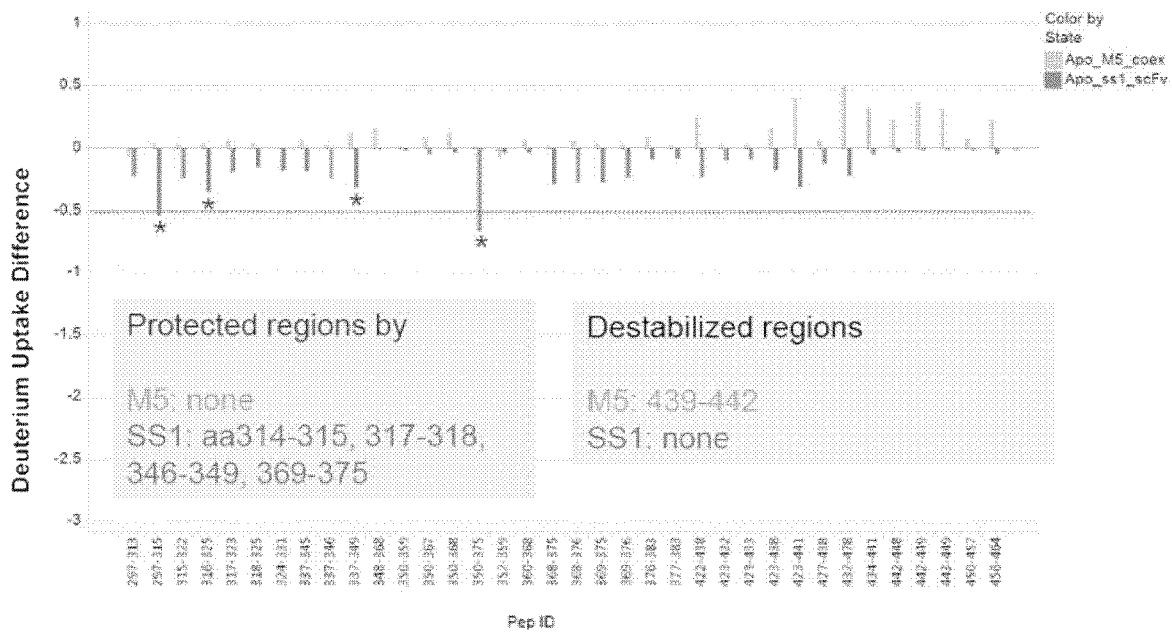
Figure 45B:
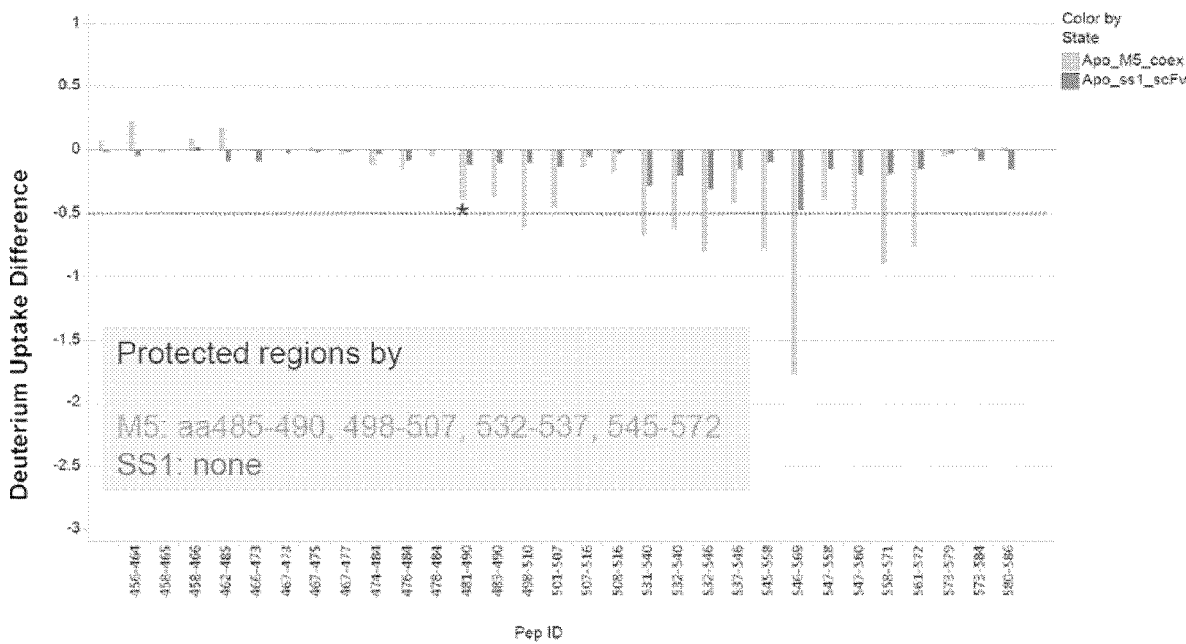

FIGS. 45A and 45B are graphic representations showing the difference in deuterium uptake of human mesothelin when in complex with S S1 (black bars) and M5 (grey bars). The difference in deuterium uptake upon antibody binding (represented on the y-axis) is depicted for each peptide fragment detected (represented on the x-axis), with peptides at amino acids 297-464 in FIG. 45A and peptides at amino acids 458-586 in FIG. 45B. All differences are relative to the deuterium uptake of unbound mesothelin (control). * denote regions of statistical significance using the Tukey test for peptides with a difference less than 0.75 Da.

Figure 47A:
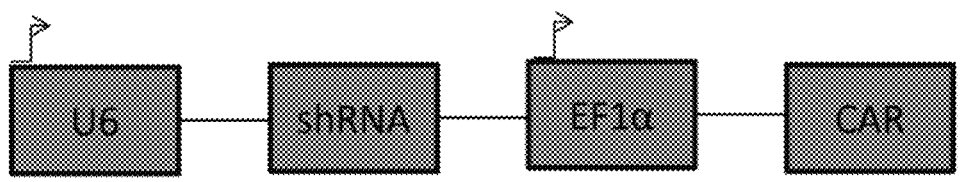
Figure 47B:
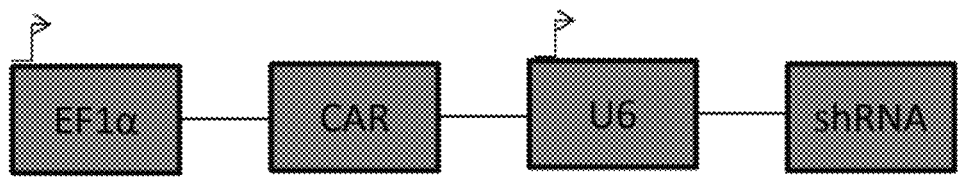
Figure 47C:
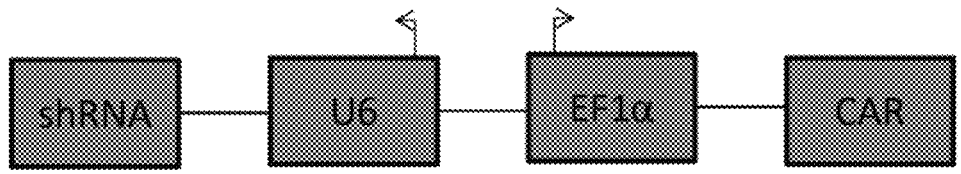
Figure 47D:
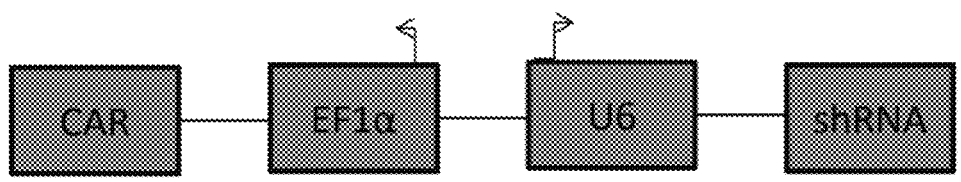
Figure 47E:
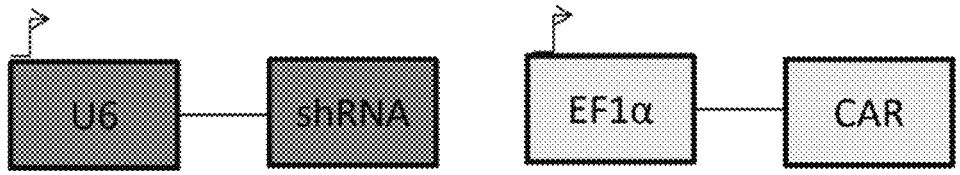

FIG. 46 is a schematic representation showing the primary sequence of antigen human mesothelin (amino acids 296-588) and the regions protected by SS1 and M5. The black bars designate the amino acids protected when complexed with SS1 (amino acids 314-315, 317-318, 346-349, and 369-375). The grey bars designate the amino acids protected when complexed with M5 (amino acids 485-490, 498-507, 532-537, and 545-572). FIGS. 47A-47E show a generic map showing different configurations of constructs encoding a CAR with a shRNA for coexpression of the CAR and an shRNA. FIG. 47A-47D show the various configurations on a single vector, e.g., where the U6 regulated shRNA is upstream or downstream of the EF1 alpha regulated CAR encoding elements. In the exemplary constructs depicted in FIGS. 47A and 47B, the transcription occurs through the U6 and EF1 alpha promoters in the same direction. In the exemplary constructs depicted in FIGS. 47C and 47D, the transcription occurs through the U6 and EF1 alpha promoters in different directions. In FIG. 47E, the shRNA (and corresponding U6 promoter) is on a first vector, and the CAR (and corresponding EF1 alpha promoter) is on a second vector.

Figure 48:
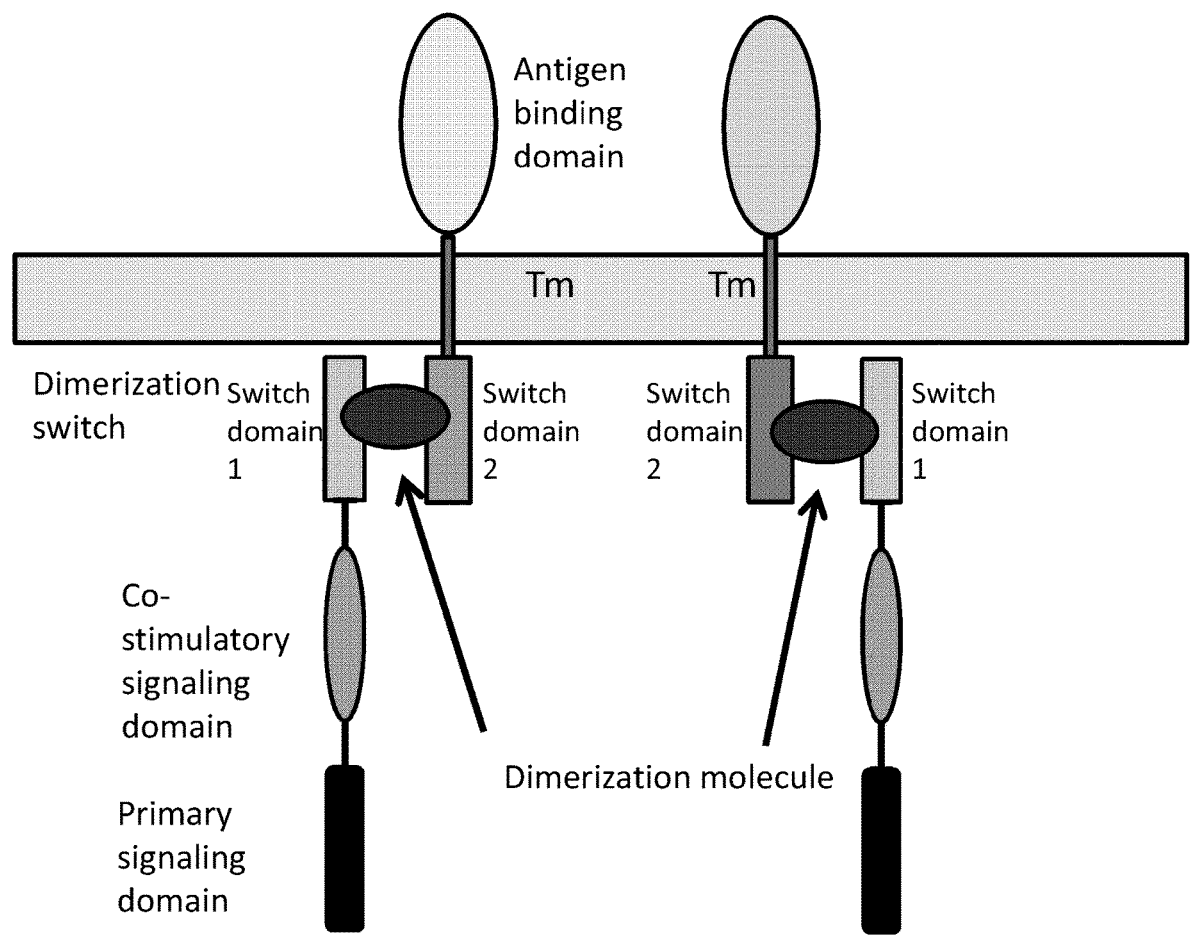

FIG. 48 depicts the structures of two exemplary RCAR configurations. The antigen binding members comprise an antigen binding domain, a transmembrane domain, and a switch domain. The intracellular binding members comprise a switch domain, a co-stimulatory signaling domain and a primary signaling domain. The two configurations demonstrate that the first and second switch domains described herein can be in different orientations with respect to the antigen binding member and the intracellular binding member. Other RCAR configurations are further described herein.

DETAILED DESCRIPTION

Definitions

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

The term "about" when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

The term "Chimeric Antigen Receptor" or alternatively a "CAR" refers to a set of polypeptides, typically two in the simplest embodiments, which when in an immune effector cell, provides the cell with specificity for a target cell, typically a cancer cell, and with intracellular signal generation. In some embodiments, a CAR comprises at least an extracellular antigen binding domain, a transmembrane domain and a cytoplasmic signaling domain (also referred to herein as "an intracellular signaling domain") comprising a functional signaling domain derived from a stimulatory molecule and/or costimulatory molecule as defined below. In some aspects, the set of polypeptides are contiguous with eachother. In some embodiments, the set of polypeptides include a dimerization switch that, upon the presence of a dimerization molecule, can couple the polypeptides to one another, e.g., can couple an antigen binding domain to an intracellular signaling domain. In one aspect, the stimulatory molecule is the zeta chain associated with the T cell receptor complex. In one aspect, the cytoplasmic signaling domain further comprises one or more functional signaling domains derived from at least one costimulatory molecule as defined below. In one aspect, the costimulatory molecule is chosen from the costimulatory molecules described herein, e.g., 4-1BB (i.e., CD137), CD27 and/or CD28. In one aspect, the CAR comprises a chimeric fusion protein comprising an extracellular antigen binding domain, a transmembrane domain and an intracellular signaling domain comprising a functional signaling domain derived from a stimulatory molecule. In one aspect, the CAR comprises a chimeric fusion protein comprising an extracellular antigen binding domain, a transmembrane domain and an intracellular signaling domain comprising a functional signaling domain derived from a costimulatory molecule and a functional signaling domain derived from a stimulatory molecule. In one aspect, the CAR comprises a chimeric fusion protein comprising an extracellular antigen binding domain, a transmembrane domain and an intracellular signaling domain comprising two functional signaling domains derived from one or more costimulatory molecule(s) and a functional signaling domain derived from a stimulatory molecule. In one aspect, the CAR comprises a chimeric fusion protein comprising an extracellular antigen binding domain, a transmembrane domain and an intracellular signaling domain comprising at least two functional signaling domains derived from one or more costimulatory molecule(s) and a functional signaling domain derived from a stimulatory molecule. In one aspect the CAR comprises an optional leader sequence at the amino-terminus (N-ter) of the CAR fusion protein. In one aspect, the CAR further comprises a leader sequence at the N-terminus of the extracellular antigen binding domain, wherein the leader sequence is optionally cleaved from the antigen binding domain (e.g., a scFv) during cellular processing and localization of the CAR to the cellular membrane.

The term "signaling domain" refers to the functional portion of a protein which acts by transmitting information within the cell to regulate cellular activity via defined signaling pathways by generating second messengers or functioning as effectors by responding to such messengers.

As used herein, the term "mesothelin" refers to the 40-kDa protein, mesothelin, which is anchored at the cell membrane by a glycosylphosphatidyl inositol (GPI) linkage and an amino-terminal 31-kDa shed fragment, called megkaryocyte potentiating factor (MPF). Both fragments contain N-glycosylation sites. The term also refers to a soluble splice variant of the 40-kDa carboxyl-terminal fragment also called "soluble mesothelin/MPF-related". Preferably, the term refers to a human mesothelin of GenBank accession number AAH03512.1, and naturally cleaved portions thereof, e.g., as expressed on a cell membrane, e.g., a cancer cell membrane.

The term "antibody" as used herein, refers to a protein, or polypeptide sequence derived from an immunoglobulin molecule which specifically binds with an antigen. Antibodies can be polyclonal or monoclonal, multiple or single chain, or intact immunoglobulins, and may be derived from natural sources or from recombinant sources. Antibodies can be tetramers of immunoglobulin molecules.

The term "antibody fragment" refers to at least one portion of an antibody, that retains the ability to specifically interact with (e.g., by binding, steric hinderance, stabilizing/ destabilizing, spatial distribution) an epitope of an antigen. Examples of antibody fragments include, but are not limited to, Fab, Fab', F(ab')$_2$, Fv fragments, scFv antibody fragments, disulfide-linked Fvs (sdFv), a Fd fragment consisting of the VH and CH1 domains, linear antibodies, single domain antibodies such as sdAb (either VL or VH), camelid VHH domains, multi-specific antibodies formed from antibody fragments such as a bivalent fragment comprising two Fab fragments linked by a disulfide brudge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can also be grafted into scaffolds based on polypeptides such as a fibronectin type III (Fn3)(see U.S. Pat. No. 6,703,199, which describes fibronectin polypeptide minibodies).

The term "scFv" refers to a fusion protein comprising at least one antibody fragment comprising a variable region of a light chain and at least one antibody fragment comprising a variable region of a heavy chain, wherein the light and heavy chain variable regions are contiguously linked, e.g., via a synthetic linker, e.g., a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The portion of the CAR of the invention comprising an antibody or antibody fragment thereof may exist in a variety of forms where the antigen binding domain is expressed as part of a contiguous polypeptide chain including, for example, a single domain antibody fragment (sdAb), a single chain antibody (scFv) a humanized antibody or bispecific antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426). In one aspect, the antigen binding domain of a CAR composition of the invention comprises an antibody fragment. In a further aspect, the CAR comprises an antibody fragment that comprises a scFv.

The term "antibody heavy chain" refers to the larger of the two types of polypeptide chains present in antibody molecules in their naturally occurring conformations, and which normally determines the class to which the antibody belongs.

The term "antibody light chain" refers to the smaller of the two types of polypeptide chains present in antibody molecules in their naturally occurring conformations. Kappa (κ) and lambda (λ) light chains refer to the two major antibody light chain isotypes.

The term "recombinant antibody" refers to an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "antigen" or "Ag" refers to a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components.

The term "compete" refers to the ability of an antigen binding domain, e.g., an antibody or fragment thereof, to interfere with binding directly or indirectly of another antigen binding domain, e.g., an antigen binding domain provided herein, e.g., an antibody or fragment thereof provided herein, to the target, e.g., mesothelin. The extent to which an antigen binding domain, e.g., an antibody or fragment thereof, is able to interfere with the binding of another antigen binding domain, e.g., an antibody or fragment thereof, to the target, and therefore whether it can be said to compete, can be determined using a competition binding assay. In some embodiments, a competition binding assay is a quantitative competition assay. For example, one particularly suitable quantitative competition assay uses a surface plasmon resonance (SPR)-based approach to measure binding, e.g., competition, between one antibody or fragment thereof and another antibody or fragment thereof for binding to an immobilized target. An exemplary SPR-based competition assay is described in Example 2 herein. Another suitable quantitative competition assay uses a FACS-based approach to measure competition between a labelled (e.g., His tagged, biotinylated or radioactively labeled, among others) antibody or fragment thereof and another antibody or fragment thereof for binding to the target.

The term "anti-cancer effect" refers to a biological effect which can be manifested by various means, including but not limited to, e.g., a decrease in tumor volume, a decrease in the number of cancer cells, a decrease in the number of metastases, an increase in life expectancy, decrease in cancer cell proliferation, decrease in cancer cell survival, or amelioration of various physiological symptoms associated with the cancerous condition. An "anti-cancer effect" can also be manifested by the ability of the peptides, polynucleotides, cells and antibodies in prevention of the occurrence of cancer in the first place. The term "anti-tumor effect" refers to a biological effect which can be manifested by various means, including but not limited to, e.g., a decrease in tumor volume, a decrease in the number of tumor cells, a decrease in tumor cell proliferation, or a decrease in tumor cell survival.

The term "autologous" refers to any material derived from the same individual to whom it is later to be re-introduced into the individual.

The term "allogeneic" refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

The term "xenogeneic" refers to a graft derived from an animal of a different species.

The term "cancer" refers to a disease characterized by the uncontrolled growth of aberrant cells. Cancer cells can spread locally or through the bloodstream and lymphatic system to other parts of the body. Examples of various cancers are described herein and include, but are not limited to, mesothelioma, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

The phrase "disease associated with expression of mesothelin" includes, but is not limited to, a disease associated with expression of mesothelin or condition associated with cells which express mesothelin including, e.g., proliferative diseases such as a cancer or malignancy or a precancerous condition such as a mesothelial hyperplasia; or a noncancer related indication associated with cells which express mesothelin. Examples of various cancers that express mesothelin include but are not limited to, mesothelioma, lung cancer, ovarian cancer, pancreatic cancer, and the like.

The term "conservative sequence modifications" refers to amino acid modifications that do not significantly affect or alter the binding characteristics of the antibody or antibody fragment containing the amino acid sequence. Such conservative modifications include amino acid substitutions, additions and deletions. Modifications can be introduced into an antibody or antibody fragment of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a CAR of the invention can be replaced with other amino acid residues from the same side chain family and the altered CAR can be tested, e.g., for the ability to bind mesothelin using the functional assays described herein.

The term "stimulation," refers to a primary response induced by binding of a stimulatory molecule (e.g., a TCR/CD3 complex or CAR) with its cognate ligand (or tumor antigen in the case of a CAR) thereby mediating a signal transduction event, such as, but not limited to, signal transduction via the TCR/CD3 complex or signal transduction via the appropriate NK receptor or signaling domains of the CAR. Stimulation can mediate altered expression of certain molecules.

The term "stimulatory molecule," refers to a molecule expressed by an immune cell (e.g., T cell, NK cell, B cell) that provides the cytoplasmic signaling sequence(s) that regulate activation of the immune cell in a stimulatory way for at least some aspect of the immune cell signaling pathway. In one aspect, the signal is a primary signal that is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or ITAM. Examples of an ITAM containing cytoplasmic signaling sequence that is of particular use in the invention includes, but is not limited to, those derived from CD3 zeta, common FcR gamma (FCER1G), Fc gamma RIIa, FcR beta (Fc Epsilon R1b), CD3 gamma, CD3 delta, CD3 epsilon, CD79a, CD79b, DAP10, and DAP12. In a specific CAR of the invention, the intracellular signaling domain in any one or more CARS of the invention comprises an intracellular signaling sequence, e.g., a primary signaling sequence of CD3-zeta. In a specific CAR of the invention, the primary signaling sequence of CD3-zeta is the sequence provided as SEQ ID NO:9, or the equivalent residues from a non-human species, e.g., mouse, rodent, monkey, ape and the like. In a specific CAR of the invention, the primary signaling sequence of CD3-zeta is the sequence as provided in SEQ ID NO:10, or the equivalent residues from a non-human species, e.g., mouse, rodent, monkey, ape and the like.

The term "antigen presenting cell" or "APC" refers to an immune system cell such as an accessory cell (e.g., a B-cell, a dendritic cell, and the like) that displays a foreign antigen complexed with major histocompatibility complexes (WIC's) on its surface. T-cells may recognize these complexes using their T-cell receptors (TCRs). APCs process antigens and present them to T-cells.

An "intracellular signaling domain," as the term is used herein, refers to an intracellular portion of a molecule. The intracellular signaling domain generates a signal that promotes an immune effector function of the CAR containing cell, e.g., a CART cell. Examples of immune effector function, e.g., in a CART cell, include cytolytic activity and helper activity, including the secretion of cytokines.

In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular domain. Exemplary costimulatory intracellular signaling domains include those derived from molecules responsible for costimulatory signals, or antigen independent stimulation. For example, in the case of a CART, a primary intracellular signaling domain can comprise a cytoplasmic sequence of a T cell receptor, and a costimulatory intracellular signaling domain can comprise cytoplasmic sequence from co-receptor or costimulatory molecule.

A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3 zeta, common FcR gamma (FCER1G), Fc gamma RIIa, FcR beta (Fc Epsilon Rib), CD3 gamma, CD3 delta, CD3 epsilon, CD79a, CD79b, DAP10, and DAP12.

The term "zeta" or alternatively "zeta chain", "CD3-zeta" or "TCR-zeta" is defined as the protein provided as GenBan Acc. No. BAG36664.1, or the equivalent residues from a non-human species, e.g., mouse, rodent, monkey, ape and the like, and a "zeta stimulatory domain" or alternatively a "CD3-zeta stimulatory domain" or a "TCR-zeta stimulatory domain" is defined as the amino acid residues from the cytoplasmic domain of the zeta chain, or functional derivatives thereof, that are sufficient to functionally transmit an initial signal necessary for T cell activation. In one aspect the cytoplasmic domain of zeta comprises residues 52 through 164 of GenBank Acc. No. BAG36664.1 or the equivalent residues from a non-human species, e.g., mouse, rodent, monkey, ape and the like, that are functional orthologs thereof. In one aspect, the "zeta stimulatory domain" or a "CD3-zeta stimulatory domain" is the sequence provided as SEQ ID NO:9. In one aspect, the "zeta stimulatory domain" or a "CD3-zeta stimulatory domain" is the sequence provided as SEQ ID NO:10.

The term a "costimulatory molecule" refers to a cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are contribute to an efficient immune response. Costimulatory molecules include, but are not limited to an MEC class I molecule, BTLA and a Toll ligand receptor, as well as OX40, CD27, CD28, CDS, ICAM-1, LFA-1 (CD11a/CD18), ICOS (CD278), and 4-1BB (CD137). Further examples of such costimulatory molecules include CDS, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, and a ligand that specifically binds with CD83

A costimulatory intracellular signaling domain can be an intracellular portion of a costimulatory molecule. A costimulatory molecule can be represented in the following protein families: TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, CD40, ICOS, BAFFR, HVEM, ICAM-1, lymphocyte function-associated antigen-1 (LFA-1), CD2, CDS, CD7, CD287, LIGHT, NKG2C, SLAMF7, NKp80, CD160, B7-H3, and a ligand that specifically binds with CD83, and the like.

The intracellular signaling domain can comprise the entire intracellular portion, or the entire native intracellular signaling domain, of the molecule from which it is derived, or a functional fragment or derivative thereof.

The term "4-1BB" refers to a member of the TNFR superfamily with an amino acid sequence provided as GenBank Acc. No. AAA62478.2, or the equivalent residues from a non-human species, e.g., mouse, rodent, monkey, ape and the like. In one aspect a "4-1BB costimulatory domain" is defined as amino acid residues 214-255 of GenBank Acc. No. AAA62478.2, or the equivalent residues from a non-human species, e.g., mouse, rodent, monkey, ape and the like. In one aspect, the "4-1BB costimulatory domain" is the sequence provided as SEQ ID NO:7 or the equivalent residues from a non-human species, e.g., mouse, rodent, monkey, ape and the like.

An "antigen presenting cell," as used herein, means an immune system cell such as an accessory cell (e.g., a B-cell, a dendritic cell, and the like) that displays foreign antigens complexed with major histocompatibility complexes (WIC's) on their surfaces. T-cells may recognize these complexes using their T-cell receptors (TCRs). APCs process antigens and present them to T-cells.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or a RNA may also include introns to the extent that the nucleotide sequence encoding the protein may in some version contain an intron(s).

The term "effective amount" or "therapeutically effective amount" is used interchangeably herein, and refer to an amount of a compound, formulation, material, or composition, as described herein effective to achieve a particular biological result. The term "endogenous" refers to any material from or produced inside an organism, cell, tissue or system.

The term "exogenous" refers to any material introduced from or produced outside an organism, cell, tissue or system.

The term "expression" refers to the transcription and/or translation of a particular nucleotide sequence driven by its promoter.

The term "transfer vector" refers to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, a polylysine compound, liposome, and the like. Examples of viral transfer vectors include, but are not limited to, adenoviral vectors, adeno-associated virus vectors, retroviral vectors, lentiviral vectors, and the like.

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic include but are not limited to, e.g., the LENTIVECTOR® gene delivery technology from Oxford BioMedica, the LENTIMAX™ vector system from Lentigen and the like. Nonclinical types of lentiviral vectors are also available and would be known to one skilled in the art.

The term "homologous" or "identity" refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

The term "humanized" refers to those forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies and antibody fragments thereof are human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody/antibody fragment can comprise residues which are found neither in the recipient antibody nor in the imported CDR or framework sequences. These modifications can further refine and optimize antibody or antibody fragment performance. In general, the humanized antibody or antibody fragment thereof will comprise a significant portion of at least one, and typically two, variable domains, in which all or substantially all of the CDR regions correspond to those of a non-human immunoglobulin and all or substantially all of the FR regions are those of a human immunoglobulin sequence. The humanized antibody or antibody fragment can also comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

The term "fully human" refers to an immunoglobulin, such as an antibody or antibody fragment, where the whole molecule is of human origin or consists of an amino acid sequence identical to a human form of the antibody or immunoglobulin.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "operably linked" or "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, where necessary to join two protein coding regions, are in the same reading frame.

The term "parenteral" administration of an immunogenic composition includes, e.g., subcutaneous (s.c.), intravenous (i.v.), intramuscular (i.m.), or intrasternal injection, intratumoral, or infusion techniques.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, a recombinant peptide, or a combination thereof.

The term "promoter" refers to a DNA sequence recognized by the synthetic machinery of the cell, or introduced synthetic machinery, required to initiate the specific transcription of a polynucleotide sequence.

The term "promoter/regulatory sequence" refers to a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "constitutive" promoter refers to a nucleotide sequence which, when operably linked with a polynucleotide which encodes or specifies a gene product, causes the gene product to be produced in a cell under most or all physiological conditions of the cell.

The term "inducible" promoter refers to a nucleotide sequence which, when operably linked with a polynucleotide which encodes or specifies a gene product, causes the gene product to be produced in a cell substantially only when an inducer which corresponds to the promoter is present in the cell.

The term "tissue-specific" promoter refers to a nucleotide sequence which, when operably linked with a polynucleotide encodes or specified by a gene, causes the gene product to be produced in a cell substantially only if the cell is a cell of the tissue type corresponding to the promoter.

The term "flexible polypeptide linker" as used in the context of a scFv refers to a peptide linker that consists of amino acids such as glycine and/or serine residues used alone or in combination, to link variable heavy and variable light chain regions together. In one embodiment, the flexible polypeptide linker is a Gly/Ser linker and comprises the amino acid sequence (Gly-Gly-Gly-Ser)$_n$ (SEQ ID NO: 38), where n is a positive integer equal to or greater than 1. For example, n=1, n=2, n=3. n=4, n=5 and n=6, n=7, n=8, n=9 and n=10. In one embodiment, the flexible polypeptide linkers include, but are not limited to, (Gly$_4$Ser)$_4$ (SEQ ID NO: 27) or (Gly$_4$Ser)$_3$ (SEQ ID NO: 28) In another embodiment, the linkers include multiple repeats of (Gly$_2$Ser), (GlySer) or (Gly$_3$Ser) (SEQ ID NO: 29). Also included within the scope of the invention are linkers described in WO2012/138475, incorporated herein by reference).

As used herein, a 5' cap (also termed an RNA cap, an RNA 7-methylguanosine cap or an RNA m$^7$G cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, "in vitro transcribed RNA" refers to RNA, preferably mRNA, that has been synthesized in vitro. Generally, the in vitro transcribed RNA is generated from an in vitro transcription vector. The in vitro transcription vector comprises a template that is used to generate the in vitro transcribed RNA.

As used herein, a "poly(A)" is a series of adenosines attached by polyadenylation to the mRNA. In the preferred embodiment of a construct for transient expression, the polyA is between 50 and 5000 (SEQ ID NO: 30), preferably greater than 64, more preferably greater than 100, most preferably greater than 300 or 400. poly(A) sequences can be modified chemically or enzymatically to modulate mRNA functionality such as localization, stability or efficiency of translation.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

As used herein, the terms "treat", "treatment" and "treating" refer to the reduction or amelioration of the progression, severity and/or duration of a proliferative disorder, or the amelioration of one or more symptoms (preferably, one or more discernible symptoms) of a proliferative disorder resulting from the administration of one or more therapies (e.g., one or more therapeutic agents such as a CAR of the invention). In specific embodiments, the terms "treat", "treatment" and "treating" refer to the amelioration of at least one measurable physical parameter of a proliferative disorder, such as growth of a tumor, not necessarily discernible by the patient. In other embodiments the terms "treat", "treatment" and "treating"-refer to the inhibition of the progression of a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size or cancerous cell count.

The term "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

The term "subject" is intended to include living organisms in which an immune response can be elicited (e.g., mammals, human).

The term a "substantially purified" cell refers to a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some aspects, the cells are cultured in vitro. In other aspects, the cells are not cultured in vitro.

The term "therapeutic" as used herein means a treatment. A therapeutic effect is obtained by reduction, suppression, remission, or eradication of a disease state.

The term "prophylaxis" as used herein means the prevention of or protective treatment for a disease or disease state.

The terms "cancer associated antigen" or "tumor antigen" interchangeably refers to a molecule (typically a protein, carbohydrate or lipid) that is expressed on the surface of a cancer cell, either entirely or as a fragment (e.g., MHC/peptide), and which is useful for the preferential targeting of a pharmacological agent to the cancer cell. In some embodiments, a tumor antigen is a marker expressed by both normal cells and cancer cells, e.g., a lineage marker, e.g., CD19 on B cells. In some embodiments, a tumor antigen is a cell surface molecule that is overexpressed in a cancer cell in comparison to a normal cell, for instance, 1-fold over expression, 2-fold overexpression, 3-fold overexpression or more in comparison to a normal cell. In some embodiments, a tumor antigen is a cell surface molecule that is inappropriately synthesized in the cancer cell, for instance, a molecule that contains deletions, additions or mutations in comparison to the molecule expressed on a normal cell. In some embodiments, a tumor antigen will be expressed exclusively on the cell surface of a cancer cell, entirely or as a fragment (e.g., MHC/peptide), and not synthesized or expressed on the surface of a normal cell. In some embodiments, the CARs of the present invention includes CARs comprising an antigen binding domain (e.g., antibody or antibody fragment) that binds to a MEC presented peptide. Normally, peptides derived from endogenous proteins fill the pockets of Major histocompatibility complex (MHC) class I molecules, and are recognized by T cell receptors (TCRs) on CD8+T lymphocytes. The MHC class I complexes are constitutively expressed by all nucleated cells. In cancer, virus-specific and/or tumor-specific peptide/MHC complexes represent a unique class of cell surface targets for immunotherapy. TCR-like antibodies targeting peptides derived from viral or tumor antigens in the context of human leukocyte antigen (HLA)-A1 or HLA-A2 have been described (see, e.g., Sastry et al., J Virol. 2011 85(5):1935-1942; Sergeeva et al., Blood, 2011 117(16):4262-4272; Verma et al., J Immunol 2010 184(4):2156-2165; Willemsen et al., Gene Ther 2001 8(21):1601-1608; Dao et al., Sci Transl Med 2013 5(176):176ra33; Tassev et al., Cancer Gene Ther 2012 19(2):84-100). For example, TCR-like antibody can be identified from screening a library, such as a human scFv phage displayed library.

The term "transfected" or "transformed" or "transduced" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The term "specifically binds," refers to an antibody, or a ligand, which recognizes and binds with a binding partner (e.g., tumor antigen) protein present in a sample, but which antibody or ligand does not substantially recognize or bind other molecules in the sample.

"Regulatable chimeric antigen receptor (RCAR)," as that term is used herein, refers to a set of polypeptides, typically two in the simplest embodiments, which when in a RCARX cell, provides the RCARX cell with specificity for a target cell, typically a cancer cell, and with regulatable intracellular signal generation or proliferation, which can optimize an immune effector property of the RCARX cell. An RCARX cell relies at least in part, on an antigen binding domain to provide specificity to a target cell that comprises the antigen bound by the antigen binding domain. In an embodiment, an RCAR includes a dimerization switch that, upon the presence of a dimerization molecule, can couple an intracellular signaling domain to the antigen binding domain.

"Membrane anchor" or "membrane tethering domain", as that term is used herein, refers to a polypeptide or moiety, e.g., a myristoyl group, sufficient to anchor an extracellular or intracellular domain to the plasma membrane.

"Switch domain," as that term is used herein, e.g., when referring to an RCAR, refers to an entity, typically a polypeptide-based entity, that, in the presence of a dimerization molecule, associates with another switch domain. The association results in a functional coupling of a first entity linked to, e.g., fused to, a first switch domain, and a second entity linked to, e.g., fused to, a second switch domain. A first and second switch domain are collectively referred to as a dimerization switch. In embodiments, the first and second switch domains are the same as one another, e.g., they are polypeptides having the same primary amino acid sequence, and are referred to collectively as a homodimerization switch. In embodiments, the first and second switch domains are different from one another, e.g., they are polypeptides having different primary amino acid sequences, and are referred to collectively as a heterodimerization switch. In embodiments, the switch is intracellular. In embodiments, the switch is extracellular. In embodiments, the switch domain is a polypeptide-based entity, e.g., FKBP or FRB-based, and the dimerization molecule is small molecule, e.g., a rapalogue. In embodiments, the switch domain is a polypeptide-based entity, e.g., an scFv that binds a myc peptide, and the dimerization molecule is a polypeptide, a fragment thereof, or a multimer of a polypeptide, e.g., a myc ligand or multimers of a myc ligand that bind to one or more myc scFvs. In embodiments, the switch domain is a polypeptide-based entity, e.g., myc receptor, and the dimerization molecule is an antibody or fragments thereof, e.g., myc antibody.

"Dimerization molecule," as that term is used herein, e.g., when referring to an RCAR, refers to a molecule that promotes the association of a first switch domain with a second switch domain. In embodiments, the dimerization molecule does not naturally occur in the subject, or does not occur in concentrations that would result in significant dimerization. In embodiments, the dimerization molecule is a small molecule, e.g., rapamycin or a rapalogue, e.g, RAD001.

The term "bioequivalent" refers to an amount of an agent other than the reference compound (e.g., RAD001), required to produce an effect equivalent to the effect produced by the reference dose or reference amount of the reference compound (e.g., RAD001). In an embodiment the effect is the level of mTOR inhibition, e.g., as measured by P70 S6 kinase inhibition, e.g., as evaluated in an in vivo or in vitro assay, e.g., as measured by an assay described herein, e.g., the Boulay assay, or measurement of phosphorylated S6 levels by western blot. In an embodiment, the effect is alteration of the ratio of PD-1 positive/PD-1 negative T cells, as measured by cell sorting. In an embodiment a bioequivalent amount or dose of an mTOR inhibitor is the amount or dose that achieves the same level of P70 S6 kinase inhibition as does the reference dose or reference amount of a reference compound. In an embodiment, a bioequivalent amount or dose of an mTOR inhibitor is the amount or dose that achieves the same level of alteration in the ratio of PD-1 positive/PD-1 negative T cells as does the reference dose or reference amount of a reference compound.

The term 'low, immune enhancing, dose" when used in conjuction with an mTOR inhibitor, e.g., an allosteric mTOR inhibitor, e.g., RAD001 or rapamycin, or a catalytic mTOR inhibitor, refers to a dose of mTOR inhibitor that partially, but not fully, inhibits mTOR activity, e.g., as measured by the inhibition of P70 S6 kinase activity. Methods for evaluating mTOR activity, e.g., by inhibition of P70 S6 kinase, are discussed herein. The dose is insufficient to result in complete immune suppression but is sufficient to enhance the immune response. In an embodiment, the low, immune enhancing, dose of mTOR inhibitor results in a decrease in the number of PD-1 positive T cells and/or an increase in the number of PD-1 negative T cells, or an increase in the ratio of PD-1 negative T cells/PD-1 positive T cells. In an embodiment, the low, immune enhancing, dose of mTOR inhibitor results in an increase in the number of naive T cells. In an embodiment, the low, immune enhancing, dose of mTOR inhibitor results in one or more of the following:

an increase in the expression of one or more of the following markers: $CD62L^{high}$, $CD127^{high}$, $CD27^+$, and BCL2, e.g., on memory T cells, e.g., memory T cell precursors;

a decrease in the expression of KLRG1, e.g., on memory T cells, e.g., memory T cell precursors; and an increase in the number of memory T cell precursors, e.g., cells with any one or combination of the following characteristics: increased $CD62L^{high}$, increased $CD127^{high}$, increased $CD27^+$, decreased KLRG1, and increased BCL2; wherein any of the changes described above occurs, e.g., at least transiently, e.g., as compared to a non-treated subject.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98%, or 99% identity, and includes subranges such as 96-99%, 96-98%, 96-97%, 97-99%, 97-98%, and 98-99% identity. This applies regardless of the breadth of the range.

Description

Provided herein are compositions of matter and methods of use for the treatment of a disease such as cancer using anti-mesothelin chimeric antigen receptors (CAR), e.g., human mesothelin CAR.

In one aspect, the invention provides a number of chimeric antigen receptors comprising an antibody or antibody fragment engineered for specific binding to a mesothelin protein. In one aspect, the invention provides a cell (e.g., T cell or NK cell) engineered to express a CAR, e.g., wherein the CAR T cell ("CART") exhibits an anticancer property. In one aspect a cell is transformed with the CAR and the CAR is expressed on the cell surface. In some embodiments, the cell (e.g., T cell or NK cell) is transduced with a viral vector encoding a CAR. In some embodiments, the viral vector is a retroviral vector. In some embodiments, the viral vector is a lentiviral vector. In some such embodiments, the cell may stably express the CAR. In another embodiment, the cell (e.g., T cell or NK cell) is transfected with a nucleic acid, e.g., mRNA, cDNA, DNA, encoding a CAR. In some such embodiments, the cell may transiently express the CAR.

In one aspect, the mesothelin protein binding portion of the CAR is a scFv antibody fragment. In one aspect such antibody fragments are functional in that they retain the equivalent binding affinity, i.e., they bind the same antigen with comparable affinity, as the IgG antibody from which it is derived. In one aspect such antibody fragments are functional in that they provide a biological response that can include, but is not limited to, activation of an immune response, inhibition of signal-transduction origination from its target antigen, inhibition of kinase activity, and the like, as will be understood by a skilled artisan. In one aspect, the mesothelin antigen binding domain of the CAR is a scFv antibody fragment that is human or humanized compared to the murine sequence of the scFv from which it is derived. In one embodiment, the human anti-mesothelin scFv antibody fragment comprises a light chain variable region and/or a heavy chain variable region provided in Table 2, or a sequence with substantial identity thereto, e.g., 95-99% identity.

In some aspects, the antibodies of the invention are incorporated into a chimeric antigen receptor (CAR). In one aspect, the CAR comprises the polypeptide sequence provided herein as SEQ ID NO: 39; SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, and SEQ ID NO: 62, or a sequence with 95-99% identify thereof.

In one aspect, the human scFv portion of a CAR is encoded by a transgene whose sequence has been codon optimized for expression in a mammalian cell. In one aspect, entire CAR construct of the invention is encoded by a transgene whose entire sequence has been codon optimized for expression in a mammalian cell. Codon optimization refers to the discovery that the frequency of occurrence of synonymous codons (i.e., codons that code for the same amino acid) in coding DNA is biased in different species. Such codon degeneracy allows an identical polypeptide to be encoded by a variety of nucleotide sequences. A variety of codon optimization methods is known in the art, and include, e.g., methods disclosed in at least U.S. Pat. Nos. 5,786,464 and 6,114,148.

In one aspect, the human mesothelin CAR molecule comprises the scFv portion provided in SEQ ID NO: 39. In one aspect, the human mesothelin CAR molecule comprises the scFv portion provided in SEQ ID NO: 40. In one aspect, the human mesothelin CAR molecule comprises the scFv portion provided in SEQ ID NO: 41. In one aspect, the human mesothelin CAR molecule comprises the scFv portion provided in SEQ ID NO: 42. In one aspect, the human mesothelin CAR molecule comprises the scFv portion provided in SEQ ID NO: 43. In one aspect, the human mesothelin CAR molecule comprises the scFv portion provided in SEQ ID NO: 44. In one aspect, the human mesothelin CAR molecule comprises the scFv portion provided in SEQ ID NO: 45. In one aspect, the human mesothelin CAR molecule comprises the scFv portion provided in SEQ ID NO: 46. In one aspect, the human mesothelin CAR molecule comprises the scFv portion provided in SEQ ID NO: 47. In one aspect, the human mesothelin CAR molecule comprises the scFv portion provided in SEQ ID NO: 48. In one aspect, the human mesothelin CAR molecule comprises the scFv portion provided in SEQ ID NO: 49. In one aspect, the human mesothelin CAR molecule comprises the scFv portion provided in SEQ ID NO: 50. In one aspect, the human mesothelin CAR molecule comprises the scFv portion provided in SEQ ID NO: 51. In one aspect, the human mesothelin CAR molecule comprises the scFv portion provided in SEQ ID NO: 52. In one aspect, the human mesothelin CAR molecule comprises the scFv portion provided in SEQ ID NO: 53. In one aspect, the human mesothelin CAR molecule comprises the scFv portion provided in SEQ ID NO: 54. In one aspect, the human mesothelin CAR molecule comprises the scFv portion provided in SEQ ID NO: 55. In one aspect, the human mesothelin CAR molecule comprises the scFv portion provided in SEQ ID NO: 56. In one aspect, the human mesothelin CAR molecule comprises the scFv portion provided in SEQ ID NO: 57. In one aspect, the human mesothelin CAR molecule comprises the scFv portion provided in SEQ ID NO: 58. In one aspect, the human mesothelin CAR molecule comprises the scFv portion provided in SEQ ID NO: 59. In one aspect, the human mesothelin CAR molecule comprises the scFv portion provided in SEQ ID NO: 60. In one aspect, the human mesothelin CAR molecule comprises the scFv portion provided in SEQ ID NO: 61. In one aspect, the human mesothelin CAR molecule comprises the scFv portion provided in SEQ ID NO: 62.

In one aspect, the CAR disclosed herein combine an antigen binding domain of a specific antibody with an intracellular signaling molecule. For example, in some aspects, the intracellular signaling molecule includes, but is not limited to, CD3-zeta chain, 4-1BB and CD28 signaling modules and combinations thereof. In one aspect, the antigen binding domain binds to mesothelin. In one aspect, the -mesothelin CAR comprises the sequence provided in Table 2.

In one aspect, the mesothelin CAR comprises a CAR selected from the sequence provided in one or more of SEQ ID NOS: 63-86. In one aspect, themesothelin CAR comprises the sequence provided in SEQ ID NO: 63. In one aspect, themesothelin CAR comprises the sequence provided in SEQ ID NO: 64. In one aspect, themesothelin CAR comprises the sequence provided in SEQ ID NO: 65. In one aspect, themesothelin CAR comprises the sequence provided in SEQ ID NO: 66. In one aspect, themesothelin CAR comprises the sequence provided in SEQ ID NO: 67. In one aspect, themesothelin CAR comprises the sequence provided in SEQ ID NO: 68. In one aspect, themesothelin CAR comprises the sequence provided in SEQ ID NO: 69. In one aspect, themesothelin CAR comprises the sequence provided in SEQ ID NO: 70. In one aspect, themesothelin CAR comprises the sequence provided in SEQ ID NO: 71. In one aspect, themesothelin CAR comprises the sequence provided in SEQ ID NO: 72. In one aspect, themesothelin CAR comprises the sequence provided in SEQ ID NO: 73. In one aspect, themesothelin CAR comprises the sequence provided in SEQ ID NO: 74. In one aspect, themesothelin CAR comprises the sequence provided in SEQ ID NO: 75. In one aspect, themesothelin CAR comprises the sequence provided in SEQ ID NO: 76. In one aspect, themesothelin CAR comprises the sequence provided in SEQ ID NO: 77. In one aspect, themesothelin CAR comprises the sequence provided in SEQ ID NO: 78. In one aspect, themesothelin CAR comprises the sequence provided in SEQ ID NO: 79. In one aspect, themesothelin CAR comprises the sequence provided in SEQ ID NO: 80. In one aspect, themesothelin CAR comprises the sequence provided in SEQ ID NO: 81. In one aspect, themesothelin CAR comprises the sequence provided in SEQ ID NO: 82. In one aspect, themesothelin CAR comprises the sequence provided in SEQ ID NO: 83. In one aspect, themesothelin CAR comprises the sequence provided in SEQ ID NO: 84. In one aspect, themesothelin CAR comprises the sequence provided in SEQ ID NO: 85. In one aspect, themesothelin CAR comprises the sequence provided in SEQ ID NO: 86.

Furthermore, the present invention provides mesothelin CAR compositions and their use in medicaments or methods for treating, among other diseases, cancer or any malignancy or autoimmune diseases involving cells or tissues which express mesothelin.

In one aspect, the invention provides a cell (e.g., T cell or NK cell) engineered to express a chimeric antigen receptor (CAR), wherein the CAR T cell ("CART") exhibits an antitumor property. A preferred antigen is mesothelin. In one aspect, the antigen binding domain of the CAR comprises a human anti-mesothelin antibody fragment. In one aspect, the antigen binding domain of the CAR comprises a human anti-mesothelin antibody fragment comprising an scFv. Accordingly, the invention provides an mesothelin CAR that comprises a human anti-mesothelin binding domain and is engineered into a T cell or NK cell and methods of their use for adoptive therapy.

In one aspect, mesothelin CAR comprises at least one intracellular signaling domain selected from the group consisting of a CD137 (4-1BB) signaling domain, a CD28 signaling domain, a CD3zeta signal domain, and any combination thereof. In one aspect, the mesothelin CAR comprises at least one intracellular signaling domain of one or more costimulatory molecule(s) other than a CD137 (4-1BB) or CD28, a CD3zeta signal domain, and any combination thereof.

Furthermore, the present invention provides mesothelin CAR compositions and their use in medicaments or methods for treating, among other diseases, cancer or any malignancy or autoimmune diseases involving cells or tissues which express mesothelin.

Chimeric Antigen Receptor (CAR)

The present invention encompasses a recombinant nucleic acid construct comprising sequences encoding a CAR, wherein the CAR comprises an antibody that binds specifically to mesothelin, e.g., a human antibody fragment that specifically binds to mesothelin. In one aspect, the mesothelin is human mesothelin, and the sequence of the antibody fragment is contiguous with, and in the same reading frame as a nucleic acid sequence encoding an intracellular signaling domain. The intracellular signaling domain can comprise a costimulatory signaling domain and/or a primary signaling domain, e.g., a zeta chain. The costimulatory signaling domain refers to a portion of the CAR comprising at least a portion of the intracellular domain of a costimulatory molecule.

In specific aspects, a CAR construct of the invention comprises a scFv domain selected from the group consisting of SEQ ID NOS: 39-62, wherein the scFv may be preceded by an optional leader sequence such as provided in SEQ ID NO: 1, and followed by an optional hinge sequence such as provided in SEQ ID NO:2 or SEQ ID NO: 3 or SEQ ID NO:4 or SEQ ID NO:5, a transmembrane region such as provided in SEQ ID NO:6, an intracellular signalling domain that includes SEQ ID NO:7 or SEQ ID NO:8 and a CD3 zeta sequence that includes SEQ ID NO:9 or SEQ ID NO: 10, wherein the domains are contiguous with and in the same reading frame to form a single fusion protein. Also included in the invention is a nucleotide sequence that encodes the polypeptide selected from the group consisting of SEQ ID NO: 87; SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, and SEQ ID NO: 110, or a sequence with 95-99% identify thereof. Also included in the invention is a nucleotide sequence that encodes the polypeptide of each of the scFv fragments selected from the group consisting of SEQ ID NO: 39; SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, and SEQ ID NO: 62, or a sequence with 95-99% identify thereof, and each of the domains of SEQ ID NOS: 1, 2, and 6-9, plus the encoded mesothelin CAR fusion protein of the invention. In one aspect an exemplary mesothelin CAR constructs comprisean optional leader sequence, an extracellular mesothelin binding domain, a hinge, a transmembrane domain, and an intracellular stimulatory domain. In one aspect, the mesothelin CAR construct comprises an optional leader sequence, a mesothelin binding domain, a hinge, a transmembrane domain, an intracellular costimulatory domain and an intracellular stimulatory domain. Specific mesothelin CAR constructs containing human scFv domains are provided as SEQ ID NOs: 87-110.

Full-length CAR sequences are also provided herein as SEQ ID NO: 63; SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, or SEQ ID NO: 86. An exemplary leader sequence is provided as SEQ ID NO: 1. An exemplary hinge/spacer sequence is provided as SEQ ID NO: 2 or SEQ ID NO:3 or SEQ ID NO:4 or SEQ ID NO:5.

An exemplary transmembrane domain sequence is provided as SEQ ID NO:6. An exemplary sequence of the intracellular signaling domain of the 4-1BB protein is provided as SEQ ID NO: 7. An exemplary sequence of the intracellular signaling domain of CD27 is provided as SEQ ID NO:8. An exemplary CD3zeta domain sequence is provided as SEQ ID NO: 9 or SEQ ID NO:10.

In one aspect, the present invention encompasses a recombinant nucleic acid construct comprising a nucleic acid molecule encoding a CAR, wherein the nucleic acid molecule comprises the nucleic acid sequence encoding an anti-mesothelin binding domain, e.g., described herein, that is contiguous with and in the same reading frame as a nucleic acid sequence encoding an intracellular signaling domain. In one aspect, the anti-mesothlin binding domain is selected from one or more of SEQ ID NOS: 87-110. In one aspect, the anti-mesothelin binding domain comprises SEQ ID NO: 87. In one aspect, the anti-mesothelin binding domain comprises SEQ ID NO: 88. In one aspect, the anti-mesothelin binding domain comprises SEQ ID NO: 89. In one aspect, the anti-mesothelin binding domain comprises SEQ ID NO: 90. In one aspect, the anti-mesothelin binding domain comprises SEQ ID NO: 91. In one aspect, the anti-mesothelin binding domain comprises SEQ ID NO: 92. In one aspect, the anti-mesothelin binding domain comprises SEQ ID NO: 93. In one aspect, the anti-mesothelin binding domain comprises SEQ ID NO: 94. In one aspect, the anti-mesothelin binding domain comprises SEQ ID NO: 95. In one aspect, the anti-mesothelin binding domain comprises SEQ ID NO: 96. In one aspect, the anti-mesothelin binding domain comprises SEQ ID NO: 97. In one aspect, the anti-mesothelin binding domain comprises SEQ ID NO: 98. In one aspect, the anti-mesothelin binding domain comprises SEQ ID NO: 99. In one aspect, the anti-mesothelin binding domain comprises SEQ ID NO: 100. In one aspect, the anti-mesothelin binding domain comprises SEQ ID NO: 101. In one aspect, the anti-mesothelin binding domain comprises SEQ ID NO: 102. In one aspect, the anti-mesothelin binding domain comprises SEQ ID NO: 103. In one aspect, the anti-mesothelin binding domain comprises SEQ ID NO: 104. In one aspect, the anti-mesothelin binding domain comprises SEQ ID NO: 105. In one aspect, the anti-mesothelin binding domain comprises SEQ ID NO: 106. In one aspect, the anti-mesothelin binding domain comprises SEQ ID NO: 107. In one aspect, the anti-mesothelin binding domain comprises SEQ ID NO: 108. In one aspect, the anti-mesothelin binding domain comprises SEQ ID NO: 109. In one aspect, the anti-mesothelin binding domain comprises SEQ ID NO: 110. In one aspect, the present invention encompasses a recombinant DNA construct comprising a transgene encoding a CAR, wherein the transgene comprises the nucleic acid sequence encoding an anti-mesothelin binding domain described herein, e.g., a human anti-mesothelin binding domain selected from one or more of SEQ ID NOS:87-110, wherein the sequence is contiguous with and in the same reading frame as the nucleic acid sequence encoding an intracellular signaling domain. An exemplary intracellular signaling domain that can be used in the CAR includes, but is not limited to, one or more intracellular signaling domains of, e.g., CD3-zeta, CD28, 4-1BB, and the like. In some instances, the CAR can comprise any combination of CD3-zeta, CD28, 4-1BB, and the like. In one aspect the nucleic acid sequence of a CAR construct of the invention is selected from one or more of SEQ ID NOS: 111-134. In one aspect the nucleic acid sequence of a CAR construct is SEQ ID NO: 111. In one aspect the nucleic acid sequence of a CAR construct is SEQ ID NO: 112. In one aspect the nucleic acid sequence of a CAR construct is SEQ ID NO: 113. In one aspect the nucleic acid sequence of a CAR construct is SEQ ID NO: 114. In one aspect the nucleic acid sequence of a CAR construct is SEQ ID NO: 115. In one aspect the nucleic acid sequence of a CAR construct is SEQ ID NO: 116. In one aspect the nucleic acid sequence of a CAR construct is SEQ ID NO: 117. In one aspect the nucleic acid sequence of a CAR construct is SEQ ID NO: 118. In one aspect the nucleic acid sequence of a CAR construct is SEQ ID NO: 119. In one aspect the nucleic acid sequence of a CAR construct is SEQ ID NO: 120. In one aspect the nucleic acid sequence of a CAR construct is SEQ ID NO: 121. In one aspect the nucleic acid sequence of a CAR construct is SEQ ID NO: 122. In one aspect the nucleic acid sequence of a CAR construct is SEQ ID NO: 123. In one aspect the nucleic acid sequence of a CAR construct is SEQ ID NO: 124. In one aspect the nucleic acid sequence of a CAR construct is SEQ ID NO: 125. In one aspect the nucleic acid sequence of a CAR construct is SEQ ID NO: 126. In one aspect the nucleic acid sequence of a CAR construct is SEQ ID NO: 127. In one aspect the nucleic acid sequence of a CAR construct is SEQ ID NO: 128. In one aspect the nucleic acid sequence of a CAR construct is SEQ ID NO: 129. In one aspect the nucleic acid sequence of a CAR construct is SEQ ID NO: 130. In one aspect the nucleic acid sequence of a CAR construct is SEQ ID NO: 131. In one aspect the nucleic acid sequence of a CAR construct is SEQ ID NO: 132. In one aspect the nucleic acid sequence of a CAR construct is SEQ ID NO: 133. In one aspect the nucleic acid sequence of a CAR construct is SEQ ID NO: 134.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the nucleic acid of interest can be produced synthetically, rather than cloned.

The present invention includes retroviral and lentiviral vector constructs expressing a CAR that can be directly transduced into a cell. The present invention also includes an RNA construct that can be directly transfected into a cell. A method for generating mRNA for use in transfection involves in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-2000 bases in length (SEQ ID NO: 35). RNA so produced can efficiently transfect different kinds of cells. In one embodiment, the template includes sequences for the CAR. In an embodiment, an RNA CAR vector is transduced into a T cell by electroporation.

Antigen Binding Domain

In one aspect, the CAR of the invention comprises a target-specific binding element otherwise referred to as an antigen binding domain. The choice of antigen binding domain depends upon the type and number of antigens that define the surface of a target cell. For example, the antigen binding domain may be chosen to recognize a antigen that acts as a cell surface marker on target cells associated with a particular disease state.

In one aspect, the CAR-mediated immune effector cell response can be directed to cells that express an antigen of interest, where the CAR comprises an antigen binding domain that specifically binds to the antigen of interest. In one aspect, the portion of the CAR comprising the antigen binding domain comprises an antigen binding domain that targets mesothelin. In one aspect, the antigen binding domain targets human mesothelin.

The antigen binding domain can be any domain that binds to the antigen including but not limited to a monoclonal antibody, a polyclonal antibody, a recombinant antibody, a human antibody, a humanized antibody, and a functional fragment thereof, including but not limited to a single-domain antibody such as a heavy chain variable domain (VH), a light chain variable domain (VL) and a variable domain (VHH) of camelid derived nanobody, and to an alternative scaffold known in the art to function as an antigen binding domain, such as a recombinant fibronectin domain, and the like. In some instances, it is beneficial for the antigen binding domain to be derived from the same species in which the CAR will ultimately be used in. For example, for use in humans, it may be beneficial for the antigen binding domain of the CAR to comprise human or humanized residues for the antigen binding domain of an antibody or antibody fragment. Thus, in one aspect, the antigen binding domain comprises a human antibody or an antibody fragment.

In one embodiment, the anti-mesothelin binding domain does not compete, or competes poorly, for binding to human mesothelin with an antigen binding domain comprising an amino acid sequence comprising SEQ ID NO: 279, e.g., murine SS1 scFv, e.g., in a competition assay described herein.

The amino acid sequence of murine SS1 scFv is provided below (SEQ ID NO: 279):

QVQLQQSGPELEKPGASVKISCKASGYSFTGYTMNWVKQSHGKSLEWIGL

ITPYNGASSYNQKFRGKATLTVDKSSSTAYMDLLSLTSEDSAVYFCARGG

YDGRGFDYWGQGTTVTVSSGGGGSGGGGSGGGGSDIELTQSPAIMSASPG

EKVTMTCSASSSVSYMHWYQQKSGTSPKRWIYDTSKLASGVPGRFSGSGS

GNSYSLTISSVEAEDDATYYCQQWSGYPLTFGAGTKLEI

In one embodiment, the anti-mesothelin binding domain competes for binding to human mesothelin with an antigen binding domain comprising a LC CDR1, LC CDR2 and LC CDR3 of an anti-mesothelin light chain amino acid sequence selected from SEQ ID NO: 43 or SEQ ID NO: 49 and an HC CDR1, HC CDR2, and HC CDR3 of an anti-mesothelin heavy chain amino acid sequence selected from SEQ ID NO: 43 or SEQ ID NO: 49, e.g., in a competition assay described herein. In one embodiment, the anti-mesothelin binding domain competes for binding to human mesothelin with an antigen binding domain comprising a LC CDR1 selected from SEQ ID NO: 203 or SEQ ID NO: 209, a LC CDR2 selected from SEQ ID NO: 227 or SEQ ID NO: 233, and a LC CDR3 selected from SEQ ID NO: 251 or SEQ ID NO: 257; and a HC CDR1 selected from SEQ ID NO: 138 or SEQ ID NO: 144, a HC CDR2 selected from SEQ ID NO: 156 or SEQ ID NO: 162, and a HC CDR3 selected from SEQ ID NO: 179 or SEQ ID NO: 185, e.g., in a competition assay described herein.

In one embodiment, the anti-mesothelin binding domain competes for binding to human mesothelin with an antigen binding domain comprising a sequence selected from SEQ ID NO: 43 or SEQ ID NO: 49, e.g., in a competition assay described herein.

In embodiments, the competition assay is an SPR-based assay. Briefly, the antigen, e.g., human mesothelin, is immobilized on a surface. Through a microflow system, a reference antibody is injected over the antigen layer. Upon binding of the reference antibody to the antigen, an increase in signal, typically expressed in response units (RU) is detected, e.g., reference signal. After a desired time, a test antibody is injected over the antigen layer. If the test antibody binds to a different region or epitope of the antigen, then an additional increase in signal is detected, e.g., a 5% or more, 10% or more, 15% or more, 20% or more, 25% or more, 30% or more, 35%, or more, 40% or more, 45% or more, 50% or more, 55% of more, 60% or more, 65% or more, 70% or more, 75% or more, 80% or more, 85% or more, 90% or more, or 95% or more increase in signal, e.g., RU, as compared to the highest signal detected upon binding of the reference antibody, e.g., the reference signal. If the test antibody binds to the same region or epitope of the antigen, then little or no increase in signal, e.g., RU, will be detected, e.g., less than 20%, less than 15%, less than 10%, less than 5%, less than 4%, less than 3%, less than 2%, or less than 1% increase in signal, e.g., RU, as compared to the highest signal detected upon binding of the reference antibody, e.g., the reference signal. When using this SPR-based competition assay, an antibody is said to compete with the reference antibody when less than 20%, less than 15%, less than 10%, less than 5%, less than 4%, less than 3%, less than 2%, or less than 1% increase in signal, e.g., RU, is detected when compared to the reference signal detected upon binding of the reference antibody to the antigen. An antibody is said to not compete, or compete poorly, with a reference antibody when a 5% or more, 10% or more, 15% or more, 20% or more, 25% or more, 30% or more, 35%, or more, 40% or more, 45% or more, 50% or more, 55% of more, 60% or more, 65% or more, 70% or more, 75% or more, 80% or more, 85% or more, 90% or more, or 95% or more increase in signal, e.g., RU, is detected when compared to the reference signal detected upon binding of the reference antibody to the antigen.

Identification of the epitope bound by the antigen binding domains described herein can be determined by various methods known in the art. For example, crystal structures can be generated containing the antigen binding domain bound to, or in complex with, the antigen. In another example, assays, e.g., a protection assay, can be performed to identify the regions of the antigen contribute to the epitope, or to identify the epitope. An exemplary protection assay, a hydrogen/deuterium exchange (HDX) mass spectrometry assay, is described further in Example 18. The HDX mass spectrometry was performed to identify the putative epitopes on human MSLN, e.g., hMSLN$_{296-588}$, e.g., SEQ ID NO: 278, for murine SS1, e.g., SEQ ID NO: 279, and the M5 scFv described herein, e.g., SEQ ID NO: 43. hMSLN$_{296-588}$, e.g., SEQ ID NO: 278, represents amino acids 296-588 of human mesothelin, e.g., the first amino acid of SEQ ID NO: 278 is amino acid 296 and the last amino acid of SEQ ID NO: 278 is amino acid 588. The amino acid sequence for human mesothelin, amino acids 296-588 is provided below: (SEQ ID NO: 278)

EVEKTACPSGKKAREIDESLIFYKKWELEACVDAALLATQMDRVNAIPFT

YEQLDVLKHKLDELYPQGYPESVIQHLGYLFLKMSPEDIRKWNVTSLETL

KALLEVNKGHEMSPQAPRRPLPQVATLIDRFVKGRGQLDKDTLDTLTAFY

PGYLCSLSPEELSSVPPSSIWAVRPQDLDTCDPRQLDVLYPKARLAFQNM

-continued
NGSEYFVKIQSFLGGAPTEDLKALSQQNVSMDLATFMKLRTDAVLPLTVA

EVQKLLGPHVEGLKAEERHRPVRDWILRQRQDDLDTLGLGLQG

The results of the HDX mass spectrometry assay indicated that one or more amino acids of 314-315, 317-318, 346-349, and 369-375 of hMSLN$_{296-588}$, e.g., SEQ ID NO: 278 contribute to the epitope recognized by SS1. The results of the HDX mass spectrometry assay indicated that one or more amino acids of 485-490, 498-507, 532-537, or 545-572 of hMSLN$_{296-588}$, e.g., SEQ ID NO: 278, contribute to the epitope recognized by an anti-mesothelin antigen binding domain described herein, e.g., M5 scFv, e.g., SEQ ID NO: 43.

In one embodiment, the anti-mesothelin binding domain described herein binds to a different epitope of human mesothelin, e.g., SEQ ID NO: 278, than the epitope of human mesothelin targeted by the antigen binding domain comprising a sequence comprising SEQ ID NO: 279, e.g., murine SS1.

In one embodiment, the epitope recognized by SS1 comprises a sequence selected from amino acids 314-315, 317-318, 346-349, or 369-375 of hMSLN$_{296-588}$, e.g., SEQ ID NO: 278, or any combination thereof. In one embodiment, the epitope recognized by SS1 comprises one or more amino acids selected from amino acids 314-315, 317-318, 346-349, or 369-375 of hMSLN$_{296-588}$, e.g., SEQ ID NO: 278.

In one embodiment, the anti-mesothelin binding domain described herein binds to the C-terminus of human mesothelin. In one embodiment, the anti-mesothelin binding domain described herein binds an epitope within amino acids 450-588 of SEQ ID NO: 278, e.g., wherein the epitope, in part or in whole, can be found within amino acids 450-588, within amino acids 480-580, or within amino acids 485-572 of SEQ ID NO: 278. In one embodiment, the epitope recognized by an anti-mesothelin binding domain described herein comprises a sequence selected from amino acids 485-490, 498-507, 532-537, or 545-572 of hMSLN$_{296-588}$, e.g., SEQ ID NO: 278, or any combination thereof. In one embodiment, the epitope recognized by an anti-mesothelin binding domain described herein comprises one or more amino acids selected from 485-490, 498-507, 532-537, or 545-572 of hMSLN$_{296-588}$, e.g., SEQ ID NO: 278, or any combination thereof.

In one embodiment, the anti-mesothelin binding domain comprises one or more (e.g., all three) light chain complementary determining region 1 (LC CDR1), light chain complementary determining region 2 (LC CDR2), and light chain complementary determining region 3 (LC CDR3) of a human anti-mesothelin binding domain selected from SEQ ID NOS: 39-62 and one or more (e.g., all three) heavy chain complementary determining region 1 (HC CDR1), heavy chain complementary determining region 2 (HC CDR2), and heavy chain complementary determining region 3 (HC CDR3) of a human anti-mesothelin binding domain selected from SEQ ID NOS: 39-62 In one embodiment, the human anti-mesothelin binding domain comprises a light chain variable region described herein (e.g., in Table 2) and/or a heavy chain variable region described herein (e.g., in Table 2). In one embodiment, the anti-mesothelin binding domain is a scFv comprising a light chain variable region and a heavy chain variable region of an amino acid sequence of Table 2. In an embodiment, the anti-mesothelin binding domain (e.g., an scFV) comprises: a light chain variable region comprising an amino acid sequence having at least one, two or three modifications (e.g., substitutions) but not more than 30, 20 or 10 modifications (e.g., substitutions) of an amino acid sequence of a light chain variable region provided in Table 2, or a sequence with 95-99% identity to an amino acid sequence of Table 2; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided in Table 2, or a sequence with 95-99% identity to an amino acid sequence of Table 2.

In one embodiment, the human anti-mesothelin binding domain comprises a sequence selected from a group consisting of SEQ ID NOS: 39-62, or a sequence with 95-99% identify thereof. In one embodiment, the nucleic acid sequence encoding the human anti-mesothelin binding domain comprises a sequence selected from a group consisting of SEQ ID NO: 87-110, or a sequence with 95-99% identify thereof. In one embodiment, the human anti-mesothelin binding domain is a scFv, and a light chain variable region comprising an amino acid sequence described herein, e.g., in Table 2 or 3, is attached to a heavy chain variable region comprising an amino acid sequence described herein, e.g., in Table 2 or 3, via a linker, e.g., a linker described herein. In one embodiment, the humanized anti-mesothelin binding domain includes a (Gly4-Ser)n linker (SEQ ID NO: 26), wherein n is 1, 2, 3, 4, 5, or 6, preferably 3 or 4. The light chain variable region and heavy chain variable region of a scFv can be, e.g., in any of the following orientations: light chain variable region-linker-heavy chain variable region or heavy chain variable region-linker-light chain variable region.

In one aspect, the antigen binding domain portion comprises one or more sequence selected from SEQ ID NOS: 39-62. In one aspect the CAR is selected from one or more sequence selected from SEQ ID NOS: 63-86.

In one aspect, the antibodies of the invention may exist in a variety of other forms including, for example, Fab, Fab', F(ab')$_2$, Fv fragments, scFv antibody fragments, disulfide-linked Fvs (sdFv), a Fd fragment consisting of the VH and CH1 domains, linear antibodies, single domain antibodies such as sdAb (either VL or VH), camelid VHH domains, multi-specific antibodies formed from antibody fragments such as a bivalent fragment comprising two Fab fragments linked by a disulfide brudge at the hinge region, and an isolated CDR or other epitope binding fragments of an antibody. In one aspect, the antibody fragment provided herein is a scFv. In some instances, a human scFv may also be derived from a yeast display library.

A display library is a collection of entities; each entity includes an accessible polypeptide component and a recoverable component that encodes or identifies the polypeptide component. The polypeptide component is varied so that different amino acid sequences are represented. The polypeptide component can be of any length, e.g. from three amino acids to over 300 amino acids. A display library entity can include more than one polypeptide component, for example, the two polypeptide chains of a Fab. In one exemplary embodiment, a display library can be used to identify an anti-mesothelin binding domain. In a selection, the polypeptide component of each member of the library is probed with mesothelin, or a fragment there, and if the polypeptide component binds to the mesothelin, the display library member is identified, typically by retention on a support.

Retained display library members are recovered from the support and analyzed. The analysis can include amplification and a subsequent selection under similar or dissimilar conditions. For example, positive and negative selections can be alternated. The analysis can also include determining the amino acid sequence of the polypeptide component, i.e., the anti-mesothelin binding domain, and purification of the polypeptide component for detailed characterization.

A variety of formats can be used for display libraries. Examples include the phage display. In phage display, the protein component is typically covalently linked to a bacteriophage coat protein. The linkage results from translation of a nucleic acid encoding the protein component fused to the coat protein. The linkage can include a flexible peptide linker, a protease site, or an amino acid incorporated as a result of suppression of a stop codon. Phage display is described, for example, in U.S. Pat. No. 5,223,409; Smith (1985) *Science* 228:1315-1317; WO 92/18619; WO 91/17271; WO 92/20791; WO 92/15679; WO 93/01288; WO 92/01047; WO 92/09690; WO 90/02809; de Haard et al. (1999) *J. Biol. Chem* 274:18218-30; Hoogenboom et al. (1998) *Immunotechnology* 4:1-20; Hoogenboom et al. (2000) *Immunol Today* 2:371-8 and Hoet et al. (2005) *Nat Biotechnol.* 23(3)344-8. Bacteriophage displaying the protein component can be grown and harvested using standard phage preparatory methods, e.g. PEG precipitation from growth media. After selection of individual display phages, the nucleic acid encoding the selected protein components can be isolated from cells infected with the selected phages or from the phage themselves, after amplification. Individual colonies or plaques can be picked, the nucleic acid isolated and sequenced.

Other display formats include cell based display (see, e.g., WO 03/029456), protein-nucleic acid fusions (see, e.g., U.S. Pat. No. 6,207,446), ribosome display (See, e.g., Mattheakis et al. (1994) *Proc. Natl. Acad. Sci. USA* 91:9022 and Hanes et al. (2000) *Nat Biotechnol.* 18:1287-92; Hanes et al. (2000) *Methods Enzymol.* 328:404-30; and Schaffitzel et al. (1999) *J Immunol Methods.* 231(1-2):119-35), and *E. coli* periplasmic display (*J Immunol Methods.* 2005 Nov. 22; PMID: 16337958).

In addition to the use of display libraries, other methods can be used to obtain an anti-mesothelin binding domain. For example, mesothelin or a fragment thereof can be used as an antigen in a non-human animal, e.g., a rodent.

In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies (Mabs) derived from the genes with the desired specificity may be produced and selected. See, e.g., XENOMOUSE™, Green et al., 1994, *Nat. Gen.* 7:13-21; U.S. 2003-0070185, WO 96/34096, published Oct. 31, 1996, and PCT Application No. PCT/US96/05928, filed Apr. 29, 1996.

In some instances, scFvs can be prepared according to method known in the art (see, for example, Bird et al., (1988) Science 242:423-426 and Huston et al., (1988) Proc. Natl. Acad. Sci. USA 85:5879-5883). ScFv molecules can be produced by linking VH and VL regions together, e.g., using flexible polypeptide linkers. The scFv molecules can comprise a linker (e.g., a Ser-Gly linker) with an optimized length and/or amino acid composition. The linker length can greatly affect how the variable regions of an scFv fold and interact. In fact, if a short polypeptide linker is employed (e.g., between 5-10 amino acids, intrachain folding is prevented. Interchain folding is also required to bring the two variable regions together to form a functional epitope binding site. For examples of linker orientation and size see, e.g., Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, is incorporated herein by reference.

An scFv can comprise a linker of at least 1, 2, 3, 4, 5, 6, 7, 8, 9, 10, 11, 12, 13, 14, 15, 16, 17, 18, 19, 20, 25, 30, 35, 40, 45, 50, or more amino acid residues between its VL and VH regions. The linker sequence may comprise any naturally occurring amino acid. In some embodiments, the linker sequence comprises amino acids glycine and serine. In another embodiment, the linker sequence comprises sets of glycine and serine repeats such as $(Gly_4Ser)_n$, where n is a positive integer equal to or greater than 1. (SEQ ID NO: 135) In one embodiment, the linker can be $(Gly_4Ser)_4$ (SEQ ID NO: 27) or $(Gly_4Ser)_3$ (SEQ ID NO: 28). Variation in the linker length may retain or enhance activity, giving rise to superior efficacy in activity studies.

Stability and Mutations

The stability of an anti-mesothelin binding domain, e.g., scFv molecules (e.g., soluble scFv), can be evaluated in reference to the biophysical properties (e.g., thermal stability) of a conventional control scFv molecule or a full length antibody. In one embodiment, the human scFv has a thermal stability that is greater than about 0.1, about 0.25, about 0.5, about 0.75, about 1, about 1.25, about 1.5, about 1.75, about 2, about 2.5, about 3, about 3.5, about 4, about 4.5, about 5, about 5.5, about 6, about 6.5, about 7, about 7.5, about 8, about 8.5, about 9, about 9.5, about 10 degrees, about 11 degrees, about 12 degrees, about 13 degrees, about 14 degrees, or about 15 degrees Celsius than a control binding molecule (e.g. a conventional scFv molecule) in the described assays.

The improved thermal stability of the anti-mesothelin binding domain, e.g., scFv, is subsequently conferred to the entire mesothelin CAR construct, leading to improved therapeutic properties of the mesothelin CAR construct. The thermal stability of the anti-mesothelin binding domain, e.g., scFv, can be improved by at least about 2° C. or 3° C. as compared to a conventional antibody. In one embodiment, the anti-mesothelin binding domain, e.g., scFv, has a 1° C. improved thermal stability as compared to a conventional antibody. In another embodiment, the anti-mesothelin binding domain, e.g., scFv, has a 2° C. improved thermal stability as compared to a conventional antibody. In another embodiment, the anti-mesothelin binding domain, e.g., scFv, has a 4, 5, 6, 7, 8, 9, 10, 11, 12, 13, 14, 15° C. improved thermal stability as compared to a conventional antibody. Comparisons can be made, for example, between the scFv molecules disclosed herein and scFv molecules or Fab fragments of an antibody from which the scFv VH and VL were derived. Thermal stability can be measured using methods known in the art. For example, in one embodiment, Tm can be measured. Methods for measuring Tm and other methods of determining protein stability are described in more detail below.

Mutations in scFv (arising through direct mutagenesis of the soluble scFv) alter the stability of the scFv and improve the overall stability of the scFv and the CART construct. Stability of the humanized scFv is compared against the murine scFv using measurements such as Tm, temperature denaturation and temperature aggregation.

In one embodiment, the anti-mesothelin binding domain, e.g., scFv, comprises at least one mutation such that the mutated anti-mesothelin binding domain, e.g., scFv, confers improved stability to the anti-mesothelin construct. In another embodiment, the anti-mesothelin binding domain, e.g., scFv, comprises at least 1, 2, 3, 4, 5, 6, 7, 8, 9, 10 mutations such that the mutated anti-mesothelin binding domain, e.g., scFv, confers improved stability to the anti-mesothelin construct. The binding capacity of the mutant scFvs can be determined using assays described in the Examples.

Binding Affinity

A wide variety of methods for determining binding affinity are known in the art. An exemplary method for determining binding affinity employs surface plasmon resonance. Surface plasmon resonance is an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jonsson, U., et al. (1993) Ann. Biol. Clin. 51:19-26; Jonsson, U., i (1991) Biotechniques 11:620-627; Johnsson, B., et al. (1995) J. Mol. Recognit. 8:125-131; and Johnnson, B., et al. (1991) Anal. Biochem. 198:268-277.

In one aspect, the portion of a CAR composition of the invention comprising an antibody or fragment thereof comprises amino acid sequences that are homologous to the amino acid sequences described herein, and wherein the antibody or fragment thereof retains the desired functional properties of the anti-mesothelin antibody fragments of the invention. In one specific aspect, the CAR composition of the invention comprises an antibody fragment. In a further aspect, that antibody fragment comprises an scFv.

In various aspects, the portion comprising an antibody or antibody fragment of the CAR composition of the invention is engineered by modifying one or more amino acids within one or both variable regions (i.e., VH and/or VL), for example within one or more CDR regions and/or within one or more framework regions. In one specific aspect, the CAR composition of the invention comprises an antibody fragment. In a further aspect, that antibody fragment comprises an scFv.

It will be understood by one of ordinary skill in the art that the antibody or antibody fragment of the invention may further be modified such that they vary in amino acid sequence (e.g., from wild-type), but not in desired activity. For example, additional nucleotide substitutions leading to amino acid substitutions at "non-essential" amino acid residues may be made to the protein For example, a nonessential amino acid residue in a molecule may be replaced with another amino acid residue from the same side chain family. In another embodiment, a string of amino acids can be replaced with a structurally similar string that differs in order and/or composition of side chain family members, i.e., a conservative substitution, in which an amino acid residue is replaced with an amino acid residue having a similar side chain, may be made.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Percent identity in the context of two or more nucleic acids or polypeptide sequences, refers to two or more sequences that are the same. Two sequences are "substantially identical" if two sequences have a specified percentage of amino acid residues or nucleotides that are the same (i.e., 60% identity, optionally 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well known in the art. Optimal alignment of sequences for comparison can be conducted, e.g., by the local homology algorithm of Smith and Waterman, (1970) Adv. Appl. Math. 2:482c, by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., (2003) Current Protocols in Molecular Biology).

Two examples of algorithms that are suitable for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information.

The percent identity between two amino acid sequences can also be determined using the algorithm of E. Meyers and W. Miller, (1988) Comput. Appl. Biosci. 4:11-17) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (1970) J. Mol. Biol. 48:444-453) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

In one aspect, the present invention contemplates modifications of the starting antibody or fragment (e.g., scFv) amino acid sequence that generate functionally equivalent molecules. For example, the VH or VL of an anti-mesothelin binding domain, e.g., scFv comprised in the CAR can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting VH or VL framework region of the anti-mesothelin binding domain, e.g., scFv. The present invention contemplates modifications of the entire CAR construct, e.g., modifications in one or more amino acid sequences of the various domains of the CAR construct in order to generate functionally equivalent molecules. The CAR construct can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting CAR construct.

Transmembrane Domain

With respect to the transmembrane domain, in various embodiments, a CAR can be designed to comprise a transmembrane domain that is attached to the extracellular domain of the CAR. A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). In one aspect, the transmembrane domain is one that is associated with one of the other domains of the CAR is used, e.g., in one embodiment, the transmembrane domain may be from the same protein that the signaling domain, costimulatory domain or the hinge domain is derived from. In another aspect, the transmembrane domain is not derived from the same protein that any other domain of the CAR is derived from. In some instances, the transmembrane domain can be selected or modified by amino acid substitution to avoid binding of such domains to the transmembrane domains of the same or different surface membrane proteins, e.g., to minimize interactions with other members of the receptor complex. In one aspect, the transmembrane domain is capable of homodimerization with another CAR on the cell surface of a CAR-expressing cell. In a different aspect, the amino acid sequence of the transmembrane domain may be modified or substituted so as to minimize interactions with the binding domains of the native binding partner present in the same CAR-expressing cell.

The transmembrane domain may be derived either from a natural or from a recombinant source. Where the source is natural, the domain may be derived from any membrane-bound or transmembrane protein. In one aspect, the transmembrane domain is capable of signaling to the intracellular domain(s) whenever the CAR has bound to a target. A transmembrane domain of particular use in this invention may include at least the transmembrane domain(s) of, e.g., the alpha, beta or zeta chain of the T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, CD154. In some embodiments, a transmembrane domain may include at least the transmembrane region(s) of, e.g., KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4

(CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKG2D, and NKG2C.

In some instances, the transmembrane domain can be attached to the extracellular region of the CAR, e.g., the antigen binding domain of the CAR, via a hinge, e.g., a hinge from a human protein. For example, in one embodiment, the hinge can be a human Ig (immunoglobulin) hinge (e.g., an IgG4 hinge, an IgD hinge), a GS linker (e.g., a GS linker described herein), a KIR2DS2 hinge or a CD8a hinge. In one embodiment, the hinge or spacer comprises (e.g., consists of) the amino acid sequence of SEQ ID NO:2. In one aspect, the transmembrane domain comprises (e.g., consists of) a transmembrane domain of SEQ ID NO: 6.

In one aspect, the hinge or spacer comprises an IgG4 hinge. For example, in one embodiment, the hinge or spacer comprises a hinge of the amino acid sequence as follows:

(SEQ ID NO: 3)
ESKYGPPCPPCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGKM.

In some embodiments, the hinge or spacer comprises a hinge encoded by a nucleotide sequence as follows:

(SEQ ID NO: 14)
GAGAGCAAGTACGGCCCTCCCTGCCCCCCTTGCCCTGCCCCCGAGTTCCT

GGGCGGACCCAGCGTGTTCCTGTTCCCCCCCAAGCCCAAGGACACCCTGA

TGATCAGCCGGACCCCCGAGGTGACCTGTGTGGTGGTGGACGTGTCCCAG

GAGGACCCCGAGGTCCAGTTCAACTGGTACGTGGACGGCGTGGAGGTGCA

CAACGCCAAGACCAAGCCCCGGGAGGAGCAGTTCAATAGCACCTACCGGG

TGGTGTCCGTGCTGACCGTGCTGCACCAGGACTGGCTGAACGGCAAGGAA

TACAAGTGTAAGGTGTCCAACAAGGGCCTGCCCAGCAGCATCGAGAAAAC

CATCAGCAAGGCCAAGGGCCAGCCTCGGGAGCCCCAGGTGTACACCCTGC

CCCCTAGCCAAGAGGAGATGACCAAGAACCAGGTGTCCCTGACCTGCCTG

GTGAAGGGCTTCTACCCCAGCGACATCGCCGTGGAGTGGGAGAGCAACGG

CCAGCCCGAGAACAACTACAAGACCACCCCCCCTGTGCTGGACAGCGACG

GCAGCTTCTTCCTGTACAGCCGGCTGACCGTGGACAAGAGCCGGTGGCAG

GAGGGCAACGTCTTTAGCTGCTCCGTGATGCACGAGGCCCTGCACAACCA

CTACACCCAGAAGAGCCTGAGCCTGTCCCTGGGCAAGATG.

In one aspect, the hinge or spacer comprises an IgD hinge. For example, in one embodiment, the hinge or spacer comprises a hinge of the amino acid sequence (SEQ ID NO: 4)
RWPESPKAQASSVPTAQPQAEGSLAKATTAPATTRNTGRGGEEKKKEKEK

EEQEERETKTPECPSHTQPLGVYLLTPAVQDLWLRDKATFTCFVVGSDLK

DAHLTWEVAGKVPTGGVEEGLLERHSNGSQSQHSRLTLPRSLWNAGTSVT

CTLNHPSLPPQRLMALREPAAQAPVKLSLNLLASSDPPEAASWLLCEVSG

FSPPNILLMVVLEDQREVNTSGFAPARPPPQPGSTTFWAWSVLRVPAPPS

PQPATYTCVVSHEDSRTLLNASRSLEVSYVTDH.

In some embodiments, the hinge or spacer comprises a hinge encoded by a nucleotide sequence of (SEQ ID NO: 15)
AGGTGGCCCGAAAGTCCCAAGGCCCAGGCATCTAGTGTTCCTACTGCACA

GCCCCAGGCAGAAGGCAGCCTAGCCAAAGCTACTACTGCACCTGCCACTA

CGCGCAATACTGGCCGTGGCGGGGAGGAGAAGAAAAAGGAGAAAGAGAAA

GAAGAACAGGAAGAGAGGGAGACCAAGACCCCTGAATGTCCATCCCATAC

CCAGCCGCTGGGCGTCTATCTCTTGACTCCCGCAGTACAGGACTTGTGGC

TTAGAGATAAGGCCACCTTTACATGTTTCGTCGTGGGCTCTGACCTGAAG

GATGCCCATTTGACTTGGGAGGTTGCCGGAAAGGTACCCACAGGGGGGGT

TGAGGAAGGGTTGCTGGAGCGCCATTCCAATGGCTCTCAGAGCCAGCACT

CAAGACTCACCCTTCCGAGATCCCTGTGGAACGCCGGGACCTCTGTCACA

TGTACTCTAAATCATCCTAGCCTGCCCCCACAGCGTCTGATGGCCCTTAG

AGAGCCAGCCGCCCAGGCACCAGTTAAGCTTAGCCTGAATCTGCTCGCCA

GTAGTGATCCCCCAGAGGCCGCCAGCTGGCTCTTATGCGAAGTGTCCGGC

TTTAGCCCGCCCAACATCTTGCTCATGTGGCTGGAGGACCAGCGAGAAGT

GAACACCAGCGGCTTCGCTCCAGCCCGGCCCCCACCCCAGCCGGGTTCTA

CCACATTCTGGGCCTGGAGTGTCTTAAGGGTCCCAGCACCACCTAGCCCC

CAGCCAGCCACATACACCTGTGTTGTGTCCCATGAAGATAGCAGGACCCT

GCTAAATGCTTCTAGGAGTCTGGAGGTTTCCTACGTGACTGACCATT.

In one aspect, the transmembrane domain may be recombinant, in which case it will comprise predominantly hydrophobic residues such as leucine and valine. In one aspect a triplet of phenylalanine, tryptophan and valine can be found at each end of a recombinant transmembrane domain.

Optionally, a short oligo- or polypeptide linker, between 2 and 10 amino acids in length may form the linkage between the transmembrane domain and the cytoplasmic signaling region of the CAR. A glycine-serine doublet provides a particularly suitable linker. For example, in one aspect, the linker comprises the amino acid sequence of GGGGSGGGGS (SEQ ID NO:5). In some embodiments, the linker is encoded by a nucleotide sequence of (SEQ ID NO: 16)
GGTGGCGGAGGTTCTGGAGGTGGAGGTTCC.

In one aspect, the hinge or spacer comprises a KIR2DS2 hinge and portions thereof.

Cytoplasmic Domain

The cytoplasmic domain or region of the CAR includes an intracellular signaling domain. An intracellular signaling domain is generally responsible for activation of at least one of the normal effector functions of the immune cell in which the CAR has been introducede. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

It is known that signals generated through the TCR alone are insufficient for full activation of the T cell and that a secondary and/or costimulatory signal is also required. Thus, T cell activation can be said to be mediated by two distinct classes of cytoplasmic signaling sequences: those that initiate antigen-dependent primary activation through the TCR (primary intracellular signaling domains) and those that act in an antigen-independent manner to provide a secondary or costimulatory signal (secondary cytoplasmic domain, e.g., a costimulatory domain).

A primary cytoplasmic signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs or ITAMs.

Examples of ITAM containing primary intracellular signaling domains that are of particular use in the invention include those of CD3 zeta, common FcR gamma (FCER1G), Fc gamma RIIa, FcR beta (Fc Epsilon R1b), CD3 gamma, CD3 delta, CD3 epsilon, CD79a, CD79b, DAP10, and DAP12. In one embodiment, a CAR of the invention comprises an intracellular signaling domain, e.g., a primary signaling domain of CD3-zeta.

In one embodiment, a primary signaling domain comprises a modified ITAM domain, e.g., a mutated ITAM domain which has altered (e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In an embodiment, a primary signaling domain comprises one, two, three, four or more ITAM motifs.

Further examples of molecules containing a primary intracellular signaling domain that are of particular use in the invention include those of DAP10, DAP12, and CD32.

The intracellular domain of the CAR can comprise the CD3-zeta signaling domain by itself or it can be combined with any other desired intracellular signaling domain(s) useful in the context of a CAR of the invention. For example, the intracellular signaling domain of the CAR can comprise a CD3 zeta chain portion and a costimulatory signaling domain. The costimulatory signaling domain refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD-1 (also known as PD1), ICOS, lymphocyte function-associated antigen-1 (LFA-1), CD2, CD7, LIGHT, NKG2C, B7-H3, and a ligand that specifically binds with CD83, and the like. For example, CD27 costimulation has been demonstrated to enhance expansion, effector function, and survival of human CART cells in vitro and augments human T cell persistence and antitumor activity in vivo (Song et al. Blood. 2012; 119(3):696-706). Further examples of such costimulatory molecules include CDS, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), NKG2D, CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, and PAG/Cbp.

The intracellular signaling domains within the cytoplasmic portion of the CAR of the invention may be linked to each other in a random or specified order. Optionally, a short oligo- or polypeptide linker, for example, between 2 and 10 amino acids (e.g., 2, 3, 4, 5, 6, 7, 8, 9, or 10 amino acids) in length may form the linkage between intracellular signaling domains. In one embodiment, a glycine-serine doublet can be used as a suitable linker. In one embodiment, a single amino acid, e.g., an alanine, a glycine, can be used as a suitable linker.

In one aspect, the intracellular signaling domain is designed to comprise two or more, e.g., 2, 3, 4, 5, or more, costimulatory signaling domains. In an embodiment, the two or more, e.g., 2, 3, 4, 5, or more, costimulatory signaling domains, are separated by a linker molecule, e.g., a linker molecule described herein. In one embodiment, the intracellular signaling domain comprises two costimulatory signaling domains. In some embodiments, the linker molecule is a glycine residue. In some embodiments, the linker is an alanine residue.

In one aspect, the intracellular signaling domain is designed to comprise the signaling domain of CD3-zeta and the signaling domain of CD28. In one aspect, the intracellular signaling domain is designed to comprise the signaling domain of CD3-zeta and the signaling domain of 4-1BB. In one aspect, the signaling domain of 4-1BB is a signaling domain of SEQ ID NO: 16. In one aspect, the signaling domain of CD3-zeta is a signaling domain of SEQ ID NO: 17.

In one aspect, the intracellular signaling domain is designed to comprise the signaling domain of CD3-zeta and the signaling domain of CD27. In one aspect, the signaling domain of CD27 comprises an amino acid sequence of QRRKYRSNKGESPVEPAEPCRYSCPREEEGSTIP-IQEDYRKPEPACSP (SEQ ID NO:8). In one aspect, the signalling domain of CD27 is encoded by a nucleic acid sequence of (SEQ ID NO: 19)
AGGAGTAAGAGGAGCAGGCTCCTGCACAGTGACTACATGAACATGACTCC

CCGCCGCCCCGGGCCCACCCGCAAGCATTACCAGCCCTATGCCCCACCAC

GCGACTTCGCAGCCTATCGCTCC.

In one aspect, the CAR-expressing cell described herein can further comprise a second CAR, e.g., a second CAR that includes a different antigen binding domain, e.g., to the same target (mesothelin) or a different target (e.g., a target other than mesothelin on stroma cells, e.g., FAP; a target other than mesothelin on prostate cancer cells, e.g., androgen receptor, OR51E2, PSMA, PSCA, PDGRF-β, TARP, GloboH, MAD-CT-1, or MAD-CT-2; a target other than mesothelin on ovararian cancer cells, e.g., Tn, PRSS21, CD171, Lewis Y, folate receptor α, claudin6, GloboH, or sperm protein 17, e.g., a target other than mesothelin on lung cancer cells, e.g., VEGF, HER3, IGF-1R, EGFR, DLL4, or Trop-2). In one embodiment, the CAR-expressing cell comprises a first CAR that targets a first antigen and includes an intracellular signaling domain having a costimulatory signaling domain but not a primary signaling domain, and a second CAR that targets a second, different, antigen and includes an intracellular signaling domain having a primary signaling domain but not a costimulatory signaling domain. Placement of a costimulatory signaling domain, e.g., 4-1BB, CD28, CD27 or OX-40, onto the first CAR, and the primary signaling domain, e.g., CD3 zeta, on the second CAR can limit the CAR activity to cells where both targets are expressed. In one embodiment, the CAR expressing cell comprises a first mesothelin CAR that includes a mesothelin binding domain, a transmembrane domain and a costimulatory domain and a second CAR that targets an antigen other than mesothelin (e.g., a target other than mesothelin on stroma cells, e.g., FAP; a target other than mesothelin on prostate cancer cells, e.g., androgen receptor, OR51E2, PSMA, PSCA, PDGRF-β, TARP, GloboH, MAD-CT-1, or MAD-CT-2; a target other than mesothelin on ovararian cancer cells, e.g., Tn, PRSS21, CD171, Lewis Y, folate receptor α, claudin6, GloboH, or sperm protein 17, e.g., a target other than mesothelin on lung cancer cells, e.g., VEGF, HER3, IGF-1R, EGFR, DLL4, or Trop-2) and includes an antigen binding domain, a transmembrane domain and a primary signaling domain. In another embodiment, the CAR expressing cell comprises a first mesothelin CAR that includes a mesothelin binding domain, a transmembrane domain and a primary signaling domain and a second CAR that targets an antigen other than mesothelin (e.g., a target other than mesothelin on stroma cells, e.g., FAP; a target other than mesothelin on prostate cancer cells, e.g., androgen receptor, OR51E2, PSMA, PSCA, PDGRF-β, TARP, GloboH, MAD-CT-1, or MAD-CT-2; a target other than mesothelin on ovararian cancer cells, e.g., Tn, PRSS21, CD171, Lewis Y, folate receptor α, claudin6, GloboH, or sperm protein 17, e.g., a target other than mesothelin on lung cancer cells, e.g., VEGF, HER3, IGF-1R, EGFR, DLL4, or Trop-2) and includes an antigen binding domain to the antigen, a transmembrane domain and a costimulatory signaling domain.

In one embodiment, the CAR-expressing cell comprises a mesothelin CAR described herein and an inhibitory CAR. In one embodiment, the inhibitory CAR comprises an antigen binding domain that binds an antigen found on normal cells but not cancer cells, e.g., normal cells that also express mesothelin. In one embodiment, the inhibitory CAR comprises the antigen binding domain, a transmembrane domain and an intracellular domain of an inhibitory molecule. For example, the intracellular domain of the inhibitory CAR can be an intracellular domain of PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 and TGFR beta.

In one embodiment, when the CAR-expressing cell comprises two or more different CARs, the antigen binding domains of the different CARs can be such that the antigen binding domains do not interact with one another. For example, a cell expressing a first and second CAR can have an antigen binding domain of the first CAR, e.g., as a fragment, e.g., an scFv, that does not form an association with the antigen binding domain of the second CAR, e.g., the antigen binding domain of the second CAR is a VHH.

In some embodiments, the antigen binding domain comprises a single domain antigen binding (SDAB) molecules include molecules whose complementary determining regions are part of a single domain polypeptide. Examples include, but are not limited to, heavy chain variable domains, binding molecules naturally devoid of light chains, single domains derived from conventional 4-chain antibodies, engineered domains and single domain scaffolds other than those derived from antibodies. SDAB molecules may be any of the art, or any future single domain molecules. SDAB molecules may be derived from any species including, but not limited to mouse, human, camel, llama, lamprey, fish, shark, goat, rabbit, and bovine. This term also includes naturally occurring single domain antibody molecules from species other than Camelidae and sharks.

In one aspect, an SDAB molecule can be derived from a variable region of the immunoglobulin found in fish, such as, for example, that which is derived from the immunoglobulin isotype known as Novel Antigen Receptor (NAR) found in the serum of shark. Methods of producing single domain molecules derived from a variable region of NAR ("IgNARs") are described in WO 03/014161 and Streltsov (2005) Protein Sci. 14:2901-2909.

According to another aspect, an SDAB molecule is a naturally occurring single domain antigen binding molecule known as heavy chain devoid of light chains. Such single domain molecules are disclosed in WO 9404678 and Hamers-Casterman, C. et al. (1993) Nature 363:446-448, for example. For clarity reasons, this variable domain derived from a heavy chain molecule naturally devoid of light chain is known herein as a VHH or nanobody to distinguish it from the conventional VH of four chain immunoglobulins. Such a VHH molecule can be derived from Camelidae species, for example in camel, llama, dromedary, alpaca and guanaco. Other species besides Camelidae may produce heavy chain molecules naturally devoid of light chain; such VHHs are within the scope of the invention.

The SDAB molecules can be recombinant, CDR-grafted, humanized, camelized, de-immunized and/or in vitro generated (e.g., selected by phage display).

It has also been discovered, that cells having a plurality of chimeric membrane embedded receptors comprising an antigen binding domain that interactions between the antigen binding domain of the receptors can be undesirable, e.g., because it inhibits the ability of one or more of the antigen binding domains to bind its cognate antigen. Accordingly, disclosed herein are cells having a first and a second non-naturally occurring chimeric membrane embedded receptor comprising antigen binding domains that minimize such interactions. Also disclosed herein are nucleic acids encoding a first and a second non-naturally occurring chimeric membrane embedded receptor comprising an antigen binding domains that minimize such interactions, as well as methods of making and using such cells and nucleic acids.

In an embodiment the antigen binding domain of one of the first and the second non-naturally occurring chimeric membrane embedded receptor, comprises an scFv, and the other comprises a single VH domain, e.g., a camelid, shark, or lamprey single VH domain, or a single VH domain derived from a human or mouse sequence.

In some embodiments, the claimed invention comprises a first and second CAR, wherein the antigen binding domain of one of the first and the second CAR does not comprise a variable light domain and a variable heavy domain. In some embodiments, the antigen binding domain of one of the first and the second CAR is an scFv, and the other is not an scFv. In some embodiments, the antigen binding domain of one of the first and the second CAR comprises a single VH domain, e.g., a camelid, shark, or lamprey single VH domain, or a single VH domain derived from a human or mouse sequence. In some embodiments, the antigen binding domain of one of the first and the second CAR comprises a nanobody. In some embodiments, the antigen binding domain of one of the first and the second CAR comprises a camelid VHH domain.

In some embodiments, the antigen binding domain of one of the first and thesecond CAR comprises an scFv, and the other comprises a single VH domain, e.g., a camelid, shark, or lamprey single VH domain, or a single VH domain derived from a human or mouse sequence. In some embodiments, the antigen binding domain of one of the first and the second CAR comprises an scFv, and the other comprises a nanobody. In some embodiments, the antigen binding domain of one of the first and the second CAR comprises comprises an scFv, and the other comprises a camelid VHH domain.

In some embodiments, when present on the surface of a cell, binding of the antigen binding domain of the first CAR to its cognate antigen is not substantially reduced by the presence of the second CAR. In some embodiments, binding of the antigen binding domain of the first CAR to its cognate antigen in the presence of the second CAR is 85%, 90%, 95%, 96%, 97%, 98% or 99% of binding of the antigen binding domain of the first CAR to its cognate antigen in the absence of the second CAR.

In some embodiments, when present on the surface of a cell, the antigen binding domains of the first and the second CAR, associate with one another less than if both were scFv antigen binding domains. In some embodiments, the antigen binding domains of the first and the second CAR, associate with one another 85%, 90%, 95%, 96%, 97%, 98% or 99% less than if both were scFv antigen binding domains.

In another aspect, the CAR-expressing cell described herein can further express another agent, e.g., an agent which enhances the activity or fitness of a CAR-expressing cell. For example, in one embodiment, the agent can be an agent which inhibits a molecule that modulates or regulates, e.g., inhibits, T cell function. In some embodiments, the molecule that modulates or regulates T cell function is an inhibitory molecule. Inhibitory molecules, e.g., PD1, can, in some embodiments, decrease the ability of a CAR-expressing cell to mount an immune effector response. Examples of inhibitory molecules include PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 and TGFR beta. In embodiments, an agent, e.g., an inhibitory nucleic acid, e.g., a dsRNA, e.g., an siRNA or shRNA; or e.g., an inhibitory protein or system, e.g., a clustered regularly interspaced short palindromic repeats (CRISPR), a transcription-activator like effector nuclease (TALEN), or a zinc finger endonuclease (ZFN), e.g., as described herein, can be used to inhibit expression of a molecule that modulates or regulates, e.g., inhibits, T-cell function in the CAR-expressing cell. In an embodiment the agent is an shRNA, e.g., an shRNA described herein. In an embodiment, the agent that modulates or regulates, e.g., inhibits, T-cell function is inhibited within a CAR-expressing cell. For example, a dsRNA molecule that inhibits expression of a molecule that modulates or regulates, e.g., inhibits, T-cell function is linked to the nucleic acid that encodes a component, e.g., all of the components, of the CAR.

In one embodiment, the agent which inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 and TGFR beta T, or a fragment of any of these (e.g., at least a portion of an extracellular domain of any of these), and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of an extracellular domain of PD1), and a second polypeptide of an intracellular signaling domain described herein (e.g., a CD28 signaling domain described herein and/or a CD3 zeta signaling domain described herein). PD1 is an inhibitory member of the CD28 family of receptors that also includes CD28, CTLA-4, ICOS, and BTLA. PD-1 is expressed on activated B cells, T cells and myeloid cells (Agata et al. 1996 Int. Immunol 8:765-75). Two ligands for PD1, PD-L1 and PD-L2 have been shown to downregulate T cell activation upon binding to PD1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094). Immune suppression can be reversed by inhibiting the local interaction of PD1 with PD-L1.

In one embodiment, the agent comprises the extracellular domain (ECD) of an inhibitory molecule, e.g., Programmed Death 1 (PD1), can be fused to a transmembrane domain and intracellular signaling domains such as 41BB and CD3 zeta (also referred to herein as a PD1 CAR). In one embodiment, the PD1 CAR, when used in combinations with a mesothelin CAR described herein, improves the persistence of the T cell. In one embodiment, the CAR is a PD1 CAR comprising the extracellular domain of PD1 indicated as underlined in SEQ ID NO: 24 and a signal sequence at amino acids 1-21 of SEQ ID NO:24. In one embodiment, the PD1 CAR comprises the amino acid sequence of SEQ ID NO:24.

(SEQ ID NO: 24)
Malpvtalllplalllhaarp<u>pqwfldspdrpwnpptfspallvvteqdn</u>

<u>atftcsfsntsesfvlnwyrmspsnqtdklaafpedrsqpgqdcrfrvtq</u>

<u>lpngrdfhmsvvrarrndsqtylcqaislapkaqikeslraelrvterra</u>

-continued evptahpspsprpaggfqtlvttttpaprpptpaptiasqplslrpeacrp aaggavhtrgldfacdiyiwaplagtcgvlllslvitlyckrgrkkllyi fkqpfmrpvqttqeedgcscrfpeeeeggcelrvkfsrsadapaykqgqn qlynelnlgrreeydvldkrrgrdpemggkprrknpqeglynelqkdkma eayseigmkgerrrgkghdglyqglstatkdtydalhmqalppr.

In one embodiment, the PD1 CAR without the N-terminal signal sequence comprises the amino acid sequence provided below (SEQ ID NO:22).

(SEQ ID NO: 22)
pqwfldspdrpwnpptfspallvvteqdnatftcsfsntsesfvlnwyrm spsnqtdklaafpedrsqpgqdcrfrvtqlpngrdfhmsvvrarrndsgt vlcqaislapkaqikeshaelrvterraevptahpspsprpaggfqtlvt ttpaprpptpaptiasqplslrpeacrpaaggavhtrgldfacdiyiwap lagtcgvlllslvitlyckrgrkkllyifkqpfmrpvqttqeedgcscrf peeeeggcelrvkfsrsadapaykqgqnqlynelnlgrreeydvldkrrg rdpemggkprrknpqeglynelqkdkmaeayseigmkgerrrgkghdgly qglstatkdtydalhmqalppr.

In one embodiment, the agent comprises a nucleic acid sequence encoding the PD1 CAR with the N-terminal signal sequence, e.g., the PD1 CAR described herein. In one embodiment, the nucleic acid sequence for the PD1 CAR is shown below, with the PD1 ECD underlined below in SEQ ID NO: 23

(SEQ ID NO: 23)
atggccctccctgtcactgccctgcttctcccctcgcactcctgctcca cgccgctagaccacccggatggtttctggactctccggatcgcccgtgga atccccaaccttctcaccggcactcttggttgtgactgagggcgataat gcgaccttcacgtgctcgttctccaacacctccgaatcattcgtgctgaa ctggtaccgcatgagcccgtcaaaccagaccgacaagctcgccgcgtttc cggaagatcggtcgcaaccgggacaggattgtcggttccgcgtgactcaa ctgccgaatggcagagacttccacatgagcgtggtccgcgctaggcgaaa cgactccgggacctacctgtgcggagccatctcgctggcgcctaaggccc aaatcaaagagagcttgagggccgaactgagagtgaccgagcgcagagct gaggtgccaactgcacatccatcccatcgcctcggcctgcgggcagtt tcagaccctggtcacgaccactccggcgccgcgcccaccgactccggccc caactatcgcgagccagcccctgtcgctgaggccggaagcatgccgcct gccgccggaggtgctgtgcatacccggggattggacttcgcatgcgacat ctacatttgggctcctctcgccggaacttgtggcgtgctccttctgtccc tggtcatcaccctgtactgcaagcgggtcggaaaaagcttctgtacatt ttcaagcagcccttcatgaggcccgtgcaaaccaccccaggaggaggacgg ttgctcctgccggttccccgaagaggaagaaggaggttgcgagctgcgcg tgaagttctcccggagcgccgacgccccgcctataagcagggccagaac cagctgtacaacgaactgaacctgggacggcgggaagagtacgatgtgct -continued ggacaagcggcgcggccgggaccccgaaatgggcgggaagcctagaagaa agaaccctcaggaaggcctgtataacgagctgcagaaggacaagatggcc gaggcctactccgaaattgggatgaagggagagcggcggagggaaaggg gcacgacggcctgtaccaaggactgtccaccgccaccaaggacacatacg atgccctgcacatgcaggcccttcccctcgc.

In another aspect, the present invention provides a population of CAR-expressing cells, e.g., CART cells. In some embodiments, the population of CAR-expressing cells comprises a mixture of cells expressing different CARs. For example, in one embodiment, the population of CART cells can include a first cell expressing a CAR having an anti-CD19 binding domain described herein, and a second cell expressing a CAR having a different anti-CD19 binding domain, e.g., an anti-mesothelin binding domain described herein that differs from the anti-mesothelin binding domain in the CAR expressed by the first cell. As another example, the population of CAR-expressing cells can include a first cell expressing a CAR that includes an anti-mesothelin binding domain, e.g., as described herein, and a second cell expressing a CAR that includes an antigen binding domain to a target other than mesothelin (e.g., a target other than mesothelin on stroma cells, e.g., FAP; a target other than mesothelin on prostate cancer cells, e.g., androgen receptor, OR51E2, PSMA, PSCA, PDGRF-β, TARP, GloboH, MAD-CT-1, or MAD-CT-2; a target other than mesothelin on ovararian cancer cells, e.g., Tn, PRSS21, CD171, Lewis Y, folate receptor α, claudin6, GloboH, or sperm protein 17, e.g., a target other than mesothelin on lung cancer cells, e.g., VEGF, HER3, IGF-1R, EGFR, DLL4, or Trop-2). In one embodiment, the population of CAR-expressing cells includes, e.g., a first cell expressing a CAR that includes a primary intracellular signaling domain, and a second cell expressing a CAR that includes a secondary signaling domain.

In another aspect, the present invention provides a population of cells wherein at least one cell in the population expresses a CAR having an anti-mesothelin binding domain described herein, and a second cell expressing another agent, e.g., an agent which enhances the activity or function of a CAR-expressing cell. For example, in one embodiment, the agent can be an agent which modulates or regulates, e.g., inhibits, T cell function. In some embodiments, the molecule that modulates or regulates T cell function is an inhibitory molecule, e.g., an agent described herein. Inhibitory molecules, e.g., can, in some embodiments, decrease the ability of a CAR-expressing cell to mount an immune effector response. Examples of inhibitory molecules include PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 and TGFR beta. In one embodiment, the agent which inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 and TGFR beta, or a fragment of any of these (e.g., at least a portion of an extracellular domain of any of these), and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of the extracellular domain of PD1), and a second polypeptide of an intracellular signaling domain described herein (e.g., a CD28 signaling domain described herein and/or a CD3 zeta signaling domain described herein).

In one aspect, the present invention provides methods comprising administering a population of CAR-expressing cells, e.g., CART cells, e.g., a mixture of cells expressing different CARS, in combination with another agent, e.g., a kinase inhibitor, such as a kinase inhibitor described herein. In another aspect, the present invention provides methods comprising administering a population of cells wherein at least one cell in the population expresses a CAR having an anti-mesoothelinbinding domain as described herein, and a second cell expressing another agent, e.g., an agent which enhances the activity or fitness of a CAR-expressing cell, in combination with another agent, e.g., a kinase inhibitor, such as a kinase inhibitor described herein.

Regulatable Chimeric Antigen Receptors

In some embodiments, a regulatable CAR (RCAR) where the CAR activity can be controlled is desirable to optimize the safety and efficacy of a CAR therapy. There are many ways CAR activities can be regulated. For example, inducible apoptosis using, e.g., a caspase fused to a dimerization domain (see, e.g., Di et al., N Egnl. J. Med. 2011 Nov. 3; 365(18):1673-1683), can be used as a safety switch in the CAR therapy of the instant invention. In an aspect, a RCAR comprises a set of polypeptides, typically two in the simplest embodiments, in which the components of a standard CAR described herein, e.g., an antigen binding domain and an intracellular signaling domain, are partitioned on separate polypeptides or members. In some embodiments, the set of polypeptides include a dimerization switch that, upon the presence of a dimerization molecule, can couple the polypeptides to one another, e.g., can couple an antigen binding domain to an intracellular signaling domain.

In an aspect, an RCAR comprises two polypeptides or members: 1) an intracellular signaling member comprising an intracellular signaling domain, e.g., a primary intracellular signaling domain described herein, and a first switch domain; 2) an antigen binding member comprising an antigen binding domain, e.g., that targets mesothelin as described herein, and a second switch domain. Optionally, the RCAR comprises a transmembrane domain described herein. In an embodiment, a transmembrane domain can be disposed on the intracellular signaling member, on the antigen binding member, or on both. (Unless otherwise indicated, when members or elements of an RCAR are described herein, the order can be as provided, but other orders are included as well. In other words, in an embodiment, the order is as set out in the text, but in other embodiments, the order can be different. E.g., the order of elements on one side of a transmembrane region can be different from the example, e.g., the placement of a switch domain relative to a intracellular signaling domain can be different, e.g., reversed).

In an embodiment, the first and second switch domains can form an intracellular or an extracellular dimerization switch. In an embodiment, the dimerization switch can be a homodimerization switch, e.g., where the first and second switch domain are the same, or a heterodimerization switch, e.g., where the first and second switch domain are different from one another.

In embodiments, an RCAR can comprise a "multi switch." A multi switch can comprise heterodimerization switch domains or homodimerization switch domains. A multi switch comprises a plurality of, e.g., 2, 3, 4, 5, 6, 7, 8, 9, or 10, switch domains, independently, on a first member, e.g., an antigen binding member, and a second member, e.g., an intracellular signaling member. In an embodiment, the first member can comprise a plurality of first switch domains, e.g., FKBP-based switch domains, and the second member can comprise a plurality of second switch domains, e.g., FRB-based switch domains. In an embodiment, the first member can comprise a first and a second switch domain, e.g., a FKBP-based switch domain and a FRB-based switch domain, and the second member can comprise a first and a second switch domain, e.g., a FKBP-based switch domain and a FRB-based switch domain.

In an embodiment, the intracellular signaling member comprises one or more intracellular signaling domains, e.g., a primary intracellular signaling domain and one or more costimulatory signaling domains.

In an embodiment, the antigen binding member may comprise one or more intracellular signaling domains, e.g., one or more costimulatory signaling domains. In an embodiment, the antigen binding member comprises a plurality, e.g., 2 or 3 costimulatory signaling domains described herein, e.g., selected from 41BB, CD28, CD27, ICOS, and OX40, and in embodiments, no primary intracellular signaling domain. In an embodiment, the antigen binding member comprises the following costimulatory signaling domains, from the extracellular to intracellular direction: 41BB-CD27; 41BB-CD27; CD27-41BB; 41BB-CD28; CD28-41BB; OX40-CD28; CD28-OX40; CD28-41BB; or 41BB-CD28. In such embodiments, the intracellular binding member comprises a CD3zeta domain. In one such embodiment the RCAR comprises (1) an antigen binding member comprising, an antigen binding domain, e.g., described herein, a transmembrane domain, and two costimulatory domains and a first switch domain; and (2) an intracellular signaling domain comprising a transmembrane domain or membrane tethering domain and at least one primary intracellular signaling domain, and a second switch domain.

An embodiment provides RCARs wherein the antigen binding member is not tethered to the surface of the CAR cell. This allows a cell having an intracellular signaling member to be conveniently paired with one or more antigen binding domains, without transforming the cell with a sequence that encodes the antigen binding member. In such embodiments, the RCAR comprises: 1) an intracellular signaling member comprising: a first switch domain, a transmembrane domain, an intracellular signaling domain, e.g., a primary intracellular signaling domain, and a first switch domain; and 2) an antigen binding member comprising: an antigen binding domain, e.g., described herein, and a second switch domain, wherein the antigen binding member does not comprise a transmembrane domain or membrane tethering domain, and, optionally, does not comprise an intracellular signaling domain. In some embodiments, the RCAR may further comprise 3) a second antigen binding member comprising: a second antigen binding domain, e.g., a second antigen binding domain that binds a different antigen than is bound by the antigen binding domain; and a second switch domain.

Also provided herein are RCARs wherein the antigen binding member comprises bispecific activation and targeting capacity. In this embodiment, the antigen binding member can comprise a plurality, e.g., 2, 3, 4, or 5 antigen binding domains, e.g., scFvs, wherein each antigen binding domain binds to a target antigen, e.g. different antigens or the same antigen, e.g., the same or different epitopes on the same antigen. In an embodiment, the plurality of antigen binding domains are in tandem, and optionally, a linker or hinge region is disposed between each of the antigen binding domains. Suitable linkers and hinge regions are described herein.

An embodiment provides RCARs having a configuration that allows switching of proliferation. In this embodiment, the RCAR comprises: 1) an intracellular signaling member comprising: optionally, a transmembrane domain or membrane tethering domain; one or more co-stimulatory signaling domain, e.g., selected from 41BB, CD28, CD27, ICOS, and OX40, and a switch domain; and 2) an antigen binding member comprising: an antigen binding domain, e.g., described herein, a transmembrane domain, and a primary intracellular signaling domain, e.g., a CD3zeta domain, wherein the antigen binding member does not comprise a switch domain, or does not comprise a switch domain that dimerizes with a switch domain on the intracellular signaling member. In an embodiment, the antigen binding member does not comprise a co-stimulatory signaling domain. In an embodiment, the intracellular signaling member comprises a switch domain from a homodimerization switch. In an embodiment, the intracellular signaling member comprises a first switch domain of a heterodimerization switch and the RCAR comprises a second intracellular signaling member which comprises a second switch domain of the heterodimerization switch. In such embodiments, the second intracellular signaling member comprises the same intracellular signaling domains as the intracellular signaling member. In an embodiment, the dimerization switch is intracellular. In an embodiment, the dimerization switch is extracellular.

In any of the RCAR configurations described here, the first and second switch domains comprise a FKBP/FRB-based switch as described herein.

Also provided herein are cells comprising an RCAR described herein. Any cell that is engineered to express a RCAR can be used as a RCARX cell. In an embodiment the RCARX cell is a T cell, and is referred to as a RCART cell. In an embodiment the RCARX cell is an NK cell, and is referred to as a RCARN cell.

Also provided herein are nucleic acids and vectors comprising RCAR encoding sequences. Sequence encoding various elements of an RCAR can be disposed on the same nucleic acid molecule, e.g., the same plasmid or vector, e.g., viral vector, e.g., lentiviral vector. In an embodiment, (i) sequence encoding an antigen binding member and (ii) sequence encoding an intracellular signaling member, can be present on the same nucleic acid, e.g., vector. Production of the corresponding proteins can be achieved, e.g., by the use of separate promoters, or by the use of a bicistronic transcription product (which can result in the production of two proteins by cleavage of a single translation product or by the translation of two separate protein products). In an embodiment, a sequence encoding a cleavable peptide, e.g., a P2A or F2A sequence, is disposed between (i) and (ii). In an embodiment, a sequence encoding an IRES, e.g., an EMCV or EV71 IRES, is disposed between (i) and (ii). In these embodiments, (i) and (ii) are transcribed as a single RNA. In an embodiment, a first promoter is operably linked to (i) and a second promoter is operably linked to (ii), such that (i) and (ii) are transcribed as separate mRNAs.

Alternatively, the sequence encoding various elements of an RCAR can be disposed on the different nucleic acid molecules, e.g., different plasmids or vectors, e.g., viral vector, e.g., lentiviral vector. E.g., the (i) sequence encoding an antigen binding member can be present on a first nucleic acid, e.g., a first vector, and the (ii) sequence encoding an intracellular signaling member can be present on the second nucleic acid, e.g., the second vector.

Dimerization Switches

Dimerization switches can be non-covalent or covalent. In a non-covalent dimerization switch, the dimerization molecule promotes a non-covalent interaction between the switch domains. In a covalent dimerization switch, the dimerization molecule promotes a covalent interaction between the switch domains.

In an embodiment, the RCAR comprises a FKBP/FRAP, or FKBP/FRB,-based dimerization switch. FKBP12 (FKBP, or FK506 binding protein) is an abundant cytoplasmic protein that serves as the initial intracellular target for the natural product immunosuppressive drug, rapamycin. Rapamycin binds to FKBP and to the large PI3K homolog FRAP (RAFT, mTOR). FRB is a 93 amino acid portion of FRAP, that is sufficient for binding the FKBP-rapamycin complex (Chen, J., Zheng, X. F., Brown, E. J. & Schreiber, S. L. (1995) *Identification of an 11-kDa FKBP12-rapamycin-binding domain within the 289-kDa FKBP12-rapamycin-associated protein and characterization of a critical serine residue*. Proc Natl Acad Sci USA 92: 4947-51.)

In embodiments, an FKBP/FRAP, e.g., an FKBP/FRB, based switch can use a dimerization molecule, e.g., rapamycin or a rapamycin analog.

The amino acid sequence of FKBP is as follows:

```
                                         (SEQ ID NO: 382)
D V P D Y A S L G G P S S P K K K R K V S R G V Q

V E T I S P G D G R T F P K R G Q T C V V H Y T G

M L E D G K K F D S S R D R N K P F K F M L G K Q

E V I R G W E E G V A Q M S V G Q R A K L T I S P

D Y A Y G A T G H P G I I P P H A T L V F D V E L

L K L E T S Y
```

In embodiments, an FKBP switch domain can comprise a FRB binding fragment of FKBP, e.g., the underlined portion of SEQ ID NO: 382, which is:

```
                                         (SEQ ID NO: 383)
V Q V E T I S P G D G R T F P K R G Q T C V V H Y

T G M L E D G K K F D S S R D R N K P F K F M L G

K Q E V I R G W E E G V A Q M S V G Q R A K L T I

S P D Y A Y G A T G H P G I I P P H A T L V F D V

E L L K L E T S
```

The amino acid sequence of FRB is as follows:

```
                                         (SEQ ID NO: 384)
ILWHEMWHEG LEEASRLYFG ERNVKGMFEV LEPLHAMMER

GPQTLKETSF NQAYGRDLME AQEWCRKYMK SGNVKDLTQA

WDLYYHVFRR ISK
```

"FKBP/FRAP, e.g., an FKPP/FRB, based switch" as that term is used herein, refers to a dimerization switch comprising: a first switch domain, comprises an FRB binding fragment or an FKBP analog, e.g., RAD001, and has at least 70, 75, 80, 85, 90, 95, 96, 97, 98, or 99% identity with, or differs by no more than 30, 25, 20, 15, 10, 5, 4, 3, 2, or 1 amino acid residues from, the FKBP sequence of SEQ ID NO: 382 or 383; and a second switch domain, which comprises an FKBP binding fragment or an FRB analog, and has at least 70, 75, 80, 85, 90, 95, 96, 97, 98, or 99% identity with, or differs by no more than 30, 25, 20, 15, 10, 5, 4, 3, 2, or 1 amino acid residues from, the FRB sequence of SEQ ID NO: 384. In an embodiment, a RCAR described herein comprises one switch domain comprises amino acid residues disclosed in SEQ ID NO: 382 (or SEQ ID NO:383), and one switch domain comprises amino acid residues disclosed in SEQ ID NO: 384.

In embodiments, the FKBP/FRB dimerization switch comprises a modified FRB switch domain that exhibits altered, e.g., increased, affinity for the dimerization molecule, e.g., rapamycin or a rapalogue, e.g., RAD001. In an embodiment, the modified FRB switch domain comprises one or more mutations, e.g., 2, 3, 4, 5, 6, 7, 8, 9, 10 or more, selected from mutations at amino acid position(s)L2031, E2032, S2035, R2036, F2039, G2040, T2098, W2101, D2102, Y2105, and F2108, where the wild-type amino acid is mutated to any other naturally-occurring amino acid. In an embodiment, a mutant FRB comprises a mutation at E2032, where E2032 is mutated to phenylalanine (E2032F), methionine (E2032M), arginine (E2032R), valine (E2032V), tyrosine (E2032Y), isoleucine (E2032I), e.g., SEQ ID NO: 385, or leucine (E2032L), e.g., SEQ ID NO: 386. In an embodiment, a mutant FRB comprises a mutation at T2098, where T2098 is mutated to phenylalanine (T2098F) or leucine (T2098L), e.g., SEQ ID NO:387. In an embodiment, a mutant FRB comprises a mutation at E2032 and at T2098, where E2032 is mutated to any amino acid, and where T2098 is mutated to any amino acid, e.g., SEQ ID NO: 388. In an embodiment, a mutant FRB comprises an E2032I and a T2098L mutation, e.g., SEQ ID NO: 389. In an embodiment, a mutant FRB comprises an E2032L and a T2098L mutation, e.g., SEQ ID NO: 340.

ance provided herein, such switches and relevant dimerization molecules will be apparent to one of ordinary skill.

Dimerization Molecule

Association between the switch domains is promoted by the dimerization molecule. In the presence of dimerization molecule interaction or association between switch domains allows for signal transduction between a polypeptide associated with, e.g., fused to, a first switch domain, and a polypeptide associated with, e.g., fused to, a second switch domain. In the presence of non-limiting levels of dimerization molecule signal transduction is increased by 1.1, 1.2, 1.3, 1.4, 1.5, 1.6, 1.7, 1.8, 1.9, 2, 5, 10, 50, 100 fold, e.g., as measured in a system described herein.

Rapamycin and rapamycin analogs (sometimes referred to as rapalogues), e.g., RAD001, can be used as dimerization molecules in a FKBP/FRB-based dimerization switch described herein. In an embodiment the dimerization molecule can be selected from rapamycin (sirolimus), RAD001 (everolimus), zotarolimus, temsirolimus, AP-23573 (ridaforolimus), biolimus and AP21967. Additional rapamycin analogs suitable for use with FKBP/FRB-based dimerization switches are further described in the section entitled "Combination Therapies", or in the subsection entitled "Exemplary mTOR inhibitors".

RNA Transfection

Disclosed herein are methods for producing an in vitro transcribed RNA CAR. The present invention also includes a CAR encoding RNA construct that can be directly transfected into a cell. A method for generating mRNA for use in transfection can involve in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-2000 bases in length (SEQ ID NO:35). RNA so produced can efficiently transfect different kinds of cells. In one aspect, the template includes sequences for the CAR.

TABLE 15

Exemplary mutant FRB having increased affinity for a dimerization molecule.

| FRB mutant | Amino Acid Sequence | SEQ ID NO: |
|---|---|---|
| E2032I mutant | ILWHEMWHEGLIEASRLYFGERNVKGMFEVLEPLHAMMERGPQTLKETSFNQAYGR DLMEAQEWCRKYMKSGNVKDLTQAWDLYYHVFRRISKTS | 385 |
| E2032L mutant | ILWHEMWHEGLLEASRLYFGERNVKGMFEVLEPLHAMMERGPQTLKETSFNQAYGR DLMEAQEWCRKYMKSGNVKDLTQAWDLYYHVFRRISKTS | 386 |
| T2098L mutant | ILWHEMWHEGLEEASRLYFGERNVKGMFEVLEPLHAMMERGPQTLKETSFNQAYGR DLMEAQEWCRKYMKSGNVKDLLQAWDLYYHVFRRISKTS | 387 |
| E2032, T2098 mutant | ILWHEMWHEGLXEASRLYFGERNVKGMFEVLEPLHAMMERGPQTLKETSFNQAYGR DLMEAQEWCRKYMKSGNVKDLXQAWDLYYHVFRRISKTS | 388 |
| E2032I, T2098L mutant | ILWHEMWHEGLIEASRLYFGERNVKGMFEVLEPLHAMMERGPQTLKETSFNQAYGR DLMEAQEWCRKYMKSGNVKDLLQAWDLYYHVFRRISKTS | 389 |
| E2032L, T2098L mutant | ILWHEMWHEGLLEASRLYFGERNVKGMFEVLEPLHAMMERGPQTLKETSFNQAYGR DLMEAQEWCRKYMKSGNVKDLLQAWDLYYHVFRRISKTS | 390 |

Other suitable dimerization switches include a GyrB-GyrB based dimerization switch, a Gibberellin-based dimerization switch, a tag/binder dimerization switch, and a halo-tag/snap-tag dimerization switch. Following the guid- In one aspect the mesothelin CAR is encoded by a messenger RNA (mRNA). In one aspect the mRNA encoding the mesothelin CAR is introduced into a T cell for production of a CART cell.

In one embodiment, the in vitro transcribed RNA CAR can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired temple for in vitro transcription is a CAR of the present invention. For example, the template for the RNA CAR comprises an extracellular region comprising a single chain variable domain of an anti-tumor antibody; a hinge region, a transmembrane domain (e.g., a transmembrane domain of CD8a); and a cytoplasmic region that includes an intracellular signaling domain, e.g., comprising the signaling domain of CD3-zeta and the signaling domain of 4-1BB.

In one embodiment, the DNA to be used for PCR contains an open reading frame. The DNA can be from a naturally occurring DNA sequence from the genome of an organism. In one embodiment, the nucleic acid can include some or all of the 5' and/or 3' untranslated regions (UTRs). The nucleic acid can include exons and introns. In one embodiment, the DNA to be used for PCR is a human nucleic acid sequence. In another embodiment, the DNA to be used for PCR is a human nucleic acid sequence including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. The term "substantially complementary" refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a nucleic acid that is normally transcribed in cells (the open reading frame), including 5' and 3' UTRs. The primers can also be designed to amplify a portion of a nucleic acid that encodes a particular domain of interest. In one embodiment, the primers are designed to amplify the coding region of a human cDNA, including all or portions of the 5' and 3' UTRs. Primers useful for PCR can be generated by synthetic methods that are well known in the art. "Forward primers" are primers that contain a region of nucleotides that are substantially complementary to nucleotides on the DNA template that are upstream of the DNA sequence that is to be amplified. The term "upstream" refers to a location 5' to the DNA sequence to be amplified relative to the coding strand. "Reverse primers" are primers that contain a region of nucleotides that are substantially complementary to a double-stranded DNA template that are downstream of the DNA sequence that is to be amplified. The term "downstream" refers to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between one and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the nucleic acid of interest. Alternatively, UTR sequences that are not endogenous to the nucleic acid of interest can be added by incorporating the UTR sequences into the forward and reverse primers or by any other modifications of the template. The use of UTR sequences that are not endogenous to the nucleic acid of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous nucleic acid. Alternatively, when a 5' UTR that is not endogenous to the nucleic acid of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be 5'UTR of an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (SEQ ID NO: 31) (size can be 50-5000 T (SEQ ID NO: 32)), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines (SEQ ID NO: 33).

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides (SEQ ID NO: 34) results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Nucleic Acid Constructs Encoding a CAR

The present invention provides CAR transgenes comprising nucleic acid sequences encoding one or more CAR constructs of the invention. In one aspect, the CAR transgene is provided as a messenger RNA transcript. In one aspect, the CAR transgene is provided as a DNA construct.

Accordingly, in one aspect, the invention pertains to an isolated nucleic acid molecule encoding a chimeric antigen receptor (CAR), wherein the CAR comprises an anti-mesothelin binding domain (e.g., a human anti-mesothelin binding domain), a transmembrane domain, and an intracellular signaling domain comprising a stimulatory domain. In one embodiment, the anti-mesothelin binding domain is an anti-mesothelin binding domain described herein, e.g., an anti-mesothelin binding domain which comprises a sequence selected from a group consisting of SEQ ID NO: 87-111, or a sequence with 95-99% identify thereof. In one embodiment, the isolated nucleic acid molecule further comprises a sequence encoding a costimulatory domain. In one embodiment, the transmembrane domain is a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In one embodiment, the transmembrane domain comprises a sequence of SEQ ID NO: 6, or a sequence with 95-99% identity thereof. In one embodiment, the anti-mesothelin binding domain is connected to the transmembrane domain by a hinge region, e.g., a hinge described herein. In one embodiment, the hinge region comprises SEQ ID NO:2 or SEQ ID NO:3 or SEQ ID NO:4 or SEQ ID NO:5, or a sequence with 95-99% identity thereof. In one embodiment, the isolated nucleic acid molecule further comprises a sequence encoding a costimulatory domain. In one embodiment, the costimulatory domain is a functional signaling domain of a protein selected from the group consisting of OX40, CD27, CD28, CDS, ICAM-1, LFA-1 (CD11a/CD18), ICOS (CD278), and 4-1BB (CD137). Further examples of such costimulatory molecules include CDS, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, and PAG/Cbp. In one embodiment, the costimulatory domain comprises a sequence of SEQ ID NO:7, or a sequence with 95-99% identity thereof. In one embodiment, the intracellular signaling domain comprises a functional signaling domain of 4-1BB and a functional signaling domain of CD3 zeta. In one embodiment, the intracellular signaling domain comprises the sequence of SEQ ID NO: 7 or SEQ ID NO: 8, or a sequence with 95-99% identity thereof, and the sequence of SEQ ID NO: 9 or SEQ ID NO: 10, or a sequence with 95-99% identity thereof, wherein the sequences comprising the intracellular signaling domain are expressed in the same frame and as a single polypeptide chain. In another aspect, the invention pertains to an isolated nucleic acid molecule encoding a CAR construct comprising a leader sequence of SEQ ID NO: 1, a scFv domain having a sequence selected from the group consisting of SEQ ID NO: 39; SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, and SEQ ID NO: 62, (or a sequence with 95-99% identify thereof), a hinge region of SEQ ID NO: 2 or SEQ ID NO:3 or SEQ ID NO:4 or SEQ ID NO:5 (or a sequence with 95-99% identity thereof), a transmembrane domain having a sequence of SEQ ID NO: 6 (or a sequence with 95-99% identity thereof), a 4-1BB costimulatory domain having a sequence of SEQ ID NO:7 (or a sequence with 95-99% identity thereof) or a CD27 costimulatory domain having a sequence of SEQ ID NO: 8 (or a sequence with 95-99% identity thereof), and a CD3 zeta stimulatory domain having a sequence of SEQ ID NO:9 or SEQ ID NO: 10 (or a sequence with 95-99% identity thereof).

In another aspect, the invention pertains to an isolated polypeptide molecule encoded by the nucleic acid molecule. In one embodiment, the isolated polypeptide molecule comprises a sequence selected from the group consisting of SEQ ID NO: 63; SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, and SEQ ID NO: 86, or a sequence with 95-99% identity thereof.

In another aspect, the invention pertains to an isolated nucleic acid molecule encoding a chimeric antigen receptor (CAR) molecule that comprises an anti-mesothelin binding domain, a transmembrane domain, and an intracellular signaling domain comprising a stimulatory domain, and wherein the nucleic acid encoding the anti-mesothelin binding domain comprises a sequence selected from the group consisting of SEQ ID NO: 111; SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO:134, or a sequence with 95-99% identify thereof.

In one embodiment, the encoded CAR molecule further comprises a sequence encoding a costimulatory domain. In one embodiment, the costimulatory domain is a functional signaling domain of a protein selected from the group consisting of OX40, CD27, CD28, CDS, ICAM-1, LFA-1 (CD11a/CD18) and 4-1BB (CD137). In one embodiment, the costimulatory domain comprises a sequence of SEQ ID NO:7. In one embodiment, the transmembrane domain is a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In one embodiment, the transmembrane domain comprises a sequence of SEQ ID NO:6. In one embodiment, the intracellular signaling domain comprises a functional signaling domain of 4-1BB and a functional signaling domain of zeta. In one embodiment, the intracellular signaling domain comprises the sequence of SEQ ID NO: 7 and the sequence of SEQ ID NO: 9, wherein the sequences comprising the intracellular signaling domain are expressed in the same frame and as a single polypeptide chain. In one embodiment, the anti-mesothelin binding domain is connected to the transmembrane domain by a hinge region. In one embodiment, the hinge region comprises SEQ ID NO:2. In one embodiment, the hinge region comprises SEQ ID NO: 3, SEQ ID NO: 4, or SEQ ID NO: 5.

In another aspect, the invention pertains to an isolated CAR molecule comprising a leader sequence of SEQ ID NO: 1, a scFv domain having a sequence selected from the group consisting of SEQ ID NOS: 39-62, or a sequence with 95-99% identify thereof, a hinge region of SEQ ID NO:2 or SEQ ID NO: 3 or SEQ ID NO: 4 or SEQ ID NO: 5, a transmembrane domain having a sequence of SEQ ID NO: 6, a 4-1BB costimulatory domain having a sequence of SEQ ID NO:7 or a CD27 costimulatory domain having a sequence of SEQ ID NO: 8, and a CD3 zeta stimulatory domain having a sequence of SEQ ID NO:9 or SEQ ID NO: 10. In one embodiment, the encoded CAR molecule comprises a sequence selected from the group consisting of SEQ ID NOS: 63-86, or a sequence with 95-99% identify thereof.

The present invention further provides vectors comprising CAR transgenes. In one aspect, a CAR vectors can be directly transduced into a cell, e.g., a T cell or NK cell. In one aspect, the vector is a cloning or expression vector, e.g., a vector including, but not limited to, one or more plasmids (e.g., expression plasmids, cloning vectors, minicircles, minivectors, double minute chromosomes), retroviral and lentiviral vector constructs. In one aspect, the vector is capable of expressing the CAR construct in mammalian T cells or NK cells. In one aspect, the mammalian T cell is a human T cell or a human NK cell.

The present invention also includes a CAR encoding RNA construct that can be directly transfected into a cell, e.g., a T cell or a NK cell. A method for generating mRNA for use in transfection involves in vitro transcription (IVT) of a template with specially designed primers, followed by polyA addition, to produce a construct containing 3' and 5' untranslated sequence ("UTR"), a 5' cap and/or Internal Ribosome Entry Site (IRES), the gene to be expressed, and a polyA tail, typically 50-2000 bases in length. RNA so produced can efficiently transfect different kinds of cells. In one aspect, the template includes sequences for the CAR.

In one aspect the mesothelin CAR transgene is encoded by a messenger RNA (mRNA). In one aspect the mRNA encoding the mesothelin CAR transgene is introduced into a T cell for production of a CART cell, or a NK cell.

Vectors

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In one embodiment, the vector comprising the nucleic acid encoding the desired CAR of the invention is a DNA, a RNA, a plasmid, an adenoviral vector, a lentivirus vector, or a retrovirus vector.

In another embodiment, the vector comprising the nucleic acid encoding the desired CAR of the invention is an adenoviral vector (A5/35). In another embodiment, the expression of nucleic acids encoding CARs can be accomplished using of transposons such as sleeping beauty, CRISPR, CAS9, and zinc finger nucleases. See, e.g., June et al. 2009 *Nature Reviews Immunology* 9.10: 704-716, incorporated herein by reference in its entirety.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription. Exemplary promoters include the CMV IE gene, EF-1α, ubiquitin C, or phosphoglycerokinase (PGK) promoters.

An example of a promoter that is capable of expressing a CAR transgene in a mammalian T cell is the EF1alpha promoter (EF1a or EF1α). The native EF1a promoter drives expression of the alpha subunit of the elongation factor-1 complex, which is responsible for the enzymatic delivery of aminoacyl tRNAs to the ribosome. The EF1a promoter has been extensively used in mammalian expression plasmids and has been shown to be effective in driving CAR expression from transgenes cloned into a lentiviral vector. See, e.g., Milone et al., Mol. Ther. 17(8): 1453-1464 (2009). In one aspect, the EF1a promoter comprises the sequence provided as SEQ ID NO:11.

Another example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HW) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the elongation factor-1α, promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter.

Such promoter regions may be linked to a reporter gene and used to evaluate agents for the ability to modulate promoter-driven transcription.

In one embodiment, the vector can further comprise a nucleic acid encoding a second CAR. In one embodiment, the second CAR includes an antigen binding domain to, e.g., a target other than mesothelin on stroma cells, e.g., FAP; a target other than mesothelin on prostate cancer cells, e.g., androgen receptor, OR51E2, PSMA, PSCA, PDGRF-β, TARP, GloboH, MAD-CT-1, or MAD-CT-2; a target other than mesothelin on ovararian cancer cells, e.g., Tn, PRSS21, CD171, Lewis Y, folate receptor α, claudin6, GloboH, or sperm protein 17; e.g., a target other than mesothelin on lung cancer cells, e.g., VEGF, HER3, IGF-1R, EGFR, DLL4, or Trop-2. In one embodiment, the vector comprises a nucleic acid sequence encoding a first CAR that targets a first antigen and includes an intracellular signaling domain having a costimulatory signaling domain but not a primary signaling domain, and a nucleic acid encoding a second CAR that targets a second, different, antigen and includes an intracellular signaling domain having a primary signaling domain but not a costimulatory signaling domain. In one embodiment, the vector comprises a nucleic acid encoding a first mesothelin CAR that includes a mesothelin binding domain, a transmembrane domain and a costimulatory domain and a nucleic acid encoding a second CAR that targets an antigen other than mesothelin (e.g., a target other than mesothelin on stroma cells, e.g., FAP; a target other than mesothelin on prostate cancer cells, e.g., androgen receptor, OR51E2, PSMA, PSCA, PDGRF-β, TARP, GloboH, MAD-CT-1, or MAD-CT-2; a target other than mesothelin on ovararian cancer cells, e.g., Tn, PRSS21, CD171, Lewis Y, folate receptor α, claudin6, GloboH, or sperm protein 17; e.g., a target other than mesothelin on lung cancer cells, e.g., VEGF, HER3, IGF-1R, EGFR, DLL4, or Trop-2) and includes an antigen binding domain, a transmembrane domain and a primary signaling domain. In another embodiment, the vector comprises a nucleic acid encoding a first mesothelin CAR that includes a mesothelin binding domain, a transmembrane domain and a primary signaling domain and a nucleic acid encoding a second CAR that targets an antigen other than mesothelin (e.g., a target other than mesothelin on stroma cells, e.g., FAP; a target other than mesothelin on prostate cancer cells, e.g., androgen receptor, OR51E2, PSMA, PSCA, PDGRF-β, TARP, GloboH, MAD-CT-1, or MAD-CT-2; a target other than mesothelin on ovararian cancer cells, e.g., Tn, PRSS21, CD171, Lewis Y, folate receptor α, claudin6, GloboH, or sperm protein 17; e.g., a target other than mesothelin on lung cancer cells, e.g., VEGF, HER3, IGF-1R, EGFR, DLL4, or Trop-2) and includes an antigen binding domain to the antigen, a transmembrane domain and a costimulatory signaling domain.

In one embodiment, the vector comprises a nucleic acid encoding a mesothelin CAR described herein and a nucleic acid encoding an inhibitory CAR. In one embodiment, the inhibitory CAR comprises an antigen binding domain that binds an antigen found on normal cells but not cancer cells, e.g., normal cells that also express CLL. In one embodiment, the inhibitory CAR comprises the antigen binding domain, a transmembrane domain and an intracellular domain of an inhibitory molecule. For example, the intracellular domain of the inhibitory CAR can be an intracellular domain of PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 and TGFR beta.

In one embodiment, the vector comprises a nucleic acid encoding a mesothelin CAR described herein and an inhibitory nucleic acid, e.g., a dsRNA, e.g., an siRNA or shRNA, e.g., as described herein.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY). A preferred method for the introduction of a polynucleotide into a host cell is lipofection, e.g., using Lipofectamine (Life Technologies).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

The present invention further provides a vector comprising a CAR encoding nucleic acid molecule. In one aspect, a CAR vector can be directly transduced into a cell, e.g., a T cell or a NK cell. In one aspect, the vector is a cloning or expression vector, e.g., a vector including, but not limited to, one or more plasmids (e.g., expression plasmids, cloning vectors, minicircles, minivectors, double minute chromosomes), retroviral and lentiviral vector constructs. In one aspect, the vector is capable of expressing the CAR construct in mammalian T cells. In one aspect, the mammalian T cell is a human T cell. In one aspect, the mammalian cell is a human NK cell.

Sources of Cells

Prior to expansion and genetic modification, a source of cells (e.g., T cells or NK cells) is obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain aspects of the present invention, any number of T cell lines available in the art, may be used. In certain aspects of the present invention, T cells can be obtained from a unit of blood collected from a subject using any number of techniques known to the skilled artisan, such as Ficoll™ separation. In one preferred aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and to place the cells in an appropriate buffer or media for subsequent processing steps. In one aspect of the invention, the cells are washed with phosphate buffered saline (PBS). In an alternative aspect, the wash solution lacks calcium and may lack magnesium or may lack many if not all divalent cations. Initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In one aspect, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as CD3+, CD28+, CD4+, CD8+, CD45RA+, and CD45RO+T cells, can be further isolated by positive or negative selection techniques. For example, in one aspect, T cells are isolated by incubation with anti-CD3/anti-CD28 (e.g., 3×28)-conjugated beads, such as DYNABEADS® M-450 CD3/CD28 T, for a time period sufficient for positive selection of the desired T cells. In one aspect, the time period is about 30 minutes. In a further aspect, the time period ranges from 30 minutes to 36 hours or longer and all integer values there between. In a further aspect, the time period is at least 1, 2, 3, 4, 5, or 6 hours. In yet another preferred aspect, the time period is 10 to 24 hours. In one aspect, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain aspects, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain aspects, it may be desirable to enrich for or positively select for regulatory T cells which typically express CD4+, CD25+, CD62Lhi, GITR+, and FoxP3+. Alternatively, in certain aspects, T regulatory cells are depleted by anti-C25 conjugated beads or other similar method of selection.

In one embodiment, a T cell population can be selected that expresses one or more of IFN-□, TNFα, IL-17A, IL-2, IL-3, IL-4, GM-CSF, IL-10, IL-13, granzyme B, and perforin, or other appropriate molecules, e.g., other cytokines. Methods for screening for cell expression can be determined, e.g., by the methods described in PCT Publication No.: WO 2013/126712.

In one embodiment, a T cell population is diaglycerol kinase (DGK)-deficient. DGK-deficient cells include cells that do not express DGK RNA or protein, or have reduced or inhibited DGK activity. DGK-deficient cells can be generated by genetic approaches, e.g., administering RNA-interfering agents, e.g., siRNA, shRNA, miRNA, to reduce or prevent DGK expression. Alternatively, DGK-deficient cells can be generated by treatment with DGK inhibitors described herein.

In one embodiment, a T cell population is Ikaros-deficient. Ikaros-deficient cells include cells that do not express Ikaros RNA or protein, or have reduced or inhibited Ikaros activity, Ikaros-deficient cells can be generated by genetic approaches, e.g., administering RNA-interfering agents, e.g., siRNA, shRNA, miRNA, to reduce or prevent Ikaros expression. Alternatively, Ikaros-deficient cells can be generated by treatment with Ikaros inhibitors, e.g., lenalidomide.

In embodiments, a T cell population is DGK-deficient and Ikaros-deficient, e.g., does not express DGK and Ikaros, or has reduced or inhibited DGK and Ikaros activity. Such DGK and Ikaros-deficient cells can be generated by any of the methods described herein.

For isolation of a desired population of cells by positive or negative selection, the concentration of cells and surface (e.g., particles such as beads) can be varied. In certain aspects, it may be desirable to significantly decrease the volume in which beads and cells are mixed together (e.g., increase the concentration of cells), to ensure maximum contact of cells and beads. For example, in one aspect, a concentration of 2 billion cells/ml is used. In one aspect, a concentration of 1 billion cells/ml is used. In a further aspect, greater than 100 million cells/ml is used. In a further aspect, a concentration of cells of 10, 15, 20, 25, 30, 35, 40, 45, or 50 million cells/ml is used. In yet one aspect, a concentration of cells from 75, 80, 85, 90, 95, or 100 million cells/ml is used. In further aspects, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (e.g., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related aspect, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one aspect, the concentration of cells used is $5 \times 10e^6$/ml. In other aspects, the concentration used can be from about $1 \times 10^5$/ml to $1 \times 10^6$/ml, and any integer value in between.

In other aspects, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain aspects, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one aspect a blood sample or an apheresis is taken from a generally healthy subject. In certain aspects, a blood sample or an apheresis is taken from a generally healthy subject who is at risk of developing a disease, but who has not yet developed a disease, and the cells of interest are isolated and frozen for later use. In certain aspects, the T cells may be expanded, frozen, and used at a later time. In certain aspects, samples are collected from a patient shortly after diagnosis of a particular disease as described herein but prior to any treatments. In a further aspect, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further aspect, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In one aspect, the cells are isolated prior to and can be frozen for later use for treatment following B-cell ablative therapy such as agents that react with CD20, e.g., Rituxan.

In a further aspect of the present invention, T cells are obtained from a patient directly following treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the invention to collect blood cells, including T cells, dendritic cells, or other cells of the hematopoietic lineage, during this recovery phase. Further, in certain aspects, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

In an embodiment, the NK cells are obtained from the subject. In another embodiment, the NK cells are an NK cell line, e.g., NK-92 cell line (Conkwest).

Allogeneic CAR

In embodiments described herein, the immune effector cell can be an allogeneic immune effector cell, e.g., T cell or NK cell. For example, the cell can be an allogeneic T cell, e.g., an allogeneic T cell lacking expression of a functional T cell receptor (TCR) and/or human leukocyte antigen (HLA), e.g., HLA class I and/or HLA class II.

A T cell lacking a functional TCR can be, e.g., engineered such that it does not express any functional TCR on its surface, engineered such that it does not express one or more subunits that comprise a functional TCR or engineered such that it produces very little functional TCR on its surface. Alternatively, the T cell can express a substantially impaired TCR, e.g., by expression of mutated or truncated forms of one or more of the subunits of the TCR. The term "substantially impaired TCR" means that this TCR will not elicit an adverse immune reaction in a host.

A T cell described herein can be, e.g., engineered such that it does not express a functional HLA on its surface. For example, a T cell described herein, can be engineered such that cell surface expression HLA, e.g., HLA class 1 and/or HLA class II, is downregulated.

In some embodiments, the T cell can lack a functional TCR and a functional HLA, e.g., HLA class I and/or HLA class II.

Modified T cells that lack expression of a functional TCR and/or HLA can be obtained by any suitable means, including a knock out or knock down of one or more subunit of TCR or HLA. For example, the T cell can include a knock down of TCR and/or HLA using siRNA, shRNA, clustered regularly interspaced short palindromic repeats (CRISPR) transcription-activator like effector nuclease (TALEN), or zinc finger endonuclease (ZFN).

In some embodiments, the allogeneic cell can be a cell which does not expresses or expresses at low levels an inhibitory molecule, e.g. by any method described herein. For example, the cell can be a cell that does not express or expresses at low levels an inhibitory molecule, e.g., that can decrease the ability of a CAR-expressing cell to mount an immune effector response. Examples of inhibitory molecules include PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 and TGFR beta. Inhibition of an inhibitory molecule, e.g., by inhibition at the DNA, RNA or protein level, can optimize a CAR-expressing cell performance. In embodiments, an inhibitory nucleic acid, e.g., an inhibitory nucleic acid, e.g., a dsRNA, e.g., an siRNA or shRNA, a clustered regularly interspaced short palindromic repeats (CRISPR), a transcription-activator like effector nuclease (TALEN), or a zinc finger endonuclease (ZFN), e.g., as described herein, can be used.

siRNA and shRNA to Inhibit TCR or HLA

In some embodiments, TCR expression and/or HLA expression can be inhibited using siRNA or shRNA that targets a nucleic acid encoding a TCR and/or HLA in a T cell.

Expression of siRNA and shRNAs in T cells can be achieved using any conventional expression system, e.g., such as a lentiviral expression system.

Exemplary shRNAs that downregulate expression of components of the TCR are described, e.g., in US Publication No.: 2012/0321667. Exemplary siRNA and shRNA that downregulate expression of HLA class I and/or HLA class II genes are described, e.g., in U.S. publication No.: US 2007/0036773.

CRISPR to Inhibit TCR or HLA

"CRISPR" or "CRISPR to TCR and/or HLA" or "CRISPR to inhibit TCR and/or HLA" as used herein refers to a set of clustered regularly interspaced short palindromic repeats, or a system comprising such a set of repeats. "Cas", as used herein, refers to a CRISPR-associated protein. A "CRISPR/Cas" system refers to a system derived from CRISPR and Cas which can be used to silence or mutate a TCR and/or HLA gene.

Naturally-occurring CRISPR/Cas systems are found in approximately 40% of sequenced eubacteria genomes and 90% of sequenced archaea. Grissa et al. (2007) *BMC Bioinformatics* 8: 172. This system is a type of prokaryotic immune system that confers resistance to foreign genetic elements such as plasmids and phages and provides a form of acquired immunity. Barrangou et al. (2007) *Science* 315: 1709-1712; Marragini et al. (2008) *Science* 322: 1843-1845.

The CRISPR/Cas system has been modified for use in gene editing (silencing, enhancing or changing specific genes) in eukaryotes such as mice or primates. Wiedenheft et al. (2012) *Nature* 482: 331-8. This is accomplished by introducing into the eukaryotic cell a plasmid containing a specifically designed CRISPR and one or more appropriate Cas.

The CRISPR sequence, sometimes called a CRISPR locus, comprises alternating repeats and spacers. In a naturally-occurring CRISPR, the spacers usually comprise sequences foreign to the bacterium such as a plasmid or phage sequence; in the TCR and/or HLA CRISPR/Cas system, the spacers are derived from the TCR or HLA gene sequence.

RNA from the CRISPR locus is constitutively expressed and processed by Cas proteins into small RNAs. These comprise a spacer flanked by a repeat sequence. The RNAs guide other Cas proteins to silence exogenous genetic elements at the RNA or DNA level. Horvath et al. (2010) *Science* 327: 167-170; Makarova et al. (2006) *Biology Direct* 1: 7. The spacers thus serve as templates for RNA molecules, analogously to siRNAs. Pennisi (2013) *Science* 341: 833-836.

As these naturally occur in many different types of bacteria, the exact arrangements of the CRISPR and structure, function and number of Cas genes and their product differ somewhat from species to species. Haft et al. (2005) *PLoS Comput. Biol.* 1: e60; Kunin et al. (2007) *Genome Biol.* 8: R61; Mojica et al. (2005) *J. Mol. Evol.* 60: 174-182; Bolotin et al. (2005) *Microbiol.* 151: 2551-2561; Pourcel et al. (2005) *Microbia* 151: 653-663; and Stern et al. (2010) *Trends. Genet.* 28: 335-340. For example, the Cse (Cas subtype, *E. coli*) proteins (e.g., CasA) form a functional complex, Cascade, that processes CRISPR RNA transcripts into spacer-repeat units that Cascade retains. Brouns et al. (2008) *Science* 321: 960-964. In other prokaryotes, Cas6 processes the CRISPR transcript. The CRISPR-based phage inactivation in *E. coli* requires Cascade and Cas3, but not Cas1 or Cas2. The Cmr (Cas RAMP module) proteins in *Pyrococcus furiosus* and other prokaryotes form a functional complex with small CRISPR RNAs that recognizes and cleaves complementary target RNAs. A simpler CRISPR system relies on the protein Cas9, which is a nuclease with two active cutting sites, one for each strand of the double helix. Combining Cas9 and modified CRISPR locus RNA can be used in a system for gene editing. Pennisi (2013) *Science* 341: 833-836.

The CRISPR/Cas system can thus be used to edit a TCR and/or HLA gene (adding or deleting a basepair), or introducing a premature stop which thus decreases expression of a TCR and/or HLA. The CRISPR/Cas system can alternatively be used like RNA interference, turning off TCR and/or HLA gene in a reversible fashion. In a mammalian cell, for example, the RNA can guide the Cas protein to a TCR and/or HLA promoter, sterically blocking RNA polymerases.

Artificial CRISPR/Cas systems can be generated which inhibit TCR and/or HLA, using technology known in the art, e.g., that described in U.S. Publication No. 20140068797, and Cong (2013) *Science* 339: 819-823. Other artificial CRISPR/Cas systems that are known in the art may also be generated which inhibit TCR and/or HLA, e.g., that described in Tsai (2014) *Nature Biotechnol.*, 32:6 569-576, U.S. Pat. Nos. 8,871,445; 8,865,406; 8,795,965; 8,771,945; and 8,697,359.

TALEN to Inhibit TCR and/or HLA

"TALEN" or "TALEN to HLA and/or TCR" or "TALEN to inhibit HLA and/or TCR" refers to a transcription activator-like effector nuclease, an artificial nuclease which can be used to edit the HLA and/or TCR gene.

TALENs are produced artificially by fusing a TAL effector DNA binding domain to a DNA cleavage domain. Transcription activator-like effects (TALEs) can be engineered to bind any desired DNA sequence, including a portion of the HLA or TCR gene. By combining an engineered TALE with a DNA cleavage domain, a restriction enzyme can be produced which is specific to any desired DNA sequence, including a HLA or TCR sequence. These can then be introduced into a cell, wherein they can be used for genome editing. Boch (2011) *Nature Biotech.* 29: 135-6; and Boch et al. (2009) *Science* 326: 1509-12; Moscou et al. (2009) *Science* 326: 3501.

TALEs are proteins secreted by *Xanthomonas* bacteria. The DNA binding domain contains a repeated, highly conserved 33-34 amino acid sequence, with the exception of the 12th and 13th amino acids. These two positions are highly variable, showing a strong correlation with specific nucleotide recognition. They can thus be engineered to bind to a desired DNA sequence.

To produce a TALEN, a TALE protein is fused to a nuclease (N), which is a wild-type or mutated FokI endonuclease. Several mutations to FokI have been made for its use in TALENs; these, for example, improve cleavage specificity or activity. Cermak et al. (2011) *Nucl. Acids Res.* 39: e82; Miller et al. (2011) *Nature Biotech.* 29: 143-8; Hockemeyer et al. (2011) *Nature Biotech.* 29: 731-734; Wood et al. (2011) *Science* 333: 307; Doyon et al. (2010) *Nature Methods* 8: 74-79; Szczepek et al. (2007) *Nature Biotech.* 25: 786-793; and Guo et al. (2010) *J. Mol. Biol.* 200: 96.

The FokI domain functions as a dimer, requiring two constructs with unique DNA binding domains for sites in the target genome with proper orientation and spacing. Both the number of amino acid residues between the TALE DNA binding domain and the FokI cleavage domain and the number of bases between the two individual TALEN binding sites appear to be important parameters for achieving high levels of activity. Miller et al. (2011) *Nature Biotech.* 29: 143-8.

A HLA or TCR TALEN can be used inside a cell to produce a double-stranded break (DSB). A mutation can be introduced at the break site if the repair mechanisms improperly repair the break via non-homologous end joining. For example, improper repair may introduce a frame shift mutation. Alternatively, foreign DNA can be introduced into the cell along with the TALEN; depending on the sequences of the foreign DNA and chromosomal sequence, this process can be used to correct a defect in the HLA or TCR gene or introduce such a defect into a wt HLA or TCR gene, thus decreasing expression of HLA or TCR.

TALENs specific to sequences in HLA or TCR can be constructed using any method known in the art, including various schemes using modular components. Zhang et al. (2011) *Nature Biotech.* 29: 149-53; Geibler et al. (2011) *PLoS ONE* 6: e19509.

Zinc Finger Nuclease to Inhibit HLA and/or TCR

"ZFN" or "Zinc Finger Nuclease" or "ZFN to HLA and/or TCR" or "ZFN to inhibit HLA and/or TCR" refer to a zinc finger nuclease, an artificial nuclease which can be used to edit the HLA and/or TCR gene.

Like a TALEN, a ZFN comprises a FokI nuclease domain (or derivative thereof) fused to a DNA-binding domain. In the case of a ZFN, the DNA-binding domain comprises one or more zinc fingers. Carroll et al. (2011) *Genetics Society of America* 188: 773-782; and Kim et al. (1996) *Proc. Natl. Acad. Sci. USA* 93: 1156-1160.

A zinc finger is a small protein structural motif stabilized by one or more zinc ions. A zinc finger can comprise, for example, Cys2His2, and can recognize an approximately 3-bp sequence. Various zinc fingers of known specificity can be combined to produce multi-finger polypeptides which recognize about 6, 9, 12, 15 or 18-bp sequences. Various selection and modular assembly techniques are available to generate zinc fingers (and combinations thereof) recognizing specific sequences, including phage display, yeast one-hybrid systems, bacterial one-hybrid and two-hybrid systems, and mammalian cells.

Like a TALEN, a ZFN must dimerize to cleave DNA. Thus, a pair of ZFNs are required to target non-palindromic DNA sites. The two individual ZFNs must bind opposite strands of the DNA with their nucleases properly spaced apart. Bitinaite et al. (1998) *Proc. Natl. Acad. Sci. USA* 95: 10570-5.

Also like a TALEN, a ZFN can create a double-stranded break in the DNA, which can create a frame-shift mutation if improperly repaired, leading to a decrease in the expression and amount of HLA and/or TCR in a cell. ZFNs can also be used with homologous recombination to mutate in the HLA or TCR gene.

ZFNs specific to sequences in HLA AND/OR TCR can be constructed using any method known in the art. See, e.g., Provasi (2011) *Nature Med.* 18: 807-815; Torikai (2013) *Blood* 122: 1341-1349; Cathomen et al. (2008) *Mol. Ther.* 16: 1200-7; and Guo et al. (2010) *J. Mol. Biol.* 400: 96; U.S. Patent Publication 2011/0158957; U.S. Patent Publication 2012/0060230.

Activation and Expansion of Cells

Cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention may be expanded by contact with a surface having attached thereto an agent that stimulates a CD3/TCR complex associated signal and a ligand that stimulates a costimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain aspects, the primary stimulatory signal and the costimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one aspect, the agent providing the costimulatory signal is bound to a cell surface and the agent providing the primary activation signal is in solution or coupled to a surface. In certain aspects, both agents can be in solution. In one aspect, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one aspect, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the costimulatory signal is an anti-CD28 antibody or antigen-binding fragment thereof; and both agents are co-immobilized to the same bead in equivalent molecular amounts. In one aspect, a 1:1 ratio of each antibody bound to the beads for CD4+ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular aspect an increase of from about 1 to about 3 fold is observed as compared to the expansion observed using a ratio of 1:1. In one aspect, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain aspects of the invention, the ratio of anti CD28 antibody to anti CD3 antibody bound to the beads is greater than 2:1. In one particular aspect, a 1:100 CD3:CD28 ratio of antibody bound to beads is used. In one aspect, a 1:75 CD3:CD28 ratio of antibody bound to beads is used. In a further aspect, a 1:50 CD3:CD28 ratio of antibody bound to beads is used. In one aspect, a 1:30 CD3:CD28 ratio of antibody bound to beads is used. In one preferred aspect, a 1:10 CD3:CD28 ratio of antibody bound to beads is used. In one aspect, a 1:3 CD3:CD28 ratio of antibody bound to the beads is used. In yet one aspect, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain aspects the ratio of cells to particles ranges from 1:100 to 100:1 and any integer values in-between and in further aspects the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one aspect, a ratio of particles to cells of 1:1 or less is used. In one particular aspect, a preferred particle: cell ratio is 1:5. In further aspects, the ratio of particles to cells can be varied depending on the day of stimulation. For example, in one aspect, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular aspect, the ratio of particles to cells is 1:1 on the first day of stimulation and adjusted to 1:5 on the third and fifth days of stimulation. In one aspect, particles are added on a daily or every other day basis to a final ratio of 1:1 on the first day, and 1:5 on the third and fifth days of stimulation. In one aspect, the ratio of particles to cells is 2:1 on the first day of stimulation and adjusted to 1:10 on the third and fifth days of stimulation. In one aspect, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type. In one aspect, the most typical ratios for use are in the neighborhood of 1:1, 2:1 and 3:1 on the first day.

In further aspects of the present invention, the cells, such as T cells, are combined with agent-coated beads, the beads and the cells are subsequently separated, and then the cells are cultured. In an alternative aspect, prior to culture, the agent-coated beads and cells are not separated but are cultured together. In a further aspect, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one aspect the cells (for example, $10^4$ to $10^9$ T cells) and beads (for example, DYNABEADS® M-450 CD3/CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain aspects, it may be desirable to significantly decrease the volume in which particles and cells are mixed together (i.e., increase the concentration of cells), to ensure maximum contact of cells and particles. For example, in one aspect, a concentration of about 2 billion cells/ml is used. In one aspect, greater than 100 million cells/ml is used. In a further aspect, a concentration of cells of 10, 15, 20, 25, 30, 35, 40, 45, or 50 million cells/ml is used. In yet one aspect, a concentration of cells from 75, 80, 85, 90, 95, or 100 million cells/ml is used. In further aspects, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain aspects. For example, using high concentration of cells allows more efficient selection of CD8+ T cells that normally have weaker CD28 expression.

In one aspect of the present invention, the mixture may be cultured for several hours (about 3 hours) to about 14 days or any hourly integer value in between. In one aspect, the mixture may be cultured for 21 days. In one aspect of the invention the beads and the T cells are cultured together for about eight days. In one aspect, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPM' 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8+). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Once a mesothelin CAR is constructed, various assays can be used to evaluate the activity of the molecule, such as but not limited to, the ability to expand T cells following antigen stimulation, sustain T cell expansion in the absence of re-stimulation, and anti-cancer activities in appropriate in vitro and animal models. Assays to evaluate the effects of a mesothelin CAR are described in further detail below Western blot analysis of CAR expression in primary T cells can be used to detect the presence of monomers and dimers. See, e.g., Milone et al., Molecular Therapy 17(8): 1453-1464 (2009). Very briefly, T cells (1:1 mixture of CD4+ and CD8+ T cells) expressing the CARs are expanded in vitro for more than 10 days followed by lysis and SDS-PAGE under reducing conditions. CARs containing the full length TCR-ζ cytoplasmic domain and the endogenous TCR-ζ chain are detected by western blotting using an antibody to the TCR-ζ chain. The same T cell subsets are used for SDS-PAGE analysis under non-reducing conditions to permit evaluation of covalent dimer formation.

In vitro expansion of CAR+ T cells following antigen stimulation can be measured by flow cytometry. For example, a mixture of CD4+ and CD8+ T cells are stimulated with αCD3/αCD28 aAPCs followed by transduction with lentiviral vectors expressing GFP under the control of the promoters to be analyzed. Exemplary promoters include the CMV IE gene, EF-1α, ubiquitin C, or phosphoglycerokinase (PGK) promoters. GFP fluorescence is evaluated on day 6 of culture in the CD4+ and/or CD8+ T cell subsets by flow cytometry. See, e.g., Milone et al., Molecular Therapy 17(8): 1453-1464 (2009). Alternatively, a mixture of CD4⁺ and CD8⁺ T cells are stimulated with αCD3/αCD28 coated magnetic beads on day 0, and transduced with CAR on day 1 using a bicistronic lentiviral vector expressing CAR along with eGFP using a 2A ribosomal skipping sequence. Cultures are re-stimulated, e.g., with K562 cells expressing hCD32 and 4-1BBL in the presence of anti-CD3 and anti-CD28 antibody (K562-BBL-3/28) following washing. Exogenous IL-2 is added to the cultures every other day at 100 IU/ml. GFP⁺ T cells are enumerated by flow cytometry using bead-based counting. See, e.g., Milone et al., Molecular Therapy 17(8): 1453-1464 (2009).

Sustained CAR⁺ T cell expansion in the absence of re-stimulation can also be measured. See, e.g., Milone et al., Molecular Therapy 17(8): 1453-1464 (2009). Briefly, mean T cell volume (fl) is measured on day 8 of culture using a Coulter Multisizer III particle counter following stimulation with αCD3/αCD28 coated magnetic beads on day 0, and transduction with the indicated CAR on day 1.

Assessment of cell proliferation and cytokine production has been previously described, e.g., at Milone et al., Molecular Therapy 17(8): 1453-1464 (2009). Briefly, assessment of CAR-mediated proliferation is performed in microtiter plates by mixing washed T cells with target cells, such as K562-Meso, Ovcar3, Ovcar8, SW1990, Panc02.03 cells expressing mesothelin or CD32 and CD137 (KT32-BBL) for a final T-cell:target cell ratio of 1:1. Anti-CD3 (clone OKT3) and anti-CD28 (clone 9.3) monoclonal antibodies are added to cultures with KT32-BBL cells to serve as a positive control for stimulating T-cell proliferation since these signals support long-term CD8⁺ T cell expansion ex vivo. T cells are enumerated in cultures using Count-Bright™ fluorescent beads (Invitrogen, Carlsbad, Calif.) and flow cytometry as described by the manufacturer. CAR⁺ T cells are identified by GFP expression using T cells that are engineered with eGFP-2A linked CAR-expressing lentiviral vectors. For CAR+ T cells not expressing GFP, the CAR+ T cells are detected with biotinylated recombinant mesothelin protein and a secondary avidin-PE conjugate. CD4+ and CD8⁺ expression on T cells are also simultaneously detected with specific monoclonal antibodies (BD Biosciences). Cytokine measurements are performed on supernatants collected 24 hours following re-stimulation using the human TH1/TH2 cytokine cytometric bead array kit (BD Biosciences, San Diego, Calif.) according the manufacturer's instructions. Fluorescence is assessed using a FACScalibur flow cytometer, and data is analyzed according to the manufacturer's instructions.

Cytotoxicity can be assessed by methods described herein, e.g., in the examples, or by a standard 51Cr-release assay. See, e.g., Milone et al., Molecular Therapy 17(8): 1453-1464 (2009). Briefly, target cells (e.g., BHK or CHO cells expressing mesothelin) are loaded with 51Cr (as NaCrO4, New England Nuclear, Boston, Mass.) at 37° C. for 2 hours with frequent agitation, washed twice in complete RPMI and plated into microtiter plates. Effector T cells are mixed with target cells in the wells in complete RPMI at varying ratios of effector cell:target cell (E:T). Additional wells containing media only (spontaneous release, SR) or a 1% solution of triton-X 100 detergent (total release, TR) are also prepared. After 4 hours of incubation at 37° C., supernatant from each well is harvested. Released $^{51}$Cr is then measured using a gamma particle counter (Packard Instrument Co., Waltham, Mass.). Each condition is performed in at least triplicate, and the percentage of lysis is calculated using the formula: % Lysis=(ER−SR)/(TR−SR), where ER represents the average 51Cr released for each experimental condition. Alternative cytotoxicity assays may also be used, such as flow based cytotoxicity assays.

Click beetle red and click beetle green luciferase can be used to simultaneously follow tumor progression and T cell trafficking, as each use the same luciferin substrate but emit light at the opposite ends of the visible light spectrum.

Other assays, including those described in the Example section herein as well as those that are known in the art can also be used to evaluate the mesothelin CAR constructs of the invention.

Therapeutic Application for Mesothelin Expressing Diseases and Disorders

The present invention provides compositions and methods for treating diseases and disorders associated with mesothelin. An example of a disease or disorder associated with mesothelin is mesothelioma.

Malignant mesothelioma is a type of cancer that occurs in the thin layer of cells lining the body's internal organs, known as the mesothelium. There are three recognized types of mesothelioma. Pleural mesothelioma (e.g., malignant pleural mesothelioma, or MPM) is the most common form of the disease, accounting for roughly 70% of cases, and occurs in the lining of the lung known as the pleura. Peritoneal mesothelioma occurs in the lining of the abdominal cavity, known as the peritoneum. Pericardial mesothelioma originates in the pericardium, which lines the heart.

A subject may be at risk to develop mesothelioma if the subject was exposed to asbestos. Exposure to asbestos and the inhalation of asbestos particles can cause mesothelioma. In most cases, mesothelioma symptoms will not appear in a subject exposed to asbestos until many years after the exposure has occurred.

Symptoms of pleural mesothelioma include, e.g., lower back pain or side chest pain, and shortness of breath. Other symptoms include difficulty swallowing, persistent cough, fever, weight loss or fatigue. Additional symptoms that some patients experience are muscle weakness, loss of sensory capability, coughing up blood, facial and arm swelling, and hoarseness. In the early stages of the disease, such as stage 1 mesothelioma, symptoms may be mild. Patients usually report pain in one area of the chest that never seems to go away, weight loss and fever.

Peritoneal mesothelioma originates in the abdomen and as a result, symptoms often include abdominal pain, weight loss, nausea, and vomiting. Fluid buildup may occur in the abdomen as well as a result of the cancer. Peritoneal mesothelioma originates in the abdomen and will frequently spread to other organs in area including the liver, spleen or bowel. Severe abdominal pain is the most common complaint that patients first experience. There may also be a discomfort level with fluid buildup in the abdomen as well. Other symptoms of peritoneal mesothelioma may include difficult bowel movements, nausea and vomiting, fever and swollen feet.

Pericardial mesothelioma is the least common form of mesothelioma. Pericardial mesothelioma, as the name suggests, involves the heart. This rare type of mesothelioma cancer invades the pericardium, the sac that surrounds the heart. As the cancer progresses, the heart is not able to deliver oxygen as efficiently to the body causing further decline in health at an increasingly rapid rate. The symptoms most commonly associated with pericardial mesothelioma mimic those of a heart attack: nausea, pain in the chest and shortness of breath.

Subjects benefiting from treatment according to the invention include subjects with a mesothelioma, or subjects suspected of having mesothelioma, e.g., as evidenced by the presence of one or more of the symptoms described herein and/or exposure to asbestos. In particular embodiments, the mesothelioma is pleural mesothelioma (e.g., malignant pleural mesothelioma). In other aspects, the subject may be treated that has a precancerous condition such as, e.g., pleural plaques, benign mesothelioma or mesothelial hyperplasia.

Another example of a disease or disorder associated with mesothelin is pancreatic cancer. Pancreatic cancers that can be treated with methods described herein include, but are not limited to, exocrine pancreatic cancers and endocrine pancreatic cancers. Exocrine pancreatic cancers include, but are not limited to, adenocarcinomas, acinar cell carcinomas, adenosquamous carcinomas, colloid carcinomas, undifferentiated carcinomas with osteoclast-like giant cells, hepatoid carcinomas, intraductal papillary-mucinous neoplasms, mucinous cystic neoplasms, pancreatoblastomas, serous cystadenomas, signet ring cell carcinomas, solid and pseuodpapillary tumors, pancreatic ductal carcinomas, and undifferentiated carcinomas. In some embodiments, the exocrine pancreatic cancer is pancreatic ductal carcinoma. Endocrine pancreatic cancers include, but are not limited to, insulinomas and glucagonomas.

In some embodiments, the pancreatic cancer is any of early stage pancreatic cancer, non-metastatic pancreatic cancer, primary pancreatic cancer, resected pancreatic cancer, advanced pancreatic cancer, locally advanced pancreatic cancer, metastatic pancreatic cancer, unresectable pancreatic cancer, pancreatic cancer in remission, recurrent pancreatic cancer, pancreatic cancer in an adjuvant setting, or pancreatic cancer in a neoadjuvant setting. In some embodiments, the pancreatic cancer is locally advanced pancreatic cancer, unresectable pancreatic cancer, or metastatic pancreatic ductal carcinoma. In some embodiments, the pancreatic cancer is resistant to the gemcitabine-based therapy. In some embodiments, the pancreatic cancer is refractory to the gemcitabine-based therapy.

In other aspects, the disorder associated with mesothelin expression is ovarian cancer. Ovarian cancer is classified according to the histology of the tumor. Surface epithelial-stromal tumor, also known as ovarian epithelial carcinoma, is the most common type of ovarian cancer. It includes serous tumor (including serous papillary cystadenocarcinoma), endometrioid tumor and mucinous cystadenocarcinoma.

The methods described herein can be used to treat various stages of ovarian cancer, e.g., stage I, stage II, stage III or stage IV. Staging can be performed, e.g., when the ovarian cancer is removed. Ovarian cancer is staged as follows:

Stage I cancer is confined to one or both ovaries. The cancer is stage II if either one or both of the ovaries is involved and has spread to the uterus and/or the fallopian tubes or other sites in the pelvis. The cancer is stage III cancer if one or both of the ovaries is involved and has spread to lymph nodes or other sites outside of the pelvis but is still within the abdominal cavity, such as the surface of the intestine or liver. The cancer is stage IV cancer if one or both ovaries are involved and the cancer has spread outside the abdomen or to the inside of the liver.

In some embodiments, the ovarian cancer is resistant to one or more chemotherapeutic agent. In some embodiments, the ovarian cancer is refractory to the one or more chemotherapeutic agent.

Other cancers that can be treated with the CAR compositions described herein include, e.g., brain cancer, bladder cancer, breast cancer, cervical cancer, colorectal cancer, liver cancer, kidney cancer, lymphoma, leukemia, lung cancer (e.g., lung adenocarcinoma), melanoma, metastatic melanoma, mesothelioma, neuroblastoma, ovarian cancer, prostate cancer, pancreatic cancer, renal cancer, skin cancer, thymoma, sarcoma, non-Hodgkin's lymphoma, Hodgkin's lymphoma, uterine cancer, and any combination thereof.

The present invention provides methods for inhibiting the proliferation or reducing a mesothelin-expressing cell population, the methods comprising contacting a population of cells comprising a mesothelin expressing cell with a mesothelin CAR-expressing cell of the invention that binds to the mesothelin-expressing cell. In a specific embodiment, the invention provides methods for inhibiting the proliferation or reducing the population of cancer cells expressing mesothelin, the methods comprising contacting the mesothelin-expressing cancer cell population with a mesothelin CAR-expressing cell of the invention that binds to the mesothelin-expressing cell. In another embodiment, the invention provides methods for inhibiting the proliferation or reducing the population of cancer cells expressing mesothelin, the methods comprising contacting the mesothelin-expressing cancer cell population with a mesothelin CAR-expressing cell of the invention that binds to the mesothelin-expressing cell. In certain embodiments, the mesothelin CAR-expressing cell of the invention reduces the quantity, number, amount or percentage of cells and/or cancer cells by at least 25%, at least 30%, at least 40%, at least 50%, at least 65%, at least 75%, at least 85%, at least 95%, or at least 99% in a subject with or animal model of mesothelioma or another cancer associated with mesothelin-expressing cells relative to a negative control. In one aspect, the subject is a human.

The invention also provides methods for preventing, treating and/or managing a disorder associated with mesothelin-expressing cells (e.g., mesothelioma), the methods comprising administering to a subject in need a mesothelioma CAR-expressing cell of the invention that binds to the mesothelin-expressing cell. In one aspect, the subject is a human.

The invention provides methods for preventing relapse of cancer associated with mesothelin-expressing cells, the methods comprising administering to a subject in need thereof a mesothelin CAR-expressing cell of the invention that binds to the mesothelin-expressing cell. In another embodiment, the methods comprise administering to the subject in need thereof an effective amount of a mesothelin CAR-expressing cell of the invention that binds to the mesothelin-expressing cell in combination with an effective amount of another therapy.

In one aspect, the invention pertains to a vector comprising a sequence encoding a mesothelin CAR operably linked to promoter for expression in mammalian immune effector cells. In one aspect, the invention provides a recombinant immune effector cell expressing the mesothelin CAR for use in treating mesothelin-expressing tumors. In one aspect, the mesothelin CAR-expressing cell of the invention is capable of contacting a tumor cell with at least one mesothelin CAR of the invention expressed on its surface such that the mesothelin CAR-expressing cell is activated in response to the antigen and the CAR-expressing cell targets the cancer cell and growth of the cancer is inhibited.

In one aspect, the invention pertains to a method of inhibiting growth of a mesothelin-expressing cancer cell, comprising contacting the tumor cell with a-mesothelin CAR-expressing cell such that the CAR-expressing cell is activated in response to the antigen and targets the cancer cell, wherein the growth of the cancer is inhibited. In one aspect, the activated CART targets and kills the cancer cell.

In one aspect, the invention pertains to a method of treating cancer in a subject. The method comprises administering to the subject a mesothelin CAR-expressing cell such that the cancer is treated in the subject. An example of a cancer that is treatable by the mesothelin CAR-expressing cell of the invention is a cancer associated with expression of mesothelin. In one aspect, the cancer associated with expression of mesothelin is selected from mesothelioma, pancreatic cancer, ovarian cancer and lung cancer.

The invention includes a type of cellular therapy where immune effector cells, e.g., T cells or NK cells, are genetically modified to express a chimeric antigen receptor (CAR) and the CAR-expressing cell is infused to a recipient in need thereof. The infused cell is able to kill tumor cells in the recipient. Unlike antibody therapies, CAR-modified immune effector cells are able to replicate in vivo resulting in long-term persistence that can lead to sustained tumor control. In various aspects, the cells administered to the patient, or their progeny, persist in the patient for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the cell to the patient.

The invention also includes a type of cellular therapy where immune effector cells are modified, e.g., by in vitro transcribed RNA, to transiently express a chimeric antigen receptor (CAR) and the CAR-expressing cell is infused to a recipient in need thereof. The infused cell is able to kill cancer cells in the recipient. Thus, in various aspects, the cells administered to the patient, is present for less than one month, e.g., three weeks, two weeks, one week, after administration of the cell to the patient.

Without wishing to be bound by any particular theory, the anti-cancer immunity response elicited by the CAR-modified immune effector cells may be an active or a passive immune response, or alternatively may be due to a direct vs indirect immune response. In one aspect, the CAR transduced T cells exhibit specific proinflammatory cytokine secretion and potent cytolytic activity in response to human cancer cells expressing mesothelin, and mediate bystander killing and mediate regression of an established human tumor. For example, antigen-less tumor cells within a heterogeneous field of mesothelin-expressing tumor may be susceptible to indirect destruction by mesothelin-redirected T cells that has previously reacted against adjacent antigen-positive cancer cells.

In one aspect, the fully-human scFv bearing CAR-modified immune effector cells of the invention may be a type of vaccine for ex vivo immunization and/or in vivo therapy in a mammal. In one aspect, the mammal is a human.

With respect to ex vivo immunization, at least one of the following occurs in vitro prior to administering the cell into a mammal: i) expansion of the cells, ii) introducing a nucleic acid encoding a CAR to the cells or iii) cryopreservation of the cells.

Ex vivo procedures are well known in the art and are discussed more fully below. Briefly, cells are isolated from a mammal (e.g., a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified immune effector cells of the invention are used in the treatment of diseases, disorders and conditions associated with expression of mesothelin. In certain aspects, the cells of the invention are used in the treatment of patients at risk for developing diseases, disorders and conditions associated with expression of mesothelin. Thus, the invention provides methods for the treatment or prevention of diseases, disorders and conditions associated with expression of mesothelin comprising administering to a subject in need thereof, a therapeutically effective amount of the CAR-modified T cells of the invention.

The CAR-modified T cells of the present invention may be administered either alone, or as a pharmaceutical composition in combination with diluents and/or with other components such as IL-2 or other cytokines or cell populations.

The present invention also provides methods for inhibiting the proliferation or reducing a mesothelin-expressing cell population, the methods comprising contacting a population of cells comprising a mesothelin-expressing cell with a mesothelin CAR-expressing cell (, e.g., a mesothelin CART also referred to as "CART-MSLN") of the invention that binds to the mesothelin-expressing cell. In a specific aspect, the invention provides methods for inhibiting the proliferation or reducing the population of cancer cells expressing mesothelin, the methods comprising contacting the mesothelin-expressing cancer cell population with a mesothelin CAR-expressing cell of the invention that binds to the mesothelin-expressing cell. In one aspect, the present invention provides methods for inhibiting the proliferation or reducing the population of cancer cells expressing mesothelin, the methods comprising contacting the mesothelin-expressing cancer cell population with a mesothelin CAR-expressing cell of the invention that binds to the mesothelin-expressing cell. In certain aspects, the mesothelin CAR-expressing cell of the invention reduces the quantity, number, amount or percentage of cells and/or cancer cells by at least 25%, at least 30%, at least 40%, at least 50%, at least 65%, at least 75%, at least 85%, at least 95%, or at least 99% in a subject with or animal model for mesothelioma or another cancer associated with mesothelin-expressing cells relative to a negative control. In one aspect, the subject is a human.

The present invention also provides methods for preventing, treating and/or managing a disease associated with mesothelin-expressing cells (e.g., mesothelioma), the methods comprising administering to a subject in need a mesothelin CAR-expressing cell of the invention that binds to the mesothelin-expressing cell. In one aspect, the subject is a human.

The present invention provides methods for preventing relapse of cancer associated with mesothelin-expressing cells, the methods comprising administering to a subject in need thereof a mesothelin CAR-expressing cell of the invention that binds to the mesothelin-expressing cell. In one aspect, the methods comprise administering to the subject in need thereof an effective amount of a mesothelin CAR-expressing cell of the invention that binds to the mesothelin-expressing cell in combination with an effective amount of another therapy.

Combination Therapies

A CAR-expressing cell described herein may be used in combination with other known agents and therapies. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

A CAR-expressing cell described herein and the at least one additional therapeutic agent can be administered simultaneously, in the same or in separate compositions, or sequentially. For sequential administration, the CAR-expressing cell described herein can be administered first, and the additional agent can be administered second, or the order of administration can be reversed.

In further aspects, a CAR-expressing cell described herein may be used in a treatment regimen in combination with surgery, chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, cyclosporin, FK506, rapamycin, mycophenolic acid, steroids, FR901228, cytokines, and irradiation. peptide vaccine, such as that described in Izumoto et al. 2008 J Neurosurg 108:963-971.

In one embodiment, a CAR-expressing cell described herein can be used in combination with a chemotherapeutic agent. Exemplary chemotherapeutic agents include an anthracycline (e.g., doxorubicin (e.g., liposomal doxorubicin)). a vinca alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzamab, gemtuzumab, rituximab, tositumomab), an antimetabolite (including, e.g., folic acid antagonists, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide).

General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, IESPA and TSPA, Thioplex®); Cyclophosphamide (Endoxan®, Cytoxan®, Neosar®, Procytox®, Revimmune®); and Bendamustine HCl (Treanda®).

Exemplary mTOR inhibitors include, e.g., temsirolimus; ridaforolimus (formally known as deferolimus, (1R,2R,4S)-4-[(2R)-2 [(1R,9S,12S,15R,16E,18R,19R,21R, 23S,24E, 26E,28Z,30S,32S,35R)-1,18-dihydroxy-19,30-dimethoxy-15,17,21,23, 29,35-hexamethyl-2,3,10,14,20-pentaoxo-11,36-dioxa-4-azatricyclo[30.3.1.04,9] hexatriaconta-16,24,26, 28-tetraen-12-yl]propyl]-2-methoxycyclohexyl dimethylphosphinate, also known as AP23573 and MK8669, and described in PCT Publication No. WO 03/064383); everolimus (Afinitor® or RAD001); rapamycin (AY22989, Sirolimus®); simapimod (CAS 164301-51-3; emsirolimus, (5-{2,4-Bis[(3S)-3-methylmorpholin-4-yl] pyrido [2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d] pyrimidin-7(8H)-one (PF04691502, CAS 1013101-36-4); and N2-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine- (SEQ ID NO: 402), inner salt (SF1126, CAS 936487-67-1), and XL765.

Exemplary immunomodulators include, e.g., afutuzumab (available from Roche®); pegfilgrastim (Neulasta®); lenalidomide (CC-5013, Revlimid®); thalidomide (Thalomid®), actimid (CC4047); and IRX-2 (mixture of human cytokines including interleukin 1, interleukin 2, and interferon γ, CAS 951209-71-5, available from IRX Therapeutics).

Exemplary anthracyclines include, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary vinca alkaloids include, e.g., vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®).

Exemplary proteosome inhibitors include bortezomib (Velcade®); carfilzomib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912).

In one embodiment, a CAR expressing cell described herein is administered to a subject in combination with a molecule targeting GITR and/or modulating GITR functions, such as a GITR agonist and/or a GITR antibody that depletes regulatory T cells (Tregs). In one embodiment, the GITR binding molecules and/or molecules modulating GITR functions (e.g., GITR agonist and/or Treg depleting GITR antibodies) are administered prior to the CAR-expressing cell. For example, in one embodiment, the GITR agonist can be administered prior to apheresis of the cells. Exemplary GITR agonists include, e.g., GITR fusion proteins and anti-GITR antibodies (e.g., bivalent anti-GITR antibodies) such as, e.g., a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In one embodiment, a CAR expressing cell described herein is administered to a subject in combination with an mTOR inhibitor, e.g., an mTOR inhibitor described herein, e.g., a rapalog such as everolimus. In one embodiment, the mTOR inhibitor is administered prior to the CAR-expressing cell. For example, in one embodiment, the mTOR inhibitor can be administered prior to apheresis of the cells.

In one embodiment, a CAR expressing cell described herein is administered to a subject in combination with a GITR agonist, e.g., a GITR agonist described herein. In one embodiment, the GITR agonist is administered prior to the CAR-expressing cell. For example, in one embodiment, the GITR agonist can be administered prior to apheresis of the cells.

In one embodiment, a CAR expressing cell described herein is administered to a subject in combination with a protein tyrosine phosphatase inhibitor, e.g., a protein tyrosine phosphatase inhibitor described herein. In one embodiment, the protein tyrosine phosphatase inhibitor is an SHP-1 inhibitor, e.g., an SHP-1 inhibitor described herein, such as, e.g., sodium stibogluconate. In one embodiment, the protein tyrosine phosphatase inhibitor is an SHP-2 inhibitor, e.g., an SHP-2 inhibitor described herein.

In one embodiment, a CAR-expressing cell described herein can be used in combination with a kinase inhibitor. In one embodiment, the kinase inhibitor is a CDK4 inhibitor, e.g., a CDK4 inhibitor described herein, e.g., a CDK4/6 inhibitor, such as, e.g., 6-Acetyl-8-cyclopentyl-5-methyl-2-(5-piperazin-1-yl-pyridin-2-ylamino)-8H-pyrido[2,3-d]pyrimidin-7-one, hydrochloride (also referred to as palbociclib or PD0332991). In one embodiment, the kinase inhibitor is a BTK inhibitor, e.g., a BTK inhibitor described herein, such as, e.g., ibrutinib. In one embodiment, the kinase inhibitor is an mTOR inhibitor, e.g., an mTOR inhibitor described herein, such as, e.g., rapamycin, a rapamycin analog, OSI-027. The mTOR inhibitor can be, e.g., an mTORC1 inhibitor and/or an mTORC2 inhibitor, e.g., an mTORC1 inhibitor and/or mTORC2 inhibitor described herein. In one embodiment, the kinase inhibitor is a MNK inhibitor, e.g., a MNK inhibitor described herein, such as, e.g., 4-amino-5-(4-fluoroanilino)-pyrazolo [3,4-d] pyrimidine. The MNK inhibitor can be, e.g., a MNK1a, MNK1b, MNK2a and/or MNK2b inhibitor. In one embodiment, the kinase inhibitor is a dual PI3K/mTOR inhibitor described herein, such as, e.g., PF-04695102. In one embodiment, the kinase inhibitor is a DGK inhibitor, e.g., a DGK inhibitor described herein, such as, e.g., DGKinh1 (D5919) or DGKinh2 (D5794).

In one embodiment, the kinase inhibitor is a CDK4 inhibitor selected from aloisine A; flavopiridol or HMR-1275, 2-(2-chlorophenyl)-5,7-dihydroxy-8-[(3S,4R)-3-hydroxy-1-methyl-4-piperidinyl]-4-chromenone; crizotinib (PF-02341066; 2-(2-Chlorophenyl)-5,7-dihydroxy-8-[(2R, 3S)-2-(hydroxymethyl)-1-methyl-3-pyrrolidinyl]-4H-1-benzopyran-4-one, hydrochloride (P276-00); 1-methyl-5-[[2-[5-(trifluoromethyl)-1H-imidazol-2-yl]-4-pyridinyl]oxy]-N-[4-(trifluoromethyl)phenyl]-1H-benzimidazol-2-amine (RAF265); indisulam (E7070); roscovitine (CYC202); palbociclib (PD0332991); dinaciclib (SCH727965); N-[5-[[(5-tert-butyloxazol-2-yl)methyl]thio]thiazol-2-yl]piperidine-4-carboxamide (BMS 387032); 4-[[9-chloro-7-(2,6-difluorophenyl)-5H-pyrimido[5,4-d][2]benzazepin-2-yl]amino]-benzoic acid (MLN8054); 5-[3-(4, 6-difluoro-1H-benzimidazol-2-yl)-1H-indazol-5-yl]-N-ethyl-4-methyl-3-pyridinemethanamine (AG-024322); 4-(2, 6-dichlorobenzoylamino)-1H-pyrazole-3-carboxylic acid N-(piperidin-4-yl)amide (AT7519); 4-[2-methyl-1-(1-methylethyl)-1H-imidazol-5-yl]-N-[4-(methylsulfonyl)phenyl]-2-pyrimidinamine (AZD5438); and XL281 (BMS908662).

In one embodiment, the kinase inhibitor is a CDK4 inhibitor, e.g., palbociclib (PD0332991), and the palbociclib is administered at a dose of about 50 mg, 60 mg, 70 mg, 75 mg, 80 mg, 90 mg, 100 mg, 105 mg, 110 mg, 115 mg, 120 mg, 125 mg, 130 mg, 135 mg (e.g., 75 mg, 100 mg or 125 mg) daily for a period of time, e.g., daily for 14-21 days of a 28 day cycle, or daily for 7-12 days of a 21 day cycle. In one embodiment, 1, 2, 3, 4, 5, 6, 7, 8, 9, 10, 11, 12 or more cycles of palbociclib are administered.

In one embodiment, the kinase inhibitor is a BTK inhibitor selected from ibrutinib (PCI-32765); GDC-0834; RN-486; CGI-560; CGI-1764; HM-71224; CC-292; ONO-4059; CNX-774; and LFM-A13. In a preferred embodiment, the BTK inhibitor does not reduce or inhibit the kinase activity of interleukin-2-inducible kinase (ITK), and is selected from GDC-0834; RN-486; CGI-560; CGI-1764; HM-71224; CC-292; ONO-4059; CNX-774; and LFM-A13.

In one embodiment, the kinase inhibitor is a BTK inhibitor, e.g., ibrutinib (PCI-32765), and the ibrutinib is administered at a dose of about 250 mg, 300 mg, 350 mg, 400 mg, 420 mg, 440 mg, 460 mg, 480 mg, 500 mg, 520 mg, 540 mg, 560 mg, 580 mg, 600 mg (e.g., 250 mg, 420 mg or 560 mg) daily for a period of time, e.g., daily for 21 day cycle cycle, or daily for 28 day cycle. In one embodiment, 1, 2, 3, 4, 5, 6, 7, 8, 9, 10, 11, 12 or more cycles of ibrutinib are administered.

In one embodiment, the kinase inhibitor is an mTOR inhibitor selected from temsirolimus; ridaforolimus (1R,2R, 4S)-4-[(2R)-2 [(1R,9S,12S,15R,16E,18R,19R,21R, 23S, 24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0$^{4,9}$] hexatriaconta-16,24,26,28-tetraen-12-yl]propyl]-2-methoxycyclohexyl dimethylphosphinate, also known as AP23573 and MK8669; everolimus (RAD001); rapamycin (AY22989); simapimod; (5-{2,4-bis[(3S)-3-methylmorpholin-4-yl]pyrido[2,3-d]pyrimidin-7-yl}-2-methoxyphenyl) methanol (AZD8055); 2-amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502); and N$^2$-[1,4-dioxo-4-[[4-(4-oxo-8-phenyl-4H-1-benzopyran-2-yl) morpholinium-4-yl]methoxy]butyl]-L-arginylglycyl-L-α-aspartylL-serine- (SEQ ID NO: 272), inner salt (SF1126); and XL765.

In one embodiment, the kinase inhibitor is an mTOR inhibitor, e.g., rapamycin, and the rapamycin is administered at a dose of about 3 mg, 4 mg, 5 mg, 6 mg, 7 mg, 8 mg, 9 mg, 10 mg (e.g., 6 mg) daily for a period of time, e.g., daily for 21 day cycle cycle, or daily for 28 day cycle. In one embodiment, 1, 2, 3, 4, 5, 6, 7, 8, 9, 10, 11, 12 or more cycles of rapamycin are administered. In one embodiment, the kinase inhibitor is an mTOR inhibitor, e.g., everolimus and the everolimus is administered at a dose of about 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg (e.g., 10 mg) daily for a period of time, e.g., daily for 28 day cycle. In one embodiment, 1, 2, 3, 4, 5, 6, 7, 8, 9, 10, 11, 12 or more cycles of everolimus are administered.

In one embodiment, the kinase inhibitor is an MNK inhibitor selected from CGP052088; 4-amino-3-(p-fluorophenylamino)-pyrazolo [3,4-d] pyrimidine (CGP57380); cercosporamide; ETC-1780445-2; and 4-amino-5-(4-fluoroanilino)-pyrazolo [3,4-d] pyrimidine.

In one embodiment, the kinase inhibitor is a dual phosphatidylinositol 3-kinase (PI3K) and mTOR inhibitor selected from 2-Amino-8-[trans-4-(2-hydroxyethoxy)cyclohexyl]-6-(6-methoxy-3-pyridinyl)-4-methyl-pyrido[2,3-d] pyrimidin-7(8H)-one (PF-04691502); N-[4-[[4-(Dimethylamino)-1-piperidinyl]carbonyl]phenyl]-N'-[4-(4,6-di-4-morpholinyl-1,3,5-triazin-2-yl)phenyl]urea (PF-05212384, PKI-587); 2-Methyl-2-{4-[3-methyl-2-oxo-8-(quinolin-3-yl)-2,3-dihydro-1H-imidazo[4,5-c]quinolin-1-yl] phenyl}propanenitrile (BEZ-235); apitolisib (GDC-0980, RG7422); 2,4-Difluoro-N-{2-(methyloxy)-5-[4-(4-pyridazinyl)-6-quinolinyl]-3-pyridinyl}benzenesulfonamide (GSK2126458); 8-(6-methoxypyridin-3-yl)-3-methyl-1-(4-(piperazin-1-yl)-3-(trifluoromethyl)phenyl)-1H-imidazo[4, 5-c]quinolin-2(3H)-one Maleic acid (NVP-BGT226); 3-[4-(4-Morpholinylpyrido[3',2':4,5]furo[3,2-d]pyrimidin-2-yl] phenol (PI-103); 5-(9-isopropyl-8-methyl-2-morpholino-9H-purin-6-yl)pyrimidin-2-amine (VS-5584, SB2343); and N-[2-[(3,5-Dimethoxyphenyl)amino]quinoxalin-3-yl]-4-[(4-methyl-3-methoxyphenyl)carbonyl]aminophenylsulfonamide (XL765).

Drugs that inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993) can also be used. In a further aspect, the cell compositions of the present invention may be administered to a patient in conjunction with (e.g., before, simultaneously or following) bone marrow transplantation, T cell ablative therapy using chemotherapy agents such as, fludarabine, external-beam radiation therapy (XRT), cyclophosphamide, and/or antibodies such as OKT3 or CAMPATH. In one aspect, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

In one embodiment, the subject can be administered an agent which reduces or ameliorates a side effect associated with the administration of a CAR-expressing cell. Side effects associated with the administration of a CAR-expressing cell include, but are not limited to CRS, and hemophagocytic lymphohistiocytosis (HLH), also termed Macrophage Activation Syndrome (MAS). Symptoms of CRS include high fevers, nausea, transient hypotension, hypoxia, and the like. CRS may include clinical constitutional signs and symptoms such as fever, fatigue, anorexia, myalgias, arthalgias, nausea, vomiting, and headache. CRS may include clinical skin signs and symptoms such as rash. CRS may include clinical gastrointestinal signs and symsptoms such as nausea, vomiting and diarrhea. CRS may include clinical respiratory signs and symptoms such as tachypnea and hypoxemia. CRS may include clinical cardiovascular signs and symptoms such as tachycardia, widened pulse pressure, hypotension, increased cardac output (early) and potentially diminished cardiac output (late). CRS may include clinical coagulation signs and symptoms such as elevated d-dimer, hypofibrinogenemia with or without bleeding. CRS may include clinical renal signs and symptoms such as azotemia. CRS may include clinical hepatic signs and symptoms such as transaminitis and hyperbilirubinemia. CRS may include clinical neurologic signs and symptoms such as headache, mental status changes, confusion, delirium, word finding difficulty or frank aphasia, hallucinations, tremor, dymetria, altered gait, and seizures.

Accordingly, the methods described herein can comprise administering a CAR-expressing cell described herein to a subject and further administering one or more agents to manage elevated levels of a soluble factor resulting from treatment with a CAR-expressing cell. In one embodiment, the soluble factor elevated in the subject is one or more of IFN-γ, TNFα, IL-2 and IL-6. In an embodiment, the factor elevated in the subject is one or more of IL-1, GM-CSF, IL-10, IL-8, IL-5 and fraktalkine. Therefore, an agent administered to treat this side effect can be an agent that neutralizes one or more of these soluble factors. In one embodiment, the agent that neutralizes one or more of these soluble forms is an antibody or antigen binding fragment thereof. Examples of such agents include, but are not limited to a steroid (e.g., corticosteroid), an inhibitor of TNFα, and an inhibitor of IL-6. An example of a TNFα inhibitor is an anti-TNFα antibody molecule such as, infliximab, adalimumab, certolizumab pegol, and golimumab. Another example of a TNFα inhibitor is a fusion protein such as entanercept. Small molecule inhibitor of TNFα include, but are not limited to, xanthine derivatives (e.g. pentoxifylline) and bupropion. An example of an IL-6 inhibitor is an anti-IL-6 antibody molecule or an anti-IL-6 receptor antibody molecule such as tocilizumab (toc), sarilumab, elsilimomab, CNTO 328, ALD518/BMS-945429, CNTO 136, CPSI-2364, CDP6038, VX30, ARGX-109, FE301, and FM101. In one embodiment, the anti-IL-6 antibody molecule is tocilizumab. An example of an IL-1R based inhibitor is anakinra.

In some embodiment, the subject is administered a corticosteroid, such as, e.g., methylprednisolone, hydrocortisone, among others.

In some embodiments, the subject is administered a vasopressor, such as, e.g., norepinephrine, dopamine, phenylephrine, epinephrine, vasopressin, or a combination thereof.

In an embodiment, the subject can be administered an antipyretic agent. In an embodiment, the subject can be administered an analgesic agent.

In one embodiment, the subject can be administered an agent which enhances the activity or fitness of a CAR-expressing cell. For example, in one embodiment, the agent can be an agent which inhibits a molecule that modulates or regulates, e.g., inhibits, T cell function. In some embodiments, the molecule that modulates or regulates T cell function is an inhibitory molecule. Inhibitory molecules, e.g., Programmed Death 1 (PD1), can, in some embodiments, decrease the ability of a CAR-expressing cell to mount an immune effector response. Examples of inhibitory molecules include PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 and TGFR beta. Inhibition of a molecule that modulates or regulates, e.g., inhibits, T cell function, e.g., by inhibition at the DNA, RNA or protein level, can optimize a CAR-expressing cell performance. In embodiments, an agent, e.g., an inhibitory nucleic acid, e.g., a dsRNA, e.g., an siRNA or shRNA; or e.g., an inhibitory protein or system, e.g., a clustered regularly interspaced short palindromic repeats (CRISPR), a transcription-activator like effector nuclease (TALEN), or a zinc finger endonuclease (ZFN), e.g., as described herein, can be used to inhibit expression of a molecule that modulates or regulates, e.g., inhibits, T-cell function in the CAR-expressing cell. In an embodiment the agent is an shRNA. In an embodiment, the agent that modulates or regulates, e.g., inhibits, T-cell function is inhibited within a CAR-expressing cell. In these embodiments, a dsRNA molecule that inhibits expression of a molecule that modulates or regulates, e.g., inhibits, T-cell function is linked to the nucleic acid that encodes a component, e.g., all of the components, of the CAR. In an embodiment, a nucleic acid molecule that encodes a dsRNA molecule that inhibits expression of the molecule that modulates or regulates, e.g., inhibits, T-cell function is operably linked to a promoter, e.g., a H1- or a U6-derived promoter such that the dsRNA molecule that inhibits expression of the molecule that modulates or regulates, e.g., inhibits, T-cell function is expressed, e.g., is expressed within a CAR-expressing cell. See e.g., Tiscornia G., "Development of Lentiviral Vectors Expressing siRNA," Chapter 3, in *Gene Transfer: Delivery and Expression of DNA and RNA* (eds. Friedmann and Rossi). Cold Spring Harbor Laboratory Press, Cold Spring Harbor, N.Y., USA, 2007; Brummelkamp T R, et al. (2002) *Science* 296: 550-553; Miyagishi M, et al. (2002) *Nat. Biotechnol.* 19: 497-500. In an embodiment the nucleic acid molecule that encodes a dsRNA molecule that inhibits expression of the molecule that modulates or regulates, e.g., inhibits, T-cell function is present on the same vector, e.g., a lentiviral vector, that comprises a nucleic acid molecule that encodes a component, e.g., all of the components, of the CAR. In such an embodiment, the nucleic acid molecule that encodes a dsRNA molecule that inhibits expression of the molecule that modulates or regulates, e.g., inhibits, T-cell function is located on the vector, e.g., the lentiviral vector, 5'- or 3'- to the nucleic acid that encodes a component, e.g., all of the components, of the CAR. The nucleic acid molecule that encodes a dsRNA molecule that inhibits expression of the molecule that modulates or regulates, e.g., inhibits, T-cell function can be transcribed in the same or different direction as the nucleic acid that encodes a component, e.g., all of the components, of the CAR. In an embodiment the nucleic acid molecule that encodes a dsRNA molecule that inhibits expression of the molecule that modulates or regulates, e.g., inhibits, T-cell function is present on a vector other than the vector that comprises a nucleic acid molecule that encodes a component, e.g., all of the components, of the CAR. In an embodiment, the nucleic acid molecule that encodes a dsRNA molecule that inhibits expression of the molecule that modulates or regulates, e.g., inhibits, T-cell function it transiently expressed within a CAR-expressing cell. In an embodiment, the nucleic acid molecule that encodes a dsRNA molecule that inhibits expression of the molecule that modulates or regulates, e.g., inhibits, T-cell function is stably integrated into the genome of a CAR-expressing cell. FIG. 47 depicts examples of vectors for expressing a component, e.g., all of the components, of the CAR with a dsRNA molecule that inhibits expression of the molecule that modulates or regulates, e.g., inhibits, T-cell function.

Examples of dsRNA molecules useful for inhibiting expression of a molecule that modulates or regulates, e.g., inhibits, T-cell function, wherein the molecule that modulates or regulates, e.g., inhibits, T-cell function is PD-1 are provided below.

Provided in Table 16 below are the names of PDCD1 (PD1) RNAi agents (derived from their position in the mouse PDCD1 gene sequence NM_008798.2), along with the SEQ ID NOs: 280-327 representing the DNA sequence. Both sense (S) and antisense (AS) sequences are presented as 19mer and 21mer sequences are in this table. Also note that the position (PoS, e.g., 176) is derived from the position number in the mouse PDCD1 gene sequence NM_008798.2. SEQ ID NOs are indicated in groups of 12 that correspond with "sense 19" SEQ ID NOs: 280-291; "sense 21" SEQ ID NOs: 292-303; "asense 21" SEQ ID NOs: 304-315; "asense 19" SEQ ID NOs: 316-327.

TABLE 16

Mouse PDCD1 (PD1) shRNA sequences

| Position on NM_008798.2 | Target region | Sense19 | Sense21 | Asense21 | Asense19 |
|---|---|---|---|---|---|
| 176 | CDS | GGAGGTCCCTCACCTTCTA (SEQ ID NO: 280) | CTGGAGGTCCCTCACCTTCTA (SEQ ID NO: 292) | TAGAAGGTGAGGGACCTCCAG (SEQ ID NO: 304) | TAGAAGGTGAGGGACCTCC (SEQ ID NO: 316) |
| 260 | CDS | CGGAGGATCTTATGCTGAA (SEQ ID NO: 281) | GTCGGAGGATCTTATGCTGAA (SEQ ID NO: 293) | TTCAGCATAAGATCCTCCGAC (SEQ ID NO: 305) | TTCAGCATAAGATCCTCCG (SEQ ID NO: 317) |
| 359 | CDS | CCCGCTTCCAGATCATACA (SEQ ID NO: 282) | TGCCCGCTTCCAGATCATACA (SEQ ID NO: 294) | TGTATGATCTGGAAGCGGGCA (SEQ ID NO: 306) | TGTATGATCTGGAAGCGGG (SEQ ID NO: 318) |
| 528 | CDS | GGAGACCTCAACAAGATAT (SEQ ID NO: 283) | CTGGAGACCTCAACAAGATAT (SEQ ID NO: 295) | ATATCTTGTTGAGGTCTCCAG (SEQ ID NO: 307) | ATATCTTGTTGAGGTCTCC (SEQ ID NO: 319) |
| 581 | CDS | AAGGCATGGTCATTGGTAT (SEQ ID NO: 284) | TCAAGGCATGGTCATTGGTAT (SEQ ID NO: 296) | ATACCAATGACCATGCCTTGA (SEQ ID NO: 308) | ATACCAATGACCATGCCTT (SEQ ID NO: 320) |
| 584 | CDS | GCATGGTCATTGGTATCAT (SEQ ID NO: 285) | AGGCATGGTCATTGGTATCAT (SEQ ID NO: 297) | ATGATACCAATGACCATGCCT (SEQ ID NO: 309) | ATGATACCAATGACCATGC (SEQ ID NO: 321) |
| 588 | CDS | GGTCATTGGTATCATGAGT (SEQ ID NO: 286) | ATGGTCATTGGTATCATGAGT (SEQ ID NO: 298) | ATGGTCATTGGTATCATGAGT (SEQ ID NO: 310) | ATGGTCATTGGTATCATGA (SEQ ID NO: 322) |
| 609 | CDS | CCTAGTGGGTATCCCTGTA (SEQ ID NO: 287) | GCCCTAGTGGGTATCCCTGTA (SEQ ID NO: 299) | GCCCTAGTGGGTATCCCTGTA (SEQ ID NO: 311) | GCCCTAGTGGGTATCCCTG (SEQ ID NO: 323) |
| 919 | CDS | GAGGATGGACATTGTTCTT (SEQ ID NO: 288) | ATGAGGATGGACATTGTTCTT (SEQ ID NO: 300) | ATGAGGATGGACATTGTTCTT (SEQ ID NO: 312) | ATGAGGATGGACATTGTTC (SEQ ID NO: 324) |
| 1021 | 3'UTR | GCATGCAGGCTACAGTTCA (SEQ ID NO: 289) | GAGCATGCAGGCTACAGTTCA (SEQ ID NO: 301) | GAGCATGCAGGCTACAGTTCA (SEQ ID NO: 313) | GAGCATGCAGGCTACAGTT (SEQ ID NO: 325) |
| 1097 | 3'UTR | CCAGCACATGCACTGTTGA (SEQ ID NO: 290) | TTCCAGCACATGCACTGTTGA (SEQ ID NO: 302) | TTCCAGCACATGCACTGTTGA (SEQ ID NO: 314) | TTCCAGCACATGCACTGTT (SEQ ID NO: 326) |

TABLE 16-continued

Mouse PDCD1 (PD1) shRNA sequences

| Position on NM_008798.2 | Target region | Sense19 | Sense21 | Asense21 | Asense19 |
|---|---|---|---|---|---|
| 1101 | 3'UTR | CACATGCACTG TTGAGTGA (SEQ ID NO: 291) | AGCACATGCAC TGTTGAGTGA (SEQ ID NO: 303) | AGCACATGCAC TGTTGAGTGA (SEQ ID NO: 315) | AGCACATGCAC TGTTGAGT (SEQ ID NO: 327) |

Provided in Table 17 below are the names of PDCD1 (PD1) RNAi agents (derived from their position in the human PDCD1 gene sequence, along with the SEQ ID NOs. 323-370 representing the DNA sequence. Both sense (S) and antisense (AS) sequences are presented as 19mer and 21mer sequences. SEQ ID NOs are indicated in groups of 12 that correspond with "sense 19" SEQ ID NOs: 328-339; "sense 21" SEQ ID NOs: 340-351; "asense 21" SEQ ID NOs: 352-363; "asense 19" SEQ ID NOs: 364-375.

TABLE 17

Human PDCD1 (PD1) shRNA sequences

| Position on NM_005018.2 | Target region | Sense19 | Asense19 | Sense21 | Asense21 |
|---|---|---|---|---|---|
| 145 | CDS | GGCCAGGATG GTTCTTAGA (SEQ ID NO: 328) | TCTAAGAACCA TCCTGGCC (SEQ ID NO: 340) | GCGGCCAGGA TGGTTCTTAGA (SEQ ID NO: 352) | TCTAAGAACCA TCCTGGCCGC (SEQ ID NO: 364) |
| 271 | CDS | GCTTCGTGCTA AACTGGTA (SEQ ID NO: 329) | TACCAGTTTAG CACGAAGC (SEQ ID NO: 341) | GAGCTTCGTGC TAAACTGGTA (SEQ ID NO: 353) | TACCAGTTTAG CACGAAGCTC (SEQ ID NO: 365) |
| 393 | CDS | GGGCGTGACTT CCACATGA (SEQ ID NO: 330) | TCATGTGGAAG TCACGCCC (SEQ ID NO: 342) | ACGGGCGTGA CTTCCACATGA (SEQ ID NO: 354) | TCATGTGGAAG TCACGCCCGT (SEQ ID NO: 366) |
| 1497 | 3'UTR | CAGGCCTAGAG AAGTTTCA (SEQ ID NO: 331) | TGAAACTTCTC TAGGCCTG (SEQ ID NO: 343) | TGCAGGCCTAG AGAAGTTTCA (SEQ ID NO: 355) | TGAAACTTCTC TAGGCCTGCA (SEQ ID NO: 367) |
| 1863 | 3'UTR | CTTGGAACCCA TTCCTGAA (SEQ ID NO: 332) | TTCAGGAATGG GTTCCAAG (SEQ ID NO: 344) | TCCTTGGAACC CATTCCTGAA (SEQ ID NO: 356) | TTCAGGAATGG GTTCCAAGGA (SEQ ID NO: 368) |
| 1866 | 3'UTR | GGAACCCATTC CTGAAATT (SEQ ID NO: 333) | AATTTCAGGAA TGGGTTCC (SEQ ID NO: 345) | TTGGAACCCAT TCCTGAAATT (SEQ ID NO: 357) | AATTTCAGGAA TGGGTTCCAA (SEQ ID NO: 369) |
| 1867 | 3'UTR | GAACCCATTCC TGAAATTA (SEQ ID NO: 334) | TAATTTCAGGA ATGGGTTC (SEQ ID NO: 346) | TGGAACCCATT CCTGAAATTA (SEQ ID NO: 358) | TAATTTCAGGA ATGGGTTCCA (SEQ ID NO: 370) |
| 1868 | 3'UTR | AACCCATTCCT GAAATTAT (SEQ ID NO: 335) | ATAATTTCAGG AAATTGGGTT (SEQ ID NO: 347) | GGAACCCATTC CTGAAATTAT (SEQ ID NO: 359) | ATAATTTCAGG AATGGGTTCC (SEQ ID NO: 371) |
| 1869 | 3'UTR | ACCCATTCCTG AAATTATT (SEQ ID NO: 336) | AATAATTTCAG GAATGGGT (SEQ ID NO: 348) | GAACCCATTCC TGAAATTATT (SEQ ID NO: 360) | AATAATTTCAG GAATGGGTTC (SEQ ID NO: 372) |
| 1870 | 3'UTR | CCCATTCCTGA AATTATTT (SEQ ID NO: 337) | AAATAATTTCA GGAATGGG (SEQ ID NO: 349) | AACCCATTCCT GAAATTATTT (SEQ ID NO: 361) | AAATAATTTCA GGAATGGGTT (SEQ ID NO: 373) |

TABLE 17-continued

Human PDCD1 (PD1) shRNA sequences

| Position on NM_005018.2 | Target region | Sense19 | Asense19 | Sense21 | Asense21 |
|---|---|---|---|---|---|
| 2079 | 3'UTR | CTGTGGTTCTA TTATATTA (SEQ ID NO: 338) | TAATATAATAGA ACCACAG (SEQ ID NO: 350) | CCCTGTGGTTC TATTATATTA (SEQ ID NO: 362) | TAATATAATAGA ACCACAGGG (SEQ ID NO: 374) |
| 2109 | 3'UTR | AAATATGAGAG CATGCTAA (SEQ ID NO: 339) | TTAGCATGCTC TCATATTT (SEQ ID NO: 351) | TTAAATATGAG AGCATGCTAA (SEQ ID NO: 363) | TTAGCATGCTC TCATATTTAA (SEQ ID NO: 375) |

In one embodiment, the inhibitor of an inhibitory signal can be, e.g., an antibody or antibody fragment that binds to an inhibitory molecule. For example, the agent can be an antibody or antibody fragment that binds to PD1, PD-L1, PD-L2 or CTLA4 (e.g., ipilimumab (also referred to as MDX-010 and MDX-101, and marketed as Yervoy®; Bristol-Myers Squibb; Tremelimumab (IgG2 monoclonal antibody available from Pfizer, formerly known as ticilimumab, CP-675,206).). In an embodiment, the agent is an antibody or antibody fragment that binds to TIM3. In an embodiment, the agent is an antibody or antibody fragment that binds to LAG3.

PD-1 is an inhibitory member of the CD28 family of receptors that also includes CD28, CTLA-4, ICOS, and BTLA. PD-1 is expressed on activated B cells, T cells and myeloid cells (Agata et al. 1996 Int. Immunol 8:765-75). Two ligands for PD-1, PD-L1 and PD-L2 have been shown to downregulate T cell activation upon binding to PD-1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094). Immune suppression can be reversed by inhibiting the local interaction of PD-1 with PD-L1. Antibodies, antibody fragments, and other inhibitors of PD-1, PD-L1 and PD-L2 are available in the art and may be used combination with a CAR of the present invention described herein. For example, nivolumab (also referred to as BMS-936558 or MDX1106; Bristol-Myers Squibb) is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449 and WO2006/121168. Pidilizumab (CT-011; Cure Tech) is a humanized IgG1k monoclonal antibody that binds to PD-1. Pidilizumab and other humanized anti-PD-1 monoclonal antibodies are disclosed in WO2009/101611. Pembrolizumab (formerly known as lambrolizumab, and also referred to as MK03475; Merck) is a humanized IgG4 monoclonal antibody that binds to PD-1. Pembrolizumab and other humanized anti-PD-1 antibodies are disclosed in U.S. Pat. No. 8,354,509 and WO2009/114335. MEDI4736 (Medimmune) is a human monoclonal antibody that binds to PDL1, and inhibits interaction of the ligand with PD1. MDPL3280A (Genentech/Roche) is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906. Other anti-PD-L1 binding agents include YW243.55.570 (heavy and light chain variable regions are shown in SEQ ID NOs 20 and 21 in WO2010/077634) and MDX-1 105 (also referred to as BMS-936559, and, e.g., anti-PD-L1 binding agents disclosed in WO2007/005874). AMP-224 (B7-DCIg; Amplimmune; e.g., disclosed in WO2010/027827 and WO2011/066342), is a PD-L2 Fc fusion soluble receptor that blocks the interaction between PD-1 and B7-H1. Other anti-PD-1 antibodies include AMP 514 (Amplimmune), among others, e.g., anti-PD-1 antibodies disclosed in U.S. Pat. No. 8,609,089, US 2010028330, and/or US 20120114649.

TIM3 (T cell immunoglobulin-3) also negatively regulates T cell function, particularly in IFN-g-secreting CD4+ T helper 1 and CD8+ T cytotoxic 1 cells, and plays a critical role in T cell exhaustion. Inhibition of the interaction between TIM3 and its ligands, e.g., galectin-9 (Ga19), phosphotidylserine (PS), and HMGB1, can increase immune response. Antibodies, antibody fragments, and other inhibitors of TIM3 and its ligands are available in the art and may be used combination with a CD19 CAR described herein. For example, antibodies, antibody fragments, small molecules, or peptide inhibitors that target TIM3 binds to the IgV domain of TIM3 to inhibit interaction with its ligands. Antibodies and peptides that inhibit TIM3 are disclosed in WO2013/006490 and US20100247521. Other anti-TIM3 antibodies include humanized versions of RMT3-23 (disclosed in Ngiow et al., 2011, Cancer Res, 71:3540-3551), and clone 8B.2C12 (disclosed in Monney et al., 2002, Nature, 415:536-541). Bi-specific antibodies that inhibit TIM3 and PD-1 are disclosed in US20130156774.

In other embodiments, the agent which enhances the activity of a CAR-expressing cell is a CEACAM inhibitor (e.g., CEACAM-1, CEACAM-3, and/or CEACAM-5 inhibitor). In one embodiment, the inhibitor of CEACAM is an anti-CEACAM antibody molecule. Exemplary anti-CEACAM-1 antibodies are described in WO 2010/125571, WO 2013/082366 WO 2014/059251 and WO 2014/022332, e.g., a monoclonal antibody 34B1, 26H7, and 5F4; or a recombinant form thereof, as described in, e.g., US 2004/0047858, U.S. Pat. No. 7,132,255 and WO 99/052552. In other embodiments, the anti-CEACAM antibody binds to CEACAM-5 as described in, e.g., Zheng et al. *PLoS One.* 2010 Sep. 2; 5(9). pii: e12529 (DOI:10:1371/journal.pone.0021146), or crossreacts with CEACAM-1 and CEACAM-5 as described in, e.g., WO 2013/054331 and US 2014/0271618.

Without wishing to be bound by theory, carcinoembryonic antigen cell adhesion molecules (CEACAM), such as CEACAM-1 and CEACAM-5, are believed to mediate, at least in part, inhibition of an anti-tumor immune response (see e.g., Markel et al. *J Immunol.* 2002 Mar. 15; 168(6): 2803-10; Markel et al. *J Immunol.* 2006 Nov. 1; 177(9): 6062-71; Markel et al. *Immunology.* 2009 February; 126(2): 186-200; Markel et al. *Cancer Immunol Immunother.* 2010 February; 59(2):215-30; Ortenberg et al. *Mol Cancer Ther.* 2012 June; 11(6):1300-10; Stern et al. *J Immunol.* 2005 Jun. 1; 174(11):6692-701; Zheng et al. *PLoS One.* 2010 Sep. 2; 5(9). pii: e12529). For example, CEACAM-1 has been described as a heterophilic ligand for TIM-3 and as playing a role in TIM-3-mediated T cell tolerance and exhaustion (see e.g., WO 2014/022332; Huang, et al. (2014) *Nature* doi:10.1038/nature13848). In embodiments, co-blockade of CEACAM-1 and TIM-3 has been shown to enhance an anti-tumor immune response in xenograft colorectal cancer models (see e.g., WO 2014/022332; Huang, et al. (2014), supra). In other embodiments, co-blockade of CEACAM-1 and PD-1 reduce T cell tolerance as described, e.g., in WO 2014/059251. Thus, CEACAM inhibitors can be used with the other immunomodulators described herein (e.g., anti-PD-1 and/or anti-TIM-3 inhibitors) to enhance an immune response against a cancer, e.g., a melanoma, a lung cancer (e.g., NSCLC), a bladder cancer, a colon cancer an ovarian cancer, and other cancers as described herein LAG3 (lymphocyte activation gene-3 or CD223) is a cell surface molecule expressed on activated T cells and B cells that has been shown to play a role in CD8+ T cell exhaustion. Antibodies, antibody fragments, and other inhibitors of LAG3 and its ligands are available in the art and may be used combination with a CD19 CAR described herein. For example, BMS-986016 (Bristol-Myers Squib) is a monoclonal antibody that targets LAG3. IMP701 (Immutep) is an antagonist LAG3 antibody and IMP731 (Immutep and GlaxoSmithKline) is a depleting LAG3 antibody. Other LAG3 inhibitors include IMP321 (Immutep), which is a recombinant fusion protein of a soluble portion of LAG3 and Ig that binds to MEC class II molecules and activates antigen presenting cells (APC). Other antibodies are disclosed, e.g., in WO2010/019570.

In some embodiments, the agent which enhances the activity of a CAR-expressing cell can be, e.g., a fusion protein comprising a first domain and a second domain, wherein the first domain is an inhibitory molecule, or fragment thereof, and the second domain is a polypeptide that is associated with a positive signal, e.g., a polypeptide comrpsing an antracellular signaling domain as described herein. In some embodiments, the polypeptide that is associated with a positive signal can include a costimulatory domain of CD28, CD27, ICOS, e.g., an intracellular signaling domain of CD28, CD27 and/or ICOS, and/or a primary signaling domain, e.g., of CD3 zeta, e.g., described herein. In one embodiment, the fusion protein is expressed by the same cell that expressed the CAR. In another embodiment, the fusion protein is expressed by a cell, e.g., a T cell that does not express a mesothelin CAR.

In one embodiment, the agent which enhances activity of a CAR-expressing cell described herein is miR-17-92.

Combination with a Low Dose of an mTOR Inhibitor

In one embodiment, the cells expressing a CAR molecule, e.g., a CAR molecule described herein, are administered in combination with a low, immune enhancing dose of an mTOR inhibitor.

In an embodiment, a dose of an mTOR inhibitor is associated with, or provides, mTOR inhibition of at least 5 but no more than 90%, at least 10 but no more than 90%, at least 15, but no more than 90%, at least 20 but no more than 90%, at least 30 but no more than 90%, at least 40 but no more than 90%, at least 50 but no more than 90%, at least 60 but no more than 90%, or at least 70 but no more than 90%.

In an embodiment, a dose of an mTOR inhibitor is associated with, or provides, mTOR inhibition of at least 5 but no more than 80%, at least 10 but no more than 80%, at least 15, but no more than 80%, at least 20 but no more than 80%, at least 30 but no more than 80%, at least 40 but no more than 80%, at least 50 but no more than 80%, or at least 60 but no more than 80%.

In an embodiment, a dose of an mTOR inhibitor is associated with, or provides, mTOR inhibition of at least 5 but no more than 70%, at least 10 but no more than 70%, at least 15, but no more than 70%, at least 20 but no more than 70%, at least 30 but no more than 70%, at least 40 but no more than 70%, or at least 50 but no more than 70%.

In an embodiment, a dose of an mTOR inhibitor is associated with, or provides, mTOR inhibition of at least 5 but no more than 60%, at least 10 but no more than 60%, at least 15, but no more than 60%, at least 20 but no more than 60%, at least 30 but no more than 60%, or at least 40 but no more than 60%.

In an embodiment, a dose of an mTOR inhibitor is associated with, or provides, mTOR inhibition of at least 5 but no more than 50%, at least 10 but no more than 50%, at least 15, but no more than 50%, at least 20 but no more than 50%, at least 30 but no more than 50%, or at least 40 but no more than 50%.

In an embodiment, a dose of an mTOR inhibitor is associated with, or provides, mTOR inhibition of at least 5 but no more than 40%, at least 10 but no more than 40%, at least 15, but no more than 40%, at least 20 but no more than 40%, at least 30 but no more than 40%, or at least 35 but no more than 40%.

In an embodiment, a dose of an mTOR inhibitor is associated with, or provides, mTOR inhibition of at least 5 but no more than 30%, at least 10 but no more than 30%, at least 15, but no more than 30%, at least 20 but no more than 30%, or at least 25 but no more than 30%.

In an embodiment, a dose of an mTOR inhibitor is associated with, or provides, mTOR inhibition of at least 1, 2, 3, 4 or 5 but no more than 20%, at least 1, 2, 3, 4 or 5 but no more than 30%, at least 1, 2, 3, 4 or 5, but no more than 35, at least 1, 2, 3, 4 or 5 but no more than 40%, or at least 1, 2, 3, 4 or 5 but no more than 45%.

In an embodiment, a dose of an mTOR inhibitor is associated with, or provides, mTOR inhibition of at least 1, 2, 3, 4 or 5 but no more than 90%.

As is discussed herein, the extent of mTOR inhibition can be expressed as the extent of P70 S6 inhibition, e.g., the extent of mTOR inhibition can be determined by the level of decrease in P70 S6 activity, e.g., by the decrease in phosphorylation of a P70 S6 substrate. The level of mTOR inhibition can be evaluated by a method described herein, e.g. by the Boulay assay.

Exemplary mTOR Inhibitors

As used herein, the term "mTOR inhibitor" refers to a compound or ligand, or a pharmaceutically acceptable salt thereof, which inhibits the mTOR kinase in a cell. In an embodiment an mTOR inhibitor is an allosteric inhibitor. In an embodiment an mTOR inhibitor is a catalytic inhibitor.

Allosteric mTOR inhibitors include the neutral tricyclic compound rapamycin (sirolimus), rapamycin-related compounds, that is compounds having structural and functional similarity to rapamycin including, e.g., rapamycin derivatives, rapamycin analogs (also referred to as rapalogs) and other macrolide compounds that inhibit mTOR activity.

Rapamycin is a known macrolide antibiotic produced by *Streptomyces hygroscopicus* having the structure shown in Formula A.

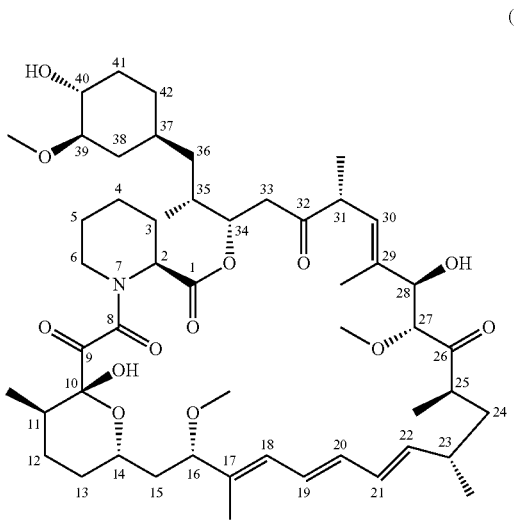

(A)

See, e.g., McAlpine, J. B., et al., J. Antibiotics (1991) 44: 688; Schreiber, S. L., et al., J. Am. Chem. Soc. (1991) 113: 7433; U.S. Pat. No. 3,929,992. There are various numbering schemes proposed for rapamycin. To avoid confusion, when specific rapamycin analogs are named herein, the names are given with reference to rapamycin using the numbering scheme of formula A.

Rapamycin analogs useful in the invention are, for example, O-substituted analogs in which the hydroxyl group on the cyclohexyl ring of rapamycin is replaced by $OR_1$ in which $R_1$ is hydroxyalkyl, hydroxyalkoxyalkyl, acylaminoalkyl, or aminoalkyl; e.g. RAD001, also known as, everolimus as described in U.S. Pat. No. 5,665,772 and WO94/09010 the contents of which are incorporated by reference. Other suitable rapamycin analogs include those substituted at the 26- or 28-position. The rapamycin analog may be an epimer of an analog mentioned above, particularly an epimer of an analog substituted in position 40, 28 or 26, and may optionally be further hydrogenated, e.g. as described in U.S. Pat. No. 6,015,815, WO95/14023 and WO99/15530 the contents of which are incorporated by reference, e.g. ABT578 also known as zotarolimus or a rapamycin analog described in U.S. Pat. No. 7,091,213, WO98/02441 and WO01/14387 the contents of which are incorporated by reference, e.g. AP23573 also known as ridaforolimus.

Examples of rapamycin analogs suitable for use in the present invention from U.S. Pat. No. 5,665,772 include, but are not limited to, 40-O-benzyl-rapamycin, 40-O-(4'-hydroxymethyl)benzyl-rapamycin, 40-O-[4'-(1,2-dihydroxyethyl)]benzyl-rapamycin, 40-O-allyl-rapamycin, 40-O-[3'-(2,2-dimethyl-1,3-dioxolan-4(S)-yl)-prop-2'-en-1'-yl]-rapamycin, (2'E,4'S)-40-O-(4',5'-dihydroxypent-2'-en-1'-yl)-rapamycin, 40-O-(2-hydroxy)ethoxycarbonylmethyl-rapamycin, 40-O-(2-hydroxy)ethyl-rapamycin, 40-O-(3-hydroxy)propyl-rapamycin, 40-O-(6-hydroxy)hexyl-rapamycin, 40-O-[2-(2-hydroxy)ethoxy]ethyl-rapamycin, 40-O-[(3S)-2,2-dimethyldioxolan-3-yl]methyl-rapamycin, 40-O-[(2S)-2,3-dihydroxyprop-1-yl]-rapamycin, 40-O-(2-acetoxy)ethyl-rapamycin, 40-O-(2-nicotinoyloxy)ethyl-rapamycin, 40-O-[2-(N-morpholino)acetoxy]ethyl-rapamycin, 40-O-(2-N-imidazolylacetoxy)ethyl-rapamycin, 40-O-[2-(N-methyl-N'-piperazinyl)acetoxy]ethyl-rapamycin, 39-O-desmethyl-39,40-O,O-ethylene-rapamycin, (26R)-26-dihydro-40-O-(2-hydroxy)ethyl-rapamycin, 40-O-(2-aminoethyl)-rapamycin, 40-O-(2-acetaminoethyl)-rapamycin, 40-O-(2-nicotinamidoethyl)-rapamycin, 40-O-(2-(N-methyl-imidazo-2'-ylcarbethoxamido)ethyl)-rapamycin, 40-O-(2-ethoxycarbonylaminoethyl)-rapamycin, 40-O-(2-tolylsulfonamidoethyl)-rapamycin and 40-O-[2-(4',5'-dicarboethoxy-1',2',3'-triazol-1'-yl)-ethyl]-rapamycin.

Other rapamycin analogs useful in the present invention are analogs where the hydroxyl group on the cyclohexyl ring of rapamycin and/or the hydroxy group at the 28 position is replaced with an hydroxyester group are known, for example, rapamycin analogs found in U.S. Pat. No. RE44,768, e.g. temsirolimus.

Other rapamycin analogs useful in the preset invention include those wherein the methoxy group at the 16 position is replaced with another substituent, preferably (optionally hydroxy-substituted) alkynyloxy, benzyl, orthomethoxybenzyl or chlorobenzyl and/or wherein the mexthoxy group at the 39 position is deleted together with the 39 carbon so that the cyclohexyl ring of rapamycin becomes a cyclopentyl ring lacking the 39 position methyoxy group; e.g. as described in WO95/16691 and WO96/41807 the contents of which are incorporated by reference. The analogs can be further modified such that the hydroxy at the 40-position of rapamycin is alkylated and/or the 32-carbonyl is reduced.

Rapamycin analogs from WO95/16691 include, but are not limited to, 16-demthoxy-16-(pent-2-ynyl)oxy-rapamycin, 16-demthoxy-16-(but-2-ynyl)oxy-rapamycin, 16-demthoxy-16-(propargyl)oxy-rapamycin, 16-demethoxy-16-(4-hydroxy-but-2-ynyl)oxy-rapamycin, 16-demthoxy-16-benzyloxy-40-O-(2-hydroxyethyl)-rapamycin, 16-demthoxy-16-benzyloxy-rapamycin, 16-demethoxy-16-ortho-methoxybenzyl-rapamycin, 16-demethoxy-40-0-(2-methoxyethyl)-16-pent-2-ynyl)oxy-rapamycin, 39-demethoxy-40-desoxy-39-formyl-42-nor-rapamycin, 39-demethoxy-40-desoxy-39-hydroxymethyl-42-nor-rapamycin, 39-demethoxy-40-desoxy-39-carboxy-42-nor-rapamycin, 39-demethoxy-40-desoxy-39-(4-methyl-piperazin-1-yl)carbonyl-42-nor-rapamycin, 39-demethoxy-40-desoxy-39-(morpholin-4-yl)carbonyl-42-nor-rapamycin, 39-demethoxy-40-desoxy-39-[N-methyl, N-(2-pyridin-2-yl-ethyl)]carbamoyl-42-nor-rapamycin and 39-demethoxy-40-desoxy-39-(p-toluenesulfonylhydrazonomethyl)-42-nor-rapamycin.

Rapamycin analogs from WO96/41807 include, but are not limited to, 32-deoxo-rapamycin, 16-O-pent-2-ynyl-32-deoxo-rapamycin, 16-O-pent-2-ynyl-32-deoxo-40-O-(2-hydroxy-ethyl)-rapamycin, 16-O-pent-2-ynyl-32-(S)-dihydro-40-O-(2-hydroxyethyl)-rapamycin, 32(S)-dihydro-40-O-(2-methoxy)ethyl-rapamycin and 32(S)-dihydro-40-O-(2-hydroxyethyl)-rapamycin.

Another suitable rapamycin analog is umirolimus as described in US2005/0101624 the contents of which are incorporated by reference.

RAD001, otherwise known as everolimus (Afinitor®), has the chemical name (1R,9S,12S,15R,16E,18R,19R,21R, 23S,24E,26E,28E,30S,32S,35R)-1,18-dihydroxy-12-{(1R)-2-[(1S,3R,4R)-4-(2-hydroxyethoxy)-3-methoxycyclohexyl]-1-methylethyl}-19,30-dimethoxy-15,17,21,23,29, 35-hexamethyl-11,36-dioxa-4-aza-tricyclo[30.3.1.04,9] hexatriaconta-16,24,26,28-tetraene-2,3,10,14,20-pentaone Further examples of allosteric mTOR inhibitors include sirolimus (rapamycin, AY-22989), 40-[3-hydroxy-2-(hydroxymethyl)-2-methylpropanoate]-rapamycin (also called temsirolimus or CCI-779) and ridaforolimus (AP-23573/

MK-8669). Other examples of allosteric mTor inhibtors include zotarolimus (ABT578) and umirolimus.

Alternatively or additionally, catalytic, ATP-competitive mTOR inhibitors have been found to target the mTOR kinase domain directly and target both mTORC1 and mTORC2. These are also more effective inhibitors of mTORC1 than such allosteric mTOR inhibitors as rapamycin, because they modulate rapamycin-resistant mTORC1 outputs such as 4EBP1-T37/46 phosphorylation and cap-dependent translation.

Catalytic inhibitors include: BEZ235 or 2-methyl-2-[4-(3-methyl-2-oxo-8-quinolin-3-yl-2,3-dihydro-imidazo[4,5-c]quinolin-1-yl)-phenyl]-propionitrile, or the monotosylate salt form. the synthesis of BEZ235 is described in WO2006/122806; CCG168 (otherwise known as AZD-8055, Chresta, C. M., et al., Cancer Res, 2010, 70(1), 288-298) which has the chemical name {5-[2,4-bis-((S)-3-methyl-morpholin-4-yl)-pyrido[2,3d]pyrimidin-7-yl]-2-methoxy-phenyl}-methanol; 3-[2,4-bis[(3S)-3-methylmorpholin-4-yl]pyrido[2,3-d]pyrimidin-7-yl]-N-methylbenzamide (WO09104019); 3-(2-aminobenzo[d]oxazol-5-yl)-1-isopropyl-1H-pyrazolo[3,4-d]pyrimidin-4-amine (WO10051043 and WO2013023184); A N-(3-(N-(3-((3,5-dimethoxyphenyl)amino)quinoxaline-2-yl)sulfamoyl)phenyl)-3-methoxy-4-methylbenzamide (WO07044729 and WO12006552); PKI-587 (Venkatesan, A. M., J. Med. Chem., 2010, 53, 2636-2645) which has the chemical name 1-[4-[4-(dimethylamino)piperidine-1-carbonyl]phenyl]-3-[4-(4,6-dimorpholino-1,3,5-triazin-2-yl)phenyl]urea; GSK-2126458 (ACS Med. Chem. Lett., 2010, 1, 39-43) which has the chemical name 2,4-difluoro-N-{2-methoxy-5-[4-(4-pyridazinyl)-6-quinolinyl]-3-pyridinyl}benzenesulfonamide; 5-(9-isopropyl-8-methyl-2-morpholino-9H-purin-6-yl)pyrimidin-2-amine (WO10114484); (E)-N-(8-(6-amino-5-(trifluoromethyl)pyridin-3-yl)-1-(6-(2-cyanopropan-2-yl)pyridin-3-yl)-3-methyl-1H-imidazo[4,5-c]quinolin-2(3H)-ylidene)cyanamide (WO12007926).

Further examples of catalytic mTOR inhibitors include 8-(6-methoxy-pyridin-3-yl)-3-methyl-1-(4-piperazin-1-yl-3-trifluoromethyl-phenyl)-1,3-dihydro-imidazo[4,5-c]quinolin-2-one (WO2006/122806) and Ku-0063794 (Garcia-Martinez J M, et al., Biochem J., 2009, 421(1), 29-42. Ku-0063794 is a specific inhibitor of the mammalian target of rapamycin (mTOR).) WYE-354 is another example of a catalytic mTor inhibitor (Yu K, et al. (2009). Biochemical, Cellular, and In vivo Activity of Novel ATP-Competitive and Selective Inhibitors of the Mammalian Target of Rapamycin. Cancer Res. 69(15): 6232-6240).

mTOR inhibitors useful according to the present invention also include prodrugs, derivatives, pharmaceutically acceptable salts, or analogs thereof of any of the foregoing.

mTOR inhibitors, such as RAD001, may be formulated for delivery based on well-established methods in the art based on the particular dosages described herein. In particular, U.S. Pat. No. 6,004,973 (incorporated herein by reference) provides examples of formulations useable with the mTOR inhibitors described herein.

Evaluation of mTOR Inhibition mTOR phosphorylates the kinase P70 S6, thereby activating P70 S6 kinase and allowing it to phosphorylate its substrate. The extent of mTOR inhibition can be expressed as the extent of P70 S6 kinase inhibition, e.g., the extent of mTOR inhibition can be determined by the level of decrease in P70 S6 kinase activity, e.g., by the decrease in phosphorylation of a P70 S6 kinase substrate. One can determine the level of mTOR inhibition, by measuring P70 S6 kinase activity (the ability of P70 S6 kinase to phsophorylate a substrate), in the absence of inhibitor, e.g., prior to administration of inhibitor, and in the presences of inhibitor, or after the administration of inhibitor. The level of inhibition of P70 S6 kinase gives the level of mTOR inhibition. Thus, if P70 S6 kinase is inhibited by 40%, mTOR activity, as measured by P70 S6 kinase activity, is inhibited by 40%. The extent or level of inhibition referred to herein is the average level of inhibition over the dosage interval. By way of example, if the inhibitor is given once per week, the level of inhibition is given by the average level of inhibition over that interval, namely a week.

Boulay et al., Cancer Res, 2004, 64:252-61, hereby incorporated by reference, teaches an assay that can be used to assess the level of mTOR inhibition (referred to herein as the Boulay assay). In an embodiment, the assay relies on the measurement of P70 S6 kinase activity from biological samples before and after administration of an mTOR inhibitor, e.g., RAD001. Samples can be taken at preselected times after treatment with an mTOR inhibitor, e.g., 24, 48, and 72 hours after treatment. Biological samples, e.g., from skin or peripheral blood mononuclear cells (PBMCs) can be used. Total protein extracts are prepared from the samples. P70 S6 kinase is isolated from the protein extracts by immunoprecipitation using an antibody that specifically recognizes the P70 S6 kinase. Activity of the isolated P70 S6 kinase can be measured in an in vitro kinase assay. The isolated kinase can be incubated with 40S ribosomal subunit substrates (which is an endogenous substrate of P70 S6 kinase) and gamma-$^{32}$P under conditions that allow phosphorylation of the substrate. Then the reaction mixture can be resolved on an SDS-PAGE gel, and $^{32}$P signal analyzed using a PhosphorImager. A $^{32}$P signal corresponding to the size of the 40S ribosomal subunit indicates phosphorylated substrate and the activity of P70 S6 kinase. Increases and decreases in kinase activity can be calculated by quantifying the area and intensity of the $^{32}$P signal of the phosphorylated substrate (e.g., using ImageQuant, Molecular Dynamics), assigning arbitrary unit values to the quantified signal, and comparing the values from after administration with values from before administration or with a reference value. For example, percent inhibition of kinase activity can be calculated with the following formula: 1−(value obtained after administration/value obtained before administration)×100. As described above, the extent or level of inhibition referred to herein is the average level of inhibition over the dosage interval.

Methods for the evaluation of kinase activity, e.g., P70 S6 kinase activity, are also provided in U.S. Pat. No. 7,727,950, hereby incorporated by reference.

The level of mTOR inhibition can also be evaluated by a change in the ration of PD1 negative to PD1 positive T cells. T cells from peripheral blood can be identified as PD1 negative or positive by art-known methods.

Low-Dose mTOR Inhibitors

Methods described herein use low, immune enhancing, dose mTOR inhibitors, doses of mTOR inhibitors, e.g., allosteric mTOR inhibitors, including rapalogs such as RAD001. In contrast, levels of inhibitor that fully or near fully inhibit the mTOR pathway are immunosuppressive and are used, e.g., to prevent organ transplant rejection. In addition, high doses of rapalogs that fully inhibit mTOR also inhibit tumor cell growth and are used to treat a variety of cancers (See, e.g., Antineoplastic effects of mammalian target of rapamycine inhibitors. Salvadori M. World J Transplant. 2012 Oct. 24; 2(5):74-83; Current and Future Treatment Strategies for Patients with Advanced Hepatocellular Carcinoma: Role of mTOR Inhibition. Finn R S. Liver Cancer. 2012 November; 1(3-4):247-256; Emerging Signaling Pathways in Hepatocellular Carcinoma. Moeini A, Cornelià H, Villanueva A. Liver Cancer. 2012 September; 1(2):83-93; Targeted cancer therapy—Are the days of systemic chemotherapy numbered? Joo W D, Visintin I, Mor G. Maturitas. 2013 Sep. 20; Role of natural and adaptive immunity in renal cell carcinoma response to VEGFR-TKIs and mTOR inhibitor. Santoni M, Berardi R, Amantini C, Burattini L, Santini D, Santoni G, Cascinu S. Int J Cancer. 2013 Oct. 2).

The present invention is based, at least in part, on the surprising finding that doses of mTOR inhibitors well below those used in current clinical settings had a superior effect in increasing an immune response in a subject and increasing the ratio of PD-1 negative T cells/PD-1 positive T cells. It was surprising that low doses of mTOR inhibitors, producing only partial inhibition of mTOR activity, were able to effectively improve immune responses in human subjects and increase the ratio of PD-1 negative T cells/PD-1 positive T cells.

Alternatively, or in addition, without wishing to be bound by any theory, it is believed that low, a low, immune enhancing, dose of an mTOR inhibitor can increase naive T cell numbers, e.g., at least transiently, e.g., as compared to a non-treated subject. Alternatively or additionally, again while not wishing to be bound by theory, it is believed that treatment with an mTOR inhibitor after a sufficient amount of time or sufficient dosing results in one or more of the following:

an increase in the expression of one or more of the following markers: $CD62L^{high}$, $CD127^{high}$, $CD27^+$, and BCL2, e.g., on memory T cells, e.g., memory T cell precursors;

a decrease in the expression of KLRG1, e.g., on memory T cells, e.g., memory T cell precursors; and an increase in the number of memory T cell precursors, e.g., cells with any one or combination of the following characteristics: increased $CD62L^{high}$, increased $CD127^{high}$, increased $CD27^+$, decreased KLRG1, and increased BCL2;

and wherein any of the changes described above occurs, e.g., at least transiently, e.g., as compared to a non-treated subject (Araki, K et al. (2009) Nature 460:108-112). Memory T cell precursors are memory T cells that are early in the differentiation program. For example, memory T cells have one or more of the following characteristics: increased $CD62L^{high}$, increased $CD127^{high}$, increased $CD27^+$, decreased KLRG1, and/or increased BCL2.

In an embodiment, the invention relates to a composition, or dosage form, of an mTOR inhibitor, e.g., an allosteric mTOR inhibitor, e.g., a rapalog, rapamycin, or RAD001, or a catalytic mTOR inhibitor, which, when administered on a selected dosing regimen, e.g., once daily or once weekly, is associated with: a level of mTOR inhibition that is not associated with complete, or significant immune suppression, but is associated with enhancement of the immune response.

An mTOR inhibitor, e.g., an allosteric mTOR inhibitor, e.g., a rapalog, rapamycin, or RAD001, or a catalytic mTOR inhibitor, can be provided in a sustained release formulation. Any of the compositions or unit dosage forms described herein can be provided in a sustained release formulation. In some embodiments, a sustained release formulation will have lower bioavailability than an immediate release formulation. E.g., in embodiments, to attain a similar therapeutic effect of an immediate release formation a sustained release formulation will have from about 2 to about 5, about 2.5 to about 3.5, or about 3 times the amount of inhibitor provided in the immediate release formulation.

In an embodiment, immediate release forms, e.g., of RAD001, typically used for one administration per week, having 0.1 to 20, 0.5 to 10, 2.5 to 7.5, 3 to 6, or about 5, mgs per unit dosage form, are provided. For once per week administrations, these immediate release formulations correspond to sustained release forms, having, respectively, 0.3 to 60, 1.5 to 30, 7.5 to 22.5, 9 to 18, or about 15 mgs of an mTOR inhibitor, e.g., an allosteric mTOR inhibitor, e.g., rapamycin or RAD001. In embodiments both forms are administered on a once/week basis.

In an embodiment, immediate release forms, e.g., of RAD001, typically used for one administration per day, having having 0.005 to 1.5, 0.01 to 1.5, 0.1 to 1.5, 0.2 to 1.5, 0.3 to 1.5, 0.4 to 1.5, 0.5 to 1.5, 0.6 to 1.5, 0.7 to 1.5, 0.8 to 1.5, 1.0 to 1.5, 0.3 to 0.6, or about 0.5 mgs per unit dosage form, are provided. For once per day administrations, these immediate release forms correspond to sustained release forms, having, respectively, 0.015 to 4.5, 0.03 to 4.5, 0.3 to 4.5, 0.6 to 4.5, 0.9 to 4.5, 1.2 to 4.5, 1.5 to 4.5, 1.8 to 4.5, 2.1 to 4.5, 2.4 to 4.5, 3.0 to 4.5, 0.9 to 1.8, or about 1.5 mgs of an mTOR inhibitor, e.g., an allosteric mTOR inhibitor, e.g., rapamycin or RAD001. For once per week administrations, these immediate release forms correspond to sustained release forms, having, respectively, 0.1 to 30, 0.2 to 30, 2 to 30, 4 to 30, 6 to 30, 8 to 30, 10 to 30, 1.2 to 30, 14 to 30, 16 to 30, 20 to 30, 6 to 12, or about 10 mgs of an mTOR inhibitor, e.g., an allosteric mTOR inhibitor, e.g., rapamycin or RAD001.

In an embodiment, immediate release forms, e.g., of RAD001, typically used for one administration per day, having having 0.01 to 1.0 mgs per unit dosage form, are provided. For once per day administrations, these immediate release forms correspond to sustained release forms, having, respectively, 0.03 to 3 mgs of an mTOR inhibitor, e.g., an allosteric mTOR inhibitor, e.g., rapamycin or RAD001. For once per week administrations, these immediate release forms correspond to sustained release forms, having, respectively, 0.2 to 20 mgs of an mTOR inhibitor, e.g., an allosteric mTOR inhibitor, e.g., rapamycin or RAD001.

In an embodiment, immediate release forms, e.g., of RAD001, typically used for one administration per week, having having 0.5 to 5.0 mgs per unit dosage form, are provided. For once per week administrations, these immediate release forms correspond to sustained release forms, having, respectively, 1.5 to 15 mgs of an mTOR inhibitor, e.g., an allosteric mTOR inhibitor, e.g., rapamycin or RAD001.

As described above, one target of the mTOR pathway is the P70 S6 kinase. Thus, doses of mTOR inhibitors which are useful in the methods and compositions described herein are those which are sufficient to achieve no greater than 80% inhibition of P70 S6 kinase activity relative to the activity of the P70 S6 kinase in the absence of an mTOR inhibitor, e.g., as measured by an assay described herein, e.g., the Boulay assay. In a further aspect, the invention provides an amount of an mTOR inhibitor sufficient to achieve no greater than 38% inhibition of P70 S6 kinase activity relative to P70 S6 kinase activity in the absence of an mTOR inhibitor.

In one aspect the dose of mTOR inhibitor useful in the methods and compositions of the invention is sufficient to achieve, e.g., when administered to a human subject, 90+/−5% (i.e., 85-95%), 89+/−5%, 88+/−5%, 87+/−5%, 86+/−5%, 85+/−5%, 84+/−5%, 83+/−5%, 82+/−5%, 81+/−5%, 80+/−5%, 79+/−5%, 78+/−5%, 77+/−5%, 76+/−5%, 75+/−5%, 74+/−5%, 73+/−5%, 72+/−5%, 71+/−5%, 70+/−5%, 69+/−

5%, 68+/−5%, 67+/−5%, 66+/−5%, 65+/−5%, 64+/−5%, 63+/−5%, 62+/−5%, 61+/−5%, 60+/−5%, 59+/−5%, 58+/−5%, 57+/−5%, 56+/−5%, 55+/−5%, 54+/−5%, 54+/−5%, 53+/−5%, 52+/−5%, 51+/−5%, 50+/−5%, 49+/−5%, 48+/−5%, 47+/−5%, 46+/−5%, 45+/−5%, 44+/−5%, 43+/−5%, 42+/−5%, 41+/−5%, 40+/−5%, 39+/−5%, 38+/−5%, 37+/−5%, 36+/−5%, 35+/−5%, 34+/−5%, 33+/−5%, 32+/−5%, 31+/−5%, 30+/−5%, 29+/−5%, 28+/−5%, 27+/−5%, 26+/−5%, 25+/−5%, 24+/−5%, 23+/−5%, 22+/−5%, 21+/−5%, 20+/−5%, 19+/−5%, 18+/−5%, 17+/−5%, 16+/−5%, 15+/−5%, 14+/−5%, 13+/−5%, 12+/−5%, 11+/−5%, or 10+/−5%, inhibition of P70 S6 kinase activity, e.g., as measured by an assay described herein, e.g., the Boulay assay.

P70 S6 kinase activity in a subject may be measured using methods known in the art, such as, for example, according to the methods described in U.S. Pat. No. 7,727,950, by immunoblot analysis of phosphoP70 S6K levels and/or phosphoP70 S6 levels or by in vitro kinase activity assays.

As used herein, the term "about" in reference to a dose of mTOR inhibitor refers to up to a +/−10% variability in the amount of mTOR inhibitor, but can include no variability around the stated dose.

In some embodiments, the invention provides methods comprising administering to a subject an mTOR inhibitor, e.g., an allosteric inhibitor, e.g., RAD001, at a dosage within a target trough level. In some embodiments, the trough level is significantly lower than trough levels associated with dosing regimens used in organ transplant and cancer patients. In an embodiment mTOR inhibitor, e.g., RAD001, or rapamycin, is administered to result in a trough level that is less than ½, ¼, 1/10, or 1/20 of the trough level that results in immunosuppression or an anticancer effect. In an embodiment mTOR inhibitor, e.g., RAD001, or rapamycin, is administered to result in a trough level that is less than ½, ¼, 1/10, or 1/20 of the trough level provided on the FDA approved packaging insert for use in immunosuppression or an anticancer indications.

In an embodiment a method disclosed herein comprises administering to a subject an mTOR inhibitor, e.g., an allosteric inhibitor, e.g., RAD001, at a dosage that provides a target trough level of 0.1 to 10 ng/ml, 0.1 to 5 ng/ml, 0.1 to 3 ng/ml, 0.1 to 2 ng/ml, or 0.1 to 1 ng/ml.

In an embodiment a method disclosed herein comprises administering to a subject an mTOR inhibitor, e.g., an allosteric inhibitor, e.g., RAD001, at a dosage that provides a target trough level of 0.2 to 10 ng/ml, 0.2 to 5 ng/ml, 0.2 to 3 ng/ml, 0.2 to 2 ng/ml, or 0.2 to 1 ng/ml.

In an embodiment a method disclosed herein comprises administering to a subject an mTOR inhibitor, e.g. an, allosteric inhibitor, e.g., RAD001, at a dosage that provides a target trough level of 0.3 to 10 ng/ml, 0.3 to 5 ng/ml, 0.3 to 3 ng/ml, 0.3 to 2 ng/ml, or 0.3 to 1 ng/ml.

In an embodiment a method disclosed herein comprises administering to a subject an mTOR inhibitor, e.g., an allosteric inhibitor, e.g., RAD001, at a dosage that provides a target trough level of 0.4 to 10 ng/ml, 0.4 to 5 ng/ml, 0.4 to 3 ng/ml, 0.4 to 2 ng/ml, or 0.4 to 1 ng/ml.

In an embodiment a method disclosed herein comprises administering to a subject an mTOR inhibitor, e.g., an allosteric inhibitor, e.g., RAD001, at a dosage that provides a target trough level of 0.5 to 10 ng/ml, 0.5 to 5 ng/ml, 0.5 to 3 ng/ml, 0.5 to 2 ng/ml, or 0.5 to 1 ng/ml.

In an embodiment a method disclosed herein comprises administering to a subject an mTOR inhibitor, e.g., an allosteric inhibitor, e.g., RAD001, at a dosage that provides a target trough level of 1 to 10 ng/ml, 1 to 5 ng/ml, 1 to 3 ng/ml, or 1 to 2 ng/ml.

As used herein, the term "trough level" refers to the concentration of a drug in plasma just before the next dose, or the minimum drug concentration between two doses.

In some embodiments, a target trough level of RAD001 is in a range of between about 0.1 and 4.9 ng/ml. In an embodiment, the target trough level is below 3 ng/ml, e.g., is between 0.3 or less and 3 ng/ml. In an embodiment, the target trough level is below 3 ng/ml, e.g., is between 0.3 or less and 1 ng/ml.

In a further aspect, the invention can utilize an mTOR inhibitor other than RAD001 in an amount that is associated with a target trough level that is bioequivalent to the specified target trough level for RAD001. In an embodiment, the target trough level for an mTOR inhibitor other than RAD001, is a level that gives the same level of mTOR inhibition (e.g., as measured by a method described herein, e.g., the inhibition of P70 S6) as does a trough level of RAD001 described herein.

Pharmaceutical Compositions: mTOR Inhibitors

In one aspect, the present invention relates to pharmaceutical compositions comprising an mTOR inhibitor, e.g., an mTOR inhibitor as described herein, formulated for use in combination with CAR cells described herein.

In some embodiments, the mTOR inhibitor is formulated for administration in combination with an additional, e.g., as described herein.

In general, compounds of the invention will be administered in therapeutically effective amounts as described above via any of the usual and acceptable modes known in the art, either singly or in combination with one or more therapeutic agents.

The pharmaceutical formulations may be prepared using conventional dissolution and mixing procedures. For example, the bulk drug substance (e.g., an mTOR inhibitor or stabilized form of the compound (e.g., complex with a cyclodextrin derivative or other known complexation agent) is dissolved in a suitable solvent in the presence of one or more of the excipients described herein. The mTOR inhibitor is typically formulated into pharmaceutical dosage forms to provide an easily controllable dosage of the drug and to give the patient an elegant and easily handleable product.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Where an mTOR inhibitor is administered in combination with (either simultaneously with or separately from) another agent as described herein, in one aspect, both components can be administered by the same route (e.g., parenterally). Alternatively, another agent may be administered by a different route relative to the mTOR inhibitor. For example, an mTOR inhibitor may be administered orally and the other agent may be administered parenterally.

Sustained Release mTOR inhibitors, e.g., allosteric mTOR inhibitors or catalytic mTOR inhibitors, disclosed herein can be provided as pharmaceutical formulations in form of oral solid dosage forms comprising an mTOR inhibitor disclosed herein, e.g., rapamycin or RAD001, which satisfy product stability requirements and/or have favorable pharmacokinetic properties over the immediate release (IR) tablets, such as reduced average plasma peak concentrations, reduced inter- and intra-patient variability in the extent of drug absorption and in the plasma peak concentration, reduced $C_{max}/C_{min}$ ratio and/or reduced food effects. Provided pharmaceutical formulations may allow for more precise dose adjustment and/or reduce frequency of adverse events thus providing safer treatments for patients with an mTOR inhibitor disclosed herein, e.g., rapamycin or RAD001.

In some embodiments, the present disclosure provides stable extended release formulations of an mTOR inhibitor disclosed herein, e.g., rapamycin or RAD001, which are multi-particulate systems and may have functional layers and coatings.

The term "extended release, multi-particulate formulation as used herein refers to a formulation which enables release of an mTOR inhibitor disclosed herein, e.g., rapamycin or RAD001, over an extended period of time e.g. over at least 1, 2, 3, 4, 5 or 6 hours. The extended release formulation may contain matrices and coatings made of special excipients, e.g., as described herein, which are formulated in a manner as to make the active ingredient available over an extended period of time following ingestion.

The term "extended release" can be interchangeably used with the terms "sustained release" (SR) or "prolonged release". The term "extended release" relates to a pharmaceutical formulation that does not release active drug substance immediately after oral dosing but over an extended in accordance with the definition in the pharmacopoeias Ph. Eur. ($7^{th}$ edition) mongraph for tablets and capsules and USP general chapter <1151> for pharmaceutical dosage forms. The term "Immediate Release" (IR) as used herein refers to a pharmaceutical formulation which releases 85% of the active drug substance within less than 60 minutes in accordance with the definition of "Guidance for Industry: "Dissolution Testing of Immediate Release Solid Oral Dosage Forms" (FDA CDER, 1997). In some embodiments, the term "immediate release" means release of everolismus from tablets within the time of 30 minutes, e.g., as measured in the dissolution assay described herein.

Stable extended release formulations of an mTOR inhibitor disclosed herein, e.g., rapamycin or RAD001, can be characterized by an in-vitro release profile using assays known in the art, such as a dissolution assay as described herein: a dissolution vessel filled with 900 mL phosphate buffer pH 6.8 containing sodium dodecyl sulfate 0.2% at 37° C. and the dissolution is performed using a paddle method at 75 rpm according to USP by according to USP testing monograph 711, and Ph.Eur. testing monograph 2.9.3. respectively.

In some embodiments, stable extended release formulations of an mTOR inhibitor disclosed herein, e.g., rapamycin or RAD001, release the mTOR inhibitor in the in-vitro release assay according to following release specifications:

0.5 h: <45%, or <40, e.g., <30%
1 h: 20-80%, e.g., 30-60%
2 h: >50%, or >70%, e.g., >75%
3 h: >60%, or >65%, e.g., >85%, e.g., >90%.

In some embodiments, stable extended release formulations of an mTOR inhibitor disclosed herein, e.g., rapamycin or RAD001, release 50% of the mTOR inhibitor not earlier than 45, 60, 75, 90, 105 min or 120 min in the in-vitro dissolution assay.

Pharmaceutical Compositions and Treatments

Pharmaceutical compositions of the present invention may comprise a CAR-expressing cell, e.g., a plurality of CAR-expressing cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

In one embodiment, the pharmaceutical composition is substantially free of, e.g., there are no detectable levels of a contaminant, e.g., selected from the group consisting of endotoxin, mycoplasma, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium and a fungus. In one embodiment, the bacterium is at least one selected from the group consisting of *Alcaligenes faecalis, Candida albicans, Escherichia coli, Haemophilus* influenza, *Neisseria meningitides, Pseudomonas aeruginosa, Staphylococcus aureus, Streptococcus pneumonia,* and *Streptococcus pyogenes* group A.

When "an immunologically effective amount," "an anti-cancer effective amount," "a cancer-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the immune effector cells described herein may be administered at a dosage of $10^4$ to $10^9$ cells/kg body weight, in some instances $10^5$ to $10^6$ cells/kg body weight, including all integer values within those ranges. The immune effector cell compositions may also be administered multiple times at these dosages. The cells can be administered by using infusion techniques that are commonly known in immunotherapy (see, e.g., Rosenberg et al., New Eng. J. of Med. 319:1676, 1988).

In certain aspects, it may be desired to administer activated immune effector cells to a subject and then subsequently redraw blood (or have an apheresis performed), activate the cells therefrom according to the present invention, and reinfuse the patient with these activated and expanded cells. This process can be carried out multiple times every few weeks. In certain aspects, the cells can be activated from blood draws of from 10 cc to 400 cc. In certain aspects, the cells are activated from blood draws of 20 cc, 30 cc, 40 cc, 50 cc, 60 cc, 70 cc, 80 cc, 90 cc, or 100 cc.

The administration of the subject compositions may be carried out in any convenient manner, including by aerosol inhalation, injection, ingestion, transfusion, implantation or transplantation. The compositions described herein may be administered to a patient trans arterially, subcutaneously, intradermally, intratumorally, intranodally, intramedullary, intramuscularly, by intravenous (i.v.) injection, or intraperitoneally. In one aspect, the T cell compositions of the present invention are administered to a patient by intradermal or subcutaneous injection. In one aspect, the immune effector cell compositions of the present invention are administered by i.v. injection. The compositions of immune effector cells may be injected directly into a tumor, lymph node, or site of infection.

In a particular exemplary aspect, subjects may undergo leukapheresis, wherein leukocytes are collected, enriched, or depleted ex vivo to select and/or isolate the cells of interest, e.g., T cells. These T cell isolates may be expanded by methods known in the art and treated such that one or more CAR constructs of the invention may be introduced, thereby creating a CAR T cell of the invention. Subjects in need thereof may subsequently undergo standard treatment with high dose chemotherapy followed by peripheral blood stem cell transplantation. In certain aspects, following or concurrent with the transplant, subjects receive an infusion of the expanded CAR T cells of the present invention. In an additional aspect, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

In one embodiment, the CAR is introduced into immune effector cells, e.g., using in vitro transcription, and the subject (e.g., human) receives an initial administration of CAR-expressingcells of the invention, and one or more subsequent administrations of the CAR-expressing cells of the invention, wherein the one or more subsequent administrations are administered less than 15 days, e.g., 14, 13, 12, 11, 10, 9, 8, 7, 6, 5, 4, 3, or 2 days after the previous administration. In one embodiment, more than one administration of the CAR-expressing cells of the invention are administered to the subject (e.g., human) per week, e.g., 2, 3, or 4 administrations of the CAR-expressing cells of the invention are administered per week. In one embodiment, the subject (e.g., human subject) receives more than one administration of the CAR-expressing cells per week (e.g., 2, 3 or 4 administrations per week) (also referred to herein as a cycle), followed by a week of no CAR-expressing cells administration, and then one or more additional administration of the CAR-expressing cells (e.g., more than one administration of the CAR-expressing cells per week) is administered to the subject. In another embodiment, the subject (e.g., human subject) receives more than one cycle of CAR-expressing cells, and the time between each cycle is less than 10, 9, 8, 7, 6, 5, 4, or 3 days. In one embodiment, the CAR-expressing cells are administered every other day for 3 administrations per week. In one embodiment, the CAR-expressing cells of the invention are administered for at least two, three, four, five, six, seven, eight or more weeks.

In one aspect, mesothelin CAR-expressing cells are generated using lentiviral viral vectors, such as lentivirus. CAR-expressing cells generated that way will have stable CAR expression.

In one aspect, the CAR-expressing cellss transiently express CAR vectors for 4, 5, 6, 7, 8, 9, 10, 11, 12, 13, 14, 15 days after transduction. Transient expression of CARs can be effected by RNA CAR vector delivery. In one aspect, the CAR RNA is transduced into the T cell by electroporation.

Figure 6:
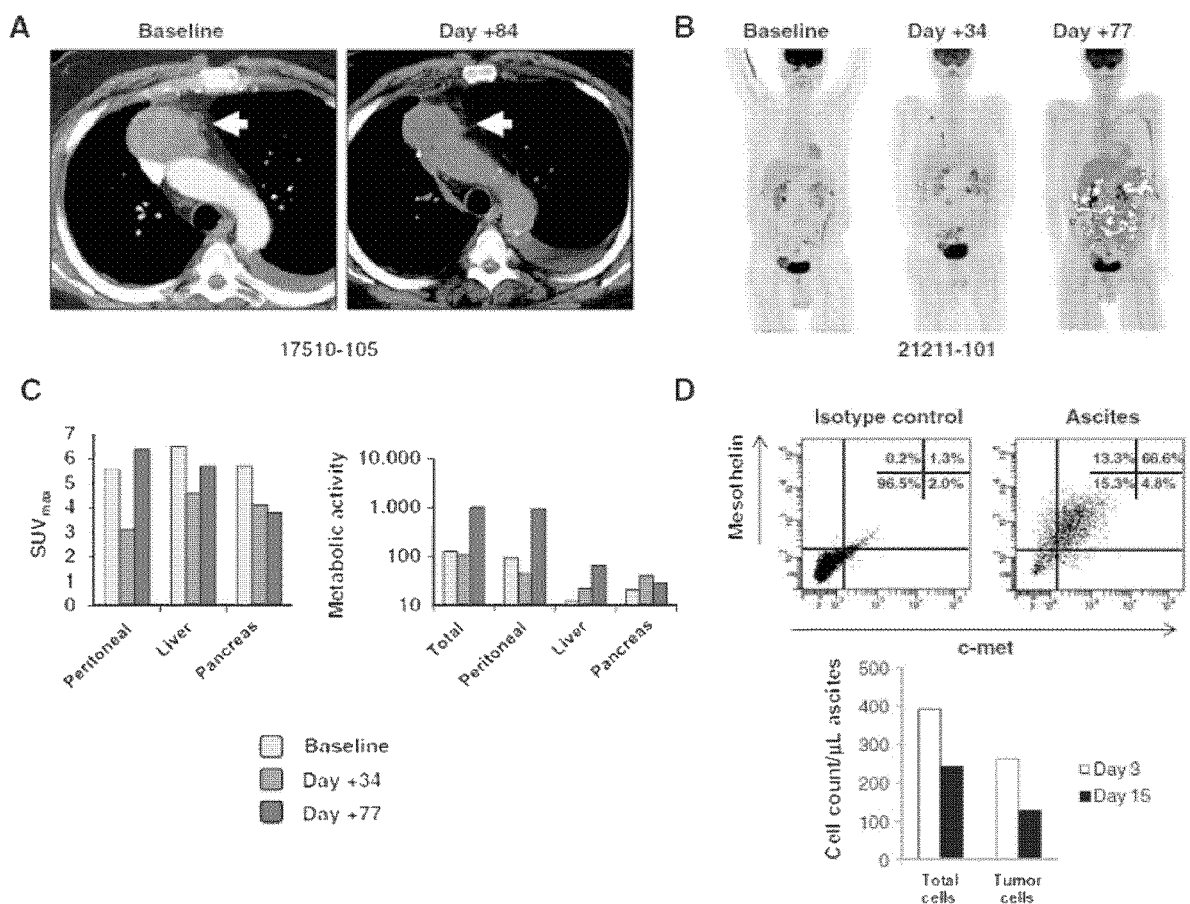
FIGS. 6A, 6B, 6C, and 6D show anti-tumor activity of CART-meso cells.

In one embodiment, the dose and/or dosing schedule is one provided in FIG. 6.

A potential issue that can arise in patients being treated using transiently expressing CAR-expressing cells (particularly with murine scFv bearing CAR-expressing cells) is anaphylaxis after multiple treatments.

Without being bound by this theory, it is believed that such an anaphylactic response might be caused by a patient developing humoral anti-CAR response, i.e., anti-CAR antibodies having an anti-IgE isotype. It is thought that a patient's antibody producing cells undergo a class switch from IgG isotype (that does not cause anaphylaxis) to IgE isotype when there is a ten to fourteen day break in exposure to antigen.

If a patient is at high risk of generating an anti-CAR antibody response during the course of transient CAR therapy (such as those generated by RNA transductions), CAR-expressing cell infusion breaks should not last more than ten to fourteen days.

Using CARs with human (instead of murine) scFvs can reduce the likelihood and intensity of a patient having an anti-CAR response.

Table 2: Amino Acid Sequences of Human scFvs and CARs (bold underline is the leader sequence and grey box is a linker sequence). In the case of the scFvs, the remaining amino acids are the heavy chain variable region and light chain variable regions, with each of the HC CDRs (HC CDR1, HC CDR2, HC CDR3) and LC CDRs (LC CDR1, LC CDR2, LCCDR3) underlined). In the case of the CARs, the further remaining amino acids are the remaining amino acids of the CARs.)

| SEQ ID NO: | Description | Amino Acid Sequence |
|---|---|---|
| 39 | M1 (ScFv domain) | QVQLQQSGAEVKKPGASVKVSCKAS<u>GYTFTGYYMH</u>WVRQ APGQGLEWMG<u>RINPNSGGTNYAQKFQG</u>RVTMTRDTSISTAYMELSRLRSEDTAVYYCAR<u>G RYYGMDVW</u>GQGTMVTVSSGGGGSGGGGSGGGGSGGGGSEIVLTQSPATLSLSPGERATIS CR<u>ASQSVSSNFA</u>WYQQRPGQAPRLLIY<u>DASNRAT</u>GIPPRFSGSGSGTDFTLTISSLEPED FAAYYC<u>HQRSNWLYT</u>FGQGTKVDIK |
| 63 | M1 (full) >ZA53-27BC (M1 ZA53-27BC R001-A11 126161) | <u>MALPVTALLLPLALLLHAARP</u>QVQLQQSGAEVKKPGASVKVSCKAS<u>GYTFTGYYMH</u>WVRQ APGQGLEWMG<u>RINPNSGGTNYAQKFQG</u>RVTMTRDTSISTAYMELSRLRSEDTAVYYCAR<u>G RYYGMDVW</u>GQGTMVTVSSGGGGSGGGGSGGGGSGGGGSEIVLTQSPATLSLSPGERATIS CR<u>ASQSVSSNFA</u>WYQQRPGQAPRLLIY<u>DASNRAT</u>GIPPRFSGSGSGTDFTLTISSLEPED FAAYYC<u>HQRSNWLYT</u>FGQGTKVDIKTTTPAPRPPTPAPTIASQPLSLRPEACRPAAGGAV HTRGLDFACDIYIWAPLAGTCGVLLLSLVITLYCKRGRKKLLYIFKQPFMRPVQTTQEED GCSCRFPEEEEGGCELRVKFSRSADAPAYKQGQNQLYNELNLGRREEYDVLDKRRGRDPE MGGKPRRKNPQEGLYNELQKDKMAEAYSEIGMKGERRRGKGHDGLYQGLSTATKDTYDAL HMQALPPR |

-continued

| SEQ ID NO: | Description | Amino Acid Sequence |
|---|---|---|
| 40 | M2 (ScFv domain) | QVQLVQSGAEVKKPGASVKVSCKAS GYTFTGYYMHWVRQ APGQGLEWMG WINPNSGGTNYAQKFQ GRVTMTRDTSISTAYMELSRLRSDDTAVYYCARD LRRTVVTPRAYYGMDVWGQGTTVTVSSGGGGSGGGGSGGGGSGGGGSDIQLTQSPSTLSA SVGDRVTITCQASQDISNSLNWYQQKAGKAPKLLIYDASTLETGVPSRFSGSGSGTDFSF TISSLQPEDIATYYCQQHDNLPLTFGQGTKVEIK |
| 64 | M2 (full) >FA56-26RC (M2 FA56-26RC R001-A10 126162 | MALPVTALLLPLALLLHAARPQVQLVQSGAEVKKPGASVKVSCKASGYTFTGYYMHWVRQ APGQGLEWMGWINPNSGGTNYAQKFQGRVTMTRDTSISTAYMELSRLRSDDTAVYYCARD LRRTVVTPRAYYGMDVWGQGTTVTVSSGGGGSGGGGSGGGGSGGGGSDIQLTQSPSTLSA SVGDRVTITCQASQDISNSLNWYQQKAGKAPKLLIYDASTLETGVPSRFSGSGSGTDFSF TISSLQPEDIATYYCQQHDNLPLTFGQGTKVEIKTTTPAPRPPTPAPTIASQPLSLRPEA CRPAAGGAVHTRGLDFACDIYIWAPLAGTCGVLLLSLVITLYCKRGRKKLLYIFKQPFMR PVQTTQEEDGCSCRFPEEEEGGCELRVKFSRSADAPAYKQGQNQLYNELNLGRREEYDVL DKRRGRDPEMGGKPRRKNPQEGLYNELQKDKMAEAYSEIGMKGERRRGKGHDGLYQGLST ATKDTYDALHMQALPPR |
| 41 | M3 (ScFv domain) | QVQLVQSGAEVKKPGAPVKVSCKASGYTFTGYYMHWVRQ APGQGLEWMGWINPNSGGTNYAQKFQGRVTMTRDTSISTAYMELSRLRSDDTAVYYCARG EWDGSYYYDYWGQGTLVTVSSGGGGSGGGGSGGGGSGGGGSDIVLTQTPSSLSASVGDRV TITCRASQSINTYLNWYQHKPGKAPKLLIYAASSLQSGVPSRFSGSGSGTDFTLTISSLQ PEDFATYYCQQSFSPLTFGGGTKLEIK |
| 65 | M3 >VA58-21LC (M3 VA58-21LC R001-A1 126163) | MALPVTALLLPLALLLHAARPQVQLVQSGAEVKKPGAPVKVSCKASGYTFTGYYMHWVRQ APGQGLEWMGWINPNSGGTNYAQKFQGRVTMTRDTSISTAYMELSRLRSDDTAVYYCARG EWDGSYYYDYWGQGTLVTVSSGGGGSGGGGSGGGGSGGGGSDIVLTQTPSSLSASVGDRV TITCRASQSINTYLNWYQHKPGKAPKLLIYAASSLQSGVPSRFSGSGSGTDFTLTISSLQ PEDFATYYCQQSFSPLTFGGGTKLEIKTTTPAPRPPTPAPTIASQPLSLRPEACRPAAGG AVHTRGLDFACDIYIWAPLAGTCGVLLLSLVITLYCKRGRKKLLYIFKQPFMRPVQTTQE EDGCSCRFPEEEEGGCELRVKFSRSADAPAYKQGQNQLYNELNLGRREEYDVLDKRRGRD PEMGGKPRRKNPQEGLYNELQKDKMAEAYSEIGMKGERRRGKGHDGLYQGLSTATKDTYD ALHMQALPPR |
| 42 | M4 (ScFv domain) | QVQLVESGGGLVQPGGSLRLSCAASGFTFSSYWMHWVRQ VPGKGLVWVSRINTDGSTTTYADSVEGRFTISRDNAKNTLYLQMNSLRDDDTAVYYCVGG HWAVWGQGTTVTVSSGGGGSGGGGSGGGGSGGGGSDIQMTQSPSTLSASVGDRVTITCRA SQSISDRLAWYQQKPGKAPKLLIYKASSLESGVPSRFSGSGSGTEFTLTISSLQPDDFAV YYCQQYGHLPMYTFGQGTKVEIK |
| 66 | M4 >DP37-07IC (M4 DP37-07IC R001-C6 126164) | MALPVTALLLPLALLLHAARPQVQLVESGGGLVQPGGSLRLSCAASGFTFSSYWMHWVRQ VPGKGLVWVSRINTDGSTTTYADSVEGRFTISRDNAKNTLYLQMNSLRDDDTAVYYCVGG HWAVWGQGTTVTVSSGGGGSGGGGSGGGGSGGGGSDIQMTQSPSTLSASVGDRVTITCRA SQSISDRLAWYQQKPGKAPKLLIYKASSLESGVPSRFSGSGSGTEFTLTISSLQPDDFAV YYCQQYGHLPMYTFGQGTKVEIKTTTPAPRPPTPAPTIASQPLSLRPEACRPAAGGAVHT RGLDFACDIYIWAPLAGTCGVLLLSLVITLYCKRGRKKLLYIFKQPFMRPVQTTQEEDGC SCRFPEEEEGGCELRVKFSRSADAPAYKQGQNQLYNELNLGRREEYDVLDKRRGRDPEMG GKPRRKNPQEGLYNELQKDKMAEAYSEIGMKGERRRGKGHDGLYQGLSTATKDTYDALHM QALPPR |
| 43 | M5 (ScFv domain) | QVQLVQSGAEVEKPGASVKVSCKASGYTFTDYYMHWVRQ APGQGLEWMGWINPNSGGTNYAQKFQGRVTMTRDTSISTAYMELSRLRSDDTAVYYCASG WDFDYWGQGTLVTVSSGGGGSGGGGSGGGGSGGGGSDIVMTQSPSSLSASVGDRVTITCR ASQSIRYYLSWYQQKPGKAPKLLIYTASILQNGVPSRFSGSGSGTDFTLTISSLQPEDFA TYYCLQTYTTPDFGPGTKVEIK |
| 67 | M5 >XP31-20LC (M5 XP31-20LC R001-B4 126165) | MALPVTALLLPLALLLHAARPQVQLVQSGAEVEKPGASVKVSCKASGYTFTDYYMHWVRQ APGQGLEWMGWINPNSGGTNYAQKFQGRVTMTRDTSISTAYMELSRLRSDDTAVYYCASG WDFDYWGQGTLVTVSSGGGGSGGGGSGGGGSGGGGSDIVMTQSPSSLSASVGDRVTITCR ASQSIRYYLSWYQQKPGKAPKLLIYTASILQNGVPSRFSGSGSGTDFTLTISSLQPEDFA TYYCLQTYTTPDFGPGTKVEIKTTTPAPRPPTPAPTIASQPLSLRPEACRPAAGGAVHTR GLDFACDIYIWAPLAGTCGVLLLSLVITLYCKRGRKKLLYIFKQPFMRPVQTTQEEDGCS CRFPEEEEGGCELRVKFSRSADAPAYKQGQNQLYNELNLGRREEYDVLDKRRGRDPEMGG KPRRKNPQEGLYNELQKDKMAEAYSEIGMKGERRRGKGHDGLYQGLSTATKDTYDALHMQ ALPPR |
| 44 | M6 (ScFv domain) | QVQLVQSGAEVKKPGASVKVSCKASGYTFTSYYMHWVRQ APGQGLEWMGIINPSGGSTSYAQKFQGRVTMTRDTSTSTVYMELSSLRSEDTAVYYCARY RLIAVAGDYYYGMDVWGQGTMVTVSSGGGGSGGGGSGGGGSGGGGSDIQMTQSPSSVSA |

| SEQ ID NO: | Description | Amino Acid Sequence |
|---|---|---|
| | | SVGDRVTITC<u>RASQGVGRWLA</u>WYQQKPGTAPKLLIY<u>AASTLQS</u>GVPSRFSGSGSGTDFTL TINNLQPEDFATYYC<u>QQANSFPLT</u>FGGGTRLEIK |
| 68 | M6 >FE10-06ID (M6 46FE10-06ID R001-A4 126166) | MALPVTALLLPLALLLHAARPQVQLVQSGAEVKKPGASVKVSCKAS<u>GYTFTSYYMH</u>WVRQ APGQGLEWMG<u>IINPSGGSTSYAQKFQG</u>RVTMTRDTSTSTVYMELSSLRSEDTAVYYCAR<u>Y RLIAVAGDYYYYGMDV</u>WGQGTMVTVSS<u>GGGGSGGGGSGGGGSGGGGS</u>DIQMTQSPSSVSA SVGDRVTITC<u>RASQGVGRWLA</u>WYQQKPGTAPKLLIY<u>AASTLQS</u>GVPSRFSGSGSGTDFTL TINNLQPEDFATYYC<u>QQANSFPLT</u>FGGGTRLEIKTTTPAPRPPTPAPTIASQPLSLRPEA CRPAAGGAVHTRGLDFACDIYIWAPLAGTCGVLLLSLVITLYCKRGRKKLLYIFKQPFMR PVQTTQEEDGCSCRFPEEEEGGCELRVKFSRSADAPAYKQGQNQLYNELNLGRREEYDVL DKRRGRDPEMGGKPRRKNPQEGLYNELQKDKMAEAYSEIGMKGERRRGKGHDGLYQGLST ATKDTYDALHMQALPPR |
| 45 | M7 (ScFv domain) | QVQLVQSGGGVVQPGRSLRLSCAAS<u>GFTFSSYAMH</u>WVRQ APGKGLEWVA<u>VISYDGSNKYYADSVKG</u>RFTISRDNSKNTLYLQMNSLRAEDTAVYYCAR<u>W KVSSSSPAFDY</u>WGQGTLVTVSS<u>GGGGSGGGGSGGGGSGGGGS</u>EIVLTQSPATLSLSPGER AILSC<u>RASQSVYTKYLG</u>WYQQKPGQAPRLLIY<u>DASTRAT</u>GIPDRFSGSGSGTDFTLTINR LEPEDFAVYYC<u>QHYGGSPLIT</u>FGQGTRLEIK |
| 69 | M7 >VE12-01CD (M7 VE12-01CD R001-A5 126167) | MALPVTALLLPLALLLHAARPQVQLVQSGGGVVQPGRSLRLSCAAS<u>GFTFSSYAMH</u>WVRQ APGKGLEWVA<u>VISYDGSNKYYADSVKG</u>RFTISRDNSKNTLYLQMNSLRAEDTAVYYCAR<u>W KVSSSSPAFDY</u>WGQGTLVTVSS<u>GGGGSGGGGSGGGGSGGGGS</u>EIVLTQSPATLSLSPGER AILSC<u>RASQSVYTKYLG</u>WYQQKPGQAPRLLIY<u>DASTRAT</u>GIPDRFSGSGSGTDFTLTINR LEPEDFAVYYC<u>QHYGGSPLIT</u>FGQGTRLEIKTTTPAPRPPTPAPTIASQPLSLRPEACRP AAGGAVHTRGLDFACDIYIWAPLAGTCGVLLLSLVITLYCKRGRKKLLYIFKQPFMRPVQ TTQEEDGCSCRFPEEEEGGCELRVKFSRSADAPAYKQGQNQLYNELNLGRREEYDVLDKR RGRDPEMGGKPRRKNPQEGLYNELQKDKMAEAYSEIGMKGERRRGKGHDGLYQGLSTATK DTYDALHMQALPPR |
| 46 | M8 (ScFv domain) | QVQLQQSGAEVKKPGASVKVSCKTS<u>GYPFTGYSLH</u>WVRQ APGQGLEWMG<u>WINPNSGGTNYAQKFQG</u>RVTMTRDTSISTAYMELSRLRSDDTAVYYCAR<u>D HYGGNSLFY</u>WGQGTLVTVSS<u>GGGGSGGGGSGGGGSGGGGS</u>DIQLTQSPSSISASVGDTVS ITC<u>RASQDSGTWLA</u>WYQQKPGKAPNLLMY<u>DASTLED</u>GVPSRFSGSASGTEFTLTVNRLQP EDSATYYC<u>QQYNSYPLT</u>FGGGTKVDIK |
| 70 | M8 >LE13-05XD (M8 LE13-05XD R001-E5 126168) | MALPVTALLLPLALLLHAARPQVQLQQSGAEVKKPGASVKVSCKTS<u>GYPFTGYSLH</u>WVRQ APGQGLEWMG<u>WINPNSGGTNYAQKFQG</u>RVTMTRDTSISTAYMELSRLRSDDTAVYYCAR<u>D HYGGNSLFY</u>WGQGTLVTVSS<u>GGGGSGGGGSGGGGSGGGGS</u>DIQLTQSPSSISASVGDTVS ITC<u>RASQDSGTWLA</u>WYQQKPGKAPNLLMY<u>DASTLED</u>GVPSRFSGSASGTEFTLTVNRLQP EDSATYYC<u>QQYNSYPLT</u>FGGGTKVDIKTTTPAPRPPTPAPTIASQPLSLRPEACRPAAGG AVHTRGLDFACDIYIWAPLAGTCGVLLLSLVITLYCKRGRKKLLYIFKQPFMRPVQTTQE EDGCSCRFPEEEEGGCELRVKFSRSADAPAYKQGQNQLYNELNLGRREEYDVLDKRRGRD PEMGGKPRRKNPQEGLYNELQKDKMAEAYSEIGMKGERRRGKGHDGLYQGLSTATKDTYD ALHMQALPPR |
| 47 | M9 (ScFv domain) | QVQLVQSGAEVKKPGASVEVSCKAS<u>GYTFTSYYMH</u>WVRQ APGQGLEWMG<u>IINPSGGSTGYAQKFQG</u>RVTMTRDTSTSTVHMELSSLRSEDTAVYYCAR<u>G GYSSSSDAFDI</u>WGQGTMVTVSS<u>GGGGSGGGGSGGGGSGGGGS</u>DIQMTQSPPSLSASVGDR VTITC<u>RASQDISSALA</u>WYQQKPGTPPKLLIY<u>DASSLES</u>GVPSRFSGSGSGTDFTLTISSL QPEDFATYYC<u>QQFSSYPLT</u>FGGGTRLEIK |
| 71 | M9 >BE15-00SD (M9 BE15-00SD R001-A3 126169) | MALPVTALLLPLALLLHAARPQVQLVQSGAEVKKPGASVEVSCKAS<u>GYTFTSYYMH</u>WVRQ APGQGLEWMG<u>IINPSGGSTGYAQKFQG</u>RVTMTRDTSTSTVHMELSSLRSEDTAVYYCAR<u>G GYSSSSDAFDI</u>WGQGTMVTVSS<u>GGGGSGGGGSGGGGSGGGGS</u>DIQMTQSPPSLSASVGDR VTITC<u>RASQDISSALA</u>WYQQKPGTPPKLLIY<u>DASSLES</u>GVPSRFSGSGSGTDFTLTISSL QPEDFATYYC<u>QQFSSYPLT</u>FGGGTRLEIKTTTPAPRPPTPAPTIASQPLSLRPEACRPAA GGAVHTRGLDFACDIYIWAPLAGTCGVLLLSLVITLYCKRGRKKLLYIFKQPFMRPVQTT QEEDGCSCRFPEEEEGGCELRVKFSRSADAPAYKQGQNQLYNELNLGRREEYDVLDKRRG RDPEMGGKPRRKNPQEGLYNELQKDKMAEAYSEIGMKGERRRGKGHDGLYQGLSTATKDT YDALHMQALPPR |
| 48 | M10 (ScFv domain) | QVQLVQSGAEVKKPGASVKVSCKAS<u>GYTFTSYGIS</u>WVRQ APGQGLEWMG<u>WISAYNGNTNYAQKLQG</u>RVTMTTDTSTSTAYMELRSLSDDTAVYYCAR<u>V AGGIYYYYGMDV</u>WGQGTTITVSS<u>GGGGSGGGGSGGGGSGGGGS</u>DIVMTQTPDSLAVSLGE RATISC<u>KSSHSVLYNRNNKNYLA</u>WYQQKPGQPPKLLFY<u>WASTRKS</u>GVPDRFSGSGSGTDF TLTISSLQPEDFATYFC<u>QQTQTFPLT</u>FGQGTRLEIN |

-continued

| SEQ ID NO: | Description | Amino Acid Sequence |
|---|---|---|
| 72 | M10 >RE16-05MD (M10 RE16-05MD R001-D10 126170) | MALPVTALLLPLALLLHAARPQVQLVQSGAEVKKPGASVKVSCKAS<u>GYTFTSYGIS</u>WVRQ APGQGLEWMG<u>WISAYNGNTNYAQKLQ</u>GRVTMTDTSTAYMELRSLRSDDTAVYYCAR<u>V AGGIYYYYGMD</u>VWGQGTTITVSS<u>GGGGSGGGGSGGGGSGGGGS</u>DIVMTQTPDSLAVSLGE RATISC<u>KSSHSVLYNRNNKNY</u>LAWYQQKPGQPPKLLFY<u>WASTRKS</u>GVPDRFSGSGSGTDF TLTISSLQPEDFATYFC<u>QQTQTFPLT</u>FGQGTRLEINTTTPAPRPPTPAPTIASQPLSLRP EACRPAAGGAVHTRGLDFACDIYIWAPLAGTCGVLLLSLVITLYCKRGRKKLLYIFKQPF MRPVQTTQEEDGCSCRFPEEEEGGCELRVKFSRSADAPAYKQGQNQLYNELNLGRREEYD VLDKRRGRDPEMGGKPRRKNPQEGLYNELQKDKMAEAYSEIGMKGERRRGKGHDGLYQGL STATKDTYDALHMQALPPR |
| 49 | M11 (ScFv domain) | QVQLQQSGAEVKKPGASVKVSCKAS<u>GYTFTGYYMH</u>WVRQ APGQGLEWMG<u>WINPNSGGTNYAQNFQ</u>GRVTMTRDTSISTAYMELRRLRSDDTAVYYCAS<u>G WDFDY</u>WGQGTLVTVSS<u>GGGGSGGGGSGGGGSGGGGS</u>DIRMTQSPSSLSASVGDRVTITC<u>R ASQSIRYYLS</u>WYQQKPGKAPKLLIY<u>TASILQN</u>GVPSRFSGSGSGTDFTLTISSLQPEDFA TYYC<u>LQTYTTPD</u>FGPGTKVEIK |
| 73 | M11 >NE10-19WD (M11 NE10-19WD R001-G2 126171) | MALPVTALLLPLALLLHAARPQVQLQQSGAEVKKPGASVKVSCKAS<u>GYTFTGYYMH</u>WVRQ APGQGLEWMG<u>WINPNSGGTNYAQNFQ</u>GRVTMTRDTSISTAYMELRRLRSDDTAVYYCAS<u>G WDFDY</u>WGQGTLVTVSS<u>GGGGSGGGGSGGGGSGGGGS</u>DIRMTQSPSSLSASVGDRVTITC<u>R ASQSIRYYLS</u>WYQQKPGKAPKLLIY<u>TASILQN</u>GVPSRFSGSGSGTDFTLTISSLQPEDFA TYYC<u>LQTYTTPD</u>FGPGTKVEIKTTTPAPRPPTPAPTIASQPLSLRPEACRPAAGGAVHTR GLDFACDIYIWAPLAGTCGVLLLSLVITLYCKRGRKKLLYIFKQPFMRPVQTTQEEDGCS CRFPEEEEGGCELRVKFSRSADAPAYKQGQNQLYNELNLGRREEYDVLDKRRGRDPEMGG KPRRKNPQEGLYNELQKDKMAEAYSEIGMKGERRRGKGHDGLYQGLSTATKDTYDALHMQ ALPPR |
| 50 | M12 (ScFv domain) | QVQLVQSGAEVKKPGASVKVSCKAS<u>GYTFTGYYMH</u>WVRQ APGQGLEWMG<u>RINPNSGGTNYAQKFQ</u>GRVTMTDTSTAYMELRSLRSDDTAVYYCAR<u>T TTSYAFDI</u>WGQGTMVTVSS<u>GGGGSGGGGSGGGGSGGGGS</u>DIQLTQSPSTLSASVGDRVTI TC<u>RASQSISTWLA</u>WYQQKPGKAPNLLIY<u>KASTLES</u>GVPSRFSGSGSGTEFTLTISSLQPD DFATYYC<u>QQYNTYSPYT</u>FGQGTKLEIK |
| 74 | M12 >DE12-14RD (M12 DE12-14RD R001-G9 126172) | MALPVTALLLPLALLLHAARPQVQLVQSGAEVKKPGASVKVSCKAS<u>GYTFTGYYMH</u>WVRQ APGQGLEWMG<u>RINPNSGGTNYAQKFQ</u>GRVTMTDTSTAYMELRSLRSDDTAVYYCAR<u>T TTSYAFDI</u>WGQGTMVTVSS<u>GGGGSGGGGSGGGGSGGGGS</u>DIQLTQSPSTLSASVGDRVTI TC<u>RASQSISTWLA</u>WYQQKPGKAPNLLIY<u>KASTLES</u>GVPSRFSGSGSGTEFTLTISSLQPD DFATYYC<u>QQYNTYSPYT</u>FGQGTKLEIKTTTPAPRPPTPAPTIASQPLSLRPEACRPAAGG AVHTRGLDFACDIYIWAPLAGTCGVLLLSLVITLYCKRGRKKLLYIFKQPFMRPVQTTQE EDGCSCRFPEEEEGGCELRVKFSRSADAPAYKQGQNQLYNELNLGRREEYDVLDKRRGRD PEMGGKPRRKNPQEGLYNELQKDKMAEAYSEIGMKGERRRGKGHDGLYQGLSTATKDTYD ALHMQALPPR |
| 51 | M13 (ScFv domain) | QVQLVQSGGGLVKPGGSLRLSCEAS<u>GFIFSDYYMG</u>WIRQ APGKGLEWVS<u>YIGRSGSSMYYADSVK</u>GRFTFSRDNAKNSLYLQMNSLRAEDTAVYYCAA<u>S PVVAATEDFQH</u>WGQGTLVTVSS<u>GGGGSGGGGSGGGGSGGGGS</u>DIVMTQTPATLSLSPGER ATLSC<u>RASQSVTSNYLA</u>WYQQKPGQAPRLLLF<u>GASTRAT</u>GIPDRFSGSGSGTDFTLTINR LEPEDFAMYYC<u>QQYGSAPVT</u>FGQGTKLEIK |
| 75 | M13 >TE13-19LD (M13 TE13-19LD R002-C3 126173) | MALPVTALLLPLALLLHAARPQVQLVQSGGGLVKPGGSLRLSCEAS<u>GFIFSDYYMG</u>WIRQ APGKGLEWVS<u>YIGRSGSSMYYADSVK</u>GRFTFSRDNAKNSLYLQMNSLRAEDTAVYYCAA<u>S PVVAATEDFQH</u>WGQGTLVTVSS<u>GGGGSGGGGSGGGGSGGGGS</u>DIVMTQTPATLSLSPGER ATLSC<u>RASQSVTSNYLA</u>WYQQKPGQAPRLLLF<u>GASTRAT</u>GIPDRFSGSGSGTDFTLTINR LEPEDFAMYYC<u>QQYGSAPVT</u>FGQGTKLEIKTTTPAPRPPTPAPTIASQPLSLRPEACRPA AGGAVHTRGLDFACDIYIWAPLAGTCGVLLLSLVITLYCKRGRKKLLYIFKQPFMRPVQT TQEEDGCSCRFPEEEEGGCELRVKFSRSADAPAYKQGQNQLYNELNLGRREEYDVLDKRR GRDPEMGGKPRRKNPQEGLYNELQKDKMAEAYSEIGMKGERRRGKGHDGLYQGLSTATKD TYDALHMQALPPR |
| 52 | M14 (ScFv domain) | QVQLVQSGAEVRAPGASVKISCKAS<u>GFTFRGYYIH</u>WVRQ APGQGLEWMG<u>IINPSGGSRAYAQKFQ</u>GRVTMTRDTSTSTVYMELSSLRSDDTAMYYCAR<u>T ASCGGDCYYLDY</u>WGQGTLVTVSS<u>GGGGSGGGGSGGGGSGGGGS</u>DIQMTQSPPTLSASVGD RVTITC<u>RASENVNIWLA</u>WYQQKPGKAPKLLIY<u>KSSSLAS</u>GVPSRFSGSGSGAEFTLTISS LQPDDFATYYC<u>QQYQSYPLT</u>FGGGTKVDIK |
| 76 | M14 >BS83-95ID (M14 | MALPVTALLLPLALLLHAARPQVQLVQSGAEVRAPGASVKISCKAS<u>GFTFRGYYIH</u>WVRQ APGQGLEWMG<u>IINPSGGSRAYAQKFQ</u>GRVTMTRDTSTSTVYMELSSLRSDDTAMYYCAR<u>T ASCGGDCYYLDY</u>WGQGTLVTVSS<u>GGGGSGGGGSGGGGSGGGGS</u>DIQMTQSPPTLSASVGD |

| SEQ ID NO: | Description | Amino Acid Sequence |
|---|---|---|
| | BS83-95ID R001-E8 126174) | RVTITC<u>RASENVNIW</u>LAWYQQKPGKAPKLLIY<u>KSSSLAS</u>GVPSRFSGSGSGAEFTLTISS LQPDDFATYYC<u>QQYQSYPLT</u>FGGGTKVDIKTTTPAPRPPTPAPTIASQPLSLRPEACRPA AGGAVHTRGLDFACDIYIWAPLAGTCGVLLLSLVITLYCKRGRKKLLYIFKQPFMRPVQT TQEEDGCSCRFPEEEEGGCELRVKFSRSADAPAYKQGQNQLYNELNLGRREEYDVLDKRR GRDPEMGGKPRRKNPQEGLYNELQKDKMAEAYSEIGMKGERRRGKGHDGLYQGLSTATKD TYDALHMQALPPR |
| 53 | M15 (ScFv domain) | QVQLVQSGGGLVQPGRSLRLSCAAS<u>GFTFDDYAMH</u>WVRQ APGKGLEWVS<u>GISWNSGSIGYADSVK</u>GRFTISRDNAKNSLYLQMNSLRAEDTAVYYCAK<u>D GSSSWSWGYFD</u>YWGQGTLVTVSS<span style="background:#ddd">GGGGSGGGGSGGGGS</span>SELTQDPAVSVALGQTVRTTC <u>QGDALRSYYAS</u>WYQQKPGQAPMLVIY<u>GKNNRPS</u>GIPDRFSGSDSGDTASLTITGAQAEDE ADYYC<u>NSRDSSGYPV</u>FGTGTKVTVL |
| 77 | M15 >H586-94XD (M15 HS86-94XD NT 127553) | MALPVTALLLPLALLLHAARPQVQLVQSGGGLVQPGRSLRLSCAAS<u>GFTFDDYAMH</u>WVRQ APGKGLEWVS<u>GISWNSGSIGYADSVK</u>GRFTISRDNAKNSLYLQMNSLRAEDTAVYYCAK<u>D GSSSWSWGYFD</u>YWGQGTLVTVSS<span style="background:#ddd">GGGGSGGGGSGGGGS</span>SELTQDPAVSVALGQTVRTTC <u>QGDALRSYYAS</u>WYQQKPGQAPMLVIY<u>GKNNRPS</u>GIPDRFSGSDSGDTASLTITGAQAEDE ADYYC<u>NSRDSSGYPV</u>FGTGTKVTVLTTTPAPRPPTPAPTIASQPLSLRPEACRPAAGGAV HTRGLDFACDIYIWAPLAGTCGVLLLSLVITLYCKRGRKKLLYIFKQPFMRPVQTTQEED GCSCRFPEEEEGGCELRVKFSRSADAPAYKQGQNQLYNELNLGRREEYDVLDKRRGRDPE MGGKPRRKNPQEGLYNELQKDKMAEAYSEIGMKGERRRGKGHDGLYQGLSTATKDTYDAL HMQALPPR |
| 54 | M16 (ScFv domain) | EVQLVESGGGLVQPGRSLRLSCAAS<u>GFTFDDYAMH</u>WVRQ APGKGLEWVS<u>GISWNSGSTGYADSVK</u>GRFTISRDNAKNSLYLQMNSLRAEDTALYYCAK<u>D SSSWYGGGSAFD</u>IWGQGTMVTVSS<span style="background:#ddd">GGGGSGGGGSGGGGS</span>SELTQEPAVSVALGQTVRIT C<u>QGDSLRSYYAS</u>WYQQKPGQAPVLVIF<u>GRSRRPS</u>GIPDRFSGSSSGNTASLIITGAQAED EADYYC<u>NSRDNTANHYV</u>FGTGTKLTVL |
| 78 | M16 >XS87-99RD (M16 XS87-99RD NT 127554) | MALPVTALLLPLALLLHAARPEVQLVESGGGLVQPGRSLRLSCAAS<u>GFTFDDYAMH</u>WVRQ APGKGLEWVS<u>GISWNSGSTGYADSVK</u>GRFTISRDNAKNSLYLQMNSLRAEDTALYYCAK<u>D SSSWYGGGSAFD</u>IWGQGTMVTVSS<span style="background:#ddd">GGGGSGGGGSGGGGS</span>SELTQEPAVSVALGQTVRIT C<u>QGDSLRSYYAS</u>WYQQKPGQAPVLVIF<u>GRSRRPS</u>GIPDRFSGSSSGNTASLIITGAQAED EADYYC<u>NSRDNTANHYV</u>FGTGTKLTVLTTTPAPRPPTPAPTIASQPLSLRPEACRPAAGG AVHTRGLDFACDIYIWAPLAGTCGVLLLSLVITLYCKRGRKKLLYIFKQPFMRPVQTTQE EDGCSCRFPEEEEGGCELRVKFSRSADAPAYKQGQNQLYNELNLGRREEYDVLDKRRGRD PEMGGKPRRKNPQEGLYNELQKDKMAEAYSEIGMKGERRRGKGHDGLYQGLSTATKDTYD ALHMQALPPR |
| 55 | M17 (ScFv domain) | EVQLVESGGGLVQPGRSLRLSCAAS<u>GFTFDDYAMH</u>WVRQ APGKGLEWVS<u>GISWNSGSTGYADSVK</u>GRFTISRDNAKNSLYLQMNSLRAEDTALYYCAK<u>D SSSWYGGGSAFD</u>IWGQGTMVTVSS<span style="background:#ddd">GGGGSGGGGSGGGGS</span>SELTQDPAVSVALGQTVRIT C<u>QGDSLRSYYAS</u>WYQQKPGQAPVLVIY<u>GKNNRPS</u>GIPDRFSGSSSGNTASLTITGAQAED EADYYC<u>NSRGSSGNHYV</u>FGTGTKVTVL |
| 79 | M17 >NS89-94MD (M17 NS89-94MD NT 127555) | MALPVTALLLPLALLLHAARPEVQLVESGGGLVQPGRSLRLSCAAS<u>GFTFDDYAMH</u>WVRQ APGKGLEWVS<u>GISWNSGSTGYADSVK</u>GRFTISRDNAKNSLYLQMNSLRAEDTALYYCAK<u>D SSSWYGGGSAFD</u>IWGQGTMVTVSS<span style="background:#ddd">GGGGSGGGGSGGGGS</span>SELTQDPAVSVALGQTVRIT C<u>QGDSLRSYYAS</u>WYQQKPGQAPVLVIY<u>GKNNRPS</u>GIPDRFSGSSSGNTASLTITGAQAED EADYYC<u>NSRGSSGNHYV</u>FGTGTKVTVLTTTPAPRPPTPAPTIASQPLSLRPEACRPAAGG AVHTRGLDFACDIYIWAPLAGTCGVLLLSLVITLYCKRGRKKLLYIFKQPFMRPVQTTQE EDGCSCRFPEEEEGGCELRVKFSRSADAPAYKQGQNQLYNELNLGRREEYDVLDKRRGRD PEMGGKPRRKNPQEGLYNELQKDKMAEAYSEIGMKGERRRGKGHDGLYQGLSTATKDTYD ALHMQALPPR |
| 56 | M18 (ScFv domain) | QVQLVQSGGGLVQPGGSLRLSCAAS<u>GFTFSSYWMH</u>WVRQ APGKGLVWVS<u>RINSDGSSTSYADSVK</u>GRFTISRDNAKNTLYLQMNSLRAEDTAVYYCVR<u>T GWVGSYYYYMDV</u>WGKGTTVTVSS<span style="background:#ddd">GGGGSGGGGSGGGGSGGGGS</span>EIVLTQSPGTLSLSPGE RATLSC<u>RASQSVSSNYLA</u>WYQQKPGQPPRLLIY<u>DVSTRAT</u>GIPARFSGGGSGTDFTLTIS SLEPEDFAVYYC<u>QQRSNWPPWT</u>FGQGTKVEIK |
| 80 | M18 >DS90-09HD (M18 DS90-09HD R003-A05 127556) | MALPVTALLLPLALLLHAARPQVQLVQSGGGLVQPGGSLRLSCAAS<u>GFTFSSYWMH</u>WVRQ APGKGLVWVS<u>RINSDGSSTSYADSVK</u>GRFTISRDNAKNTLYLQMNSLRAEDTAVYYCVR<u>T GWVGSYYYYMDV</u>WGKGTTVTVSS<span style="background:#ddd">GGGGSGGGGSGGGGSGGGGS</span>EIVLTQSPGTLSLSPGE RATLSC<u>RASQSVSSNYLA</u>WYQQKPGQPPRLLIY<u>DVSTRAT</u>GIPARFSGGGSGTDFTLTIS SLEPEDFAVYYC<u>QQRSNWPPWT</u>FGQGTKVEIKTTTPAPRPPTPAPTIASQPLSLRPEACR PAAGGAVHTRGLDFACDIYIWAPLAGTCGVLLLSLVITLYCKRGRKKLLYIFKQPFMRPV |

-continued

| SEQ ID NO: | Description | Amino Acid Sequence |
|---|---|---|
| | | QTTQEEDGCSCRFPEEEEGGCELRVKFSRSADAPAYKQGQNQLYNELNLGRREEYDVLDK RRGRDPEMGGKPRRKNPQEGLYNELQKDKMAEAYSEIGMKGERRRGKGHDGLYQGLSTAT KDTYDALHMQALPPR |
| 57 | M19 (ScFv domain) | QVQLVQSGGGVVQPGRSLRLSCAASGFTFSSYGMHWVRQ APGKGLEWVAVISYDGSNKYYADSVKGRFTISRDNSKNTLYLQMNSLRAEDTAVYYCAKG YSRYYYYGMDVWGQGTTVTVSSGGGGSGGGGSGGGGSGGGGSEIVMTQSPATLSLSPGER AILSCRASQSVYTKYLGWYQQKPGQAPRLLIYDASTRATGIPDRFSGSGSGTDFTLTINR LEPEDFAVYYCQHYGGSPLITFGQGTKVDIK |
| 81 | M19 >TS92-04BD (M19 TS92-04BD R003-C06 127557) | MALPVTALLLPLALLLHAARPQVQLVQSGGGVVQPGRSLRLSCAASGFTFSSYGMHWVRQ APGKGLEWVAVISYDGSNKYYADSVKGRFTISRDNSKNTLYLQMNSLRAEDTAVYYCAKG YSRYYYYGMDVWGQGTTVTVSSGGGGSGGGGSGGGGSGGGGSEIVMTQSPATLSLSPGER AILSCRASQSVYTKYLGWYQQKPGQAPRLLIYDASTRATGIPDRFSGSGSGTDFTLTINR LEPEDFAVYYCQHYGGSPLITFGQGTKVDIKTTTPAPRPPTPAPTIASQPLSLRPEACRP AAGGAVHTRGLDFACDIYIWAPLAGTCGVLLLSLVITLYCKRGRKKLLYIFKQPFMRPVQ TTQEEDGCSCRFPEEEEGGCELRVKFSRSADAPAYKQGQNQLYNELNLGRREEYDVLDKR RGRDPEMGGKPRRKNPQEGLYNELQKDKMAEAYSEIGMKGERRRGKGHDGLYQGLSTATK DTYDALHMQALPPR |
| 58 | M20 (ScFv domain) | QVQLVQSGGGLVQPGGSLRLSCAASGFTFSSYAMSWVRQ APGKGLEWVSAISGSGGSTYYADSVKGRFTISRDNSKNTLYLQMNSLRAEDTAVYYCAKR EAAAGHDWYFDLWGRGTLVTVSSGGGGSGGGGSGGGGSGGGGSDIRVTQSPSSLSASVGD RVTITCRASQSISSYLNWYQQKPGKAPKLLIYAASSLQSGVPSRFSGSGSGTDFTLTISS LQPEDFATYYCQQSYSIPLTFGQGTKVEIK |
| 82 | M20 >JS93-08WD (M20 JS93-08WD R003-E07 127558) | MALPVTALLLPLALLLHAARPQVQLVQSGGGLVQPGGSLRLSCAASGFTFSSYAMSWVRQ APGKGLEWVSAISGSGGSTYYADSVKGRFTISRDNSKNTLYLQMNSLRAEDTAVYYCAKR EAAAGHDWYFDLWGRGTLVTVSSGGGGSGGGGSGGGGSGGGGSDIRVTQSPSSLSASVGD RVTITCRASQSISSYLNWYQQKPGKAPKLLIYAASSLQSGVPSRFSGSGSGTDFTLTISS LQPEDFATYYCQQSYSIPLTFGQGTKVEIKTTTPAPRPPTPAPTIASQPLSLRPEACRPA AGGAVHTRGLDFACDIYIWAPLAGTCGVLLLSLVITLYCKRGRKKLLYIFKQPFMRPVQT TQEEDGCSCRFPEEEEGGCELRVKFSRSADAPAYKQGQNQLYNELNLGRREEYDVLDKRR GRDPEMGGKPRRKNPQEGLYNELQKDKMAEAYSEIGMKGERRRGKGHDGLYQGLSTATKD TYDALHMQALPPR |
| 275 | Ss1 (scFv domain) | QVQLQQSGPELEKPGASVKISCKASGYSFTGYTMNWVKQSHGKSLEWIGLITPYNGASS YNQKFRGKATLTVDKSSSTAYMDLLSLTSEDSAVYFCARGGYDGRGFDYWGQGTTVTVS SGGGGSGGGGSGGGGSDIELTQSPAIMSASPGEKVTMTCSASSSVSYMHWYQQKSGTSP KRWIYDTSKLASGVPGRFSGSGSGNSYSLTISSVEAEDDATYYCQQWSGYPLTFGAGTK LEI |
| 391 | Ss1 (full) | MALPVTALLLPLALLLHAARPQVQLQQSGPELEKPGASVKISCKASGYSFTGYTMNWVK QSHGKSLEWIGLITPYNGASSYNQKFRGKATLTVDKSSSTAYMDLLSLTSEDSAVYFCA RGGYDGRGFDYWGQGTTVTVSSGGGGSGGGGSGGGGSDIELTQSPAIMSASPGEKVTMT CSASSSVSYMHWYQQKSGTSPKRWIYDTSKLASGVPGRFSGSGSGNSYSLTISSVEAED DATYYCQQWSGYPLTFGAGTKLEITTTPAPRPPTPAPTIASQPLSLRPEACRPAAGGAV HTRGLDFACDIYIWAPLAGTCGVLLLSLVITLYCKRGRKKLLYIFKQPFMRPVQTTQEE DGCSCRFPEEEEGGCELRVKFSRSADAPA |

TABLE 3

Nucleic Acid Sequences encoding CAR molecules (underlined is the leader sequence)

| SEQ ID NO: | Desc. | Nucleic Acid Sequence |
|---|---|---|
| 87 | M1 (ScFv domain) >ZA53-27BC (M1) | CAAGTCCAACTGCAGCAGTCAGGAGCGGAAGTGAAGAAACCAGGAGCGTCAGTCAAAGTGTCGTGCAAGGCTAGCGGCTA CACCTTCACCGGCTACTA CATGCACTGGGTTCGACAGGCTCCAGGGCAGGGTCTGGAGTGGATGGGCCGCATCAACCCGAATTCCGGTGGGACTAACT ACGCCCAGAAGTTCCAGGGAAGAGTGACCATGACTAGGGACACGTCGATCAGCACTGCGTACATGGAACTGAGCGCCTG CGGTCCGAGGATACTGCCGTCTACTACTGCGCACGCGGAAGGTACTATGGAATGGACGTGTGGGGCCAAGGGACTATGGT GACTGTGAGCTCGGGAGGGGGAGGGTCCGGTGGCGGGGATCAGGAGGAGGAGGATCAGGGGGGAGGAGGTTCCGAAATTG TCCTCACCCAGAGACCCGGCAACCCTCTCACTTTCCCGGGAGAGCGCGCAACCATCTCTTGCCGGGCTAGCCAATCCGTG TCGTCCAATTTCGCCTGGTACCAGCAACGGCCGGGACAAGCCCCTAGACTCCTGATCTACGACGCCAGCAACAGAGCGAC TGGAATTCCTCCACGCTTTTCGGGATCAGGCTCCGGTACCGACTTCACCCTGACTATCTCGTCGCTCGAACCCGAGGATT TCGCCGCCTACTACTGTCATCAGCGGTCGAACTGGTTGTATACGTTTGGCCAGGGCACCAAGGTGGATATCAAG |

TABLE 3-continued

Nucleic Acid Sequences encoding CAR molecules (underlined is the leader sequence)

| SEQ ID NO:Desc. | Nucleic Acid Sequence |
|---|---|
| 111M1 (Full) >ZA53-27BC (M1) | <u>ATGGCCCTCCCTGTCACCGCCCTGCTGCTTCCGCTGGCTCTTCTGCTCCACGCCGCTCGGCCC</u>CAAGTCCAACTGCAGCA<br>G<br>TCAGGAGCGGAAGTGAAGAAACCAGGAGCGTCAGTCAAAGTGTCGTGCAAGGCTAGCGGCTACACCTTCACCGGCTACTA<br>CATGCACTGGGTTCGACAGGCTCCAGGGCAGGGTCTGGAGTGGATGGGCCGCATCAACCCGAATTCCGGTGGGACTAACT<br>ACGCCCAGAAGTTCCAGGGAAGAGTGACCATGACTAGGGACACGTCGATCAGCACTGCGTACATGGAACTGAGCCGCCTG<br>CGGTCCGAGGATACTGCCGTCTACTACTGCGCACGCGGAAGGTACTATGGAATGGACGTGTGGGGCCAAGGGACTATGGT<br>GACTGTGAGCTCGGGAGGGGGAGGCTCCGGTGGCGGGGGATCAGGAGGAGGAGGATCAGGGGGAGGAGGTTCCGAAATTG<br>TCCTCACCCAGAGCCCGGCAACCCTCTCACTTTCCCGGGAGACCGCGCAACCATCTCTTGCCGGGCTAGCCAATCCGTG<br>TCGTCCAATTTCGCCTGGTACCAGCAACGGCCGGGACAAGCCCCTAGACTCCTGATCTACGACGCCAGCAACAGAGCGAC<br>TGGAATTCCTCCACGCTTTTCGGGATCAGGCTCCGGTACCGACTTCACCCTGACTATCTCGTCGCTCGAACCCGAGGATT<br>TCGCCGCCTACTACTGTCATCAGCGGTCGAACTGGTTGTATACCTTTGGCCAGGGCACCAAGGTGGATATCAAGACCACT<br>ACCCCAGCACCGAGGCCACCCACCCCGGCTCCTACCATCGCCTCCCAGCCTCTGTCCCTGCGTCCGGAGGCATGTAGACC<br>CGCAGCTGGTGGGCCGTGCATACCCGGGTCTTGACTTCGCCTGCGATATCTACATTTGGGCCCCTCTGGCTGGTACTT<br>GCGGGGTCCTGCTGCTTTCACTCGTGATCACTCTTTACTGTAAGCGCGGTCGGAAGAAGCTGCTGTACATCTTTAAGCAA<br>CCCTTCATGAGGCCTGTGCAGACTACTCAAGAGGAGGACGGCTGTTCATGCCGGTTCCCAGAGGAGGAGGAAGGCGCTG<br>CGAACTGCGCGTGAAATTCAGCCGCAGCGCAGATGCTCCAGCCTACAAGCAGGGGCAGAACCAGCTCTACAACGAACTCA<br>ATCTTGGTCGGAGAGAGGAGTACGACGTGCTGGACAAGCGGAGAGGACGGGACCCAGAAATGGGCGGGAAGCCGCGCAGA<br>AAGAATCCCCAAGAGGGCCTGTACAACGAGCTCCAAAAGGATAAGATGGCAGAAGCCTATAGCGAGATTGGTATGAAAGG<br>GGAACGCAGAAGAGGCAAAGGCCACGACGGACTGTACCAGGGACTCAGCACCGCCACCAAGGACACCTATGACGCTCTTC<br>ACATGCAGGCCCTGCCGCCTCGG |
| 88M2 (ScFv domain) >FA56-26RC (M2) | CAAGTCCAACTCGTCCAGTCAGGAGCAGAAGTCAAGAAACCAGGTGCTAGCGTGAAAGTGTCGTGCAAGGCGTCGGGATA<br>CACTTTCACCGGATACTAC<br>ATGCACTGGGTCCGCCAGGCCCCCGGACAAGGACTGGAATGGATGGGCTGGATCAACCCGAATAGCGGGGGAACTAATTA<br>CGCCCAGAAGTTTCAGGGACGAGTGACCATGACCCGCGATACCTCTATCTCGACCGCCTACATGGAGCTCTCCAGACTGC<br>GCTCCGACGATACTGCAGTGTACTACTGCGCCCGGGACCTGAGGCGGACTGTGGTTACTCCTCGCGCCTATATGGCATG<br>GACGTGTGGGGCCAAGGAACTACTGTGACTGTGAGCTCGGGAGGCGGTGGGTCAGGCGGAGGAGGGTCGGGCGGTGGTGG<br>CTCGGGAGGGGGAGGAAGCGACATTCAACTTACGCAGAGCCCGTCAACCCTGTCAGCGTCAGTGGGAGATCGGGTGACCA<br>TCACGTGTCAGGCCAGCCAGGATATCTCCAACTCGCTCAACTGGTACCAGCAAAAGGCGGGTAAAGCTCCGAAGCTGCTG<br>ATCTACGACGCTTCCACCCTCGAGACTGGAGTCCCATCCAGATTTTCCGGGTCAGGAAGCGGCACCGATTTCTCCTTCAC<br>CATTTCGTCCTTGCAACCGGAGGACATCGCAACCTACTACTGCCAGCAGCATGACAACTTGCCTCTGACGTTCGGGCAGG<br>GCACCAAGGTGGAAATCAAG |
| 112M2 (Full) >FA56-26RC (M2) | <u>ATGGCCCTCCCTGTCACCGCCCTGCTGCTTCCGCTGGCTCTTCTGCTCCACGCCGCTCGGCCC</u>CAAGTCCAACTCGTCCA<br>GTCAGGAGCAGAAGTCAAGAAACCAGGTGCTAGCGTGAAAGTGTCGTGCAAGGCGTCGGGATACACTTTCACCGGATACT<br>AC<br>ATGCACTGGGTCCGCCAGGCCCCCGGACAAGGACTGGAATGGATGGGCTGGATCAACCCGAATAGCGGGGGAACTAATTA<br>CGCCCAGAAGTTTCAGGGACGAGTGACCATGACCCGCGATACCTCTATCTCGACCGCCTACATGGAGCTCTCCAGACTGC<br>GCTCCGACGATACTGCAGTGTACTACTGCGCCCGGGACCTGAGGCGGACTGTGGTTACTCCTCGCGCCTATATGGCATG<br>GACGTGTGGGGCCAAGGAACTACTGTGACTGTGAGCTCGGGAGGCGGTGGGTCAGGCGGAGGAGGGTCGGGCGGTGGTGG<br>CTCGGGAGGGGGAGGAAGCGACATTCAACTTACGCAGAGCCCGTCAACCCTGTCAGCGTCAGTGGGAGATCGGGTGACCA<br>TCACGTGTCAGGCCAGCCAGGATATCTCCAACTCGCTCAACTGGTACCAGCAAAAGGCGGGTAAAGCTCCGAAGCTGCTG<br>ATCTACGACGCTTCCACCCTCGAGACTGGAGTCCCATCCAGATTTTCCGGGTCAGGAAGCGGCACCGATTTCTCCTTCAC<br>CATTTCGTCCTTGCAACCGGAGGACATCGCAACCTACTACTGCCAGCAGCATGACAACTTGCCTCTGACGTTCGGGCAGG<br>GCACCAAGGTGGAAATCAAGACCACTACCCCAGCACCGAGGCCACCCACCCCGGCTCCTACCATCGCCTCCCAGCCTCTG<br>TCCCTGCGTCCGGAGGCATGTAGACCCGCAGCTGGTGGGCCGTGCATACCCGGGTCTTGACTTCGCCTGCGATATCTA<br>CATTTGGGCCCCTCTGGCTGGTACTTGCGGGGTCCTGCTGCTTTCACTCGTGATCACTCTTTACTGTAAGCGCGGTCGGA<br>AGAAGCTGCTGTACATCTTTAAGCAACCCTTCATGAGGCCTGTGCAGACTACTCAAGAGGACGGCTGTTCATGCCGG<br>TTCCCAGAGGAGGAGGAAGGCGGCTGCGAACTGCGCGTGAAATTCAGCCGCAGCGCAGATGCTCCAGCCTACAAGCAGGG<br>GCAGAACCAGCTCTACAACGAACTCAATCTTGGTCGGAGAGAGGAGTACGACGTGCTGGACAAGCGGAGAGGACGGGACC<br>CAGAAATGGGCGGGAAGCCGCGCAGAAAGAATCCCCAAGAGGGCCTGTACAACGAGCTCCAAAAGGATAAGATGGCAGAA<br>GCCTATAGCGAGATTGGTATGAAAGGGGAACGCAGAAGAGGCAAAGGCCACGACGGACTGTACCAGGGACTCAGCACCGC<br>CACCAAGGACACCTATGACGCTCTTCACATGCAGGCCCTGCCGCCTCGG |
| 89M3 (ScFv domain) >VA58-21LC (M3) | CAAGTCCAACTCGTCCAA<br>TCAGGAGCGGAAGTCAAAAAGCCCGGAGCTCCAGTGAAAGTGTCATGCAAGGCCTCCGGCTACACCTTCACCGGTTACTA<br>TATGCACTGGGTGCGCCAGGCCCCGGGCCAGGGGTTGGAATGGATGGGATGGATCAATCCAAACTCGGGTGGGACTAACT<br>ACGCCCAGAAGTTCCAAGGACGGGTGACCATGACTAGGGACACCTCGATCTCCACCGCATACATGGAGCTTAGCAGACTC<br>CGCTCCGACGATACCGCAGTCTACTATTGCGCGCGGGGAGAGTGGGACGGATCGTACTACTACGATTACTGGGGCCAGGG<br>AACTCTGGTGACTGTTTCCTCGGGTGGAGGAGGTTCAGGCGGAGGCGGCTCGGGCGGGGAGGATCTGGAGGAGGAGGGT<br>CCGACATTGTGCTGACCCAAACTCCTTCGTCCCTGTCGGCCAGCGTGGGCGACCGCGTGACGATTACGTGCAGAGCTAGC<br>CAATCCATCAATACTTACCTCAACTGGTACCAGCATAAGCCGGGAAAGCACCAAAGCTGCTGATCTACGCCGCCTCATC<br>CTTGCAGAGCGGTGTGCCTTCACGCTTTAGCGGATCGGGATCGGGAACGGATTTCACCCTGACTATCAGCTCCCTCCAGC<br>CGGAGGATTTTGCGACCTACTACTGTCAGCAGAGCTTCTCACCGCTGACTTTCGGCGGCGGGACCAAGCTGGAAATCAAG |
| 113M3 (Full) >VA58-21LC (M3) | <u>ATGGCCCTCCCTGTCACCGCCCTGCTGCTTCCGCTGGCTCTTCTGCTCCACGCCGCTCGGCCC</u>CAAGTCCAACTCGTCCA<br>A<br>TCAGGAGCGGAAGTCAAAAAGCCCGGAGCTCCAGTGAAAGTGTCATGCAAGGCCTCCGGCTACACCTTCACCGGTTACTA<br>TATGCACTGGGTGCGCCAGGCCCCGGGCCAGGGGTTGGAATGGATGGATGGATCAATCCAAACTCGGGTGGGACTAACT<br>ACGCCCAGAAGTTCCAAGGACGGGTGACCATGATTAGGGACACCTCGATCTCCACCGCATACATGGAGCTTAGCAGACTC<br>CGCTCCGACGATACCGCAGTCTACTATTGCGCGCGGGGAGAGTGGGACGGATCGTACTACTACGATTACTGGGGCCAGGG<br>AACTCTGGTGACTGTTTCCTCGGGTGGAGGAGGTTCAGGCGGAGGCGGCTCGGGCGGGGAGGATCTGGAGGAGGAGGGT<br>CCGACATTGTGCTGACCCAAACTCCTTCGTCCCTGTCGGCCAGCGTGGGCGACCGCGTGACGATTACGTGCAGAGCTAGC<br>CAATCCATCAATACTTACCTCAACTGGTACCAGCATAAGCCGGGAAAGCACCAAAGCTGCTGATCTACGCCGCCTCATC |

TABLE 3-continued

Nucleic Acid Sequences encoding CAR molecules (underlined is the leader sequence)

| SEQ ID NO:Desc. | Nucleic Acid Sequence |
|---|---|
| | CTTGCAGAGCGGTGTGCCTTCACGCTTTAGCGGATCGGGATCGGGAACGGATTTCACCCTGACTATCAGCTCCCTCCAGC CGGAGGATTTTGCGACCTACTACTGTCAGCAGAGCTTCTCACCGCTGACTTTCGGCGGCGGGACCAAGCTGGAAATCAAG ACCACTACCCCAGCACCGAGGCCACCCACCCCGGCTCCTACCATCGCCTCCCAGCCTCTGTCCCTGCGTCCGGAGGCATG TAGACCCGCAGCTGGTGGGGCCGTGCATACCCGGGGTCTTGACTTCGCCTGCGATATCTACATTTGGGCCCCTCTGGCTG GTACTTGCGGGGTCCTGCTGCTTTCACTCGTGATCACTCTTTACTGTAAGCGCGGTCGGAAGAAGCTGCTGTACATCTTT AAGCAACCCTTCATGAGGCCTGTGCAGACTACTCAAGAGGAGGACGGCTGTTCATGCCGGTTCCCAGAGGAGGAGGAAGG CGGCTGCGAACTGCGCGTGAAATTCAGCCGCAGCGCAGATGCTCCAGCCTACAAGCAGGGGCAGAACCAGCTCTACAACG AACTCAATCTTGGTCGGAGAGAGGAGTACGACGTGCTGGACAAGCGGAGAGGACGGGACCCAGAAATGGGCGGGAAGCCG CGCAGAAAGAATCCCCAAGAGGGCCTGTACAACGAGCTCCAAAAGGATAAGATGGCAGAAGCCTATAGCGAGATTGGTAT GAAAGGGGAACGCAGAAGAGGCAAAGGCCACGACGGACTGTACCAGGGACTCAGCACCGCCACCAAGGACACCTATGACG CTCTTCACATGCAGGCCCTGCCGCCTCGG |
| 90M4 (ScFv domain) >DP37- 07IC (M4) | CAAGTGCAACTCGTTGAA TCAGGTGGAGGTTTGGTGCAACCCGGAGGATCTCTCAGACTGTCGTGTGCGGCGTCCGGGTTCACCTTTTCGTCCTACTG GATGCACTGGGTGCGCCAGGTGCCGGGAAAAGGACTGGTGTGGGTGTCCAGAATCAACACCGACGGGTCAACGACTACCT ACGCAGATAGCGTGGAAGGTCGGTTCACCATTTCGCGGGACAACGCTAAAAACACTCTGTACCTTCAGATGAATTCACTG CGCGATGACGACACCGCAGTCTACTACTGCGTCGGTGGACACTGGGCGGTCTGGGGACAGGGAACTACGGTGACTGTGTC CAGCGGCGGGGAGGAAGCGGCGGAGGGGGAGCGGAGGCGGAGGATCAGGAGGAGGCGGCTCCGATATCCAGATGACCC AGTCGCCATCGACCCTCTCCGCTAGCGTGGGGGATAGGGTCACTATCACTTGCCGAGCCAGCCAATCCATTAGCGACCGG CTTGCCTGGTACCAACAGAAACCTGGAAAGGCCCCGAAGCTGCTCATCTACAAGGCCTCGTCACTGGAGTCGGGAGTCCC GTCCCGCTTTTCCGGCTCGGGCTCAGGCACCGAGTTCACTCTGACCATCTCGAGCCTGCAGCCGGACGATTTCGCCGTGT ATTACTGCCAGCAATACGGACATCTCCCAATGTACACGTTCGGTCAGGGCACCAAGGTCGAAATCAAG |
| 114M4 >DP37- 07IC (M4) | <u>ATGGCCCTCCCTGTCACCGCCCTGCTGCTTCCGCTGGCTCTTCTGCTCCACGCCGCTCGGCCC</u>AAGTGCAACTCGTTGA A TCAGGTGGAGGTTTGGTGCAACCCGGAGGATCTCTCAGACTGTCGTGTGCGGCGTCCGGGTTCACCTTTTCGTCCTACTG GATGCACTGGGTGCGCCAGGTGCCGGGAAAAGGACTGGTGTGGGTGTCCAGAATCAACACCGACGGGTCAACGACTACCT ACGCAGATAGCGTGGAAGGTCGGTTCACCATTTCGCGGGACAACGCTAAAAACACTCTGTACCTTCAGATGAATTCACTG CGCGATGACGACACCGCAGTCTACTACTGCGTCGGTGGACACTGGGCGGTCTGGGGACAGGGAACTACGGTGACTGTGTC CAGCGGCGGGGAGGAAGCGGCGGAGGGGGAGCGGAGGCGGAGGATCAGGAGGAGGCGGCTCCGATATCCAGATGACCC AGTCGCCATCGACCCTCTCCGCTAGCGTGGGGGATAGGGTCACTATCACTTGCCGAGCCAGCCAATCCATTAGCGACCGG CTTGCCTGGTACCAACAGAAACCTGGAAAGGCCCCGAAGCTGCTCATCTACAAGGCCTCGTCACTGGAGTCGGGAGTCCC GTCCCGCTTTTCCGGCTCGGGCTCAGGCACCGAGTTCACTCTGACCATCTCGAGCCTGCAGCCGGACGATTTCGCCGTGT ATTACTGCCAGCAATACGGACATCTCCCAATGTACACGTTCGGTCAGGGCACCAAGGTCGAAATCAAGACCACTACCCA GCACCGAGGCCACCCACCCCGGCTCCTACCATCGCCTCCCAGCCTCTGTCCCTGCGTCCGGAGGCATGTAGACCCGCAGC TGGTGGGGCCGTGCATACCCGGGGTCTTGACTTCGCCTGCGATATCTACATTTGGGCCCCTCTGGCTGGTACTTGCGGGG TCCTGCTGCTTTCACTCGTGATCACTCTTTACTGTAAGCGCGGTCGGAAGAAGCTGCTGTACATCTTTAAGCAACCCTTC ATGAGGCCTGTGCAGACTACTCAAGAGGAGGACGGCTGTTCATGCCGGTTCCCAGAGGAGGAGGAAGGCGGCTGCGAACT GCGCGTGAAATTCAGCCGCAGCGCAGATGCTCCAGCCTACAAGCAGGGGCAGAACCAGCTCTACAACGAACTCAATCTTG GTCGGAGAGAGGAGTACGACGTGCTGGACAAGCGGAGAGGACGGGACCCAGAAATGGGCGGGAAGCCGCGCAGAAAGAAT CCCCAAGAGGGCCTGTACAACGAGCTCCAAAAGGATAAGATGGCAGAAGCCTATAGCGAGATTGGTATGAAAGGGGAACG CAGAAGAGGCAAAGGCCACGACGGACTGTACCAGGGACTCAGCACCGCCACCAAGGACACCTATGACGCTCTTCACATGC AGGCCCTGCCGCCTCGG |
| 91M5 (ScFv domain) >XP31- 20LC (M5) | CAAGTCCAACTCGTTCAATCAGGCGCAGAAGTCGAAAAGCCCGGAGCATCAGTCAAAGTCTCTTGCAAGGCTTCCGGCTA CACCTTCACGGACTACTAC ATGCACTGGGTGCGCCAGGCTCCAGGCCAGGGACTGGAGTGGATGGGATGGATCAACCCGAATTCCGGGGGAACTAACTA CGCCCAGAAGTTTCAGGGCCGGGTGACTATGACTCGCGATACCTCGATCTCGACTGCGTACATGGAGCTCAGCCGCCTCC GGTCGGACGATACCGCCGTGTACTATTGTGCGTCGGGATGGGACTTCGACTACTGGGGGCAGGGCACTCTGGTCACTGTG TCAAGCGGAGGAGGTGGATCAGGTGGAGGTGGAAGCGGGGGAGGAGGTTCCGGCGGCGGAGGATCAGATATCGTGATGAC GCAATCGCCTTCCTCGTTGTCCGCATCCGTGGGAGACAGGGTGACCATTACTTGCAGAGCGTCCCAGTCCATTCGGTACT ACCTGTCGTGGTACCAGCAGAAGCCGGGAAAGCCCCAAAACTGCTTATCTATACTGCCTCGATCCTCCAAAACGGCGTG CCATCAAGATTCAGCGGTTCGGGCAGCGGGACCGACTTTACCCTGACTATCAGCAGCCTGCAGCCGGAAGATTTCGCCAC GTACTACTGCCTGCAAACCTACACCACCCCGGACTTCGGACCTGGAACCAAGGTGGAGATCAAG |
| 115M5 (Full) >XP31- 20LC (M5) | <u>ATGGCCCTCCCTGTCACCGCCCTGCTGCTTCCGCTGGCTCTTCTGCTCCACGCCGCTCGGCCC</u>AAGTCCAACTCGTTCA ATCAGGCGCAGAAGTCGAAAAGCCCGGAGCATCAGTCAAAGTCTCTTGCAAGGCTTCCGGCTACACCTTCACGGACTACT AC ATGCACTGGGTGCGCCAGGCTCCAGGCCAGGGACTGGAGTGGATGGGATGGATCAACCCGAATTCCGGGGGAACTAACTA CGCCCAGAAGTTTCAGGGCCGGGTGACTATGACTCGCGATACCTCGATCTCGACTGCGTACATGGAGCTCAGCCGCCTCC GGTCGGACGATACCGCCGTGTACTATTGTGCGTCGGGATGGGACTTCGACTACTGGGGGCAGGGCACTCTGGTCACTGTG TCAAGCGGAGGAGGTGGATCAGGTGGAGGTGGAAGCGGGGGAGGAGGTTCCGGCGGCGGAGGATCAGATATCGTGATGAC GCAATCGCCTTCCTCGTTGTCCGCATCCGTGGGAGACAGGGTGACCATTACTTGCAGAGCGTCCCAGTCCATTCGGTACT ACCTGTCGTGGTACCAGCAGAAGCCGGGAAAGCCCCAAAACTGCTTATCTATACTGCCTCGATCCTCCAAAACGGCGTG CCATCAAGATTCAGCGGTTCGGGCAGCGGGACCGACTTTACCCTGACTATCAGCAGCCTGCAGCCGGAAGATTTCGCCAC GTACTACTGCCTGCAAACCTACACCACCCCGGACTTCGGACCTGGAACCAAGGTGGAGATCAAGACCACTACCCAGCAC CGAGGCCACCCACCCCGGCTCCTACCATCGCCTCCCAGCCTCTGTCCCTGCGTCCGGAGGCATGTAGACCCGCAGCTGGT GGGGCCGTGCATACCCGGGGTCTTGACTTCGCCTGCGATATCTACATTTGGGCCCCTCTGGCTGGTACTTGCGGGGTCCT GCTGCTTTCACTCGTGATCACTCTTTACTGTAAGCGCGGTCGGAAGAAGCTGCTGTACATCTTTAAGCAACCCTTCATGA GGCCTGTGCAGACTACTCAAGAGGAGGACGGCTGTTCATGCCGGTTCCCAGAGGAGGAGGAAGGCGGCTGCGAACTGCGC GTGAAATTCAGCCGCAGCGCAGATGCTCCAGCCTACAAGCAGGGGCAGAACCAGCTCTACAACGAACTCAATCTTGGTCG GAGAGAGGAGTACGACGTGCTGGACAAGCGGAGAGGACGGGACCCAGAAATGGGCGGGAAGCCGCGCAGAAAGAATCCCC |

TABLE 3-continued

Nucleic Acid Sequences encoding CAR molecules (underlined is the leader sequence)

| SEQ ID NO:Desc. | Nucleic Acid Sequence |
|---|---|
| | AAGAGGGCCTGTACAACGAGCTCCAAAAGGATAAGATGGCAGAAGCCTATAGCGAGATTGGTATGAAAGGGGAACGCAGA<br>AGAGGCAAAGGCCACGACGGACTGTACCAGGGACTCAGCACCGCCACCAAGGACACCTATGACGCTCTTCACATGCAGGC<br>CCTGCCGCCTCGG |
| 92 M6<br>(ScFv<br>domain)<br>>FE10-<br>06ID<br>(M6) | CAAGTGCAACTCGTCCAGTCAGGTGCAGAAGTGAAGAAACCCGGAGCGTCAGTCAAAGTGTCATGCAAGGCGTCAGGCTA<br>CACCTTCACCAGCTACTAC<br>ATGCACTGGGTGCGGCAGGCCCCAGGCCAAGGCTTGGAGTGGATGGGAATCATTAACCCGTCAGGAGGCTCCACCTCCTA<br>CGCCCAGAAGTTTCAGGGAAGAGTGACGATGACTCGGGATACGTCGACCTCGACCGTGTACATGGAACTGAGCTCGCTGC<br>GCTCCGAGGACACTGCTGTGTACTACTGCGCACGGTACAGACTCATTGCCGTGGCAGGAGACTACTACTACTATGGCATG<br>GACGTCTGGGGGCAGGGCACTATGGTCACTGTGTCGTCCGGCGGAGGAGGCTCGGGTGGAGGAGGTAGCGGAGGAGGGGG<br>AAGCGGAGGGGGGGGCTCCGATATCCAGATGACTCAGTCGCCTTCCTCCGTGTCGGCCTCGGTTGGAGATCGCGTCACCA<br>TCACTTGTCGAGCTTCCCAAGGAGTCGGTAGGTGGCTGGCGTGGTACCAGCAAAAGCCGGGAACTGCCCCGAAGCTCCTG<br>ATCTACGCGGCTAGCACCCTGCAGTCGGGAGTGCCATCCCGCTTCAGCGGATCTGGGTCAGGTACCGACTTCACCCTTAC<br>GATCAACAATCTCCAGCCGGAGGACTTTGCCACCTATTACTGCCAACAGGCCAACAGCTTCCCTCTGACTTTCGGAGGGG<br>GCACTCGCCTGGAAATCAAG |
| 116 M6<br>(Full)<br>>FE10-<br>06ID<br>(M6) | <u>ATGGCCCTCCCTGTCACCGCCCTGCTGCTTCCGCTGGCTCTTCTGCTCCACGCCGCTCGG</u>CCCCAAGTGCAACTCGTCCA<br>GTCAGGTGCAGAAGTGAAGAAACCCGGAGCGTCAGTCAAAGTGTCATGCAAGGCGTCAGGCTACACCTTCACCAGCTACT<br>AC<br>ATGCACTGGGTGCGGCAGGCCCCAGGCCAAGGCTTGGAGTGGATGGGAATCATTAACCCGTCAGGAGGCTCCACCTCCTA<br>CGCCCAGAAGTTTCAGGGAAGAGTGACGATGACTCGGGATACGTCGACCTCGACCGTGTACATGGAACTGAGCTCGCTGC<br>GCTCCGAGGACACTGCTGTGTACTACTGCGCACGGTACAGACTCATTGCCGTGGCAGGAGACTACTACTACTATGGCATG<br>GACGTCTGGGGGCAGGGCACTATGGTCACTGTGTCGTCCGGCGGAGGAGGCTCGGGTGGAGGAGGTAGCGGAGGAGGGGG<br>AAGCGGAGGGGGGGGCTCCGATATCCAGATGACTCAGTCGCCTTCCTCCGTGTCGGCCTCGGTTGGAGATCGCGTCACCA<br>TCACTTGTCGAGCTTCCCAAGGAGTCGGTAGGTGGCTGGCGTGGTACCAGCAAAAGCCGGGAACTGCCCCGAAGCTCCTG<br>ATCTACGCGGCTAGCACCCTGCAGTCGGGAGTGCCATCCCGCTTCAGCGGATCTGGGTCAGGTACCGACTTCACCCTTAC<br>GATCAACAATCTCCAGCCGGAGGACTTTGCCACCTATTACTGCCAACAGGCCAACAGCTTCCCTCTGACTTTCGGAGGGG<br>GCACTCGCCTGGAAATCAAGACCACTACCCAGCACCGAGGCCACCCACCCCGGCTCCTACCATCGCCTCCCAGCCTCTG<br>TCCCTGCGTCCGGAGGCATGTAGACCCGCAGCTGGTGGGCCGTGCATACCCGGGGTCTTGACTTCGCCTGCGATATCTA<br>CATTTGGGCCCCTCTGGCTGGTACTTGCGGGGTCCTGCTGCTTTCACTCGTGATCACTCTTTACTGTAAGCGCGGTCGGA<br>AGAAGCTGCTGTACATCTTTAAGCAACCCTTCATGAGGCCTGTGCAGACTACTCAAGAGGAGGACGGCTGTTCATGCCGG<br>TTCCCAGAGGAGGAGGAAGGCGGCTGCGAACTGCGCGTGAAATTCAGCCGCGACGCCAGATGCTCCAGCCTACAAGCAGGG<br>GCAGAACCAGCTCTACAACGAACTCAATCTTGGTCGGAGAGAGGAGTACGACGTGCTGGACAAGCGGAGAGGACGGGACC<br>CAGAAATGGGCGGAAGCCGCGCAGAAAGAATCCCCAAGAGGGCCTGTACAACGAGCTCCAAAAGGATAAGATGGCAGAA<br>GCCTATAGCGAGATTGGTATGAAAGGGGAACGCAGAAGAGGCAAAGGCCACGACGGACTGTACCAGGGACTCAGCACCGC<br>CACCAAGGACACCTATGACGCTCTTCACATGCAGGCCCTGCCGCCTCGG |
| 93 M7<br>(ScFv<br>domain)<br>>VE12-<br>01CD<br>(M7) | CAAGTGCAATTGGTTCAA<br>TCAGGAGGAGGAGTGGTGCAACCTGGAAGATCTCTCAGACTGTCGTGTGCGGCATCGGGATTCACTTTCTCATCATACGC<br>AATGCACTGGGTCCGCCAGGCCCCGGGCAAAGGCTTGGAATGGGTGGCGGTCATTTCATACGACGGCTCGAACAAGTACT<br>ACGCTGACAGCGTGAAGGGACGCTTTACTATTTCCCGGGACAATTCGAAGAACACTCTGTACCTCCAGATGAACTCCCTT<br>AGGGCTGAGGACACCGCCGTCTACTACTGCGCACGCTGGAAAGTGTCGTCCAGCTCCCCAGCTTTTGACTACTGGGGACA<br>GGGAACCCTTGTGACCGTGTCGTCCGGTGGAGGGGGAAGCGGCGGAGGGGGATCAGGTGGCGGCGGATCGGGAGGCGGGG<br>GATCAGAAATCGTGCTGACTCAGTCCCCGGCCACGCTGTCTCTCAGCCCGGGAGAAGAGAGCGATCCTGTCCTGCCGCGCC<br>TCGCAGAGCGTGTACACTAAGTACCTGGGGTGGTACCAGCAGAAACCGGGTCAAGCGCCTCGGCTGCTGATCTACGATGC<br>CTCCACCCGGGCCACCGGAATCCCCGATCGGTTCTCCGGCAGCGGCTCGGGAACTGATTTCACGCTGACCATCAATCGCC<br>TGGAGCCGGAAGATTTCGCCGTCTATTACTGCCAGCATTACGGCGGGAGCCCACTCATCACCTTCGGTCAAGGAACCCGA<br>CTCGAAATCAAG |
| 117 M7<br>(Full)<br>>VE12-<br>01CD<br>(M7) | <u>ATGGCCCTCCCTGTCACCGCCCTGCTGCTTCCGCTGGCTCTTCTGCTCCACGCCGCTCGG</u>CCCCAAGTGCAATTGGTTCA<br>A<br>TCAGGAGGAGGAGTGGTGCAACCTGGAAGATCTCTCAGACTGTCGTGTGCGGCATCGGGATTCACTTTCTCATCATACGC<br>AATGCACTGGGTCCGCCAGGCCCCGGGCAAAGGCTTGGAATGGGTGGCGGTCATTTCATACGACGGCTCGAACAAGTACT<br>ACGCTGACAGCGTGAAGGGACGCTTTACTATTTCCCGGGACAATTCGAAGAACACTCTGTACCTCCAGATGAACTCCCTT<br>AGGGCTGAGGACACCGCCGTCTACTACTGCGCACGCTGGAAAGTGTCGTCCAGCTCCCCAGCTTTTGACTACTGGGGACA<br>GGGAACCCTTGTGACCGTGTCGTCCGGTGGAGGGGGAAGCGGCGGAGGGGGATCAGGTGGCGGCGGATCGGGAGGCGGGG<br>GATCAGAAATCGTGCTGACTCAGTCCCCGGCCACGCTGTCTCTCAGCCCGGGAGAAGAGAGCGATCCTGTCCTGCCGCGCC<br>TCGCAGAGCGTGTACACTAAGTACCTGGGGTGGTACCAGCAGAAACCGGGTCAAGCGCCTCGGCTGCTGATCTACGATGC<br>CTCCACCCGGGCCACCGGAATCCCCGATCGGTTCTCCGGCAGCGGCTCGGGAACTGATTTCACGCTGACCATCAATCGCC<br>TGGAGCCGGAAGATTTCGCCGTCTATTACTGCCAGCATTACGGCGGGAGCCCACTCATCACCTTCGGTCAAGGAACCCGA<br>CTCGAAATCAAGACCACTACCCAGCACCGAGGCCACCCACCCCGGCTCCTACCATCGCCTCCCAGCCTCTGTCCCTGCG<br>TCCGGAGGCATGTAGACCCGCAGCTGGTGGGCCGTGCATACCCGGGTCTTGACTTCGCCTGCGATATCTACATTTGGG<br>CCCCTCTGGCTGGTACTTGCGGGGTCCTGCTGCTTTCACTCGTGATCACTCTTTACTGTAAGCGCGGTCGGAAGAAGCTG<br>CTGTACATCTTTAAGCAACCCTTCATGAGGCCTGTGCAGACTACTCAAGAGGAGGACGGCTGTTCATGCCGGTTCCCAGA<br>GGAGGAGGAAGGCGGCTGCGAACTGCGCGTGAAATTCAGCCGCAGCGCAGATGCTCCAGCCTACAAGCAGGGCAGAACC<br>AGCTCTACAACGAACTCAATCTTGGTCGGAGAGAGGAGTACGACGTGCTGGACAAGCGGAGAGGACGGGACCCAGAAATG<br>GGCGGAAGCCGCGCAGAAAGAATCCCCAAGAGGGCCTGTACAACGAGCTCCAAAAGGATAAGATGGCAGAAGCCTATAG<br>CGAGATTGGTATGAAAGGGGAACGCAGAAGAGGCAAAGGCCACGACGGACTGTACCAGGGACTCAGCACCGCCACCAAGG<br>ACACCTATGACGCTCTTCACATGCAGGCCCTGCCGCCTCGG |
| 94 M8<br>(ScFv<br>domain)<br>>LE13- | CAAGTCCAACTCCAGCAG<br>TCAGGTGCAGAAGTCAAAAAGCCAGGAGCATCCGTGAAGGTTTCGTGCAAGACTTCCGGCTACCCTTTTACCGGGTACTC<br>CCTCCATTGGGTGAGACAAGCACCGGGCCAGGGACTGGAGTGGATGGGATGGATCAACCCAAATTCGGGCGGCACCAACT<br>ATGCGCAGAAGTTCCAGGGACGGGTGACCATGACTCGCGACACTTCGATCTCCACTGCCTACATGGAGCTGTCCCGCTTG |

TABLE 3-continued

Nucleic Acid Sequences encoding CAR molecules (underlined is the leader sequence)

| SEQ ID NO:Desc. | Nucleic Acid Sequence |
|---|---|
| 05XD (M8) | AGATCTGACGACACGGCCGTCTACTACTGCGCCCGGGATCACTACGGAGGTAATTCGCTGTTCTACTGGGGGCAGGGAAC<br>CCTTGTGACTGTGTCCTCGGGTGGTGGAGGGTCAGGAGGCGGAGGCTCAGGGGGAGGAGGTAGCGGAGGAGGCGGATCAG<br>ACATCCAACTGACCCAGTCACCATCCTCCATCTCGGCTAGCGTCGGAGACACCGTGTCGATTACTTGTAGGGCCTCCCAA<br>GACTCAGGGACGTGGCTGGCGTGGTATCAGCAAAAACCGGGCAAAGCTCCGAACCTGTTGATGTACGACGCCAGCACCCT<br>CGAAGATGGAGTGCCTAGCCGCTTCAGCGGAAGCGCCTCGGGCACTGAATTCACGCTGACTGTGAATCGGCTCCAGCCGG<br>AGGATTCGGCGACCTACTACTGCCAGCAGTACAACAGCTACCCCCTGACCTTTGGAGGCGGGACCAAGGTGGATATCAAG |
| 118M8 (Full) >LE13-05XD (M8) | <u>ATGGCCCTCCCTGTCACCGCCCTGCTGCTTCCGCTGGCTCTTCTGCTCCACGCCGCTCGGCCC</u>AAGTCCAACTCCAGCA<br>G<br>TCAGGTGCAGAAGTCAAAAAGCCAGGAGCATCCGTGAAGGTTTCGTGCAAGACTTCCGGCTACCCTTTTACCGGGTACTC<br>CCTCCATTGGGTGAGACAAGCACCGGGCCAGGATTGGAGTGGATGGGATGGATCAACCCAAATTCGGGCGGCACCAACT<br>ATGCGCAGAAGTTCCAGGGACGGGTGACCATGACTCGCGACACTTCGATCTCCACTGCCTACATGGAGCTGTCCCGCTTG<br>AGATCTGACGACACGGCCGTCTACTACTGCGCCCGGGATCACTACGGAGGTAATTCGCTGTTCTACTGGGGGCAGGGAAC<br>CCTTGTGACTGTGTCCTCGGGTGGTGGAGGGTCAGGAGGCGGAGGCTCAGGGGGAGGAGGTAGCGGAGGAGGCGGATCAG<br>ACATCCAACTGACCCAGTCACCATCCTCCATCTCGGCTAGCGTCGGAGACACCGTGTCGATTACTTGTAGGGCCTCCCAA<br>GACTCAGGGACGTGGCTGGCGTGGTATCAGCAAAAACCGGGCAAAGCTCCGAACCTGTTGATGTACGACGCCAGCACCCT<br>CGAAGATGGAGTGCCTAGCCGCTTCAGCGGAAGCGCCTCGGGCACTGAATTCACGCTGACTGTGAATCGGCTCCAGCCGG<br>AGGATTCGGCGACCTACTACTGCCAGCAGTACAACAGCTACCCCCTGACCTTTGGAGGCGGGACCAAGGTGGATATCAAG<br>ACCACTACCCAGCACCGAGGCCACCCACCCCGGCTCCTACCATCGCCTCCCAGCCTCTGTCCCTGCGTCCGGAGGCATG<br>TAGACCCGCAGCTGGTGGGGCCGTGCATACCCGGGGTCTTGACTTCGCCTGCGATATCTACATTTGGGCCCCTCTGGCTG<br>GTACTTGCGGGGTCCTGCTGCTTTCACTCGTGATCACTCTTTACTGTAAGCGCGGTCGGAAGAAGCTGCTGTACATCTTT<br>AAGCAACCCTTCATGAGGCCTGTGCAGACTACTCAAGAGGAGGACGGCTGTTCATGCCGGTTCCCAGAGGAGGAGGAAGG<br>CGGCTGCGAACTGCGCGTGAAATTCAGCCGCAGCGCAGATGCTCCAGCCTACAAGCAGGGGCAGAACCAGCTCTACAACG<br>AACTCAATCTTGGTCGGAGAGAGGAGTACGACGTGCTGGACAAGCGGAGAGGACGGGACCCAGAAATGGGCGGGAAGCCG<br>CGCAGAAAGAATCCCAAGAGGGCCTGTACAACGAGCTCCAAAAGGATAAGATGGCAGAAGCCTATAGCGAGATTGGTAT<br>GAAAGGGGAACGCAGAAGAGGCAAAGGCCACGACGGACTGTACCAGGGACTCAGCACCGCCACCAAGGACACCTATGACG<br>CTCTTCACATGCAGGCCCTGCCGCCTCGG |
| 95M9 (ScFv domain) >BE15-00SD (M9) | CAAGTGCAACTCGTCCAG<br>TCAGGTGCAGAAGTGAAGAAACCAGGAGCGTCCGTCGAAGTGTCGTGTAAGGCGTCCGGCTACACTTTCACCTCGTACTA<br>CATGCACTGGGTGCGGCAGGCCCCGGGACAAGGCCTCGAATGGATGGGAATCATCAACCCGAGCGGAGGCTCGACTGGTT<br>ACGCCCAGAAGTTCCAGGGAAGGGTGACGATGACCCGCGATACCTCGACTTCGACCGTTCATATGGAGCTCTCGTCCCTG<br>CGGAGCGAGGACACTGCTGTCTACTATTGCGCGCGGGGAGGATACTCTAGCTCCTCCGATGCATTTGACATTTGGGGCCA<br>GGGAACTATGGTGACCGTGTCATCAGGCGGAGGTGGATCAGGAGGAGGAGGTCGGGAGGGGGAGGCAGCGGCGGGGGTG<br>GGTCGGACATTCAGATGACGCAGTCCCCTCCTAGCCTGAGCGCCTCGGTGGGTGACAGAGTGACCATCACTTGCAGAGCC<br>TCGCAAGACATCTCCTCCGCATTGGCTTGGTACCAGCAAAAGCCGGGCACTCCGCCGAAACTGCTCATCTACGATGCCTC<br>CTCACTGGAGTCAGGAGTCCCATCTCGCTTCTCGGGGTCAGGAAGCGGCACCGATTTTACCCTTACCATCTCCAGCCTGC<br>AGCCCGAGGACTTCGCCACGTACTACTGCCAACAGTTCAGCTCCTACCCACTGACCTTCGGGGGCGGAACTCGCCTGGAA<br>ATCAAG |
| 119M9 (Full) >BE15-00SD (M9) | <u>ATGGCCCTCCCTGTCACCGCCCTGCTGCTTCCGCTGGCTCTTCTGCTCCACGCCGCTCGGCCC</u>AAGTGCAACTCGTCCA<br>G<br>TCAGGTGCAGAAGTGAAGAAACCAGGAGCGTCCGTCGAAGTGTCGTGTAAGGCGTCCGGCTACACTTTCACCTCGTACTA<br>CATGCACTGGGTGCGGCAGGCCCCGGGACAAGGCCTCGAATGGATGGGAATCATCAACCCGAGCGGAGGCTCGACTGGTT<br>ACGCCCAGAAGTTCCAGGGAAGGGTGACGATGACCCGCGATACCTCGACTTCGACCGTTCATATGGAGCTCTCGTCCCTG<br>CGGAGCGAGGACACTGCTGTCTACTATTGCGCGCGGGGAGGATACTCTAGCTCCTCCGATGCATTTGACATTTGGGGCCA<br>GGGAACTATGGTGACCGTGTCATCAGGCGGAGGTGGATCAGGAGGAGGAGGTCGGGAGGGGGAGGCAGCGGCGGGGGTG<br>GGTCGGACATTCAGATGACGCAGTCCCCTCCTAGCCTGAGCGCCTCGGTGGGTGACAGAGTGACCATCACTTGCAGAGCC<br>TCGCAAGACATCTCCTCCGCATTGGCTTGGTACCAGCAAAAGCCGGGCACTCCGCCGAAACTGCTCATCTACGATGCCTC<br>CTCACTGGAGTCAGGAGTCCCATCTCGCTTCTCGGGGTCAGGAAGCGGCACCGATTTTACCCTTACCATCTCCAGCCTGC<br>AGCCCGAGGACTTCGCCACGTACTACTGCCAACAGTTCAGCTCCTACCCACTGACCTTCGGGGGCGGAACTCGCCTGGAA<br>ATCAAGACCACTACCCAGCACCGAGGCCACCCACCCCGGCTCCTACCATCGCCTCCCAGCCTCTGTCCCTGCGTCCGGA<br>GGCATGTAGACCCGCAGCTGGTGGGGCCGTGCATACCCGGGGTCTTGACTTCGCCTGCGATATCTACATTTGGGCCCCTC<br>TGGCTGGTACTTGCGGGGTCCTGCTGCTTTCACTCGTGATCACTCTTTACTGTAAGCGCGGTCGGAAGAAGCTGCTGTAC<br>ATCTTTAAGCAACCCTTCATGAGGCCTGTGCAGACTACTCAAGAGGAGGACGGCTGTTCATGCCGGTTCCCAGAGGAGGA<br>GGAAGGCGGCTGCGAACTGCGCGTGAAATTCAGCCGCAGCGCAGATGCTCCAGCCTACAAGCAGGGGCAGAACCAGCTCT<br>ACAACGAACTCAATCTTGGTCGGAGAGAGGAGTACGACGTGCTGGACAAGCGGAGAGGACGGGACCCAGAAATGGGCGGG<br>AAGCCGCGCAGAAAGAATCCCAAGAGGGCCTGTACAACGAGCTCCAAAAGGATAAGATGGCAGAAGCCTATAGCGAGAT<br>TGGTATGAAAGGGGAACGCAGAAGAGGCAAAGGCCACGACGGACTGTACCAGGGACTCAGCACCGCCACCAAGGACACCT<br>ATGACGCTCTTCACATGCAGGCCCTGCCGCCTCGG |
| 96M10 (ScFv domain) >RE16-05MD (M10) | CAAGTGCAACTCGTCCAGAGCGGAGCAGAAGTCAAGAAGCCAGGAGCGTCAGTGAAAGTGTCATGCAAGGCCAGCGGCTA<br>TACCTTTACTTCGTATGGG<br>ATCTCCTGGGTGCGGCAGGCACCGGGCCAAGGACTGGAGTGGATGGGATGGATCTCAGCCTACAACGGTAACACCAACTA<br>CGCCCAGAAGCTGCAAGGACGCGTGACCATGACTACTGATACGAGCACCTCCACTGCCTACATGGAATTGCGGTCCCTTC<br>GGTCGGACGATACTGCTGTGTACTACTGCGCAAGAGTCGCCGGAGGGATTCATACTACTACGGCATGGACGTCTGGGGA<br>CAGGGAACCACCATTACGGTGTCGAGCGGAGGAGGCTCGGGGGAGGAGGAAGCGGAGGTGGCGGCTCGGGGGCGG<br>CGGATCGGACATTGTGATGACCCAGACTCCTGACTCCTGGCTGTTTCGTTGGGAGAGCGCGCGACTATCTCGTGTAAGT<br>CCAGCCACTCAGTCCTGTACAATGCAATAACAAGAACTACCTCGCGTGGTACCAGCAAAAACGGGTCAGCCGCCTAAA<br>CTCCTGTTCTACTGGGCCTCCACCAGAAAGAGCGGGGTGCCAGATCGATTCTCTGGATCAGGATCAGGTACCGACTTTAC<br>GCTGACCATCTCGTCCCTGCAGCCGGAGGATTTCGCGACTTACTTCTGCCAGCAGACTCAGACTTTCCCCCTCACCTTCG<br>GTCAAGGCACCAGGCTGGAAATCAAT |

TABLE 3-continued

Nucleic Acid Sequences encoding CAR molecules (underlined is the leader sequence)

| SEQ ID NO:Desc. | Nucleic Acid Sequence |
|---|---|
| 120M10 (Full) >RE16-05MD (M10) | <u>ATGGCCCTCCCTGTCACCGCCCTGCTGCTTCCGCTGGCTCTTCTGCTCCACGCCGCTCGGCCCC</u>AAGTGCAACTCGTCCA GAGCGGAGCAGAAGTCAAGAAGCCAGGAGCGTCAGTGAAAGTGTCATGCAAGGCCAGCGGCTATACCTTTACTTCGTATG GG ATCTCCTGGGTGCGGCAGGCACCGGGCCAAGGACTGGAGTGGATGGGATGGATCTCAGCCTACAACGGTAACACCAACTA CGCCCAGAAGCTGCAAGGACGCGTGACCATGACTACTGATACGAGCACCTCCACTGCCTACATGGAATTGCGGTCCCTTC GGTCGGACGATACTGCTGTGTACTACTGCGCAAGAGTCGCCGGAGGGATCTACTACTACTACGGCATGGACGTCTGGGGA CAGGGAACCACCATTACGGTGTCGAGCGGAGGGGGAGGCTCGGGGGAGGAGGAAGCGGAGGTGGCGGCTCCGGGGCGG CGGATCGGACATTGTGATGACCCAGACTCCTGACTCCCTGGCTGTTTCGTTGGGAGAGCGCGCGACTATCTCGTGTAAGT CCAGCCACTCAGTCCTGTACAATCGCAATAACAAGAACTACCTCGCGTGGTACCAGCAAAAACCGGGTCAGCCGCCTAAA CTCCTGTTCTACTGGGCCTCCACCAGAAAGAGCGGGGTGCCAGATCGATTCTCTGGATCAGGATCAGGTACCGACTTTAC GCTGACCATCTCGTCCCTGCAGCCGGAGGATTTCGCGACTTACTTCTGCCAGCAGACTCAGACTTTCCCCCTCACCTTCG GTCAAGGCACCAGGCTGGAAATCAATACCACTACCCCAGCACCGAGGCACCCACCCCGGCTCCTACCATCGCCTCCCAG CCTCTGTCCCTGCGTCCGAGGCATGTAGACCCGCAGCTGGTGGGGCCGTGCATACCCGGGGTCTTGACTTCGCCTGCGA TATCTACATTTGGGCCCCTCTGGCTGGTACTTGCGGGGTCCTGCTGCTTTCACTCGTGATCACTCTTTACTGTAAGCGCG GTCGGAAGAAGCTGCTGTACATCTTTAAGCAACCCTTCATGAGGCCTGTGCAGACTACTCAAGAGGAGGACGGCTGTTCA TGCCGGTTCCCAGAGGAGGAGGAAGGCGGCTGCGAACTGCGCGTGAAATTCAGCCGCAGCGCAGATGCTCCAGCCTACA AGCAGGGGCAGAACCAGCTCTACAACGAACTCAATCTTGGTCGGAGAGAGGAGTACGACGTGCTGGACAAGCGGAGAGGAC GGGACCCAGAAATGGGCGGGAAGCCGCGCAGAAAGAATCCCCAAGAGGGCCTGTACAACGAGCTCCAAAAGGATAAGATG GCAGAAGCCTATAGCGAGATTGGTATGAAAGGGGAACGCAGAAGAGGCAAAGGCCACGACGGACTGTACCAGGGACTCAG CACCGCCACCAAGGACACCTATGACGCTCTTCACATGCAGGCCCTGCCGCCTCGG |
| 97M11 (ScFv domain) >NE10-19WD (M11) | CAAGTCCAATTGCAGCAGAGCGGAGCAGAAGTGAAGAAGCCAGGAGCGTCAGTCAAAGTGTCGTGTAAGGCGTCAGGATA CACCTTCACGGGATACTAC ATGCACTGGGTGCGCCAGGCCCCGGGCCAAGGACTCGAGTGGATGGGCTGGATCAACCCTAACTCTGGAGGCACCAACTA CGCCCAGAATTTCCAAGGCAGAGTGACCATGACCCGGGACACCTCCATCTCGACTGCCTATATGGAACTGCGGCGGCTGC GCTCGGACGATACTGCTGTGTATTACTGCGCCAGCGGCTGGGACTTTGACTACTGGGGACAGGGTACTCTGGTGACTGTT TCCTCGGGAGGAGGCGGATCGGGTGGAGGAGGTAGCGGGGGAGGGGGCTCGGGAGGCGGAGGCAGCGATATTCGCATGAC TCAATCGCCGTCCTCCCTGAGCGCTAGCGTGGGAGATCGAGTCACCATCACTTGCAGAGCGTCACAGTCGATTCGCTACT ACCTGTCCTGGTACCAGCAGAAACCGGGAAAGGCACCAAAGCTTCTGATCTACACGGCCTCCATCCTGCAAATGGTGTC CCATCAAGGTTCTCCGGGTCAGGGAGCGGCACTGACTTCACTCTCACCATCTCCTCACTCCAGCCCGAGGACTTTGCAAC CTACTACTGCCTCCAGACGTACACCACCCCCGGATTTCGGTCCTGGAACCAAGGTGGAAATCAAA |
| 121M11 (Full) >NE10-19WD (M11) | <u>ATGGCCCTCCCTGTCACCGCCCTGCTGCTTCCGCTGGCTCTTCTGCTCCACGCCGCTCGGCCCC</u>AAGTCCAATTGCAGCA GAGCGGAGCAGAAGTGAAGAAGCCAGGAGCGTCAGTCAAAGTGTCGTGTAAGGCGTCAGGATACACCTTCACGGGATACT AC ATGCACTGGGTGCGCCAGGCCCCGGGCCAAGGACTCGAGTGGATGGGCTGGATCAACCCTAACTCTGGAGGCACCAACTA CGCCCAGAATTTCCAAGGCAGAGTGACCATGACCCGGGACACCTCCATCTCGACTGCCTATATGGAACTGCGGCGGCTGC GCTCGGACGATACTGCTGTGTATTACTGCGCCAGCGGCTGGGACTTTGACTACTGGGGACAGGGTACTCTGGTGACTGTT TCCTCGGGAGGAGGCGGATCGGGTGGAGGAGGTAGCGGGGGAGGGGGCTCGGGAGGCGGAGGCAGCGATATTCGCATGAC TCAATCGCCGTCCTCCCTGAGCGCTAGCGTGGGAGATCGAGTCACCATCACTTGCAGAGCGTCACAGTCGATTCGCTACT ACCTGTCCTGGTACCAGCAGAAACCGGGAAAAGGCACCAAAGCTTCTGATCTACACGGCCTCCATCCTGCAAATGGTGTC CCATCAAGGTTCTCCGGGTCAGGGAGCGGCACTGACTTCACTCTCACCATCTCCTCACTCCAGCCCGAGGACTTTGCAAC CTACTACTGCCTCCAGACGTACACCACCCCCGGATTTCGGTCCTGGAACCAAGGTGGAAATCAAAACCACTACCCCAGCAC CGAGGCACCCACCCCGGCTCCTACCATCGCCTCCCAGCCTCTGTCCCTGCGTCCGGAGGCATGTAGACCCGCAGCTGGT GGGGCCGTGCATACCCGGGGTCTTGACTTCGCCTGCGATATCTACATTTGGGCCCCTCTGGCTGGTACTTGCGGGGTCCT GCTGCTTTCACTCGTGATCACTCTTTACTGTAAGCGCGGTCGGAAGAAGCTGCTGTACATCTTTAAGCAACCCTTCATGA GGCCTGTGCAGACTACTCAAGAGGAGGACGGCTGTTCATGCCGGTTCCCAGAGGAGGAGGAAGGCGGCTGCGAACTGCGC GTGAAATTCAGCCGCAGCGCAGATGCTCCAGCCTACAAGCAGGGGCAGAACCAGCTCTACAACGAACTCAATCTTGGTCG GAGAGAGGAGTACGACGTGCTGGACAAGCGGAGAGGACGGGACCCAGAAATGGGCGGGAAGCCGCGCAGAAAGAATCCCC AAGAGGGCCTGTACAACGAGCTCCAAAAGGATAAGATGGCAGAAGCCTATAGCGAGATTGGTATGAAAGGGGAACGCAGA AGAGGCAAAGGCCACGACGGACTGTACCAGGGACTCAGCACCGCCACCAAGGACACCTATGACGCTCTTCACATGCAGGC CCTGCCGCCTCGG |
| 98M12 (ScFv domain) >DE12-14RD (M12) | CAAGTCCAACTCGTCCAA AGCGGAGCAGAAGTCAAAAAGCCAGGAGCGTCGGTGAAAGTGTCTTGCAAAGCCAGCGGCTACACCTTCACGGGTTACTA CATGCACTGGGTGCGCCAGGCGCCCGGGCCAGGGGCTGGAGTGGATGGGCCGGATTAACCCTAACAGCGGGGGAACTAATT ACGCTCAGAAGTTCCAGGGTAGAGTCACCATGACTACGGACACTTCCACTTCCACCGCCTATATGGAACTGCGCTCCCTC CGCTCAGATGATACTGCCGTGTATTACTGCGCGCGGACTACCACGTCATACGCATTTGACATCTGGGGCCAGGGAACTAT GGTGACCGTGAGCTCGGGCGGAGGCGGTTCAGGGGGAGGAGGAAGCGGAGGAGGAGGATCGGGAGGAGGTGGCTCCGATA TCCAGCTGACTCAGTCCCCGAGCACCCTGTCGGCGTCGGTGGGGACAGGGTTACCATCACCTGTAGAGCTTCCCAATCC ATTTCGACTTGGCTGGCCTGGTACCAGCAAAAGCCGGGAAAGGCCCCTAATTTGCTTATCTACAAGGCATCGACCCTCGA AAGCGGTGTGCCCTCCCGGTTTTCGGGATCAGGATCAGGGACCGAGTTCACCCTGACCATCTCATCCCTCCAGCCGGACG ACTTCGCCACTTACTACTGCCAGCAGTACAACACCTACTCGCCATACACTTTCGGCCAAGGCACCAAGCTGGAGATCAAG |
| 122M12 (Full) >DE12-14RD (M12) | <u>ATGGCCCTCCCTGTCACCGCCCTGCTGCTTCCGCTGGCTCTTCTGCTCCACGCCGCTCGGCCCC</u>AAGTCCAACTCGTCCA A AGCGGAGCAGAAGTCAAAAAGCCAGGAGCGTCGGTGAAAGTGTCTTGCAAAGCCAGCGGCTACACCTTCACGGGTTACTA CATGCACTGGGTGCGCCAGGCGCCCGGGCCAGGGGCTGGAGTGGATGGGCCGGATTAACCCTAACAGCGGGGGAACTAATT ACGCTCAGAAGTTCCAGGGTAGAGTCACCATGACTACGGACACTTCCACTTCCACCGCCTATATGGAACTGCGCTCCCTC CGCTCAGATGATACTGCCGTGTATTACTGCGCGCGGACTACCACGTCATACGCATTTGACATCTGGGGCCAGGGAACTAT GGTGACCGTGAGCTCGGGCGGAGGCGGTTCAGGGGGAGGAGGAAGCGGAGGAGGAGGATCGGGAGGAGGTGGCTCCGATA TCCAGCTGACTCAGTCCCCGAGCACCCTGTCGGCGTCGGTGGGGACAGGGTTACCATCACCTGTAGAGCTTCCCAATCC ATTTCGACTTGGCTGGCCTGGTACCAGCAAAAGCCGGGAAAGGCCCCTAATTTGCTTATCTACAAGGCATCGACCCTCGA |

TABLE 3-continued

Nucleic Acid Sequences encoding CAR molecules (underlined is the leader sequence)

| SEQ ID NO:Desc. | Nucleic Acid Sequence |
|---|---|
| | AAGCGGTGTGCCCTCCCGGTTTTCGGGATCAGGATCAGGGACCGAGTTCACCCTGACCATCTCATCCCTCCAGCCGGACG ACTTCGCCACTTACTACTGCCAGCAGTACAACACCTACTCGCCATACACTTTCGGCCAAGGCACCAAGCTGGAGATCAAG ACCACTACCCCAGCACCGAGGCCACCCACCCCGGCTCCTACCATCGCCTCCCAGCCTCTGTCCCTGCGTCCGGAGGCATG TAGACCCGCAGCTGGTGGGGCCGTGCATACCCGGGGTCTTGACTTCGCCTGCGATATCTACATTTGGGCCCCTCTGGCTG GTACTTGCGGGGTCCTGCTGCTTTCACTCGTGATCACTCTTTACTGTAAGCGCGGTCGGAAGAAGCTGCTGTACATCTTT AAGCAACCCTTCATGAGGCCTGTGCAGACTACTCAAGAGGAGGACGGCTGTTCATGCCGGTTCCCAGAGGAGGAGGAAGG CGGCTGCGAACTGCGCGTGAAATTCAGCCGCAGCGCAGATGCTCCAGCCTACAAGCAGGGGCAGAACCAGCTCTACAACG AACTCAATCTTGGTCGGAGAGAGGAGTACGACGTGCTGGACAAGCGGAGAGGACGGGACCCAGAAATGGGCGGGAAGCCG CGCAGAAAGAATCCCCAAGAGGGCCTGTACAACGAGCTCCAAAAGGATAAGATGGCAGAAGCCTATAGCGAGATTGGTAT GAAAGGGGAACGCAGAAGAGGCAAAGGCCACGACGGACTGTACCAGGGACTCAGCACCGCCACCAAGGACACCTATGACG CTCTTCACATGCAGGCCCTGCCGCCTCGG |
| 99M13 (ScFv domain) >TE13-19LD (M13) | CAAGTTCAACTCGTGCAATCAGGTGGAGGACTCGTCAAACCCGGAGGATCATTGAGACTGTCATGCGAAGCGAGCGGTTT TATCTTCTCCGATTACTAT ATGGGATGGATTCGGCAGGCCCCGGGAAAGGGACTCGAATGGGTGTCATACATCGGAAGGTCAGGCTCGTCCATGTACTA CGCAGACTCGGTGAAAGGCAGATTCACCTTTAGCCGGGACAACGCCAAGAATTCCCTCTACTTGCAGATGAACAGCCTGC GAGCCGAGGATACTGCTGTCTACTACTGTGCCGCGTCGCCGGTGGTGGCAGCTACTGAAGATTTCCAGCACTGGGGACAG GGAACTCTGGTCACGGTGTCGAGCGGTGGGGGCGGAAGCGGAGGCGGAGGATCGGGCGGCGGAGGTTCGGGGGGCGGAGG GTCTGACATCGTGATGACCCAAACCCCAGCCACCCTGAGCCTCTCCCCTGGAGAGCGCGCGACTCTTTCGTGCCGCGCTT CCCAGTCAGTGACCAGCAATTACTTGGCTTGGTACCAACAGAAGCCGGGACAGGCGCCACGGCTGCTGCTTTTTGGTGCC AGCACTCGCGCCACCGGAATCCCGGATCGCTTCTCGGGCTCAGGGTCCGGGACGGACTTCACCCTGACTATCAACCGGCT GGAACCTGAGGACTTCGCGATGTACTACTGCCAGCAGTACGGCTCCGCACCAGTCACTTTCGGACAAGGCACCAAGCTGG AGATCAAG |
| 123M13 (Full) >TE13-19LD (M13) | <u>ATGGCCCTCCCTGTCACCGCCCTGCTGCTTCCGCTGGCTCTTCTGCTCCACGCCGCTCGGCCC</u>AAGTTCAACTCGTGCA ATCAGGTGGAGGACTCGTCAAACCCGGAGGATCATTGAGACTGTCATGCGAAGCGAGCGGTTTTATCTTCTCCGATTACT AT ATGGGATGGATTCGGCAGGCCCCGGGAAAGGGACTCGAATGGGTGTCATACATCGGAAGGTCAGGCTCGTCCATGTACTA CGCAGACTCGGTGAAAGGCAGATTCACCTTTAGCCGGGACAACGCCAAGAATTCCCTCTACTTGCAGATGAACAGCCTGC GAGCCGAGGATACTGCTGTCTACTACTGTGCCGCGTCGCCGGTGGTGGCAGCTACTGAAGATTTCCAGCACTGGGGACAG GGAACTCTGGTCACGGTGTCGAGCGGTGGGGGCGGAAGCGGAGGCGGAGGATCGGGCGGCGGAGGTTCGGGGGGCGGAGG GTCTGACATCGTGATGACCCAAACCCCAGCCACCCTGAGCCTCTCCCCTGGAGAGCGCGCGACTCTTTCGTGCCGCGCTT CCCAGTCAGTGACCAGCAATTACTTGGCTTGGTACCAACAGAACCCGGGACAGGCGCCACGGCTGCTGCTTTTTGGTGCC AGCACTCGCGCCACCGGAATCCCGGATCGCTTCTCGGGCTCAGGGTCCGGGACGGACTTCACCCTGACTATCAACCGGCT GGAACCTGAGGACTTCGCGATGTACTACTGCCAGCAGTACGGCTCCGCACCAGTCACTTTCGGACAAGGCACCAAGCTGG AGATCAAGACCACTACCCCAGCACCGAGGCCACCCACCCCGGCTCCTACCATCGCCTCCCAGCCTCTGTCCCTGCGTCCG GAGGCATGTAGACCCGCAGCTGGTGGGGCCGTGCATACCCGGGGTCTTGACTTCGCCTGCGATATCTACATTTGGGCCCC TCTGGCTGGTACTTGCGGGGTCCTGCTGCTTTCACTCGTGATCACTCTTTACTGTAAGCGCGGTCGGAAGAAGCTGCTGT ACATCTTTAAGCAACCCTTCATGAGGCCTGTGCAGACTACTCAAGAGGAGGACGGCTGTTCATGCCGGTTCCCAGAGGAG GAGGAAGGCGGCTGCGAACTGCGCGTGAAATTCAGCCGCAGCGCAGATGCTCCAGCCTACAAGCAGGGGCAGAACCAGCT CTACAACGAACTCAATCTTGGTCGGAGAGAGGAGTACGACGTGCTGGACAAGCGGAGAGGACGGGACCCAGAAATGGGCG GGAAGCCGCGCAGAAAGAATCCCCAAGAGGGCCTGTACAACGAGCTCCAAAAGGATAAGATGGCAGAAGCCTATAGCGAG ATTGGTATGAAAGGGGAACGCAGAAGAGGCAAAGGCCACGACGGACTGTACCAGGGACTCAGCACCGCCACCAAGGACAC CTATGACGCTCTTCACATGCAGGCCCTGCCGCCTCGG |
| 100M14 (ScFv domain) >BS83-95ID (M14) | CAAGTCCAACTCGTCCAGTCGGGAGCAGAAGTTAGAGCACCAGGAGCGTCAGTGAAATCTCATGCAAGGCCTCGGGCTT CACGTTCCGCGGATACTAC ATCCACTGGGTGCGCCAAGCCCCGGGTCAGGGATTGGAGTGGATGGGAATCATTAACCCATCAGGAGGGAGCCGGGCTTA CGCGCAGAAGTTCCAGGGACGCGTCACTATGACCCGAGATACTTCCACCTCGACTGTGTACATGGAACTCTCGTCCCTGA GGTCCGACGACACTGCGATGTATTACTGTGCTCGGACTGCCAGCTGCGGTGGGGACTGTTACTACCTCGATTACTGGGGC CAGGGAACTCTGGTGACCGTGTCCAGCGGAGGTGGCGGGTCAGGGGTGGCGGAAGCGGAGGCGGCGGTTCAGGCGGAGG AGGCTCGGACATCCAAATGACGCAATCGCCGCCTACCCTGAGCCGCTTCCGTGGAGATCGGGTGACCATTACTTGCAGAG CATCCGAGAACGTCAATATCGGCTGGCCTGGTACCAACAGAAACCGGGAAGGCCCCTAAACTGCTGATCTACAAGTCG AGCAGCCTGCCTCTGGAGTGCCCTCCCGCTTCGGGCTCGGATCAGGAGCGGAATTCACCCTCACCATCTCCTCCCT GCAGCCAGATGACTTTGCCACCTACTACTGCCAGCAGTACCAGAGCTATCCGTTGACCTTTGGGGAGGCACTAAAGTGG ACATCAAG |
| 124M14 (Full) >BS83-95ID (M14) | <u>ATGGCCCTCCCTGTCACCGCCCTGCTGCTTCCGCTGGCTCTTCTGCTCCACGCCGCTCGGCCC</u>AAGTCCAACTCGTCCA GTCGGGAGCAGAAGTTAGAGCACCAGGAGCGTCAGTGAAATCTCATGCAAGGCCTCGGGCTTCACGTTCCGCGGATACT AC ATCCACTGGGTGCGCCAAGCCCCGGGTCAGGGATTGGAGTGGATGGGAATCATTAACCCATCAGGAGGGAGCCGGGCTTA CGCGCAGAAGTTCCAGGGACGCGTCACTATGACCCGAGATACTTCCACCTCGACTGTGTACATGGAACTCTCGTCCCTGA GGTCCGACGACACTGCGATGTATTACTGTGCTCGGACTGCCAGCTGCGGTGGGGACTGTTACTACCTCGATTACTGGGGC CAGGGAACTCTGGTGACCGTGTCCAGCGGAGGTGGCGGGTCAGGGGTGGCGGAAGCGGAGGCGGCGGTTCAGGCGGAGG AGGCTCGGACATCCAAATGACGCAATCGCCGCCTACCCTGAGCCGCTTCCGTGGAGATCGGGTGACCATTACTTGCAGAG CATCCGAGAACGTCAATATCGGCTGGCCTGGTACCAACAGAAACCGGGAAGGCCCCTAAACTGCTGATCTACAAGTCG AGCAGCCTGCCTCTGGAGTGCCCTCCCGCTTCGGGCTCGGATCAGGAGCGGAATTCACCCTCACCATCTCCTCCCT GCAGCCAGATGACTTTGCCACCTACTACTGCCAGCAGTACCAGAGCTATCCGTTGACCTTTGGGGAGGCACTAAAGTGG ACATCAAGACCACTACCCCAGCACCGAGGCCACCCACCCCGGCTCCTACCATCGCCTCCCAGCCTCTGTCCCTGCGTCCG GAGGCATGTAGACCCGCAGCTGGTGGGGCCGTGCATACCCGGGGTCTTGACTTCGCCTGCGATATCTACATTTGGGCCCC TCTGGCTGGTACTTGCGGGGTCCTGCTGCTTTCACTCGTGATCACTCTTTACTGTAAGCGCGGTCGGAAGAAGCTGCTGT ACATCTTTAAGCAACCCTTCATGAGGCCTGTGCAGACTACTCAAGAGGAGGACGGCTGTTCATGCCGGTTCCCAGAGGAG GAGGAAGGCGGCTGCGAACTGCGCGTGAAATTCAGCCGCAGCGCAGATGCTCCAGCCTACAAGCAGGGGCAGAACCAGCT CTACAACGAACTCAATCTTGGTCGGAGAGAGGAGTACGACGTGCTGGACAAGCGGAGAGGACGGGACCCAGAAATGGGCG |

TABLE 3-continued

Nucleic Acid Sequences encoding CAR molecules (underlined is the leader sequence)

| SEQ ID NO:Desc. | Nucleic Acid Sequence |
|---|---|
| | GGAAGCCGCGCAGAAAGAATCCCCAAGAGGGCCTGTACAACGAGCTCCAAAAGGATAAGATGGCAGAAGCCTATAGCGAG<br>ATTGGTATGAAAGGGGAACGCAGAAGAGGCAAAGGCCACGACGGACTGTACCAGGGACTCAGCACCGCCACCAAGGACAC<br>CTATGACGCTCTTCACATGCAGGCCCTGCCGCCTCGG |
| 101 M15<br>(ScFv<br>domain)<br>>HS86-<br>94XD<br>(M15) | CAAGTTCAACTCGTTCAA<br>TCAGGTGGAGGACTCGTGCAACCAGGAAGATCACTCAGACTCAGCTGCGCCGCGTCGGGATTCACTTTCGATGACTACGC<br>AATGCACTGGGTGCGGCAGGCCCCGGGCAAAGGACTGGAATGGGTGAGCGGAATTAGCTGGAACTCGGGGTCCATCGGGT<br>ACGCCGACTCGGTGAAGGGACGCTTTACGATCTCCCGGGACAATGCCAAGAACTCCCTGTATTTGCAGATGAACTCCTTG<br>AGGGCTGAGGACACCGCCGTGTACTACTGCGCTAAAGATGGATCATCGTCCTGGTCCTGGGGATACTTCGATTACTGGGG<br>CCAGGGCACTCTGGTGACCGTGTCGTCAGGCGGTGGAGGGTCGGCGGAGGAGGTAGCGGAGGCGGAGGGAGCAGCTCTG<br>AACTGACCCAAGACCCGGCGGTGTCGGTCGCCCTTGGTCAGACTGTGCGGACTACCTGTCAGGGGACGCGCGCTGCGCTCG<br>TACTACGCTTCATGGTACCAGCAGAAGCCCGGACAGGCACCTATGTGGTCATCTACGAAAGAATAACGCCCATCCGG<br>CATCCCGGATCGCTTCTCGGGTTCGGACAGCGGCGACACCGCATCCCTGACGATCACTGGAGCGCAGGCCGAGGATGAAG<br>CCGACTACTACTGCAATTCCCGAGATTCAAGCGGCTACCCTGTGTTTGGGACCGGAACTAAGGTCACCGTCCTG |
| 125 M15<br>(Full)<br>>HS86-<br>94XD<br>(M15) | <u>ATGGCCCTCCCTGTCACCGCCCTGCTGCTTCCGCTGGCTCTTCTGCTCCACGCCGCTCGGCCCC</u>AAGTTCAACTCGTTCA<br>A<br>TCAGGTGGAGGACTCGTGCAACCAGGAAGATCACTCAGACTCAGCTGCGCCGCGTCGGGATTCACTTTCGATGACTACGC<br>AATGCACTGGGTGCGGCAGGCCCCGGGCAAAGGACTGGAATGGGTGAGCGGAATTAGCTGGAACTCGGGGTCCATCGGGT<br>ACGCCGACTCGGTGAAGGGACGCTTTACGATCTCCCGGGACAATGCCAAGAACTCCCTGTATTTGCAGATGAACTCCTTG<br>AGGGCTGAGGACACCGCCGTGTACTACTGCGCTAAAGATGGATCATCGTCCTGGTCCTGGGGATACTTCGATTACTGGGG<br>CCAGGGCACTCTGGTGACCGTGTCGTCAGGCGGTGGAGGGTCGGCGGAGGAGGTAGCGGAGGCGGAGGGAGCAGCTCTG<br>AACTGACCCAAGACCCGGCGGTGTCGGTCGCCCTTGGTCAGACTGTGCGGACTACCTGTCAGGGGACGCGCGCTGCGCTCG<br>TACTACGCTTCATGGTACCAGCAGAAGCCCGGACAGGCACCTATGTGGTCATCTACGAAAGAATAACGCCCATCCGG<br>CATCCCGGATCGCTTCTCGGGTTCGGACAGCGGCGACACCGCATCCCTGACGATCACTGGAGCGCAGGCCGAGGATGAAG<br>CCGACTACTACTGCAATTCCCGAGATTCAAGCGGCTACCCTGTGTTTGGGACCGGAACTAAGGTCACCGTCCTGACCACT<br>ACCCCAGCACCGAGGCCACCCACCCCGGCTCCTACCATCGCCTCCCAGCCTCTGTCCCTGCGTCCGGAGGCATGTAGACC<br>CGCAGCTGGTGGGCCGTGCATACCCGGGGTCTTGACTTCGCCTGCGATATCTACATTTGGGCCCCTCTGGCTGGTACTT<br>GCGGGGTCCTGCTGCTTTCACTCGTGATCACTCTTTACTGTAAGCGCGGTCGGAAGAAGCTGCTGTACATCTTTAAGCAA<br>CCCTTCATGAGGCCTGTGCAGACTACTCAAGAGGAGGACGGCTGTTCATGCCGGTTCCCAGAGGAGGAGGAAGGCGGCTG<br>CGAACTGCGCGTGAAATTCAGCCGCAGCGCAGATGCTCCAGCCTACAAGCAGGGGCAGAACCAGCTCTACAACGAACTCA<br>ATCTTGGTCGGAGAGAGGAGTACGACGTGCTGGACAAGCGGAGAGGACGGGACCCAGAAATGGGCGGGAAGCCGCGCAGA<br>AAGAATCCCCAAGAGGGCCTGTACAACGAGCTCCAAAAGGATAAGATGGCAGAAGCCTATAGCGAGATTGGTATGAAAGG<br>GGAACGCAGAAGAGGCAAAGGCCACGACGGACTGTACCAGGGACTCAGCACCGCCACCAAGGACACCTATGACGCTCTTC<br>ACATGCAGGCCCTGCCGCCTCGG |
| 102 M16<br>(ScFv<br>domain)<br>>XS87-<br>99RD<br>(M16) | GAAGTGCAACTCGTGGAA<br>TCTGGTGGAGGACTTGTGCAACCTGGAAGATCGTTGAGACTCTCATGTGCTGCCTCCGGGTTCACCTTTGACGACTACGC<br>CATGCACTGGGTGCGCCAGGCACCAGGAAAGGGTCTGGAGTGGGTTTCGGGTATCTCGTGGAACTCCGGGAGCACTGGCT<br>ACGCTGATTCGGTGAAAGGCCGGTTTACCATCTCCCGAGACAATGCGAAGAATTCCCTCTATCTGCAGATGAACAGCCTC<br>CGGGCCGAGGATACTGCCCTGTACTACTGCGCCAAGGATAGCTCATCATGGTACGGAGGTGGATCGGCTTTCGATATCTG<br>GGGCCAGGGCACGATGGTCACCGTGTCCTCGGGGGGCGGAGGCTCCGGGGAGGAGGTAGCGGAGGAGGAGGATCGAGCT<br>CAGAGTTGACTCAAGAACCCGCAGTGTCCGTGGCACTGGGCCAAACCGTCAGGATCACTTGCCAGGGAGACAGCCTGAGG<br>TCGTACTACGCGTCCTGGTACCAGCAGAAGCCGGGACAGGCCCGGTCCTGGTCATTTTCGGACGCTCAAGACGCCCATC<br>GGGCATCCCGGACCGGTTCAGCGGAAGCTCCTCGGGAAACACCGCGTCACTTATCATTACCGGCGCACAGGCTGAGGACG<br>AAGCGGATTACTACTGCAACTCCCGCGACAATACTGCCAACCATTACGTGTTCGGGACCGGAACGAAACTGACTGTCCTG |
| 126 M16<br>(Full)<br>>XS87-<br>99RD<br>(M16) | <u>ATGGCCCTCCCTGTCACCGCCCTGCTGCTTCCGCTGGCTCTTCTGCTCCACGCCGCTCGGCCC</u>GAAGTGCAACTCGTGGA<br>A<br>TCTGGTGGAGGACTTGTGCAACCTGGAAGATCGTTGAGACTCTCATGTGCTGCCTCCGGGTTCACCTTTGACGACTACGC<br>CATGCACTGGGTGCGCCAGGCACCAGGAAAGGGTCTGGAGTGGGTTTCGGGTATCTCGTGGAACTCCGGGAGCACTGGCT<br>ACGCTGATTCGGTGAAAGGCCGGTTTACCATCTCCCGAGACAATGCGAAGAATTCCCTCTATCTGCAGATGAACAGCCTC<br>CGGGCCGAGGATACTGCCCTGTACTACTGCGCCAAGGATAGCTCATCATGGTACGGAGGTGGATCGGCTTTCGATATCTG<br>GGGCCAGGGCACGATGGTCACCGTGTCCTCGGGGGGCGGAGGCTCCGGGGAGGAGGTAGCGGAGGAGGAGGATCGAGCT<br>CAGAGTTGACTCAAGAACCCGCAGTGTCCGTGGCACTGGGCCAAACCGTCAGGATCACTTGCCAGGGAGACAGCCTGAGG<br>TCGTACTACGCGTCCTGGTACCAGCAGAAGCCGGGACAGGCCCGGTCCTGGTCATTTTCGGACGCTCAAGACGCCCATC<br>GGGCATCCCGGACCGGTTCAGCGGAAGCTCCTCGGGAAACACCGCGTCACTTATCATTACCGGCGCACAGGCTGAGGACG<br>AAGCGGATTACTACTGCAACTCCCGCGACAATACTGCCAACCATTACGTGTTCGGGACCGGAACGAAACTGACTGTCCTG<br>ACCACTACCCCAGCACCGAGGCCACCCACCCCGGCTCCTACCATCGCCTCCCAGCCTCTGTCCCTGCGTCCGGAGGCATG<br>TAGACCCGCAGCTGGTGGGCCGTGCATACCCGGGGTCTTGACTTCGCCTGCGATATCTACATTTGGGCCCCTCTGGCTG<br>GTACTTGCGGGGTCCTGCTGCTTTCACTCGTGATCACTCTTTACTGTAAGCGCGGTCGGAAGAAGCTGCTGTACATCTTT<br>AAGCAACCCTTCATGAGGCCTGTGCAGACTACTCAAGAGGAGGACGGCTGTTCATGCCGGTTCCCAGAGGAGGAGGAAGG<br>CGGCTGCGAACTGCGCGTGAAATTCAGCCGCAGCGCAGATGCTCCAGCCTACAAGCAGGGGCAGAACCAGCTCTACAACG<br>AACTCAATCTTGGTCGGAGAGAGGAGTACGACGTGCTGGACAAGCGGAGAGGACGGGACCCAGAAATGGGCGGGAAGCCG<br>CGCAGAAAGAATCCCCAAGAGGGCCTGTACAACGAGCTCCAAAAGGATAAGATGGCAGAAGCCTATAGCGAGATTGGTAT<br>GAAAGGGGAACGCAGAAGAGGCAAAGGCCACGACGGACTGTACCAGGGACTCAGCACCGCCACCAAGGACACCTATGACG<br>CTCTTCACATGCAGGCCCTGCCGCCTCGG |
| 103 M17<br>(ScFv<br>domain)<br>>NS89-<br>94MD<br>(M17) | GAAGTTCAATTGGTGGAA<br>TCTGGAGGAGGACTTGTGCAACCCGGTAGATCTCTGAGACTGTCCTGTGCGGCATCGGGATTCACCTTCGACGACTACGC<br>TATGCACTGGGTGAGACAAGCCCTGGAAAGGACTGGAGTGGGTGTCAGGCATTCCTGGAATAGCGGGTCCACTGGAT<br>ACGCCGATTCGGTCAAGGGTCGCTTCACCATTTCCCGGGACAATGCCAAGAACTCCCTGTACCTTCAAATGAACTCCCTC<br>CGGGCCGAGGATACCGCCCTACTACTGCGCCAAAGACAGCTCGTCATGTATGGCGGAGGGTCGGCATTTGACATCTG<br>GGACAGGGAACTATGGTGACTGTGTCATCAGGAGGCGGCGGAAGCGGCGGCGGCGGGTCCGGCGGAGGAGGGTCGTCCA |

TABLE 3-continued

Nucleic Acid Sequences encoding CAR molecules (underlined is the leader sequence)

| SEQ ID NO:Desc. | Nucleic Acid Sequence |
|---|---|
| | GCGAACTCACCCAAGATCCAGCAGTGAGCGTCGCGCTGGGCCAGACCGTCAGGATCACGTGCCAGGGAGATTCACTGCGC<br>TCATACTACGCGTCCTGGTACCAGCAGAAGCCGGGGCAGGCCCCGGTCCTCGTGATCTACGGAAAGAACAACCGCCCGTC<br>GGGTATCCCAGACCGCTTTTCGGGTAGCTCCAGCGGAAATACGGCTAGCCTGACCATCACTGGAGCACAGGCTGAGGATG<br>AAGCGGACTACTACTGCAATTCGCGGGGCTCATCGGGGAACCATTACGTGTTCGGAACTGGTACCAAGGTGACTGTCCTG |
| 127M17<br>(Full)<br>>NS89-<br>94MD<br>(M17) | <u>ATGGCCCTCCCTGTCACCGCCCTGCTGCTTCCGCTGGCTCTTCTGCTCCACGCCGCTCGGCCC</u>GAAGTTCAATTGGTGGA<br>A<br>TCTGGAGGAGGACTTGTGCAACCCGGTAGATCTCTGAGACTGTCCTGTGCGGCATCGGGATTCACCTTCGACGACTACGC<br>TATGCACTGGGTGAGACAAGCCCCTGGAAAAGGACTGGAGTGGGTGTCAGGCATCTCCTGGAATAGCGGGTCCACTGGAT<br>ACGCCGATTCGGTCAAGGGTCGCTTCACCATTTCCCGGGACAATGCCAAGAACTCCCTGTACCTTCAAATGAACTCCCTC<br>CGGGCCGAGGATACCGCCCTCTACTACTGCGCCAAAGACAGCTCGTCATGGTATGGCGGAGGGTCGGCATTTGACATCTG<br>GGGACAGGGAACTATGGTGACTGTGTCATCAGGAGGCGGCGGAAGCGGCGGCGGCGGGTCCGGCGGAGGAGGGTCGTCCA<br>GCGAACTCACCCAAGATCCAGCAGTGAGCGTCGCGCTGGGCCACACCGTCAGGATCACGTGCCAGGGAGATTCACTGCGC<br>TCATACTACGCGTCCTGGTACCAGCAGAAGCCGGGGCAGGCCCCGGTCCTCGTGATCTACGGAAAGAACAACCGCCCGTC<br>GGGTATCCCAGACCGCTTTTCGGGTAGCTCCAGCGGAAATACGGCTAGCCTGACCATCACTGGAGCACAGGCTGAGGATG<br>AAGCGGACTACTACTGCAATTCGCGGGGCTCATCGGGGAACCATTACGTGTTCGGAACTGGTACCAAGGTGACTGTCCTG<br>ACCACTACCCCAGCACCGAGGCCACCCACCCCGGCTCCTACCATCGCCTCCCAGCCTCTGTCCCTGCGTCCGGAGGCATG<br>TAGACCCGCAGCTGGTGGGGCCGTGCATACCCGGGTCTTGACTTCGCCTGCGATATCTACATTTGGGCCCCTCTGGCTG<br>GTACTTGCGGGGTCCTGCTGCTTTCACTCGTGATCACTCTTTACTGTAAGCGCGGTCGGAAGAAGCTGCTGTACATCTTT<br>AAGCAACCCTTCATGAGGCCTGTGCAGACTACTCAAGAGGAGGACGGCTGTTCATGCCGGTTCCCAGAGGAGGAGGAAGG<br>CGGCTGCGAACTGCGCGTGAAATTCAGCCGCAGCGCAGATGCTCCAGCCTACAAGCAGGGGCAGAACCAGCTCTACAACG<br>AACTCAATCTTGGTCGGAGAGAGGAGTACGACGTGCTGGACAAGCGGAGAGGACGGGACCCAGAAATGGGCGGGAAGCCG<br>CGCAGAAAGAATCCCCAAGAGGGCCTGTACAACGAGCTCCAAAAGGATAAGATGGCAGAAGCCTATAGCGAGATTGGTAT<br>GAAAGGGGAACGCAGAAGAGGCAAAGGCCACGACGGACTGTACCAGGGACTCAGCACCGCCACCAAGGACACCTATGACG<br>CTCTTCACATGCAGGCCCTGCCGCCTCGG |
| 104M18<br>(ScFv<br>domain)<br>>DS90-<br>09HD<br>(M18) | CAAGTGCAGCTCGTTCAATCAGGCGGAGGACTCGTTCAACCAGGAGGATCATTGCGACTCTCATGTGCGGCCTCTGGATT<br>CACGTTTAGCTCATATTGG<br>ATGCACTGGGTGCGGCAGGCGCCGGGGAAAGGTCTGGTGTGGGTCAGCCGCATCAACTCAGACGGCTCCTCGACTTCGTA<br>CGCCGACTCCGTGAAGGGACGCTTTACCATTTCCCGCGACAACGCCAAGAATACCCTTTACCTTCAGATGAACTCCCTCC<br>GCGCTGAGGATACCGCCGTGTACTACTGCGTGAGGACTGGCTGGGTCGGCAGCTACTACTACATGGACGTGTGGGGC<br>AAAGGAACTACTGTCACCGTGTCAAGCGGCGGTGGAGGTTCCGGCGGGGAGGATCGGGGGGGGCGGATCGGGTGGCGG<br>AGGATCGGAGATCGTGTTGACCCAGTCGCCGGGAACCCTGTCGCTGTCGCCTGGGGAGAGAGCAACTCTGTCCTGCCGGG<br>CTTCCCAGTCGGTGTCGAGCAATTACCTGGCATGGTACCAACACAAGCGGGACAGCCGCCACGCCTGCTGATCTATGAC<br>GTGTCAACTCGGGCAACTGGAATCCCTGCGCGGTTCAGCGGCGGAGGGAGCGGTACCGATTTCACCCTGACTATTTCCTC<br>CCTCGAACCAGAAGATTTCGCCGTCTACTACTGCCAGCAGAGAAGCAACTGGCCGCCCTGGACGTTCGGACAAGGAACCA<br>AGGTCGAAATCAAG |
| 128M18<br>(Full)<br>>DS90-<br>09HD<br>(M18) | <u>ATGGCCCTCCCTGTCACCGCCCTGCTGCTTCCGCTGGCTCTTCTGCTCCACGCCGCTCGGCCC</u>CAAGTGCAGCTCGTTCA<br>ATCAGGCGGAGGACTCGTTCAACCAGGAGGATCATTGCGACTCTCATGTGCGGCCTCTGGATTCACGTTTAGCTCATATT<br>GG<br>ATGCACTGGGTGCGGCAGGCGCCGGGGAAAGGTCTGGTGTGGGTCAGCCGCATCAACTCAGACGGCTCCTCGACTTCGTA<br>CGCCGACTCCGTGAAGGGACGCTTTACCATTTCCCGCGACAACGCCAAGAATACCCTTTACCTTCAGATGAACTCCCTCC<br>GCGCTGAGGATACCGCCGTGTACTACTGCGTGAGGACTGGCTGGGTCGGCAGCTACTACTACATGGACGTGTGGGGC<br>AAAGGAACTACTGTCACCGTGTCAAGCGGCGGTGGAGGTTCCGGCGGGGAGGATCGGGGGGGGCGGATCGGGTGGCGG<br>AGGATCGGAGATCGTGTTGACCCAGTCGCCGGGAACCCTGTCGCTGTCGCCTGGGGAGAGAGCAACTCTGTCCTGCCGGG<br>CTTCCCAGTCGGTGTCGAGCAATTACCTGGCATGGTACCAACAGAAGCGGGACAGCCGCCACGCCTGCTGATCTATGAC<br>GTGTCAACTCGGGCAACTGGAATCCCTGCGCGGTTCAGCGGCGGAGGGAGCGGTACCGATTTCACCCTGACTATTTCCTC<br>CCTCGAACCAGAAGATTTCGCCGTCTACTACTGCCAGCAGAGAAGCAACTGGCCGCCCTGGACGTTCGGACAAGGAACCA<br>AGGTCGAAATCAAGACCACTACCCCAGCACCGAGGCCACCCACCCCGGCTCCTACCATCGCCTCCCAGCCTCTGTCCCTG<br>CGTCCGGAGGCATGTAGACCCGCAGCTGGTGGGGCCGTGCATACCCGGGTCTTGACTTCGCCTGCGATATCTACATTTG<br>GGCCCCTCTGGCTGGTACTTGCGGGGTCCTGCTGCTTTCACTCGTGATCACTCTTTACTGTAAGCGCGGTCGGAAGAAGC<br>TGCTGTACATCTTTAAGCAACCCTTCATGAGGCCTGTGCAGACTACTCAAGAGGAGGACGGCTGTTCATGCCGGTTCCCA<br>GAGGAGGAGGAAGGCGGCTGCGAACTGCGCGTGAAATTCAGCCGCAGCGCAGATGCTCCAGCCTACAAGCAGGGGCAGAA<br>CCAGCTCTACAACGAACTCAATCTTGGTCGGAGAGAGGAGTACCACGTGCTGGACAAGCGGAGAGGACGGGACCCAGAAA<br>TGGGCGGGAAGCCGCGCAGAAAGAATCCCCAAGAGGGCCTGTACAACGAGCTCCAAAAGGATAAGATGGCAGAAGCCTAT<br>AGCGAGATTGGTATGAAAGGGGAACGCAGAAGAGGCAAAGGCCACGACGGACTGTACCAGGGACTCAGCACCGCCACCAA<br>GGACACCTATGACGCTCTTCACATGCAGGCCCTGCCGCCTCGG |
| 105M19<br>(ScFv<br>domain)<br>>TS92-<br>04BD<br>(M19) | CAAGTGCAATTGGTTCAA<br>TCAGGAGGAGGAGTCGTGCAGCCCGGAAGATCGTTGAGACTGTCATGTGCCGCGAGCGGCTTTACTTTCTCAAGCTACGG<br>AATGCATTGGGTGCGACAGGCTCCGGGAAAAGGACTGGAATGGGTCGCAGTGATCTCATACGACGGCTCGAACAAGTACT<br>ACGCCGACTCCGTCAAGGGTCGGTTCACGATTTCGCGCGATAATTCCAAGAACACTCTGTACCTCCAAATGAACAGCCTC<br>CGGGCAGAGGACACCGCCGTCTACTACTGCGTCAGCTACTACTATGGAATGGATGTGTGGGGCCA<br>GGGAACTACCGTGACGGTGTCGTCCGGCGGCGGTGGGTCGGCGGAGGCGGATCAGGTGGAGGTGGAAGCGGAGGAGGAG<br>GGAGCGAAATCGTCATGACTCAGTCCCCTGCTACCCTTTCTCTCGCCGGAGAAAGAGCCATCCTGAGCTGCCGGGCC<br>TCCCAGAGCGTGTACACCAATACCTGGGATGGTACCAGCAGAAGCCGGGCAGGCACCAAGGCCTGATCTACGATGC<br>GTCCACCCGCGCGACTGGTATCCCAGACCGCTTTTCCGGCTCGGGGTCAGGGACTGACTTCACCCTTACTATCAATCGGC<br>TCGAGCCTGAGGATTTCGCCGTGTATTACTGCCAGCACTACGGAGGGTCCCCGCTGATTACCTTCGGCCAAGGCACCAAA<br>GTGGACATCAAG |

TABLE 3-continued

Nucleic Acid Sequences encoding CAR molecules (underlined is the leader sequence)

| SEQ ID NO:Desc. | Nucleic Acid Sequence |
|---|---|
| 129M19 (Full) >TS92- 04BD (M19) | <u>ATGGCCCTCCCTGTCACCGCCCTGCTGCTTCCGCTGGCTCTTCTGCTCCACGCCGCTCGGCCC</u>AAGTGCAATTGGTTCA<br>A<br>TCAGGAGGAGGAGTCGTGCAGCCCGGAAGATCGTTGAGACTGTCATGTGCCGCGAGCGGCTTTACTTTCTCAAGCTACGG<br>AATGCATTGGGTGCGACAGGCTCCGGAAAAGGACTGGAATGGGTCGCAGTGATCTCATACGACGGCTCGAACAAGTACT<br>ACGCCGACTCCGTCAAGGGTCGGTTCACGATTTCGCGCGATAATTCCAAGAACACTCTGTACCTCCAAATGAACAGCCTC<br>CGGGCAGAGGACACCGCCGTCTACTACTGCGCTAAGGGATACTCGCGCTACTACTACTATGGAATGGATGTGTGGGGCCA<br>GGGAACTACCGTGACGGTGTCGTCCGGCGGCGGTGGGTCGGGCGGAGGCGGATCAGGTGGAGGTGGAAGCGGAGGAGGAG<br>GGAGCGAAATCGTCATGACTCAGTCCCCTGCTACCCTTTCTCTGTCGCCGGGAGAAAGAGCCATCCTGAGCTGCCGGGCC<br>TCCCAGAGCGTGTACACCAAATACCTGGGATGGTACCAGCAGAAGCCGGGGCAGGCACCAAGGCTCCTGATCTACGATGC<br>GTCCACCCGCGCGACTGGTATCCCAGACCGCTTTTCCGGCTCAGGGGTCAGGGACTGACTTCACCCTTACTATCAATCGGC<br>TCGAGCCTGAGGATTTCGCCGTGTATTACTGCCAGCACTACGGAGGGTCCCCGCTGATTACCTTCGGCCAAGGCACCAAA<br>GTGGACATCAAGACCACTACCCCAGCACCGAGGCCACCCACCCCGGCTCCTACCATCGCCTCCCAGCCTCTGTCCCTGCG<br>TCCGGAGGCATGTAGACCCGCAGCTGGTGGGGCCGTGCATACCCGGGGTCTTGACTTCGCCTGCGATATCTACATTTGGG<br>CCCCTCTGGCTGGTACTTGCGGGGTCCTGCTGCTTTCACTCGTGATCACTCTTTACTGTAAGCGCGGTCGGAAGAAGCTG<br>CTGTACATCTTTAAGCAACCCTTCATGAGGCCTGTGCAGACTACTCAAGAGGAGGACGGCTGTTCATGCCGGTTCCCAGA<br>GGAGGAGGAAGGCGGCTGCGAACTGCGCGTGAAATTCAGCCGCAGCGCAGATGCTCCAGCCTACAAGCAGGGGCAGAACC<br>AGCTCTACAACGAACTCAATCTTGGTCGGAGAGAGGAGTACGACGTGCTGGACAAGCGGAGAGGACGGGACCCAGAAATG<br>GGCGGGAAGCCGCGCAGAAAGAATCCCCAAGAGGGCCTGTACAACGAGCTCCAAAAGGATAAGATGGCAGAAGCCTATAG<br>CGAGATTGGTATGAAAGGGGAACGCAGAAGAGGCAAAGGCCACGACGGACTGTACCAGGGACTCAGCACCGCCACCAAGG<br>ACACCTATGACGCTCTTCACATGCAGGCCCTGCCGCCTCGG |
| 106M20 (ScFv domain) >JS93- 08WD (M20) | CAAGTGCAACTTGTTCAATCAGGAGGAGGACTCGTTCAACCCGGAGGATCACTGCGACTCTCATGTGCAGCGTCGGGGTT<br>CACCTTCTCCAGCTACGCA<br>ATGTCCTGGGTGCGCCAAGCCCCTGGAAAAGGCCTGGAGTGGGTGTCGGCCATCTCTGGGAGCGGGGGATCAACTTACTA<br>CGCTGACTCCGTCAAGGGCCGCTTTACCATCTCCCGGGACAACAGCAAGAACACTCTCTATCTCCAGATGAACTCGCTGA<br>GAGCCGAAGATACCGCTGTCTACTACTGCGCGGAAGAGAGAAGCTGCCGCAGGGCACGATTGGTACTTCGACTTGTGGGGC<br>AGGGGCACCCTTGTGACCGTGTCCTCCGGTGGAGGCGGATCAGGAGGTGGGGGATCGGGTGGAGGAGGAAGCGGAGGCGG<br>CGGTTCGGACATTGCGTCACCCAGTCACCGAGCTCCCTCAGCGCATCGGTGGGCGACCGGGTCACTATCACTTGCCGGG<br>CGTCCCAGTCGATCTCATCGTATCTGAATTGGTACCAGCAGAAACCGGGAAAGGCGCCGAAGCTGTTGATCTACGCTGCC<br>AGCTCCCTGCAGTCGGGTGTGCCATCACGCTTTTCCGGCTCGGGATCGGGAACCGATTTCACTCTGACGATCTCTAGCCT<br>GCAGCCAGAAGATTTCGCCACTTACTACTGCCAGCAGTCCTACAGCATCCCTCTGACTTTCGGACAAGGGACGAAAGTGG<br>AGATTAAG |
| 130M20 (Full) >JS93- 08WD (M20) | <u>ATGGCCCTCCCTGTCACCGCCCTGCTGCTTCCGCTGGCTCTTCTGCTCCACGCCGCTCGGCCC</u>AAGTGCAACTTGTTCA<br>ATCAGGAGGAGGACTCGTTCAACCCGGAGGATCACTGCGACTCTCATGTGCAGCGTCGGGGTTCACCTTCTCCAGCTACG<br>CA<br>ATGTCCTGGGTGCGCCAAGCCCCTGGAAAAGGCCTGGAGTGGGTGTCGGCCATCTCTGGGAGCGGGGGATCAACTTACTA<br>CGCTGACTCCGTCAAGGGCCGCTTTACCATCTCCCGGGACAACAGCAAGAACACTCTCTATCTCCAGATGAACTCGCTGA<br>GAGCCGAAGATACCGCTGTCTACTACTGCGCGGAAGAGAGAAGCTGCCGCAGGGCACGATTGGTACTTCGACTTGTGGGGC<br>AGGGGCACCCTTGTGACCGTGTCCTCCGGTGGAGGCGGATCAGGAGGTGGGGGATCGGGTGGAGGAGGAAGCGGAGGCGG<br>CGGTTCGGACATTGCGTCACCCAGTCACCGAGCTCCCTCAGCGCATCGGTGGGCGACCGGGTCACTATCACTTGCCGGG<br>CGTCCCAGTCGATCTCATCGTATCTGAATTGGTACCAGCAGAAACCGGGAAAGGCGCCGAAGCTGTTGATCTACGCTGCC<br>AGCTCCCTGCAGTCGGGTGTGCCATCACGCTTTTCCGGCTCGGGATCGGGAACCGATTTCACTCTGACGATCTCTAGCCT<br>GCAGCCAGAAGATTTCGCCACTTACTACTGCCAGCAGTCCTACAGCATCCCTCTGACTTTCGGACAAGGGACGAAAGTGG<br>AGATTAAGACCACTACCCAGCACCGAGGCCACCCACCCCGGCTCCTACCATCGCCTCCCAGCCTCTGTCCCTGCGTCCG<br>GAGGCATGTAGACCCGCAGCTGGTGGGGCCGTGCATACCCGGGGTCTTGACTTCGCCTGCGATATCTACATTTGGGCCCC<br>TCTGGCTGGTACTTGCGGGGTCCTGCTGCTTTCACTCGTGATCACTCTTTACTGTAAGCGCGGTCGGAAGAAGCTGCTGT<br>ACATCTTTAAGCAACCCTTCATGAGGCCTGTGCAGACTACTCAAGAGGAGGACGGCTGTTCATGCCGGTTCCCAGAGGAG<br>GAGGAAGGCGGCTGCGAACTGCGCGTGAAATTCAGCCGCAGCGCAGATGCTCCAGCCTACAAGCAGGGGCAGAACCAGCT<br>CTACAACGAACTCAATCTTGGTCGGAGAGAGGAGTACGACGTGCTGGACAAGCGGAGAGGACGGGACCCAGAAATGGGCG<br>GGAAGCCGCGCAGAAAGAATCCCCAAGAGGGCCTGTACAACGAGCTCCAAAAGGATAAGATGGCAGAAGCCTATAGCGAG<br>ATTGGTATGAAAGGGGAACGCAGAAGAGGCAAAGGCCACGACGGACTGTACCAGGGACTCAGCACCGCCACCAAGGACAC<br>CTATGACGCTCTTCACATGCAGGCCCTGCCGCCTCGG |
| 107M21 (ScFv domain) >ZS95- 03QD (M21) | CAAGTCCAACTCGTTCAGTCATGGGCAGAAGTCAAGAAACCCGGTGCAAGCGTCAAAGTGTCGTGTAAGGCCTCCGGCTA<br>CACTTTCACTTCCTACTAC<br>ATGCACTGGGTGCGCCAAGCCCCGGGACAGGGCCTTGAATGGATGGGCATCATCAACCCATCAGGAGGTTCCACGAGCTA<br>CGCGCAGAAGTTCCAGGGGAGAGTGACGATGACTAGAGATACCTCCACGAGCACCGTCTACATGGAGCTGTCGAATCTGC<br>GGTCAGAGGACACTGCTGTGTATTACTGCGCGCGCTCCCCGCGGGTGACCACTGGCTACTTTGACTACTGGGGACAAGGG<br>ACCCTGGTGACCGTCAGCTCGGGAGGCGGAGGATCGGGAGGTGGAGGGTCCGGTGGAGGCGGCTCTGGAGGAGGCGGGTC<br>GGACATTCAATTGACCCAGAGCCCATCCACCCTCTCAGCCTCGGTGGGGATAGGGTGACTATCACTTGCCGGGCCTCCC<br>AGTCAATTTCCAGCTGGCTGGCTTGGTACCAGCAAAAGCCTGGAAAGGCACCGAAGCTCCTGATCTACAAGGCCTCATCT<br>CTGGAATCAGGAGTGCCTTCGCGCTTCAGCGGAAGCGGCTCGGGAACTGAGTTTACCCTGACCATCTCGAGCCTGCAGCC<br>AGATGACTTCGCGACCTATTACTGCCAGCAGTACTCGTCCTACCCGTTGACTTTCGGAGGAGGTACCCGCCTCGAAATCA<br>AA |
| 131M21 (Full) >ZS95- 03QD (M21) | <u>ATGGCCCTCCCTGTCACCGCCCTGCTGCTTCCGCTGGCTCTTCTGCTCCACGCCGCTCGGCCC</u>AAGTCCAACTCGTTCA<br>GTCATGGGCAGAAGTCAAGAAACCCGGTGCAAGCGTCAAAGTGTCGTGTAAGGCCTCCGGCTACACTTTCACTTCCTACT<br>AC<br>ATGCACTGGGTGCGCCAAGCCCCGGGACAGGGCCTTGAATGGATGGGCATCATCAACCCATCAGGAGGTTCCACGAGCTA<br>CGCGCAGAAGTTCCAGGGGAGAGTGACGATGACTAGAGATACCTCCACGAGCACCGTCTACATGGAGCTGTCGAATCTGC<br>GGTCAGAGGACACTGCTGTGTATTACTGCGCGCGCTCCCCGCGGGTGACCACTGGCTACTTTGACTACTGGGGACAAAGGG<br>ACCCTGGTGACCGTCAGCTCGGGAGGCGGAGGATCGGGAGGTGGAGGGTCCGGTGGAGGCGGCTCTGGAGGAGGCGGGTC |

TABLE 3-continued

Nucleic Acid Sequences encoding CAR molecules (underlined is the leader sequence)

| SEQ ID NO: Desc. | Nucleic Acid Sequence |
|---|---|
| | GGACATTCAATTGACCCAGAGCCCATCCACCCTCTCAGCCTCGGTGGGGATAGGGTGACTATCACTTGCCGGGCCTCCC<br>AGTCAATTTCCAGCTGGCTGGCTTGGTACCAGCAAAAGCCTGGAAAGGCACCGAAGCTCCTGATCTACAAGGCCTCATCT<br>CTGGAATCAGGAGTGCCTTCGCGCTTCAGCGGAAGCGGCTCGGGAACTGAGTTTACCCTGACCATCTCGAGCCTGCAGCC<br>AGATGACTTCGCGACCTATTACTGCCAGCAGTACTCGTCCTACCCGTTGACTTTCGGAGGAGGTACCCGCCTCGAAATCA<br>AAACCACTACCCCAGCACCGAGGCCACCCACCCCGGCTCCTACCATCGCCTCCCAGCCTCTGTCCCTGCGTCCGGAGGCA<br>TGTAGACCCGCAGCTGGTGGGGCCGTGCATACCCGGGGTCTTGACTTCGCCTGCGATATCTACATTTGGGCCCCTCTGGC<br>TGGGTACTTGCGGGGTCCTGCTGCTTTCACTCGTGATCACTCTTTACTGTAAGCGCGGTCGGAAGAAGCTGCTGTACATCT<br>TTAAGCAACCCTTCATGAGGCCTGTGCAGACTACTCAAGAGGAGGACGGCTGTTCATGCCGGTTCCCAGAGGAGGAGGAA<br>GGCGGCTGCGAACTGCGCGTGAAATTCAGCCGCAGCGCAGATGCTCCAGCCTACAAGCAGGGGCAGAACCAGCTCTACAA<br>CGAACTCAATCTTGGTCGGAGAGAGGAGTACGACGTGCTGGACAAGCGGAGAGGACGGGACCCAGAAATGGGCGGGAAGC<br>CGCGCAGAAAGAATCCCCAAGAGGGCCTGTACAACGAGCTCAAAAGGATAAGATGGCAGAAGCCTATAGCGAGATTGGT<br>ATGAAAGGGGAACGCAGAAGAGGCAAAGGCCACGACGGACTGTACCAGGGACTCAGCACCGCCACCAAGGACACCTATGA<br>CGCTCTTCACATGCAGGCCCTGCCGCCTCGG |
| 108 M22<br>(ScFv<br>domain)<br>>PS96-<br>08LD<br>(M22) | CAAGTCCAACTCGTCCAGTCCGGTGCAGAAGTCAGAAGGCCAGGAGCAAGCGTGAAGATCTCGTGTAGAGCGTCAGGAGA<br>CACCAGCACTCGCCATTAC<br>ATCCACTGGCTGCGCCAGGCTCCGGGCCAAGGGCCGGAGTGGATGGGTGTGATCAACCCGACTACGGGACCGGCTACCGG<br>AAGCCCTGCGTACGCACAGATGCTGCAGGGACGGGTGACTATGACCCGCGATACTAGCACTAGGACCGTGTACATGGAAC<br>TCCGCTCGTTGCGGTTCGAAGATACCGCCGTCTACTACTGCGCCCGGTCCGTGGTGGGCCGAAGCGCCCCTTACTACTTC<br>GATTACTGGGGACAGGGCACTCTGGTGACCGTTAGCTCCGGTGGGGAGGCTCGGGTGGAGGCGGATCGGGAGGAGGAGG<br>CAGCGGTGGAGGGGGATCGGACATTCAGATGACCCAGTCACCCTCCTCCCTCTCAGCCTCGGTCGGGGACCGGGTGACCA<br>TTACGTGCAGAGCCTCACAAGGGATCTCGGACTACTCCGCCTGGTACCAGCAGAAACCGGGAAAAGCGCCAAAGCTCCTG<br>ATCTACGCCGCGAGCACCCTGCAATCAGGAGTGCCATCGCGCTTTTCTGGATCGGGCTCAGGGACTGACTTCACGCTGAC<br>TATCTCCTACCTTCAGTCCGAGGATTTCGCTACCTACTACTGCCAACAGTATTACTCCTATCCCCTGACCTTTGGCGGAG<br>GCACTAAGGTGGACATCAAG |
| 132 M22<br>(Full)<br>>PS96-<br>08LD<br>(M22) | <u>ATGGCCCTCCCTGTCACCGCCCTGCTGCTTCCGCTGGCTCTTCTGCTCCACGCCGCTCGGCCC</u>CAAGTCCAACTCGTCCA<br>GTCCGGTGCAGAAGTCAGAAGGCCAGGAGCAAGCGTGAAGATCTCGTGTAGAGCGTCAGGAGACACCAGCACTCGCCATT<br>AC<br>ATCCACTGGCTGCGCCAGGCTCCGGGCCAAGGGCCGGAGTGGATGGGTGTGATCAACCCGACTACGGGACCGGCTACCGG<br>AAGCCCTGCGTACGCACAGATGCTGCAGGGACGGGTGACTATGACCCGCGATACTAGCACTAGGACCGTGTACATGGAAC<br>TCCGCTCGTTGCGGTTCGAAGATACCGCCGTCTACTACTGCGCCCGGTCCGTGGTGGGCCGAAGCGCCCCTTACTACTTC<br>GATTACTGGGGACAGGGCACTCTGGTGACCGTTAGCTCCGGTGGGGAGGCTCGGGTGGAGGCGGATCGGGAGGAGGAGG<br>CAGCGGTGGAGGGGGATCGGACATTCAGATGACCCAGTCACCCTCCTCCCTCTCAGCCTCGGTCGGGGACCGGGTGACCA<br>TTACGTGCAGAGCCTCACAAGGGATCTCGGACTACTCCGCCTGGTACCAGCAGAAACCGGGAAAAGCGCCAAAGCTCCTG<br>ATCTACGCCGCGAGCACCCTGCAATCAGGAGTGCCATCGCGCTTTTCTGGATCGGGCTCAGGGACTGACTTCACGCTGAC<br>TATCTCCTACCTTCAGTCCGAGGATTTCGCTACCTACTACTGCCAACAGTATTACTCCTATCCCCTGACCTTTGGCGGAG<br>GCACTAAGGTGGACATCAAGACCACTACCCCAGCACCGAGGCCACCCACCCCGGCTCCTACCATCGCCTCCCAGCCTCTG<br>TCCCTGCGTCCGGAGGCATGTAGACCCGCAGCTGGTGGGGCCGTGCATACCCGGGGTCTTGACTTCGCCTGCGATATCTA<br>CATTTGGGCCCCTCTGGCTGGTACTTGCGGGGTCCTGCTGCTTTACTCGTGATCACTCTTTACTGTAAGCGCGGTCGGA<br>AGAAGCTGCTGTACATCTTTAAGCAACCCTTCATGAGGCCTGTGCAGACTACTCAAGAGGAGGACGGCTGTTCATGCCGG<br>TTCCCAGAGGAGGAGGAAGGCGGCTGCGAACTGCGCGTGAAATTCAGCCGCAGCGCAGATGCTCCAGCCTACAAGCAGGG<br>GCAGAACCAGCTCTACAACGAACTCAATCTTGGTCGGAGAGAGGAGTACGACGTGCTGGACAAGCGGAGAGGACGGGACC<br>CAGAAATGGGCGGGAAGCCGCGCAGAAAGAATCCCCAAGAGGGCCTGTACAACGAGCTCCAAAAGGATAAGATGGCAGAA<br>GCCTATAGCGAGATTGGTATGAAAGGGGAACGCAGAAGAGGCAAAGGCCACGACGGACTGTACCAGGGACTCAGCACCGC<br>CACCAAGGACACCTATGACGCTCTTCACATGCAGGCCCTGCCGCCTCGG |
| 109 M23<br>(ScFv<br>domain)<br>>XH66-<br>84HE<br>(M23) | CAAGTCCAACTCCAGCAATCGGGAGCAGAAGTCAAGAAACCAGGCGCATCGGTGAAAGTGTCGTGTAAGGCGTCAGGGTA<br>CACCTTCACCAACTACTAT<br>ATGCACTGGGTGCGCCAGGCTCCAGGCCAGGGGTTGGAGTGGATGGGGATCATCAATCCGTCAGGTGGCTACACCACTTA<br>CGCTCAGAAGTTCCAGGGACGCCTCACTATGACTCGCGATACTAGCACCTCCACGGTGTACATGGAACTGTCATCGCTGA<br>GGTCCGAAGATACCGCCGTCTACTACTGCGCACGGATCAGATCCTGCGGAGGAGATTGTTACTACTTTGACAACTGGGGA<br>CAGGGCACCCTTGTTACTGTGTCATCGGGAGGAGGGGAAGCGGAGGAGGTGGATCAGGCGGCGGTGGCAGCGGGGGCGG<br>AGGATCGGACATTCAGCTGACTCAGTCCCCCTCCACTTTGTCGGCCAGCGTGGGAGACAGAGTGACCATCACTTGCCGGG<br>CGTCCGAGAACGTCAATATCTGGCTGGCCTGGTACCAGCAAAAGCCTGGAAAAGCCCCGAAGCTGCTCATCTATAAGTCA<br>TCCAGCCTGGCGTCTGGTGTGCCGTCGCGGTTCTCCGGCAGCGGGAGCGGAGCCGAGTTCACTCTCACCATTTCGAGCCT<br>TCAACCGGACGATTTCGCCACCTACTACTGCCAGCAGTACCAATCCTACCCTCTGACGTTTGGAGGTGGAACCAAGGTGG<br>ACATCAAG |
| 133 M23<br>(Full)<br>>XH66-<br>84HE<br>(M23) | <u>ATGGCCCTCCCTGTCACCGCCCTGCTGCTTCCGCTGGCTCTTCTGCTCCACGCCGCTCGGCCC</u>CAAGTCCAACTCCAGCA<br>ATCGGGAGCAGAAGTCAAGAAACCAGGCGCATCGGTGAAAGTGTCGTGTAAGGCGTCAGGGTACACCTTCACCAACTACT<br>AT<br>ATGCACTGGGTGCGCCAGGCTCCAGGCCAGGGGTTGGAGTGGATGGGGATCATCAATCCGTCAGGTGGCTACACCACTTA<br>CGCTCAGAAGTTCCAGGGACGCCTCACTATGACTCGCGATACTAGCACCTCCACGGTGTACATGGAACTGTCATCGCTGA<br>GGTCCGAAGATACCGCCGTCTACTACTGCGCACGGATCAGATCCTGCGGAGGAGATTGTTACTACTTTGACAACTGGGGA<br>CAGGGCACCCTTGTTACTGTGTCATCGGGAGGAGGGGAAGCGGAGGAGGTGGATCAGGCGGCGGTGGCAGCGGGGGCGG<br>AGGATCGGACATTCAGCTGACTCAGTCCCCCTCCACTTTGTCGGCCAGCGTGGGAGACAGAGTGACCATCACTTGCCGGG<br>CGTCCGAGAACGTCAATATCTGGCTGGCCTGGTACCAGCAAAAGCCTGGAAAAGCCCCGAAGCTGCTCATCTATAAGTCA<br>TCCAGCCTGGCGTCTGGTGTGCCGTCGCGGTTCTCCGGCAGCGGGAGCGGAGCCGAGTTCACTCTCACCATTTCGAGCCT<br>TCAACCGGACGATTTCGCCACCTACTACTGCCAGCAGTACCAATCCTACCCTCTGACGTTTGGAGGTGGAACCAAGGTGG<br>ACATCAAGACCACTACCCCAGCACCGAGGCCACCCACCCCGGCTCCTACCATCGCCTCCCAGCCTCTGTCCCTGCGTCCG<br>GAGGCATGTAGACCCGCAGCTGGTGGGGCCGTGCATACCCGGGGTCTTGACTTCGCCTGCGATATCTACATTTGGGCCCC<br>TCTGGCTGGTACTTGCGGGGTCCTGCTGCTTTCACTCGTGATCACTCTTTACTGTAAGCGCGGTCGGAAGAAGCTGCTGT<br>ACATCTTTAAGCAACCCTTCATGAGGCCTGTGCAGACTACTCAAGAGGAGGACGGCTGTTCATGCCGGTTCCCAGAGGAG |

TABLE 3-continued

Nucleic Acid Sequences encoding CAR molecules (underlined is the leader sequence)

| SEQ ID NO:Desc. | Nucleic Acid Sequence |
|---|---|
| | GAGGAAGGCGGCTGCGAACTGCGCGTGAAATTCAGCCGCAGCGCAGATGCTCCAGCCTACAAGCAGGGGCAGAACCAGCT<br>CTACAACGAACTCAATCTTGGTCGGAGAGAGGAGTACGACGTGCTGGACAAGCGGAGAGGACGGGACCCAGAAATGGGCG<br>GGAAGCCGCGCAGAAAGAATCCCCAAGAGGGCCTGTACAACGAGCTCCAAAAGGATAAGATGGCAGAAGCCTATAGCGAG<br>ATTGGTATGAAGGGGAACGCAGAAGAGGCAAAGGCCACGACGGACTGTACCAGGGACTCAGCACCGCCACCAAGGACAC<br>CTATGACGCTCTTCACATGCAGGCCCTGCCGCCTCGG |
| 110M24<br>(ScFv<br>domain)<br>>NH67-<br>89CE<br>(M24) | CAAATCACTCTGAAAGAA<br>TCTGGACCGGCCCTGGTTAAGCCGACTCAAACGCTCACCCTTACTTGCACCTTCAGCGGATTCTCACTCAGCACTGCTGG<br>TGTGCACGTCGGATGGATTAGACAGCCGCCTGGAAAGGCCCTGGAATGGCTCGCCCTCATCTCCTGGGCCGATGACAAGA<br>GATACAGGCCCTCGCTTCGATCCCGGTTGGACATTACCCGGGTGACCTCGAAAGATCAGGTGGTGCTCTCAATGACCAAT<br>ATGCAGCCGGAGGACACCGCTACGTACTACTGCGCACTGCAAGGATTTGACGGCTACGAGGCTAACTGGGGACCAGGTAC<br>TCTGGTCACCGTGAGCTCCGGCGGGGGAGGATCAGGCGGGGGGGGGTCAGGAGGCGGAGGCTCCGGTGGAGGAGGATCGG<br>ATATCGTCATGACCCAGTCCCCAAGCTCGCTGAGCGCGTCAGCGGGCGACCGCGTGACTATCACTTGCCGGGCCAGCCGC<br>GGCATCTCCTCCGCACTGGCGTGGTACCAGCAGAAGCCTGGAAAACCGCCAAAGCTCCTGATCTATGATGCCTCCAGCCT<br>GGAGTCAGGTGTCCCCAGCCGCTTCTCGGGTTCGGGCTCGGGAACCGACTTCACTTTGACCATCGACTCGCTGGAACCGG<br>AAGATTTCGCAACCTACTACTGTCAGCAGTCCTACTCGACCCCTTGGACTTTTGGACAAGGGACGAAGGTGGACATCAAG |
| 134M24<br>(Full)<br>>NH67-<br>89CE<br>(M24) | <u>ATGGCCCTCCCTGTCACCGCCCTGCTGCTTCCGCTGGCTCTTCTGCTCCACGCCGCTCGGCCCC</u>AAATCACTCTGAAAGA<br>A<br>TCTGGACCGGCCCTGGTTAAGCCGACTCAAACGCTCACCCTTACTTGCACCTTCAGCGGATTCTCACTCAGCACTGCTGG<br>TGTGCACGTCGGATGGATTAGACAGCCGCCTGGAAAGGCCCTGGAATGGCTCGCCCTCATCTCCTGGGCCGATGACAAGA<br>GATACAGGCCCTCGCTTCGATCCCGGTTGGACATTACCCGGGTCACCTCGAAAGATCAGGTGGTGCTCTCAATGACCAAT<br>ATGCAGCCGGAGGACACCGCTACGTACTACTGCGCACTGCAAGGATTTGACGGCTACGAGGCTAACTGGGGACCAGGTAC<br>TCTGGTCACCGTGAGCTCCGGCGGGGGAGGATCAGGCGGGGGGGGTCAGGAGGCGGAGGCTCCGGTGGAGGAGGATCGG<br>ATATCGTCATGACCCAGTCCCCAAGCTCGCTGAGCGCGTCAGCCGGCGACCGCGTGACTATCACTTGCCGGGCCAGCCGC<br>GGCATCTCCTCCGCACTGGCGTGGTACCAGCAGAAGCCTGGAAAACCGCCAAAGCTCCTGATCTATGATGCCTCCAGCCT<br>GGAGTCAGGTGTCCCCAGCCGCTTCTCGGGTTCGGGCTCGGGAACCGACTTCACTTTGACCATCGACTCGCTGGAACCGG<br>AAGATTTCGCAACCTACTACTGTCAGCAGTCCTACTCGACCCCTTGGACTTTTGGACAAGGGACGAAGGTGGACATCAAG<br>ACCACTACCCAGCACCGAGGCCACCCACCCCGGCTCCTACCATCGCCTCCCAGCCTCTGTCCCTGCTCCGGAGGCATG<br>TAGACCCGCAGCTGGTGGGCCGTGCATACCCGGGTCTTGACTTCGCCTGCGATATCTACATTTGGGCCCCTCTGGCTG<br>GTACTTGCGGGGTCCTGCTGCTTTCACTCGTGATCACTCTTTACTGTAAGCGCGGTCGGAAGAAGCTGCTGTACATCTTT<br>AAGCAACCCTTCATGAGGCCTGTGCAGACTACTCAAGAGGAGGACGGCTGTTCATGCCGGTTCCCAGAGGAGGAGGAAGG<br>CGGCTGCGAACTGCGCGTGAAATTCAGCCGCAGCGCAGATGCTCCAGCCTACAAGCAGGGGCAGAACCAGCTCTACAACG<br>AACTCAATCTTGGTCGGAGAGAGGAGTACGACGTGCTGGACAACCGGAGAGGACGGGACCCAGAAATGGGCGGGAAGCCG<br>CGCAGAAAGAATCCCCAAGAGGGCCTGTACAACGAGCTCCAAAAGGATAAGATGGCAGAAGCCTATAGCGAGATTGGTAT<br>GAAAGGGGAACGCAGAAGAGGCAAAGGCCACGACGGACTGTACCAGGGACTCAGCACCGCCACCAAGGACACCTATGACG<br>CTCTTCACATGCAGGCCCTGCCGCCTCGG |
| 392Ss1<br>(scFv<br>domain) | CAAGTCCAGCTCCAGCAGTCGGGCCCAGAGTTGGAGAAGCCTGGGGCGAGCGTGAAGAT<br>CTCATGCAAAGCCTCAGGCTACTCCTTTACTGGATACACGATGAATTGGGTGAAACAGT<br>CGCATGGAAAGTCACTGGAATGGATCGGTCTGATTACGCCCTACAACGGCGCCTCCAGC<br>TACAACCAGAAGTTCAGGGGAAAGGCGACCCTTACTGTCGACAAGTCGTCAAGCACCGC<br>CTACATGGACCTCCTGTCCCTGACCTCCGAAGATAGCGCGGTCTACTTTTGTGCACGCG<br>GAGGTTACGATGGACGGGATTCGACTACTGGGGCCAGGGAACCACTGTCACCGTGTCG<br>AGCGGAGGCGGAGGGAGCGGAGGAGGAGGCAGCGGAGGTGGAGGGTCGGATATCGAACT<br>CACTCAGTCCCCAGCAATCATGTCCGCTTCACCGGGAGAAAAGGTGACCATGACTTGCT<br>CGGCCTCCTCGTCCGTGTCATACATGCACTGGTACCAACAAAAATCGGGGACCTCCCCT<br>AAGAGATGGATCTACGATACCAGCAAACTGGCTTCAGGCGTGCCGGGACGCTTCTCGGG<br>TTCGGGGAGCGGAAATTCGTATTCGTTGACCATTTCGTCCGTGGAAGCCGAGGACGACG<br>CAACTTATTACTGCCAACAGTGGTCAGGCTACCCGCTCACTTTCGGAGCCGGCACTAAG<br>CTGGAGATC |
| 393Ss1(full) | <u>ATGGCCCTCCCTGTCACCGCCCTGCTGCTTCCGCTGGCTCTTCTGCTCCACGCCGCTCG<br>GCCCC</u>AAGTCCAGCTCCAGCAGTCGGGCCCAGAGTTGGAGAAGCCTGGGGCGAGCGTGA<br>AGATCTCATGCAAAGCCTCAGGCTACTCCTTTACTGGATACACGATGAATTGGGTGAAA<br>CAGTCGCATGGAAAGTCACTGGAATGGATCGGTCTGATTACGCCCTACAACGGCGCCTC<br>CAGCTACAACCAGAAGTTCAGGGGAAAGGCGACCCTTACTGTCGACAAGTCGTCAAGCA<br>CCGCCTACATGGACCTCCTGTCCCTGACCTCCGAAGATAGCGCGGTCTACTTTTGTGCA<br>CGCGGAGGTTACGATGGACGGGATTCGACTACTGGGGCCAGGGAACCACTGTCACCGT<br>GTCGAGCGGAGGCGGAGGGAGCGGAGGAGGAGGCAGCGGAGGTGGAGGGTCGGATATCG<br>AACTCACTCAGTCCCCAGCAATCATGTCCGCTTCACCGGGAGAAAAGGTGACCATGACT<br>TGCTCGGCCTCCTCGTCCGTGTCATACATGCACTGGTACCAACAAAAATCGGGGACCTC<br>CCCTAAGAGATGGATCTACGATACCAGCAAACTGGCTTCAGGCGTGCCGGGACGCTTCT<br>CGGGTTCGGGGAGCGGAAATTCGTATTCGTTGACCATTTCGTCCGTGGAAGCCGAGGAC<br>GACGCAACTTATTACTGCCAACAGTGGTCAGGCTACCCGCTCACTTTCGGAGCCGGCAC<br>TAAGCTGGAGATCACCACTACCCCAGCACCGAGGCCACCCACCCCGGCTCCTACCATCG<br>CCTCCCAGCCTCTGTCCCTGCTCCGGAGGCATGTAGACCCGCAGCTGGTGGGCCGTG<br>CATACCCGGGTCTTGACTTCGCCTGCGATATCTACATTTGGGCCCCTCTGGCTGGTAC<br>TTGCGGGGTCCTGCTGCTTTCACTCGTGATCACTCTTTACTGTAAGCGCGGTCGGAAGA<br>AGCTGCTGTACATCTTTAAGCAACCCTTCATGAGGCCTGTGCAGACTACTCAAGAGGAG<br>GACGGCTGTTCATGCCGGTTCCCAGAGGAGGAGGAAGGCGGCTGCGAACTGCGCGTGAA<br>ATTCAGCCGCAGCGCAGATGCTCCAGCC |

TABLE 4

Amino acid sequences for the heavy chain (HC) CDR1, CDR2, and CDR3 regions of human anti-mesothelin scFvs

| Descrip. | HC-CDR1 | SEQ ID NO: | HC-CDR2 | SEQ ID NO: | HC-CDR3 | SEQ ID NO: |
|---|---|---|---|---|---|---|
| M1 | GYTFTGYYMH | 136 | RINPNSGGTNYAQKFQG | 155 | GRYYGMDV | 175 |
| M2 | GYTFTGYYMH | 136 | WINPNSGGTNYAQKFQG | 156 | DLRRTVVTPRAYYGMDV | 176 |
| M3 | GYTFTGYYMH | 136 | WINPNSGGTNYAQKFQG | 156 | GEWDGSYYYDY | 177 |
| M4 | GFTFSSYWMH | 137 | RINTDGSTTTYADSVEG | 157 | GHWAV | 178 |
| M5 | GYTFTDYYMH | 138 | WINPNSGGTNYAQKFQG | 156 | GWDFDY | 179 |
| M6 | GYTFTSYYMH | 139 | IINPSGGSTSYAQKFQ | 158 | YRLIAVAGDYYYGMDV | 180 |
| M7 | GFTFSSYAMH | 140 | VISYDGSNKYYADSVKG | 274 | WKVSSSSPAFDY | 181 |
| M8 | GYPFTGYSLH | 141 | WINPNSGGTNYAQKFQG | 159 | DHYGGNSLFY | 182 |
| M9 | GYTFTSYYMH | 142 | IINPSGGSTGYAQKFQG | 160 | GGYSSSSDAFDI | 183 |
| M10 | GYTFTSYGIS | 143 | WISAYNGNTNYAQKLQ | 161 | VAGGIYYYYGMDV | 184 |
| M11 | GYTFTGYYMH | 144 | WINPNSGGTNYAQNFQG | 162 | GWDFDY | 185 |
| M12 | GYTFTGYYMH | 144 | RINPNSGGTNYAQKFQG | 163 | TTTSYAFDI | 186 |
| M13 | GFIFSDYYMG | 145 | YIGRSGSSMYYADSVKG | 164 | SPVVAATEDFQH | 187 |
| M14 | GFTFRGYYIH | 146 | IINPSGGSRAYAQKFQG | 165 | TASCGGDCYYLDY | 188 |
| M15 | GFTFDDYAMH | 147 | GISWNSGSIGYADSVK | 166 | DGSSSWSWGYFDY | 189 |
| M16 | GFTFDDYAMH | 147 | GISWNSGSTGYADSVKG | 167 | DSSSWYGGGSAFDI | 190 |
| M17 | GFTFDDYAMH | 147 | GISWNSGSTGYADSVKG | 167 | DSSSWYGGGSAFDI | 191 |
| M18 | GFTFSSYWMH | 148 | RINSDGSSTSYADSVKG | 168 | TGWVGSYYYYMDV | 192 |
| M19 | GFTFSSYGMH | 149 | VISYDGSNKYYADSVKG | 169 | GYSRYYYYGMDV | 193 |
| M20 | GFTFSSYAMS | 150 | AISGSGGSTYYADSVKG | 170 | REAAAGHDWYFDL | 194 |
| M21 | GYTFTSYYMH | 151 | IINPSGGSTSYAQKFQG | 171 | SPRVTTGYFDY | 195 |
| M22 | GDTSTRHYIH | 152 | VINPTTGPATGSPAYAQMLQG | 172 | SVVGRSAPYYFDY | 196 |
| M23 | GYTFTNYYMH | 153 | IINPSGGYTTYAQKFQG | 173 | IRSCGGDCYYFDN | 197 |
| M24 | GFSLSTAGVHVG | 154 | LISWADDKRYRPSLRS | 174 | QGFDGYEAN | 198 |
| Ss1 | GYSFTGYTMN | 394 | LITPYNGASSYNQKFRG | 395 | GGYDGRGFDY | 396 |

TABLE 5

Amino acid sequences for the light chain (LC) CDR1, CDR2, and CDR3 regions of human anti-mesothelin scFvs

| Description | LC-CDR1 | SEQ ID NO: | LC-CDR2 | SEQ ID NO: | LC-CDR3 | SEQ ID NO: |
|---|---|---|---|---|---|---|
| M1 | RASQSVSSNFA | 199 | DASNRAT | 223 | HQRSNWLYT | 247 |
| M2 | QASQDISNSLN | 200 | DASTLET | 224 | QQHDNLPLT | 248 |
| M3 | RASQSINTYLN | 201 | AASSLQS | 225 | QQSFSPLT | 249 |
| M4 | RASQSISDRLA | 202 | KASSLES | 226 | QQYGHLPMYT | 250 |
| M5 | RASQSIRYYLS | 203 | TASILQN | 227 | LQTYTTPD | 251 |

TABLE 5-continued

Amino acid sequences for the light chain (LC) CDR1, CDR2, and CDR3 regions of human anti-mesothelin scFvs

| Description | LC-CDR1 | SEQ ID NO: | LC-CDR2 | SEQ ID NO: | LC-CDR3 | SEQ ID NO: |
|---|---|---|---|---|---|---|
| M6 | RASQGVGRWLA | 204 | AASTLQS | 228 | QQANSFPLT | 252 |
| M7 | RASQSVYTKYLG | 205 | DASTRAT | 229 | QHYGGSPLIT | 253 |
| M8 | RASQDSGTWLA | 206 | DASTLED | 230 | QQYNSYPLT | 254 |
| M9 | RASQDISSALA | 207 | DASSLES | 231 | QQFSSYPLT | 255 |
| M10 | KSSHSVLYNRNNKNYLA | 208 | WASTRKS | 232 | QQTQTFPLT | 256 |
| M11 | RASQSIRYYLS | 209 | TASILQN | 233 | LQTYTTPD | 257 |
| M12 | RASQSISTWLA | 210 | KASTLES | 234 | QQYNTYSPYT | 258 |
| M13 | RASQSVTSNYLA | 211 | GASTRAT | 235 | QQYGSAPVT | 259 |
| M14 | RASENVNIWLA | 212 | KSSSLAS | 236 | QQYQSYPLT | 260 |
| M15 | QGDALRSYYAS | 213 | GKNNRPS | 237 | NSRDSSGYPV | 261 |
| M16 | QGDSLRSYYAS | 214 | GRSRRPS | 238 | NSRDNTANHYV | 262 |
| M17 | QGDSLRSYYAS | 215 | GKNNRPS | 239 | NSRGSSGNHYV | 263 |
| M18 | RASQSVSSNYLA | 216 | DVSTRAT | 240 | QQRSNWPPWT | 264 |
| M19 | RASQSVYTKYLG | 217 | DASTRAT | 241 | QHYGGSPLIT | 265 |
| M20 | RASQSISSYLN | 218 | AASSLQS | 242 | QQSYSIPLT | 266 |
| M21 | RASQSISSWLA | 219 | KASSLES | 243 | QQYSSYPLT | 267 |
| M22 | RASQGISDYS | 220 | AASTLQS | 244 | QQYYSYPLT | 268 |
| M23 | RASENVNIWLA | 221 | KSSSLAS | 245 | QQYQSYPLT | 269 |
| M24 | RASRGISSALA | 222 | DASSLES | 246 | QQSYSTPWT | 270 |
| Ss1 | SASSSVSYMH | 397 | DTSKLAS | 398 | QQWSGYPLT | 399 |

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1

Generating CAR Constructs

ScFv to be used in the final CAR construct were derived from the pannings of human scFV libraries.
The amino acid sequences of the human scFv fragments are provided above in Table 2 and the nucleic acid sequences of the human scFv fragments are provided above in Table 3. Full CAR constructs were generated using the scFv fragments of Table 2 with additional sequences, SEQ ID NOs: 1-2, 6-7, 9-10, 12-13, 17-18, 20-21, and 36-37, shown below, to generate full CAR constructs.

leader (amino acid sequence)
(SEQ ID NO: 1)
MALPVTALLLPLALLLHAARP leader (nucleic acid sequence)
(SEQ ID NO: 12)
ATGGCCCTCCCTGTCACCGCCCTGCTGCTTCCGCTGGCTCTTCTGCTCCA

CGCCGCTCGGCCC

CD8 hinge (amino acid sequence)
(SEQ ID NO: 2)
TTTPAPRPPTPAPTIASQPLSLRPEACRPAAGGAVHTRGLDFACD CD8 hinge (nucleic acid sequence)
(SEQ ID NO: 13)
ACCACTACCCCAGCACCGAGGCCACCCACCCCGGCTCCTACCATCGCCTC

CCAGCCTCTGTCCCTGCGTCCGGAGGCATGTAGACCCGCAGCTGGTGGGG

CCGTGCATACCCGGGGTCTTGACTTCGCCTGCGAT

CD8 transmembrane (amino acid sequence)
(SEQ ID NO: 6)
IYIWAPLAGTCGVLLLSLVITLYC

CD8 transmembrane (nucleic acid sequence)
(SEQ ID NO: 17)
ATCTACATTTGGGCCCCTCTGGCTGGTACTTGCGGGGTCCTGCTGCTTTC

ACTCGTGATCACTCTTTACTGT 4-1BB Intracellular domain (amino acid sequence)
(SEQ ID NO: 7)
KRGRKKLLYIFKQPFMRPVQTTQEEDGCSCRFPEEEEGGCEL 4-1BB Intracellular domain (nucleic acid sequence)
(SEQ ID NO: 18)
AAGCGCGGTCGGAAGAAGCTGCTGTACATCTTTAAGCAACCCTTCATGAG

GCCTGTGCAGACTACTCAAGAGGAGGACGGCTGTTCATGCCGGTTCCCAG

AGGAGGAGGAAGGCGGCTGCGAACTG

CD3 zeta domain (amino acid sequence)
(SEQ ID NO: 9)
RVKFSRSADAPAYKQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

CD3 zeta (nucleic acid sequence)
(SEQ ID NO: 20)
CGCGTGAAATTCAGCCGCAGCGCAGATGCTCCAGCCTACAAGCAGGGGCA

GAACCAGCTCTACAACGAACTCAATCTTGGTCGGAGAGAGGAGTACGACG

TGCTGGACAAGCGGAGAGGACGGGACCCAGAAATGGGCGGGAAGCCGCGC

AGAAAGAATCCCCAAGAGGGCCTGTACAACGAGCTCCAAAAGGATAAGAT

GGCAGAAGCCTATAGCGAGATTGGTATGAAAGGGGAACGCAGAAGAGGCA

AAGGCCACGACGGACTGTACCAGGGACTCAGCACCGCCACCAAGGACACC

TATGACGCTCTTCACATGCAGGCCCTGCCGCCTCGG

CD3 zeta domain (amino acid sequence;
NCBI Reference Sequence NM_000734.3)
(SEQ ID NO: 10)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

CD3 zeta (nucleic acid sequence; NCBI Reference
Sequence NM_000734.3);
(SEQ ID NO: 21)
AGAGTGAAGTTCAGCAGGAGCGCAGACGCCCCCGCGTACCAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGAGA

AGGAAGAACCCTCAGGAAGGCCTGTACAATGAACTGCAGAAAGATAAGAT

GGCGGAGGCCTACAGTGAGATTGGGATGAAAGGCGAGCGCCGGAGGGGCA

AGGGGCACGATGGCCTTTACCAGGGTCTCAGTACAGCCACCAAGGACACC

TACGACGCCCTTCACATGCAGGCCCTGCCCCCTCGC

IgG4 Hinge (amino acid sequence)
(SEQ ID NO: 36)
ESKYGPPCPPCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGKM

IgG4 Hinge (nucleotide sequence)
(SEQ ID NO: 37)
GAGAGCAAGTACGGCCCTCCCTGCCCCCCTTGCCCTGCCCCCGAGTTCCT

CGGACCCAGCGTGTTCCTGTTCCCCCCCAAGCCCAAGGACACCCTGATGA

TCGGGAGCCGGACCCCCGAGGTGACCTGTGTGGTGGTGGACGTGTCCCAG

GAGGACCCCGAGGTCCAGTTCAACTGGTACGTGGACGGCGTGGAGGTGCA

CAACGCCAAGACCAAGCCCCGGGAGGAGCAGTTCAATAGCACCTACCGGG

TGGTGTCCGTGCTGACCGTGCTGCACCAGGACTGGCTGAACGGCAAGGAA

TACAAGTGTAAGGTGTCCAACAAGGGCCTGCCCAGCAGCATCGAGAAAAC

CATCAGCAAGGCCAAGGGCCAGCCTCGGGAGCCCCAGGTGTACACCCTGC

CCCCTAGCCAAGAGGAGATGACCAAGAACCAGGTGTCCCTGACCTGCCTG

GTGAAGGGCTTCTACCCCAGCGACATCGCCGTGGAGTGGGAGAGCAACGG

CCAGCCCGAGAACAACTACAAGACCACCCCCCCTGTGCTGGACAGCGACG

GCAGCTTCTTCCTGTACAGCCGGCTGACCGTGGACAAGAGCCGGTGGCAG

GAGGGCAACGTCTTTAGCTGCTCCGTGATGCACGAGGCCCTGCACAACCA

CTACACCCAGAAGAGCCTGAGCCTGTCCCTGGGCAAGATG

These clones all contained a Q/K residue
change in the signal domain of the co-
stimulatory domain derived from CD3zeta chain.

The CAR scFv fragments were then cloned into lentiviral vectors to create a full length CAR construct in a single coding frame, and using the EF1 alpha promoter for expression (SEQ ID NO: 11).

EF1 alpha promoter
(SEQ ID NO: 11)
CGTGAGGCTCCGGTGCCCGTCAGTGGGCAGAGCGCACATCGCCCACAGTC

CCCGAGAAGTTGGGGGGAGGGGTCGGCAATTGAACCGGTGCCTAGAGAAG

GTGGCGCGGGGTAAACTGGGAAAGTGATGTCGTGTACTGGCTCCGCCTTT

TTCCCGAGGGTGGGGGAGAACCGTATATAAGTGCAGTAGTCGCCGTGAAC

GTTCTTTTTCGCAACGGGTTTGCCGCCAGAACACAGGTAAGTGCCGTGTG

TGGTTCCCGCGGGCCTGGCCTCTTTACGGGTTATGGCCCTTGCGTGCCTT

GAATTACTTCCACCTGGCTGCAGTACGTGATTCTTGATCCCGAGCTTCGG

GTTGGAAGTGGGTGGGAGAGTTCGAGGCCTTGCGCTTAAGGAGCCCCTTC

GCCTCGTGCTTGAGTTGAGGCCTGGCCTGGGCGCTGGGGCCGCCGCGTGC

GAATCGGTGGCACCTTCGCGCCTGTCTCGCTGCTTTCGATAAGTCTCTA

GCCATTTAAAATTTTTGATGACCTGCTGCGACGCTTTTTTTCTGGCAAGA

TAGTCTTGTAAATGCGGGCCAAGATCTGCACACTGGTATTTCGGTTTTTG

GGGCCGCGGGCGGCGACGGGGCCCGTGCGTCCCAGCGCACATGTTCGGCG

AGGCGGGGCCTGCGAGCGCGGCCACCGAGAATCGGACGGGGGTAGTCTCA

AGCTGGCCGGCCTGCTCTGGTGCCTGGCCTCGCGCCGCCGTGTATCGCCC

CGCCCTGGGCGGCAAGGCTGGCCCGGTCGGCACCAGTTGCGTGAGCGGAA

AGATGGCCGCTTCCCGGCCCTGCTGCAGGGAGCTCAAAATGGAGGACGCG

GCGCTCGGGAGAGCGGGCGGGTGAGTCACCCACACAAAGGAAAAGGGCCT

TTCCGTCCTCAGCCGTCGCTTCATGTGACTCCACGGAGTACCGGGCGCCG

TCCAGGCACCTCGATTAGTTCTCGAGCTTTTGGAGTACGTCGTCTTTAGG

-continued

TTGGGGGGAGGGGTTTTATGCGATGGAGTTTCCCCACACTGAGTGGGTGG

AGACTGAAGTTAGGCCAGCTTGGCACTTGATGTAATTCTCCTTGGAATTT

GCCCTTTTTGAGTTTGGATCTTGGTTCATTCTCAAGCCTCAGACAGTGGT

TCAAAGTTTTTTTCTTCCATTTCAGGTGTCGTGA.

Gly/Ser (SEQ ID NO: 25)

GGGGS

Gly/Ser (SEQ ID NO: 26): This sequence may encompass 1-6 "Gly Gly Gly Gly Ser" repeating units Gly/Ser (SEQ ID NO: 27)

GGGGSGGGGS GGGGSGGGGS GGGGSGGGGS

Gly/Ser (SEQ ID NO: 28)

GGGGSGGGGS GGGGSGGGGS

Gly/Ser (SEQ ID NO: 29)

GGGGSGGGGS GGGGS

Gly/Ser (SEQ ID NO: 29)

GGGS

PolyA (SEQ ID NO: 30)

This sequence may encompass 50-5000 adenines.

PolyA (SEQ ID NO: 31)

```
aaaaaaaaaa aaaaaaaaaa aaaaaaaaaa aaaaaaaaaa aaaaaaaaaa aaaaaaaaaa    60
aaaaaaaaaa aaaaaaaaaa aaaaaaaaaa aaaaaaaaaa aaaaaaaaaa aaaaaaaaaa   120
aaaaaaaaaa aaaaaaaaaa aaaaaaaaaa aaaaaaaaaa aaaaaaaaaa aaaaaaaaaa   180
aaaaaaaaaa aaaaaaaaaa aaaaaaaaaa aaaaaaaaaa aaaaaaaaaa aaaaaaaaaa   240
aaaaaaaaaa aaaaaaaaaa aaaaaaaaaa aaaaaaaaaa aaaaaaaaaa aaaaaaaaaa   300
aaaaaaaaaa aaaaaaaaaa aaaaaaaaaa aaaaaaaaaa aaaaaaaaaa aaaaaaaaaa   360
aaaaaaaaaa aaaaaaaaaa aaaaaaaaaa aaaaaaaaaa aaaaaaaaaa aaaaaaaaaa   420
aaaaaaaaaa aaaaaaaaaa aaaaaaaaaa aaaaaaaaaa aaaaaaaaaa aaaaaaaaaa   480
aaaaaaaaaa aaaaaaaaaa aaaaaaaaaa aaaaaaaaaa aaaaaaaaaa aaaaaaaaaa   540
aaaaaaaaaa aaaaaaaaaa aaaaaaaaaa aaaaaaaaaa aaaaaaaaaa aaaaaaaaaa   600
aaaaaaaaaa aaaaaaaaaa aaaaaaaaaa aaaaaaaaaa aaaaaaaaaa aaaaaaaaaa   660
aaaaaaaaaa aaaaaaaaaa aaaaaaaaaa aaaaaaaaaa aaaaaaaaaa aaaaaaaaaa   720
aaaaaaaaaa aaaaaaaaaa aaaaaaaaaa aaaaaaaaaa aaaaaaaaaa aaaaaaaaaa   780
aaaaaaaaaa aaaaaaaaaa aaaaaaaaaa aaaaaaaaaa aaaaaaaaaa aaaaaaaaaa   840
aaaaaaaaaa aaaaaaaaaa aaaaaaaaaa aaaaaaaaaa aaaaaaaaaa aaaaaaaaaa   900
aaaaaaaaaa aaaaaaaaaa aaaaaaaaaa aaaaaaaaaa aaaaaaaaaa aaaaaaaaaa   960
aaaaaaaaaa aaaaaaaaaa aaaaaaaaaa aaaaaaaaaa aaaaaaaaaa aaaaaaaaaa  1020
aaaaaaaaaa aaaaaaaaaa aaaaaaaaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaaaaa aaaaaaaaaa aaaaaaaaaa aaaaaaaaaa  1200
aaaaaaaaaa aaaaaaaaaa aaaaaaaaaa aaaaaaaaaa aaaaaaaaaa aaaaaaaaaa  1260
aaaaaaaaaa aaaaaaaaaa aaaaaaaaaa aaaaaaaaaa aaaaaaaaaa aaaaaaaaaa  1320
aaaaaaaaaa aaaaaaaaaa aaaaaaaaaa aaaaaaaaaa aaaaaaaaaa aaaaaaaaaa  1380
aaaaaaaaaa aaaaaaaaaa aaaaaaaaaa aaaaaaaaaa aaaaaaaaaa aaaaaaaaaa  1440
aaaaaaaaaa aaaaaaaaaa aaaaaaaaaa aaaaaaaaaa aaaaaaaaaa aaaaaaaaaa  1500
aaaaaaaaaa aaaaaaaaaa aaaaaaaaaa aaaaaaaaaa aaaaaaaaaa aaaaaaaaaa  1560
aaaaaaaaaa aaaaaaaaaa aaaaaaaaaa aaaaaaaaaa aaaaaaaaaa aaaaaaaaaa  1620
aaaaaaaaaa aaaaaaaaaa aaaaaaaaaa aaaaaaaaaa aaaaaaaaaa aaaaaaaaaa  1680
aaaaaaaaaa aaaaaaaaaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
```

-continued

```
aaaaaaaaaa aaaaaaaaaa aaaaaaaaaa aaaaaaaaaa aaaaaaaaaa aaaaaaaaaa    1860
aaaaaaaaaa aaaaaaaaaa aaaaaaaaaa aaaaaaaaaa aaaaaaaaaa aaaaaaaaaa    1920
aaaaaaaaaa aaaaaaaaaa aaaaaaaaaa aaaaaaaaaa aaaaaaaaaa aaaaaaaaaa    1980
aaaaaaaaaa aaaaaaaaaa aaaaaaaaaa aaaaaaaaaa aaaaaaaaaa aaaaaaaaaa    2040
aaaaaaaaaa aaaaaaaaaa aaaaaaaaaa aaaaaaaaaa aaaaaaaaaa aaaaaaaaaa    2100
aaaaaaaaaa aaaaaaaaaa aaaaaaaaaa aaaaaaaaaa aaaaaaaaaa aaaaaaaaaa    2160
aaaaaaaaaa aaaaaaaaaa aaaaaaaaaa aaaaaaaaaa aaaaaaaaaa aaaaaaaaaa    2220
aaaaaaaaaa aaaaaaaaaa aaaaaaaaaa aaaaaaaaaa aaaaaaaaaa aaaaaaaaaa    2280
aaaaaaaaaa aaaaaaaaaa aaaaaaaaaa aaaaaaaaaa aaaaaaaaaa aaaaaaaaaa    2340
aaaaaaaaaa aaaaaaaaaa aaaaaaaaaa aaaaaaaaaa aaaaaaaaaa aaaaaaaaaa    2400
aaaaaaaaaa aaaaaaaaaa aaaaaaaaaa aaaaaaaaaa aaaaaaaaaa aaaaaaaaaa    2460
aaaaaaaaaa aaaaaaaaaa aaaaaaaaaa aaaaaaaaaa aaaaaaaaaa aaaaaaaaaa    2520
aaaaaaaaaa aaaaaaaaaa aaaaaaaaaa aaaaaaaaaa aaaaaaaaaa aaaaaaaaaa    2580
aaaaaaaaaa aaaaaaaaaa aaaaaaaaaa aaaaaaaaaa aaaaaaaaaa aaaaaaaaaa    2640
aaaaaaaaaa aaaaaaaaaa aaaaaaaaaa aaaaaaaaaa aaaaaaaaaa aaaaaaaaaa    2700
aaaaaaaaaa aaaaaaaaaa aaaaaaaaaa aaaaaaaaaa aaaaaaaaaa aaaaaaaaaa    2760
aaaaaaaaaa aaaaaaaaaa aaaaaaaaaa aaaaaaaaaa aaaaaaaaaa aaaaaaaaaa    2820
aaaaaaaaaa aaaaaaaaaa aaaaaaaaaa aaaaaaaaaa aaaaaaaaaa aaaaaaaaaa    2880
aaaaaaaaaa aaaaaaaaaa aaaaaaaaaa aaaaaaaaaa aaaaaaaaaa aaaaaaaaaa    2940
aaaaaaaaaa aaaaaaaaaa aaaaaaaaaa aaaaaaaaaa aaaaaaaaaa aaaaaaaaaa    3000
aaaaaaaaaa aaaaaaaaaa aaaaaaaaaa aaaaaaaaaa aaaaaaaaaa aaaaaaaaaa    3060
aaaaaaaaaa aaaaaaaaaa aaaaaaaaaa aaaaaaaaaa aaaaaaaaaa aaaaaaaaaa    3120
aaaaaaaaaa aaaaaaaaaa aaaaaaaaaa aaaaaaaaaa aaaaaaaaaa aaaaaaaaaa    3180
aaaaaaaaaa aaaaaaaaaa aaaaaaaaaa aaaaaaaaaa aaaaaaaaaa aaaaaaaaaa    3240
aaaaaaaaaa aaaaaaaaaa aaaaaaaaaa aaaaaaaaaa aaaaaaaaaa aaaaaaaaaa    3300
aaaaaaaaaa aaaaaaaaaa aaaaaaaaaa aaaaaaaaaa aaaaaaaaaa aaaaaaaaaa    3360
aaaaaaaaaa aaaaaaaaaa aaaaaaaaaa aaaaaaaaaa aaaaaaaaaa aaaaaaaaaa    3420
aaaaaaaaaa aaaaaaaaaa aaaaaaaaaa aaaaaaaaaa aaaaaaaaaa aaaaaaaaaa    3480
aaaaaaaaaa aaaaaaaaaa aaaaaaaaaa aaaaaaaaaa aaaaaaaaaa aaaaaaaaaa    3540
aaaaaaaaaa aaaaaaaaaa aaaaaaaaaa aaaaaaaaaa aaaaaaaaaa aaaaaaaaaa    3600
aaaaaaaaaa aaaaaaaaaa aaaaaaaaaa aaaaaaaaaa aaaaaaaaaa aaaaaaaaaa    3660
aaaaaaaaaa aaaaaaaaaa aaaaaaaaaa aaaaaaaaaa aaaaaaaaaa aaaaaaaaaa    3720
aaaaaaaaaa aaaaaaaaaa aaaaaaaaaa aaaaaaaaaa aaaaaaaaaa aaaaaaaaaa    3780
aaaaaaaaaa aaaaaaaaaa aaaaaaaaaa aaaaaaaaaa aaaaaaaaaa aaaaaaaaaa    3840
aaaaaaaaaa aaaaaaaaaa aaaaaaaaaa aaaaaaaaaa aaaaaaaaaa aaaaaaaaaa    3900
aaaaaaaaaa aaaaaaaaaa aaaaaaaaaa aaaaaaaaaa aaaaaaaaaa aaaaaaaaaa    3960
aaaaaaaaaa aaaaaaaaaa aaaaaaaaaa aaaaaaaaaa aaaaaaaaaa aaaaaaaaaa    4020
aaaaaaaaaa aaaaaaaaaa aaaaaaaaaa aaaaaaaaaa aaaaaaaaaa aaaaaaaaaa    4080
aaaaaaaaaa aaaaaaaaaa aaaaaaaaaa aaaaaaaaaa aaaaaaaaaa aaaaaaaaaa    4140
aaaaaaaaaa aaaaaaaaaa aaaaaaaaaa aaaaaaaaaa aaaaaaaaaa aaaaaaaaaa    4200
```

```
-continued
aaaaaaaaaa aaaaaaaaaa aaaaaaaaaa aaaaaaaaaa aaaaaaaaaa aaaaaaaaaa    4260
aaaaaaaaaa aaaaaaaaaa aaaaaaaaaa aaaaaaaaaa aaaaaaaaaa aaaaaaaaaa    4320
aaaaaaaaaa aaaaaaaaaa aaaaaaaaaa aaaaaaaaaa aaaaaaaaaa aaaaaaaaaa    4380
aaaaaaaaaa aaaaaaaaaa aaaaaaaaaa aaaaaaaaaa aaaaaaaaaa aaaaaaaaaa    4440
aaaaaaaaaa aaaaaaaaaa aaaaaaaaaa aaaaaaaaaa aaaaaaaaaa aaaaaaaaaa    4500
aaaaaaaaaa aaaaaaaaaa aaaaaaaaaa aaaaaaaaaa aaaaaaaaaa aaaaaaaaaa    4560
aaaaaaaaaa aaaaaaaaaa aaaaaaaaaa aaaaaaaaaa aaaaaaaaaa aaaaaaaaaa    4620
aaaaaaaaaa aaaaaaaaaa aaaaaaaaaa aaaaaaaaaa aaaaaaaaaa aaaaaaaaaa    4680
aaaaaaaaaa aaaaaaaaaa aaaaaaaaaa aaaaaaaaaa aaaaaaaaaa aaaaaaaaaa    4740
aaaaaaaaaa aaaaaaaaaa aaaaaaaaaa aaaaaaaaaa aaaaaaaaaa aaaaaaaaaa    4800
aaaaaaaaaa aaaaaaaaaa aaaaaaaaaa aaaaaaaaaa aaaaaaaaaa aaaaaaaaaa    4860
aaaaaaaaaa aaaaaaaaaa aaaaaaaaaa aaaaaaaaaa aaaaaaaaaa aaaaaaaaaa    4920
aaaaaaaaaa aaaaaaaaaa aaaaaaaaaa aaaaaaaaaa aaaaaaaaaa aaaaaaaaaa    4980
aaaaaaaaaa aaaaaaaaaa                                                5000

PolyA
                                                    (SEQ ID NO: 32)
tttttttttt tttttttttt tttttttttt tttttttttt tttttttttt tttttttttt     60
tttttttttt tttttttttt tttttttttt tttttttttt                          100
```

This sequence may encompass 50-5000 thymines.

```
PolyA
                                                    (SEQ ID NO: 33)
tttttttttt tttttttttt tttttttttt tttttttttt tttttttttt tttttttttt     60
tttttttttt tttttttttt tttttttttt tttttttttt tttttttttt tttttttttt    120
tttttttttt tttttttttt tttttttttt tttttttttt tttttttttt tttttttttt    180
tttttttttt tttttttttt tttttttttt tttttttttt tttttttttt tttttttttt    240
tttttttttt tttttttttt tttttttttt tttttttttt tttttttttt tttttttttt    300
tttttttttt tttttttttt tttttttttt tttttttttt tttttttttt tttttttttt    360
tttttttttt tttttttttt tttttttttt tttttttttt tttttttttt tttttttttt    420
tttttttttt tttttttttt tttttttttt tttttttttt tttttttttt tttttttttt    480
tttttttttt tttttttttt tttttttttt tttttttttt tttttttttt tttttttttt    540
tttttttttt tttttttttt tttttttttt tttttttttt tttttttttt tttttttttt    600
tttttttttt tttttttttt tttttttttt tttttttttt tttttttttt tttttttttt    660
tttttttttt tttttttttt tttttttttt tttttttttt tttttttttt tttttttttt    720
tttttttttt tttttttttt tttttttttt tttttttttt tttttttttt tttttttttt    780
tttttttttt tttttttttt tttttttttt tttttttttt tttttttttt tttttttttt    840
tttttttttt tttttttttt tttttttttt tttttttttt tttttttttt tttttttttt    900
tttttttttt tttttttttt tttttttttt tttttttttt tttttttttt tttttttttt    960
tttttttttt tttttttttt tttttttttt tttttttttt tttttttttt tttttttttt   1020
tttttttttt tttttttttt tttttttttt tttttttttt tttttttttt tttttttttt   1080
tttttttttt tttttttttt tttttttttt tttttttttt tttttttttt tttttttttt   1140
tttttttttt tttttttttt tttttttttt tttttttttt tttttttttt tttttttttt   1200
tttttttttt tttttttttt tttttttttt tttttttttt tttttttttt tttttttttt   1260
```

-continued

```
tttttttttt tttttttttt tttttttttt tttttttttt tttttttttt tttttttttt   1320
tttttttttt tttttttttt tttttttttt tttttttttt tttttttttt tttttttttt   1380
tttttttttt tttttttttt tttttttttt tttttttttt tttttttttt tttttttttt   1440
tttttttttt tttttttttt tttttttttt tttttttttt tttttttttt tttttttttt   1500
tttttttttt tttttttttt tttttttttt tttttttttt tttttttttt tttttttttt   1560
tttttttttt tttttttttt tttttttttt tttttttttt tttttttttt tttttttttt   1620
tttttttttt tttttttttt tttttttttt tttttttttt tttttttttt tttttttttt   1680
tttttttttt tttttttttt tttttttttt tttttttttt tttttttttt tttttttttt   1740
tttttttttt tttttttttt tttttttttt tttttttttt tttttttttt tttttttttt   1800
tttttttttt tttttttttt tttttttttt tttttttttt tttttttttt tttttttttt   1860
tttttttttt tttttttttt tttttttttt tttttttttt tttttttttt tttttttttt   1920
tttttttttt tttttttttt tttttttttt tttttttttt tttttttttt tttttttttt   1980
tttttttttt tttttttttt tttttttttt tttttttttt tttttttttt tttttttttt   2040
tttttttttt tttttttttt tttttttttt tttttttttt tttttttttt tttttttttt   2100
tttttttttt tttttttttt tttttttttt tttttttttt tttttttttt tttttttttt   2160
tttttttttt tttttttttt tttttttttt tttttttttt tttttttttt tttttttttt   2220
tttttttttt tttttttttt tttttttttt tttttttttt tttttttttt tttttttttt   2280
tttttttttt tttttttttt tttttttttt tttttttttt tttttttttt tttttttttt   2340
tttttttttt tttttttttt tttttttttt tttttttttt tttttttttt tttttttttt   2400
tttttttttt tttttttttt tttttttttt tttttttttt tttttttttt tttttttttt   2460
tttttttttt tttttttttt tttttttttt tttttttttt tttttttttt tttttttttt   2520
tttttttttt tttttttttt tttttttttt tttttttttt tttttttttt tttttttttt   2580
tttttttttt tttttttttt tttttttttt tttttttttt tttttttttt tttttttttt   2640
tttttttttt tttttttttt tttttttttt tttttttttt tttttttttt tttttttttt   2700
tttttttttt tttttttttt tttttttttt tttttttttt tttttttttt tttttttttt   2760
tttttttttt tttttttttt tttttttttt tttttttttt tttttttttt tttttttttt   2820
tttttttttt tttttttttt tttttttttt tttttttttt tttttttttt tttttttttt   2880
tttttttttt tttttttttt tttttttttt tttttttttt tttttttttt tttttttttt   2940
tttttttttt tttttttttt tttttttttt tttttttttt tttttttttt tttttttttt   3000
tttttttttt tttttttttt tttttttttt tttttttttt tttttttttt tttttttttt   3060
tttttttttt tttttttttt tttttttttt tttttttttt tttttttttt tttttttttt   3120
tttttttttt tttttttttt tttttttttt tttttttttt tttttttttt tttttttttt   3180
tttttttttt tttttttttt tttttttttt tttttttttt tttttttttt tttttttttt   3240
tttttttttt tttttttttt tttttttttt tttttttttt tttttttttt tttttttttt   3300
tttttttttt tttttttttt tttttttttt tttttttttt tttttttttt tttttttttt   3360
tttttttttt tttttttttt tttttttttt tttttttttt tttttttttt tttttttttt   3420
tttttttttt tttttttttt tttttttttt tttttttttt tttttttttt tttttttttt   3480
tttttttttt tttttttttt tttttttttt tttttttttt tttttttttt tttttttttt   3540
tttttttttt tttttttttt tttttttttt tttttttttt tttttttttt tttttttttt   3600
tttttttttt tttttttttt tttttttttt tttttttttt tttttttttt tttttttttt   3660
```

```
tttttttttt tttttttttt tttttttttt tttttttttt tttttttttt tttttttttt   3720
tttttttttt tttttttttt tttttttttt tttttttttt tttttttttt tttttttttt   3780
tttttttttt tttttttttt tttttttttt tttttttttt tttttttttt tttttttttt   3840
tttttttttt tttttttttt tttttttttt tttttttttt tttttttttt tttttttttt   3900
tttttttttt tttttttttt tttttttttt tttttttttt tttttttttt tttttttttt   3960
tttttttttt tttttttttt tttttttttt tttttttttt tttttttttt tttttttttt   4020
tttttttttt tttttttttt tttttttttt tttttttttt tttttttttt tttttttttt   4080
tttttttttt tttttttttt tttttttttt tttttttttt tttttttttt tttttttttt   4140
tttttttttt tttttttttt tttttttttt tttttttttt tttttttttt tttttttttt   4200
tttttttttt tttttttttt tttttttttt tttttttttt tttttttttt tttttttttt   4260
tttttttttt tttttttttt tttttttttt tttttttttt tttttttttt tttttttttt   4320
tttttttttt tttttttttt tttttttttt tttttttttt tttttttttt tttttttttt   4380
tttttttttt tttttttttt tttttttttt tttttttttt tttttttttt tttttttttt   4440
tttttttttt tttttttttt tttttttttt tttttttttt tttttttttt tttttttttt   4500
tttttttttt tttttttttt tttttttttt tttttttttt tttttttttt tttttttttt   4560
tttttttttt tttttttttt tttttttttt tttttttttt tttttttttt tttttttttt   4620
tttttttttt tttttttttt tttttttttt tttttttttt tttttttttt tttttttttt   4680
tttttttttt tttttttttt tttttttttt tttttttttt tttttttttt tttttttttt   4740
tttttttttt tttttttttt tttttttttt tttttttttt tttttttttt tttttttttt   4800
tttttttttt tttttttttt tttttttttt tttttttttt tttttttttt tttttttttt   4860
tttttttttt tttttttttt tttttttttt tttttttttt tttttttttt tttttttttt   4920
tttttttttt tttttttttt tttttttttt tttttttttt tttttttttt tttttttttt   4980
tttttttttt tttttttttt                                                5000
```

This sequence may encompass 100-5000 adenines.

```
aaaaaaaaaa aaaaaaaaaa aaaaaaaaaa aaaaaaaaaa aaaaaaaaaa aaaaaaaaaa     60
aaaaaaaaaa aaaaaaaaaa aaaaaaaaaa aaaaaaaaaa aaaaaaaaaa aaaaaaaaaa    120
aaaaaaaaaa aaaaaaaaaa aaaaaaaaaa aaaaaaaaaa aaaaaaaaaa aaaaaaaaaa    180
aaaaaaaaaa aaaaaaaaaa aaaaaaaaaa aaaaaaaaaa aaaaaaaaaa aaaaaaaaaa    240
aaaaaaaaaa aaaaaaaaaa aaaaaaaaaa aaaaaaaaaa aaaaaaaaaa aaaaaaaaaa    300
aaaaaaaaaa aaaaaaaaaa aaaaaaaaaa aaaaaaaaaa aaaaaaaaaa aaaaaaaaaa    360
aaaaaaaaaa aaaaaaaaaa aaaaaaaaaa aaaaaaaaaa aaaaaaaaaa aaaaaaaaaa    420
aaaaaaaaaa aaaaaaaaaa aaaaaaaaaa aaaaaaaaaa aaaaaaaaaa aaaaaaaaaa    480
aaaaaaaaaa aaaaaaaaaa aaaaaaaaaa aaaaaaaaaa aaaaaaaaaa aaaaaaaaaa    540
aaaaaaaaaa aaaaaaaaaa aaaaaaaaaa aaaaaaaaaa aaaaaaaaaa aaaaaaaaaa    600
aaaaaaaaaa aaaaaaaaaa aaaaaaaaaa aaaaaaaaaa aaaaaaaaaa aaaaaaaaaa    660
aaaaaaaaaa aaaaaaaaaa aaaaaaaaaa aaaaaaaaaa aaaaaaaaaa aaaaaaaaaa    720
aaaaaaaaaa aaaaaaaaaa aaaaaaaaaa aaaaaaaaaa aaaaaaaaaa aaaaaaaaaa    780
aaaaaaaaaa aaaaaaaaaa aaaaaaaaaa aaaaaaaaaa aaaaaaaaaa aaaaaaaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaaaaaa    960
```

```
aaaaaaaaaa aaaaaaaaaa aaaaaaaaaa aaaaaaaaaa aaaaaaaaaa aaaaaaaaaa   1020
aaaaaaaaaa aaaaaaaaaa aaaaaaaaaa aaaaaaaaaa aaaaaaaaaa aaaaaaaaaa   1080
aaaaaaaaaa aaaaaaaaaa aaaaaaaaaa aaaaaaaaaa aaaaaaaaaa aaaaaaaaaa   1140
aaaaaaaaaa aaaaaaaaaa aaaaaaaaaa aaaaaaaaaa aaaaaaaaaa aaaaaaaaaa   1200
aaaaaaaaaa aaaaaaaaaa aaaaaaaaaa aaaaaaaaaa aaaaaaaaaa aaaaaaaaaa   1260
aaaaaaaaaa aaaaaaaaaa aaaaaaaaaa aaaaaaaaaa aaaaaaaaaa aaaaaaaaaa   1320
aaaaaaaaaa aaaaaaaaaa aaaaaaaaaa aaaaaaaaaa aaaaaaaaaa aaaaaaaaaa   1380
aaaaaaaaaa aaaaaaaaaa aaaaaaaaaa aaaaaaaaaa aaaaaaaaaa aaaaaaaaaa   1440
aaaaaaaaaa aaaaaaaaaa aaaaaaaaaa aaaaaaaaaa aaaaaaaaaa aaaaaaaaaa   1500
aaaaaaaaaa aaaaaaaaaa aaaaaaaaaa aaaaaaaaaa aaaaaaaaaa aaaaaaaaaa   1560
aaaaaaaaaa aaaaaaaaaa aaaaaaaaaa aaaaaaaaaa aaaaaaaaaa aaaaaaaaaa   1620
aaaaaaaaaa aaaaaaaaaa aaaaaaaaaa aaaaaaaaaa aaaaaaaaaa aaaaaaaaaa   1680
aaaaaaaaaa aaaaaaaaaa aaaaaaaaaa aaaaaaaaaa aaaaaaaaaa aaaaaaaaaa   1740
aaaaaaaaaa aaaaaaaaaa aaaaaaaaaa aaaaaaaaaa aaaaaaaaaa aaaaaaaaaa   1800
aaaaaaaaaa aaaaaaaaaa aaaaaaaaaa aaaaaaaaaa aaaaaaaaaa aaaaaaaaaa   1860
aaaaaaaaaa aaaaaaaaaa aaaaaaaaaa aaaaaaaaaa aaaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaaaaaaa aaaaaaaaaa aaaaaaaaaa aaaaaaaaaa aaaaaaaaaa aaaaaaaaaa   2040
aaaaaaaaaa aaaaaaaaaa aaaaaaaaaa aaaaaaaaaa aaaaaaaaaa aaaaaaaaaa   2100
aaaaaaaaaa aaaaaaaaaa aaaaaaaaaa aaaaaaaaaa aaaaaaaaaa aaaaaaaaaa   2160
aaaaaaaaaa aaaaaaaaaa aaaaaaaaaa aaaaaaaaaa aaaaaaaaaa aaaaaaaaaa   2220
aaaaaaaaaa aaaaaaaaaa aaaaaaaaaa aaaaaaaaaa aaaaaaaaaa aaaaaaaaaa   2280
aaaaaaaaaa aaaaaaaaaa aaaaaaaaaa aaaaaaaaaa aaaaaaaaaa aaaaaaaaaa   2340
aaaaaaaaaa aaaaaaaaaa aaaaaaaaaa aaaaaaaaaa aaaaaaaaaa aaaaaaaaaa   2400
aaaaaaaaaa aaaaaaaaaa aaaaaaaaaa aaaaaaaaaa aaaaaaaaaa aaaaaaaaaa   2460
aaaaaaaaaa aaaaaaaaaa aaaaaaaaaa aaaaaaaaaa aaaaaaaaaa aaaaaaaaaa   2520
aaaaaaaaaa aaaaaaaaaa aaaaaaaaaa aaaaaaaaaa aaaaaaaaaa aaaaaaaaaa   2580
aaaaaaaaaa aaaaaaaaaa aaaaaaaaaa aaaaaaaaaa aaaaaaaaaa aaaaaaaaaa   2640
aaaaaaaaaa aaaaaaaaaa aaaaaaaaaa aaaaaaaaaa aaaaaaaaaa aaaaaaaaaa   2700
aaaaaaaaaa aaaaaaaaaa aaaaaaaaaa aaaaaaaaaa aaaaaaaaaa aaaaaaaaaa   2760
aaaaaaaaaa aaaaaaaaaa aaaaaaaaaa aaaaaaaaaa aaaaaaaaaa aaaaaaaaaa   2820
aaaaaaaaaa aaaaaaaaaa aaaaaaaaaa aaaaaaaaaa aaaaaaaaaa aaaaaaaaaa   2880
aaaaaaaaaa aaaaaaaaaa aaaaaaaaaa aaaaaaaaaa aaaaaaaaaa aaaaaaaaaa   2940
aaaaaaaaaa aaaaaaaaaa aaaaaaaaaa aaaaaaaaaa aaaaaaaaaa aaaaaaaaaa   3000
aaaaaaaaaa aaaaaaaaaa aaaaaaaaaa aaaaaaaaaa aaaaaaaaaa aaaaaaaaaa   3060
aaaaaaaaaa aaaaaaaaaa aaaaaaaaaa aaaaaaaaaa aaaaaaaaaa aaaaaaaaaa   3120
aaaaaaaaaa aaaaaaaaaa aaaaaaaaaa aaaaaaaaaa aaaaaaaaaa aaaaaaaaaa   3180
aaaaaaaaaa aaaaaaaaaa aaaaaaaaaa aaaaaaaaaa aaaaaaaaaa aaaaaaaaaa   3240
aaaaaaaaaa aaaaaaaaaa aaaaaaaaaa aaaaaaaaaa aaaaaaaaaa aaaaaaaaaa   3300
aaaaaaaaaa aaaaaaaaaa aaaaaaaaaa aaaaaaaaaa aaaaaaaaaa aaaaaaaaaa   3360
```

```
                                                       -continued
aaaaaaaaaa aaaaaaaaaa aaaaaaaaaa aaaaaaaaaa aaaaaaaaaa aaaaaaaaaa    3420
aaaaaaaaaa aaaaaaaaaa aaaaaaaaaa aaaaaaaaaa aaaaaaaaaa aaaaaaaaaa    3480
aaaaaaaaaa aaaaaaaaaa aaaaaaaaaa aaaaaaaaaa aaaaaaaaaa aaaaaaaaaa    3540
aaaaaaaaaa aaaaaaaaaa aaaaaaaaaa aaaaaaaaaa aaaaaaaaaa aaaaaaaaaa    3600
aaaaaaaaaa aaaaaaaaaa aaaaaaaaaa aaaaaaaaaa aaaaaaaaaa aaaaaaaaaa    3660
aaaaaaaaaa aaaaaaaaaa aaaaaaaaaa aaaaaaaaaa aaaaaaaaaa aaaaaaaaaa    3720
aaaaaaaaaa aaaaaaaaaa aaaaaaaaaa aaaaaaaaaa aaaaaaaaaa aaaaaaaaaa    3780
aaaaaaaaaa aaaaaaaaaa aaaaaaaaaa aaaaaaaaaa aaaaaaaaaa aaaaaaaaaa    3840
aaaaaaaaaa aaaaaaaaaa aaaaaaaaaa aaaaaaaaaa aaaaaaaaaa aaaaaaaaaa    3900
aaaaaaaaaa aaaaaaaaaa aaaaaaaaaa aaaaaaaaaa aaaaaaaaaa aaaaaaaaaa    3960
aaaaaaaaaa aaaaaaaaaa aaaaaaaaaa aaaaaaaaaa aaaaaaaaaa aaaaaaaaaa    4020
aaaaaaaaaa aaaaaaaaaa aaaaaaaaaa aaaaaaaaaa aaaaaaaaaa aaaaaaaaaa    4080
aaaaaaaaaa aaaaaaaaaa aaaaaaaaaa aaaaaaaaaa aaaaaaaaaa aaaaaaaaaa    4140
aaaaaaaaaa aaaaaaaaaa aaaaaaaaaa aaaaaaaaaa aaaaaaaaaa aaaaaaaaaa    4200
aaaaaaaaaa aaaaaaaaaa aaaaaaaaaa aaaaaaaaaa aaaaaaaaaa aaaaaaaaaa    4260
aaaaaaaaaa aaaaaaaaaa aaaaaaaaaa aaaaaaaaaa aaaaaaaaaa aaaaaaaaaa    4320
aaaaaaaaaa aaaaaaaaaa aaaaaaaaaa aaaaaaaaaa aaaaaaaaaa aaaaaaaaaa    4380
aaaaaaaaaa aaaaaaaaaa aaaaaaaaaa aaaaaaaaaa aaaaaaaaaa aaaaaaaaaa    4440
aaaaaaaaaa aaaaaaaaaa aaaaaaaaaa aaaaaaaaaa aaaaaaaaaa aaaaaaaaaa    4500
aaaaaaaaaa aaaaaaaaaa aaaaaaaaaa aaaaaaaaaa aaaaaaaaaa aaaaaaaaaa    4560
aaaaaaaaaa aaaaaaaaaa aaaaaaaaaa aaaaaaaaaa aaaaaaaaaa aaaaaaaaaa    4620
aaaaaaaaaa aaaaaaaaaa aaaaaaaaaa aaaaaaaaaa aaaaaaaaaa aaaaaaaaaa    4680
aaaaaaaaaa aaaaaaaaaa aaaaaaaaaa aaaaaaaaaa aaaaaaaaaa aaaaaaaaaa    4740
aaaaaaaaaa aaaaaaaaaa aaaaaaaaaa aaaaaaaaaa aaaaaaaaaa aaaaaaaaaa    4800
aaaaaaaaaa aaaaaaaaaa aaaaaaaaaa aaaaaaaaaa aaaaaaaaaa aaaaaaaaaa    4860
aaaaaaaaaa aaaaaaaaaa aaaaaaaaaa aaaaaaaaaa aaaaaaaaaa aaaaaaaaaa    4920
aaaaaaaaaa aaaaaaaaaa aaaaaaaaaa aaaaaaaaaa aaaaaaaaaa aaaaaaaaaa    4980
aaaaaaaaaa aaaaaaaaaa                                                5000

PolyA (SEQ ID NO: 34)
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa aaaaaaaaaa aaaaaaaaaa aaaaaaaaaa aaaaaaaaaa aaaaaaaaaa     300
aaaaaaaaaa aaaaaaaaaa aaaaaaaaaa aaaaaaaaaa aaaaaaaaaa aaaaaaaaaa     360
aaaaaaaaaa aaaaaaaaaa aaaaaaaaaa aaaaaaaaaa                           400

PolyA (SEQ ID NO: 35)
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa aaaaaaaaaa aaaaaaaaaa aaaaaaaaaa aaaaaaaaaa aaaaaaaaaa     300
```

-continued

```
aaaaaaaaaa aaaaaaaaaa aaaaaaaaaa aaaaaaaaaa aaaaaaaaaa aaaaaaaaaa    360
aaaaaaaaaa aaaaaaaaaa aaaaaaaaaa aaaaaaaaaa aaaaaaaaaa aaaaaaaaaa    420
aaaaaaaaaa aaaaaaaaaa aaaaaaaaaa aaaaaaaaaa aaaaaaaaaa aaaaaaaaaa    480
aaaaaaaaaa aaaaaaaaaa aaaaaaaaaa aaaaaaaaaa aaaaaaaaaa aaaaaaaaaa    540
aaaaaaaaaa aaaaaaaaaa aaaaaaaaaa aaaaaaaaaa aaaaaaaaaa aaaaaaaaaa    600
aaaaaaaaaa aaaaaaaaaa aaaaaaaaaa aaaaaaaaaa aaaaaaaaaa aaaaaaaaaa    660
aaaaaaaaaa aaaaaaaaaa aaaaaaaaaa aaaaaaaaaa aaaaaaaaaa aaaaaaaaaa    720
aaaaaaaaaa aaaaaaaaaa aaaaaaaaaa aaaaaaaaaa aaaaaaaaaa aaaaaaaaaa    780
aaaaaaaaaa aaaaaaaaaa aaaaaaaaaa aaaaaaaaaa aaaaaaaaaa aaaaaaaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaaaaaaaa   1020
aaaaaaaaaa aaaaaaaaaa aaaaaaaaaa aaaaaaaaaa aaaaaaaaaa aaaaaaaaaa   1080
aaaaaaaaaa aaaaaaaaaa aaaaaaaaaa aaaaaaaaaa aaaaaaaaaa aaaaaaaaaa   1140
aaaaaaaaaa aaaaaaaaaa aaaaaaaaaa aaaaaaaaaa aaaaaaaaaa aaaaaaaaaa   1200
aaaaaaaaaa aaaaaaaaaa aaaaaaaaaa aaaaaaaaaa aaaaaaaaaa aaaaaaaaaa   1260
aaaaaaaaaa aaaaaaaaaa aaaaaaaaaa aaaaaaaaaa aaaaaaaaaa aaaaaaaaaa   1320
aaaaaaaaaa aaaaaaaaaa aaaaaaaaaa aaaaaaaaaa aaaaaaaaaa aaaaaaaaaa   1380
aaaaaaaaaa aaaaaaaaaa aaaaaaaaaa aaaaaaaaaa aaaaaaaaaa aaaaaaaaaa   1440
aaaaaaaaaa aaaaaaaaaa aaaaaaaaaa aaaaaaaaaa aaaaaaaaaa aaaaaaaaaa   1500
aaaaaaaaaa aaaaaaaaaa aaaaaaaaaa aaaaaaaaaa aaaaaaaaaa aaaaaaaaaa   1560
aaaaaaaaaa aaaaaaaaaa aaaaaaaaaa aaaaaaaaaa aaaaaaaaaa aaaaaaaaaa   1620
aaaaaaaaaa aaaaaaaaaa aaaaaaaaaa aaaaaaaaaa aaaaaaaaaa aaaaaaaaaa   1680
aaaaaaaaaa aaaaaaaaaa aaaaaaaaaa aaaaaaaaaa aaaaaaaaaa aaaaaaaaaa   1740
aaaaaaaaaa aaaaaaaaaa aaaaaaaaaa aaaaaaaaaa aaaaaaaaaa aaaaaaaaaa   1800
aaaaaaaaaa aaaaaaaaaa aaaaaaaaaa aaaaaaaaaa aaaaaaaaaa aaaaaaaaaa   1860
aaaaaaaaaa aaaaaaaaaa aaaaaaaaaa aaaaaaaaaa aaaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaaaaaaa aaaaaaaaaa                                               2000

Gly/Ser (SEQ ID NO: 38): This sequence may encompass 1-10
"Gly Gly Gly Ser" repeating units
GGGSGGGSGG GSGGGSGGGS GGGSGGGSGG GSGGGSGGGS
```

Example 2

Expression and Characterization of Human Anti-mesothelin scFv Constructs for CAR Therapy Additional analysis was performed to characteraize the human anti-mesothelin scFv constructs, e.g., mass spectrometry analysis, size exclusion chromatography, and surface plasmon resonance (SPR). Binding affinity and epitope binding (compared to SS1 epitope) on the extracellular domain of mesothelin was determined by SPR. The assays and results from this analysis are described below.

Expression of scFv Candidates and Biotinylated Human Mesothelin

To assess the binding and biophysical characteristics of human anti-mesothelin scFvs identified by phage panning, scFv constructs were transiently produced and purified from HEK293F cells along with human mesothelin extracellular domain (human MSLN ECD). SS1 scFv, which is a murine anti-mesothelin scFv, was also produced as a reference. The human anti-mesothelin scFvs tested were M5, M11, M12, M14, M16, M17, M21 and M23 (see Table 14). The plasmids encoding the amino acids for the scFv constructs of M5 (SEQ ID NO: 43), M11 (SEQ ID NO: 49), M12 (SEQ ID NO: 50), M14 (SEQ ID NO: 52), M16 (SEQ ID NO: 54), M17 (SEQ ID NO: 55), M21 (SEQ ID NO: 59), M23 (SEQ ID NO: 61) and SS1 (SEQ ID NO: 275) and human MSLN ECD (SEQ ID NO: 276) were synthesized externally. ScFvs were produced with a 7x (SEQ ID NO: 400) or 8xHis (SEQ ID NO: 401) Tag on the C-terminus of the constructs. The human scFv constructs (M5, M11, M12, M14, M16, M17, M21, and M23) had a short linker sequence comprising the sequence GS linking the C-terminus of the scFv to the N-terminus of an 8xHis (SEQ ID NO: 401) Tag, e.g., GSHHHHHHHH (SEQ ID NO: 277). Human mesothelin ECD was produced with a C-terminal Avi-Tag (SEQ ID NO: 276) and was site selectively biotinylated in vitro with BirA enzyme from Avidity, LLC. Transient expression and purification in HEK293F cells was performed with standard methodology. For scFvs, briefly, 100 ml of HEK293F cells at 3x106cells/ml were transfected with 100 µg plasmid and 300 µg polyethylenimine. The cells were incubated at 37° C. with 8% CO2 and rotated at 80 rpm. After six days, the cells were harvested by centrifugation at 3500 g for 20 minutes. The supernatant was purified by binding the scFv to 200 µl Ni-NTA agarose beads (Qiagen) overnight at 4° C. The protein was eluted with 200 µl300 mM imidazole, and dialyzed against phosphate buffered saline.

The sequence of the SS1 scFv with the His Tag is provided below:

```
                                                  (SEQ ID NO: 275)
QVQLQQSGPELEKPGASVKISCKASGYSFTGYTMNWVKQSHGKSLEWIGL

ITPYNGASSYNQKFRGKATLTVDKSSSTAYMDLLSLTSEDSAVYFCARGG

YDGRGFDYWGQGTTVTVSSGGGGSGGGGSGGGGSDIELTQSPAIMSASPG

EKVTMTCSASSSVSYMHWYQQKSGTSPKRWIYDTSKLASGVPGRFSGSGS

GNSYSLTISSVEAEDDATYYCQQWSGYPLTFGAGTKLEIEFGSHHHHHHH
```

The sequence of the human mesothelin ECD with the C-terminal Avi-Tag is provided below:

```
                                                  (SEQ ID NO: 276)
DAAQPAASEVEKTACPSGKKAREIDESLIFYKKWELEACVDAALLATQMD

RVNAIPFTYEQLDVLKHKLDELYPQGYPESVIQHLGYLFLKMSPEDIRKW

NVTSLETLKALLEVNKGHEMSPQVATLIDRFVKGRGQLDKDTLDTLTAFY

PGYLCSLSPEELSSVPPSSIWAVRPQDLDTCDPRQLDVLYPKARLAFQNM

NGSEYFVKIQSFLGGAPTEDLKALSQQNVSMDLATFMKLRTDAVLPLTVA

EVQKLLGPHVEGLKAEERHRPVRDWILRQRQDDLDTLGLGLQGTRGSHHH

HHHEFRHDSGLNDIFEAQKIEWHE
```

Mass Spectrometry Analysis

To confirm identity, purified scFvs were analyzed with high-performance liquid chromatography coupled to mass spectrometry (HPLC-MS). 1 µg each was injected onto a Poros R1/10 2.1 mm×100 mm column (Life Technologies) heated to 60° C. Separation was performed on a Waters BioAcquity UPLC. Mobile Phase A was 0.1% formic acid; mobile phase B was 0.1% formic acid in 25% acetonitrile, 75% isopropanol. The scFvs were eluted at 0.5 mL/min using a gradient from 25-50% mobile phase B in 15 minutes. Mass spectrometry detection was performed with a Waters Xevo-Tof instrument operating in electrospray positive ion mode scanning from 600-4000 m/z with a cone voltage ramp of 20-50V. The resulting mass spectra were averaged across the width of the peak and deconvoluted using the MaxEnt1 algorithm from Waters to determine the masses of the expressed scFvs.

Size Exclusion Chromatography Analysis

Size exclusion chromatography was performed to determine the oligomerization states of the expressed scFvs. 25 µg each was injected onto a TSKGel Super SW3000 4.6 mm×300 mm column (Tosoh Bioscience) heated to 35° C. The scFvs were eluted at 0.3 mL/min in 750 mM arginine, 1 mM EDTA, 20 mM sodium phosphate, 250 mM sodium chloride, pH 7.2; the UV absorbance was monitored at 280 nm.

Surface Plasmon Resonance (SPR)

Binding affinity of purified scFvs was measured on a Biacore T200 system. Briefly, recombinant human biotinylated mesothelin ECD was immobilized on a streptavidin (SA) sensor chip surface at a density of 150 RU. Purified scFv was injected over the chip under constant flow rate at three-fold serial dilutions. Association and dissociation rates of the protein complex were monitored for 270 seconds and 400 seconds, respectively. Double referencing was performed against a blank immobilized flow cell and a buffer blank. Affinity was determined with a Langmuir 1:1 binding model when possible, for those scFVs where accurate fitting was not possible due to fast on and off rates, the steady state model was used.

To determine the relative binding epitope of each of the scFvs in comparison to SS1, 50 nM SS1 was captured by biotinylated mesothelin ECD immobilized on a streptavidin sensor chip at a contact time of 180 seconds resulting in a relative density of 70 RU. Purified scFv at 100 nM (M5, M11, M12, M14, M16, M17, MM21, or M23) was then immediately injected over the chip to minimize dissociation of the SS1/mesothelin complex. Binding of the secondary scFv was monitored for 270 seconds.

Results

The observed masses for the scFvs, determined by HPLC-MS, were consistent with the theoretical values based on the amino acid sequences. Expressed scFvs ranged from 43% monomer to >98% monomer based upon analytical size exclusion chromatography. The selected scFvs represented a broad range of affinities from 0.9 nM to 114 nM compared to SS1 control scFV which had an apparent affinity of 0.1 nM for mesothelin ECD (Table 14). Representative SPR sensograms for SS1, M5, and M11 are shown in FIGS. 41A, B and C, respectively.

Relative epitope binning (FIG. 42) suggests M12, M14, M16, M17, M21, M23 are competitive binders with SS1 to human mesothelin while M5 and M11 appear to bind to a unique epitope, as judged by the increased response in the assay upon their injection.

TABLE 14

Characteristics of anti-human Mesothelin scFvs

| Sample | Identity Theor. Mass | Identity Obs. Mass | SEC[1] % Monomer | Affinity[2] Fit | Affinity[2] ka (1/Ms) | Affinity[2] kd (1/s) | Affinity[2] KD (nM) |
|---|---|---|---|---|---|---|---|
| M5   | 26866 | 26865 | 82%    | 1:1 Binding          | 4.20E+04 | 1.13E−03 | 26.9 |
| M11[3] | 26949 | 26948 | ND[3]  | Steady State Affinity | —        | —        | 64.7 |
| M12  | 27261 | 27260 | 70%    | Steady State Affinity | —        | —        | 307  |
| M14  | 27420 | 27422 | 74.5%  | 1:1 Binding          | 2.75E+06 | 2.51E−03 | 0.9  |
| M16  | 27127 | 27128 | 94.5%  | 1:1 Binding          | 1.74E+05 | 3.95E−03 | 22.7 |
| M17  | 26890 | 26891 | >98%   | 1:1 Binding          | 5.22E+05 | 1.45E−02 | 27.8 |
| M21  | 27412 | 27411 | >98%   | Steady State Affinity | —        | —        | 110  |
| M23  | 27602 | 27604 | 91%    | Steady State Affinity | —        | —        | 114  |
| SS1  | 26504 | 26503 | 43%    | 1:1 Binding          | 5.55E+06 | 5.60E−04 | 0.1  |

[1]High aggregate content/low % monomer may result in less accurate affinity determinations due to potential avidity effects.
[2]Affinity was determined with 1:1 binding model when possible, for those scFvs where accurate fitting was not possible due to fast on and off rates, steady state model was used.
[3]Not determined, low concentration precluded accurate determination of % monomer.

Example 3

Analysis and in vitro Activity of Human scFv Bearing CARTs

Single chain variable fragments for anti-MSLN antibodies were cloned into lentiviral CAR expression vectors with the CD3zeta chain and the 4-1BB costimulatory molecule and the optimal constructs are selected based on the quantity and quality of the effector T cell responses of MSLN CAR transduced T cells ("CART-MSLN" or "CART-MSLN T cells") in response to MSLN expressing ("MSLN+") targets. Effector T cell responses include, but are not limited to, cellular expansion, proliferation, doubling, cytokine production and target cell killing or cytolytic activity (degranulation).

Generation of CART-MSLN

The human scFv encoding lentiviral transfer vectors are used to produce the genomic material packaged into the VSVg psuedotyped lentiviral particles. Lentiviral transfer vector DNA is mixed with the three packaging components of VSVg, gag/pol and rev in combination with lipofectamine reagent to transfect them together in to Lenti-X 293T cells (Clontech).

After 30 hours, the media was collected, filtered and stored at −80 C. The therapeutic CART-MSLN were generated by starting with the blood from a normal apheresed donor whose naïve T cells are obtained by negative selection for T cells, CD4+ and CD8+ lymphocytes. These cells are activated by CD3×28 beads (Dynabeads® Human T-Expander CD3/CD28, Invitrogen) at a ratio of 1:3 in RPMI1640, 10% heat-inactivated fetal calf serum (FCS), 2 mM L-glutamine, 1× Penicillin/Streptomycin, 100 µM non-essential amino acids, 1 mM NaPyruvate, 10 mM Hepes, and 55 µM 2-mercaptoethanol at 37° C., 5% $CO_2$. T cells were cultured at 1×10⁶ T cells in 0.5 mL medium per well of a 24-well plate. After 24 hours, the T cells are blasting and 0.5 mL of non-concentrated, or smaller volumes of concentrated viral supernatant is added. The T cells begin to divide in a logarithmic growth pattern, which is monitored by measuring the cell counts per mL, and T cells are diluted in fresh medium every two days. As the T cells begin to rest down after approximately 10 days, the logarithmic growth wanes. The combination of slowing growth rate and T cell size approaching ~300 fl determines the state for T cells to be cryopreserved for later analysis.

Before cryopreserving, percentage of cells transduced (expressing the mesothelin-specific CAR on the cell surface) and their relative fluorescence intensity of that expression were determined by flow cytometric analysis on a FACS-Cantoll or FACS Fortessa. Comparing histogram plots of relative fluorescent intensity from that FACS showed the percentage of transduced T cells. The virus transduction show comparable expression levels correlating with transduction efficiency, percent cells transduced. The results indicate that there is no detectable negative effect of the human scFv bearing CAR-MSLN on the cells ability to expand normally when compared to the untransduced T cells ("UTD") and SS1 CART-MSLN.

Evaluating cytolytic activity and cytokine secretion of CART-MSLN redirected T cells.

To evaluate the functional abilities of CART-MSLN T cells to kill and secrete cytokines, the cells were thawed and allowed to recover overnight. In addition to the human scFv bearing CART-MSLN, the CART-MSLN bearing the murine scFv "SS1" (see WO2013/040577) was used as a control. The control SS1 scFV bearing CART-MSLN (also referred to as SS1 CART-MSLN) was used in all assays to compare assay variation and/or act as a control. The SS1 scFV bearing CART cells, as well as all the other human scFv bearing MSLN-CARTs, were produced in research grade (i.e., not clinical grade) manufacturing conditions. CD19-BBz or Iso 1-BBz was used as non-targeting CAR for background CART effect.

T cell killing was directed towards K562, a chronic myelogenous leukemia cell line. K652 MSLN+ (K562-Meso) cells were generated by transduction. Non-MSLN expressing K5652 were used as a control. For the flow based cytotoxicity assay, the target cells are stained with Carboxyfluorescein succinimidyl ester (CSFE) quantitate their presence. The cytolytic activities of CART-MSLN were measured at a titration of effector:target cell ratios of 10:1, 3:1, and 1:1 where effectors were defined as T cells expressing the anti-MSLN chimeric receptor. Assays were initiated by mixing an appropriate number of T cells with a constant number of targets cells. After 20 hours, the plates were centrifuged and the total volume of each mixture was removed. The remaining cell pellet in each well was washed and cells were stained with live/dead marker 7AAD. After the final wash, the pelleted cells were re-suspended in a specific volume with a predetermined number of counting beads. Cell staining data was collected by CantoII flow cytometry and analyzed with FloJo software using beads to quantitate results.

Plots from 20 hour flow-based killing assays using titrating Effector to Target (E:T) ratios with effector CART-MSLN cells targeting CSFE labeled K562 (FIG. 3A. non-expressing MSLN controls) and K562-Meso (FIG. 3B, K562 cells transduced to express MSLN). Comparing these killing curves, titrating the amount of effector cells shows that those cells expressing MSLN are destroyed. T cells from the same donor and that were transduced with either human scFv bearing CAR-MSLN cells or SS1 CAR-MSLN cells were able to kill selectively MSLN+ targets. The cytolytic activities of all CART-MSLN cells are similar and comparable to the murine SS1 CART-MSLN. They show that all CART-MSLN cells become Mesothelin reactive upon transduction and gain the ability to kill target cells expressing high levels of Mesothelin. For measuring cytokine production of human scFv bearing CART-MSLN, cells were thawed and allowed to recover overnight. In addition to the humanized CART-MSLN, the SS1 CART-MSLN (murine scFv) was used for comparative purposes. CD19-BBz CART was used as a non-targeting control for background CART cell effect. SS1 CART-MSLN was used in all assays to compare assay variation. The T cells were directed towards K562, a chronic myelogenous leukemia cell line (both MSLN+ and MSLN), the MLSN-expressing ovarian cancer cell line Ovcar8, and the pancreatic cancer lines SW1990 and Panc0203. When analyzing MSLN expression by flow cytometry, we detected 10-fold lower expression of MSLN on Ovcar8 compared to MSLN+K562 cells; SW1990 expressed 10-fold less than Ovcar8. MSLN expression on Panc0203 was not detectable by flow cytometry, but was positive by RNA analysis. In addition, PMA/Ionomycin was used to evaluate the potential of T cells to respond to the endogenous immunological signals. The assay tests only an effector:target ratio of 1:1. The assay is run for 24 hours after mixing of the cells, when the media is removed for cytokine analysis using the IFN-☐ CBA-Flex kit for human cytokine detection.

Background levels of cytokine produced from CART-MSLN cells after exposure to the control K562 cells not expressing MSLN were analyzed. The potential cytokine secretion from stimulation of the T cells with PMA/Ionomycin indicates that the cell populations have slightly variable potential to secrete cytokine. Differences were dealt with by normalizing the specific IFN☐ release over the maximum release (PMA/Ionomycin).

Data shows that most human scFv bearing CART-MSLN and the murine SS1 CART-MSLN produced IFNγ when cultured with K562 overexpressig MSLN. When cultured with cancer cells endogenously expressing MSLN (at lower levels), only few CARTs responded (M5, 11, 14, 15, 16, 17 and SS1), while the two CARTs M5 and M11 showed superior IFNγ levels. The lower endogenous MSLN levels they might better reflect naturally expressed levels of mesothelin on tumor cells, those CART having those scFVs might have an enhanced therapeutic response than CARTs having the SS1 construct.

Example 4

Clinical Trial for Lentiviral Generated CARTs

Patients will be selected from those have mesothelin expressing cancers, such as serious epithelial ovarian cancer, malignant plural mesothelioma, or pancreatic cancer.

The manufacture and release testing of CART-MSLN cells will be performed by the Clinical Cell and Vaccine Production (CVPF) at the University of Pennsylvania. CART-MSLN product will be manufactured from the patients' apheresis product.

An about 10-liter apheresis procedure will be carried out at the University of Pennsylvania Apheresis center (4 weeks prior to first dose of CAR T cells). PBMCs from a patient are obtained for CAR T cells during this procedure. From a single leukapheresis, the intention is to harvest at least $5 \times 10^9$ white blood cells to manufacture CAR T cells. Baseline blood leukocytes for FDA look-back requirements and for research are also obtained and cryopreserved. The mesothelin-modified T cell product is expected to be ready for release approximately 4 weeks later.

Lentiviral generated CARTs were made as described in Example 2 using cells isolated from each patient, i.e., autologous T cells. The CART-MSLN made from each patients T cells express human scFvs (including M5 and M11), or SS1.

At the end of cell cultures, the cells are cryopreserved in infusible cryomedia in bags. The dose is $1-5 \times 10^7$ CAR T cells for Cohort 1, $1-5 \times 10^8$ CAR transduced cells for Cohort 2 and 3, calculated as a range of 2-50% transduced cells in total cells. Bags containing autologous modified CAR T cell products will be stored in a controlled and monitored freezer at the CVPF at the Hospital of the University of Pennsylvania. Infusion bags will be stored in the freezer until needed.

Each dose will be packed and cryopreserved in 1 infusion bag at in a volume dependent on the total cell number, a function of the transduction efficiency; the minimum volume will be 10 mL per bag. Each bag will contain an aliquot (volume dependent upon total cell dose) of cryomedia.

Cohort 1 subjects (N=3-6) will receive a single flat intravenous dose of autologous $1-5 \times 10^7$ CART-MSLN cells on day 0. Cohort 2 subjects (N=3-6) will receive a single flat intravenous dose of autologous $1-5 \times 10^8$ CART-MSLN cells on day 0. Subjects in Cohort 1 and 2 will not receive any lymphodepleting chemotherapy prior to CART-MSLN cells. Cohort 3 (N=6) will receive 1.5 grams/m$^2$ of cyclophosphamide intravenously two days prior to a single flat intravenous dose of autologous $1-5 \times 10^8$ CART-MSLN cells.

It is anticipated that patients receiving cyclophosphamide may experience nausea and vomiting as a side effect of the treatment. Anti-emetic prophylaxis premedication for nausea can be administered prior to infusion of chemotherapy according to the institutional standards. Choice of specific agent will be left to the discretion of the investigator, though corticosteroids should not be used due to their immunosuppressive effects.

Side effects following T cell infusions may include transient fever, chills, rigors, myalgias/arthralgias, headache, fatigue, and/or nausea. Subjects will be pre-medicated with acetaminophen 650 mg by mouth and diphenhydramine hydrochloride by mouth or W prior to CAR T cell infusion. If Benadryl is contraindicated, an H2-blocker, such as ranitidine, will be administered. These medications may be repeated every six hours as needed. A course of non-steroidal anti-inflammatory medication may be prescribed if the patient continues to have fever not relieved by acetaminophen. It is recommended that patients do not receive systemic corticosteroids such as hydrocortisone, prednisone, prednisolone (Solu-Medrol), or dexamethasone (Decadron). If corticosteroids are required for an acute infusional reaction, an initial dose of hydrocortisone 100 mg is recommended.

One bag of CART-MSLN cells will be transported by the study coordinator or CVPF stuff on dry ice from CVPF to the subject's bedside in the CTRC.

Transfected T cells will be thawed by a member of CVPF staff in a 37° C. water bath at subject's bedside. The bag will be gently massaged until the cells have just thawed. If the CAR T cell product appears to have a damaged or leaking bag, or otherwise appears to be compromised, it should not be infused, and should be returned to the CVPF as specified below.

Cells will be infused to the subject while cold within approximately 10-15 minutes after thaw. The transfected T cells will be infused intravenously rapidly through an 18 gauge latex free Y-type blood set with 3-way stopcock. No leukocyte filter at infusion. Dosing will take place by gravity infusion. If the infusion rate by gravity is too slow, the transfected T cell drug product may be drawn into a syringe via the stopcock and manually infused at the required rate. There should be no frozen clumps left in the bag.

Prior to the infusion, two individuals will independently verify the information on the label of each bag in the presence of the subject and confirm that the information correctly matches the participant.

Patients will be monitored during and after infusion of the transfected T cells. Temperature, blood pressure, heart rate, respiratory rate and pulse oximetry will be obtained and recorded immediately prior to dosing and every 15 minutes for 2 hours following infusion completion.

Emergency medical equipment (i.e. a crash cart) must be available for an emergency situation during the infusion in the event that the subject has an allergic response, or severe hypotensive crisis, or any other reaction to the infusion.

If no symptoms occur and subject's vital signs remain normal 2 hours after the infusion, the subject will be discharged home with instructions to return to the hospital should any symptoms develop. If a vital sign measurement is not stable, it will continue to be obtained approximately every 15 minutes until the subject's vital signs stabilize or the physician releases the patient. The subject will be asked not to leave until the physician considers that it is safe for him or her to do so.

Within 60 minutes (±5 minutes) following completion of transduced CAR T cell dosing, a blood sample will be obtained for a baseline determination of transduced CAR T cell number and cytokine levels.

Subjects will be instructed to return to the CTRC or Perelman Center in 24 hours after the first infusion for blood tests and follow-up examination according to the SOE.

For CARTs bearing scFv doses of cells can be repeated as needed.

Descriptive statistics will be applied to determine the relative persistence and trafficking to blood (and optionally tumor) of the CART-MSLN cells. Data regarding the number of CAR T cells in blood, HAMA levels, and the tracking of soluble biomarker levels will be presented graphically. Correlations with radiographic and other standard measures of tumor burden will be determined. We will compute 95% confidence intervals for proportions and means.

Adverse events will be collected and evaluated for all patients during the protocol specified AE reporting periods. AEs will be graded for severity using the National Cancer Institute (NCI)—Common Toxicity Criteria (v4). All adverse events will be described and exact 95% confidence intervals will be produced for adverse event rates, both overall and within major categories. The data will be monitored continuously for evidence of excessive toxicity. Results will be tabulated and summarized.

Rates of clinical responses will be summarized in exact 95% confidence intervals. Distributions of progression-free and overall survival and duration of clinical response will be presented graphically using Kaplan-Meier curves. The two-year survival rates will be presented. Preliminary evidence of efficacy will be determined by monitoring tumor response rates in those subjects with measurable disease. Tumor response will be assessed using radiographic imaging (i.e. CT imaging) and serum biomarkers at Day 28, Months 3 and 6 after infusion.

Radiographic responses will be measured according to Response Evaluation Criteria in Solid Tumors (RECIST 1.1), modified RECIST criteria for pleural mesothelioma, and Immune-Related Response Criteria (iRRC).

Serum biomarker responses will be evaluated according to standards for each disease; additionally all subjects will have SMRP measured. For example, subjects with pancreatic cancer will have monitoring in levels of CA19-9, CEA and serum mesothelin related protein [SMRP]) following CAR T cell administration. Subjects with ovarian cancer will have serum levels of CA125 monitored, an also SMRP. Subjects with mesothelioma will have serum levels of SMRP measured. In all cases, serum biomarkers will not be used as the sole measurement of tumor response, given that CART-MSLN cells may affect the assays used in these biomarker measurements.

Data will be analyzed descriptively for overall response rates, progression-free survival, and overall survival.

PFS and OS up to 2 years post-infusion or until subjects initiate a cancer-related therapy will be evaluated.

Safety assessments including blood monitoring of cytokine levels will be performed. Subjects will be enrolled serially. Infusions will be staggered to allow 28 days of safety assessment between enrolled subjects in each cohort.

Example 5

Clinical Trial for RNA Generated CARTs

Autologous T cells are engineered to express an extracellular a SS1 CAR construct that recognized mesothelin, along with transmembrane domain, in addition to human 4-1BB and CD3zeta signaling domains described above. See, e.g., WO2013/040577, Example 1.

Production of CAR-containing Nucleic Acids

SS1-CARs are constructed according as follows. CARs containing human anti-mesothelin scFvs are also constructed using similar methods.

Two different plasmids were utilized to clone the ss1.bbz fragment. The mesothelin scFv fragment (ss1) was first cloned by the Translational Research Program (TRP) laboratory from the previously published construct of Dr. Pastan (Chowdhury et al., 1998). The human CD8α hinge and transmembrane domain together with 41BB and CD3ζ sequence was cloned by PCR from the pELNS.CD19-BB-ζ plasmid described previously (Milone et al., 2009). Sequences for the hinge, transmembrane, and intracellular signaling domains are disclosed herein. The ss1.bbz fragment was first cloned in pGEM.GFP.64A vector (provided by Eli Gilboa and described in Boczkowsk, D et al., 2000).

Figure 1:
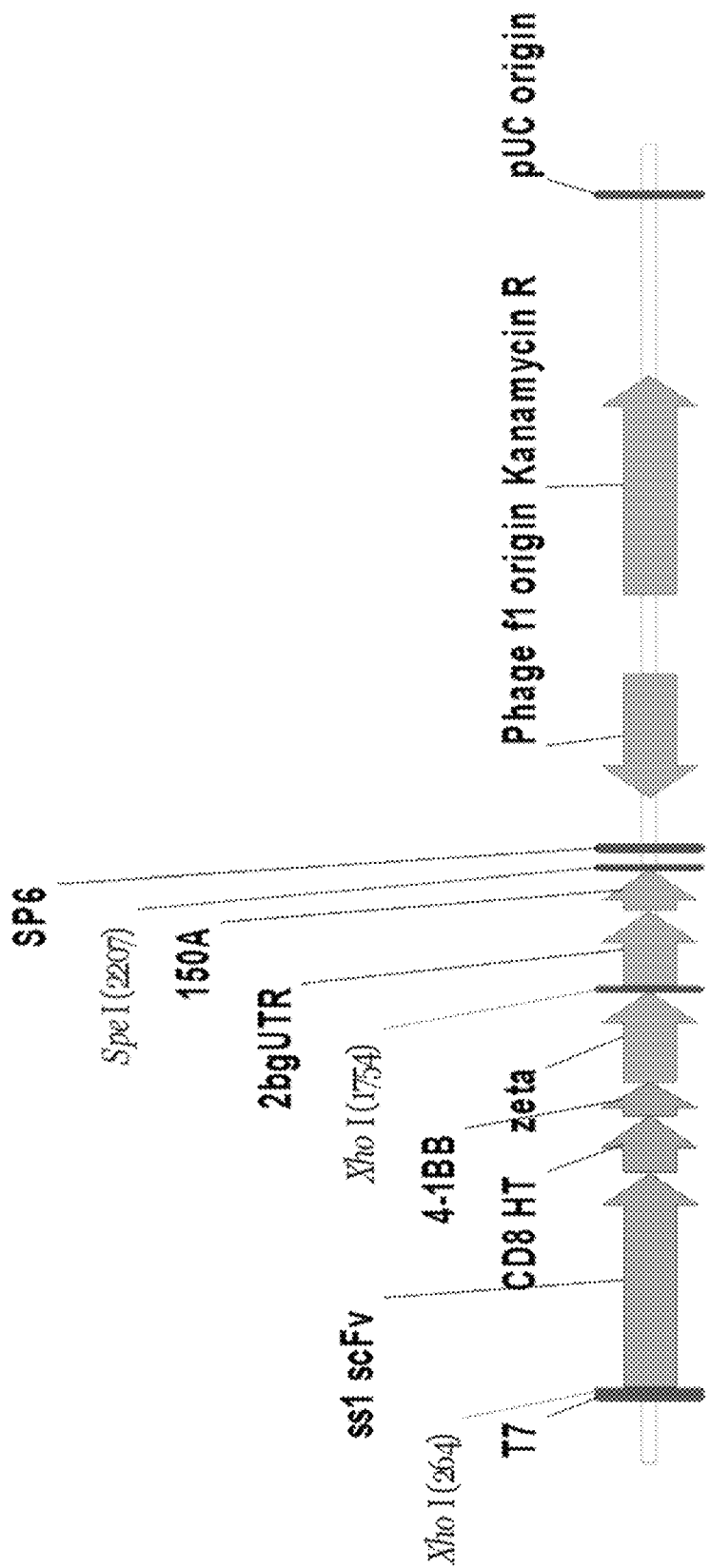
FIG. 1 is a schematic of the pD-A.anti-meso BD.OF.BBZ.2bg.150A plasmid. Figure discloses "150A" as SEQ ID NO: 271.
Figure 5:
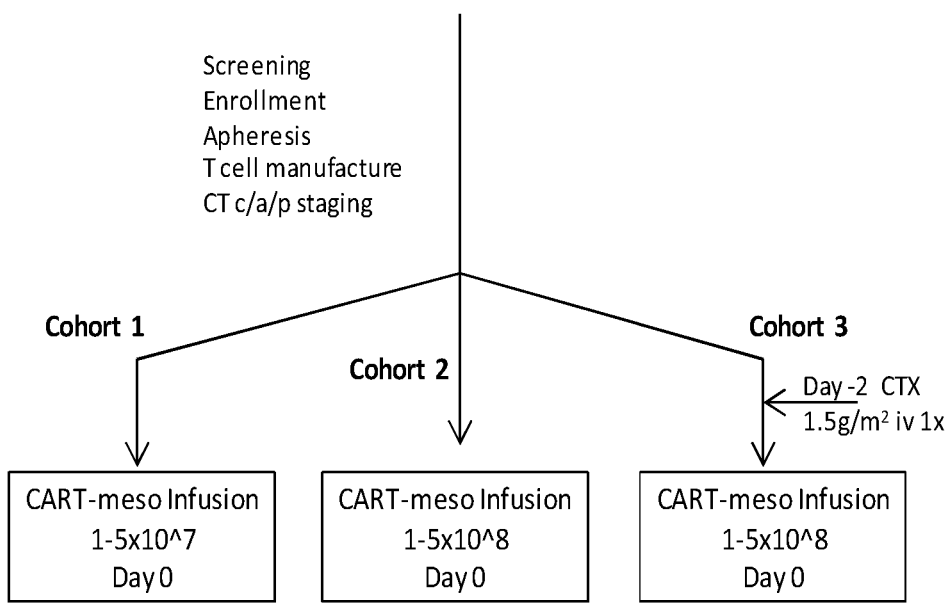
FIG. 5 shows a clinical trial design for mesothelin CARTs made by transducing a CAR construct with a lentiviral vector.

This vector was modified by addition of two 3'UTR beta globin repeats and 150 bp of polyA sequence (SEQ ID NO: 271)(replacing the 64 polyA sequence (SEQ ID NO: 273) in pGEM.GFP.64A) for enhanced transgene expression (Holtkamp 2006). The GMP-compliant plasmid for clinical use was derived by subcloning the ss1.bbz.2bgUTR.150A fragment from pGEM into the pDrive vector. The pDrive cloning vector (Qiagen) is designed for highly efficient cloning of PCR products through UA hybridization. It allows for both ampicillin and kanamycin selection of recombinant clones, and comes with universal sequencing primer sites, and both T7 and SP6 promoters for in vitro transcription. First, ss1.bbz.2bgUTR.150A was cut from pGEM vector by Hind III and NdeI (Fill-in blunt) and subcloned into pDrive cut by KpnI and NotI (Fill-in blunt). The insert with correct orientation was sequence confirmed to generate pDrive.ss1.bbz.2bgUTR.150A. Ampicillin resistance gene in pDrive vectors was deleted by double digestion with AhdI and BciVI. To eliminate potential aberrant proteins translated from internal open reading frames (ORF) inside the CAR ORFs, all internal ORF that were larger than 60 bp in size were mutated by mutagenesis PCR, while the ORF of ss1 CAR was maintained intact. The resulting plasmid was designated pD-A.ss1.bbz.OF.2bg.150A, as shown in FIG. 1.

Production of CAR nucleic acids for introduction into autologous T cells were prepared as follows. The final pD-A.ss1.bbz.OF.2bg.150A construct was introduced into OneShot TOP10 Chemically Competent E Coli cells (Invitrogen) as per CVPF SOP 1188. Up to 10 mg plasmid DNA prepared as one batch was generated using the QIAfilter Plasmid Giga DNA isolation kit as per SOP 1191, from two 1.25 liters of LB-media containing 100 µg/ml kanamycin. 1 mg of DNA at a time was linearized with SpeI restriction enzyme overnight at 37° C. Linearization was confirmed by gel electrophoresis prior to large scale purification using the Qiagen Plasmid Maxi Kit.

RNA was transcribed from the plasmids by utilizing the mScript mRNA system and was isolated using the RNeasy Maxi kit (Qiagen). The in vitro transcribed RNA was cryopreserved in aliquots of 0.5 mL at a concentration of 1 mg/mL. RNA quality and quantity was analyzed by 1% agarose gel electrophoresis after 15 min denaturation at 70° C. in mRNA denaturation buffer (Invitrogen, Carlsbad, Calif.) and quantified by UV spectrophotometry (0D260/280).

CAR T Cells Product Manufacturing.

A 7 to 12-liter apheresis procedure is performed about 4 weeks prior to first dose of CAR T cells. PBMC are obtained for CAR T cells during this procedure. From a single leukapheresis, the intention is to harvest at least 5×109 white blood cells to manufacture CAR T cells.

CD3+ T-cells are enriched from a leukapheresis product by depletion of monocytes via counterflow centrifugal elutriation on the CaridianBCT Elutra, which employs a single use closed system disposable set. On day 0, the T cell manufacturing process is initiated with activation with anti-CD3/CD28 monoclonal antibody-coated magnetic beads, and expansion is initiated in a static tissue culture bag. At day 5, cells will be transferred to a WAVE bioreactor if needed for additional expansion. At the end of the culture, cells are depleted of the magnetic beads, washed, and concentrated using the Haemonetics Cell Saver system. The post-harvest cells are incubated overnight at 37° C. for electroporation the next morning. Cells are washed and resuspended in Electroporation Buffer (Maxcyte) and loaded into the Maxcyte processing assembly. Cells are electroporated with the ss1 RNA, and allowed to recover for 4 hours and then formulated in infusible cryopreservation media.

Packaging $1 \times 10^8$ or $1 \times 10^9 \pm 20\%$ modified CAR T cells will be supplied in W infusion bags maintained on wet ice. Each bag will contain an aliquot (volume dependent upon dose) of cryomedia containing the following infusible grade reagents (% v/v): 31.25 plasmalyte-A, 31.25 dextrose (5%), 0.45 NaCl, up to 7.50 DMSO, 1.00 dextran 40, and 5.00 human serum albumin. Bags can be frozen at −135° C.

CAR T Cells Product Stability

The ss1 CAR T cells will be cryopreserved 4 hours post-electroporation, and thawed and administered within a three month window after T cell manufacturing. We have demonstrated that mesothelin scFv expression of the cryopreserved ss1CAR T cells approximately 30 days at ≤−130° C. was 97.4%, almost identical to time of cryopreservation (96.9%), and other cryopreserved T cell products are stable for at least 6 months. Viability post-thaw, based on Trypan blue counts was 75.2% as compared to 98.7%. The expression data suggests that the final product is stable during storage for the trial, and that the sentinel vial for additional doses should meet release criteria of 70% viability and ≥20% CAR expression. Additional vials of ss1 CAR T cells will be thawed at 3, 6, 9, and 12 months post cryopreservation, and viability and transgene expression tested to generate further product stability data.

Clinical Trial Procedure and Results: A Phase I clinical trial of autologous mesothelin re-directed T cells administered to patients with malignant pleural mesothelioma is performed as follows. Similar procedures can be utilized for a study for treating patients with pancreatic cancer.

Dosages

Cohort 1 patients (n=3) will receive a single infusion of $1 \times 10^8$ using flat dosing with anti-meso RNA CAR T cells on day 0 and one infusion of $1 \times 10^9$ RNA CAR T cells on day 7, providing the patients meet the protocol-specified safety assessments before the day 7 infusion.

Cohort 2 patients (n=6) will be given 2 cycles of modified CAR T cells. One cycle consists of 3 infusions every other day (Monday, Wednesday, Friday). Cycle 1 consists of 3 doses of $1 \times 10^8$ CAR T cells dosed on MWF (day 0, 2, 4); cycle 2 consists of 3 doses of $1 \times 10^9$ CAR T cells dosed on MWF (day 7, 9, 11).

The target dose per infusion is 1×108 cells (one dose for Cohort 1 and week 1 doses for Cohort 2) and $1 \times 10^9 \pm 20\%$ cells (one dose for Cohort 1 and week 2 doses for Cohort 2). The minimally acceptable dose is $1 \times 10^8$. If the total cell expansion is lower than the total acceptable cell dose, the patient may undergo a second apheresis in an attempt to expand more cells and fulfill the total target dose. If there are contraindications for the second apheresis or if the second apheresis and expansion fails to produce the minimally acceptable dose, the dose will be deemed a manufacturing failure. For Cohort 1 patients, as many mesothelin CAR electroporated T cells as possible will be manufactured/ frozen to reduce the probability subjects will undergo a second leukapheresis in the case they will follow Extended Cohort 1 regimen.

Dose de-escalation will occur if more than one patient develops a DLT from modified CAR T cell infusion. In the event of DLT, we will dose de-escalate by 10-fold. Thus, if toxicity occurs during cycle 1 at $10^8$ CAR T cells, then all infusions (doses 1 to 6) would be reduced to $10^7$ CAR T cells. In the event of unmanageable toxicity at $10^7$ CAR T cells, the trial would be stopped.

A potential issue that can arise in patients being treated using transiently expressing CAR T cells (particularly with murine scFv bearing CARTs) is anaphylaxis after multiple treatments.

Without being bound by this theory, it is believed that such an anaphylactic response might be caused by a patient developing humoral anti-CAR response, i.e., anti-CAR antibodies having an anti-IgE isotype. It is thought that a patient's antibody producing cells undergo a class switch from IgG isotype (that does not cause anaphylaxis) to IgE isotype when there is a ten to fourteen day break in exposure to antigen. Therefore, for transient CARTs (such as those generated by RNA electroporation), CART infusion breaks should last more than ten to fourteen days.

In addition, using CARS with human (instead of murine) scFvs could reduce the likelihood and intensity of a patient having an anti-CAR response.

Study Procedure

The study consists of 1) a screening phase, 2) an intervention phase consisting of apheresis, CAR T cell infusion, side effect assessment, and optional tumor biopsy, and 3) follow up visits.

Screening and Baseline Assessment

An investigator must explain the nature of the study protocol and risks associated with the protocol in detail to the subject. The subject must sign and date the written informed consent prior to study participation. Informed consent process and date will be recorded in the subject's medical record and on the CRF. Informed consent must be obtained before protocol procedures are performed. If a procedure required for screening was performed prior to signing the informed consent and the procedure meets the time limits of the protocol, this procedure may be used for the screening evaluation.

The screening procedures (not required for determination of eligibility) will be completed within 6 weeks of first dose of CAR T cells (unless otherwise noted in the SOE). In the event that a second apheresis is needed to expand additional T cells and reach the target cell dose, this time window will not cover all the procedures. Thus, in this specific situation, a 6-8 week period is allowed for performing the baseline scans.

Screening procedures include:

Informed consent

Confirm an ECOG performance status ≤1

Determination of manufacturing efficiency (for the first 2 patients): a blood sample is sent to the CVPF to determine T cell manufacturing feasibility. In approximately 1 week, the CVPF will return a result as to whether the subjects PBMC are likely to be adequate for large scale CAR T cell manufacturing process. Results must be known before performing any additional study procedures.

Complete medical history

Physical examination including vital signs, height, weight and oxygen saturation Review of concomitant medications Hematology (WBC with differential, RBC, Hct, Hgb and platelets)

PT and PTT

Chemistry (sodium, potassium, chloride, bicarbonate, urea nitrogen, creatinine, glucose, total protein, albumin, calcium, alkaline phosphatase, total bilirubin, ALT, AST)

Viral screens: HIV, HCV, HBV and serology for CMV

Autoantibody panel: ANA, ESR

Urinalysis 12 lead Electrocardiogram (ECG)

Serum βHCG pregnancy (women of childbearing potential)

Spirometry and DLCO

Tumor assessment Chest CT Scan with contrast, other radiographic evaluations as clinically indicated. PET/CT scan is optional.

Pathological confirmation of epithelial or mixed (biphasic) mesothelioma and stain for mesothelin by protocol specific pathologist.

Leukapheresis

A 7 to 12-liter apheresis procedure will be carried out at the University of Pennsylvania Apheresis center (4 weeks prior to first dose of CAR T cells). PBMC are obtained for CAR T cells during this procedure. From a single leukapheresis, the intention is to harvest at least 5×10$^9$ white blood cells to manufacture CAR T cells. If the harvest is unsuccessful, patients will have the option to undergo a second leukapheresis. Baseline blood leukocytes for FDA look-back requirements and for research are also obtained and cryopreserved. The mesothelin-modified T cell product is expected to be ready for release approximately 4 weeks later. All patients will have the standard leukapheresis screening prior to the procedure.

Pre-Infusion Assessment (Study Day −3, Prior to First Dose)

This safety assessment includes physical exam (e.g., vital signs, weight, etc.), review of concomitant medications, performance status, chemistry, CBC with differential, pregnancy test (urin) urinalysis, EKG, CXR, and research blood specimens.

CAR T Cell Administration

Prior to each CAR T cell infusion patients will have limited problem oriented PE, review of adverse events, ECOG performance status, CBC, chemistry, and urinalysis. Subjects will return to HUP 1 day after CAR T cell infusion (D1, D3, D8 and D10) to have limited problem oriented PE, review of adverse events, concomitant medications, ECOG performance status, CBC and chemistry. On day 7, Cohort 1 patients will also have an EKG. On Day 14 Cohort 2 patients will also have a CXR and EKG.

CAR T cells will be administered as described above. Subjects' vital signs will be assessed and pulse oximetry will be done prior to dosing, at the end of the infusion and every 15 minutes thereafter for 2 hours and until these are stable.

Post-infusion Assessment

Cytokine levels in blood will be monitored at 1 h, 4 h, 1 day and 3 days following first infusion and at 1 h, 4 h, 1 day and 3 days, 7 days and 14 days following the second infusion for patients of Cohort 1. Blood collection for engraftment analysis (flow cytometry and RT-PCR) will be collected for 21 days following the first infusion.

For Cohort 2 (and Extended Cohort 1) patients, cytokine levels will be monitored at 1 h following each infusion and at additional time points according to the SOE. The primary safety and engraftment data is collected for 35 days following the first (Day 0) CAR T cell administration.

1 day after the CAR T cell infusion, blood is drawn for flow cytometry and RT-PCR in order to evaluate for circulating CAR T cells. Peripheral blood samples will be processed to isolate: a) peripheral blood mononuclear cells (PBMC) to evaluate immune cell phenotype and function, b) RNA to quantify short term persistence and distribution of infused CAR T cells and c) serum to quantify and evaluate immune cell subset and soluble immune and growth factors, evaluate the development of anti-infused cell immune responses, and perform protoarray analyses to evaluate the development of humoral anti-tumor immune responses via immune epitope spreading.

Subjects will be assessed on month 2 and 3 (Cohort 1), and months 2, 3, and 6 following the last CAR T cell infusion (Cohort 2 and extended Cohort 1) for safety assessment as described above.

Tumor Biopsy and Mini-apheresis

For Cohort 2 and extended Cohort 1: If tumor is visibly accessible or accessible by image-guided biopsy, eligible subjects will undergo direct tumor biopsy or biopsy under image guidance to evaluate the presence of CAR T cells and mesothelin expression. This is to be scheduled at Day 14 after T cell infusion for Cohort 2 subjects. The frequency of total tumor-infiltrating lymphocytes and T cell subsets as well as the expression of molecular markers of T cell antitumor response will be measured. These will be compared to baseline values on stored surgical tumor specimens, if available. Subjects will be given the option to refuse tumor biopsy. Intracavitary fluid may also be submitted as biopsy.

A mini-apheresis (2 L) is done for research purposes and for FDA "lookback" purposes to archive CAR T cells for safety analysis at day 21 post-infusion. A blood sample may be collected in lieu of leukapheresis.

Tumor Response Assessment

Tumor response will be assessed at Day 35 and Month 2 for Cohort 1 and Day 35, Months 2 and 6 following the last CAR T cell infusion for Cohort 2 (and Extended Cohort 1), or until the patient requires alternative MPM therapy. Tumor assessment will be done by CT scan with contrast for chest and other procedures as clinically indicated.

The above example can be done using human bearing scFv CARTs, using for example the scFvs in CAR constructs M5, M11, M14, M15, M16 and M17.

Example 6

CART-MSLN Induce Anti-tumor Activity in Solid Malignancies

This example present two case reports from ongoing clinical trials indicating that adoptive transfer of mRNA CAR T cells (PBMCs were electroporated with mesothelin CAR construct) that target mesothelin (CART-MSLN) is feasible and safe without overt evidence of off-tumor on-target toxicity against normal tissues. These cases also demonstrate that CART-MSLN can infiltrate and have anti-tumor activity in solid malignancies, such as malignant plural mesothelioma (MPM) and pancreatic cancer.

Subject 17510-105 had MPM and was given 3 infusions of CARTmeso. Subject 21211-101 had metastatic pancreatic cancer (PDA) and was given 8 doses of CARTmeso by intravenous infusion and 2 intratumoral injections. Both patients were elderly and had advanced chemotherapy-refractory cancer with extensive tumor burden at the time of enrollment.

Anti-tumor Clinical Activity of CART Meso Cells

Both cases were evaluated for tumor response by computed tomography (CT) imagining. In addition, the PDA patient was evaluated by [18F]2-fluoro-2-deoxy-D-glucose (FDG) avidity on positron emission tomography/computed tomography (PET/CT) imaging before and after infusions (FIG. 6) The MPM patient had stable disease after receiving CARTmeso infusions, however, developed a confirmed partial response after receiving one infusion of CARTmeso cells on Schedule 2 (FIG. 6A). The PDA patient had stable disease after 3 weeks of intravenous CARTmeso therapy. By FDG PET/Ct imaging, a decrease in the maximum standardized uptake value (SUVmax) was seen in all sites of disease. To further this metabolic response, changes in the mean volumetric product (MVPmean) for each disease site were determined (FIGS. 6B, 6C, and 6D). A decrease in MVPmean was observed only in the peritoneal lesions. To further understand the impact of CARTmeso cell therapy on peritoneal tumor burden, ascites fluid was analysed by flow cytometry. Analysis of the ascitic fluid on days +3 and +15 after beginning therapy revealed a 40% decrease in the concentration of tumor cells that co-expressed mesothelin and c-met. (FIG. 6D). Overall, these findings suggest a role for CARTmeso cell infusions in inducing an anti-tumor effect in these patients.

Serological tumor markers was also evaluated in both patients. Serum mesothelin-related peptide (SMRP) and CA19-9 levels were measured pre- and post-CARTmeso cell infusions. For the MPM patient, SMRP levels declined after receiving the first infusion on Schedule 2, coinciding with the reduction of tumor burden seen by CT imaging. For the PDA patient, CA19-9 levels increased slowly over the course of treatment but remained stable for 1 month. After completion of the intra-tumoral injections of CARTmeso cells, CA19-9 levels rose consistent with disease progression.

In Vivo Persistence and Trafficking of CARTmeso Cells

Figure 7:
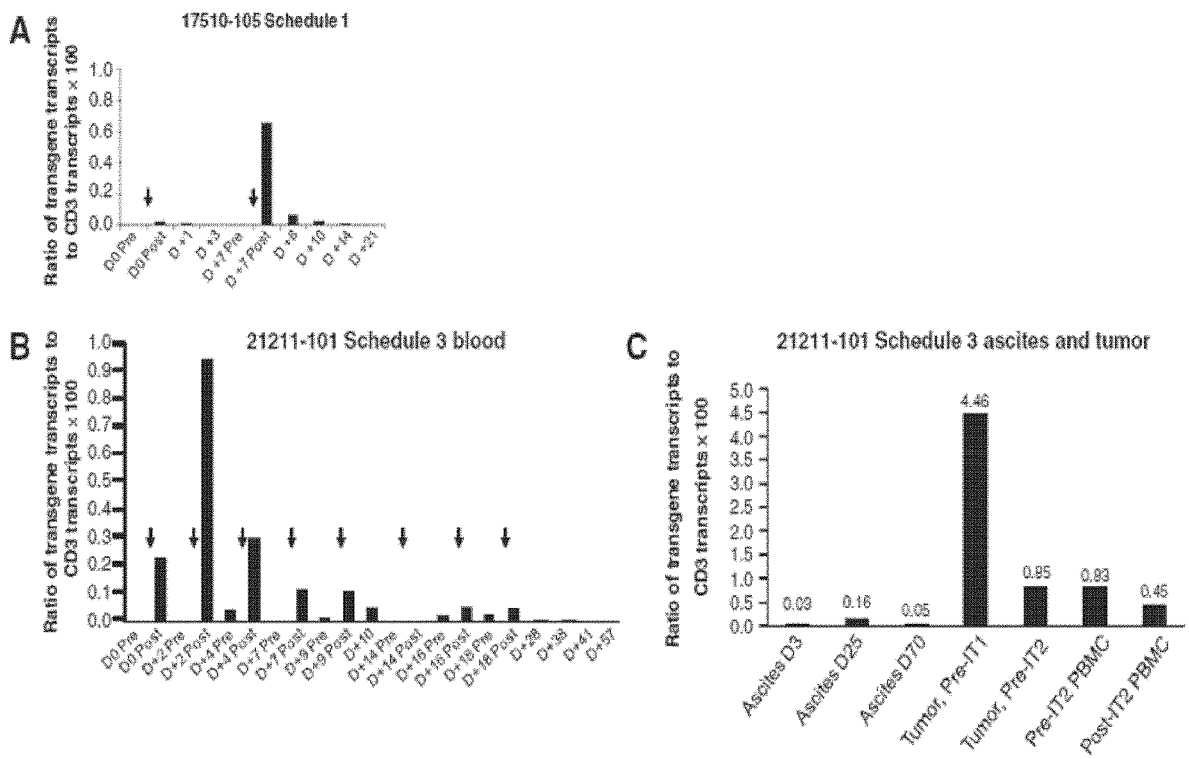
FIGS. 7A, 7B, and 7C show the in vivo persistence of CARTmeso cells and trafficking to primary and metastatic tumor sites.
Figure 8:
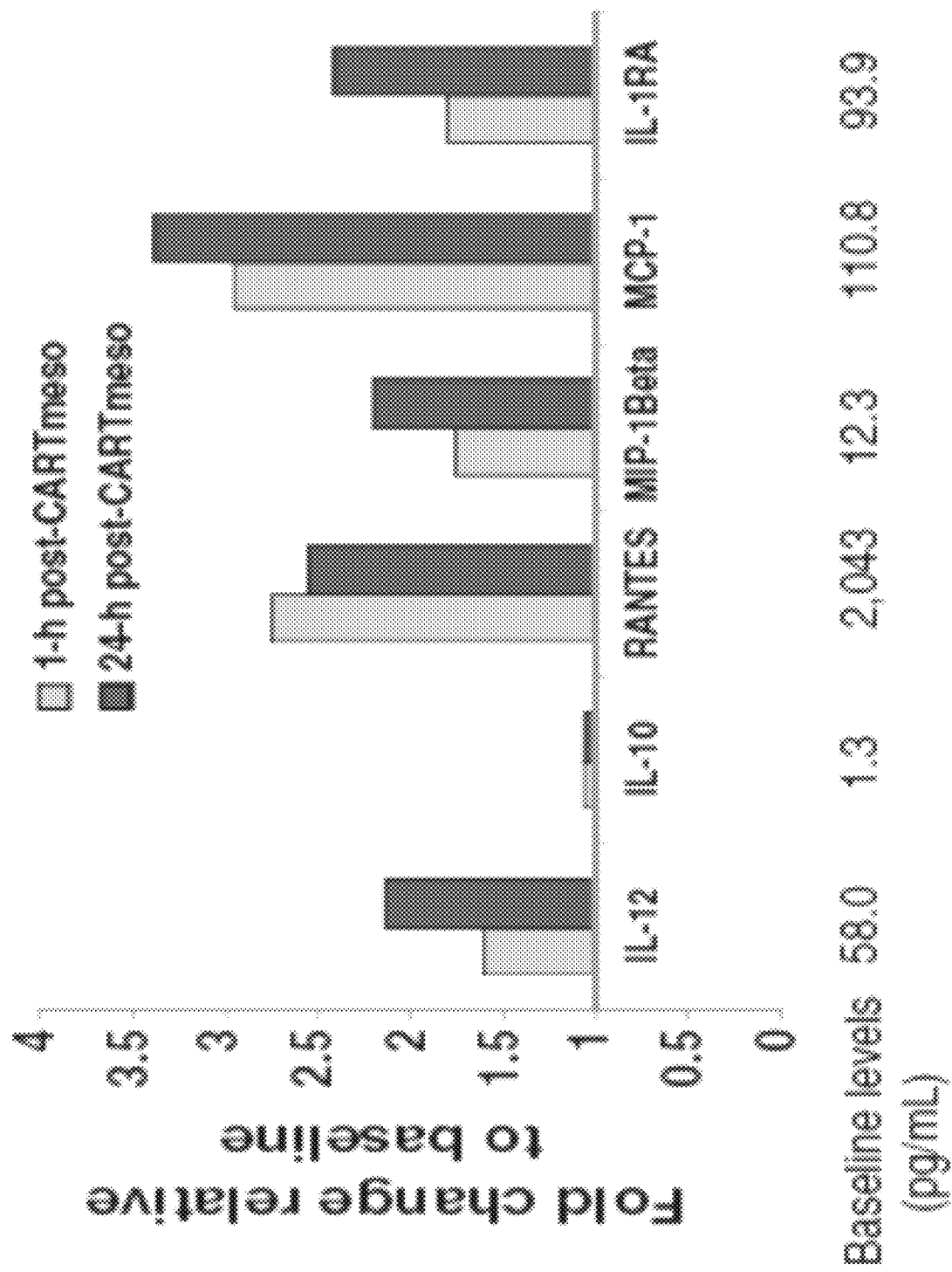
FIG. 8 shows cytokine and chemokines in the serum after CARTmeso cell infusion.

A qPCR assay was develed to detect and quantify the persistence of CARTmeso cells in patients following infusion. Analysis of peripheral blood, ascites, and tumor samples from the two patients are presented in FIG. 7. CARTmeso transgene was detected in both patient immediately after each infusion. In agreement with the biodegradable nature of the CARTmeso transgene, levels were observed to progressively decrease on successive days.

Trafficking of CARTmeso cells in tumor tissues was evaluated in the PDA patient by collecting ascites at serial time point and by tumor biopsy.

Induction of Humoral Epitope Spreading after CART-meso Cell Infusion

The hypothesis that CARTmeso cells, if able to recognize and lyse primary tumor cells in vivo, might elicit a systemic anti-tumor immune response was tested. High-throughput serological analysis was performed to measure induction of antibody responses to antigens to detect the development of a polyclonal immune response that may have occurred as a result of tumor destruction and epitope spreading. These analysis were accomplished using an unbiased interrogation of treatment-induced igG responses to almost 10,000 independent human proteins. In PDA patient, new antibody responses were detected at day +44 to more than 100 proteins. Similarly, elevated antibody responses to a subset of proteins was observed for the MPM patient. Overall, these antibody immune responses observed in both patients are consistent with CAR T cell-mediated tumor destruction leading to the release of self-proteins that are cross-presented in a classical process of epitope spreading.

Pre- and post-treatment sera of both patients for the induction of anti-tumor immune responses was also examined by immunoblotting using purified tumor associated proteins or protein lysates from human MPM or PDA cell lines. Anti-tumor immune responses were defined by the presence of new bands or increases in the intensity of pre-existing bands on immunoblots (FIG. 9) In both patients, antibody pattern alterations were seen during treatment, e.g., increases in antibodies detecting proteins present in allogeneic tumor cell lines. These findings along with the protoarray analysis suggest that an antitumor humoral immune response was induced by CARTmeso cell infusion.

Example 7

Combination Treatment to Improve CART Function in Solid Tumors

Immunotherapy using adoptively transferred tumor infiltrating lymphocytes (TILs) is limited by T cell functional inactivation within the solid tumor microenvironment. In this study, human T cells expressing meso CAR were injected intravensously into immunodeficient mice bearing large, established human mesothelin-expressing mesothelioma flank tumors. Analysis of the isolated meso-CAR T cells (mesoCART) showed rapid loss of effector functions that appeared to be multifactorial. The results from these experiments demonstrate that inhibitors of mechanisms that cause loss of effector function of mesoCART may be useful to in a combination therapy to enhance efficacy of mesoCART treatment in vivo.

Materials and Methods

Generation of mesoCAR and Lentivirus Vector Preparation. Lentiviral constructs containing mesothelin CAR ss1 were prepared as described previously. Human mesothelin CAR constructs and T cells expressing the same can also be generated using methods previously described.

Cell Lines. A human mesothelioma cell line derived from a patient's tumor was used—EMP (parental). Since EMP did not have baseline expression of the tumor-associated antigen (TAA) mesothelin, it was transfected with a lentivirus to stably express human mesothelin (the transduced cell line was named EMMESO). Cells were also transduced to stably express firefly luciferase (called EMPfluc, EMMESOffluc).

T Cell Effector Assays. Effector T cells were cocultured with firefly luciferase expressing tumor cells at different ratios for a specified period time. At the end of the co-culture incubation period, supernatant was saved for IFN levels by ELISA (Biolegend #430106), wells were washed, and remaining tumor cells were lysed with 1× cell lysis buffer for 30 minutes. The luciferase activity in the lysates was analyzed using the Luciferase Assay System on a GloMax Multi Detection System (Promega.) Results are reported as percent killing based on luciferase activity in wells with tumor, but no T cells. (% killing=100−((RLU from well with effector and target cell coculture)/(RLU from well with target cells)× 100)). Effector-to-target ratios represent total T cells per target cell.

Animals. All animal experiments were approved by the appropriate Institutional Animal Care and Use Committee. NOD/scid/IL2rγ−/− (NSG) mice were bred in the Animal Services Unit of the Wistar Institute and Children's Hospital of Philadelphia. Female mice were used for experiments at 10 to 16 weeks of age.

In Vivo Xenograft Experiments. $5 \times 10^6$ EMMESO tumor cells were injected in the flanks of NSG mice in a solution of X-Vivo media (Lonza) and Matrigel (BD Biosciences). After tumors were established (100-200 mm$^3$), the mice were randomly assigned to one of three intravenous (tail-vein) treatment groups: 1) $20 \times 10^6$ non-transduced (NT) T cells (Dynabead® activated T cells), 2) $20 \times 10^6$ mesoCAR T cells (Dynabead® activated T cells transduced with meso-CAR) 3) saline. Tumors were measured using calipers and tumor volume was calculated using the formula $(\pi/6)*$ (length)*(width). Groups contained 10 mice each. The in vivo experiments were repeated three times.

Results

Hypofunction Observed in Tumor Infiltrating CARTs

Figure 10:
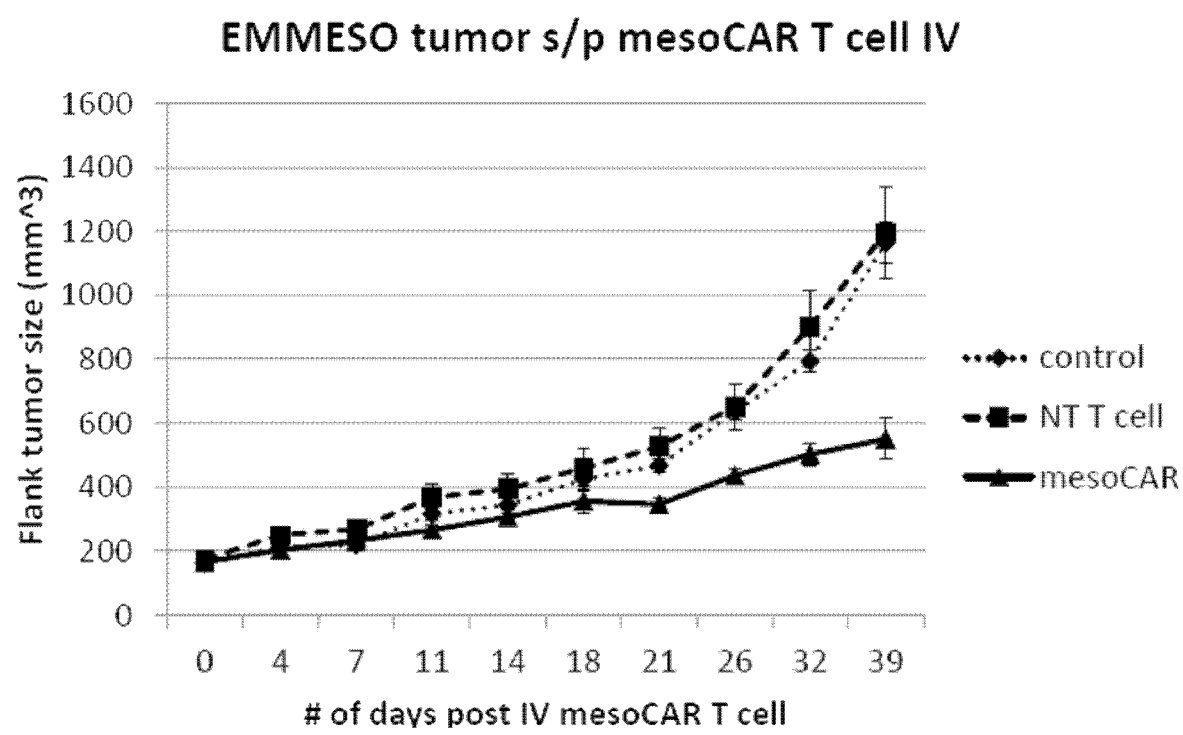
FIG. 10 shows tumor growth in NSG mice injected with EMMESO tumor cells.

The human mesothelin-expressing mesothelioma tumor cell line EMMESO was injected into the flanks of NSG mice and allowed to grow to a size between 100 and 200 mm3. At that time, tumor-bearing mice were given one intravenous injection of 20 million T cells (mesoCAR expression was approximately 50% (data not shown)). Significant tumor growth slowing was seen after a delay 14 days (FIG. 10), however, unlike our experience with another mesothelioma cell line (Carpenito et al., *Proc Natl Acad Sci USA*, 106(9): 3360-65 (2009), Zhao et al., *Cancer Res*, 70(22):9053-61 (2010).) no tumor regression or cures were noted. Injection of non-transduced T cells had minimal anti-tumor effects when compared to the saline treated control (FIG. 10), indicating that the reduction in tumor growth observed in animals treated with T cells expressing mesoCAR was the result of the mesoCAR.

Various analyses were performed to understand why tumor regressions were not observed after CART treatment. EMMESCO tumors were examined and mesoCARTs were found to be present in large numbers, however, the T cells present had become hypofunctional. Given that the level of CAR expression on the CAR TILs was equal or greater to that of the cells prior to injection (FIGS. 11A and 11B), we compared their functional activity. We isolated and analyzed the mesoCAR TILs from EMMESO tumors 40 days after injection (all studies were started immediately after isolation) and compared them to the same batch of mesoCAR T cells that had been used for the original injection and frozen away ("cryo mesoCAR"). These cells were studied after thawing and incubating in 37° C./5% CO2 for 18 hrs. When cryo mesoCAR T cells and flank mesoCAR TILs were added to cultured EMMESO cells expressing firefly luciferase (EMMESOffluc) at a 20:1 ratio for 18 hours, the cryo mesoCAR T cells were highly efficient in killing tumor cells (>95%), while the mesoCAR TILs killed only about 10% of the tumor cells over this same time period (FIG. 11C, p<0.001).

Additional analysis also demonstrated that the mesoCAR T cells did not produce cytokines, such as IL-2 and IFNg, after exposure to antigen or PMA/Ionomycin. In contrast, the cryo-meso CAR T cells produced cytokines. The meso-CAR T cells also demonstrated reduced signaling, by reduced or absence of phosph-ERK expression by immunoblotting 20 minutes after exposure to anti-CD3/CD28-coated beads. In contrast, cryo-meso CAR T cells retained phosphor-ERK expression after exposure to the beads.

Human mesoCAR TILs Express Increased Levels of Inhibitory Receptors

Next, the expression of four inhibitory receptors (IR) that have been previously described in hypofunctional TILs isolated from humans was evaluated using flow cytometry on: i) the cryo mesoCAR T cells that were used for injection, ii) freshly isolated mesoCAR TILs from Day 39 from EMMESO, and iii) "recovered" mesoCAR TILs that had been removed from the tumor for 24 hours (Table 6). CAR TILs expressed high levels of inhibitory receptors. These levels were generally much lower after 24 hours of recovery away from the tumor microenvironment. For the CD4 CAR TILs, PD-1 went from 73% to 53%, LAG-3 went from 63% to 3%, and TIM3 went from 24% to 1%. 2B4 expression was high and remained elevated after rest (67% to 88%). For the CD8 CAR TILs, PD-1 went from 26% to 21%, LAG-3 went from 48% to 13%, and TIM3 went from 56% to 1%. 2B4 expression was high and remained elevated after rest (96% to 98%).

TABLE 6

Expression of inhibitor receptors (IRs) on TILs

| EMMESO TIL | Percent positive CD4 T cells | | | Percent positive CD8 T cells | | |
|---|---|---|---|---|---|---|
| | Cryo Meso CAR T cells | Fresh TIL | Recovered TIL | Cryo Meso CAR T cells | Fresh TIL | Recovered TIL |
| PD-1 | 37.2 (947) | 73.0 (1492) | 53.0 (1081) | 5.4 (326) | 26.0 (420) | 21.0 (360) |
| LAG-3 | 44.7 (2585) | 62.8 (3845) | 3.0 (1968) | 85.2 (4609) | 48.0 (4376) | 13.0 (3161) |
| 2B4 | 4.5 (215) | 67.0 (1102) | 88.0 (351) | 60.0 (2974) | 96.0 (6303) | 98.0 (5917) |
| TIM3 | 1.9 (945) | 24.0 (1253) | 1.0 (200) | 2.4 (941) | 56.0 (1408) | 1.0 (435) |

Three of these IR's were also evaluated on the human T cells that could be isolated from the spleens of the EMMESO mice. Interestingly, the expression levels of PD-1, TIM3, and LAG3 were all lower on the splenic T cells compared with the TILs (Table 7), supporting a key role for the tumor microenvironment in the upregulation

TABLE 7

Comparison of expression of inhibitor receptors on TILs and splenic cells

| EMMESO TIL | Percent positive CD4 T cells | | Percent positive CD8 T cells | |
|---|---|---|---|---|
| | Fresh TIL | Splenic T cells | Fresh TIL | Splenic T cells |
| PD-1 | 73 | 46 (22) | 26 | 15 (17) |
| LAG-3 | 63 | 32 (132) | 48 | 15 (11) |
| TIM3 | 24 | 17 (9) | 56 | 31 (8) |

Human mesoCAR TILs Express Increased Levels of Intracellular Inhibitory Enzymes.

The expression levels of two intrinsic inhibitors of T cell function that have been implicated in TIL dysfunction, SHP-1 and DGK, was examined using immunoblotting (FIG. 12). The levels of both isoforms of DGK (alpha and zeta), as well as the phosphorylated form of SHP1 (pSHP1), were significantly elevated in mesoCAR TILs that were freshly isolated from EMMESO flank tumor compared to overnight-rested TILs. This was also confirmed for DGK using flow cytometry where 23% of fresh EMMESO TILs expressed DGK. Expression was undetectable after overnight rest.

Block of Inhibitors in Human mesoCAR T Cells Enhances their Ex Vivo Killing Function.

Given these expression data, the potential functional importance of specific inhibitory pathways in mesoCAR TILs was studied by introducing available blocking agents during the ex vivo killing and cytokine release assays. Addition of an anti-PDL1 antibody significantly restored the killing activity and ability to secrete IFNby the mesoCAR TILs (FIGS. 13A and 13B). The relatively high dose of 10 ug/ml anti-PDL1 antibody was based on previously published investigations on cancer immunotherapy. Addition of either a type I or type II DGK inhibitor significantly increased the killing ability (FIG. 13C), but without significantly increasing tumor-induced IFN secretion (FIG. 13D). Addition of the SHP1 inhibitor, sodium stibogluconate (SSG), slightly inhibited the killing ability of cryo meso-CAR T cells (FIG. 13E), as well as significantly increasing tumor-induced IFN secretion (FIG. 13F) of the mesoCAR TILs. Dose response curves were performed for both DGK inhibitors and for SSG, and the highest doses which did not induced direct tumor cell killing were used.

Taken together, the results from these experiments demonstrate that hypofunction of CARTs in vivo is reversible. Specifically, modulation of the inhibitor mechanisms that reduce CART function can increase effector function, and therefore, may increase therapeutic efficacy. Inhibitors of inhibitor receptors, such as PD-1, LAG3, and TIM3, may be useful in combination therapy with CARTs for increased efficacy.

Example 8

Characterization of Human Meso CAR

Generation of Human CART-MSLN

PBMCs from a normal subject were isolated from a blood sample. PBMCs were transduced with lentivirus constructs containing the human mesothelin CARs described herein. Transduction and culturing of the cells to produce CART-MSLN are described in the previous examples. The CARTs produced express mesothelin CARS with scFv constructs including M1, M2, M3, M4, M5, M6, M7, M8, M9, M10, M11, M12, M13, M14, M15, M16, M17, M18, M19, M20, M21, M22, M23, and M24. Control CARTs were also generated, including CART expressing CAR-ss1 (murine anti-mesothelin scFv) (for positive control), and anti-CD19 CART (for negative control).

Cytokine Assay

Cytokine production after stimulation by tumor cells was assessed. CARTs expressing M5, M11, M17, M21, ss1, and CAR19 were mixed with different tumor cell lines at a 1:1 effector to target ratio, and plated at 50,000 cell per well. The tumor cell lines were K562-meso (CIVIL cell line expressing mesothelin), Ovcar3 (ovarian cancer), Ovcar8 (ovarian cancer), and SW1990 (pancreatic adenocarcinoma). After 24 hours, CBA analysis was performed to determine cytokine expression and/or secretion of IFNγ, TNF, IL-2, and IL-4.

As shown in FIG. 15A, CART-MSLN21 (M21) leads to the strongest activation by K562-Meso. CART-MSLN5 and CART-MSLN11 were stimulated by SW1990 to produce IFNγ. The production/secretion of IL-2 was similar for the tested CART-MSLN (FIG. 15C). As shown in FIG. 15D, there was hardly any production of IL-4. Other studies also showed very little production of IL-10.

Killing Assay

The ability for the CART-MSLN to target and kill tumor cells was also assessed in vitro. A luciferase-based assay was used, with tumor cell lines expressing luciferase reporters. Target cells (tumor cells) were plated at 20,000 targets/well. CART-MSLN were added at varying effector:target ratios, from 10:1, 5:1, 2.5:1, and 1:1. The cells were cultured for 20 hours, and the luminescence of each well was detected to determine the percentage of target cells killed. Luciferase-expressing Ovcar3 (ovarian cancer) and U87 mg (glioblastoma) cell lines were used as target cells.

As shown in FIG. 16A, CARTs expressing M5, M11, M17 and ss1 performed similarly well in killing target tumor cells. No killing was observed for CART-MSLN21. In contrast, no killing was observed for any of the CART constructs for glioblastoma cells (FIG. 16B). Similar results were obtained for the panel of human meso CARs, where M11, M5, M17, and SS1 had the highest specific killing of Ovcar3 cells (FIGS. 17A and 17B).

In Vivo Mouse Model

Anti-tumor activity of CART-MSLN was assessed in vivo in an Ovcar8 xenograft model. $10 \times 10^6$ Ovcar8 cells were implanted subcutaneously on day 0 in NSG mice. At day 14, $2 \times 10^6$ CART cells (CARTs expressing M5, M11, M17, M21, SS1, and CD19, or untransduced cells; $10 \times 10^6$ total T cells) in a 100 µl dose was administered intravenously. Mice and tumors were monitored for about 40 days after tumor cell implantation.

Results from this experiment show that CART expressing M5 and M11 exhibit strong anti-tumor activity in this model (FIG. 18). When compared to the mock treated group, M5 and M11-treated mice exhibited statistically significant tumor reduction ($p<0.05$).

A second in vivo xenograft experiment was performed to assess the anti-tumor activity of a second set of CART-MSLN cells. $10 \times 10^6$ OVCAR8-mcherry cells were injected into NSG mice. Once tumors were 150-250 mm$^2$, mice were randomized into treatment groups. CARTs expressing M12, M14, M16, 1V123, ss1, CD19, or untreated cells were injected at a dose of $10 \times 10^6$ T cells in 100 µl. About 40% of T cells were expressing CAR, and therefore at the administered dosage, about $4 \times 10^6$ CART cells were delivered to each animal. Results from this experiment show that the CART expressing the human anti-MSLN (M12, M14, M16 and M23) did not have an effect on tumor growth (FIG. 19). These results taken together with the results from the first set of CART-MSLN assessed indicate that M5 and M11 have specific anti-tumor activity in comparison with the other CART-MSLN tested, and thereby demonstrate their potential for further investigation for cancer therapy. In addition, CART-SS1 did not exhibit any anti-tumor activity in the first xenograft or the second xenograft experiment, further indicating that M5 and M11 containing CART-MSLN are more effective at reducing tumor growth.

Example 9

DGK Inhibition Augments CART Efficacy

Previous studies, for example, the experiments discussed in Example 6, have suggested that CAR T cells lose efficacy over time in vivo (e.g., in the tumor microenvironment). Specifically, mesoCAR T cells that were injected into a tumor mouse model were isolated from tumors after T cell infusion (e.g., 39 days after, hereinafter referred to as tumor infiltrating lymphocytes, TILs) and were assessed for their functional activity in comparison to freshly thawed mesoCAR T cells. The results showed that in ex vivo killing assays and IFNγ release assays, the mesoCAR T cells isolated from the tumor had reduced ability to kill tumor cells (FIG. 20A), reduced IFNg production (FIG. 20B), and reduced ERK signaling (as shown by phosphorylation in western blot analysis, FIG. 20C) in response to antigen or CD3/CD28 stimuli (indicating reduced T cell activation.

Inhibitory mechanisms that possibly explain the decrease in CAR T cell activity in vivo over time include: soluble factors (TGFb, PGE2, adenosine, IL10, RAGE ligands, etc.), cell to cell contact (PD-1, LAG3, CTLA4, TIM3, CD160, etc.), and intrinsic activation-induced intracellular negative feedback systems (diaglycerol kinases: α and ζ isoforms, Egrs (2 and 3), SHP-1, NFAT2, BLIMP-1, Itch, GRAIL, Cbl-b, Ikaros, etc.). T cell activation can induce factors such as DGK. DGK, in turn, inhibits DAG signaling by phosphorylating DAG. This limits DAG-induced activation of the RAS-ERK-AP1 pathway that leads to T cell activation. Previous studies have shown that mice deficient in DGKα or DGKζ results in CD4 T cells that demonstrate enhanced signal transduction and appear more resistant to anergy-inducing stimuli.

In Vitro Cytoxicity and Cytokine Release Assays

To investigate the effect of DGK inhibition on CART cell efficacy, transgenic mice with deletions in DGK genes DGKα, DGKζ, or both were utilized. Splenic T cells from wild-type and DGK-deficient mice were isolated, and transduced to express mesoCAR (SS1 BBZ) using retrovirus. MIGR1 CAR was used as a control.

A cytotoxicity assay was performed using similar methods to those described in previous Examples. Wild-type and DGK-deficient (KO) mesoCAR expressing cells were incubated at various effector:target ratios and cytotoxicity (% of target cells killed) was quantified (FIG. 21). As shown in FIG. 21, deletion of DGKs markedly enhanced effector function of CAR T cells, especially at low effector:target ratios.

Similarly, IFNγ release was examined in response to target cells at varying effector:target ratios after 18 hours. As shown in FIG. 22, deletion of DGKs was found to markedly enhance effector function of the mesoCAR T cells, especially at low effector:target ratios.

Western blot analysis of DGK-deficient mesoCAR T cells in comparison to wild-type mesoCAR T cells showed increased ERK phosphorylation (FIG. 23), indicating that presence of DGK suppresses ERK signaling, while deletion of DGK results in increased ERK signaling. The increase in ERK signaling in the DGK deleted background suggests that inhibition of DGK results in activation of the Ras-ERK-AP1 pathway, and therefore, T cell activation.

Recent studies have shown that TGFβ modulates the functionality of tumor-infiltrating CD8 T cells though interfering with RAS/ERK signal transduction, the same signaling molecules by which DGK deficiency confers augmented T cell effects. Sensitivity of the DGK-deficient mesoCAR T cells to TGFβ was examined. WT and DGK-deficient mesoCAR T cells was incubated with mesothelin-expressing AE17 tumor cells + or −10 ng/ml of TGFβ for 18 hours. Cytotoxicity and IFNg production by these T cells was measured. As shown in FIG. 24, TGFβ inhibited killing by 50% in WT CAR T cells (arrows). However, this TGFβ-induced inhibition was not observed in CAR T cells with DGK deletion, demonstrating that DGK-deficient cells are not sensitive to TGFβ modulation, and are more resistant to inhibitor stimuli such as TGFβ, which may contribute to the increase in T cell activity.

Therapeutic Efficacy of mesoCAR and DGK Inhibition In Vivo

Next, therapeutic efficacy of mesoCAR T cells was examined in the context of DGK inhibition or deficiency. AE17meso tumor cells (mesothelioma cells) were injected subcutaneously into C57BL/6 mice. When tumors reached 100 mm$^3$ (approximately a week later), 10 million meso- CAR T cells were injected intravenously via tail vein. Tumor volumes were then followed over at least 18 days.

DGK-deficient mesoCAR T cells demonstrated enhanced and prolonged anti-tumor activity compared to wild-type (WT) mesoCAR and untreated cells (FIG. 25A). Specifically, each of the three DGK-deficient mesoCAR T cells was shown to inhibit tumor growth by volume compared to WT and untreated cells up to 18 days after injection. DGKz-deficient cells expressing mesoCAR were also shown to persist and proliferate better than wild-type meso CAR T cells in mice (FIG. 25B).

These results taken together show that DGK inhibition in combination with mesoCAR T cell treatment can improve mesoCAR T cell activation and anti-tumor activity in therapy.

Example 10

Inhibition of Ikaros Augments Anti-tumor Capacity of CAR-T Cells

One of the major hurdles in CAR T cell therapy is up-regulation of intrinsic negative regulators of T cell signaling, such as diacylglycerol kinase (DGK). As described in Example 9, CAR T cells have been shown to lose efficacy in vivo over time. Inhibition of negative regulators of T cell function such as DGK was shown to enhance activity and function of CAR-expressing T cells.

Another important negative regulator of T cell function is the transcription factor Ikaros. Unlike DGKs which act mainly in proximal TCR signaling, Ikaros is a zinc finger DNA binding protein that negatively regulates gene expression through the recruitment of chromatin remodeling complexes, such as Sin3A, CtBP, and HDACs. Ikaros plays a role in regulating cytokine production and cytolytic function in CD4+ T cells and CD8+ T cells, In this example, anti-tumor efficacy of retrovirally-transduced CAR T cells with reduced Ikaros expression was examined in vitro and in vivo.

Materials and Methods

Cell Lines. Mouse AE17 mesothelioma cells were described in Jackman et al., *J Immunol.* 2003; 171:5051-63). Human mesothelin were introduced into AE17 cells by lentiviral transduction. 3T3Balb/C cells, were purchased from the American Type Culture Collection. Mouse FAP expressing 3T3BALB/C (3T3.FAP) cells were created by lentiviral transduction of the FAP-3T3 parental line with murine FAP.

Animals. Pathogen-free C57BL/6 mice were purchased from Charles River Laboratories Inc. (Wilmington, Mass.). Ikaros DN+/− mice contain one wildtype Ikaros allele and one Ikaros allele with a deletion of a DNA binding domain (Winandy et al., Cell. 1995; 83:289-99). Ikzf1+/− mice have one wildtype Ikaros allele and one allele with deletion of exon 7 (Avitahl et al., *Immunity.* 1999; 10:333-43). Animals used for all experiments were female mice between 6 and 12 weeks old and were housed in pathogen-free animal facilities.

Isolation, Transduction and Expansion of Primary Mouse T lymphocytes. Primary murine splenic T cells were isolated using the "Pan T cell Negative Selection" kit as suggested by the manufacturer (Miltenyi Biotec), and activated in 24-well plates ($4 \times 10^6$ cells/well in 2 mL supplemented RPMI-1640 with 100 U/mL IL-2) pre-coated with −CD3 (1 µg/mL) and −CD28 (2 µg/mL). After 48 hours, cells ($1 \times 10^6$ cells/well) were mixed with retrovirus (1 mL crude viral supernatant) in a 24-well plate coated withRetronectin (50 µg/mL; Clontech) and centrifuged, without braking, at room temperature for 45 minutes at 1200 g. After overnight incubation, cells were expanded with 50 U/mL of IL-2 for additional 48 hours.

Antigen- or antibody-coated beads. Recombinant mesothelin-extracellular domain protein, bovine serum albumin (Fisher Scientific) or anti-CD3/anti-CD28 antibodies (eBioscience) were chemically crosslinked to tosylactivated 4.5 µm Dynabeads (Invitrogen, #140-13) per manufacturers' instructions.

Immunoblotting. Anti-mesothelin-CAR transduced T cells were incubated either with BSA-, mesothelin-, or anti-CD3 antibody-coated beads (at 2:1 bead to T cell ratio) for 5 and 20 min. Total cell lysates were then prepared and immunoblotted for phosphorylated ERK, phosphorylated AKT, phosphorylated IKK, phosphorylated JNK, phosphorylated Lck, phosphorylated PKC, phosphorylated PLC, or phosphorylated ZAP70. All anti-phospho-protein antibodies were purchased from Cell Signaling, with exception of anti-phospho-Lck, which was purchased from Sigma Aldrich. A C-terminus reactive goat anti-mouse antibody to Ikaros (SC-9861) and a goat anti-mouse actin antibody (SC-1615) were purchased from Santa Cruz. (β-actin expression levels were determined to normalize the differences in loading.

Cytotoxicity and IFN ELISA. AE17, AE17.meso, 3T3 and 3T3.FAP cells were transduced with luciferase as described (Moon et al., *Clinical Cancer Research.* 2011; 17:4719-30). T cells and target cells were co-cultured at the indicated ratios, in triplicate, in 96-well round bottom plates. After 18 hours, the culture supernatants were collected for IFN analysis using an ELISA (mouse IFN, BDOpEIA). Cytotoxicity of transduced T cells was determined by detecting the remaining luciferase activity from the cell lysate using a previously described assay (Riese et al., *Cancer Res.* 2013; 73:3566-77).

CAR T cell transfer into mice bearing established tumors. Mice were injected subcutaneously with $2 \times 10^6$ AE17.meso tumor cells into the dorsal-lateral flank of C57BL/6 mice. Mice bearing large established tumors (100-150 mm³) were randomly assigned to receive either wildtype CAR T cells, Ikaros-deficient CAR T cells or remained untreated (minimum, five mice per group, each experiment repeated at least once). $1 \times 10^7$ T cells were administered through the tail vein. Tumor size was measured by electronic scales and calipers, respectively.

For Day 9 T cell activity assessment, spleen and tumors were processed into single cell suspensions as previously described (Moon et al., *Clinical Cancer Research.* 2014; 20(16):4262-73). Splenocytes and tumor single cell suspensions were re-stimulated with soluble anti-CD3/CD28 antibodies (1.0 µg/ml) or with phorbol ester/ionomycin (PMA/I: 30 ng/ml, 1 uM) for 4-6 hours in the presence of Golgi Stop (BD Biosciences, 0.66 µl/ml) and then harvested for flow cytometric analysis.

Flow cytometric assays. Fluorochrome conjugated antibodies against anti-mouse IFN-γ (XMG1), anti-mouse CD25 (PC61), anti-mouse IL-2 (JES6-1A12), anti-mouse CD8 (53-6.7), anti-mouse CD44 (IM7), and anti-mouse CD4 (GK1.5) were purchased from Biolegend. Fixable, Live/Dead Aqua stain (L34957) was purchased from Invitrogen. Fluorochrome antibody to anti-mouse Granzyme B (NGZB) and FoxP3 (FJK-16s) was purchased from eBioscience. Fluorochrome antibodies to anti-mouse TNF-α (MP6-XT22) and anti-mouse CD69 (H1.2F3) were purchased from BD Biosciences. For intracellular cytokine staining, cells were treated with Golgi Stop (BD Biosciences, 0.66 µg/ml) for 4-6 hours. Following harvesting, cells were fixed with 1% paraformaldehyde for 30 minutes, spun down and washed once with FACS buffer. Cells were then washed with BD Perm Wash (BD Biosciences) 2 times and then stained with cytokine antibodies for 45 minutes at room temperature. Cells were washed 2 times in BD Perm Wash and then re-suspended in FACS Buffer. For transcription factor staining, cells were surfaced stained with fluorochrome-labeled primary antibodies for 20 minutes on ice. After washing in FACS buffer, cells were fixed with Fix/Perm buffer from eBioscience. Following fixation, cells were permeabilized and stained with APC anti-mouse FoxP3. For Ikaros staining, rabbit anti-mouse Ikaros (Abcam, ab26083, 1:2000) was used following fixation and permeabilization with the eBioscience FoxP3 kit. Following staining with the Ikaros antibody, cells were washed and then stained with a PE-labeled anti-rabbit secondary antibody (1:2000). Following completion of stains, cells were processed on a CyanADP (Beckman Coulter) for flow cytometric analysis.

Statistical Analysis. All statistical tests were done with GraphPad Prism. Two-way ANOVA was conducted with post-hoc testing, with * $p<0.05$,  $p<0.01$, * $p<0.001$, and **** $p<0.0001$. Data are presented as mean+/−SEM.

Results

Cytokine Production and Cytolytic Mediator Release in CAR-expressing T Cells with Reduced Levels of Ikaros are Augmented Given that cytolytic T lymphocytes (CTLs) with reduced Ikaros have enhanced effector function in vitro and in vivo (O'Brien, et al., *J Immunol.* 2014; 192:5118-29), experiments were performed to test if depletion of Ikaros could improve the efficacy of CAR T therapy. T cells isolated from wild type C57BL/6 and Ikaros-haplodeficient mice (Ikzf1+/−) in the C57BL/6 background were retrovirally-transduced to express a mesothelin CAR. Following ex vivo activation, transduction, and expansion in IL2, it was confirmed that, in comparison to wild-type (WT) CAR T cells, Ikzf1+/− CAR T cells continued to express less Ikaros protein by flow cytometry and western blot (FIG. 26A).

Figure 26B:
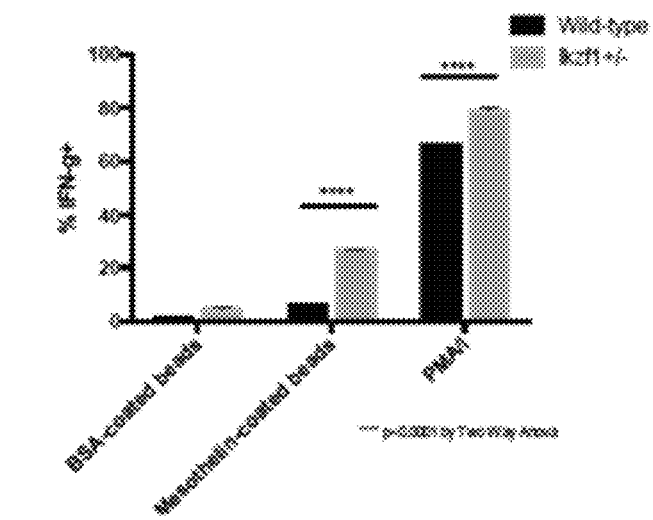
Figure 26C:
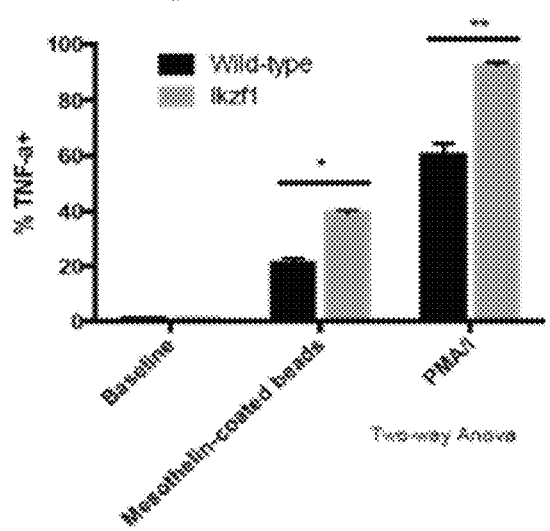
Figure 26D:
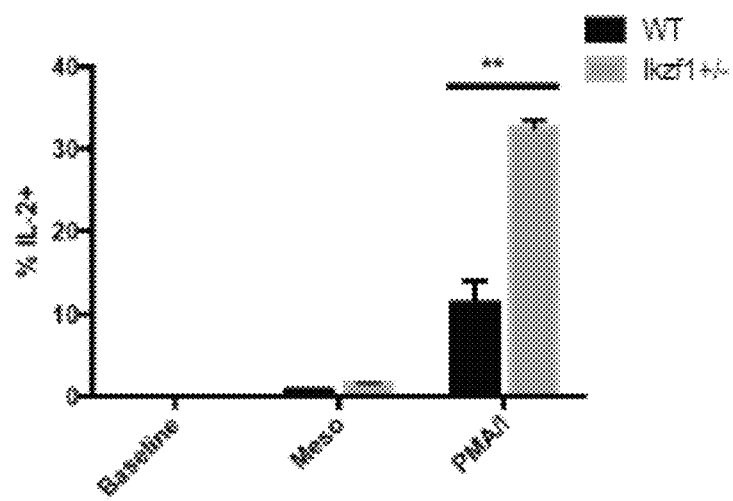

Since Ikaros is a transcriptional repressor for multi-cytokine gene loci (Thomas et al., *J Immunol.* 2007; 179: 7305-15; Bandyopadhyay et al., *Blood.* 2006; 109:2878-2886; Thomas et al., *J of Biological Chemistry.* 2010; 285:2545-53; and O'Brien et al., *J Immunol.* 2014; 192: 5118-29), it was next examined if reduction of Ikaros resulted in autocrine cytokine production by CAR T cells and also whether or not the Ikaros-haplodeficient CAR T cells responded better than their WT counterparts to their target antigen. Both WT and Ikzf1+/− CAR T cells were stimulated with beads coated with either BSA-(control) or mesothelin (the CAR antigen) at a 2:1 bead: T cell ratio for 6 hours, and analyzed their ability to produce IFNγ, TNRβ and IL2 by flow cytometry. At baseline (BSA stimulation), there was an ~3-fold increase in IFN-producing Ikzf1+/− CAR T cells compared to WT CAR T cells (4.35% vs 1.4%, FIG. 26B), but there was no significant difference in the % IL2 producing cells (FIG. 26D). Following stimulation with mesothelin-coated beads, there was a dramatic increase in the % IFN-γ cytokine-producing Ikzf1+/− CAR T cells (25%) while the response was modest in WT CAR T cells (7%). An increase in TNFα production was also seen (FIG. 26C). To investigate if this augmentation in cytokine production was generalized across different stimuli or limited to CAR antigen, both WT and Ikzf1+/− CAR T cells were treated with PMA and ionomycin for 6 hours. In this case, more IFN γ, TNF-β and IL-2 cytokine-producing cells were observed in the Ikzf1+/− CAR T cell compared to their WT counterparts (FIGS. 26B-26D). These data support the hypothesis that Ikaros is one of the limiting factors that suppresses cytokine production of T cells, or CAR T cells.

Figure 26E:
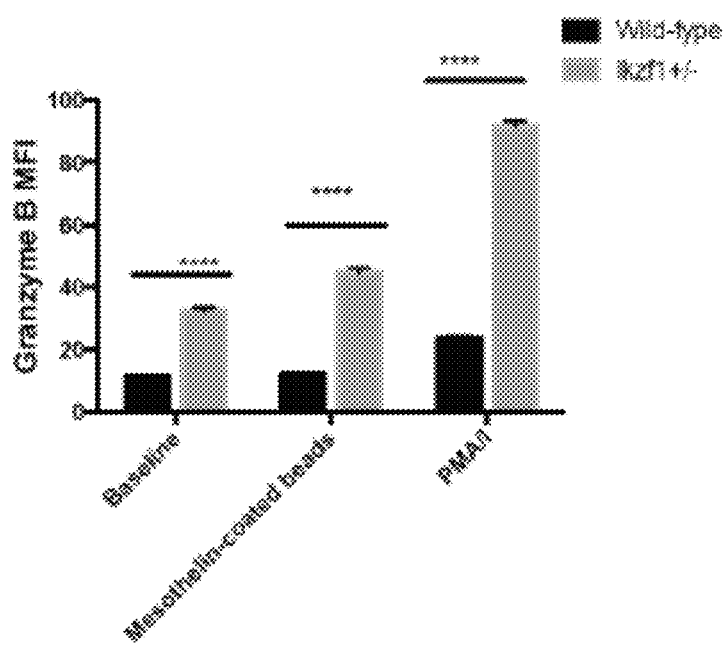
Figure 26F:
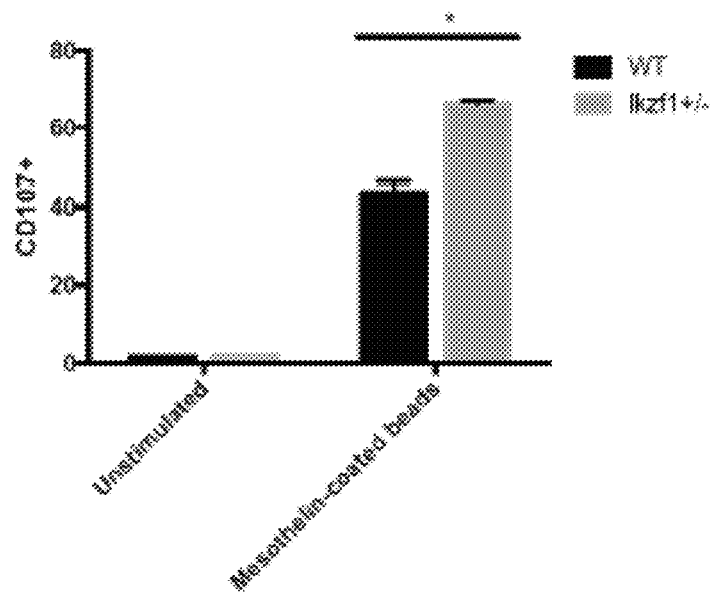

An important cytotoxic mediator, granzyme B, was shown to be up-regulated in CD3/CD28-activated Ikaros-deficient OT-I cells, and this increased their cytolytic activity against OVA-expressing EL4 tumor cells (O'Brien et al., *J Immunol.* 2014; 192:5118-29). It was hypothesized that granzyme B production would also be enhanced in Ikzf+/− T cells bearing CAR. Both WT and Ikzf1+/− CAR T cells were stimulated with either BSA-(baseline) or mesothelin-(CAR antigen) coated beads at 2:1 bead: T cell ratio for 6 hours. PMA/ionomycin was used as the positive control for the assay. Similar to the data above, granzyme B level was higher in Ikzf+/− CAR T cells than in WT CAR T cells at baseline (BSA stimulation; FIG. 26E). After stimulation with either mesothelin-coated beads or PMA/Ionomycin, granzyme B level increased in both WT and Ikzf+/− CAR T cells but the production was much higher in the Ikzf+/−CAR T cells (FIG. 26E). To determine if there was also a difference in degranulation of CAR T cells with reduced Ikaros, CD107a expression after antigen stimulation was assessed. Wild-type transduced T cells had moderate levels of CD107a expression following antigen re-stimulation, however, the T cells with reduced Ikaros demonstrated enhanced CD107a up-regulation (FIG. 26F). Thus, in response to re-stimulation, the CTLs with reduced Ikaros degranulate more and release more cytotoxic mediators in comparison to their wild-type counterparts.

Depleting Ikaros with a Dominant Negative Allele Enhances CAR T Cell Function

In addition to the cells with lower levels of Ikaros, T cells from mice expressing one dominant-negative allele of Ikaros (IkDN) were studied. Transgenic mice expressing IkDN have normal lymphoid development but have peripheral T cells with 90% reduced Ikaros DNA binding activity (Thomas et al., *J Immunol.* 2007; 179:7305-15; and Winandy et al., *Cell.* 1995; 83:289-99). T cells isolated from spleens of WT and IkDN mice were activated with plate-bound anti-CD3/CD28 antibodies, transduced with mesothelin CAR, followed by expansion with IL2. Knockdown of Ikaros in IkDN CAR T cells was confirmed by western. WT and IkDN CAR T cells were re-challenged with either BSA- or mesothelin-coated beads at 2:1 bead:T cell ratio for 6 hours, and analyzed their ability to produce IFN and IL2, as well as to de-granulate in response to CAR antigen. Similar to the Ikzf1+/− data above, some autocrine IFNγ production at baseline was observed (FIG. 27A), but not with IL2 (BSA stimulation; FIG. 27B). Upon ligation of the CAR with its target antigen, mesothelin, IkDN T cells made more IFNγ than WT T cells (Mesothelin stimulation; FIG. 27A). De-granulation, as measured by CD107a up-regulation, was also similar in both wild-type and IkDN CAR T cells (FIG. 27D).

Depletion of Ikaros Did not Augment Activation and Signaling of CAR T Cells Following Antigen Stimulation Given that depletion in Ikaros augmented cytokine release and increased the Granzyme B levels and CD107a expression of CAR T cells, possible mechanisms were explored. It is plausible that these changes in effector function could be due to differences in the activation of the wild-type and Ikzf1+/− transduced T cells. Thus, the levels of CD69, CD25 and 4-1BB (markers of T cell activation) were measured by flow cytometry after stimulating with mesothelin-coated beads for 6 and 24 hours. CD69, an early activation marker, was up-regulated to the same extent by both the wild-type and Ikzf1+/− cells (FIG. 28A). With longer stimulation, the wild-type and Ikzf1+/− CAR-expressing T cells continued to express similar levels of CD69, but Ikzf1+/− transduced T cells exhibited increased CD25 expression (FIG. 28B). This may not directly indicate a difference in T cell activation, however, as increased IL-2 by Ikzf1+/− cells (FIG. 28D) can act in a positive feed-forward loop on CD25, the IL-2Ra (Depper et al., *Proc Natl Acad of Sci USA*. 1985; 82:4230-4; and Nakajima et al., *Immunity*. 1997; 7:691-701). 4-1BB, a member of the TNF Receptor superfamily is also expressed on activated T cells (Vinay et al., *Seminars in Immunology*. 1998; 10:481-9) and was expressed at similar levels by CAR transduced wild-type and Ikzf1+/− T cells following antigen stimulation (FIG. 28C). Thus, functional differences between our WT and Ikzf1+/− transduced T cells were not due to differences in T cell activation.

The experiments described in Example 9 and Riese et al., *Cancer Research*. 2013; 73:3566-77, demonstrate that depletion of the enzyme diacylglycerol kinase (DGK) in CAR T cells resulted in an increase in RAS/ERK signaling, which correlated well with enhanced activation of CAR T cells. Some signaling pathways in WT and Ikaros-deficient T cells after TCR stimulation with CD3/CD28 antibodies were examined. Lysates from stimulated T cells were prepared and immunoblotted for various phospho-proteins implicated in proximal (PLC and Lck) and distal (ERK1/2, JNK, AKT and IKKa) signaling from the TCR. There was a constitutive low-level baseline activation of some TCR signaling proteins in Ikaros-deficient T cells, including Lck, ERK and AKT (FIG. 28D). With TCR/CD28 stimulation, all proteins studied were phosphorylated to the same level when comparing WT and Ikaros-deficient T cells, with the exception of phospho-IKK, which was slightly higher in Ikaros-deficient T cells 20 minutes after stimulation. To determine if the NFB pathway was enhanced in T cells with reduced Ikaros level, the same blot was re-probed for IB, the downstream target for IKK. There was no difference in IB degradation between both WT and Ikaros-depleted T cells. To study CAR signaling, both WT and IkDN mesothelin CAR transduced T cells were re-stimulated with mesothelin-coated beads. Similar to the data with CD3/CD28 stimulation, no difference was found in phosphorylation of PLC and ERK (FIG. 28E). Together, these data indicate that depletion in Ikaros does not alter TCR/CAR-mediated signaling.

Reduction of Ikaros in CAR T Cells Augments their Response Against their Target Cells.

Figure 29B:
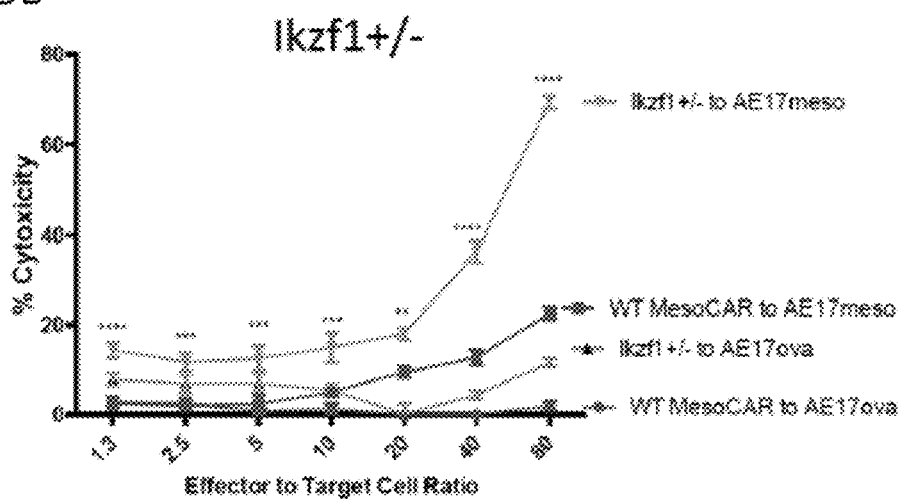
Figure 29C:
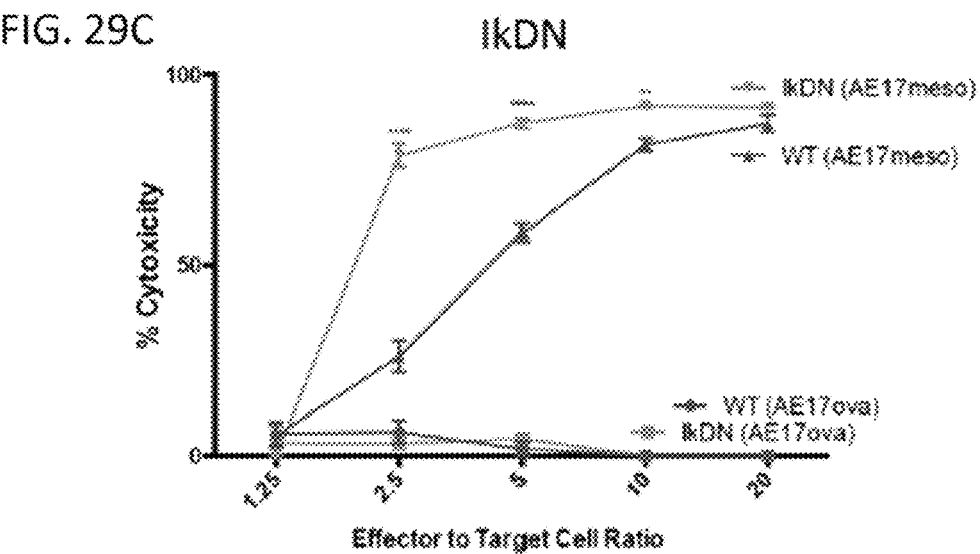
Figure 29D:
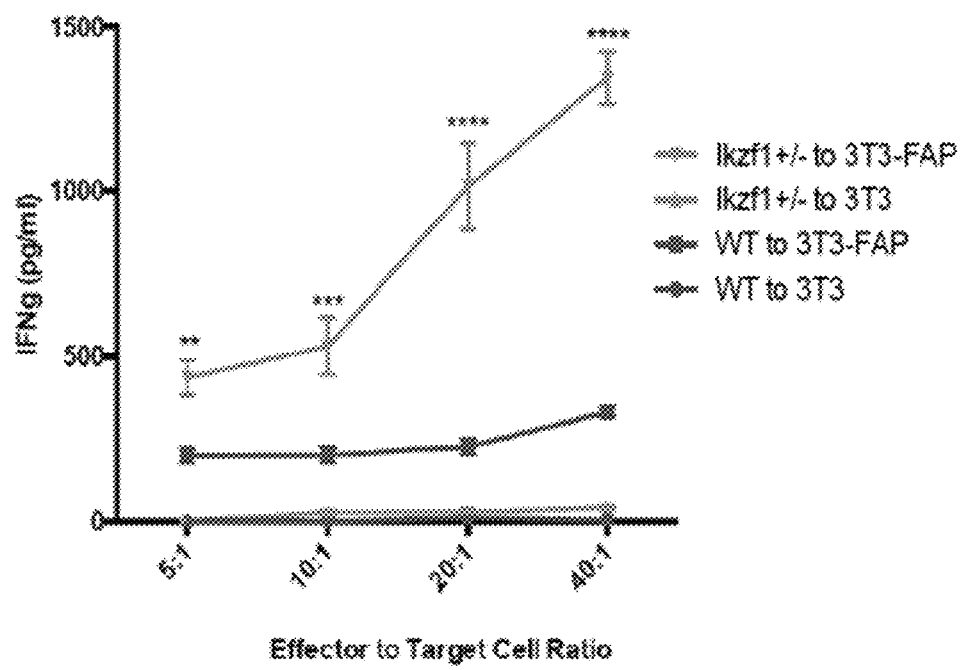
Figure 29E:
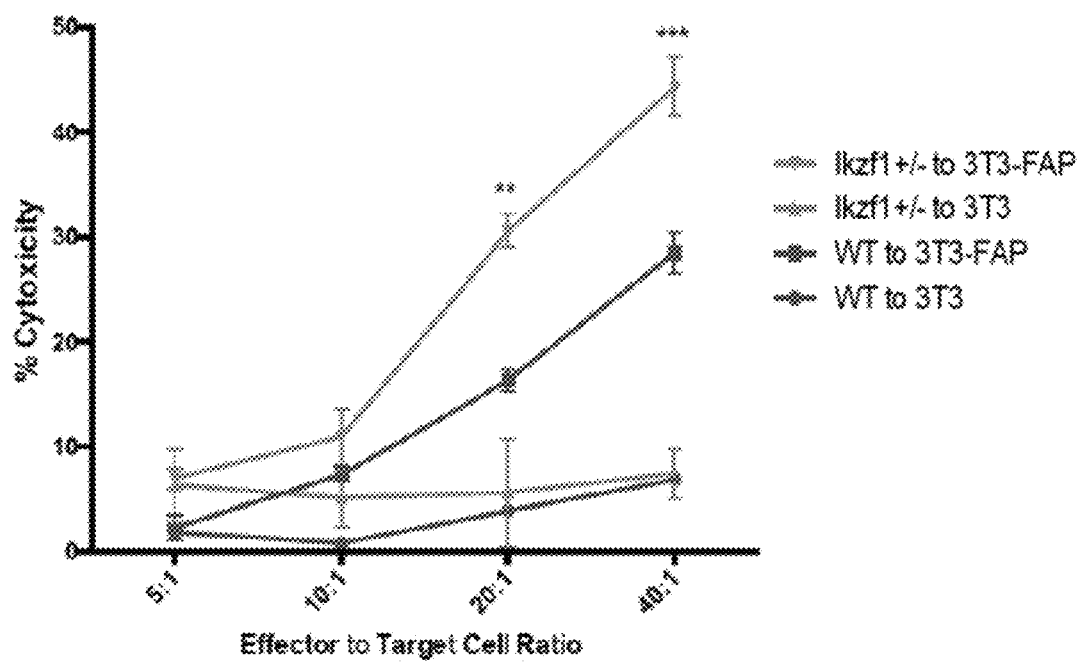

Given the increased production of effector factors by CAR T cells with reduced Ikaros, their efficacy against their target tumor cells in vitro was tested. Wild-type, Ikzf1+/− and IkDN T cells expressing mesoCAR were mixed at different ratios with the parental tumor cell line, AE17 or the mesothelin-expressing cell line, AE17meso. When mixed with the parental cell line, both the wild-type, Ikzf1+/− and IkDN T cells failed to produce IFN-γ or lyse cells in response to AE17 (FIGS. 29A, 29B and 29C). In contrast, when reacted with AE17meso, IFN-γ production and cytolysis by wild-type T cells increased as the E:T ratio increased (FIGS. 29B and 29C). However, both the Ikzf1+/− and IkDN T cells produced significantly more IFN-γ and had significantly increased tumor lysis than wild-type T cells, even at the lowest E:T ratio 1.3:1 (FIGS. 29B, and 29C).

To study the generalizability of this effect, T cells expressing a different CAR construct, which targets fibroblast activation protein (FAP-CAR) and has the same intracellular signaling domain as the mesothelin CAR used above, were examined. The efficacy of comparably transduced FAP-CAR splenic T cells isolated from WT C57BL/6 was compared to those from Ikzf1+/− mice. Ikzf1+/−FAP-CAR T cells were more efficient in lysing 3T3.FAP cells (FIG. 29D) and in secreting more IFN (FIG. 29E) than WT FAP CAR T cells, with retention of specificity in vitro.

Depletion of Ikaros Enhances the Efficacy of CAR T Cells Against Established Tumors The capability of mesothelin-specific T cells with reduced Ikaros (Ikzf1+/− and IkDN) to control growth of established AE17meso tumors in mice was next examined. Two million of AE17meso tumor cells were injected into the flanks of syngenic C57BL/6 mice and allowed to form large established tumors (~100-150 mm$^3$). Ten million CAR T cells prepared from WT or Ikaros-deficient (Ikzf1+/− and IkDN) mice were then adoptively transferred into those tumor-bearing mice, and tumor measurements were followed. Mild tumor growth inhibition was induced by wild-type transduced mesoCAR T cells, while both Ikzf1+/− and IkDN transduced mesoCAR T cells inhibited growth of AE17meso tumors significantly more (FIGS. 30A and 30B).

It was also studied if reduction of Ikaros could enhance the therapeutic potential of FAP-CAR T cells. Mice with established AE17meso tumors (100-150 mm$^3$) were adoptively transferred with 10 millions wild-type or Ikzf1+/− transduced anti-mouse FAP CAR T cells. Mice receiving wild-type transduced cells provided minimal tumor delay and the AE17meso tumors continued to grow (FIG. 30C). In contrast, the Ikzf1+/− transduced T cells were able to significantly delay tumor growth.

Ikzf1+/− CAR T Cells Persist Longer and More Resistant to Immunosuppressive Tumor Microenvironment than WT CAR T Cells Given the enhanced efficacy of the Ikaros-inhibited CAR T cells, the possible mechanisms using the Ikzf1+/− mesoCAR T cells were explored. To further interrogate how these mesoCAR T cells operate in an immunosuppressive tumor microenvironment in vivo, tumors at 3 and 9 days post-adoptive transfer were harvested and assessed their number and functionality. These two time points allowed characterization of their activity at early and late time points during the anti-tumor immune response.

At Day 3 post-transfer, we observed a similar frequency of wild-type and Ikzf1+/− mesoCAR T cells in both the spleens (FIG. 31A) and tumors (FIG. 31B). These similar levels indicate that both the wild-type and Ikzf1+/− mesoCAR T cells initially traffic equally well to the tumor. In assessing the Day 9 timepoint, the number of both wild-type mesoCAR T cells Ikzf1+/− mesoCAR T cells declined in the spleen. However, when the tumors were examined at this time point, there was a significant increase in the number of Ikzf1+/− mesoCAR T cells compared with WT mesoCAR T cells (FIG. 31B). These data show that the Ikzf1+/− mesoCAR T cells either persist or proliferate better than WT mesoCAR T cells in the immunosuppressive microenvironment.

Tumor infiltrating lymphocytes (TILs) become hypofunctional in response to their cognate antigens within the immunosuppressive tumor microenvironment, and is a key phenomenon associated with tumor progression (Prinz et al., *J Immunol*. 2012; 188:5990-6000; and Kerkar et al., *Cancer Res*. 2012; 72:3125-30). Although there were more Ikzf1+/− mesoCAR T cells in the tumors at Day 9, they could still be adversely affected by the tumor microenvironment. To evaluate functionality, CD3/CD28 antibodies were used to stimulate TILs isolated from wild-type and Ikzf1+/− mesoCAR T cells at Day 9 post-transfer and characterized differences in lytic mediator production. At Day 9 post-transfer, the wild-type mesoCAR T cells in the spleen continued to produce some moderate levels of IFN (FIG. 31C). As expected, isolated wild-type T cells from the tumors produced much less of this cytokine in comparison to wild-type T cells isolated from the spleen. This indicates that the wild-type TILs begin to become hypofunctional at Day 9 post transfer. In contrast, splenic Ikzf1+/− mesoCAR T cells continued to produce more IFN- at baseline and upon stimulation (FIG. 31C). Compared to the wild-type TILs, the Ikzf1+/−TILs produced higher amounts of IFNγ. These data indicate that Ikzf1+/−TILs could be less sensitive to the immunosuppressive tumor microenvironment.

Bypassing the proximal defect of TCR signaling often seen in TILs (Prinz, P U et al., *J. Immunol.* 2012; 188:5990-6000) can be achieved through use of PMA/Ionomycin (PMA/I) (Prinz et al., *J Immunol.* 2012; 188:5990-6000). Wild-type and Ikzf1+/− mesoCAR T cells were re-stimulated with PMA/I to determine if TCR-stimulation insensitive wild-type and Ikzf1+/−TILs were still capable making cytokines in response to other stimuli. At Day 9 post-transfer, the wild-type TILs demonstrated a noticeable drop in IFN-γ production (FIG. 31C), and this was partially restored through stimulation with PMA/I (FIG. 31D). However, stimulation of splenic and tumor isolated Ikzf1+/− mesoCAR T cells still resulted in increased levels of IFN-γ in comparison to wild-type transferred cells. Through bypassing any defects in TCR signaling via PMA/I stimulation, these results demonstrate that IFNγ production differs at the chromatin level and is likely due to differential Ikaros function.

Figure 31E:
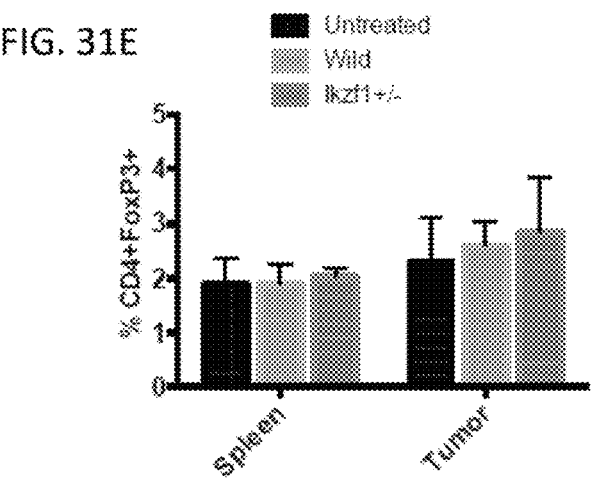
Figure 31F:
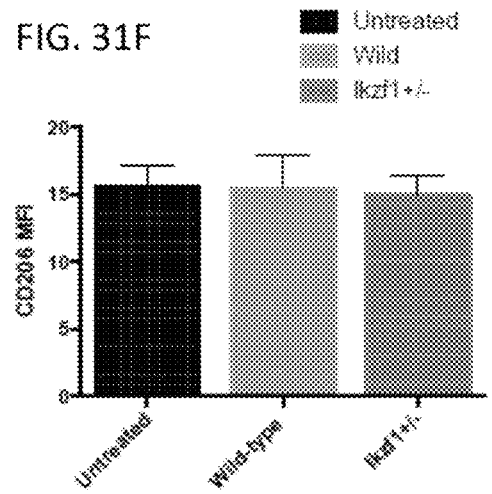

In light of the increased anti-tumor activity by the transferred Ikzf1+/− T cells, the impacts on the composition of the immunosuppressive tumor microenvironment was also examined and the number of regulatory T cells (Tregs) and Myeloid Derived Suppressor Cells (MDSCs) was evaluated at Day 9. At Day 9 post-transfer, similar levels of Tregs in hosts that received wild-type or Ikzf1+/− mesoCAR T cells was observed (FIG. 31E). The presence of Ly6G−/CD11b+/CD206+ macrophages was determined, which are typically characterized as immunosuppressive and pro-tumorigenic M2 macrophages. In the Day 9 treated groups, that CD206 expression was similar in all 3 groups (untreated, wild-type, and Ikzf1+/−) (FIG. 31F).

T Cells with Reduced Ikaros are Less Sensitive to Soluble Inhibitory Factors TGF and Adenosine To further characterize the interaction of the immunosuppressive tumor microenvironment with the mesoCAR T cells, an in vitro culture system was utilized. Soluble inhibitory factors such as IDO, IL-10, Adenosine, and TGF-β (Wang et al., *Oncoimmunology.* 2013; 2: e26492) have been shown to contribute to inhibiting infiltrating tumor lymphocytes. The effects of select inhibitory factors in vitro on the Ikaros-deficient CAR T cells was tested to determine if the immunosuppressive environment could impact their lytic function. Wild-type CAR T cells had a 50% reduction in their ability to make IFN-γ and had a reduction in their lytic function in the presence of TGF-β and Adenosine (FIG. 32). CAR T cells with reduced levels of Ikaros (Ikzf1+/− and IkDN) continued to produce more IFN γ than their wild-type counterparts in the absence of inhibitors and were only marginally inhibited in the presence of TGF β and Adenosine (FIG. 32A). Increased lytic function in Ikzf1+/− and IkDN CAR T cells in comparison to wild-type T cells was observed (FIG. 32B). These data demonstrate that the T cells with reduced Ikaros are less sensitive to TGFβ and adenosine inhibition.

Discussion

In this example, a new approach for enabling CAR-expressing T cells to survive and enhance their effector functions in the tumor environment has been identified: inactivation of the transcriptional repressor Ikaros, which is known to inhibit a diverse array of genes involved in T cell function, e.g., cytokine genes (IL2 and IFNγ), cytolytic mediators (granzyme B), and the key T-box transcription factors that influence T cell differentiation (R-Bet and Eomes).

Figure 30:
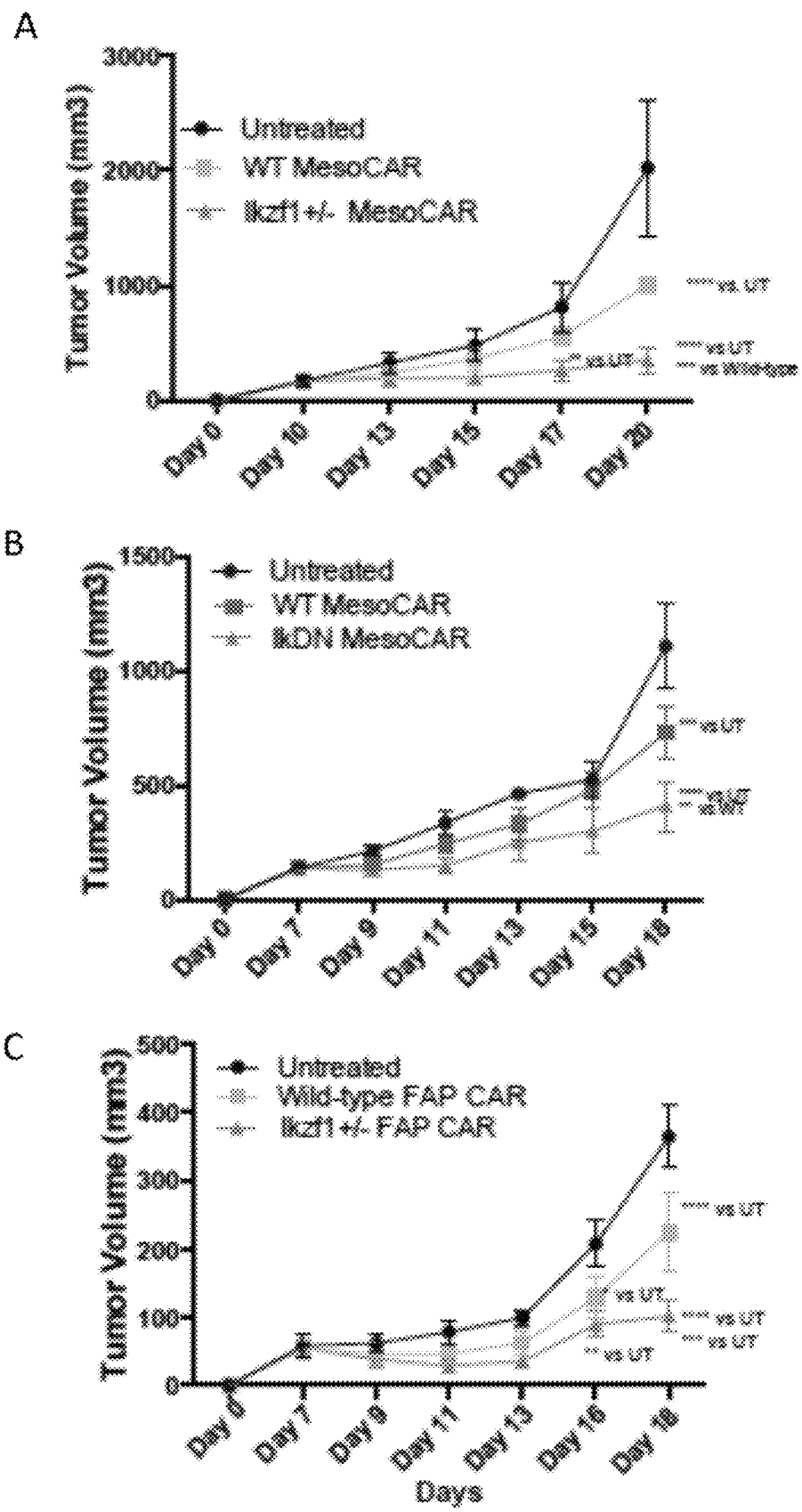

An important finding from the experiments described above is that CAR T cells that were deficient in Ikaros function were significantly better than wild type CAR T cells in restricting tumor growth (FIG. 30). These results were observed in multiple tumor models and using two different CAR constructs. Due to the high number of genes that Ikaros regulates, it is plausible that Ikaros may regulate many pathways that are normally sensitive to immunosuppression. Increased IFN-g production by lowering Ikaros level in CAR T cells can result in up-regulation of Class I MHC expression on the tumor, and thereby improving its immunogenicity, improving anti-angiogenic activity, and driving STAT1 mediated function of Th1 cells. A possible effect of increased IFNγ could have been an alternation of the macrophage phenotype within the tumors, however, no differences in the total number of macrophages, nor the proportion of M2-like macrophages (as measured by CD206 expression) was observed. The increased IL-2 production could have also increased the formation of CD4 Treg cells, however, no differences were observed when comparing the tumors treated with WT CAR T cells with Ikaros-deficient CAR T cells.

An increased number of tumor infiltrating lymphocytes nine days after injection was observed. This was not likely due to increased trafficking, since the number of WT versus Ikaros-deficient TIL was similar at Day 3. Instead, these results suggest that Ikaros-deficient TIL showed increased proliferation or decreased antigen-induced cell death (AICD). In vitro studies suggest that AICD was similar between the two types of T cells, making it more likely that the difference was due to increased proliferation. This would be consistent with the increased IL-2 produced by these cells. In addition to increased persistence, the Ikaros-deficient TIL appeared to be less hypofunctional. When tumor-infiltrating CAR T cells were re-stimulated with anti-CD3 antibody or PMA and ionomycin, CAR T1Ls with Ikaros deficiency were able to make more IFNγ than their wild-type counterparts (FIGS. 31C and 31D).

The in vitro studies allowed further studies of the mechanistic underpinnings of the observed increased anti-tumor efficacy in vivo. Consistent with the known inhibitor functions of Ikaros, deletion of one Ikaros allele (Ikzf+/−) or replacing one of its alleles with an Ikaros dominant negative construct (IkDN) resulted in T cells that had some increased baseline autocrine IFNγ and Granzyme B production (FIG. 26), but more importantly, showed markedly augmented cytokine secretion and granule release after TCR or CAR stimulation in vitro. This was accompanied by increased tumor cell killing in vitro. To test whether or not Ikaros-deficient CAR T cells have lower activation threshold than WT CAR T cells, Dynabeads were coated with 10-fold less mesothelin protein and it was shown that Ikzf+/− CAR T cells could still respond to the mesothelin antigen at low-density to make IFNγ and TNF-α but the WT CAR T cells could not. The Ikaros-disabled CAR T cells were also more resistant to inhibition by known immunosuppressive factors such as TGF-β and adenosine (FIG. 32). This may be due to the fact that cytokine (i.e. IL2 and IFNγ and T cell effector (i.e. granzyme B) genes are more accessible for transcription in Ikaros-deficient T cells following TCR/CAR activation.

This appears to help compensate for suboptimal T cell activation within immunosuppressive tumor microenvironment.

In previous studies, e.g., Example 9, a similar phenotype (i.e. increase in cytolysis and IFN production) has been observed in CAR T cells through depletion of DGKs, enzymes that metabolize the second messenger diacylglycerol and limit RAS/ERK activation. With DGK deletion, however, clear changes were observed in the CAR/TCR signaling pathway. Specifically, RAS/ERK activation was dramatically enhanced after both TCR and CAR activation. This resulted in enhanced activation, as measured by increased CD69 upregulation, however production of effector molecules such as TRAIL, FasL and IFNγ. Perforin and Granzyme B were similar between WT and DGK-deficient CAR T cells. A very different phenotype in this study with Ikaros-deficient CAR T cells. In contrast to the DGK-deficient CAR T cells, the Ikaros-deficient CAR T cells had similar CAR/TCR activation as shown by CD69 and CD25 upregulation (FIG. 28), and similar CAR/TCR signaling as measured by phosphorylation of multiple TCR signaling molecules (FIG. 34) and calcium signaling. Unlike DGK-deficient T cells, Ikaros-depleted CAR T cells had higher granzyme B and IFN levels at baseline (FIGS. 26 and 27), as well as constitutive low level activation of some TCR signaling cascades such as ERK and Akt (FIG. 28). This baseline activation may be due to induction of T-bet (Thomas et al., *J of Biol Chemistry.* 2010; 285:2545-53), which cooperates with other transcription factor like Eomes to transactivate IFN and granzyme B gene expression (Pearce et al., *Science.* 2003; 302:1041-3; and Intelkofer et al., *Nat Immunol.* 2005; 6:1236-44).

These findings raise the possibility that therapeutically targeting Ikaros in transduced human T cells (in clinical trials) might be beneficial using either genetic or biochemical approaches. Genetic approaches could mimic these results in mice and include knockdown of Ikaros in CAR T cells using shRNA or use of a dominant negative construct to compete with endogenous Ikaros. Another option would be to use a pharmacological inhibitor to lower Ikaros levels transiently. Recent reports have indicated that the immunomodulatory drug, Lenalidomide, targets Ikaros for ubiquitin-mediated degradation by the E3 ligase complex CRL4CRBN (Gandhi et al., *Br J HaematoL* 2013; 164:811-21; Kronke et al, *Science.* 2014; 343:301-5; and Sakamaki et al., *Leukemia.* 2013; 28:329-37). CD3-stimulated human T cells treated with Lenalidomide produce more IL-2 (Gandhi et al., *Br J Haematol.* 2013; 164:811-21), a key trait of T cells with reduced Ikaros levels. In preliminary studies, TCR/CD28 stimulated mesothelin-CAR transduced human PBMCs in vitro produce more IL-2 and IFNγ after pretreatment with lenalidomide. Thus, the combination of CAR T cell therapy with in vivo administration of Lenalidomide may provide a therapeutic strategy for reversal of T cell hypofunction through inhibition of Ikaros.

In conclusion, this example demonstrates for the first time that targeting a transcriptional repressor can enhance CAR-mediated anti-tumor immunity. The mechanisms involved enhanced cytokine and effector function without alterations in signal transduction. Translating this approach into the clinic can be pursued through the use of shRNA, a dominant negative construct, or a pharmacological inhibitor (like Lenalidomide) to target Ikaros in CAR-expressing T cells.

Example 11

Meso-CART in Human Ovarian Cancer

In this example, the safety of intravenous infusion of autologous T cells transduced to express a mesothelin CAR was determined in a human patient with advanced recurrent serou ovarian cancer.

A single patient treatment protocol was modeled after a planned Phase I study (as described in Example 3) to assess the safety and feasibility of infusing autologous T cells expressing mesothelin CAR (mesoCART). T cells from the patient were transduced to express a CAR comprising an extracellular anti-mesothelin single chain variable fragment (scFv) fused to 4-1BB and TCRzeta signaling domains. $3 \times 10^7$ mesoCAR T cells/m$^2$, for a total of $4.65 \times 10^7$ meso CAR T cells, were infused into the patient. No lymphodepletion with chemotherapy was given prior to infusion.

The mesoCART infusion had no acute toxic effects. The patient experienced grade 3 bilateral pleural effusions, dyspnea, fever, hypotension, and aspiration. There were no clinical toxicities due to off tumor/on target effects of the meso CART cells, such as pericarditis or peritonitis. The patient was treated with tocilizumab (anti-IL6) on Day 21 after infusion for suspected cytokine release syndrome (CRS), based on unexplained fevers, hypotension requiring pressors, elevated serum levels of ferritin (>7000 ng/mL) and CRP (>160 mg/L).

The mesoCAR T cells were detectable in peripheral blood samples, as well as tumor samples from liver and peritoneum, with highest numbers in pericardial and pleural fluid. Cytokine evaluation showed a marked increase in IL-6 within the pleural fluid (>80-fold increase over baseline), peaking at Day 22-23. Evaluation of the blood also revealed elevation of IL-6 levels in the blood (15-fold increase over baseline at Day 22). No elevation in TNFα or IFNγ levels was detected.

Preliminary results showed that CT imaging of abdomen and pelvis performed Day 21 showed peritoneal carcinomatosis minimally improved compared to a CT imaging two weeks prior. Specifically, one tumor decreased from 3.4×3.1 cm to 3.0×2.6 cm. Cytology from the left sided pleural fluid showed malignancy on Day 8 after infusion, but at Day 21 and Day 26, there was no evidence of malignancy.

These results showed that infusion of meso CART cells without lymphodepletion was found to be feasible and safe. There was no evidence of toxicity with infusion, or life-threatening pericarditis or peritonitis. Also, there was clinical evidence of treatment efficacy as evidenced by the disappearance of malignant pleural effusions.

Example 12

Transient Expression of CARS with Varying Intracellular Signaling Domains

In this example, the use of distinct costimulatory domains in the CAR architecture and its effects on cell longevity, memory differentiation, and cell metabolism characteristics are examined.

A novel system of in vitro T cell stimulation was developed to study the consequences of a single round of CAR-specific stimulation and analyze signaling through various CAR signaling endodomains. In vitro transcribed mRNA encoding anti-mesothelin SS1-CAR constructs with varying intracellular signaling domains of CD3zeta, CD28:z, and 4-1BB:z were electroporated into primary resting human T cells. Greater than 90% CAR-positive T cell populations were achieved by this method. Upon verifying CAR expression, the T cells were stimulated with recombinant mesothelin immobilized on beads and then cultured. Since the RNA is transiently expressed, the CAR disappears from the cell surface after one round of stimulation, allowing the unambiguous analysis of signaling through the CAR alone (i.e., without subsequent signaling from additional mesothelin binding events). This approach thus obviated the requirement for stimulation through the endogenous T cell receptor and permitted for the first time an analysis of the consequences of signaling through the surrogate antigen of CAR T cells. These experiments were conducted on primary peripheral blood T cells, sorted naïve T cells and cord blood cells.

The various CAR constructs (SS-1 with CD3zeta, SS1 with CD28:z, and SS1 with 4-1BB:z) were expressed at equivalent levels on the surface of T cells. All signaling domains were demonstrated to have comparable and specific cytolytic capabilities when cultured with target cells that expressed mesothelin.

Primary T cells stimulated through the 4-1BBz-containing CARs showed superior survival and expansion profiles when compared to CD28-based CARs. Both 4-1BB and CD28-based CARs exhibited more than 5 population doublings. However, the 4-1BB-based CAR T cels1 proliferated for longer in vitro. Phenotypic analysis of the 4-1BB-based CAR T cells revealed that an increased population of cells with central-memory surface markers was generated. In contrast, the CD28-based CARs rapidly differentiated to an effector memory pool of CAR T cells.

CD28z-containing CARS yielded a significantly higher proportion of effector memory cells, with a modest increase in expression of inhibitory PD-1, TIM3 and LAG3 molecules relative to their 4-1BBz counterparts. These results remained consistent whether starting populations of bulk peripheral blood T cells, naïve (CD45RO-CD95-CD62L+CCR7+ sorted) peripheral blood T cells, or cord blood T cells were used.

Metabolic profiling of the mesothelin-stimulated CAR T cells using the Sea-Horse assay (Seahorse Biosciences) in culture revealed a substantial increase in lipid oxidation in 4-1BBz-CAR stimulated cells compared to their CD28z counterparts. Additionally, microarray studies have revealed a unique gene signature in cells that are recovered after stimulation through the different CAR signaling domains.

Together, these results show that CAR T cells exhibit differential survival and function depending on the costimulatory domains. This system also allows for rapid characterization and functional analysis of new CAR designs.

Example 13

Effects of mTOR Inhibition on Immunosenescence in the Elderly

One of the pathways most clearly linked to aging is the mTOR pathway. The mTOR inhibitor rapamycin has been shown to extend lifespan in mice and improve a variety of aging-related conditions in old mice (Harrison, D E et al. (2009) Nature 460:392-395; Wilkinson J E et al. (2012) Aging Cell 11:675-682; and Flynn, J M et al. (2013) Aging Cell 12:851-862). Thus, these findings indicate that mTOR inhibitors may have beneficial effects on aging and aging-related conditions in humans.

An age-related phenotype that can be studied in a short clinical trial timeframe is immunosenescence. Immunosenescence is the decline in immune function that occurs in the elderly, leading to an increased susceptibility to infection and a decreased response to vaccination, including influenza vaccination. The decline in immune function with age is due to an accumulation of immune defects, including a decrease in the ability of hematopoietic stem cells (HSCs) to generate naïve lymphocytes, and an increase in the numbers of exhausted PD-1 positive lymphocytes that have defective responses to antigenic stimulation (Boraschi, D et al. (2013) Sci. Transl. Med. 5:185ps8; Lages, C S et al. (2010) Aging Cell 9:785-798; and Shimatani, K et al., (2009) Proc. Natl. Acad. Sci. USA 106:15807-15812). Studies in elderly mice showed that 6 weeks of treatment with the mTOR inhibitor rapamycin rejuvenated HSC function leading to increased production of naïve lymphocytes, improved response to influenza vaccination, and extended lifespan (Chen, C et al. (2009) Sci. Signal. 2:ra75).

To assess the effects of mTOR inhibition on human aging-related phenotypes and whether the mTOR inhibitor RAD001 ameliorates immunosenescence, the response to influenza vaccine in elderly volunteers receiving RAD001 or placebo was evaluated. The findings presented herein suggest that RAD001 enhanced the response to influenza vaccine in elderly volunteers at doses that were well tolerated. RAD001 also reduced the percentage of programmed death (PD)-1 positive CD4 and CD8 T lymphocytes that accumulate with age. These results show that mTOR inhibition has beneficial effects on immunosenescence in elderly volunteers.

As described herein, a 6 week treatment with the mTOR inhibitor RAD001, an analog of rapamycin, improved the response to influenza vaccination in elderly human volunteers.

Methods

Study Population

Elderly volunteers >=65 years of age without unstable underlying medical diseases were enrolled at 9 sites in New Zealand and Australia. Exclusion criteria at screening included hemoglobin <9.0 g/dL, white blood cell count <3,500/mm$^3$, neutrophil count <2,000/mm$^3$, or platelet count <125,000/mm$^3$, uncontrolled diabetes, unstable ischemic heart disease, clinically significant underlying pulmonary disease, history of an immunodeficiency or receiving immunosuppressive therapy, history of coagulopathy or medical condition requiring long-term anticoagulation, estimated glomerular filtration rate <30 ml/min, presence of severe uncontrolled hypercholesterolemia (>350 mg/dL, 9.1 mmol/L) or hypertriglyceridemia (>500 mg/dL, 5.6 mmol/L).

Baseline demographics between the treatment arms were similar (Table 8). Of the 218 subjects enrolled, 211 completed the study. Seven subjects withdrew from the study. Five subjects withdrew due to adverse events (AEs), one subject withdrew consent, and one subject left the study as a result of a protocol violation.

TABLE 8

Demographic and Baseline characteristics of the Study Patients

| Population | | RAD001 0.5 mg daily N = 53 | RAD001 5 mg weekly N = 53 | RAD001 20 mg weekly N = 53 | Placebo pooled N = 59 | Total N = 218 |
|---|---|---|---|---|---|---|
| Age (Years) | Mean (SD) | 70.8 (5.0) | 72.0 (5.3) | 71.4 (5.2) | 71.1 (5.1) | 71.3 (5.2) |
| Gender | Male- n (%) | 34 (64%) | 27 (51%) | 32 (60%) | 31 (53%) | 124 (57%) |
| BMI* (kg/m2) | Mean (SD) | 27.4 (4.2) | 28.8 (5.0) | 28.0 (4.1) | 28.0 (4.2) | 28.0 (4.4) |
| Race - n (%) | Caucasian | 48 (91%) | 50 (94%) | 46 (87%) | 54 (92%) | 198 (91%) |
| | Other | 5 (9%) | 3 (6%) | 7 (13%) | 5 (8%) | 20 (9%) |

*The body-mass index is weight in kilograms divided by the square of the height in meters Study Design and Conduct From December 2011 to April 2012, 218 elderly volunteers were enrolled in a randomized, observer-blind, placebo-controlled trial. The subjects were randomized to treatment arms using a validated automated randomization system with a ratio of RAD001 to placebo of 5:2 in each treatment arm. The treatment arms were:

RAD001 0.5 mg daily or placebo
RAD001 5 mg weekly or placebo
RAD001 20 mg weekly or placebo The trial was observer-blind because the placebo in the RAD001 0.5 mg daily and 20 mg weekly cohorts differed slightly from the RAD001 tablets in those cohorts. The study personnel evaluating the subjects did not see the study medication and therefore were fully blinded. The treatment duration for all cohorts was 6 weeks during which time subjects underwent safety evaluations in the clinic every 2 weeks. After subjects had been dosed for 4 weeks, RAD001 steady state levels were measured pre-dose and at one hour post dose. After completing the 6 week course of study drug, subjects were given a 2 week drug free break to reverse any possible RAD001-induced immunosuppression, and then were given a 2012 seasonal influenza vaccination (Agrippal®, Novartis Vaccines and Diagnostics, Siena, Italy) containing the strains H1N1 A/California/07/2009, H3N2 A/Victoria/210/2009, B/Brisbane/60/2008. Four weeks after influenza vaccination, subjects had serum collected for influenza titer measurements. Antibody titers to the 3 influenza vaccine strains as well as to 2 heterologous strains (A/H1N1 strain A/New Jersy/8/76 and A/H3N2 strain A/Victoria/361/11) were measured by standard hemagglutination inhibition assay (Kendal, A P et al. (1982) *Concepts and procedures for laboratory-based influenza surveillance*. Atlanta: Centers for Disease Control and Prevention B17-B35). Levels of IgG and IgM specific for the A/H1N1/California/07/2009 were measured in serum samples taken before and 4 weeks after influenza vaccination as described previously (Spensieri, F. et al. (2013) *Proc. Natl. Acad. Sci. USA* 110:14330-14335). Results were expressed as fluorescence intensity.

All subjects provided written informed consent. The study was conducted in accordance with the principals of Good Clinical Practice and was approved by the appropriate ethics committees and regulatory agencies.

Safety

Adverse event assessment and blood collection for hematologic and biochemical safety assessments were performed during study visits. Adverse event information was also collected in diaries that subjects filled out at home during the 6 weeks they were on study drug. Data on all adverse events were collected from the time of informed consent until 30 days after the last study visit. Events were classified by the investigators as mild, moderate or severe.

Statistical Analysis

The primary analysis of geometric mean titer ratios was done using a normal Bayesian regression model with non-informative priors. This model was fitted to each antibody titer on the log scale. The primary outcome in each model was the Day 84 measurement. The Day 63 measurement was included in the outcome vector. The model fitted using SAS 9.2 proc mixed with the prior statement. The covariance structure of the matrix was considered as unstructured (option type=UN). A flat prior was used. For the secondary analysis of seroconversion rates, logistic regression was used.

The intention to treat population was defined as all subjects who received at least one full dose of study drug and who had no major protocol deviations impacting efficacy data. 199 out of the total of 218 subjects enrolled in the study were in the intention to treat population.

Immunophenotyping

Peripheral blood mononuclear cells were isolated from whole blood collected at 3 time points: baseline; after 6 weeks of study drug treatment; and at the end of study when subjects had been off study drug for 6 weeks and 4 weeks after influenza vaccination. Seventy-six PBMC subsets were analyzed by flow cytometry using 8-color immunophenotyping panels at the Human Immune Monitoring Center at Stanford University, CA, USA as described previously (Maecker, H T et al. (2012) *Nat Rev Immunol.* 12:191-200). Seventy-six PBMC subsets were analyzed by flow cytometry using 8-color lyophilized immunophenotyping panels (BD Lyoplate, BD Biosciences, San Diego, Calif.). PBMC samples with viability >80% and yield of $2 \times 10^6$ cells or greater were included in the analysis.

Relative changes of the immunophenotypes from baseline to Week 6 of study drug treatment and from baseline to the end of study (Week 12) were calculated for each of the RAD001 dosing cohorts. Student T test was conducted to examine if the relative change of the immunophenotypes from baseline to the two blood sampling time points was significantly different from zero, respectively, within each dosing group after adjusting for placebo effect. Missing data imputation in treatment effect analysis was not conducted. Therefore if a patient has a missing phenotype data at baseline, this patient was not be included in the analysis for this phenotype. If a patient had a missing phenotype data at 6 or 12 weeks, then this patient did not contribute to the analysis of this phenotype for the affected timepoint.

608 tests in 76 phenotypes under 3 dosing groups were conducted to compare the treatment effect against the placebo effect. Stratified false discovery rate (FDR) control methodology was implemented to control the occurrence of false positives associated with multiple testing yet provide considerably better power. The cell type group was taken as the stratification factor and conducted FDR (q-value) calculation within each stratum respectively. All null-hypotheses were rejected at 0.05 significance level with corresponding q-value ≤0.1. The multiple testing adjustment strategy with rejecting at 0.05 significance level and corresponding q<0.1 ensured that less than 10% of the findings are false.

In a second analysis, the immunophenotype changes between pooled treatment and placebo groups, where all three RAD001 dosing groups were combined. To determine which immunophenotype changes differed between the treated and placebo groups, within-patient cell count ratios for each measured phenotype were calculated between baseline and Week 6 of study drug treatment and between baseline and the end of study (Week 12). The ratios were log transformed, and analyzed by analysis of covariance at each time point in order to detect a difference between the pooled treatment and placebo groups. 152 tests in 76 phenotypes were performed to compare the pooled treatment effect against the placebo effect. Stratified false discovery rate (FDR) control methodology was implemented to control the occurrence of false positives associated with multiple testing yet provide considerably better power (Benjamini, Y. et al. (1995) *J. Roy. Statist.* 57:289-300; and Sun, L. et al. (2006) *Genet. Epidemiol.* 30:519-530). The cell type group was taken as the stratification factor and FDR (q-value) calculation was conducted within each stratum respectively. All null-hypotheses at 0.05 significance level and q-value less than 20% were rejected. This can be interpreted as rejecting only those hypotheses with P values less than 0.05 and less than 20% probability that the each observed significant result is due to multiple testing.

Results

In general, RAD001 was well tolerated, particularly the 0.5 mg daily and 5 mg weekly dosing regimens. No deaths occurred during the study. Three subjects experienced four serious adverse events (SAEs) that were assessed as unrelated to RAD001. The 4 SAEs were retinal hemorrhage of the left eye with subsequent blindness in a subject with normal platelet counts who had completed a 6 week course of 5 mg weekly RAD001 6 weeks previously; severe back pain in a subject treated with placebo and severe gastroenteritis in a subject treated with placebo. A list of treatment-related adverse events (AEs) with an incidence >2% in any treatment group is provided in Table 9. The most common RAD001-related AE was mouth ulcer that, in the majority of cases, was of mild severity. Overall, subjects who received RAD001 had a similar incidence of severe AEs as those treated with placebo. Only one severe AE was assessed as related to RAD001 mouth ulcers in a subject treated with 20 mg weekly RAD001.

TABLE 9

Incidence of treatment-related AEs >2% in any treatment group by preferred term

| | RAD001 0.5 mg daily N = 53 n (%) | RAD001 5 mg weekly N = 53 n (%) | RAD001 20 mg weekly N = 53 n (%) | Placebo, pooled N = 59 n (%) | Total N = 218 n (%) |
|---|---|---|---|---|---|
| Total AE(s) | 35 | 46 | 109 | 21 | 211 |
| Patients with AE(s) | 22 (41.5%) | 20 (37.7%) | 27 (50.9%) | 12 (20.3%) | 81 (37.2%) |
| Mouth ulceration | 6 (11.3%) | 2 (3.8%) | 9 (17.0%) | 3 (5.1%) | 20 (9.2%) |
| Headache | 0 | 2 (3.8%) | 9 (17.0%) | 1 (1.7%) | 12 (5.5%) |
| Blood cholesterol increased | 2 (3.8%) | 2 (3.8%) | 2 (3.8%) | 0 | 6 (2.8%) |
| Diarrhea | 1 (1.9%) | 4 (7.5%) | 1 (1.9%) | 0 | 6 (2.8%) |
| Dyspepsia | 0 | 3 (5.7%) | 2 (3.8%) | 1 (1.7%) | 6 (2.8%) |
| Fatigue | 0 | 2 (3.8%) | 4 (7.5%) | 0 | 6 (2.8%) |
| Low density lipoprotein increased | 2 (3.8%) | 1 (1.9%) | 2 (3.8%) | 0 | 5 (2.3%) |
| Tongue ulceration | 3 (5.7%) | 1 (1.9%) | 0 | 1 (1.7%) | 5 (2.3%) |
| Insomnia | 1 (1.9%) | 2 (3.8%) | 1 (1.9%) | 0 | 4 (1.8%) |
| Dry mouth | 0 | 0 | 2 (3.8%) | 1 (1.7%) | 3 (1.4%) |
| Neutropenia | 0 | 0 | 3 (5.7%) | 0 | 3 (1.4%) |
| Oral pain | 0 | 2 (3.8%) | 1 (1.9%) | 0 | 3 (1.4%) |
| Pruritus | 0 | 2 (3.8%) | 1 (1.9%) | 0 | 3 (1.4%) |
| Conjunctivitis | 0 | 2 (3.8%) | 0 | 0 | 2 (0.9%) |
| Erythema | 0 | 2 (3.8%) | 0 | 0 | 2 (0.9%) |
| Limb discomfort | 0 | 2 (3.8%) | 0 | 0 | 2 (0.9%) |
| Mucosal inflammation | 0 | 0 | 2 (3.8%) | 0 | 2 (0.9%) |
| Paresthesia oral | 2 (3.8%) | 0 | 0 | 0 | 2 (0.9%) |
| Stomatitis | 0 | 0 | 2 (3.8%) | 0 | 2 (0.9%) |
| Thrombocytopenia | 0 | 0 | 2 (3.8%) | 0 | 2 (0.9%) |
| Urinary tract infection | 0 | 0 | 2 (3.8%) | 0 | 2 (0.9%) |

The ability of RAD001 to improve immune function in elderly volunteers was evaluated by measuring the serologic response to the 2012 seasonal influenza vaccine. The hemagglutination inhibition (HI) geometric mean titers (GMT) to each of the 3 influenza vaccine strains at baseline and 4 weeks after influenza vaccination are provided in Table 10. The primary analysis variable was the HI GMT ratio (4 weeks post vaccination/baseline). The study was powered to be able to demonstrate that in at least 2 out of 3 influenza vaccine strains there was 1) a ≥1.2-fold GMT increase relative to placebo; and 2) a posterior probability no lower than 80% that the placebo-corrected GMT ratio exceeded 1. This endpoint was chosen because a 1.2-fold increase in the influenza GMT ratio induced by the MF-59 vaccine adjuvant was associated with a decrease in influenza illness (Job, A et al. (2005) *Epidemiol Infect* 133:687-693).

TABLE 10

HI GMTs for each influenza vaccine strain at baseline and at 4 weeks after influenza vaccination

| Influenza Vaccine Strain | | Time | RAD001 0.5 mg daily N = 50 | RAD001 5 mg weekly N = 49 | RAD001 20 mg weekly N = 49 | Placebo N = 55 |
|---|---|---|---|---|---|---|
| A/H1N1 | GMT (CV %) | Baseline | 102.8 (186.9) | 84.2 (236.4) | 90.1 (188.4) | 103.2 (219.7) |
| | | Week 4 | 190.2 (236.9) | 198.73 (195.6) | 129.7 (175.9) | 169.4 (259.8) |
| | GMT ratio (CV %) | | 2.6 (302.5) | 2.5 (214.3) | 1.8 (201.5) | 2.0 (132.7) |
| A/H3N2 | GMT (CV %) | Baseline | 106.8 (168.2) | 126.04 (162.6) | 137.1 (211.5) | 131.7 (162.3) |
| | | Week 4 | 194.4 (129.1) | 223.0 (118.8) | 223.0 (163.6) | 184.3 (153.2) |
| | GMT ratio (CV %) | | 2.1 (152.6) | 2.0 (189.2) | 2.1 (277.3) | 1.6 (153.6) |
| B | GMT (CV %) | Baseline | 44.2 (96.6) | 64.8 (87.3) | 58.0 (156.0) | 57.0 (112.6) |
| | | Week 4 | 98.4 (94.8) | 117.3 (99.9) | 99.2 (124.1) | 114.6 (136.7) |
| | GMT ratio (CV %) | | 2.5 (111.2) | 2.2 (112.8) | 2.1 (126.5) | 2.2 (109.2) |

Baseline indicates 2 weeks prior to influenza vaccination
Week 4 indicates 4 weeks after influenza vaccination
N is number of subjects per cohort
GMT is geometric mean titer
GMT ratio is the GMT at week 4 post vaccination/GMT at baseline
CV % indicates coefficient of variation In the intent-to-treat (ITT) population, the low, immune enhancing, dose RAD001 (0.5 mg daily or 5 mg weekly) cohorts but not higher dose (20 mg weekly) cohort met the primary endpoint of the study (FIG. 33A). This demonstrates that there is a distinct immunomodulatory mechanism of RAD001 at the lower doses, and that at the higher dose the known immunosuppressive effects of mTOR inhibition may come into play. Furthermore, the results suggest a trend toward improved immune function in the elderly after low, immune enhancing, dose RAD001 treatment.

In a subgroup analysis, the subset of subjects with low baseline influenza titers (≤1:40) experienced a greater RAD001-associated increase in titers than did the ITT population (FIG. 33B). These data show that RAD001 is particularly effective at enhancing the influenza vaccine response of subjects who did not have protective (>1:40) titers at baseline, and therefore were at highest risk of influenza illness.

Scatter plots of RAD001 concentration versus increase in titer to each influenza vaccine strain show an inverse exposure/response relationship (FIG. 34). Modeling and simulation based on mTOR mediated phosphorylation of S6 kinase (S6K) predicts that the 20 mg weekly dosing regimen inhibits mTOR-mediated S6K activity almost completely, the 5 mg weekly dosing regimen inhibits S6K activity by over 50%, and the 0.5 mg daily dosing regiment inhibits S6K phosphorylation by approximately 38% during the dosing interval (Tanaka, C et al. (2008) *J. Clin. Oncol* 26:1596-1602). Thus, partial mTOR inhibition, e.g., mTOR-mediated S6K phosphorylation, with low, immune enhancing, dose RAD001 may be as, if not more effective, than near complete mTOR inhibition with high dose RAD001 at enhancing the immune response of the elderly.

Rates of seroconversion 4 weeks after influenza vaccination were also evaluated. Seroconversion was defined as the change from a negative pre-vaccination titer (i.e., HI titer <1:10) to post-vaccination HI titer ≥1:40 or at least 4-fold increase from a non-negative (≥1:10) pre-vaccination HI titer. In the intention-to-treat population, seroconversion rates for the H3N2 and B strains were increased in the RAD001 as compared to the placebo cohorts although the increases did not meet statistical significance (Table 11). In the subpopulation of subjects with baseline influenza titers <=1:40, RAD001 treatment also increased the rates of seroconversion to the H3N2 and B strains, and these results reached statistical significance for the B strain in the 0.5 mg daily dosing cohort. These data further show that RAD001 enhanced the serologic response to influenza vaccination in the elderly.

TABLE 11

Percent of subjects with seroconversion to influenza 4 weeks after vaccination

| | Placebo N = 54 | 0.5 mg N = 48 | 5 mg N = 49 | 20 mg N = 48 |
|---|---|---|---|---|
| Intention to Treat Population | | | | |
| H1N1 | 24 | 27 | 27 | 17 |
| H3N2 | 17 | 27 | 24 | 25 |
| B | 17 | 27 | 22 | 19 |
| Subjects with Baseline Titers <=40 | | | | |
| H1N1 | 40 | 42 | 45 | 36 |
| H3N2 | 42 | 64 | 53 | 71 |
| B | 16 | 40* | 33 | 28 |

*Odds ratio for seroconversion between RAD001 and Placebo significantly different than 1 (two-sided p-value < 0.05 obtained by logistic regression with treatment as fixed effect)

Current seasonal influenza vaccines often provide inadequate protection against continuously emerging strains of influenza that present as variants of previously circulating viruses. However, mice vaccinated against influenza in the presence of the mTOR inhibitor rapamycin, as compared to placebo, developed a broader serologic response to influenza. The broader serologic response included antibodies to conserved epitopes expressed by multiple subtypes of influenza that provided protection against infection with heterologous strains of influenza not contained in the vaccine (Keating, R et al. (2013) Nat Immunology 14:2166-2178). To determine if RAD001 broadened the serologic response to influenza in the elderly volunteers, HI titers to 2 heterologous strains of influenza not contained in the influenza vaccine (A/H1N1 strain A/New Jersey/8/76 and A/H3N2 strain A/Victoria/361/11) were measured. The increase in the HI GMT ratios for the heterologous strains was higher in the RAD001 as compared to placebo cohorts (FIG. 35). In addition, seroconversion rates for the heterologous strains were higher in the RAD001 as compared to placebo cohorts. The increase in seroconversion rates in the 5 and 20 mg weekly RAD001 dosing cohorts was statistically significant for the H3N2 heterologous strain (Table 12). The H3N2 seroconversion rate for the pooled RAD001 cohorts was 39% versus 20% for the placebo cohort (p=0.007). The results presented herein suggest that mTOR inhibition broadens the serologic response of elderly volunteers to influenza vaccination, and increases antibody titers to heterologous strains of influenza not contained in the seasonal influenza vaccine.

Broadened serologic response to heterologous strains of influenza in mice treated with rapamycin has been associated with an inhibition of class switching in B cells and an increase in anti-influenza IgM levels (Keating, R. et al. (2013) Nat Immunol 14:2166-2178). However, inhibition of class switching may not be involved in the broadened serologic response in humans treated with RAD001 because the post-vaccination anti-influenza IgM and IgG levels did not differ between RAD001 and placebo treated cohorts (FIG. 36).

TABLE 12

Percentage of subjects who seroconvert to heterologous strains of influenza 4 weeks after seasonal influenza vaccination

|  | Placebo, pooled | RAD001 0.5 mg daily | RAD001 5 mg weekly | RAD001 20 mg weekly |
|---|---|---|---|---|
| A/H1N1 strain: A/NewJersey/8/76 | 7% | 17% | 16% | 8% |
| A/H3N2 strain: A/Victoria/361/11 | 20% | 38% | 39%* | 40%* |

*Odds ratio for seroconversion between RAD001 and Placebo significantly different than 1 (two-sided p-value < 0.05 obtained by logistic regression with treatment as fixed effect)

To address the mechanism by which RAD001 enhanced immune function in elderly volunteers, immunophenotyping was performed on PBMC samples obtained from subjects at baseline, after 6 weeks of study drug treatment and 4 weeks after influenza vaccination (6 weeks after study drug discontinuation). Although the percentage of most PBMC subsets did not differ between the RAD001 and placebo cohorts, the percentage of PD-1 positive CD4 and CD8 cells was lower in the RAD001 as compared to placebo cohorts (FIG. 37). PD-1 positive CD4 and CD8 cells accumulate with age and have defective responses to antigen stimulation because PD-1 inhibits T cell receptor-induced T cell proliferation, cytokine production and cytolytic function (Lages, C S et al. (2010) Aging Cell 9:785-798). There was an increase in percentage of PD-1 positive T cells over time in the placebo cohort. At week 12 (4 weeks post-vaccination) this increase may have been due to influenza vaccination since influenza virus has been shown to increase PD-1 positive T cells (Erikson, J J et al. (2012) JCI 122:2967-2982). However the percentage of CD4 PD-1 positive T cells decreased from baseline at week 6 and 12 in all RAD001 cohorts (FIG. 37A). The percentage of CD8 PD-1 positive cells also decreased from baseline at both week 6 and 12 in the two lower dose RAD001 cohorts (FIG. 37B). The percentage of PD-1 negative CD4 T cells was evaluated and increased in the RAD001 cohorts as compared to the placebo cohorts (FIG. 37C).

Under more stringent statistical analysis, where the results from the RAD001 cohorts were pooled and adjusted for differences in baseline PD-1 expression, there was a statistically significant decrease of 30.2% in PD-1 positive CD4 T cells at week 6 in the pooled RAD cohort (n=84) compared to placebo cohort (n=25) with p=0.03 (q=0.13) (FIG. 38A). The decrease in PD-1 positive CD4 T cells at week 12 in the pooled RAD as compared to the placebo cohort is 32.7% with p=0.05 (q=0.19). FIG. 38B shows a statistically significant decrease of 37.4% in PD-1 positive CD8 T cells at week 6 in the pooled RAD001 cohort (n=84) compared to placebo cohort (n=25) with p=0.008 (q=0.07). The decrease in PD-1 positive CD8 T cells at week 12 in the pooled RAD001 as compared to the placebo cohort is 41.4% with p=0.066 (q=0.21). Thus, the results from FIGS. 37 and 38 together suggest that the RAD001-associated decrease in the percentage of PD-1 positive CD4 and CD8 T cells may contribute to enhanced immune function.

Conclusion

In conclusion, the data presented herein show that the mTOR inhibitor RAD001 ameliorates the age-related decline in immunological function of the human elderly as assessed by response to influenza vaccination, and that this amelioration is obtained with an acceptable risk/benefit balance. In a study of elderly mice, 6 weeks treatment with the mTOR inhibitor rapamycin not only enhanced the response to influenza vaccination but also extended lifespan, suggesting that amelioration of immunosenescence may be a marker of a more broad effect on aging-related phenotypes.

Since RAD001 dosing was discontinued 2 weeks prior to vaccination, the immune enhancing effects of RAD001 may be mediated by changes in a relevant cell population that persists after discontinuation of drug treatment. The results presented herein show that RAD001 decreased the percentage of exhausted PD-1 positive CD4 and CD8 T cells as compared to placebo. PD-1 expression is induced by TCR signaling and remains high in the setting of persistent antigen stimulation including chronic viral infection. While not wishing to be bound by theory, is possible that RAD001 reduced chronic immune activation in elderly volunteers and thereby led to a decrease in PD-1 expression. RAD001 may also directly inhibit PD-1 expression as has been reported for the immunophilin cyclosporine A (Oestreich, K J et al. (2008) J Immunol. 181:4832-4839). A RAD001-induced reduction in the percentage of PD-1 positive T cells is likely to improve the quality of T cell responses. This is consistent with previous studies showing that mTOR inhibition improved the quality of memory CD8 T cell response to vaccination in mice and primates (Araki, K et al. (2009) Nature 460:108-112). In aged mice, mTOR inhibition has also been shown to increase the number of hematopoietic stem cells, leading to increased production of naïve lymphocytes (Chen, C et al. (2009) Sci Signal 2:ra75). Although significant differences in the percentages of naïve lymphocytes in the RAD001 versus placebo cohorts were not detected in this example, this possible mechanism may be further investigated.

The mechanism by which RAD001 broadened the serologic response to heterologous strains of influenza may be further investigated. Rapamycin has also been shown to inhibit class switching in B cells after influenza vaccination. As a result, a unique repertoire of anti-influenza antibodies was generated that promoted cross-strain protection against lethal infection with influenza virus subtypes not contained in the influenza vaccine (Keating, R et al. (2013) *Nat Immunol.* 14:2166-2178). The results described herein did not show that RAD001 altered B cell class switching in the elderly subjects who had discontinued RAD001 2 weeks prior to influenza vaccination. Although the underlying mechanism requires further elucidation, the increased serologic response to heterologous influenza strains described herein may confer enhanced protection to influenza illness in years when there is a poor match between the seasonal vaccine and circulating strains of influenza in the community.

The effect of RAD001 on influenza antibody titers was comparable to the effect of the MF59 vaccine adjuvant that is approved to enhance the response of the elderly to influenza vaccination (Podda, A (2001) *Vaccine* 19:2673-2680). Therefore, RAD001-driven enhancement of the antibody response to influenza vaccination may translate into clinical benefit as demonstrated with MF59-adjuvanted influenza vaccine in the elderly (Job, A et al. (2005) *Epidemiol Infect.* 133:687-693). However, RAD001 is also used to suppress the immune response of organ transplant patients. These seemingly paradoxical findings raise the possibility that the immunomodulatory effects of mTOR inhibitors may be dose and/or antigen-dependent (Ferrer, I R et al. (2010) *J Immunol.* 185:2004-2008). A trend toward an inverse RAD001 exposure/vaccination response relationship was seen herein. It is possible that complete mTOR inhibition suppresses immune function through the normal cyclophilin-rapamycin mechanism, whereas partial mTOR inhibition, at least in the elderly, enhances immune function due to a distinct aging-related phenotype inhibition. Of interest, mTOR activity is increased in a variety of tissues including hematopoietic stem cells in aging animal models (Chen C. et al. (2009) *Sci Signal* 2:ra75 and Barns, M. et al. (2014) *Int J Biochem Cell Biol.* 53:174-185). Thus, turning down mTOR activity to levels seen in young tissue, as opposed to more complete suppression of mTOR activity, may be of clinical benefit in aging indications.

The safety profile of mTOR inhibitors such as RAD001 in the treatment of aging-related indications has been of concern. The toxicity of RAD001 at doses used in oncology or organ transplant indications includes rates of stomatitis, diarrhea, nausea, cytopenias, hyperlipidemia, and hyperglycemia that would be unacceptable for many aging-related indications. However, these AEs are related to the trough levels of RAD001 in blood. Therefore the RAD001 dosing regimens used in this study were chosen to minimize trough levels. The average RAD001 trough levels of the 0.5 mg daily, 5 mg weekly and 20 mg weekly dosing cohorts were 0.9 ng/ml, below 0.3 ng/ml (the lower limit of quantification), and 0.7 ng/ml, respectively. These trough levels are significantly lower than the trough levels associated with dosing regimens used in organ transplant and cancer patients. In addition, the limited 6 week course of treatment decreased the risk of adverse events. These findings suggest that the dosing regimens used in this study may have an acceptable risk/benefit for some conditions of the elderly. Nonetheless, significant numbers of subjects in the experiments described hereindeveloped mouth ulcers even when dosed as low as 0.5 mg daily. Therefore the safety profile of low, immune enhancing, dose RAD001 warrants further study. Development of mTOR inhibitors with cleaner safety profiles than currently available rapalogs may provide better therapeutic options in the future for aging-associated conditions.

Example 14

Enhancement of Immune Response to Vaccine in Elderly Subjects

Immune function declines in the elderly, leading to an increase incidence of infection and a decreased response to vaccination. As a first step in determining if mTOR inhibition has anti-aging effects in humans, a randomized placebo-controlled trial was conducted to determine if the mTOR inhibitor RAD001 reverses the aging-related decline in immune function as assessed by response to vaccination in elderly volunteers. In all cases, appropriate patent consents were obtained and the study was approved by national health authorities.

The following 3 dosing regimens of RAD001 were used in the study:
20 mg weekly (trough level: 0.7 ng/ml)
5 mg weekly (trough level was below detection limits)
0.5 mg daily (trough level: 0.9 ng/ml)

These dosing regimens were chosen because they have lower trough levels than the doses of RAD001 approved for transplant and oncology indications. Trough level is the lowest level of a drug in the body. The trough level of RAD001 associated with the 10 mg daily oncology dosing regimen is approximately 20 ng/ml. The trough level associated with the 0.75-1.5 mg bid transplant dosing regimen is approximately 3 ng/ml. In contrast, the trough level associated with the dosing regimens used in our immunization study were 3-20 fold lower.

Since RAD001-related AEs are associated with trough levels, the 3 dosing regimens were predicted to have adequate safety for normal volunteers. In addition, the 3 doses were predicted to give a range of mTOR inhibition. P70 S6 Kinase (P70 S6K) is a downstream target that is phosphorylated by mTOR. Levels of P70 S6K phosphorylation serve as a measure of mTOR activity. Based on modeling and simulation of P70 S6K phosphorylation data obtained in preclinical and clinical studies of RAD001, 20 mg weekly was predicted to almost fully inhibit mTOR activity for a full week, whereas 5 mg weekly and 0.5 mg daily were predicted to partially inhibit mTOR activity.

Elderly volunteers >=65 years of age were randomized to one of the 3 RAD001 treatment groups (50 subjects per arm) or placebo (20 subjects per arm). Subjects were treated with study drug for 6 weeks, given a 2 week break, and then received influenza (Aggrippal, Novartis) and pneumoccal (Pneumovax 23, Merck), vaccinations. Response to influenza vaccination was assessed by measuring the geometric mean titers (GMTs) by hemagglutination inhibition assay to the 3 influenza strains (H1N1, H3N2 and B influenza subtypes) in the influenza vaccine 4 weeks after vaccination. The primary endpoints of the study were (1) safety and tolerability and (2) a 1.2 fold increase in influenza titers as compared to placebo in 2/3 of the influenza vaccine strains 4 weeks after vaccination. This endpoint was chosen because a 1.2 fold increase in influenza titers is associated with a decrease in influenza illness post vaccination, and therefore is clinically relevant. The 5 mg weekly and 0.5 mg daily doses were well tolerated and unlike the 20 mg weekly dose, met the GMT primary endpoint (FIG. 33A). Not only did RAD001 improve the response to influenza vaccination, it also improved the response to pneumococcal vaccination as compared to placebo in elderly volunteers. The pneumococcal vaccine contains antigens from 23 pneumococcal serotypes. Antibody titers to 7 of the serotypes were measured in our subjects. Antibody titers to 6/7 serotypes were increased in all 3 RAD cohorts compared to placebo.

The combined influenza and pneumococcal titer data suggest that partial (less than 80-100%) mTOR inhibition is more effective at reversing the aging-related decline in immune function than more complete mTOR inhibition.

Example 15

Low Dose mTOR Inhibition Increases Energy and Exercise

In preclinical models, mTOR inhibition with the rapalog rapamycin increases spontaneous physical activity in old mice (Wilkinson et al. Rapamycin slows aging in mice. (2012) *Aging Cell;* 11:675-82). Of interest, subjects in the 0.5 mg daily dosing cohort described in Example 2 also reported increased energy and exercise ability as compared to placebo in questionnaires administered one year after dosing (FIG. 39). These data suggest that partial mTOR inhibition with rapalogs may have beneficial effects on aging-related morbidity beyond just immune function.

Example 16

P70 S6 Kinase Inhibition with RAD001

Figure 40:
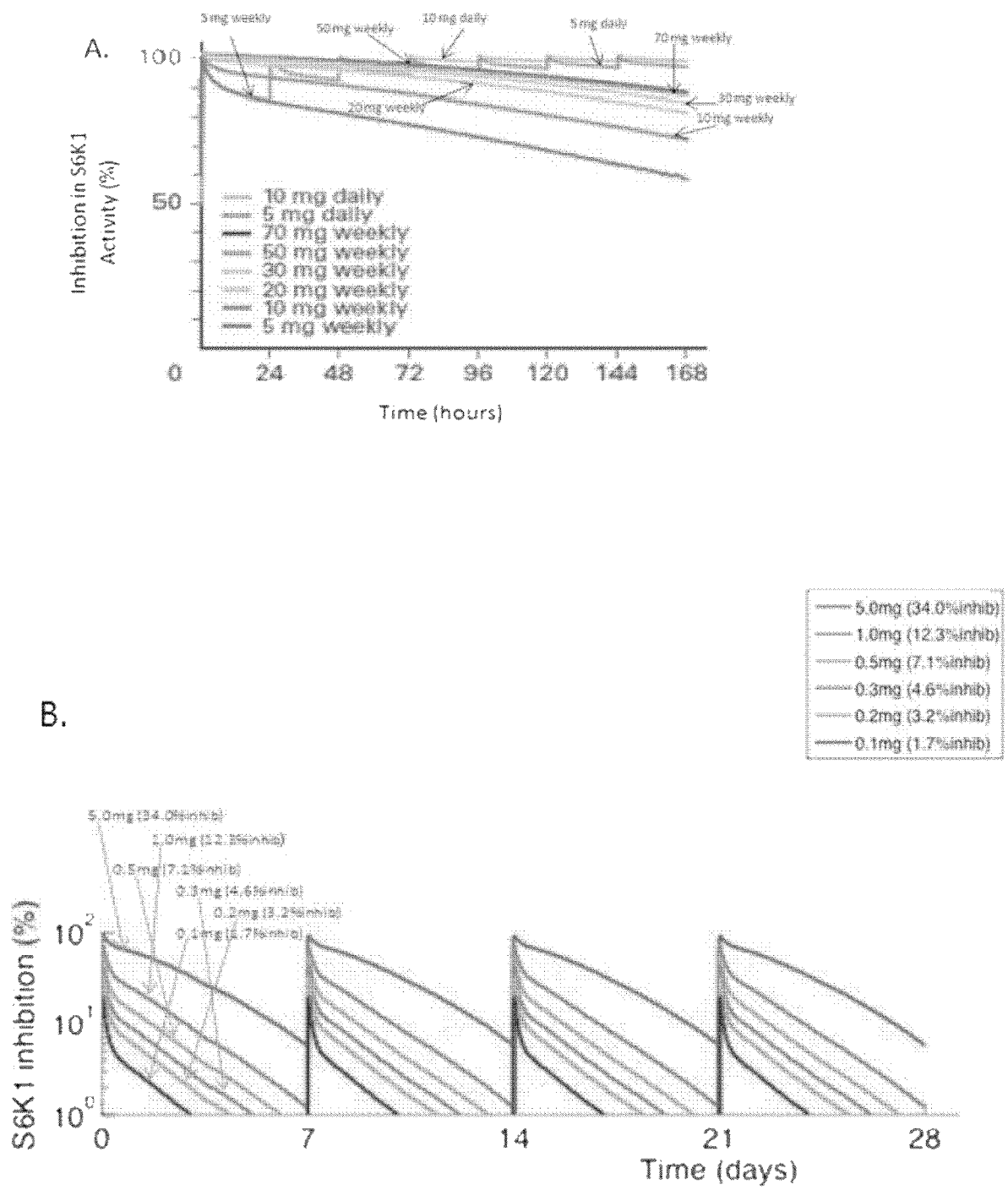

Modeling and simulation were performed to predict daily and weekly dose ranges of RAD001 that are predicted to partially inhibit mTOR activity. As noted above, P70 S6K is phosphorylated by mTOR and is the downstream target of mTOR that is most closely linked to aging because knockout of P70 S6K increases lifespan. Therefore modeling was done of doses of RAD001 that partially inhibit P70 S6K activity. Weekly dosing in the range of >=0.1 mg and <20 mg are predicted to achieve partial inhibition of P70 S6K activity (FIG. 40).

For daily dosing, concentrations of RAD001 from 30 pM to 4 nM partially inhibited P70 S6K activity in cell lines (Table 13). These serum concentrations are predicted to be achieved with doses of RAD001>=0.005 mg to <1.5 mg daily.

TABLE 13

Percent inhibition of P70 S6K activity in HeLa cells in vitro

| | RAD001 concentration | | | | | |
|---|---|---|---|---|---|---|
| | 0 | 6 pM | 32 pM | 160 pM | 800 pM | 4 nM | 20 nM |
| % P70 S6K inhibition | 0 | 0 | 18 | 16 | 62 | 90 | 95 |

Conclusion

Methods of treating aging-related morbidity, or generally enhancing an immune response, with doses of mTOR inhibitors that only partially inhibit P70 S6K. The efficacy of partial mTOR inhibition with low doses of RAD001 in aging indications is an unexpected finding. RAD001 dose ranges between >=0.1 mg to <20 mg weekly and >=0.005 mg to <1.5 mg daily will achieve partial mTOR inhibition and therefore are expected to have efficacy in aging-related morbidity or in the enhancement of the immune response.

Example 17

MSLN CART in Ovarian Cancer

Anti-tumor activity of a single dose of $2\times10^6$ mesothelin CAR T cells was previously assessed in an in vivo ovarian tumor mouse model, as described in Example 8. In order to see if the anti-tumor activity with the M5 and M11 CAR T cells in this model, as described in Example 8, could be increased, the CAR T cells were administered a higher dose of $4\times10^6$ mesothelin CAR T cells 14 days after tumor implantation when the tumor volumes were an average of 150 mm$^3$, and a follow-up identical dose of CAR T cells was administered. Half of the mice were given the second identical dose of the CAR T cells five days later to see if this would enhance the anti-tumor activity seen previously in this model.

Materials and Methods:

Cell Line: OVCAR8 is a human ovarian cancer cell line that was derived from a 64 year old female patient with ovarian adenocarcinoma, and has been transduced to express mCherry. Cells were grown in RMPI medium containing 10% fetal bovine serum. This cell line grows adherent in tissue culture flasks. This cell line forms tumors in mice when implanted subcutaneously in the flank and mixed with matrigel. The addition of matrigel to the cells during the implantation allow for a matrix to develop in the flank of the mouse that provides a structure for the tumor cells to start growing on. Over 10-12 days, the matrigel plug degrades and the solid tumor that remains is made up of tumor cells and surrounding stromal cells. The OVCAR8 cells have been modified to express mCherry, so that that tumor cell growth can also be monitored by imaging the mice.

Mice: 6 week old NSG (NOD.Cg-Prkdc$^{scid}$Il2rg$^{tm1Wjl}$/SzJ) mice were received from the Jackson Laboratory (stock number 005557). Animals were allowed to acclimate in the Novartis NIBRI animal facility for at least 3 days prior to experimentation. Animals were handled in accordance with Novartis ACUC regulations and guidelines. Electronic transponders for animal identification were implanted on the left flank one day prior to tumor implantation. Mice were shaved on the right flank prior to tumor implantation.

Tumor implantation: OVCAR8 cells in log phase were harvested after tyrpsinization with 0.25% trypsin-EDTA. The cells were washed in 50 ml falcon tubes at 1200 rpm for 5 minutes, once in growth media and then two times in cold sterile PBS. The cells were resuspended in PBS at a concentration of $100\times10^6$ per ml and kept on ice. The PBS solution containing the cells was then mixed 1:1 with matrigel, resulting in a final concentration of $50\times10^6$ cells per ml of PBS-matrigel. The cells were placed on ice and immediately implanted in mice. Tumors were implanted subcutaneously in 200 ul on the right flank.

The OVCAR8 model endogenously expresses mesothelin and thus, can be used to test the in vivo efficacy of mesothelin directed CAR T cells. This model grows well when implanted subcutaneously in the flank of mice and can be calipered for tumor volume measurements. Upon implantation of $10\times10^6$ tumor cells in a 50:50 mix of PBS and matrigel, the tumors establish and can be accurately measured in one week. Within 13-15 days, the mean tumor volume is 100-200 mm$^3$, with tumors reaching an endpoint volume (1000-1200 mm$^3$) by 60-65 days. Anti-tumor activities of therapeutic agents are often tested once tumors are fully engrafted and matrigel resorbed. Thus, there is a large window with this model during which the anti-tumor activity of the CAR T cells can be observed.

CAR T cell dosing: Mice were dosed with 4×10⁶ CAR T cells (13.3×10⁶ total T cells) 14 days after tumor implantation. Cells were partially thawed in a 37 degree Celsius water bath and then completely thawed by the addition of 1 ml of cold sterile PBS to the tube containing the cells. The thawed cells were transferred to a 15 ml falcon tube and adjusted to a final volume of 10 mls with PBS. The cells were washed twice at 1000 rpm for 10 minutes each time and then counted on a hemocytometer. T cells were then resuspended at a concentration of 133×10⁶ cells per ml of cold PBS and kept on ice until the mice were dosed. The mice were injected intravenously via the tail vein with 100 ul of the T cells for a dose of 4×10⁶ CAR T cells (13.3×10⁶ total T cells) per mouse. Seven mice per group were either treated with 100 ul of PBS alone (PBS) or T cells transduced with an isotype CAR (Isotype). 14 mice per group were treated with either the SS1 mesothelin CAR T cells, M5 mesothelin CAR T cells, or M11 mesothelin CAR T cells. Five days later the SS1, M5, and M11 groups were split in half and seven mice in each group were treated with an identical second dose of the CAR T cells. The groups were identified as SS1 single (one dose of SS1 CAR T cells), SS1 double (two doses of SS1 CAR T cells), M5 single (one dose of the M5 CAR T cells), M5 double (two doses of the M5 CAR T cells), M11 single (one dose of the M11 CAR T cells), M11 double (two doses of the M11 CAR T cells). The isotype T cells, SS1 T cells, M5 T cells, and M11 T cells were all prepared from the same donor in parallel.

Animal monitoring: The health status of the mice was monitored daily, including twice weekly body weight measurements. The percent change in body weight was calculated as $(BW_{current} - BW_{initial})/(BW_{initial}) \times 100\%$. Tumors were monitored 2-3 times weekly by calipering and tumor volumes (TV) were calculated using the ellipsoid formula: $TV(mm^3) = ((length \times width) \times 3.14159))/6$. Tumor volumes are reported as the mean+/−standard error of the mean (SEM). Percent treatment/control (T/C) values were calculated using the following formula:

% $T/C = 100 \times \Delta T/\Delta C$ if $\Delta T \geq 0$;

% Regression = $100 \times \Delta T/T_{initial}$ if $\Delta T < 0$;

where T=mean tumor volume of the drug-treated group on the final day of the study; $T_{initial}$=mean tumor volume of the drug-treated group on initial day of dosing; ΔT=mean tumor volume of the drug-treated group on the final day of the study—mean tumor volume of the drug treated group on the initial day of dosing; C=mean tumor volume of the control group on the final day of the study; and ΔC=mean tumor volume of the control group on the final day of the study—mean tumor volume of the control group on the initial day of dosing. T/C values in the range of 100%-42% are interpreted to have no or minimal anti-tumor activity; T/C values that are ≤42% and >10% are interpreted to have anti-tumor activity or tumor growth inhibition. T/C values ≤10% or regression values ≥−10% are interpreted to be tumor stasis. Regression values <−10% are reported as regression.

Results:

The anti-tumor activity of mesothelin CAR T cells were assessed in a subcutaneous ovarian adenocarcinoma xenograft model. Following tumor cell implantation on day 0, tumor bearing mice were randomized into treatment groups and were administered 4×10⁶ CAR T cells (13.3×10⁶ total T cells) intravenously via the lateral tail vein on day 14 after tumor implantation. A second identical dose of T cells was given to half of the mice 5 days later. Tumor growth and animal health were monitored until animals achieved endpoint. The mice in all groups were euthanized between days 57 and 62 when tumors were beginning to show signs of ulceration leading to a change in animal body condition scores.

The mean+/−SEM tumor volume for all treatment groups is plotted in FIG. 43. The PBS treatment group, which did not receive any T cells, demonstrates baseline OVCAR8 tumor growth kinetics in subcutaneously implanted NSG mice. The Isotype treatment group received T cells transduced with a control CAR. These cells serve as a T cell control to show the non-specific response of human donor T cells in this model. Both the PBS and the Isotype treatment groups demonstrate continuous tumor progression throughout this study. The Isotype group shows a slight slower tumor growth, due to the background activity of the donor T cells. Similar to previous studies a single dose of 4×10⁶ CAR+ T cells leads to no changes in tumor growth for the SS1 treated group. A double dose of the SS1 CAR T cells similarly led to no changes in OVCAR8 tumor growth. The M5 and M11 single dose groups show clear anti-tumor activity, as they did previously when dosed with 2×10⁶ CAR+ T cells. Both the M5 and M11 double dose groups show an increased anti-tumor activity as compared with the single dose groups. The tumors in these groups show regression as opposed to tumor growth inhibition. The M5 double dose group demonstrates a complete regression in four out of seven mice with no tumor measureable for multiple time points.

Change in tumor volume versus the Isotype group (delta T/C %) was calculated on day 52, which is the last tumor volume measurement before mice were removed due to tumors ulcerating. Table 14 shows the delta T/C values for each group. Both the SS1 single and double dose groups show no anti-tumor activity, similar to the PBS control treated group. The M5 single dose group shows tumor growth inhibition with a delta T/C value of 30.28%, while the M5 double dose group shows regression with a regression value of −63.90%. The M11 single dose group shows minimal anti-tumor activity with a delta T/C value of 52.91%, while the M11 double dose group also demonstrates regression with a regression value of −15.80%.

TABLE 14

Delta T/C (Treatment Tumor Volume/Control)

| Group | Day | Delta T/C (%) | Regression (%) |
|---|---|---|---|
| PBS | 52 | 162.23 | NA |
| Isotype | 52 | 100.00 | NA |
| SS1 Single | 52 | 172.05 | NA |
| SS1 Double | 52 | 166.15 | NA |
| M5 Single | 52 | 30.28 | NA |
| M5 Double | 52 | NA | −63.90 |
| M11 Single | 52 | 52.91 | NA |
| M11 Double | 52 | NA | −15.80 |

Discussion:

This study demonstrated that the mesothelin specific CAR T cells (M5 and M11), when dosed a second time five days after an initial T cell dose, are capable of leading to the regression of OVCAR8 tumors. This response along with the anti-tumor activity following a single dose of both the M5 and M11 CAR T cells are durable. In addition, four out of seven mice in the M5 double dose group demonstrate a complete regression with no tumor measureable by caliper or palpation.

As seen previously, e.g., in Example 8, a single dose of 2×10⁶ CAR T cells of the M5 or M11 CAR T cells shows anti-tumor activity and what appears to be stasis in the OVCAR8 xenograft model in NSG mice. In this study, a single dose of 4×10⁶ M5 or M11 CAR T cells shows the same result. Compared to the Isotype CAR T cells or the SS1 CAR T cells, the M5 and the M11 groups show clear anti-tumor activity even as a single dose (FIG. 43). Administering a second dose of the SS1 CAR T cells does not show an increased anti-tumor response. However, administering a second dose of the M5 or M11 CAR T cells results in an enhanced anti-tumor response and leads to regression of the tumors in both of these groups.

The increased anti-tumor activity of the M5 and M11 CAR T cells can be attributed to several mechanisms. The first is that a larger dose of CAR T cells achieves regression in the OVCAR8 model. Increasing the dose of CAR T cells, e.g., to 8×10⁶ CAR T cells, e.g., in a single dose, may increase anti-tumor activity and result in regression. Another mechanism is that additional doses of CAR T cells improve anti-tumor activity and tumor regression. For example, the initial dose may result in some anti-tumor activity due to the expansion of the CAR T cells and the production of cytokines by the T cells. Giving an additional dose, e.g., a second dose five days later while the cells are still undergoing expansion, may increase the activity of the cells due to the cytokines already being produced by the earlier administered CAR T cells.

In addition, previous studies have shown the infiltration of CAR T cells into the OVCAR8 tumors. Infiltration of CAR T cells is also studied in the mice that have received a double dose of the CAR T cells to determine if there is a greater infiltration of CD8⁺ (cytotoxic) T cells. The persistence of the CAR T cells is also evaluated through an analysis of the cells in the spleen and bone marrow of these mice.

Example 18

Epitope Mapping by Hydrogen-Deuterium Exchange-Mass Spectrometry

Hydrogen-deuterium exchange (HDX) mass spectrometry was performed to predict the regions of mesothelin that contribute to the epitopes recognized by scFv constructs SS1 and M5. In HDX, the hydrogens of the amide backbone of a target protein are exchanged with deuterium. Interaction between the target protein and a binding protein, e.g., an antibody, "protects" regions of the target protein from solvent accessibility, thereby preventing hydrogen exchange at the interface between the target protein and the binding protein. Accordingly, HDX mass spectrometry can be used to probe for mapping protein binding interfaces, e.g., predicting the epitope of an antibody.

As described in Example 2, analysis of scFv constructs M5, M11, M12, M14, M16, M17, M21, and M23 by SPR-based epitope binning against SS1 indicated that M5 and M11 bind to a different epitope than SS1. To gain insight into the regions of the human mesothelin that may be bound by SS1 and M5, HDX mass spectrometry was performed as follows.

Cloning of Expression Plasmids

A DNA fragment corresponding to amino acids Val 297-Gly 588 of Mesothelin (Uniprot Q13421) was cloned into a mammalian expression vector using the restriction sites HindIII and EcoRI at the 5' and 3' respectively. Subsequently, a secretion signal was inserted at amino terminus corresponding to the amino acids METDTLLLWVLLL-WVPGSTGDAAQPAASE (SEQ ID NO: 376). At the carboxyl terminus, a V5-His tag corresponding to the amino acids TRGSGKPIPNPLLGLDSTRTGHHHHHHHHH-HHH (SEQ ID NO: 377) was also inserted.

The three predicted glycosylation sites were mutated: N388Q, N496Q and N523Q. The final expressed sequence is provided below:

Glycosylation Deficient Mesothelin
(296-588; N388Q, N496Q, N523Q)

(SEQ ID NO: 378)
METDTLLLWVLLLWVPGSTGDAAQPAASEVEKTACPSGKKAREIDESLIF

YKKWELEACVDAALLATQMDRVNAIPFTYEQLDVLKHKLDELYPQGYPES

VIQHLGYLFLKMSPEDIRKWQVTSLETLKALLEVNKGHEMSPQVATLIDR

FVKGRGQLDKDTLDTLTAFYPGYLCSLSPEELSSVPPSSIWAVRPQDLDT

CDPRQLDVLYPKARLAFQNMQGSEYFVKIQSFLGGAPTEDLKALSQQQVS

MDLATFMKLRTDAVLPLTVAEVQKLLGPHVEGLKAEERHRPVRDWILRQR

QDDLDTLGLGLQGTRGSGKPIPNPLLGLDSTRTGHHHHHHHHHHHH

The scFv corresponding to the M5 IgG (e.g., SEQ ID NO: 43) was similarly cloned into a mammalian expression vector with the N-terminal leader MALPVTALLLPLALLL-HAARP (SEQ ID NO: 379) and a C-terminal eight histidine purification tag GSHHHHHHHH (SEQ ID NO: 380). The final expressed sequence is provided below:

(SEQ ID NO: 381)
MALPVTALLLPLALLLHAARPQVQLVQSGAEVEKPGASVKVSCKASGYTF

TDYYMHWVRQAPGQGLEWMGWINPNSGGTNYAQKFQGRVTMTRDTSISTA

YMELSRLRSDDTAVYYCASGWDFDYWGQGTLVTVSSGGGGSGGGGSGGGG

SGGGGSDIVMTQSPSSLSASVGDRVTITCRASQSIRYYLSWYQQKPGKAP

KLLIYTASILQNGVPSRFSGSGSGTDFTLTISSLQPEDFATYYCLQTYTT

PDFGPGTKVEIKGSHHHHHHHH

Protein Expression and Purification

Both the Mesothelin and scFv M5 were expressed under the control of a CMV promoter in the Expi293 expression system (Life Technologies). The mesothelin and scFv plasmids were co-transfected into 2 L of Expi293 cells at a density of 2.3×10⁶ cells/mL and viability >97% using 1 mg of each purified plasmid and 5 mg of polyethylenimine (PEI) in Opti-MEM media (Life Technologies). Mesothelin was also transfected alone following a similar protocol but into 1 L of cells using 1 mg of plasmid DNA and 2.5 mg of PEI. The transfection proceeded for 5 days and then the cells were harvested when the viability reached 80%.

Once the viability dropped to 80%, the cells and conditioned media were collected and spun down at 4000×g for 10 minutes. The conditioned media was then filtered through a 0.22 µM filter to clear any debris and then stirred overnight with Roche's cOmplete His-Tag Purification Resin at 4° C. A total of 3 mL of beads was added to the scFv-M5/Mesothelin conditioned media and 1.5 mL of beads was added to the Mesothelin alone media.

The following morning, the beads were loaded onto a Bio-Rad Econo-Column and washed with 15 column volumes of 50 mM Tris.Cl pH=8.0, 300 mM NaCl and then 8 column volumes of 50 mM Tris.Cl pH=8.0, 300 mM NaCl, 20 mM Imidazole. The proteins were then eluted from the column with 50 mM Tris.Cl pH=8.0, 300 mM NaCl, 250 mM Imidazole. The eluted sample was collected and concentrated to 6 mL and loaded onto a Superdex 75 16/60 column connected to an AKTAxpress (GE) in 20 mM HEPES pH=7.4, 150 mM NaCl. Elutions corresponding to the expected size of the mesothelin:M5 complex or Mesothelin alone were collected and concentrated to 5 mg/mL.

Epitope Mapping by Hydrogen-deuterium Exchange/mass Spectrometry

Hydrogen-deuterium exchange (HDx) in combination with mass spectrometry (MS) (Woods V L, Hamuro Y (2001) High Resolution, High-Throughput Amide Deuterium Exchange-Mass Spectrometry (DXMS) Determination of Protein Binding Site Structure and Dynamics: Utility in Pharmaceutical Design. *J. Cell. Biochem. Supp.*; 84(37): 89-98.) was used to map the putative binding site of scFv antibodies M5 and SS1 on human mesothelin(296-588), referred to herein as $hMSLN_{296-588}$ (SEQ ID No 278). In HDx, exchangeable amide hydrogens of proteins are replaced by deuterium. This process is sensitive to protein structure/dynamics and solvent accessibility and, therefore, able to report on locations that undergo a decrease in deuterium uptake upon ligand binding.

HDx/MS experiments were performed using methods similar to those described in the literature (Chalmers M J, Busby S A, Pascal B D, He Y, Hendrickson C L, Marshall A G, Griffin P R (2006) Probing protein ligand interactions by automated hydrogen/deuterium exchange mass spectrometry. *Anal. Chem.*; 78(4): 1005-1014. Chalmers, 2006). The experiments were performed on a Waters HDx/MS platform, which included a LEAP autosampler, nanoACQUITY UPLC, and Synapt G2 mass spectrometer. The deuterium buffer used to label the protein backbone of $hMSLN_{296-588}$ with deuterium was 25 mM HEPES, 150 mM NaCl, pH 7.4; the overall percentage of deuterium in the solution was 94.5%. For $hMSLN_{296-588}$ deuterium labeling experiments in the absence of antibody, 400 pmol of $hMSLN_{296-588}$, volume of 6.9 µl, was diluted using 100 µl of the deuterium buffer for 15 minutes at 4° C. The labeling reaction was then quenched with 100 µl of chilled quench buffer at 2° C. for three minutes followed by injected onto the LC-MS system for automated pepsin digestion and peptide analysis.

For $hMSLN_{296-588}$ deuterium labeling experiments in the presence of scFv M5, 400 pmol of $hMSLN_{296-588}$ co-expressed with M5, volume of 6.9 µl, was diluted using 100 µl of the deuterium buffer for 15 minutes at 4° C. The labeling reaction was then quenched with 100 µl of chilled quench buffer at 2° C. for three minutes followed by injected onto the LC-MS system for automated pepsin digestion and peptide analysis. For $hMSLN_{296-588}$ deuterium labeling experiments in the presence of scFv SS1, 400 pmol of $hMSLN_{296-588}$ is combined with 480 pmol of SS1 scFv. After incubation of SS1 with $hMSLN_{296-588}$ for 30 minutes at 4° C., the total volume of 6.9 µl was diluted using 100 µl of the deuterium buffer for 15 minutes at 4° C. The labeling reaction was then quenched with 100 µl of chilled quench buffer at 2° C. for three minutes, and then injected onto the LC-MS system for automated pepsin digestion and peptide analysis.

All deuterium exchange experiments were quenched using 0.5 M TCEP and 3 M urea (pH=2.6). After quenching, the exchanged antigen was subjected to on-line pepsin digestion using a Poroszyme Immobilized Pepsin column (2.1×30 mm) at 12° C. followed by trapping on a Waters Vanguard HSS T3 trapping column. Peptides were eluted from the trapping column and separated on a Waters BEH C18 1×100 mm column (maintained at 1° C.) at a flow rate of 40 µl/min using a binary 8.4 minute gradient of 2 to 35% B (mobile phase A was 99.9% water and 0.1% formic acid; mobile phase B was 99.9% acetonitrile and 0.1% formic acid).

Peptides from $hMSLN_{296-588}$ that were monitored by the deuterium exchange experiments are indicated in FIG. 44 (each bar represents a peptide). Over 80% coverage of $hMSLN_{296-588}$ was achieved.

For differential experiments between antibody (M5 or SS1) bound and unbound states it is informative to examine the difference in deuterium uptake between the two states. In FIGS. 45A and 45B a negative value indicates that the mesothelin-antibody complex undergoes less deuterium uptake relative to mesothelin alone. A decrease in deuterium uptake can be due to protection of the region from exchangeable deuterium or stabilization of the hydrogen bonding network. In contrast, a positive value indicates that the complex undergoes more deuterium uptake relative to mesothelin alone. An increase in deuterium uptake can be due to destabilization of hydrogen bonding networks (i.e. localized unfolding of the protein).

Differential deuterium exchange between apo mesolethin and mesothelin complexed with either SS1 or M5 were considered significant if: 1) if the difference is greater than 0.75 Da or, in cases, where the difference is equal to or less than 0.75 Da, 2) the difference is greater than 0.2 Da and statistically significant (p<0.01) when using the Tukey test. See, e.g., Houde D, Berkowitz S A, Engen J R (2010) The Utility of Hydrogen/Deuterium Exchange Mass Spectrometry in Biopharmaceutical Comparability Studies. *J. Pharma. Sci.*; 100(6): 2071-2086; Chalmers, M J, Pascal B D, Willis S, Zhang J, iturria S J, Dodge J A, Griffin P R (2011) Methods for the Analysis of High Precision Differential Hydrogen Deuterium Exchange Data *Int. J. Mass Spectrom.*; 302(1-3): 59-68.

FIG. 45A shows the differential deuterium uptake of the M5-mesothelin complex (black bars) and the differential uptake of the SS1-mesothelin complex (grey bars) from amino acid position 297 to 464 on mesothelin. Over this region binding of M5 to mesothelin caused no protection and there is some very slight destabilization observed. In contrast, the binding of SS1 to mesothelin caused significant protection in the following peptides: 297-315, 315-322, 316-325, 337-346, 337-349, 350-375, and 369-376. Protection in the peptides 297-315, 315-322, 316-325, 337-346, 337-349 is consistent with the published crystallography structure where residues E313, F317, K319, P343, and Y346 form a significant part of the epitope (Ma J, Tang W K, Esser L, Pastan I, Xia D (2012) Recognition of Mesotehlin by the Therapuetic Antibody MORAb-009 *J. Biol. Chem.*; (287)40: 33123-33131.) FIG. 45B shows the differential deuterium uptake for the amino acid positions 458-586 on mesothelin. Over this region, binding of M5, caused significant protection in the following peptides: 481-490, 483-490, 498-510, 501-507, 531-540, 532-540, 532-546, 537-546, 545-558, 546-569, 547-560, 558-571, 561-572. By comparing the protection of overlapping peptides, we deduce that the regions 485-490, 498-507, 532-537, and 545-572 are significantly protected in the M5-mesothelin complex. In contrast, the SS1-mesothelin complex does not contain any peptides in the region 458-586 that are significantly protected using the criteria stated above.

FIG. 46 provides a summary of the protected regions for both the M5 and SS1 complex. These data indicate that M5 protects exclusively towards the C-terminal side of mesothelin, and that amino acid residues 485-490, 498-507, 532-537, and 545-572may contribute to the M5-mesothelin interaction. In contrast, SS1 protects exclusively towards the N-terminal side of mesothelin and there was no observed overlap in the regions protected by SS1and those protected by M5. The observation of two distinct protection patterns for SS1 and M5 indicate that M5likely binds a distinct epitope from that bound by SS1. M11is expected to bind to a similar region of MSLN as compared to M5, M11and M5 have high homology I both light and heavy chains including identical CDR3regions.

EQUIVALENTS

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

SEQUENCE LISTING

```
<160> NUMBER OF SEQ ID NOS: 402

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met Ala Leu Pro Val Thr Ala Leu Leu Leu Pro Leu Ala Leu Leu Leu
1               5                   10                  15

His Ala Ala Arg Pro
            20

<210> SEQ ID NO 2
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 3
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60
```

```
Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys Met
225                 230

<210> SEQ ID NO 4
<211> LENGTH: 282
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Arg Trp Pro Glu Ser Pro Lys Ala Gln Ala Ser Ser Val Pro Thr Ala
  1               5                  10                  15

Gln Pro Gln Ala Glu Gly Ser Leu Ala Lys Ala Thr Thr Ala Pro Ala
             20                  25                  30

Thr Thr Arg Asn Thr Gly Arg Gly Gly Glu Glu Lys Lys Lys Glu Lys
         35                  40                  45

Glu Lys Glu Glu Gln Glu Glu Arg Glu Thr Lys Thr Pro Glu Cys Pro
 50                  55                  60

Ser His Thr Gln Pro Leu Gly Val Tyr Leu Leu Thr Pro Ala Val Gln
 65                  70                  75                  80

Asp Leu Trp Leu Arg Asp Lys Ala Thr Phe Thr Cys Phe Val Val Gly
                 85                  90                  95

Ser Asp Leu Lys Asp Ala His Leu Thr Trp Glu Val Ala Gly Lys Val
            100                 105                 110

Pro Thr Gly Gly Val Glu Glu Gly Leu Leu Glu Arg His Ser Asn Gly
        115                 120                 125

Ser Gln Ser Gln His Ser Arg Leu Thr Leu Pro Arg Ser Leu Trp Asn
130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
```

```
            180                 185                 190
Trp Leu Leu Cys Glu Val Ser Gly Phe Ser Pro Pro Asn Ile Leu Leu
        195                 200                 205

Met Trp Leu Glu Asp Gln Arg Glu Val Asn Thr Ser Gly Phe Ala Pro
    210                 215                 220

Ala Arg Pro Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
                245                 250                 255

Cys Val Val Ser His Glu Asp Ser Arg Thr Leu Leu Asn Ala Ser Arg
                260                 265                 270

Ser Leu Glu Val Ser Tyr Val Thr Asp His
        275                 280

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Gly Gly Ser Gly Gly Gly Gly Ser
1               5                   10

<210> SEQ ID NO 6
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 7
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 8
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 8

Gln Arg Arg Lys Tyr Arg Ser Asn Lys Gly Glu Ser Pro Val Glu Pro
1               5                   10                  15

Ala Glu Pro Cys Arg Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45

<210> SEQ ID NO 9
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 10
<211> LENGTH: 112
<212> TYPE: PRT
<213> ORGANISM: Homo sapiens

<400> SEQUENCE: 10

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 11
<211> LENGTH: 1184
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 11

```
cgtgaggctc cggtgcccgt cagtgggcag agcgcacatc gcccacagtc cccgagaagt      60
tgggggagg  ggtcggcaat tgaaccggtg cctagagaag gtggcgcggg gtaaactggg     120
aaagtgatgt cgtgtactgg ctccgccttt ttcccgaggg tgggggagaa ccgtatataa     180
gtgcagtagt cgccgtgaac gttcttttc  gcaacgggtt tgccgccaga acacaggtaa     240
gtgccgtgtg tggttcccgc gggcctggcc tctttacggg ttatggccct tgcgtgcctt     300
gaattacttc cacctggctg cagtacgtga ttcttgatcc cgagcttcgg gttggaagtg     360
ggtgggagag ttcgaggcct tgcgcttaag gagccccttc gcctcgtgct tgagttgagg     420
cctggcctgg gcgctgggc  cgccgcgtgc gaatctggtg gcaccttcgc gcctgtctcg     480
ctgctttcga taagtctcta gccatttaaa attttttgatg acctgctgcg acgcttttt     540
tctggcaaga tagtcttgta aatgcgggcc aagatctgca cactggtatt tcggtttttg     600
ggccgcggg  cggcgacggg gcccgtgcgt cccagcgcac atgttcggcg aggcggggcc     660
tgcgagcgcg gccaccgaga tcggacggg  ggtagtctca agctggccgg cctgctctgg     720
tgcctggcct cgcgccgccg tgtatcgccc cgccctgggc ggcaaggctg gcccggtcgg     780
caccagttgc gtgagcggaa agatggccgc ttcccggccc tgctgcaggg agctcaaaat     840
ggaggacgcg gcgctcggga gagcgggcgg gtgagtcacc cacacaaagg aaaagggcct     900
ttccgtcctc agccgtcgct tcatgtgact ccacggagta ccgggcgccg tccaggcacc     960
tcgattagtt ctcgagcttt tggagtacgt cgtctttagg ttgggggag  gggttttatg    1020
cgatggagtt tccccacact gagtgggtgg agactgaagt taggccagct tggcacttga    1080
tgtaattctc cttggaattt gccctttttg agtttggatc ttggttcatt ctcaagcctc    1140
agacagtggt tcaaagtttt tttcttccat ttcaggtgtc gtga                     1184
```

<210> SEQ ID NO 12
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12

```
atggccctgc ctgtgacagc cctgctgctg cctctggctc tgctgctgca tgccgctaga     60
ccc                                                                   63
```

<210> SEQ ID NO 13
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

```
accacgacgc cagcgccgcg accaccaaca ccggcgccca ccatcgcgtc gcagcccctg      60
tccctgcgcc cagaggcgtg ccggccagcg gcgggggggcg cagtgcacac gagggggctg    120
gacttcgcct gtgat                                                     135
```

<210> SEQ ID NO 14

<211> LENGTH: 690
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

| | |
|---|---|
| gagagcaagt acggccctcc ctgccccct tgccctgccc ccgagttcct gggcggaccc | 60 |
| agcgtgttcc tgttccccc caagcccaag gacaccctga tgatcagccg gaccccgag | 120 |
| gtgacctgtg tggtggtgga cgtgtcccag gaggaccccg aggtccagtt caactggtac | 180 |
| gtggacggcg tggaggtgca caacgccaag accaagcccc gggaggagca gttcaatagc | 240 |
| acctaccggg tggtgtccgt gctgaccgtg ctgcaccagg actggctgaa cggcaaggaa | 300 |
| tacaagtgta aggtgtccaa caaggggcctg cccagcagca tcgagaaaac catcagcaag | 360 |
| gccaagggcc agcctcggga gccccaggtg tacaccctgc cccctagcca agaggagatg | 420 |
| accaagaacc aggtgtccct gacctgcctg gtgaagggct tctacccag cgacatcgcc | 480 |
| gtggagtggg agagcaacgg ccagcccgag aacaactaca agaccacccc ccctgtgctg | 540 |
| gacagcgacg gcagcttctt cctgtacagc cggctgaccg tggacaagag ccggtggcag | 600 |
| gagggcaacg tctttagctg ctccgtgatg cacgaggccc tgcacaacca ctacacccag | 660 |
| aagagcctga gcctgtccct gggcaagatg | 690 |

<210> SEQ ID NO 15
<211> LENGTH: 847
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

| | |
|---|---|
| aggtggcccg aaagtcccaa ggcccaggca tctagtgttc ctactgcaca gccccaggca | 60 |
| gaaggcagcc tagccaaagc tactactgca cctgccacta cgcgcaatac tggccgtggc | 120 |
| ggggaggaga agaaaaagga gaaagagaaa gaagaacagg aagagaggga gaccaagacc | 180 |
| cctgaatgtc catcccatac ccagccgctg ggcgtctatc tcttgactcc cgcagtacag | 240 |
| gacttgtggc ttagagataa ggccacctttt acatgtttcg tcgtgggctc tgacctgaag | 300 |
| gatgcccatt tgacttggga ggttgccgga aaggtaccca caggggggt tgaggaaggg | 360 |
| ttgctggagc gccattccaa tggctctcag agccagcact caagactcac ccttccgaga | 420 |
| tccctgtgga acgccgggac tctgtcaca tgtactctaa atcatcctag cctgccccca | 480 |
| cagcgtctga tggcccttag agagccagcc gcccaggcac cagttaagct tagcctgaat | 540 |
| ctgctcgcca gtagtgatcc cccagaggcc gccagctggc tcttatgcga agtgtccggc | 600 |
| tttagcccgc ccaacatctt gctcatgtgg ctggaggacc agcgagaagt gaacaccagc | 660 |
| ggcttcgctc cagcccggcc cccaccccag ccgggttcta ccacattctg ggcctggagt | 720 |
| gtcttaaggg tcccagcacc acctagcccc cagccagcca catacacctg tgttgtgtcc | 780 |
| catgaagata gcaggaccct gctaaatgct tctaggagtc tggaggtttc ctacgtgact | 840 |
| gaccatt | 847 |

<210> SEQ ID NO 16
<211> LENGTH: 30
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 16
ggtggcggag gttctggagg tggaggttcc                                          30

<210> SEQ ID NO 17
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
atctacatct gggcgccctt ggccgggact tgtggggtcc ttctcctgtc actggttatc         60 acccttact gc                                                              72

<210> SEQ ID NO 18
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
aaacggggca gaaagaaact cctgtatata ttcaaacaac catttatgag accagtacaa         60
actactcaag aggaagatgg ctgtagctgc cgatttccag aagaagaaga aggaggatgt        120
gaactg                                                                   126

<210> SEQ ID NO 19
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
aggagtaaga ggagcaggct cctgcacagt gactacatga acatgactcc ccgccgcccc         60
gggcccaccc gcaagcatta ccagccctat gccccaccac gcgacttcgc agcctatcgc        120
tcc                                                                      123

<210> SEQ ID NO 20
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
agagtgaagt tcagcaggag cgcagacgcc cccgcgtaca agcagggcca gaaccagctc         60
tataacgagc tcaatctagg acgaagagag gagtacgatg tttggacaa gagacgtggc        120 cgggaccctg agatgggggg aaagccgaga aggaagaacc ctcaggaagg cctgtacaat        180
gaactgcaga agataagat ggcggaggcc tacagtgaga ttgggatgaa aggcgagcgc        240
cggaggggca aggggcacga tggcctttac caggtctca gtacagccac caaggacacc        300
tacgacgccc ttcacatgca ggccctgccc cctcgc                                  336
```

<210> SEQ ID NO 21
<211> LENGTH: 336
<212> TYPE: DNA
<213> ORGANISM: Homo sapiens

<400> SEQUENCE: 21

```
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatggggggg aaagccgaga aggaagaacc ctcaggaagg cctgtacaat     180
gaactgcaga aagataagat ggcggaggcc tacagtgaga ttgggatgaa aggcgagcgc     240
cggaggggca aggggcacga tggcctttac cagggtctca gtacagccac caaggacacc     300
tacgacgccc ttcacatgca ggccctgccc cctcgc                               336
```

<210> SEQ ID NO 22
<211> LENGTH: 373
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Thr Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190

Ala Cys Asp Ile Tyr Ile Trp Ala Pro Leu Ala Gly Thr Cys Gly Val
        195                 200                 205

Leu Leu Leu Ser Leu Val Ile Thr Leu Tyr Cys Lys Arg Gly Arg Lys
    210                 215                 220

Lys Leu Leu Tyr Ile Phe Lys Gln Pro Phe Met Arg Pro Val Gln Thr
225                 230                 235                 240

Thr Gln Glu Glu Asp Gly Cys Ser Cys Arg Phe Pro Glu Glu Glu Glu
                245                 250                 255
```

Gly Gly Cys Glu Leu Arg Val Lys Phe Ser Arg Ser Ala Asp Ala Pro
            260                 265                 270

Ala Tyr Lys Gln Gly Gln Asn Gln Leu Tyr Asn Glu Leu Asn Leu Gly
        275                 280                 285

Arg Arg Glu Glu Tyr Asp Val Leu Asp Lys Arg Gly Arg Asp Pro
    290                 295                 300

Glu Met Gly Gly Lys Pro Arg Arg Lys Asn Pro Gln Glu Gly Leu Tyr
305                 310                 315                 320

Asn Glu Leu Gln Lys Asp Lys Met Ala Glu Ala Tyr Ser Glu Ile Gly
                325                 330                 335

Met Lys Gly Glu Arg Arg Arg Gly Lys Gly His Asp Gly Leu Tyr Gln
            340                 345                 350

Gly Leu Ser Thr Ala Thr Lys Asp Thr Tyr Asp Ala Leu His Met Gln
        355                 360                 365

Ala Leu Pro Pro Arg
        370

<210> SEQ ID NO 23
<211> LENGTH: 1182
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

| | | | |
|---|---|---|---|
| atggccctcc ctgtcactgc cctgcttctc cccctcgcac tcctgctcca cgccgctaga | | | 60 |
| ccacccggat ggtttctgga ctctccggat cgccgtggaa tcccccaac cttctcaccg | | | 120 |
| gcactcttgg ttgtgactga gggcgataat gcgaccttca cgtgctcgtt ctccaacacc | | | 180 |
| tccgaatcat tcgtgctgaa ctggtaccgc atgagcccgt caaaccagac cgacaagctc | | | 240 |
| gccgcgtttc cggaagatcg gtcgcaaccg ggacaggatt gtcggttccg cgtgactcaa | | | 300 |
| ctgccgaatg gcagagactt ccacatgagc gtggtccgcg ctaggcgaaa cgactccggg | | | 360 |
| acctacctgt gcggagccat ctcgctggcg cctaaggccc aaatcaaaga gagcttgagg | | | 420 |
| gccgaactga gagtgaccga gcgcagagct gaggtgccaa ctgcacatcc atccccatcg | | | 480 |
| cctcggcctg cggggcagtt tcagaccctg gtcacgacca ctccggcgcc gcgcccaccg | | | 540 |
| actccggccc caactatcgc gagccagccc ctgtcgctga ggccggaagc atgccgccct | | | 600 |
| gccgccggag gtgctgtgca tacccgggga ttggacttcg catgcgacat ctacatttgg | | | 660 |
| gctcctctcg ccggaacttg tggcgtgctc cttctgtccc tggtcatcac cctgtactgc | | | 720 |
| aagcggggtc ggaaaaagct tctgtacatt ttcaagcagc ccttcatgag gcccgtgcaa | | | 780 |
| accacccagg aggaggacgg ttgctcctgc cggttccccg aagaggaaga aggaggttgc | | | 840 |
| gagctgcgcg tgaagttctc ccggagcgcc gacgcccccg cctataagca gggccagaac | | | 900 |
| cagctgtaca cgaactgaa cctgggacgg cgggaagagt acgatgtgct ggacaagcgg | | | 960 |
| cgcggccggg accccgaaat gggcgggaag cctagaagaa gaaccctca ggaaggcctg | | | 1020 |
| tataacgagc tgcagaagga caagatggcc gaggcctact ccgaaattgg gatgaaggga | | | 1080 |
| gagcggcgga ggggaaaggg cacgacggc ctgtaccaag actgtccac cgccaccaag | | | 1140 |
| gacacatacg atgccctgca catgcaggcc cttccccctc gc | | | 1182 |

<210> SEQ ID NO 24
<211> LENGTH: 394

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Met Ala Leu Pro Val Thr Ala Leu Leu Leu Pro Leu Ala Leu Leu Leu
  1               5                  10                  15
His Ala Ala Arg Pro Pro Gly Trp Phe Leu Asp Ser Pro Asp Arg Pro
             20                  25                  30
Trp Asn Pro Pro Thr Phe Ser Pro Ala Leu Leu Val Val Thr Glu Gly
         35                  40                  45
Asp Asn Ala Thr Phe Thr Cys Ser Phe Ser Asn Thr Ser Glu Ser Phe
     50                  55                  60
Val Leu Asn Trp Tyr Arg Met Ser Pro Ser Asn Gln Thr Asp Lys Leu
 65                  70                  75                  80
Ala Ala Phe Pro Glu Asp Arg Ser Gln Pro Gly Gln Asp Cys Arg Phe
                 85                  90                  95
Arg Val Thr Gln Leu Pro Asn Gly Arg Asp Phe His Met Ser Val Val
            100                 105                 110
Arg Ala Arg Arg Asn Asp Ser Gly Thr Tyr Leu Cys Gly Ala Ile Ser
        115                 120                 125
Leu Ala Pro Lys Ala Gln Ile Lys Glu Ser Leu Arg Ala Glu Leu Arg
    130                 135                 140
Val Thr Glu Arg Arg Ala Glu Val Pro Thr Ala His Pro Ser Pro Ser
145                 150                 155                 160
Pro Arg Pro Ala Gly Gln Phe Gln Thr Leu Val Thr Thr Thr Pro Ala
                165                 170                 175
Pro Arg Pro Pro Thr Pro Ala Pro Thr Ile Ala Ser Gln Pro Leu Ser
            180                 185                 190
Leu Arg Pro Glu Ala Cys Arg Pro Ala Ala Gly Gly Ala Val His Thr
        195                 200                 205
Arg Gly Leu Asp Phe Ala Cys Asp Ile Tyr Ile Trp Ala Pro Leu Ala
    210                 215                 220
Gly Thr Cys Gly Val Leu Leu Leu Ser Leu Val Ile Thr Leu Tyr Cys
225                 230                 235                 240
Lys Arg Gly Arg Lys Lys Leu Leu Tyr Ile Phe Lys Gln Pro Phe Met
                245                 250                 255
Arg Pro Val Gln Thr Thr Gln Glu Glu Asp Gly Cys Ser Cys Arg Phe
            260                 265                 270
Pro Glu Glu Glu Glu Gly Gly Cys Glu Leu Arg Val Lys Phe Ser Arg
        275                 280                 285
Ser Ala Asp Ala Pro Ala Tyr Lys Gln Gly Gln Asn Gln Leu Tyr Asn
    290                 295                 300
Glu Leu Asn Leu Gly Arg Arg Glu Glu Tyr Asp Val Leu Asp Lys Arg
305                 310                 315                 320
Arg Gly Arg Asp Pro Glu Met Gly Gly Lys Pro Arg Arg Lys Asn Pro
                325                 330                 335
Gln Glu Gly Leu Tyr Asn Glu Leu Gln Lys Asp Lys Met Ala Glu Ala
            340                 345                 350
Tyr Ser Glu Ile Gly Met Lys Gly Glu Arg Arg Arg Gly Lys Gly His
        355                 360                 365
Asp Gly Leu Tyr Gln Gly Leu Ser Thr Ala Thr Lys Asp Thr Tyr Asp
    370                 375                 380
```

Ala Leu His Met Gln Ala Leu Pro Pro Arg
385                 390

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Gly Gly Gly Ser
1               5

<210> SEQ ID NO 26
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(30)
<223> OTHER INFORMATION: This sequence may encompass 1-6 "Gly Gly Gly
      Gly Ser" repeating units wherein some positions may be absent
<220> FEATURE:
<223> OTHER INFORMATION: See specification as filed for detailed
      description of substitutions and preferred embodiments

<400> SEQUENCE: 26

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 27
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Gly Gly Gly Ser Gly Gly Gly Gly Ser Gly Gly Gly Gly Ser Gly
1               5                   10                  15

Gly Gly Gly Ser
            20

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Gly Gly Gly Ser Gly Gly Gly Gly Ser Gly Gly Gly Gly Ser
1               5                   10                  15

<210> SEQ ID NO 29
<211> LENGTH: 4
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 29

Gly Gly Gly Ser
1

<210> SEQ ID NO 30
<211> LENGTH: 5000
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(5000)
<223> OTHER INFORMATION: This sequence may encompass 50-5,000
      nucleotides wherein some positions may be absent
<220> FEATURE:
<223> OTHER INFORMATION: See specification as filed for detailed
      description of substitutions and preferred embodiments

<400> SEQUENCE: 30
aaaaaaaaaa aaaaaaaaaa aaaaaaaaaa aaaaaaaaaa aaaaaaaaaa aaaaaaaaaa     60
aaaaaaaaaa aaaaaaaaaa aaaaaaaaaa aaaaaaaaaa aaaaaaaaaa aaaaaaaaaa    120
aaaaaaaaaa aaaaaaaaaa aaaaaaaaaa aaaaaaaaaa aaaaaaaaaa aaaaaaaaaa    180
aaaaaaaaaa aaaaaaaaaa aaaaaaaaaa aaaaaaaaaa aaaaaaaaaa aaaaaaaaaa    240
aaaaaaaaaa aaaaaaaaaa aaaaaaaaaa aaaaaaaaaa aaaaaaaaaa aaaaaaaaaa    300
aaaaaaaaaa aaaaaaaaaa aaaaaaaaaa aaaaaaaaaa aaaaaaaaaa aaaaaaaaaa    360
aaaaaaaaaa aaaaaaaaaa aaaaaaaaaa aaaaaaaaaa aaaaaaaaaa aaaaaaaaaa    420
aaaaaaaaaa aaaaaaaaaa aaaaaaaaaa aaaaaaaaaa aaaaaaaaaa aaaaaaaaaa    480
aaaaaaaaaa aaaaaaaaaa aaaaaaaaaa aaaaaaaaaa aaaaaaaaaa aaaaaaaaaa    540
aaaaaaaaaa aaaaaaaaaa aaaaaaaaaa aaaaaaaaaa aaaaaaaaaa aaaaaaaaaa    600
aaaaaaaaaa aaaaaaaaaa aaaaaaaaaa aaaaaaaaaa aaaaaaaaaa aaaaaaaaaa    660
aaaaaaaaaa aaaaaaaaaa aaaaaaaaaa aaaaaaaaaa aaaaaaaaaa aaaaaaaaaa    720
aaaaaaaaaa aaaaaaaaaa aaaaaaaaaa aaaaaaaaaa aaaaaaaaaa aaaaaaaaaa    780
aaaaaaaaaa aaaaaaaaaa aaaaaaaaaa aaaaaaaaaa aaaaaaaaaa aaaaaaaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaaaaaaaa   1020
aaaaaaaaaa aaaaaaaaaa aaaaaaaaaa aaaaaaaaaa aaaaaaaaaa aaaaaaaaaa   1080
aaaaaaaaaa aaaaaaaaaa aaaaaaaaaa aaaaaaaaaa aaaaaaaaaa aaaaaaaaaa   1140
aaaaaaaaaa aaaaaaaaaa aaaaaaaaaa aaaaaaaaaa aaaaaaaaaa aaaaaaaaaa   1200
aaaaaaaaaa aaaaaaaaaa aaaaaaaaaa aaaaaaaaaa aaaaaaaaaa aaaaaaaaaa   1260
aaaaaaaaaa aaaaaaaaaa aaaaaaaaaa aaaaaaaaaa aaaaaaaaaa aaaaaaaaaa   1320
aaaaaaaaaa aaaaaaaaaa aaaaaaaaaa aaaaaaaaaa aaaaaaaaaa aaaaaaaaaa   1380
aaaaaaaaaa aaaaaaaaaa aaaaaaaaaa aaaaaaaaaa aaaaaaaaaa aaaaaaaaaa   1440
aaaaaaaaaa aaaaaaaaaa aaaaaaaaaa aaaaaaaaaa aaaaaaaaaa aaaaaaaaaa   1500
aaaaaaaaaa aaaaaaaaaa aaaaaaaaaa aaaaaaaaaa aaaaaaaaaa aaaaaaaaaa   1560
```

```
aaaaaaaaaa aaaaaaaaaa aaaaaaaaaa aaaaaaaaaa aaaaaaaaaa aaaaaaaaaa   1620
aaaaaaaaaa aaaaaaaaaa aaaaaaaaaa aaaaaaaaaa aaaaaaaaaa aaaaaaaaaa   1680
aaaaaaaaaa aaaaaaaaaa aaaaaaaaaa aaaaaaaaaa aaaaaaaaaa aaaaaaaaaa   1740
aaaaaaaaaa aaaaaaaaaa aaaaaaaaaa aaaaaaaaaa aaaaaaaaaa aaaaaaaaaa   1800
aaaaaaaaaa aaaaaaaaaa aaaaaaaaaa aaaaaaaaaa aaaaaaaaaa aaaaaaaaaa   1860
aaaaaaaaaa aaaaaaaaaa aaaaaaaaaa aaaaaaaaaa aaaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaaaaaaa aaaaaaaaaa aaaaaaaaaa aaaaaaaaaa aaaaaaaaaa aaaaaaaaaa   2040
aaaaaaaaaa aaaaaaaaaa aaaaaaaaaa aaaaaaaaaa aaaaaaaaaa aaaaaaaaaa   2100
aaaaaaaaaa aaaaaaaaaa aaaaaaaaaa aaaaaaaaaa aaaaaaaaaa aaaaaaaaaa   2160
aaaaaaaaaa aaaaaaaaaa aaaaaaaaaa aaaaaaaaaa aaaaaaaaaa aaaaaaaaaa   2220
aaaaaaaaaa aaaaaaaaaa aaaaaaaaaa aaaaaaaaaa aaaaaaaaaa aaaaaaaaaa   2280
aaaaaaaaaa aaaaaaaaaa aaaaaaaaaa aaaaaaaaaa aaaaaaaaaa aaaaaaaaaa   2340
aaaaaaaaaa aaaaaaaaaa aaaaaaaaaa aaaaaaaaaa aaaaaaaaaa aaaaaaaaaa   2400
aaaaaaaaaa aaaaaaaaaa aaaaaaaaaa aaaaaaaaaa aaaaaaaaaa aaaaaaaaaa   2460
aaaaaaaaaa aaaaaaaaaa aaaaaaaaaa aaaaaaaaaa aaaaaaaaaa aaaaaaaaaa   2520
aaaaaaaaaa aaaaaaaaaa aaaaaaaaaa aaaaaaaaaa aaaaaaaaaa aaaaaaaaaa   2580
aaaaaaaaaa aaaaaaaaaa aaaaaaaaaa aaaaaaaaaa aaaaaaaaaa aaaaaaaaaa   2640
aaaaaaaaaa aaaaaaaaaa aaaaaaaaaa aaaaaaaaaa aaaaaaaaaa aaaaaaaaaa   2700
aaaaaaaaaa aaaaaaaaaa aaaaaaaaaa aaaaaaaaaa aaaaaaaaaa aaaaaaaaaa   2760
aaaaaaaaaa aaaaaaaaaa aaaaaaaaaa aaaaaaaaaa aaaaaaaaaa aaaaaaaaaa   2820
aaaaaaaaaa aaaaaaaaaa aaaaaaaaaa aaaaaaaaaa aaaaaaaaaa aaaaaaaaaa   2880
aaaaaaaaaa aaaaaaaaaa aaaaaaaaaa aaaaaaaaaa aaaaaaaaaa aaaaaaaaaa   2940
aaaaaaaaaa aaaaaaaaaa aaaaaaaaaa aaaaaaaaaa aaaaaaaaaa aaaaaaaaaa   3000
aaaaaaaaaa aaaaaaaaaa aaaaaaaaaa aaaaaaaaaa aaaaaaaaaa aaaaaaaaaa   3060
aaaaaaaaaa aaaaaaaaaa aaaaaaaaaa aaaaaaaaaa aaaaaaaaaa aaaaaaaaaa   3120
aaaaaaaaaa aaaaaaaaaa aaaaaaaaaa aaaaaaaaaa aaaaaaaaaa aaaaaaaaaa   3180
aaaaaaaaaa aaaaaaaaaa aaaaaaaaaa aaaaaaaaaa aaaaaaaaaa aaaaaaaaaa   3240
aaaaaaaaaa aaaaaaaaaa aaaaaaaaaa aaaaaaaaaa aaaaaaaaaa aaaaaaaaaa   3300
aaaaaaaaaa aaaaaaaaaa aaaaaaaaaa aaaaaaaaaa aaaaaaaaaa aaaaaaaaaa   3360
aaaaaaaaaa aaaaaaaaaa aaaaaaaaaa aaaaaaaaaa aaaaaaaaaa aaaaaaaaaa   3420
aaaaaaaaaa aaaaaaaaaa aaaaaaaaaa aaaaaaaaaa aaaaaaaaaa aaaaaaaaaa   3480
aaaaaaaaaa aaaaaaaaaa aaaaaaaaaa aaaaaaaaaa aaaaaaaaaa aaaaaaaaaa   3540
aaaaaaaaaa aaaaaaaaaa aaaaaaaaaa aaaaaaaaaa aaaaaaaaaa aaaaaaaaaa   3600
aaaaaaaaaa aaaaaaaaaa aaaaaaaaaa aaaaaaaaaa aaaaaaaaaa aaaaaaaaaa   3660
aaaaaaaaaa aaaaaaaaaa aaaaaaaaaa aaaaaaaaaa aaaaaaaaaa aaaaaaaaaa   3720
aaaaaaaaaa aaaaaaaaaa aaaaaaaaaa aaaaaaaaaa aaaaaaaaaa aaaaaaaaaa   3780
aaaaaaaaaa aaaaaaaaaa aaaaaaaaaa aaaaaaaaaa aaaaaaaaaa aaaaaaaaaa   3840
aaaaaaaaaa aaaaaaaaaa aaaaaaaaaa aaaaaaaaaa aaaaaaaaaa aaaaaaaaaa   3900
```

```
aaaaaaaaaa aaaaaaaaaa aaaaaaaaaa aaaaaaaaaa aaaaaaaaaa aaaaaaaaaa    3960
aaaaaaaaaa aaaaaaaaaa aaaaaaaaaa aaaaaaaaaa aaaaaaaaaa aaaaaaaaaa    4020
aaaaaaaaaa aaaaaaaaaa aaaaaaaaaa aaaaaaaaaa aaaaaaaaaa aaaaaaaaaa    4080
aaaaaaaaaa aaaaaaaaaa aaaaaaaaaa aaaaaaaaaa aaaaaaaaaa aaaaaaaaaa    4140
aaaaaaaaaa aaaaaaaaaa aaaaaaaaaa aaaaaaaaaa aaaaaaaaaa aaaaaaaaaa    4200
aaaaaaaaaa aaaaaaaaaa aaaaaaaaaa aaaaaaaaaa aaaaaaaaaa aaaaaaaaaa    4260
aaaaaaaaaa aaaaaaaaaa aaaaaaaaaa aaaaaaaaaa aaaaaaaaaa aaaaaaaaaa    4320
aaaaaaaaaa aaaaaaaaaa aaaaaaaaaa aaaaaaaaaa aaaaaaaaaa aaaaaaaaaa    4380
aaaaaaaaaa aaaaaaaaaa aaaaaaaaaa aaaaaaaaaa aaaaaaaaaa aaaaaaaaaa    4440
aaaaaaaaaa aaaaaaaaaa aaaaaaaaaa aaaaaaaaaa aaaaaaaaaa aaaaaaaaaa    4500
aaaaaaaaaa aaaaaaaaaa aaaaaaaaaa aaaaaaaaaa aaaaaaaaaa aaaaaaaaaa    4560
aaaaaaaaaa aaaaaaaaaa aaaaaaaaaa aaaaaaaaaa aaaaaaaaaa aaaaaaaaaa    4620
aaaaaaaaaa aaaaaaaaaa aaaaaaaaaa aaaaaaaaaa aaaaaaaaaa aaaaaaaaaa    4680
aaaaaaaaaa aaaaaaaaaa aaaaaaaaaa aaaaaaaaaa aaaaaaaaaa aaaaaaaaaa    4740
aaaaaaaaaa aaaaaaaaaa aaaaaaaaaa aaaaaaaaaa aaaaaaaaaa aaaaaaaaaa    4800
aaaaaaaaaa aaaaaaaaaa aaaaaaaaaa aaaaaaaaaa aaaaaaaaaa aaaaaaaaaa    4860
aaaaaaaaaa aaaaaaaaaa aaaaaaaaaa aaaaaaaaaa aaaaaaaaaa aaaaaaaaaa    4920
aaaaaaaaaa aaaaaaaaaa aaaaaaaaaa aaaaaaaaaa aaaaaaaaaa aaaaaaaaaa    4980
aaaaaaaaaa aaaaaaaaaa                                                5000

<210> SEQ ID NO 31
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
tttttttttt tttttttttt tttttttttt tttttttttt tttttttttt tttttttttt      60
tttttttttt tttttttttt tttttttttt tttttttttt                           100

<210> SEQ ID NO 32
<211> LENGTH: 5000
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(5000)
<223> OTHER INFORMATION: This sequence may encompass 50-5,000
      nucleotides wherein some positions may be absent
<220> FEATURE:
<223> OTHER INFORMATION: See specification as filed for detailed
      description of substitutions and preferred embodiments

<400> SEQUENCE: 32
tttttttttt tttttttttt tttttttttt tttttttttt tttttttttt tttttttttt      60
tttttttttt tttttttttt tttttttttt tttttttttt tttttttttt tttttttttt     120
tttttttttt tttttttttt tttttttttt tttttttttt tttttttttt tttttttttt     180
tttttttttt tttttttttt tttttttttt tttttttttt tttttttttt tttttttttt     240
```

| | |
|---|---|
| tttttttttt tttttttttt tttttttttt tttttttttt tttttttttt tttttttttt | 300 |
| tttttttttt tttttttttt tttttttttt tttttttttt tttttttttt tttttttttt | 360 |
| tttttttttt tttttttttt tttttttttt tttttttttt tttttttttt tttttttttt | 420 |
| tttttttttt tttttttttt tttttttttt tttttttttt tttttttttt tttttttttt | 480 |
| tttttttttt tttttttttt tttttttttt tttttttttt tttttttttt tttttttttt | 540 |
| tttttttttt tttttttttt tttttttttt tttttttttt tttttttttt tttttttttt | 600 |
| tttttttttt tttttttttt tttttttttt tttttttttt tttttttttt tttttttttt | 660 |
| tttttttttt tttttttttt tttttttttt tttttttttt tttttttttt tttttttttt | 720 |
| tttttttttt tttttttttt tttttttttt tttttttttt tttttttttt tttttttttt | 780 |
| tttttttttt tttttttttt tttttttttt tttttttttt tttttttttt tttttttttt | 840 |
| tttttttttt tttttttttt tttttttttt tttttttttt tttttttttt tttttttttt | 900 |
| tttttttttt tttttttttt tttttttttt tttttttttt tttttttttt tttttttttt | 960 |
| tttttttttt tttttttttt tttttttttt tttttttttt tttttttttt tttttttttt | 1020 |
| tttttttttt tttttttttt tttttttttt tttttttttt tttttttttt tttttttttt | 1080 |
| tttttttttt tttttttttt tttttttttt tttttttttt tttttttttt tttttttttt | 1140 |
| tttttttttt tttttttttt tttttttttt tttttttttt tttttttttt tttttttttt | 1200 |
| tttttttttt tttttttttt tttttttttt tttttttttt tttttttttt tttttttttt | 1260 |
| tttttttttt tttttttttt tttttttttt tttttttttt tttttttttt tttttttttt | 1320 |
| tttttttttt tttttttttt tttttttttt tttttttttt tttttttttt tttttttttt | 1380 |
| tttttttttt tttttttttt tttttttttt tttttttttt tttttttttt tttttttttt | 1440 |
| tttttttttt tttttttttt tttttttttt tttttttttt tttttttttt tttttttttt | 1500 |
| tttttttttt tttttttttt tttttttttt tttttttttt tttttttttt tttttttttt | 1560 |
| tttttttttt tttttttttt tttttttttt tttttttttt tttttttttt tttttttttt | 1620 |
| tttttttttt tttttttttt tttttttttt tttttttttt tttttttttt tttttttttt | 1680 |
| tttttttttt tttttttttt tttttttttt tttttttttt tttttttttt tttttttttt | 1740 |
| tttttttttt tttttttttt tttttttttt tttttttttt tttttttttt tttttttttt | 1800 |
| tttttttttt tttttttttt tttttttttt tttttttttt tttttttttt tttttttttt | 1860 |
| tttttttttt tttttttttt tttttttttt tttttttttt tttttttttt tttttttttt | 1920 |
| tttttttttt tttttttttt tttttttttt tttttttttt tttttttttt tttttttttt | 1980 |
| tttttttttt tttttttttt tttttttttt tttttttttt tttttttttt tttttttttt | 2040 |
| tttttttttt tttttttttt tttttttttt tttttttttt tttttttttt tttttttttt | 2100 |
| tttttttttt tttttttttt tttttttttt tttttttttt tttttttttt tttttttttt | 2160 |
| tttttttttt tttttttttt tttttttttt tttttttttt tttttttttt tttttttttt | 2220 |
| tttttttttt tttttttttt tttttttttt tttttttttt tttttttttt tttttttttt | 2280 |
| tttttttttt tttttttttt tttttttttt tttttttttt tttttttttt tttttttttt | 2340 |
| tttttttttt tttttttttt tttttttttt tttttttttt tttttttttt tttttttttt | 2400 |
| tttttttttt tttttttttt tttttttttt tttttttttt tttttttttt tttttttttt | 2460 |
| tttttttttt tttttttttt tttttttttt tttttttttt tttttttttt tttttttttt | 2520 |
| tttttttttt tttttttttt tttttttttt tttttttttt tttttttttt tttttttttt | 2580 |

| | | | | | | |
|---|---|---|---|---|---|---|
| tttttttttt | tttttttttt | tttttttttt | tttttttttt | tttttttttt | tttttttttt | 2640 |
| tttttttttt | tttttttttt | tttttttttt | tttttttttt | tttttttttt | tttttttttt | 2700 |
| tttttttttt | tttttttttt | tttttttttt | tttttttttt | tttttttttt | tttttttttt | 2760 |
| tttttttttt | tttttttttt | tttttttttt | tttttttttt | tttttttttt | tttttttttt | 2820 |
| tttttttttt | tttttttttt | tttttttttt | tttttttttt | tttttttttt | tttttttttt | 2880 |
| tttttttttt | tttttttttt | tttttttttt | tttttttttt | tttttttttt | tttttttttt | 2940 |
| tttttttttt | tttttttttt | tttttttttt | tttttttttt | tttttttttt | tttttttttt | 3000 |
| tttttttttt | tttttttttt | tttttttttt | tttttttttt | tttttttttt | tttttttttt | 3060 |
| tttttttttt | tttttttttt | tttttttttt | tttttttttt | tttttttttt | tttttttttt | 3120 |
| tttttttttt | tttttttttt | tttttttttt | tttttttttt | tttttttttt | tttttttttt | 3180 |
| tttttttttt | tttttttttt | tttttttttt | tttttttttt | tttttttttt | tttttttttt | 3240 |
| tttttttttt | tttttttttt | tttttttttt | tttttttttt | tttttttttt | tttttttttt | 3300 |
| tttttttttt | tttttttttt | tttttttttt | tttttttttt | tttttttttt | tttttttttt | 3360 |
| tttttttttt | tttttttttt | tttttttttt | tttttttttt | tttttttttt | tttttttttt | 3420 |
| tttttttttt | tttttttttt | tttttttttt | tttttttttt | tttttttttt | tttttttttt | 3480 |
| tttttttttt | tttttttttt | tttttttttt | tttttttttt | tttttttttt | tttttttttt | 3540 |
| tttttttttt | tttttttttt | tttttttttt | tttttttttt | tttttttttt | tttttttttt | 3600 |
| tttttttttt | tttttttttt | tttttttttt | tttttttttt | tttttttttt | tttttttttt | 3660 |
| tttttttttt | tttttttttt | tttttttttt | tttttttttt | tttttttttt | tttttttttt | 3720 |
| tttttttttt | tttttttttt | tttttttttt | tttttttttt | tttttttttt | tttttttttt | 3780 |
| tttttttttt | tttttttttt | tttttttttt | tttttttttt | tttttttttt | tttttttttt | 3840 |
| tttttttttt | tttttttttt | tttttttttt | tttttttttt | tttttttttt | tttttttttt | 3900 |
| tttttttttt | tttttttttt | tttttttttt | tttttttttt | tttttttttt | tttttttttt | 3960 |
| tttttttttt | tttttttttt | tttttttttt | tttttttttt | tttttttttt | tttttttttt | 4020 |
| tttttttttt | tttttttttt | tttttttttt | tttttttttt | tttttttttt | tttttttttt | 4080 |
| tttttttttt | tttttttttt | tttttttttt | tttttttttt | tttttttttt | tttttttttt | 4140 |
| tttttttttt | tttttttttt | tttttttttt | tttttttttt | tttttttttt | tttttttttt | 4200 |
| tttttttttt | tttttttttt | tttttttttt | tttttttttt | tttttttttt | tttttttttt | 4260 |
| tttttttttt | tttttttttt | tttttttttt | tttttttttt | tttttttttt | tttttttttt | 4320 |
| tttttttttt | tttttttttt | tttttttttt | tttttttttt | tttttttttt | tttttttttt | 4380 |
| tttttttttt | tttttttttt | tttttttttt | tttttttttt | tttttttttt | tttttttttt | 4440 |
| tttttttttt | tttttttttt | tttttttttt | tttttttttt | tttttttttt | tttttttttt | 4500 |
| tttttttttt | tttttttttt | tttttttttt | tttttttttt | tttttttttt | tttttttttt | 4560 |
| tttttttttt | tttttttttt | tttttttttt | tttttttttt | tttttttttt | tttttttttt | 4620 |
| tttttttttt | tttttttttt | tttttttttt | tttttttttt | tttttttttt | tttttttttt | 4680 |
| tttttttttt | tttttttttt | tttttttttt | tttttttttt | tttttttttt | tttttttttt | 4740 |
| tttttttttt | tttttttttt | tttttttttt | tttttttttt | tttttttttt | tttttttttt | 4800 |
| tttttttttt | tttttttttt | tttttttttt | tttttttttt | tttttttttt | tttttttttt | 4860 |
| tttttttttt | tttttttttt | tttttttttt | tttttttttt | tttttttttt | tttttttttt | 4920 |
| tttttttttt | tttttttttt | tttttttttt | tttttttttt | tttttttttt | tttttttttt | 4980 | tttttttttt tttttttttt                                                    5000

<210> SEQ ID NO 33
<211> LENGTH: 5000
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(5000)
<223> OTHER INFORMATION: This sequence may encompass 100-5,000
      nucleotides wherein some positions may be absent
<220> FEATURE:
<223> OTHER INFORMATION: See specification as filed for detailed
      description of substitutions and preferred embodiments

<400> SEQUENCE: 33
aaaaaaaaaa aaaaaaaaaa aaaaaaaaaa aaaaaaaaaa aaaaaaaaaa aaaaaaaaaa          60
aaaaaaaaaa aaaaaaaaaa aaaaaaaaaa aaaaaaaaaa aaaaaaaaaa aaaaaaaaaa         120
aaaaaaaaaa aaaaaaaaaa aaaaaaaaaa aaaaaaaaaa aaaaaaaaaa aaaaaaaaaa         180
aaaaaaaaaa aaaaaaaaaa aaaaaaaaaa aaaaaaaaaa aaaaaaaaaa aaaaaaaaaa         240
aaaaaaaaaa aaaaaaaaaa aaaaaaaaaa aaaaaaaaaa aaaaaaaaaa aaaaaaaaaa         300
aaaaaaaaaa aaaaaaaaaa aaaaaaaaaa aaaaaaaaaa aaaaaaaaaa aaaaaaaaaa         360
aaaaaaaaaa aaaaaaaaaa aaaaaaaaaa aaaaaaaaaa aaaaaaaaaa aaaaaaaaaa         420
aaaaaaaaaa aaaaaaaaaa aaaaaaaaaa aaaaaaaaaa aaaaaaaaaa aaaaaaaaaa         480
aaaaaaaaaa aaaaaaaaaa aaaaaaaaaa aaaaaaaaaa aaaaaaaaaa aaaaaaaaaa         540
aaaaaaaaaa aaaaaaaaaa aaaaaaaaaa aaaaaaaaaa aaaaaaaaaa aaaaaaaaaa         600
aaaaaaaaaa aaaaaaaaaa aaaaaaaaaa aaaaaaaaaa aaaaaaaaaa aaaaaaaaaa         660
aaaaaaaaaa aaaaaaaaaa aaaaaaaaaa aaaaaaaaaa aaaaaaaaaa aaaaaaaaaa         720
aaaaaaaaaa aaaaaaaaaa aaaaaaaaaa aaaaaaaaaa aaaaaaaaaa aaaaaaaaaa         780
aaaaaaaaaa aaaaaaaaaa aaaaaaaaaa aaaaaaaaaa aaaaaaaaaa aaaaaaaaaa         840
aaaaaaaaaa aaaaaaaaaa aaaaaaaaaa aaaaaaaaaa aaaaaaaaaa aaaaaaaaaa         900
aaaaaaaaaa aaaaaaaaaa aaaaaaaaaa aaaaaaaaaa aaaaaaaaaa aaaaaaaaaa         960
aaaaaaaaaa aaaaaaaaaa aaaaaaaaaa aaaaaaaaaa aaaaaaaaaa aaaaaaaaaa        1020
aaaaaaaaaa aaaaaaaaaa aaaaaaaaaa aaaaaaaaaa aaaaaaaaaa aaaaaaaaaa        1080
aaaaaaaaaa aaaaaaaaaa aaaaaaaaaa aaaaaaaaaa aaaaaaaaaa aaaaaaaaaa        1140
aaaaaaaaaa aaaaaaaaaa aaaaaaaaaa aaaaaaaaaa aaaaaaaaaa aaaaaaaaaa        1200
aaaaaaaaaa aaaaaaaaaa aaaaaaaaaa aaaaaaaaaa aaaaaaaaaa aaaaaaaaaa        1260
aaaaaaaaaa aaaaaaaaaa aaaaaaaaaa aaaaaaaaaa aaaaaaaaaa aaaaaaaaaa        1320
aaaaaaaaaa aaaaaaaaaa aaaaaaaaaa aaaaaaaaaa aaaaaaaaaa aaaaaaaaaa        1380
aaaaaaaaaa aaaaaaaaaa aaaaaaaaaa aaaaaaaaaa aaaaaaaaaa aaaaaaaaaa        1440
aaaaaaaaaa aaaaaaaaaa aaaaaaaaaa aaaaaaaaaa aaaaaaaaaa aaaaaaaaaa        1500
aaaaaaaaaa aaaaaaaaaa aaaaaaaaaa aaaaaaaaaa aaaaaaaaaa aaaaaaaaaa        1560
aaaaaaaaaa aaaaaaaaaa aaaaaaaaaa aaaaaaaaaa aaaaaaaaaa aaaaaaaaaa        1620
aaaaaaaaaa aaaaaaaaaa aaaaaaaaaa aaaaaaaaaa aaaaaaaaaa aaaaaaaaaa        1680
aaaaaaaaaa aaaaaaaaaa aaaaaaaaaa aaaaaaaaaa aaaaaaaaaa aaaaaaaaaa        1740

```
aaaaaaaaaa aaaaaaaaaa aaaaaaaaaa aaaaaaaaaa aaaaaaaaaa aaaaaaaaaa   1800
aaaaaaaaaa aaaaaaaaaa aaaaaaaaaa aaaaaaaaaa aaaaaaaaaa aaaaaaaaaa   1860
aaaaaaaaaa aaaaaaaaaa aaaaaaaaaa aaaaaaaaaa aaaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaaaaaaa aaaaaaaaaa aaaaaaaaaa aaaaaaaaaa aaaaaaaaaa aaaaaaaaaa   2040
aaaaaaaaaa aaaaaaaaaa aaaaaaaaaa aaaaaaaaaa aaaaaaaaaa aaaaaaaaaa   2100
aaaaaaaaaa aaaaaaaaaa aaaaaaaaaa aaaaaaaaaa aaaaaaaaaa aaaaaaaaaa   2160
aaaaaaaaaa aaaaaaaaaa aaaaaaaaaa aaaaaaaaaa aaaaaaaaaa aaaaaaaaaa   2220
aaaaaaaaaa aaaaaaaaaa aaaaaaaaaa aaaaaaaaaa aaaaaaaaaa aaaaaaaaaa   2280
aaaaaaaaaa aaaaaaaaaa aaaaaaaaaa aaaaaaaaaa aaaaaaaaaa aaaaaaaaaa   2340
aaaaaaaaaa aaaaaaaaaa aaaaaaaaaa aaaaaaaaaa aaaaaaaaaa aaaaaaaaaa   2400
aaaaaaaaaa aaaaaaaaaa aaaaaaaaaa aaaaaaaaaa aaaaaaaaaa aaaaaaaaaa   2460
aaaaaaaaaa aaaaaaaaaa aaaaaaaaaa aaaaaaaaaa aaaaaaaaaa aaaaaaaaaa   2520
aaaaaaaaaa aaaaaaaaaa aaaaaaaaaa aaaaaaaaaa aaaaaaaaaa aaaaaaaaaa   2580
aaaaaaaaaa aaaaaaaaaa aaaaaaaaaa aaaaaaaaaa aaaaaaaaaa aaaaaaaaaa   2640
aaaaaaaaaa aaaaaaaaaa aaaaaaaaaa aaaaaaaaaa aaaaaaaaaa aaaaaaaaaa   2700
aaaaaaaaaa aaaaaaaaaa aaaaaaaaaa aaaaaaaaaa aaaaaaaaaa aaaaaaaaaa   2760
aaaaaaaaaa aaaaaaaaaa aaaaaaaaaa aaaaaaaaaa aaaaaaaaaa aaaaaaaaaa   2820
aaaaaaaaaa aaaaaaaaaa aaaaaaaaaa aaaaaaaaaa aaaaaaaaaa aaaaaaaaaa   2880
aaaaaaaaaa aaaaaaaaaa aaaaaaaaaa aaaaaaaaaa aaaaaaaaaa aaaaaaaaaa   2940
aaaaaaaaaa aaaaaaaaaa aaaaaaaaaa aaaaaaaaaa aaaaaaaaaa aaaaaaaaaa   3000
aaaaaaaaaa aaaaaaaaaa aaaaaaaaaa aaaaaaaaaa aaaaaaaaaa aaaaaaaaaa   3060
aaaaaaaaaa aaaaaaaaaa aaaaaaaaaa aaaaaaaaaa aaaaaaaaaa aaaaaaaaaa   3120
aaaaaaaaaa aaaaaaaaaa aaaaaaaaaa aaaaaaaaaa aaaaaaaaaa aaaaaaaaaa   3180
aaaaaaaaaa aaaaaaaaaa aaaaaaaaaa aaaaaaaaaa aaaaaaaaaa aaaaaaaaaa   3240
aaaaaaaaaa aaaaaaaaaa aaaaaaaaaa aaaaaaaaaa aaaaaaaaaa aaaaaaaaaa   3300
aaaaaaaaaa aaaaaaaaaa aaaaaaaaaa aaaaaaaaaa aaaaaaaaaa aaaaaaaaaa   3360
aaaaaaaaaa aaaaaaaaaa aaaaaaaaaa aaaaaaaaaa aaaaaaaaaa aaaaaaaaaa   3420
aaaaaaaaaa aaaaaaaaaa aaaaaaaaaa aaaaaaaaaa aaaaaaaaaa aaaaaaaaaa   3480
aaaaaaaaaa aaaaaaaaaa aaaaaaaaaa aaaaaaaaaa aaaaaaaaaa aaaaaaaaaa   3540
aaaaaaaaaa aaaaaaaaaa aaaaaaaaaa aaaaaaaaaa aaaaaaaaaa aaaaaaaaaa   3600
aaaaaaaaaa aaaaaaaaaa aaaaaaaaaa aaaaaaaaaa aaaaaaaaaa aaaaaaaaaa   3660
aaaaaaaaaa aaaaaaaaaa aaaaaaaaaa aaaaaaaaaa aaaaaaaaaa aaaaaaaaaa   3720
aaaaaaaaaa aaaaaaaaaa aaaaaaaaaa aaaaaaaaaa aaaaaaaaaa aaaaaaaaaa   3780
aaaaaaaaaa aaaaaaaaaa aaaaaaaaaa aaaaaaaaaa aaaaaaaaaa aaaaaaaaaa   3840
aaaaaaaaaa aaaaaaaaaa aaaaaaaaaa aaaaaaaaaa aaaaaaaaaa aaaaaaaaaa   3900
aaaaaaaaaa aaaaaaaaaa aaaaaaaaaa aaaaaaaaaa aaaaaaaaaa aaaaaaaaaa   3960
aaaaaaaaaa aaaaaaaaaa aaaaaaaaaa aaaaaaaaaa aaaaaaaaaa aaaaaaaaaa   4020
aaaaaaaaaa aaaaaaaaaa aaaaaaaaaa aaaaaaaaaa aaaaaaaaaa aaaaaaaaaa   4080
```

```
aaaaaaaaaa aaaaaaaaaa aaaaaaaaaa aaaaaaaaaa aaaaaaaaaa aaaaaaaaaa    4140
aaaaaaaaaa aaaaaaaaaa aaaaaaaaaa aaaaaaaaaa aaaaaaaaaa aaaaaaaaaa    4200
aaaaaaaaaa aaaaaaaaaa aaaaaaaaaa aaaaaaaaaa aaaaaaaaaa aaaaaaaaaa    4260
aaaaaaaaaa aaaaaaaaaa aaaaaaaaaa aaaaaaaaaa aaaaaaaaaa aaaaaaaaaa    4320
aaaaaaaaaa aaaaaaaaaa aaaaaaaaaa aaaaaaaaaa aaaaaaaaaa aaaaaaaaaa    4380
aaaaaaaaaa aaaaaaaaaa aaaaaaaaaa aaaaaaaaaa aaaaaaaaaa aaaaaaaaaa    4440
aaaaaaaaaa aaaaaaaaaa aaaaaaaaaa aaaaaaaaaa aaaaaaaaaa aaaaaaaaaa    4500
aaaaaaaaaa aaaaaaaaaa aaaaaaaaaa aaaaaaaaaa aaaaaaaaaa aaaaaaaaaa    4560
aaaaaaaaaa aaaaaaaaaa aaaaaaaaaa aaaaaaaaaa aaaaaaaaaa aaaaaaaaaa    4620
aaaaaaaaaa aaaaaaaaaa aaaaaaaaaa aaaaaaaaaa aaaaaaaaaa aaaaaaaaaa    4680
aaaaaaaaaa aaaaaaaaaa aaaaaaaaaa aaaaaaaaaa aaaaaaaaaa aaaaaaaaaa    4740
aaaaaaaaaa aaaaaaaaaa aaaaaaaaaa aaaaaaaaaa aaaaaaaaaa aaaaaaaaaa    4800
aaaaaaaaaa aaaaaaaaaa aaaaaaaaaa aaaaaaaaaa aaaaaaaaaa aaaaaaaaaa    4860
aaaaaaaaaa aaaaaaaaaa aaaaaaaaaa aaaaaaaaaa aaaaaaaaaa aaaaaaaaaa    4920
aaaaaaaaaa aaaaaaaaaa aaaaaaaaaa aaaaaaaaaa aaaaaaaaaa aaaaaaaaaa    4980
aaaaaaaaaa aaaaaaaaaa                                                5000

<210> SEQ ID NO 34
<211> LENGTH: 400
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(400)
<223> OTHER INFORMATION: This sequence may encompass 100-400 nucleotides
      wherein some positions may be absent
<220> FEATURE:
<223> OTHER INFORMATION: See specification as filed for detailed
      description of substitutions and preferred embodiments

<400> SEQUENCE: 34
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa aaaaaaaaaa aaaaaaaaaa aaaaaaaaaa aaaaaaaaaa aaaaaaaaaa     300
aaaaaaaaaa aaaaaaaaaa aaaaaaaaaa aaaaaaaaaa aaaaaaaaaa aaaaaaaaaa     360
aaaaaaaaaa aaaaaaaaaa aaaaaaaaaa aaaaaaaaaa                           400

<210> SEQ ID NO 35
<211> LENGTH: 2000
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(2000)
<223> OTHER INFORMATION: This sequence may encompass 50-2,000
      nucleotides wherein some positions may be absent
<220> FEATURE:
```

<223> OTHER INFORMATION: See specification as filed for detailed
       description of substitutions and preferred embodiments

<400> SEQUENCE: 35

```
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa aaaaaaaaaa aaaaaaaaaa aaaaaaaaaa aaaaaaaaaa aaaaaaaaaa     300
aaaaaaaaaa aaaaaaaaaa aaaaaaaaaa aaaaaaaaaa aaaaaaaaaa aaaaaaaaaa     360
aaaaaaaaaa aaaaaaaaaa aaaaaaaaaa aaaaaaaaaa aaaaaaaaaa aaaaaaaaaa     420
aaaaaaaaaa aaaaaaaaaa aaaaaaaaaa aaaaaaaaaa aaaaaaaaaa aaaaaaaaaa     480
aaaaaaaaaa aaaaaaaaaa aaaaaaaaaa aaaaaaaaaa aaaaaaaaaa aaaaaaaaaa     540
aaaaaaaaaa aaaaaaaaaa aaaaaaaaaa aaaaaaaaaa aaaaaaaaaa aaaaaaaaaa     600
aaaaaaaaaa aaaaaaaaaa aaaaaaaaaa aaaaaaaaaa aaaaaaaaaa aaaaaaaaaa     660
aaaaaaaaaa aaaaaaaaaa aaaaaaaaaa aaaaaaaaaa aaaaaaaaaa aaaaaaaaaa     720
aaaaaaaaaa aaaaaaaaaa aaaaaaaaaa aaaaaaaaaa aaaaaaaaaa aaaaaaaaaa     780
aaaaaaaaaa aaaaaaaaaa aaaaaaaaaa aaaaaaaaaa aaaaaaaaaa aaaaaaaaaa     840
aaaaaaaaaa aaaaaaaaaa aaaaaaaaaa aaaaaaaaaa aaaaaaaaaa aaaaaaaaaa     900
aaaaaaaaaa aaaaaaaaaa aaaaaaaaaa aaaaaaaaaa aaaaaaaaaa aaaaaaaaaa     960
aaaaaaaaaa aaaaaaaaaa aaaaaaaaaa aaaaaaaaaa aaaaaaaaaa aaaaaaaaaa    1020
aaaaaaaaaa aaaaaaaaaa aaaaaaaaaa aaaaaaaaaa aaaaaaaaaa aaaaaaaaaa    1080
aaaaaaaaaa aaaaaaaaaa aaaaaaaaaa aaaaaaaaaa aaaaaaaaaa aaaaaaaaaa    1140
aaaaaaaaaa aaaaaaaaaa aaaaaaaaaa aaaaaaaaaa aaaaaaaaaa aaaaaaaaaa    1200
aaaaaaaaaa aaaaaaaaaa aaaaaaaaaa aaaaaaaaaa aaaaaaaaaa aaaaaaaaaa    1260
aaaaaaaaaa aaaaaaaaaa aaaaaaaaaa aaaaaaaaaa aaaaaaaaaa aaaaaaaaaa    1320
aaaaaaaaaa aaaaaaaaaa aaaaaaaaaa aaaaaaaaaa aaaaaaaaaa aaaaaaaaaa    1380
aaaaaaaaaa aaaaaaaaaa aaaaaaaaaa aaaaaaaaaa aaaaaaaaaa aaaaaaaaaa    1440
aaaaaaaaaa aaaaaaaaaa aaaaaaaaaa aaaaaaaaaa aaaaaaaaaa aaaaaaaaaa    1500
aaaaaaaaaa aaaaaaaaaa aaaaaaaaaa aaaaaaaaaa aaaaaaaaaa aaaaaaaaaa    1560
aaaaaaaaaa aaaaaaaaaa aaaaaaaaaa aaaaaaaaaa aaaaaaaaaa aaaaaaaaaa    1620
aaaaaaaaaa aaaaaaaaaa aaaaaaaaaa aaaaaaaaaa aaaaaaaaaa aaaaaaaaaa    1680
aaaaaaaaaa aaaaaaaaaa aaaaaaaaaa aaaaaaaaaa aaaaaaaaaa aaaaaaaaaa    1740
aaaaaaaaaa aaaaaaaaaa aaaaaaaaaa aaaaaaaaaa aaaaaaaaaa aaaaaaaaaa    1800
aaaaaaaaaa aaaaaaaaaa aaaaaaaaaa aaaaaaaaaa aaaaaaaaaa aaaaaaaaaa    1860
aaaaaaaaaa aaaaaaaaaa aaaaaaaaaa aaaaaaaaaa aaaaaaaaaa aaaaaaaaaa    1920
aaaaaaaaaa aaaaaaaaaa aaaaaaaaaa aaaaaaaaaa aaaaaaaaaa aaaaaaaaaa    1980
aaaaaaaaaa aaaaaaaaaa                                                2000
```

<210> SEQ ID NO 36
<211> LENGTH: 230
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 36

| Glu | Ser | Lys | Tyr | Gly | Pro | Pro | Cys | Pro | Pro | Cys | Pro | Ala | Pro | Glu | Phe |
|---|---|---|---|---|---|---|---|---|---|---|---|---|---|---|---|
| 1 | | | | 5 | | | | | 10 | | | | | 15 | |

| Leu | Gly | Gly | Pro | Ser | Val | Phe | Leu | Phe | Pro | Pro | Lys | Pro | Lys | Asp | Thr |
|---|---|---|---|---|---|---|---|---|---|---|---|---|---|---|---|
| | | | | 20 | | | | | 25 | | | | | 30 | |

| Leu | Met | Ile | Ser | Arg | Thr | Pro | Glu | Val | Thr | Cys | Val | Val | Val | Asp | Val |
|---|---|---|---|---|---|---|---|---|---|---|---|---|---|---|---|
| | | | 35 | | | | | 40 | | | | | 45 | | |

| Ser | Gln | Glu | Asp | Pro | Glu | Val | Gln | Phe | Asn | Trp | Tyr | Val | Asp | Gly | Val |
|---|---|---|---|---|---|---|---|---|---|---|---|---|---|---|---|
| | 50 | | | | | 55 | | | | | 60 | | | | |

| Glu | Val | His | Asn | Ala | Lys | Thr | Lys | Pro | Arg | Glu | Glu | Gln | Phe | Asn | Ser |
|---|---|---|---|---|---|---|---|---|---|---|---|---|---|---|---|
| 65 | | | | | 70 | | | | | 75 | | | | | 80 |

| Thr | Tyr | Arg | Val | Val | Ser | Val | Leu | Thr | Val | Leu | His | Gln | Asp | Trp | Leu |
|---|---|---|---|---|---|---|---|---|---|---|---|---|---|---|---|
| | | | | 85 | | | | | 90 | | | | | 95 | |

| Asn | Gly | Lys | Glu | Tyr | Lys | Cys | Lys | Val | Ser | Asn | Lys | Gly | Leu | Pro | Ser |
|---|---|---|---|---|---|---|---|---|---|---|---|---|---|---|---|
| | | | | 100 | | | | | 105 | | | | | 110 | |

| Ser | Ile | Glu | Lys | Thr | Ile | Ser | Lys | Ala | Lys | Gly | Gln | Pro | Arg | Glu | Pro |
|---|---|---|---|---|---|---|---|---|---|---|---|---|---|---|---|
| | | | 115 | | | | | 120 | | | | | 125 | | |

| Gln | Val | Tyr | Thr | Leu | Pro | Pro | Ser | Gln | Glu | Glu | Met | Thr | Lys | Asn | Gln |
|---|---|---|---|---|---|---|---|---|---|---|---|---|---|---|---|
| | 130 | | | | | 135 | | | | | 140 | | | | |

| Val | Ser | Leu | Thr | Cys | Leu | Val | Lys | Gly | Phe | Tyr | Pro | Ser | Asp | Ile | Ala |
|---|---|---|---|---|---|---|---|---|---|---|---|---|---|---|---|
| 145 | | | | | 150 | | | | | 155 | | | | | 160 |

| Val | Glu | Trp | Glu | Ser | Asn | Gly | Gln | Pro | Glu | Asn | Asn | Tyr | Lys | Thr | Thr |
|---|---|---|---|---|---|---|---|---|---|---|---|---|---|---|---|
| | | | | 165 | | | | | 170 | | | | | 175 | |

| Pro | Pro | Val | Leu | Asp | Ser | Asp | Gly | Ser | Phe | Phe | Leu | Tyr | Ser | Arg | Leu |
|---|---|---|---|---|---|---|---|---|---|---|---|---|---|---|---|
| | | | 180 | | | | | 185 | | | | | 190 | | |

| Thr | Val | Asp | Lys | Ser | Arg | Trp | Gln | Glu | Gly | Asn | Val | Phe | Ser | Cys | Ser |
|---|---|---|---|---|---|---|---|---|---|---|---|---|---|---|---|
| | | 195 | | | | | 200 | | | | | 205 | | | |

| Val | Met | His | Glu | Ala | Leu | His | Asn | His | Tyr | Thr | Gln | Lys | Ser | Leu | Ser |
|---|---|---|---|---|---|---|---|---|---|---|---|---|---|---|---|
| 210 | | | | | 215 | | | | | 220 | | | | | |

| Leu | Ser | Leu | Gly | Lys | Met |
|---|---|---|---|---|---|
| 225 | | | | 230 | |

<210> SEQ ID NO 37
<211> LENGTH: 690
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 37

```
gagagcaagt acggccctcc ctgccccct  tgccctgccc  ccgagttcct gggcggaccc      60
agcgtgttcc tgttcccccc caagcccaag  acaccctga  tgatcagccg gaccccgag     120
gtgacctgtg tggtggtgga cgtgtcccag  gaggacccg  aggtccagtt caactggtac     180
gtggacggcg tggaggtgca caacgccaag  accaagcccc gggaggagca gttcaatagc     240
acctaccggg tggtgtccgt gctgaccgtg  ctgcaccagg actggctgaa cggcaaggaa     300
tacaagtgta aggtgtccaa caagggcctg  cccagcagca tcgagaaaac catcagcaag     360
gccaagggcc agcctcggga gccccaggtg  tacaccctgc cccctagcca agaggagatg     420
accaagaacc aggtgtccct gacctgcctg  gtgaagggct  ctacccccag cgacatcgcc     480
gtggagtggg agagcaacgg ccagcccgag  aacaactaca gaccacccc  ccctgtgctg     540
```

```
gacagcgacg gcagcttctt cctgtacagc cggctgaccg tggacaagag ccggtggcag    600
gagggcaacg tctttagctg ctccgtgatg cacgaggccc tgcacaacca ctacacccag    660
aagagcctga gcctgtccct gggcaagatg                                     690
```

<210> SEQ ID NO 38
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(40)
<223> OTHER INFORMATION: This sequence may encompass 1-10 "Gly Gly Gly
      Ser" repeating units wherein some positions may be absent
<220> FEATURE:
<223> OTHER INFORMATION: See specification as filed for detailed
      description of substitutions and preferred embodiments

<400> SEQUENCE: 38

```
Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40
```

<210> SEQ ID NO 39
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

```
Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Gly Arg Tyr Tyr Gly Met Asp Val Trp Gly Gln Gly Thr Met
            100                 105                 110

Val Thr Val Ser Ser Gly Gly Gly Gly Ser Gly Gly Gly Gly Ser Gly
        115                 120                 125

Gly Gly Ser Gly Gly Gly Gly Ser Glu Ile Val Leu Thr Gln Ser
    130                 135                 140

Pro Ala Thr Leu Ser Leu Ser Pro Gly Glu Arg Ala Thr Ile Ser Cys
145                 150                 155                 160

Arg Ala Ser Gln Ser Val Ser Ser Asn Phe Ala Trp Tyr Gln Gln Arg
                165                 170                 175

Pro Gly Gln Ala Pro Arg Leu Leu Ile Tyr Asp Ala Ser Asn Arg Ala
```

```
            180                 185                 190
Thr Gly Ile Pro Pro Arg Phe Ser Gly Ser Gly Ser Gly Thr Asp Phe
        195                 200                 205

Thr Leu Thr Ile Ser Ser Leu Glu Pro Glu Asp Phe Ala Ala Tyr Tyr
        210                 215                 220

Cys His Gln Arg Ser Asn Trp Leu Tyr Thr Phe Gly Gln Gly Thr Lys
225                 230                 235                 240

Val Asp Ile Lys

<210> SEQ ID NO 40
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Leu Arg Arg Thr Val Val Thr Pro Arg Ala Tyr Tyr Gly
            100                 105                 110

Met Asp Val Trp Gly Gln Gly Thr Thr Val Thr Val Ser Ser Gly Gly
        115                 120                 125

Gly Gly Ser Gly Gly Gly Gly Ser Gly Gly Gly Gly Ser Gly Gly Gly
    130                 135                 140

Gly Ser Asp Ile Gln Leu Thr Gln Ser Pro Ser Thr Leu Ser Ala Ser
145                 150                 155                 160

Val Gly Asp Arg Val Thr Ile Thr Cys Gln Ala Ser Gln Asp Ile Ser
                165                 170                 175

Asn Ser Leu Asn Trp Tyr Gln Gln Lys Ala Gly Lys Ala Pro Lys Leu
            180                 185                 190

Leu Ile Tyr Asp Ala Ser Thr Leu Glu Thr Gly Val Pro Ser Arg Phe
        195                 200                 205

Ser Gly Ser Gly Ser Gly Thr Asp Phe Ser Phe Thr Ile Ser Ser Leu
    210                 215                 220

Gln Pro Glu Asp Ile Ala Thr Tyr Tyr Cys Gln Gln His Asp Asn Leu
225                 230                 235                 240

Pro Leu Thr Phe Gly Gln Gly Thr Lys Val Glu Ile Lys
                245                 250

<210> SEQ ID NO 41
<211> LENGTH: 246
<212> TYPE: PRT
<213> ORGANISM: Artificial Sequence
<220> FEATURE:
<223> OTHER INFORMATION: Description of Artificial Sequence: Synthetic
```

<400> SEQUENCE: 41

```
Gln Val Gln Leu Val Gln Ser Gly Ala Glu Val Lys Lys Pro Gly Ala
1               5                   10                  15

Pro Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Glu Trp Asp Gly Ser Tyr Tyr Tyr Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Asp Ile Val Leu
    130                 135                 140

Thr Gln Thr Pro Ser Ser Leu Ser Ala Ser Val Gly Asp Arg Val Thr
145                 150                 155                 160

Ile Thr Cys Arg Ala Ser Gln Ser Ile Asn Thr Tyr Leu Asn Trp Tyr
                165                 170                 175

Gln His Lys Pro Gly Lys Ala Pro Lys Leu Leu Ile Tyr Ala Ala Ser
            180                 185                 190

Ser Leu Gln Ser Gly Val Pro Ser Arg Phe Ser Gly Ser Gly Ser Gly
        195                 200                 205

Thr Asp Phe Thr Leu Thr Ile Ser Ser Leu Gln Pro Glu Asp Phe Ala
    210                 215                 220

Thr Tyr Tyr Cys Gln Gln Ser Phe Ser Pro Leu Thr Phe Gly Gly Gly
225                 230                 235                 240

Thr Lys Leu Glu Ile Lys
                245
```

<210> SEQ ID NO 42
<211> LENGTH: 242
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Val Pro Gly Lys Gly Leu Val Trp Val
        35                  40                  45

Ser Arg Ile Asn Thr Asp Gly Ser Thr Thr Tyr Ala Asp Ser Val
    50                  55                  60

Glu Gly Arg Phe Thr Ile Ser Arg Asp Asn Ala Lys Asn Thr Leu Tyr
65                  70                  75                  80

Leu Gln Met Asn Ser Leu Arg Asp Asp Asp Thr Ala Val Tyr Tyr Cys
```

```
                    85                  90                  95
Val Gly Gly His Trp Ala Val Trp Gly Gln Gly Thr Thr Val Thr Val
                100                 105                 110

Ser Ser Gly Gly Gly Ser Gly Gly Gly Ser Gly Gly Gly
        115                 120                 125

Ser Gly Gly Gly Ser Asp Ile Gln Met Thr Gln Ser Pro Ser Thr
        130                 135                 140

Leu Ser Ala Ser Val Gly Asp Arg Val Thr Ile Thr Cys Arg Ala Ser
145                 150                 155                 160

Gln Ser Ile Ser Asp Arg Leu Ala Trp Tyr Gln Gln Lys Pro Gly Lys
                165                 170                 175

Ala Pro Lys Leu Leu Ile Tyr Lys Ala Ser Ser Leu Glu Ser Gly Val
                180                 185                 190

Pro Ser Arg Phe Ser Gly Ser Gly Ser Gly Thr Glu Phe Thr Leu Thr
                195                 200                 205

Ile Ser Ser Leu Gln Pro Asp Asp Phe Ala Val Tyr Tyr Cys Gln Gln
        210                 215                 220

Tyr Gly His Leu Pro Met Tyr Thr Phe Gly Gln Gly Thr Lys Val Glu
225                 230                 235                 240

Ile Lys

<210> SEQ ID NO 43
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Val Gln Leu Val Gln Ser Gly Ala Glu Val Glu Lys Pro Gly Ala
1               5                   10                  15

Ser Val Lys Val Ser Cys Lys Ala Ser Gly Tyr Thr Phe Thr Asp Tyr
                20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Ser Gly Trp Asp Phe Asp Tyr Trp Gly Gln Gly Thr Leu Val Thr
                100                 105                 110

Val Ser Ser Gly Gly Gly Gly Ser Gly Gly Gly Gly Ser Gly Gly Gly
                115                 120                 125

Gly Ser Gly Gly Gly Gly Ser Asp Ile Val Met Thr Gln Ser Pro Ser
        130                 135                 140

Ser Leu Ser Ala Ser Val Gly Asp Arg Val Thr Ile Thr Cys Arg Ala
145                 150                 155                 160

Ser Gln Ser Ile Arg Tyr Tyr Leu Ser Trp Tyr Gln Gln Lys Pro Gly
                165                 170                 175

Lys Ala Pro Lys Leu Leu Ile Tyr Thr Ala Ser Ile Leu Gln Asn Gly
                180                 185                 190

Val Pro Ser Arg Phe Ser Gly Ser Gly Ser Gly Thr Asp Phe Thr Leu
```

```
                195                 200                 205
Thr Ile Ser Ser Leu Gln Pro Glu Asp Phe Ala Thr Tyr Tyr Cys Leu
    210                 215                 220
Gln Thr Tyr Thr Thr Pro Asp Phe Gly Pro Gly Thr Lys Val Glu Ile
225                 230                 235                 240
Lys

<210> SEQ ID NO 44
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Arg Leu Ile Ala Val Ala Gly Asp Tyr Tyr Tyr Tyr Gly
            100                 105                 110

Met Asp Val Trp Gly Gln Gly Thr Met Val Thr Val Ser Ser Gly Gly
        115                 120                 125

Gly Gly Ser Gly Gly Gly Gly Ser Gly Gly Gly Gly Ser Gly Gly Gly
    130                 135                 140

Gly Ser Asp Ile Gln Met Thr Gln Ser Pro Ser Ser Val Ser Ala Ser
145                 150                 155                 160

Val Gly Asp Arg Val Thr Ile Thr Cys Arg Ala Ser Gln Gly Val Gly
                165                 170                 175

Arg Trp Leu Ala Trp Tyr Gln Gln Lys Pro Gly Thr Ala Pro Lys Leu
            180                 185                 190

Leu Ile Tyr Ala Ala Ser Thr Leu Gln Ser Gly Val Pro Ser Arg Phe
        195                 200                 205

Ser Gly Ser Gly Ser Gly Thr Asp Phe Thr Leu Thr Ile Asn Asn Leu
    210                 215                 220

Gln Pro Glu Asp Phe Ala Thr Tyr Tyr Cys Gln Gln Ala Asn Ser Phe
225                 230                 235                 240

Pro Leu Thr Phe Gly Gly Gly Thr Arg Leu Glu Ile Lys
                245                 250

<210> SEQ ID NO 45
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45
```

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Lys Val Ser Ser Ser Pro Ala Phe Asp Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Gly Ser Gly Gly Gly Ser Glu Ile Val
    130                 135                 140

Leu Thr Gln Ser Pro Ala Thr Leu Ser Leu Ser Pro Gly Glu Arg Ala
145                 150                 155                 160

Ile Leu Ser Cys Arg Ala Ser Gln Ser Val Tyr Thr Lys Tyr Leu Gly
                165                 170                 175

Trp Tyr Gln Gln Lys Pro Gly Gln Ala Pro Arg Leu Leu Ile Tyr Asp
            180                 185                 190

Ala Ser Thr Arg Ala Thr Gly Ile Pro Asp Arg Phe Ser Gly Ser Gly
            195                 200                 205

Ser Gly Thr Asp Phe Thr Leu Thr Ile Asn Arg Leu Glu Pro Glu Asp
        210                 215                 220

Phe Ala Val Tyr Tyr Cys Gln His Tyr Gly Gly Ser Pro Leu Ile Thr
225                 230                 235                 240

Phe Gly Gln Gly Thr Arg Leu Glu Ile Lys
                245                 250

<210> SEQ ID NO 46
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Val Gln Leu Gln Gln Ser Gly Ala Glu Val Lys Lys Pro Gly Ala
1               5                   10                  15

Ser Val Lys Val Ser Cys Lys Thr Ser Gly Tyr Pro Phe Thr Gly Tyr
            20                  25                  30

Ser Leu His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Tyr Gly Gly Asn Ser Leu Phe Tyr Trp Gly Gln Gly

```
                 100                 105                 110
Thr Leu Val Thr Val Ser Ser Gly Gly Gly Ser Gly Gly Gly
            115                 120                 125

Ser Gly Gly Gly Ser Gly Gly Gly Ser Asp Ile Gln Leu Thr
130                 135                 140

Gln Ser Pro Ser Ser Ile Ser Ala Ser Val Gly Asp Thr Val Ser Ile
145                 150                 155                 160

Thr Cys Arg Ala Ser Gln Asp Ser Gly Thr Trp Leu Ala Trp Tyr Gln
                165                 170                 175

Gln Lys Pro Gly Lys Ala Pro Asn Leu Leu Met Tyr Asp Ala Ser Thr
            180                 185                 190

Leu Glu Asp Gly Val Pro Ser Arg Phe Ser Gly Ser Ala Ser Gly Thr
            195                 200                 205

Glu Phe Thr Leu Thr Val Asn Arg Leu Gln Pro Glu Asp Ser Ala Thr
            210                 215                 220

Tyr Tyr Cys Gln Gln Tyr Asn Ser Tyr Pro Leu Thr Phe Gly Gly Gly
225                 230                 235                 240

Thr Lys Val Asp Ile Lys
            245

<210> SEQ ID NO 47
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Val Gln Leu Val Gln Ser Gly Ala Glu Val Lys Lys Pro Gly Ala
1               5                   10                  15

Ser Val Glu Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Gly Tyr Ala Gln Lys Phe
    50                  55                  60

Gln Gly Arg Val Thr Met Thr Arg Asp Thr Ser Thr Ser Thr Val His
65                  70                  75                  80

Met Glu Leu Ser Ser Leu Arg Ser Glu Asp Thr Ala Val Tyr Tyr Cys
                85                  90                  95

Ala Arg Gly Gly Tyr Ser Ser Ser Asp Ala Phe Asp Ile Trp Gly
            100                 105                 110

Gln Gly Thr Met Val Thr Val Ser Ser Gly Gly Gly Ser Gly Gly
        115                 120                 125

Gly Gly Ser Gly Gly Gly Ser Gly Gly Gly Ser Asp Ile Gln
130                 135                 140

Met Thr Gln Ser Pro Ser Ser Leu Ser Ala Ser Val Gly Asp Arg Val
145                 150                 155                 160

Thr Ile Thr Cys Arg Ala Ser Gln Asp Ile Ser Ser Ala Leu Ala Trp
                165                 170                 175

Tyr Gln Gln Lys Pro Gly Thr Pro Pro Lys Leu Leu Ile Tyr Asp Ala
            180                 185                 190

Ser Ser Leu Glu Ser Gly Val Pro Ser Arg Phe Ser Gly Ser Gly Ser
        195                 200                 205
```

```
Gly Thr Asp Phe Thr Leu Thr Ile Ser Ser Leu Gln Pro Glu Asp Phe
            210                 215                 220

Ala Thr Tyr Tyr Cys Gln Gln Phe Ser Ser Tyr Pro Leu Thr Phe Gly
225                 230                 235                 240

Gly Gly Thr Arg Leu Glu Ile Lys
                245

<210> SEQ ID NO 48
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Ala Gly Ile Tyr Tyr Tyr Gly Met Asp Val Trp
                100                 105                 110

Gly Gln Gly Thr Thr Ile Thr Val Ser Ser Gly Gly Gly Gly Ser Gly
            115                 120                 125

Gly Gly Gly Ser Gly Gly Gly Ser Gly Gly Gly Ser Asp Ile
        130                 135                 140

Val Met Thr Gln Thr Pro Asp Ser Leu Ala Val Ser Leu Gly Glu Arg
145                 150                 155                 160

Ala Thr Ile Ser Cys Lys Ser Ser His Ser Val Leu Tyr Asn Arg Asn
                165                 170                 175

Asn Lys Asn Tyr Leu Ala Trp Tyr Gln Gln Lys Pro Gly Gln Pro Pro
            180                 185                 190

Lys Leu Leu Phe Tyr Trp Ala Ser Thr Arg Lys Ser Gly Val Pro Asp
        195                 200                 205

Arg Phe Ser Gly Ser Gly Ser Gly Thr Asp Phe Thr Leu Thr Ile Ser
    210                 215                 220

Ser Leu Gln Pro Glu Asp Phe Ala Thr Tyr Phe Cys Gln Gln Thr Gln
225                 230                 235                 240

Thr Phe Pro Leu Thr Phe Gly Gln Gly Thr Arg Leu Glu Ile Asn
                245                 250                 255

<210> SEQ ID NO 49
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49
```

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Asn Phe
    50                  55                  60

Gln Gly Arg Val Thr Met Thr Arg Asp Thr Ser Ile Ser Thr Ala Tyr
65                  70                  75                  80

Met Glu Leu Arg Arg Leu Arg Ser Asp Asp Thr Ala Val Tyr Tyr Cys
                85                  90                  95

Ala Ser Gly Trp Asp Phe Asp Tyr Trp Gly Gln Gly Thr Leu Val Thr
            100                 105                 110

Val Ser Gly Gly Gly Gly Ser Gly Gly Gly Ser Gly Gly Gly
            115                 120                 125

Gly Ser Gly Gly Gly Gly Ser Asp Ile Arg Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Ser Ile Arg Tyr Tyr Leu Ser Trp Tyr Gln Gln Lys Pro Gly
                165                 170                 175

Lys Ala Pro Lys Leu Leu Ile Tyr Thr Ala Ser Ile Leu Gln Asn Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Leu
210                 215                 220

Gln Thr Tyr Thr Thr Pro Asp Phe Gly Pro Gly Thr Lys Val Glu Ile
225                 230                 235                 240

Lys

<210> SEQ ID NO 50
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Thr Thr Thr Ser Tyr Ala Phe Asp Ile Trp Gly Gln Gly Thr
            100                 105                 110

```
Met Val Thr Val Ser Ser Gly Gly Gly Ser Gly Gly Gly Ser
            115                 120                 125

Gly Gly Gly Gly Ser Gly Gly Gly Ser Asp Ile Gln Leu Thr Gln
        130                 135                 140

Ser Pro Ser Thr Leu Ser Ala Ser Val Gly Asp Arg Val Thr Ile Thr
145                 150                 155                 160

Cys Arg Ala Ser Gln Ser Ile Ser Thr Trp Leu Ala Trp Tyr Gln Gln
                165                 170                 175

Lys Pro Gly Lys Ala Pro Asn Leu Leu Ile Tyr Lys Ala Ser Thr Leu
                180                 185                 190

Glu Ser Gly Val Pro Ser Arg Phe Ser Gly Ser Gly Ser Gly Thr Glu
            195                 200                 205

Phe Thr Leu Thr Ile Ser Ser Leu Gln Pro Asp Asp Phe Ala Thr Tyr
        210                 215                 220

Tyr Cys Gln Gln Tyr Asn Thr Tyr Ser Pro Tyr Thr Phe Gly Gln Gly
225                 230                 235                 240

Thr Lys Leu Glu Ile Lys
                245

<210> SEQ ID NO 51
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Val Gln Leu Val Gln Ser Gly Gly Gly Leu Val Lys Pro Gly Gly
1               5                   10                  15

Ser Leu Arg Leu Ser Cys Glu Ala Ser Gly Phe Ile Phe Ser Asp Tyr
            20                  25                  30

Tyr Met Gly Trp Ile Arg Gln Ala Pro Gly Lys Gly Leu Glu Trp Val
        35                  40                  45

Ser Tyr Ile Gly Arg Ser Gly Ser Ser Met Tyr Tyr Ala Asp Ser Val
    50                  55                  60

Lys Gly Arg Phe Thr Phe Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ala Ser Pro Val Val Ala Thr Glu Asp Phe Gln His Trp Gly
                100                 105                 110

Gln Gly Thr Leu Val Thr Val Ser Ser Gly Gly Gly Ser Gly Gly
            115                 120                 125

Gly Gly Ser Gly Gly Gly Ser Gly Gly Gly Ser Asp Ile Val
        130                 135                 140

Met Thr Gln Thr Pro Ala Thr Leu Ser Leu Ser Pro Gly Glu Arg Ala
145                 150                 155                 160

Thr Leu Ser Cys Arg Ala Ser Gln Ser Val Thr Ser Asn Tyr Leu Ala
                165                 170                 175

Trp Tyr Gln Gln Lys Pro Gly Gln Ala Pro Arg Leu Leu Phe Gly
                180                 185                 190

Ala Ser Thr Arg Ala Thr Gly Ile Pro Asp Arg Phe Ser Gly Ser Gly
            195                 200                 205

Ser Gly Thr Asp Phe Thr Leu Thr Ile Asn Arg Leu Glu Pro Glu Asp
        210                 215                 220
```

```
Phe Ala Met Tyr Tyr Cys Gln Gln Tyr Gly Ser Ala Pro Val Thr Phe
225                 230                 235                 240

Gly Gln Gly Thr Lys Leu Glu Ile Lys
            245

<210> SEQ ID NO 52
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Val Gln Leu Val Gln Ser Gly Ala Glu Val Arg Ala Pro Gly Ala
1               5                   10                  15

Ser Val Lys Ile Ser Cys Lys Ala Ser Gly Phe Thr Phe Arg Gly Tyr
            20                  25                  30

Tyr Ile His Trp Val Arg Gln Ala Pro Gly Gln Gly Leu Glu Trp Met
        35                  40                  45

Gly Ile Ile Asn Pro Ser Gly Gly Ser Arg Ala Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Asp Asp Thr Ala Met Tyr Tyr Cys
                85                  90                  95

Ala Arg Thr Ala Ser Cys Gly Gly Asp Cys Tyr Tyr Leu Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ser Gly Gly Gly Gly Ser Asp Ile
    130                 135                 140

Gln Met Thr Gln Ser Pro Pro Thr Leu Ser Ala Ser Val Gly Asp Arg
145                 150                 155                 160

Val Thr Ile Thr Cys Arg Ala Ser Glu Asn Val Asn Ile Trp Leu Ala
                165                 170                 175

Trp Tyr Gln Gln Lys Pro Gly Lys Ala Pro Lys Leu Leu Ile Tyr Lys
            180                 185                 190

Ser Ser Ser Leu Ala Ser Gly Val Pro Ser Arg Phe Ser Gly Ser Gly
        195                 200                 205

Ser Gly Ala Glu Phe Thr Leu Thr Ile Ser Ser Leu Gln Pro Asp Asp
    210                 215                 220

Phe Ala Thr Tyr Tyr Cys Gln Gln Tyr Gln Ser Tyr Pro Leu Thr Phe
225                 230                 235                 240

Gly Gly Gly Thr Lys Val Asp Ile Lys
            245

<210> SEQ ID NO 53
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Val Gln Leu Val Gln Ser Gly Gly Gly Leu Val Gln Pro Gly Arg
1               5                   10                  15
```

```
Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Ser Ser Ser Trp Ser Trp Gly Tyr Phe Asp Tyr Trp
            100                 105                 110

Gly Gln Gly Thr Leu Val Thr Val Ser Ser Gly Gly Gly Ser Gly
        115                 120                 125

Gly Gly Gly Ser Gly Gly Gly Ser Ser Glu Leu Thr Gln Asp
130                 135                 140

Pro Ala Val Ser Val Ala Leu Gly Gln Thr Val Arg Thr Thr Cys Gln
145                 150                 155                 160

Gly Asp Ala Leu Arg Ser Tyr Tyr Ala Ser Trp Tyr Gln Gln Lys Pro
                165                 170                 175

Gly Gln Ala Pro Met Leu Val Ile Tyr Gly Lys Asn Asn Arg Pro Ser
            180                 185                 190

Gly Ile Pro Asp Arg Phe Ser Gly Ser Asp Ser Gly Asp Thr Ala Ser
        195                 200                 205

Leu Thr Ile Thr Gly Ala Gln Ala Glu Asp Glu Ala Asp Tyr Tyr Cys
    210                 215                 220

Asn Ser Arg Asp Ser Ser Gly Tyr Pro Val Phe Gly Thr Gly Thr Lys
225                 230                 235                 240

Val Thr Val Leu

<210> SEQ ID NO 54
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Ser Ser Trp Tyr Gly Gly Gly Ser Ala Phe Asp Ile
            100                 105                 110

Trp Gly Gln Gly Thr Met Val Thr Val Ser Ser Gly Gly Gly Gly Ser
        115                 120                 125
```

```
Gly Gly Gly Gly Ser Gly Gly Gly Ser Ser Glu Leu Thr Gln
            130                 135             140

Glu Pro Ala Val Ser Val Ala Leu Gly Gln Thr Val Arg Ile Thr Cys
145                 150                 155                 160

Gln Gly Asp Ser Leu Arg Ser Tyr Tyr Ala Ser Trp Tyr Gln Gln Lys
                165                 170                 175

Pro Gly Gln Ala Pro Val Leu Val Ile Phe Gly Arg Ser Arg Arg Pro
            180                 185                 190

Ser Gly Ile Pro Asp Arg Phe Ser Gly Ser Ser Ser Gly Asn Thr Ala
            195                 200                 205

Ser Leu Ile Ile Thr Gly Ala Gln Ala Glu Asp Glu Ala Asp Tyr Tyr
210                 215                 220

Cys Asn Ser Arg Asp Asn Thr Ala Asn His Tyr Val Phe Gly Thr Gly
225                 230                 235                 240

Thr Lys Leu Thr Val Leu
                245
```

<210> SEQ ID NO 55
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Ser Trp Tyr Gly Gly Ser Ala Phe Asp Ile
                100                 105                 110

Trp Gly Gln Gly Thr Met Val Thr Val Ser Ser Gly Gly Gly Gly Ser
            115                 120                 125

Gly Gly Gly Gly Ser Gly Gly Gly Ser Ser Glu Leu Thr Gln
            130                 135             140

Asp Pro Ala Val Ser Val Ala Leu Gly Gln Thr Val Arg Ile Thr Cys
145                 150                 155                 160

Gln Gly Asp Ser Leu Arg Ser Tyr Tyr Ala Ser Trp Tyr Gln Gln Lys
                165                 170                 175

Pro Gly Gln Ala Pro Val Leu Val Ile Tyr Gly Lys Asn Asn Arg Pro
            180                 185                 190

Ser Gly Ile Pro Asp Arg Phe Ser Gly Ser Ser Ser Gly Asn Thr Ala
            195                 200                 205

Ser Leu Thr Ile Thr Gly Ala Gln Ala Glu Asp Glu Ala Asp Tyr Tyr
210                 215                 220

Cys Asn Ser Arg Gly Ser Ser Gly Asn His Tyr Val Phe Gly Thr Gly
```

```
225                 230                 235                 240

Thr Lys Val Thr Val Leu
                245

<210> SEQ ID NO 56
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Thr Gly Trp Val Gly Ser Tyr Tyr Tyr Met Asp Val Trp
            100                 105                 110

Gly Lys Gly Thr Thr Val Thr Val Ser Ser Gly Gly Gly Gly Ser Gly
        115                 120                 125

Gly Gly Gly Ser Gly Gly Gly Gly Ser Gly Gly Gly Gly Ser Glu Ile
    130                 135                 140

Val Leu Thr Gln Ser Pro Gly Thr Leu Ser Leu Ser Pro Gly Glu Arg
145                 150                 155                 160

Ala Thr Leu Ser Cys Arg Ala Ser Gln Ser Val Ser Ser Asn Tyr Leu
                165                 170                 175

Ala Trp Tyr Gln Gln Lys Pro Gly Gln Pro Pro Arg Leu Leu Ile Tyr
            180                 185                 190

Asp Val Ser Thr Arg Ala Thr Gly Ile Pro Ala Arg Phe Ser Gly Gly
        195                 200                 205

Gly Ser Gly Thr Asp Phe Thr Leu Thr Ile Ser Ser Leu Glu Pro Glu
    210                 215                 220

Asp Phe Ala Val Tyr Tyr Cys Gln Gln Arg Ser Asn Trp Pro Pro Trp
225                 230                 235                 240

Thr Phe Gly Gln Gly Thr Lys Val Glu Ile Lys
                245                 250

<210> SEQ ID NO 57
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
```

```
            20                  25                  30
Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Gly Tyr Ser Arg Tyr Tyr Tyr Gly Met Asp Val Trp Gly
            100                 105                 110

Gln Gly Thr Thr Val Thr Val Ser Ser Gly Gly Gly Ser Gly Gly
            115                 120                 125

Gly Gly Ser Gly Gly Gly Ser Gly Gly Gly Ser Glu Ile Val
        130                 135                 140

Met Thr Gln Ser Pro Ala Thr Leu Ser Leu Ser Pro Gly Glu Arg Ala
145                 150                 155                 160

Ile Leu Ser Cys Arg Ala Ser Gln Ser Val Tyr Thr Lys Tyr Leu Gly
                165                 170                 175

Trp Tyr Gln Gln Lys Pro Gly Gln Ala Pro Arg Leu Leu Ile Tyr Asp
                180                 185                 190

Ala Ser Thr Arg Ala Thr Gly Ile Pro Asp Arg Phe Ser Gly Ser Gly
            195                 200                 205

Ser Gly Thr Asp Phe Thr Leu Thr Ile Asn Arg Leu Glu Pro Glu Asp
        210                 215                 220

Phe Ala Val Tyr Tyr Cys Gln His Tyr Gly Gly Ser Pro Leu Ile Thr
225                 230                 235                 240

Phe Gly Gln Gly Thr Lys Val Asp Ile Lys
                245                 250

<210> SEQ ID NO 58
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Val Gln Leu Val Gln Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Arg Glu Ala Ala Gly His Asp Trp Tyr Phe Asp Leu Trp
            100                 105                 110

Gly Arg Gly Thr Leu Val Thr Val Ser Ser Gly Gly Gly Gly Ser Gly
            115                 120                 125
```

```
Gly Gly Gly Ser Gly Gly Gly Gly Ser Gly Gly Gly Gly Ser Asp Ile
        130                 135                 140

Arg Val Thr Gln Ser Pro Ser Ser Leu Ser Ala Ser Val Gly Asp Arg
145                 150                 155                 160

Val Thr Ile Thr Cys Arg Ala Ser Gln Ser Ile Ser Ser Tyr Leu Asn
                165                 170                 175

Trp Tyr Gln Gln Lys Pro Gly Lys Ala Pro Lys Leu Leu Ile Tyr Ala
                180                 185                 190

Ala Ser Ser Leu Gln Ser Gly Val Pro Ser Arg Phe Ser Gly Ser Gly
                195                 200                 205

Ser Gly Thr Asp Phe Thr Leu Thr Ile Ser Ser Leu Gln Pro Glu Asp
210                 215                 220

Phe Ala Thr Tyr Tyr Cys Gln Gln Ser Tyr Ser Ile Pro Leu Thr Phe
225                 230                 235                 240

Gly Gln Gly Thr Lys Val Glu Ile Lys
                245

<210> SEQ ID NO 59
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gln Val Gln Leu Val Gln Ser Trp Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Asn Leu Arg Ser Glu Asp Thr Ala Val Tyr Tyr Cys
                85                  90                  95

Ala Arg Ser Pro Arg Val Thr Thr Gly Tyr Phe Asp Tyr Trp Gly Gln
                100                 105                 110

Gly Thr Leu Val Thr Val Ser Ser Gly Gly Gly Gly Ser Gly Gly Gly
            115                 120                 125

Gly Ser Gly Gly Gly Gly Ser Gly Gly Gly Gly Ser Asp Ile Gln Leu
        130                 135                 140

Thr Gln Ser Pro Ser Thr Leu Ser Ala Ser Val Gly Asp Arg Val Thr
145                 150                 155                 160

Ile Thr Cys Arg Ala Ser Gln Ser Ile Ser Ser Trp Leu Ala Trp Tyr
                165                 170                 175

Gln Gln Lys Pro Gly Lys Ala Pro Lys Leu Leu Ile Tyr Lys Ala Ser
                180                 185                 190

Ser Leu Glu Ser Gly Val Pro Ser Arg Phe Ser Gly Ser Gly Ser Gly
                195                 200                 205

Thr Glu Phe Thr Leu Thr Ile Ser Ser Leu Gln Pro Asp Asp Phe Ala
            210                 215                 220

Thr Tyr Tyr Cys Gln Gln Tyr Ser Ser Tyr Pro Leu Thr Phe Gly Gly
225                 230                 235                 240
```

```
Gly Thr Arg Leu Glu Ile Lys
                245

<210> SEQ ID NO 60
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gln Val Gln Leu Val Gln Ser Gly Ala Glu Val Arg Arg Pro Gly Ala
1               5                   10                  15

Ser Val Lys Ile Ser Cys Arg Ala Ser Gly Asp Thr Ser Thr Arg His
            20                  25                  30

Tyr Ile His Trp Leu Arg Gln Ala Pro Gly Gln Gly Pro Glu Trp Met
        35                  40                  45

Gly Val Ile Asn Pro Thr Thr Gly Pro Ala Thr Gly Ser Pro Ala Tyr
    50                  55                  60

Ala Gln Met Leu Gln Gly Arg Val Thr Met Thr Arg Asp Thr Ser Thr
65                  70                  75                  80

Arg Thr Val Tyr Met Glu Leu Arg Ser Leu Arg Phe Glu Asp Thr Ala
                85                  90                  95

Val Tyr Tyr Cys Ala Arg Ser Val Val Gly Arg Ser Ala Pro Tyr Tyr
            100                 105                 110

Phe Asp Tyr Trp Gly Gln Gly Thr Leu Val Thr Val Ser Ser Gly Gly
        115                 120                 125

Gly Gly Ser Gly Gly Gly Ser Gly Gly Gly Ser Gly Gly Gly
    130                 135                 140

Gly Ser Asp Ile Gln Met Thr Gln Ser Pro Ser Ser Leu Ser Ala Ser
145                 150                 155                 160

Val Gly Asp Arg Val Thr Ile Thr Cys Arg Ala Ser Gln Gly Ile Ser
                165                 170                 175

Asp Tyr Ser Ala Trp Tyr Gln Gln Lys Pro Gly Lys Ala Pro Lys Leu
            180                 185                 190

Leu Ile Tyr Ala Ala Ser Thr Leu Gln Ser Gly Val Pro Ser Arg Phe
        195                 200                 205

Ser Gly Ser Gly Ser Gly Thr Asp Phe Thr Leu Thr Ile Ser Tyr Leu
    210                 215                 220

Gln Ser Glu Asp Phe Ala Thr Tyr Tyr Cys Gln Gln Tyr Tyr Ser Tyr
225                 230                 235                 240

Pro Leu Thr Phe Gly Gly Gly Thr Lys Val Asp Ile Lys
                245                 250

<210> SEQ ID NO 61
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30
```

Tyr Met His Trp Val Arg Gln Ala Pro Gly Gln Gly Leu Glu Trp Met
         35                  40                  45

Gly Ile Ile Asn Pro Ser Gly Gly Tyr Thr Thr Tyr Ala Gln Lys Phe
 50                  55                  60

Gln Gly Arg Leu Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ile Arg Ser Cys Gly Asp Cys Tyr Tyr Phe Asp Asn Trp
                100                 105                 110

Gly Gln Gly Thr Leu Val Thr Val Ser Ser Gly Gly Gly Gly Ser Gly
            115                 120                 125

Gly Gly Gly Ser Gly Gly Gly Ser Gly Gly Gly Ser Asp Ile
        130                 135                 140

Gln Leu Thr Gln Ser Pro Ser Thr Leu Ser Ala Ser Val Gly Asp Arg
145                 150                 155                 160

Val Thr Ile Thr Cys Arg Ala Ser Glu Asn Val Asn Ile Trp Leu Ala
                165                 170                 175

Trp Tyr Gln Gln Lys Pro Gly Lys Ala Pro Lys Leu Leu Ile Tyr Lys
                180                 185                 190

Ser Ser Ser Leu Ala Ser Gly Val Pro Ser Arg Phe Ser Gly Ser Gly
                195                 200                 205

Ser Gly Ala Glu Phe Thr Leu Thr Ile Ser Ser Leu Gln Pro Asp Asp
            210                 215                 220

Phe Ala Thr Tyr Tyr Cys Gln Gln Tyr Gln Ser Tyr Pro Leu Thr Phe
225                 230                 235                 240

Gly Gly Gly Thr Lys Val Asp Ile Lys
                245

<210> SEQ ID NO 62
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Ile Thr Leu Lys Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ala
                 20                  25                  30

Gly Val His Val Gly Trp Ile Arg Gln Pro Pro Gly Lys Ala Leu Glu
             35                  40                  45

Trp Leu Ala Leu Ile Ser Trp Ala Asp Asp Lys Arg Tyr Arg Pro Ser
 50                  55                  60

Leu Arg Ser Arg Leu Asp Ile Thr Arg Val Thr Ser Lys Asp Gln Val
 65                  70                  75                  80

Val Leu Ser Met Thr Asn Met Gln Pro Glu Asp Thr Ala Thr Tyr Tyr
                 85                  90                  95

Cys Ala Leu Gln Gly Phe Asp Gly Tyr Glu Ala Asn Trp Gly Pro Gly
                100                 105                 110

Thr Leu Val Thr Val Ser Ser Gly Gly Gly Gly Ser Gly Gly Gly Gly
            115                 120                 125

Ser Gly Gly Gly Gly Ser Gly Gly Gly Gly Ser Asp Ile Val Met Thr

```
                130                 135                 140
Gln Ser Pro Ser Ser Leu Ser Ala Ser Ala Gly Asp Arg Val Thr Ile
145                 150                 155                 160

Thr Cys Arg Ala Ser Arg Gly Ile Ser Ser Ala Leu Ala Trp Tyr Gln
                165                 170                 175

Gln Lys Pro Gly Lys Pro Pro Lys Leu Leu Ile Tyr Asp Ala Ser Ser
                180                 185                 190

Leu Glu Ser Gly Val Pro Ser Arg Phe Ser Gly Ser Gly Ser Gly Thr
                195                 200                 205

Asp Phe Thr Leu Thr Ile Asp Ser Leu Glu Pro Glu Asp Phe Ala Thr
                210                 215                 220

Tyr Tyr Cys Gln Gln Ser Tyr Ser Thr Pro Trp Thr Phe Gly Gln Gly
225                 230                 235                 240

Thr Lys Val Asp Ile Lys
                245

<210> SEQ ID NO 63
<211> LENGTH: 488
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Ala Glu Val
                20                  25                  30

Lys Lys Pro Gly Ala Ser Val Lys Val Ser Cys Lys Ala Ser Gly Tyr
            35                  40                  45

Thr Phe Thr Gly Tyr Tyr Met His Trp Val Arg Gln Ala Pro Gly Gln
        50                  55                  60

Gly Leu Glu Trp Met Gly Arg Ile Asn Pro Asn Ser Gly Gly Thr Asn
65                  70                  75                  80

Tyr Ala Gln Lys Phe Gln Gly Arg Val Thr Met Thr Arg Asp Thr Ser
                85                  90                  95

Ile Ser Thr Ala Tyr Met Glu Leu Ser Arg Leu Arg Ser Glu Asp Thr
            100                 105                 110

Ala Val Tyr Tyr Cys Ala Arg Gly Arg Tyr Tyr Gly Met Asp Val Trp
        115                 120                 125

Gly Gln Gly Thr Met Val Thr Val Ser Ser Gly Gly Gly Gly Ser Gly
    130                 135                 140

Gly Gly Gly Ser Gly Gly Gly Ser Gly Gly Gly Ser Glu Ile
145                 150                 155                 160

Val Leu Thr Gln Ser Pro Ala Thr Leu Ser Leu Ser Pro Gly Glu Arg
                165                 170                 175

Ala Thr Ile Ser Cys Arg Ala Ser Gln Ser Val Ser Ser Asn Phe Ala
            180                 185                 190

Trp Tyr Gln Gln Arg Pro Gly Gln Ala Pro Arg Leu Leu Ile Tyr Asp
        195                 200                 205

Ala Ser Asn Arg Ala Thr Gly Ile Pro Pro Arg Phe Ser Gly Ser Gly
    210                 215                 220

Ser Gly Thr Asp Phe Thr Leu Thr Ile Ser Ser Leu Glu Pro Glu Asp
225                 230                 235                 240
```

Phe Ala Ala Tyr Tyr Cys His Gln Arg Ser Asn Trp Leu Tyr Thr Phe
                245                 250                 255

Gly Gln Gly Thr Lys Val Asp Ile Lys Thr Thr Thr Pro Ala Pro Arg
            260                 265                 270

Pro Pro Thr Pro Ala Pro Thr Ile Ala Ser Gln Pro Leu Ser Leu Arg
            275                 280                 285

Pro Glu Ala Cys Arg Pro Ala Ala Gly Gly Ala Val His Thr Arg Gly
            290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
            355                 360                 365

Glu Glu Glu Gly Gly Cys Glu Leu Arg Val Lys Phe Ser Arg Ser Ala
            370                 375                 380

Asp Ala Pro Ala Tyr Lys Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
            435                 440                 445

Glu Ile Gly Met Lys Gly Glu Arg Arg Arg Gly Lys Gly His Asp Gly
            450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485

<210> SEQ ID NO 64
<211> LENGTH: 497
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Lys Val Ser Cys Lys Ala Ser Gly Tyr
            35                  40                  45

Thr Phe Thr Gly Tyr Tyr Met His Trp Val Arg Gln Ala Pro Gly Gln
            50                  55                  60

Gly Leu Glu Trp Met Gly Trp Ile Asn Pro Asn Ser Gly Gly Thr Asn
65                  70                  75                  80

Tyr Ala Gln Lys Phe Gln Gly Arg Val Thr Met Thr Arg Asp Thr Ser
                85                  90                  95

Ile Ser Thr Ala Tyr Met Glu Leu Ser Arg Leu Arg Ser Asp Asp Thr
            100                 105                 110

Ala Val Tyr Tyr Cys Ala Arg Asp Leu Arg Arg Thr Val Thr Pro
            115                 120                 125

Arg Ala Tyr Tyr Gly Met Asp Val Trp Gly Gln Gly Thr Thr Val Thr
130                 135                 140

Val Ser Gly Gly Gly Gly Ser Gly Gly Gly Ser Gly Gly Gly
145                 150                 155                 160

Gly Ser Gly Gly Gly Ser Asp Ile Gln Leu Thr Gln Ser Pro Ser
            165                 170                 175

Thr Leu Ser Ala Ser Val Gly Asp Arg Val Thr Ile Thr Cys Gln Ala
            180                 185                 190

Ser Gln Asp Ile Ser Asn Ser Leu Asn Trp Tyr Gln Gln Lys Ala Gly
            195                 200                 205

Lys Ala Pro Lys Leu Leu Ile Tyr Asp Ala Ser Thr Leu Glu Thr Gly
            210                 215                 220

Val Pro Ser Arg Phe Ser Gly Ser Gly Ser Gly Thr Asp Phe Ser Phe
225                 230                 235                 240

Thr Ile Ser Ser Leu Gln Pro Glu Asp Ile Ala Thr Tyr Tyr Cys Gln
            245                 250                 255

Gln His Asp Asn Leu Pro Leu Thr Phe Gly Gln Gly Thr Lys Val Glu
            260                 265                 270

Ile Lys Thr Thr Thr Pro Ala Pro Arg Pro Pro Thr Pro Ala Pro Thr
            275                 280                 285

Ile Ala Ser Gln Pro Leu Ser Leu Arg Pro Glu Ala Cys Arg Pro Ala
            290                 295                 300

Ala Gly Gly Ala Val His Thr Arg Gly Leu Asp Phe Ala Cys Asp Ile
305                 310                 315                 320

Tyr Ile Trp Ala Pro Leu Ala Gly Thr Cys Gly Val Leu Leu Leu Ser
            325                 330                 335

Leu Val Ile Thr Leu Tyr Cys Lys Arg Gly Arg Lys Lys Leu Leu Tyr
            340                 345                 350

Ile Phe Lys Gln Pro Phe Met Arg Pro Val Gln Thr Thr Gln Glu Glu
            355                 360                 365

Asp Gly Cys Ser Cys Arg Phe Pro Glu Glu Glu Glu Gly Gly Cys Glu
            370                 375                 380

Leu Arg Val Lys Phe Ser Arg Ser Ala Asp Ala Pro Ala Tyr Lys Gln
385                 390                 395                 400

Gly Gln Asn Gln Leu Tyr Asn Glu Leu Asn Leu Gly Arg Arg Glu Glu
            405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
            435                 440                 445

Lys Asp Lys Met Ala Glu Ala Tyr Ser Glu Ile Gly Met Lys Gly Glu
            450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
            485                 490                 495

Arg

<210> SEQ ID NO 65
<211> LENGTH: 490
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 65

```
Met Ala Leu Pro Val Thr Ala Leu Leu Leu Pro Leu Ala Leu Leu Leu
 1               5                  10                  15

His Ala Ala Arg Pro Gln Val Gln Leu Val Gln Ser Gly Ala Glu Val
                20                  25                  30

Lys Lys Pro Gly Ala Pro Val Lys Val Ser Cys Lys Ala Ser Gly Tyr
            35                  40                  45

Thr Phe Thr Gly Tyr Tyr Met His Trp Val Arg Gln Ala Pro Gly Gln
        50                  55                  60

Gly Leu Glu Trp Met Gly Trp Ile Asn Pro Asn Ser Gly Gly Thr Asn
 65                  70                  75                  80

Tyr Ala Gln Lys Phe Gln Gly Arg Val Thr Met Thr Arg Asp Thr Ser
                85                  90                  95

Ile Ser Thr Ala Tyr Met Glu Leu Ser Arg Leu Arg Ser Asp Asp Thr
            100                 105                 110

Ala Val Tyr Tyr Cys Ala Arg Gly Glu Trp Asp Gly Ser Tyr Tyr Tyr
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

Ser Asp Ile Val Leu Thr Gln Thr Pro Ser Ser Leu Ser Ala Ser Val
                165                 170                 175

Gly Asp Arg Val Thr Ile Thr Cys Arg Ala Ser Gln Ser Ile Asn Thr
            180                 185                 190

Tyr Leu Asn Trp Tyr Gln His Lys Pro Gly Lys Ala Pro Lys Leu Leu
        195                 200                 205

Ile Tyr Ala Ala Ser Ser Leu Gln Ser Gly Val Pro Ser Arg Phe Ser
    210                 215                 220

Gly Ser Gly Ser Gly Thr Asp Phe Thr Leu Thr Ile Ser Ser Leu Gln
225                 230                 235                 240

Pro Glu Asp Phe Ala Thr Tyr Tyr Cys Gln Gln Ser Phe Ser Pro Leu
                245                 250                 255

Thr Phe Gly Gly Gly Thr Lys Leu Glu Ile Lys Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380
```

```
Ser Ala Asp Ala Pro Ala Tyr Lys Gln Gly Gln Asn Gln Leu Tyr Asn
385                 390                 395                 400

Glu Leu Asn Leu Gly Arg Arg Glu Tyr Asp Val Leu Asp Lys Arg
            405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
            435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
            485                 490
```

<210> SEQ ID NO 66
<211> LENGTH: 486
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Trp Met His Trp Val Arg Gln Val Pro Gly Lys
    50                  55                  60

Gly Leu Val Trp Val Ser Arg Ile Asn Thr Asp Gly Ser Thr Thr Thr
65                  70                  75                  80

Tyr Ala Asp Ser Val Glu Gly Arg Phe Thr Ile Ser Arg Asp Asn Ala
                85                  90                  95

Lys Asn Thr Leu Tyr Leu Gln Met Asn Ser Leu Arg Asp Asp Asp Thr
            100                 105                 110

Ala Val Tyr Tyr Cys Val Gly Gly His Trp Ala Val Trp Gly Gln Gly
        115                 120                 125

Thr Thr Val Thr Val Ser Ser Gly Gly Gly Ser Gly Gly Gly Gly
    130                 135                 140

Ser Gly Gly Gly Gly Ser Gly Gly Gly Ser Asp Ile Gln Met Thr
145                 150                 155                 160

Gln Ser Pro Ser Thr Leu Ser Ala Ser Val Gly Asp Arg Val Thr Ile
                165                 170                 175

Thr Cys Arg Ala Ser Gln Ser Ile Ser Asp Arg Leu Ala Trp Tyr Gln
            180                 185                 190

Gln Lys Pro Gly Lys Ala Pro Lys Leu Leu Ile Tyr Lys Ala Ser Ser
        195                 200                 205

Leu Glu Ser Gly Val Pro Ser Arg Phe Ser Gly Ser Gly Ser Gly Thr
    210                 215                 220

Glu Phe Thr Leu Thr Ile Ser Ser Leu Gln Pro Asp Asp Phe Ala Val
225                 230                 235                 240

Tyr Tyr Cys Gln Gln Tyr Gly His Leu Pro Met Tyr Thr Phe Gly Gln
                245                 250                 255
```

-continued

```
Gly Thr Lys Val Glu Ile Lys Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
450                 455                 460

Gln Gly Leu Ser Thr Ala Thr Lys Asp Thr Tyr Asp Ala Leu His Met
465                 470                 475                 480

Gln Ala Leu Pro Pro Arg
                485
```

<210> SEQ ID NO 67
<211> LENGTH: 485
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 67

```
Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Glu Lys Pro Gly Ala Ser Val Lys Val Ser Cys Lys Ala Ser Gly Tyr
        35                  40                  45

Thr Phe Thr Asp Tyr Tyr Met His Trp Val Arg Gln Ala Pro Gly Gln
    50                  55                  60

Gly Leu Glu Trp Met Gly Trp Ile Asn Pro Asn Ser Gly Gly Thr Asn
65                  70                  75                  80

Tyr Ala Gln Lys Phe Gln Gly Arg Val Thr Met Thr Arg Asp Thr Ser
                85                  90                  95

Ile Ser Thr Ala Tyr Met Glu Leu Ser Arg Leu Arg Ser Asp Asp Thr
            100                 105                 110

Ala Val Tyr Tyr Cys Ala Ser Gly Trp Asp Phe Asp Tyr Trp Gly Gln
```

```
            115                 120                 125
Gly Thr Leu Val Thr Val Ser Ser Gly Gly Gly Ser Gly Gly
        130                 135                 140
Gly Ser Gly Gly Gly Ser Gly Gly Gly Ser Asp Ile Val Met
145                 150                 155                 160
Thr Gln Ser Pro Ser Ser Leu Ser Ala Ser Val Gly Asp Arg Val Thr
                165                 170                 175
Ile Thr Cys Arg Ala Ser Gln Ser Ile Arg Tyr Tyr Leu Ser Trp Tyr
            180                 185                 190
Gln Gln Lys Pro Gly Lys Ala Pro Lys Leu Leu Ile Tyr Thr Ala Ser
                195                 200                 205
Ile Leu Gln Asn Gly Val Pro Ser Arg Phe Ser Gly Ser Gly Ser Gly
            210                 215                 220
Thr Asp Phe Thr Leu Thr Ile Ser Ser Leu Gln Pro Glu Asp Phe Ala
225                 230                 235                 240
Thr Tyr Tyr Cys Leu Gln Thr Tyr Thr Thr Pro Asp Phe Gly Pro Gly
                245                 250                 255
Thr Lys Val Glu Ile Lys Thr Thr Thr Pro Ala Pro Arg Pro Pro Thr
            260                 265                 270
Pro Ala Pro Thr Ile Ala Ser Gln Pro Leu Ser Leu Arg Pro Glu Ala
                275                 280                 285
Cys Arg Pro Ala Ala Gly Gly Ala Val His Thr Arg Gly Leu Asp Phe
            290                 295                 300
Ala Cys Asp Ile Tyr Ile Trp Ala Pro Leu Ala Gly Thr Cys Gly Val
305                 310                 315                 320
Leu Leu Leu Ser Leu Val Ile Thr Leu Tyr Cys Lys Arg Gly Arg Lys
                325                 330                 335
Lys Leu Leu Tyr Ile Phe Lys Gln Pro Phe Met Arg Pro Val Gln Thr
            340                 345                 350
Thr Gln Glu Glu Asp Gly Cys Ser Cys Arg Phe Pro Glu Glu Glu Glu
                355                 360                 365
Gly Gly Cys Glu Leu Arg Val Lys Phe Ser Arg Ser Ala Asp Ala Pro
            370                 375                 380
Ala Tyr Lys Gln Gly Gln Asn Gln Leu Tyr Asn Glu Leu Asn Leu Gly
385                 390                 395                 400
Arg Arg Glu Glu Tyr Asp Val Leu Asp Lys Arg Arg Gly Arg Asp Pro
                405                 410                 415
Glu Met Gly Gly Lys Pro Arg Arg Lys Asn Pro Gln Glu Gly Leu Tyr
            420                 425                 430
Asn Glu Leu Gln Lys Asp Lys Met Ala Glu Ala Tyr Ser Glu Ile Gly
            435                 440                 445
Met Lys Gly Glu Arg Arg Arg Gly Lys Gly His Asp Gly Leu Tyr Gln
            450                 455                 460
Gly Leu Ser Thr Ala Thr Lys Asp Thr Tyr Asp Ala Leu His Met Gln
465                 470                 475                 480
Ala Leu Pro Pro Arg
            485

<210> SEQ ID NO 68
<211> LENGTH: 497
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 68

| | | | | | | | | | | | | | | |
|---|---|---|---|---|---|---|---|---|---|---|---|---|---|---|
| Met | Ala | Leu | Pro | Val | Thr | Ala | Leu | Leu | Pro | Leu | Ala | Leu | Leu | Leu |
| 1 | | | | 5 | | | | | 10 | | | | | 15 |
| His | Ala | Ala | Arg | Pro | Gln | Val | Gln | Leu | Val | Gln | Ser | Gly | Ala | Glu | Val |
| | | | 20 | | | | | 25 | | | | | 30 | | |
| Lys | Lys | Pro | Gly | Ala | Ser | Val | Lys | Val | Ser | Cys | Lys | Ala | Ser | Gly | Tyr |
| | | 35 | | | | | 40 | | | | | 45 | | | |
| Thr | Phe | Thr | Ser | Tyr | Tyr | Met | His | Trp | Val | Arg | Gln | Ala | Pro | Gly | Gln |
| | 50 | | | | | 55 | | | | | 60 | | | | |
| Gly | Leu | Glu | Trp | Met | Gly | Ile | Ile | Asn | Pro | Ser | Gly | Gly | Ser | Thr | Ser |
| 65 | | | | 70 | | | | | 75 | | | | | 80 | |
| Tyr | Ala | Gln | Lys | Phe | Gln | Gly | Arg | Val | Thr | Met | Thr | Arg | Asp | Thr | Ser |
| | | | 85 | | | | | 90 | | | | | 95 | | |
| Thr | Ser | Thr | Val | Tyr | Met | Glu | Leu | Ser | Ser | Leu | Arg | Ser | Glu | Asp | Thr |
| | | | 100 | | | | | 105 | | | | | 110 | | |
| Ala | Val | Tyr | Tyr | Cys | Ala | Arg | Tyr | Arg | Leu | Ile | Ala | Val | Ala | Gly | Asp |
| | | | 115 | | | | | 120 | | | | | 125 | | |
| Tyr | Tyr | Tyr | Tyr | Gly | Met | Asp | Val | Trp | Gly | Gln | Gly | Thr | Met | Val | Thr |
| | 130 | | | | | 135 | | | | | 140 | | | | |
| Val | Ser | Ser | Gly | Gly | Gly | Gly | Ser | Gly | Gly | Gly | Ser | Gly | Gly | Gly |
| 145 | | | | | 150 | | | | | 155 | | | | | 160 |
| Gly | Ser | Gly | Gly | Gly | Gly | Ser | Asp | Ile | Gln | Met | Thr | Gln | Ser | Pro | Ser |
| | | | | 165 | | | | | 170 | | | | | 175 | |
| Ser | Val | Ser | Ala | Ser | Val | Gly | Asp | Arg | Val | Thr | Ile | Thr | Cys | Arg | Ala |
| | | | 180 | | | | | 185 | | | | | 190 | | |
| Ser | Gln | Gly | Val | Gly | Arg | Trp | Leu | Ala | Trp | Tyr | Gln | Gln | Lys | Pro | Gly |
| | | | 195 | | | | | 200 | | | | | 205 | | |
| Thr | Ala | Pro | Lys | Leu | Leu | Ile | Tyr | Ala | Ala | Ser | Thr | Leu | Gln | Ser | Gly |
| | | 210 | | | | | 215 | | | | | 220 | | | |
| Val | Pro | Ser | Arg | Phe | Ser | Gly | Ser | Gly | Ser | Gly | Thr | Asp | Phe | Thr | Leu |
| 225 | | | | | 230 | | | | | 235 | | | | | 240 |
| Thr | Ile | Asn | Asn | Leu | Gln | Pro | Glu | Asp | Phe | Ala | Thr | Tyr | Tyr | Cys | Gln |
| | | | | 245 | | | | | 250 | | | | | 255 | |
| Gln | Ala | Asn | Ser | Phe | Pro | Leu | Thr | Phe | Gly | Gly | Gly | Thr | Arg | Leu | Glu |
| | | | 260 | | | | | 265 | | | | | 270 | | |
| Ile | Lys | Thr | Thr | Thr | Pro | Ala | Pro | Arg | Pro | Pro | Thr | Pro | Ala | Pro | Thr |
| | | 275 | | | | | 280 | | | | | 285 | | | |
| Ile | Ala | Ser | Gln | Pro | Leu | Ser | Leu | Arg | Pro | Glu | Ala | Cys | Arg | Pro | Ala |
| | | 290 | | | | | 295 | | | | | 300 | | | |
| Ala | Gly | Gly | Ala | Val | His | Thr | Arg | Gly | Leu | Asp | Phe | Ala | Cys | Asp | Ile |
| 305 | | | | | 310 | | | | | 315 | | | | | 320 |
| Tyr | Ile | Trp | Ala | Pro | Leu | Ala | Gly | Thr | Cys | Gly | Val | Leu | Leu | Leu | Ser |
| | | | | 325 | | | | | 330 | | | | | 335 | |
| Leu | Val | Ile | Thr | Leu | Tyr | Cys | Lys | Arg | Gly | Arg | Lys | Lys | Leu | Leu | Tyr |
| | | | | 340 | | | | | 345 | | | | | 350 | |
| Ile | Phe | Lys | Gln | Pro | Phe | Met | Arg | Pro | Val | Gln | Thr | Thr | Gln | Glu | Glu |
| | | | 355 | | | | | 360 | | | | | 365 | | |
| Asp | Gly | Cys | Ser | Cys | Arg | Phe | Pro | Glu | Glu | Glu | Glu | Gly | Gly | Cys | Glu |
| | | | 370 | | | | | 375 | | | | | 380 | | |
| Leu | Arg | Val | Lys | Phe | Ser | Arg | Ser | Ala | Asp | Ala | Pro | Ala | Tyr | Lys | Gln |
| 385 | | | | | 390 | | | | | 395 | | | | | 400 |
| Gly | Gln | Asn | Gln | Leu | Tyr | Asn | Glu | Leu | Asn | Leu | Gly | Arg | Arg | Glu | Glu |

```
            405                 410                 415
Tyr Asp Val Leu Asp Lys Arg Arg Gly Arg Asp Pro Glu Met Gly Gly
                420                 425                 430

Lys Pro Arg Arg Lys Asn Pro Gln Glu Gly Leu Tyr Asn Glu Leu Gln
            435                 440                 445

Lys Asp Lys Met Ala Glu Ala Tyr Ser Glu Ile Gly Met Lys Gly Glu
        450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg

<210> SEQ ID NO 69
<211> LENGTH: 494
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Gly Gly Val
                20                  25                  30

Val Gln Pro Gly Arg Ser Leu Arg Leu Ser Cys Ala Ala Ser Gly Phe
            35                  40                  45

Thr Phe Ser Ser Tyr Ala Met His Trp Val Arg Gln Ala Pro Gly Lys
        50                  55                  60

Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Trp Lys Val Ser Ser Ser Pro Ala
        115                 120                 125

Phe Asp Tyr Trp Gly Gln Gly Thr Leu Val Thr Val Ser Ser Gly Gly
    130                 135                 140

Gly Gly Ser Gly Gly Gly Gly Ser Gly Gly Gly Gly Ser Gly Gly Gly
145                 150                 155                 160

Gly Ser Glu Ile Val Leu Thr Gln Ser Pro Ala Thr Leu Ser Leu Ser
                165                 170                 175

Pro Gly Glu Arg Ala Ile Leu Ser Cys Arg Ala Ser Gln Ser Val Tyr
            180                 185                 190

Thr Lys Tyr Leu Gly Trp Tyr Gln Gln Lys Pro Gly Gln Ala Pro Arg
        195                 200                 205

Leu Leu Ile Tyr Asp Ala Ser Thr Arg Ala Thr Gly Ile Pro Asp Arg
    210                 215                 220

Phe Ser Gly Ser Gly Ser Gly Thr Asp Phe Thr Leu Thr Ile Asn Arg
225                 230                 235                 240

Leu Glu Pro Glu Asp Phe Ala Val Tyr Tyr Cys Gln His Tyr Gly Gly
                245                 250                 255

Ser Pro Leu Ile Thr Phe Gly Gln Gly Thr Arg Leu Glu Ile Lys Thr
```

```
                    260                 265                 270
Thr Thr Pro Ala Pro Arg Pro Thr Pro Ala Pro Thr Ile Ala Ser
            275                 280                 285

Gln Pro Leu Ser Leu Arg Pro Glu Ala Cys Arg Pro Ala Gly Gly
            290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Ser Leu Val Ile
            325                 330                 335

Thr Leu Tyr Cys Lys Arg Gly Arg Lys Lys Leu Leu Tyr Ile Phe Lys
            340                 345                 350

Gln Pro Phe Met Arg Pro Val Gln Thr Thr Gln Glu Glu Asp Gly Cys
            355                 360                 365

Ser Cys Arg Phe Pro Glu Glu Glu Glu Gly Gly Cys Glu Leu Arg Val
            370                 375                 380

Lys Phe Ser Arg Ser Ala Asp Ala Pro Ala Tyr Lys Gln Gly Gln Asn
385                 390                 395                 400

Gln Leu Tyr Asn Glu Leu Asn Leu Gly Arg Arg Glu Glu Tyr Asp Val
            405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
            435                 440                 445

Met Ala Glu Ala Tyr Ser Glu Ile Gly Met Lys Gly Glu Arg Arg Arg
450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
            485                 490

<210> SEQ ID NO 70
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Ala Glu Val
            20                  25                  30

Lys Lys Pro Gly Ala Ser Val Lys Val Ser Cys Lys Thr Ser Gly Tyr
            35                  40                  45

Pro Phe Thr Gly Tyr Ser Leu His Trp Val Arg Gln Ala Pro Gly Gln
        50                  55                  60

Gly Leu Glu Trp Met Gly Trp Ile Asn Pro Asn Ser Gly Gly Thr Asn
65                  70                  75                  80

Tyr Ala Gln Lys Phe Gln Gly Arg Val Thr Met Thr Arg Asp Thr Ser
            85                  90                  95

Ile Ser Thr Ala Tyr Met Glu Leu Ser Arg Leu Arg Ser Asp Asp Thr
            100                 105                 110

Ala Val Tyr Tyr Cys Ala Arg Asp His Tyr Gly Gly Asn Ser Leu Phe
            115                 120                 125
```

Tyr Trp Gly Gln Gly Thr Leu Val Thr Val Ser Ser Gly Gly Gly
            130                 135                 140

Ser Gly Gly Gly Ser Gly Gly Gly Ser Gly Gly Gly Ser
145                 150                 155                 160

Asp Ile Gln Leu Thr Gln Ser Pro Ser Ser Ile Ser Ala Ser Val Gly
                165                 170                 175

Asp Thr Val Ser Ile Thr Cys Arg Ala Ser Gln Asp Ser Gly Thr Trp
            180                 185                 190

Leu Ala Trp Tyr Gln Gln Lys Pro Gly Lys Ala Pro Asn Leu Leu Met
        195                 200                 205

Tyr Asp Ala Ser Thr Leu Glu Asp Gly Val Pro Ser Arg Phe Ser Gly
210                 215                 220

Ser Ala Ser Gly Thr Glu Phe Thr Leu Thr Val Asn Arg Leu Gln Pro
225                 230                 235                 240

Glu Asp Ser Ala Thr Tyr Tyr Cys Gln Gln Tyr Asn Ser Tyr Pro Leu
                245                 250                 255

Thr Phe Gly Gly Gly Thr Lys Val Asp Ile Lys Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Gly Lys Gly His
450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
            485                 490

<210> SEQ ID NO 71
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

```
Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Glu Val Ser Cys Lys Ala Ser Gly Tyr
        35                  40                  45

Thr Phe Thr Ser Tyr Tyr Met His Trp Val Arg Gln Ala Pro Gly Gln
    50                  55                  60

Gly Leu Glu Trp Met Gly Ile Ile Asn Pro Ser Gly Gly Ser Thr Gly
65                  70                  75                  80

Tyr Ala Gln Lys Phe Gln Gly Arg Val Thr Met Thr Arg Asp Thr Ser
            85                  90                  95

Thr Ser Thr Val His Met Glu Leu Ser Ser Leu Arg Ser Glu Asp Thr
            100                 105                 110

Ala Val Tyr Tyr Cys Ala Arg Gly Gly Tyr Ser Ser Ser Ser Asp Ala
        115                 120                 125

Phe Asp Ile Trp Gly Gln Gly Thr Met Val Thr Val Ser Ser Gly Gly
    130                 135                 140

Gly Gly Ser Gly Gly Gly Ser Gly Gly Gly Gly Ser Gly Gly Gly Gly
145                 150                 155                 160

Gly Ser Asp Ile Gln Met Thr Gln Ser Pro Pro Ser Leu Ser Ala Ser
            165                 170                 175

Val Gly Asp Arg Val Thr Ile Thr Cys Arg Ala Ser Gln Asp Ile Ser
            180                 185                 190

Ser Ala Leu Ala Trp Tyr Gln Gln Lys Pro Gly Thr Pro Pro Lys Leu
        195                 200                 205

Leu Ile Tyr Asp Ala Ser Ser Leu Glu Ser Gly Val Pro Ser Arg Phe
    210                 215                 220

Ser Gly Ser Gly Ser Gly Thr Asp Phe Thr Leu Thr Ile Ser Ser Leu
225                 230                 235                 240

Gln Pro Glu Asp Phe Ala Thr Tyr Tyr Cys Gln Gln Phe Ser Ser Tyr
            245                 250                 255

Pro Leu Thr Phe Gly Gly Gly Thr Arg Leu Glu Ile Lys Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
            325                 330                 335

Tyr Cys Lys Arg Gly Arg Lys Lys Leu Leu Tyr Ile Phe Lys Gln Pro
        340                 345                 350

Phe Met Arg Pro Val Gln Thr Thr Gln Glu Glu Asp Gly Cys Ser Cys
    355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Lys Gln Gly Gln Asn Gln Leu
385                 390                 395                 400

Tyr Asn Glu Leu Asn Leu Gly Arg Arg Glu Glu Tyr Asp Val Leu Asp
            405                 410                 415
```

```
Lys Arg Arg Gly Arg Asp Pro Glu Met Gly Lys Pro Arg Arg Lys
            420                 425                 430

Asn Pro Gln Glu Gly Leu Tyr Asn Glu Leu Gln Lys Asp Lys Met Ala
            435                 440                 445

Glu Ala Tyr Ser Glu Ile Gly Met Lys Gly Glu Arg Arg Arg Gly Lys
450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 72
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
                20                  25                  30

Lys Lys Pro Gly Ala Ser Val Lys Val Ser Cys Lys Ala Ser Gly Tyr
            35                  40                  45

Thr Phe Thr Ser Tyr Gly Ile Ser Trp Val Arg Gln Ala Pro Gly Gln
        50                  55                  60

Gly Leu Glu Trp Met Gly Trp Ile Ser Ala Tyr Asn Gly Asn Thr Asn
65                  70                  75                  80

Tyr Ala Gln Lys Leu Gln Gly Arg Val Thr Met Thr Thr Asp Thr Ser
                85                  90                  95

Thr Ser Thr Ala Tyr Met Glu Leu Arg Ser Leu Arg Ser Asp Asp Thr
            100                 105                 110

Ala Val Tyr Tyr Cys Ala Arg Val Ala Gly Gly Ile Tyr Tyr Tyr Tyr
        115                 120                 125

Gly Met Asp Val Trp Gly Gln Gly Thr Thr Ile Thr Val Ser Ser Gly
    130                 135                 140

Gly Gly Gly Ser Gly Gly Gly Gly Ser Gly Gly Gly Gly Ser Gly Gly
145                 150                 155                 160

Gly Gly Ser Asp Ile Val Met Thr Gln Thr Pro Asp Ser Leu Ala Val
                165                 170                 175

Ser Leu Gly Glu Arg Ala Thr Ile Ser Cys Lys Ser Ser His Ser Val
            180                 185                 190

Leu Tyr Asn Arg Asn Asn Lys Asn Tyr Leu Ala Trp Tyr Gln Gln Lys
        195                 200                 205

Pro Gly Gln Pro Pro Lys Leu Leu Phe Tyr Trp Ala Ser Thr Arg Lys
    210                 215                 220

Ser Gly Val Pro Asp Arg Phe Ser Gly Ser Gly Ser Gly Thr Asp Phe
225                 230                 235                 240

Thr Leu Thr Ile Ser Ser Leu Gln Pro Glu Asp Phe Ala Thr Tyr Phe
                245                 250                 255

Cys Gln Gln Thr Gln Thr Phe Pro Leu Thr Phe Gly Gln Gly Thr Arg
            260                 265                 270

Leu Glu Ile Asn Thr Thr Thr Pro Ala Pro Arg Pro Pro Thr Pro Ala
        275                 280                 285
```

```
Pro Thr Ile Ala Ser Gln Pro Leu Ser Leu Arg Pro Glu Ala Cys Arg
    290                 295                 300

Pro Ala Ala Gly Gly Ala Val His Thr Arg Gly Leu Asp Phe Ala Cys
305                 310                 315                 320

Asp Ile Tyr Ile Trp Ala Pro Leu Ala Gly Thr Cys Gly Val Leu Leu
                325                 330                 335

Leu Ser Leu Val Ile Thr Leu Tyr Cys Lys Arg Gly Arg Lys Lys Leu
            340                 345                 350

Leu Tyr Ile Phe Lys Gln Pro Phe Met Arg Pro Val Gln Thr Thr Gln
        355                 360                 365

Glu Glu Asp Gly Cys Ser Cys Arg Phe Pro Glu Glu Glu Glu Gly Gly
    370                 375                 380

Cys Glu Leu Arg Val Lys Phe Ser Arg Ser Ala Asp Ala Pro Ala Tyr
385                 390                 395                 400

Lys Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
    450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg

<210> SEQ ID NO 73
<211> LENGTH: 485
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Ala Glu Val
            20                  25                  30

Lys Lys Pro Gly Ala Ser Val Lys Val Ser Cys Lys Ala Ser Gly Tyr
        35                  40                  45

Thr Phe Thr Gly Tyr Tyr Met His Trp Val Arg Gln Ala Pro Gly Gln
    50                  55                  60

Gly Leu Glu Trp Met Gly Trp Ile Asn Pro Asn Ser Gly Gly Thr Asn
65                  70                  75                  80

Tyr Ala Gln Asn Phe Gln Gly Arg Val Thr Met Thr Arg Asp Thr Ser
                85                  90                  95

Ile Ser Thr Ala Tyr Met Glu Leu Arg Arg Leu Arg Ser Asp Asp Thr
            100                 105                 110

Ala Val Tyr Tyr Cys Ala Ser Gly Trp Asp Phe Asp Tyr Trp Gly Gln
        115                 120                 125

Gly Thr Leu Val Thr Val Ser Ser Gly Gly Gly Gly Ser Gly Gly Gly
    130                 135                 140
```

-continued

Gly Ser Gly Gly Gly Ser Gly Gly Gly Ser Asp Ile Arg Met
145                 150                 155                 160

Thr Gln Ser Pro Ser Ser Leu Ser Ala Ser Val Gly Asp Arg Val Thr
                165                 170                 175

Ile Thr Cys Arg Ala Ser Gln Ser Ile Arg Tyr Tyr Leu Ser Trp Tyr
            180                 185                 190

Gln Gln Lys Pro Gly Lys Ala Pro Lys Leu Leu Ile Tyr Thr Ala Ser
        195                 200                 205

Ile Leu Gln Asn Gly Val Pro Ser Arg Phe Ser Gly Ser Gly Ser Gly
210                 215                 220

Thr Asp Phe Thr Leu Thr Ile Ser Ser Leu Gln Pro Glu Asp Phe Ala
225                 230                 235                 240

Thr Tyr Tyr Cys Leu Gln Thr Tyr Thr Thr Pro Asp Phe Gly Pro Gly
                245                 250                 255

Thr Lys Val Glu Ile Lys Thr Thr Thr Pro Ala Pro Arg Pro Pro Thr
            260                 265                 270

Pro Ala Pro Thr Ile Ala Ser Gln Pro Leu Ser Leu Arg Pro Glu Ala
        275                 280                 285

Cys Arg Pro Ala Ala Gly Gly Ala Val His Thr Arg Gly Leu Asp Phe
290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
        355                 360                 365

Gly Gly Cys Glu Leu Arg Val Lys Phe Ser Arg Ser Ala Asp Ala Pro
370                 375                 380

Ala Tyr Lys Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
450                 455                 460

Gly Leu Ser Thr Ala Thr Lys Asp Thr Tyr Asp Ala Leu His Met Gln
465                 470                 475                 480

Ala Leu Pro Pro Arg
                485

<210> SEQ ID NO 74
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Met Ala Leu Pro Val Thr Ala Leu Leu Leu Pro Leu Ala Leu Leu Leu

-continued

```
1               5                   10                  15
His Ala Ala Arg Pro Gln Val Gln Leu Val Gln Ser Gly Ala Glu Val
                20                  25                  30
Lys Lys Pro Gly Ala Ser Val Lys Val Ser Cys Lys Ala Ser Gly Tyr
                35                  40                  45
Thr Phe Thr Gly Tyr Tyr Met His Trp Val Arg Gln Ala Pro Gly Gln
        50                  55                  60
Gly Leu Glu Trp Met Gly Arg Ile Asn Pro Asn Ser Gly Gly Thr Asn
65                  70                  75                  80
Tyr Ala Gln Lys Phe Gln Gly Arg Val Thr Met Thr Thr Asp Thr Ser
                85                  90                  95
Thr Ser Thr Ala Tyr Met Glu Leu Arg Ser Leu Arg Ser Asp Asp Thr
                100                 105                 110
Ala Val Tyr Tyr Cys Ala Arg Thr Thr Thr Ser Tyr Ala Phe Asp Ile
                115                 120                 125
Trp Gly Gln Gly Thr Met Val Thr Val Ser Ser Gly Gly Gly Gly Ser
        130                 135                 140
Gly Gly Gly Gly Ser Gly Gly Gly Ser Gly Gly Gly Gly Ser Asp
145                 150                 155                 160
Ile Gln Leu Thr Gln Ser Pro Ser Thr Leu Ser Ala Ser Val Gly Asp
                165                 170                 175
Arg Val Thr Ile Thr Cys Arg Ala Ser Gln Ser Ile Ser Thr Trp Leu
                180                 185                 190
Ala Trp Tyr Gln Gln Lys Pro Gly Lys Ala Pro Asn Leu Leu Ile Tyr
                195                 200                 205
Lys Ala Ser Thr Leu Glu Ser Gly Val Pro Ser Arg Phe Ser Gly Ser
                210                 215                 220
Gly Ser Gly Thr Glu Phe Thr Leu Thr Ile Ser Ser Leu Gln Pro Asp
225                 230                 235                 240
Asp Phe Ala Thr Tyr Tyr Cys Gln Gln Tyr Asn Thr Tyr Ser Pro Tyr
                245                 250                 255
Thr Phe Gly Gln Gly Thr Lys Leu Glu Ile Lys Thr Thr Thr Pro Ala
                260                 265                 270
Pro Arg Pro Pro Thr Pro Ala Pro Thr Ile Ala Ser Gln Pro Leu Ser
                275                 280                 285
Leu Arg Pro Glu Ala Cys Arg Pro Ala Ala Gly Gly Ala Val His Thr
                290                 295                 300
Arg Gly Leu Asp Phe Ala Cys Asp Ile Tyr Ile Trp Ala Pro Leu Ala
305                 310                 315                 320
Gly Thr Cys Gly Val Leu Leu Leu Ser Leu Val Ile Thr Leu Tyr Cys
                325                 330                 335
Lys Arg Gly Arg Lys Lys Leu Leu Tyr Ile Phe Lys Gln Pro Phe Met
                340                 345                 350
Arg Pro Val Gln Thr Thr Gln Glu Glu Asp Gly Cys Ser Cys Arg Phe
                355                 360                 365
Pro Glu Glu Glu Glu Gly Gly Cys Glu Leu Arg Val Lys Phe Ser Arg
                370                 375                 380
Ser Ala Asp Ala Pro Ala Tyr Lys Gln Gly Gln Asn Gln Leu Tyr Asn
385                 390                 395                 400
Glu Leu Asn Leu Gly Arg Arg Glu Glu Tyr Asp Val Leu Asp Lys Arg
                405                 410                 415
Arg Gly Arg Asp Pro Glu Met Gly Gly Lys Pro Arg Arg Lys Asn Pro
                420                 425                 430
```

```
Gln Glu Gly Leu Tyr Asn Glu Leu Gln Lys Asp Lys Met Ala Glu Ala
            435                 440                 445

Tyr Ser Glu Ile Gly Met Lys Gly Glu Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 75
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Gly Gly Leu
            20                  25                  30

Val Lys Pro Gly Gly Ser Leu Arg Leu Ser Cys Glu Ala Ser Gly Phe
        35                  40                  45

Ile Phe Ser Asp Tyr Tyr Met Gly Trp Ile Arg Gln Ala Pro Gly Lys
    50                  55                  60

Gly Leu Glu Trp Val Ser Tyr Ile Gly Arg Ser Gly Ser Ser Met Tyr
65                  70                  75                  80

Tyr Ala Asp Ser Val Lys Gly Arg Phe Thr Phe Ser Arg Asp Asn Ala
                85                  90                  95

Lys Asn Ser Leu Tyr Leu Gln Met Asn Ser Leu Arg Ala Glu Asp Thr
            100                 105                 110

Ala Val Tyr Tyr Cys Ala Ala Ser Pro Val Val Ala Ala Thr Glu Asp
        115                 120                 125

Phe Gln His Trp Gly Gln Gly Thr Leu Val Thr Val Ser Ser Gly Gly
    130                 135                 140

Gly Gly Ser Gly Gly Gly Gly Ser Gly Gly Gly Gly Ser Gly Gly Gly
145                 150                 155                 160

Gly Ser Asp Ile Val Met Thr Gln Thr Pro Ala Thr Leu Ser Leu Ser
                165                 170                 175

Pro Gly Glu Arg Ala Thr Leu Ser Cys Arg Ala Ser Gln Ser Val Thr
            180                 185                 190

Ser Asn Tyr Leu Ala Trp Tyr Gln Gln Lys Pro Gly Gln Ala Pro Arg
        195                 200                 205

Leu Leu Leu Phe Gly Ala Ser Thr Arg Ala Thr Gly Ile Pro Asp Arg
    210                 215                 220

Phe Ser Gly Ser Gly Ser Gly Thr Asp Phe Thr Leu Thr Ile Asn Arg
225                 230                 235                 240

Leu Glu Pro Glu Asp Phe Ala Met Tyr Tyr Cys Gln Gln Tyr Gly Ser
                245                 250                 255

Ala Pro Val Thr Phe Gly Gln Gly Thr Lys Leu Glu Ile Lys Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
```

```
                290                 295                 300
Val His Thr Arg Gly Leu Asp Phe Ala Cys Asp Ile Tyr Ile Trp Ala
305                 310                 315                 320

Pro Leu Ala Gly Thr Cys Gly Val Leu Leu Ser Leu Val Ile Thr
                325                 330                 335

Leu Tyr Cys Lys Arg Gly Arg Lys Leu Leu Tyr Ile Phe Lys Gln
                340                 345                 350

Pro Phe Met Arg Pro Val Gln Thr Thr Gln Glu Glu Asp Gly Cys Ser
                355                 360                 365

Cys Arg Phe Pro Glu Glu Glu Gly Gly Cys Glu Leu Arg Val Lys
                370                 375                 380

Phe Ser Arg Ser Ala Asp Ala Pro Ala Tyr Lys Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
                420                 425                 430

Lys Asn Pro Gln Glu Gly Leu Tyr Asn Glu Leu Gln Lys Asp Lys Met
                435                 440                 445

Ala Glu Ala Tyr Ser Glu Ile Gly Met Lys Gly Glu Arg Arg Arg Gly
                450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490

<210> SEQ ID NO 76
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
                20                  25                  30

Arg Ala Pro Gly Ala Ser Val Lys Ile Ser Cys Lys Ala Ser Gly Phe
                35                  40                  45

Thr Phe Arg Gly Tyr Tyr Ile His Trp Val Arg Gln Ala Pro Gly Gln
                50                  55                  60

Gly Leu Glu Trp Met Gly Ile Ile Asn Pro Ser Gly Gly Ser Arg Ala
65                  70                  75                  80

Tyr Ala Gln Lys Phe Gln Gly Arg Val Thr Met Thr Arg Asp Thr Ser
                85                  90                  95

Thr Ser Thr Val Tyr Met Glu Leu Ser Ser Leu Arg Ser Asp Asp Thr
                100                 105                 110

Ala Met Tyr Tyr Cys Ala Arg Thr Ala Ser Cys Gly Gly Asp Cys Tyr
                115                 120                 125

Tyr Leu Asp Tyr Trp Gly Gln Gly Thr Leu Val Thr Val Ser Ser Gly
                130                 135                 140

Gly Gly Gly Ser Gly Gly Gly Gly Ser Gly Gly Gly Gly Ser Gly Gly
145                 150                 155                 160
```

```
Gly Gly Ser Asp Ile Gln Met Thr Gln Ser Pro Thr Leu Ser Ala
            165                 170                 175

Ser Val Gly Asp Arg Val Thr Ile Thr Cys Arg Ala Ser Glu Asn Val
        180                 185                 190

Asn Ile Trp Leu Ala Trp Tyr Gln Gln Lys Pro Gly Lys Ala Pro Lys
            195                 200                 205

Leu Leu Ile Tyr Lys Ser Ser Leu Ala Ser Gly Val Pro Ser Arg
        210                 215                 220

Phe Ser Gly Ser Gly Ser Gly Ala Glu Phe Thr Leu Thr Ile Ser Ser
225                 230                 235                 240

Leu Gln Pro Asp Asp Phe Ala Thr Tyr Tyr Cys Gln Gln Tyr Gln Ser
            245                 250                 255

Tyr Pro Leu Thr Phe Gly Gly Gly Thr Lys Val Asp Ile Lys Thr Thr
            260                 265                 270

Thr Pro Ala Pro Arg Pro Pro Thr Pro Ala Pro Thr Ile Ala Ser Gln
            275                 280                 285

Pro Leu Ser Leu Arg Pro Glu Ala Cys Arg Pro Ala Ala Gly Gly Ala
            290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
            325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
            355                 360                 365

Cys Arg Phe Pro Glu Glu Glu Glu Gly Gly Cys Glu Leu Arg Val Lys
            370                 375                 380

Phe Ser Arg Ser Ala Asp Ala Pro Ala Tyr Lys Gln Gly Gln Asn Gln
385                 390                 395                 400

Leu Tyr Asn Glu Leu Asn Leu Gly Arg Arg Glu Glu Tyr Asp Val Leu
            405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
            435                 440                 445

Ala Glu Ala Tyr Ser Glu Ile Gly Met Lys Gly Glu Arg Arg Arg Gly
            450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
            485                 490

<210> SEQ ID NO 77
<211> LENGTH: 488
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Gly Gly Leu
            20                  25                  30
```

-continued

Val Gln Pro Gly Arg Ser Leu Arg Leu Ser Cys Ala Ala Ser Gly Phe
         35                  40                  45

Thr Phe Asp Asp Tyr Ala Met His Trp Val Arg Gln Ala Pro Gly Lys
     50                  55                  60

Gly Leu Glu Trp Val Ser Gly Ile Ser Trp Asn Ser Gly Ser Ile Gly
 65              70                  75                      80

Tyr Ala Asp Ser Val Lys Gly Arg Phe Thr Ile Ser Arg Asp Asn Ala
                 85                  90                  95

Lys Asn Ser Leu Tyr Leu Gln Met Asn Ser Leu Arg Ala Glu Asp Thr
             100                 105                 110

Ala Val Tyr Tyr Cys Ala Lys Asp Gly Ser Ser Trp Ser Trp Gly
             115                 120                 125

Tyr Phe Asp Tyr Trp Gly Gln Gly Thr Leu Val Thr Val Ser Ser Gly
         130                 135                 140

Gly Gly Gly Ser Gly Gly Gly Ser Gly Gly Gly Ser Ser
145                 150                 155                 160

Glu Leu Thr Gln Asp Pro Ala Val Ser Val Ala Leu Gly Gln Thr Val
                 165                 170                 175

Arg Thr Thr Cys Gln Gly Asp Ala Leu Arg Ser Tyr Tyr Ala Ser Trp
             180                 185                 190

Tyr Gln Gln Lys Pro Gly Gln Ala Pro Met Leu Val Ile Tyr Gly Lys
             195                 200                 205

Asn Asn Arg Pro Ser Gly Ile Pro Asp Arg Phe Ser Gly Ser Asp Ser
210                 215                 220

Gly Asp Thr Ala Ser Leu Thr Ile Thr Gly Ala Gln Ala Glu Asp Glu
225                 230                 235                 240

Ala Asp Tyr Tyr Cys Asn Ser Arg Asp Ser Ser Gly Tyr Pro Val Phe
                 245                 250                 255

Gly Thr Gly Thr Lys Val Thr Val Leu Thr Thr Pro Ala Pro Arg
             260                 265                 270

Pro Pro Thr Pro Ala Pro Thr Ile Ala Ser Gln Pro Leu Ser Leu Arg
         275                 280                 285

Pro Glu Ala Cys Arg Pro Ala Ala Gly Gly Ala Val His Thr Arg Gly
         290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
             325                 330                 335

Gly Arg Lys Lys Leu Leu Tyr Ile Phe Lys Gln Pro Phe Met Arg Pro
             340                 345                 350

Val Gln Thr Thr Gln Glu Glu Asp Gly Cys Ser Cys Arg Phe Pro Glu
         355                 360                 365

Glu Glu Glu Gly Gly Cys Glu Leu Arg Val Lys Phe Ser Arg Ser Ala
370                 375                 380

Asp Ala Pro Ala Tyr Lys Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
             405                 410                 415

Arg Asp Pro Glu Met Gly Gly Lys Pro Arg Arg Lys Asn Pro Gln Glu
             420                 425                 430

Gly Leu Tyr Asn Glu Leu Gln Lys Asp Lys Met Ala Glu Ala Tyr Ser
             435                 440                 445

```
Glu Ile Gly Met Lys Gly Glu Arg Arg Gly Lys Gly His Asp Gly
    450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485

<210> SEQ ID NO 78
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Arg Ser Leu Arg Leu Ser Cys Ala Ala Ser Gly Phe
        35                  40                  45

Thr Phe Asp Asp Tyr Ala Met His Trp Val Arg Gln Ala Pro Gly Lys
    50                  55                  60

Gly Leu Glu Trp Val Ser Gly Ile Ser Trp Asn Ser Gly Ser Thr Gly
65                  70                  75                  80

Tyr Ala Asp Ser Val Lys Gly Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110

Ala Leu Tyr Tyr Cys Ala Lys Asp Ser Ser Ser Trp Tyr Gly Gly Gly
        115                 120                 125

Ser Ala Phe Asp Ile Trp Gly Gln Gly Thr Met Val Thr Val Ser Ser
    130                 135                 140

Gly Gly Gly Gly Ser Gly Gly Gly Ser Gly Gly Gly Gly Ser Ser
145                 150                 155                 160

Ser Glu Leu Thr Gln Glu Pro Ala Val Ser Val Ala Leu Gly Gln Thr
                165                 170                 175

Val Arg Ile Thr Cys Gln Gly Asp Ser Leu Arg Ser Tyr Tyr Ala Ser
            180                 185                 190

Trp Tyr Gln Gln Lys Pro Gly Gln Ala Pro Val Leu Val Ile Phe Gly
        195                 200                 205

Arg Ser Arg Arg Pro Ser Gly Ile Pro Asp Arg Phe Ser Gly Ser Ser
    210                 215                 220

Ser Gly Asn Thr Ala Ser Leu Ile Ile Thr Gly Ala Gln Ala Glu Asp
225                 230                 235                 240

Glu Ala Asp Tyr Tyr Cys Asn Ser Arg Asp Asn Thr Ala Asn His Tyr
                245                 250                 255

Val Phe Gly Thr Gly Thr Lys Leu Thr Val Leu Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320
```

```
Gly Thr Cys Gly Val Leu Leu Ser Leu Val Ile Thr Leu Tyr Cys
            325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
            355                 360                 365

Pro Glu Glu Glu Glu Gly Gly Cys Glu Leu Arg Val Lys Phe Ser Arg
370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
            435                 440                 445

Tyr Ser Glu Ile Gly Met Lys Gly Glu Arg Arg Arg Gly Lys Gly His
            450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 79
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Arg Ser Leu Arg Leu Ser Cys Ala Ala Ser Gly Phe
        35                  40                  45

Thr Phe Asp Asp Tyr Ala Met His Trp Val Arg Gln Ala Pro Gly Lys
    50                  55                  60

Gly Leu Glu Trp Val Ser Gly Ile Ser Trp Asn Ser Gly Ser Thr Gly
65                  70                  75                  80

Tyr Ala Asp Ser Val Lys Gly Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110

Ala Leu Tyr Tyr Cys Ala Lys Asp Ser Ser Ser Trp Tyr Gly Gly Gly
        115                 120                 125

Ser Ala Phe Asp Ile Trp Gly Gln Gly Thr Met Val Thr Val Ser Ser
    130                 135                 140

Gly Gly Gly Gly Ser Gly Gly Gly Ser Gly Gly Gly Gly Ser Ser
145                 150                 155                 160

Ser Glu Leu Thr Gln Asp Pro Ala Val Ser Val Ala Leu Gly Gln Thr
                165                 170                 175

Val Arg Ile Thr Cys Gln Gly Asp Ser Leu Arg Ser Tyr Tyr Ala Ser
```

```
            180                 185                 190

Trp Tyr Gln Gln Lys Pro Gly Gln Ala Pro Val Leu Val Ile Tyr Gly
            195                 200                 205

Lys Asn Asn Arg Pro Ser Gly Ile Pro Asp Arg Phe Ser Gly Ser Ser
        210                 215                 220

Ser Gly Asn Thr Ala Ser Leu Thr Ile Thr Gly Ala Gln Ala Glu Asp
225                 230                 235                 240

Glu Ala Asp Tyr Tyr Cys Asn Ser Arg Gly Ser Ser Gly Asn His Tyr
                245                 250                 255

Val Phe Gly Thr Gly Thr Lys Val Thr Val Leu Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
        290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
        450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 80
<211> LENGTH: 495
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Gly Gly Leu
            20                  25                  30

Val Gln Pro Gly Gly Ser Leu Arg Leu Ser Cys Ala Ala Ser Gly Phe
        35                  40                  45
```

```
Thr Phe Ser Ser Tyr Trp Met His Trp Val Arg Gln Ala Pro Gly Lys
 50                  55                  60

Gly Leu Val Trp Val Ser Arg Ile Asn Ser Asp Gly Ser Ser Thr Ser
 65                  70                  75                  80

Tyr Ala Asp Ser Val Lys Gly Arg Phe Thr Ile Ser Arg Asp Asn Ala
                 85                  90                  95

Lys Asn Thr Leu Tyr Leu Gln Met Asn Ser Leu Arg Ala Glu Asp Thr
                100                 105                 110

Ala Val Tyr Tyr Cys Val Arg Thr Gly Trp Val Gly Ser Tyr Tyr Tyr
            115                 120                 125

Tyr Met Asp Val Trp Gly Lys Gly Thr Thr Val Thr Val Ser Ser Gly
130                 135                 140

Gly Gly Gly Ser Gly Gly Gly Ser Gly Gly Gly Ser Gly Gly
145                 150                 155                 160

Gly Gly Ser Glu Ile Val Leu Thr Gln Ser Pro Gly Thr Leu Ser Leu
                165                 170                 175

Ser Pro Gly Glu Arg Ala Thr Leu Ser Cys Arg Ala Ser Gln Ser Val
            180                 185                 190

Ser Ser Asn Tyr Leu Ala Trp Tyr Gln Gln Lys Pro Gly Gln Pro Pro
            195                 200                 205

Arg Leu Leu Ile Tyr Asp Val Ser Thr Arg Ala Thr Gly Ile Pro Ala
210                 215                 220

Arg Phe Ser Gly Gly Ser Gly Thr Asp Phe Thr Leu Thr Ile Ser
225                 230                 235                 240

Ser Leu Glu Pro Glu Asp Phe Ala Val Tyr Tyr Cys Gln Gln Arg Ser
                245                 250                 255

Asn Trp Pro Pro Trp Thr Phe Gly Gln Gly Thr Lys Val Glu Ile Lys
                260                 265                 270

Thr Thr Thr Pro Ala Pro Arg Pro Pro Thr Pro Ala Pro Thr Ile Ala
            275                 280                 285

Ser Gln Pro Leu Ser Leu Arg Pro Glu Ala Cys Arg Pro Ala Ala Gly
            290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
            355                 360                 365

Cys Ser Cys Arg Phe Pro Glu Glu Glu Glu Gly Gly Cys Glu Leu Arg
370                 375                 380

Val Lys Phe Ser Arg Ser Ala Asp Ala Pro Ala Tyr Lys Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
            435                 440                 445

Lys Met Ala Glu Ala Tyr Ser Glu Ile Gly Met Lys Gly Glu Arg Arg
450                 455                 460

Arg Gly Lys Gly His Asp Gly Leu Tyr Gln Gly Leu Ser Thr Ala Thr
```

```
                465                 470                 475                 480
Lys Asp Thr Tyr Asp Ala Leu His Met Gln Ala Leu Pro Pro Arg
                    485                 490                 495

<210> SEQ ID NO 81
<211> LENGTH: 494
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Gly Gly Val
                20                  25                  30

Val Gln Pro Gly Arg Ser Leu Arg Leu Ser Cys Ala Ala Ser Gly Phe
            35                  40                  45

Thr Phe Ser Ser Tyr Gly Met His Trp Val Arg Gln Ala Pro Gly Lys
        50                  55                  60

Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Lys Gly Tyr Ser Arg Tyr Tyr Tyr Tyr Gly
        115                 120                 125

Met Asp Val Trp Gly Gln Gly Thr Thr Val Thr Val Ser Ser Gly Gly
    130                 135                 140

Gly Gly Ser Gly Gly Gly Gly Ser Gly Gly Gly Gly Ser Gly Gly Gly
145                 150                 155                 160

Gly Ser Glu Ile Val Met Thr Gln Ser Pro Ala Thr Leu Ser Leu Ser
                165                 170                 175

Pro Gly Glu Arg Ala Ile Leu Ser Cys Arg Ala Ser Gln Ser Val Tyr
            180                 185                 190

Thr Lys Tyr Leu Gly Trp Tyr Gln Gln Lys Pro Gly Gln Ala Pro Arg
        195                 200                 205

Leu Leu Ile Tyr Asp Ala Ser Thr Arg Ala Thr Gly Ile Pro Asp Arg
    210                 215                 220

Phe Ser Gly Ser Gly Ser Gly Thr Asp Phe Thr Leu Thr Ile Asn Arg
225                 230                 235                 240

Leu Glu Pro Glu Asp Phe Ala Val Tyr Tyr Cys Gln His Tyr Gly Gly
                245                 250                 255

Ser Pro Leu Ile Thr Phe Gly Gln Gly Thr Lys Val Asp Ile Lys Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335
```

Thr Leu Tyr Cys Lys Arg Gly Arg Lys Leu Leu Tyr Ile Phe Lys
            340                 345                 350

Gln Pro Phe Met Arg Pro Val Gln Thr Thr Gln Glu Glu Asp Gly Cys
        355                 360                 365

Ser Cys Arg Phe Pro Glu Glu Glu Gly Cys Glu Leu Arg Val
    370                 375                 380

Lys Phe Ser Arg Ser Ala Asp Ala Pro Ala Tyr Lys Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490

<210> SEQ ID NO 82
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Ala Met Ser Trp Val Arg Gln Ala Pro Gly Lys
    50                  55                  60

Gly Leu Glu Trp Val Ser Ala Ile Ser Gly Ser Gly Gly Ser Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Lys Arg Glu Ala Ala Ala Gly His Asp Trp
        115                 120                 125

Tyr Phe Asp Leu Trp Gly Arg Gly Thr Leu Val Thr Val Ser Ser Gly
    130                 135                 140

Gly Gly Gly Ser Gly Gly Gly Gly Ser Gly Gly Gly Gly Ser Gly Gly
145                 150                 155                 160

Gly Gly Ser Asp Ile Arg Val Thr Gln Ser Pro Ser Ser Leu Ser Ala
                165                 170                 175

Ser Val Gly Asp Arg Val Thr Ile Thr Cys Arg Ala Ser Gln Ser Ile
            180                 185                 190

Ser Ser Tyr Leu Asn Trp Tyr Gln Gln Lys Pro Gly Lys Ala Pro Lys
        195                 200                 205

-continued

```
Leu Leu Ile Tyr Ala Ala Ser Ser Leu Gln Ser Gly Val Pro Ser Arg
    210                 215                 220

Phe Ser Gly Ser Gly Ser Gly Thr Asp Phe Thr Leu Thr Ile Ser Ser
225                 230                 235                 240

Leu Gln Pro Glu Asp Phe Ala Thr Tyr Tyr Cys Gln Gln Ser Tyr Ser
                245                 250                 255

Ile Pro Leu Thr Phe Gly Gln Gly Thr Lys Val Glu Ile Lys Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Lys Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490
```

<210> SEQ ID NO 83
<211> LENGTH: 491
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

```
Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Trp Ala Glu Val
            20                  25                  30

Lys Lys Pro Gly Ala Ser Val Lys Val Ser Cys Lys Ala Ser Gly Tyr
        35                  40                  45

Thr Phe Thr Ser Tyr Tyr Met His Trp Val Arg Gln Ala Pro Gly Gln
    50                  55                  60

Gly Leu Glu Trp Met Gly Ile Ile Asn Pro Ser Gly Gly Ser Thr Ser
```

```
            65                  70                  75                  80
Tyr Ala Gln Lys Phe Gln Gly Arg Val Thr Met Thr Arg Asp Thr Ser
                85                  90                  95

Thr Ser Thr Val Tyr Met Glu Leu Ser Asn Leu Arg Ser Glu Asp Thr
            100                 105                 110

Ala Val Tyr Tyr Cys Ala Arg Ser Pro Arg Val Thr Thr Gly Tyr Phe
            115                 120                 125

Asp Tyr Trp Gly Gln Gly Thr Leu Val Thr Val Ser Ser Gly Gly Gly
            130                 135                 140

Gly Ser Gly Gly Gly Ser Gly Gly Gly Ser Gly Gly Gly Gly
145                 150                 155                 160

Ser Asp Ile Gln Leu Thr Gln Ser Pro Ser Thr Leu Ser Ala Ser Val
                165                 170                 175

Gly Asp Arg Val Thr Ile Thr Cys Arg Ala Ser Gln Ser Ile Ser Ser
            180                 185                 190

Trp Leu Ala Trp Tyr Gln Gln Lys Pro Gly Lys Ala Pro Lys Leu Leu
            195                 200                 205

Ile Tyr Lys Ala Ser Ser Leu Glu Ser Gly Val Pro Ser Arg Phe Ser
210                 215                 220

Gly Ser Gly Ser Gly Thr Glu Phe Thr Leu Thr Ile Ser Ser Leu Gln
225                 230                 235                 240

Pro Asp Asp Phe Ala Thr Tyr Tyr Cys Gln Gln Tyr Ser Ser Tyr Pro
            245                 250                 255

Leu Thr Phe Gly Gly Gly Thr Arg Leu Glu Ile Lys Thr Thr Thr Pro
            260                 265                 270

Ala Pro Arg Pro Pro Thr Pro Ala Pro Thr Ile Ala Ser Gln Pro Leu
            275                 280                 285

Ser Leu Arg Pro Glu Ala Cys Arg Pro Ala Ala Gly Gly Ala Val His
            290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
            325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
            355                 360                 365

Phe Pro Glu Glu Glu Glu Gly Gly Cys Glu Leu Arg Val Lys Phe Ser
370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
                435                 440                 445

Ala Tyr Ser Glu Ile Gly Met Lys Gly Glu Arg Arg Arg Gly Lys Gly
            450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
            485                 490
```

```
<210> SEQ ID NO 84
<211> LENGTH: 497
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
                20                  25                  30

Arg Arg Pro Gly Ala Ser Val Lys Ile Ser Cys Arg Ala Ser Gly Asp
            35                  40                  45

Thr Ser Thr Arg His Tyr Ile His Trp Leu Arg Gln Ala Pro Gly Gln
        50                  55                  60

Gly Pro Glu Trp Met Gly Val Ile Asn Pro Thr Thr Gly Pro Ala Thr
65                  70                  75                  80

Gly Ser Pro Ala Tyr Ala Gln Met Leu Gln Gly Arg Val Thr Met Thr
                85                  90                  95

Arg Asp Thr Ser Thr Arg Thr Val Tyr Met Glu Leu Arg Ser Leu Arg
            100                 105                 110

Phe Glu Asp Thr Ala Val Tyr Tyr Cys Ala Arg Ser Val Val Gly Arg
        115                 120                 125

Ser Ala Pro Tyr Tyr Phe Asp Tyr Trp Gly Gln Gly Thr Leu Val Thr
    130                 135                 140

Val Ser Ser Gly Gly Gly Gly Ser Gly Gly Gly Ser Gly Gly Gly
145                 150                 155                 160

Gly Ser Gly Gly Gly Gly Ser Asp Ile Gln Met Thr Gln Ser Pro Ser
                165                 170                 175

Ser Leu Ser Ala Ser Val Gly Asp Arg Val Thr Ile Thr Cys Arg Ala
            180                 185                 190

Ser Gln Gly Ile Ser Asp Tyr Ser Ala Trp Tyr Gln Gln Lys Pro Gly
        195                 200                 205

Lys Ala Pro Lys Leu Leu Ile Tyr Ala Ala Ser Thr Leu Gln Ser Gly
    210                 215                 220

Val Pro Ser Arg Phe Ser Gly Ser Gly Ser Gly Thr Asp Phe Thr Leu
225                 230                 235                 240

Thr Ile Ser Tyr Leu Gln Ser Glu Asp Phe Ala Thr Tyr Tyr Cys Gln
                245                 250                 255

Gln Tyr Tyr Ser Tyr Pro Leu Thr Phe Gly Gly Gly Thr Lys Val Asp
            260                 265                 270

Ile Lys Thr Thr Thr Pro Ala Pro Arg Pro Pro Thr Pro Ala Pro Thr
        275                 280                 285

Ile Ala Ser Gln Pro Leu Ser Leu Arg Pro Glu Ala Cys Arg Pro Ala
    290                 295                 300

Ala Gly Gly Ala Val His Thr Arg Gly Leu Asp Phe Ala Cys Asp Ile
305                 310                 315                 320

Tyr Ile Trp Ala Pro Leu Ala Gly Thr Cys Gly Val Leu Leu Leu Ser
                325                 330                 335

Leu Val Ile Thr Leu Tyr Cys Lys Arg Gly Arg Lys Lys Leu Leu Tyr
            340                 345                 350

Ile Phe Lys Gln Pro Phe Met Arg Pro Val Gln Thr Thr Gln Glu Glu
```

```
                355                 360                 365
Asp Gly Cys Ser Cys Arg Phe Pro Glu Glu Glu Gly Gly Cys Glu
            370                 375                 380
Leu Arg Val Lys Phe Ser Arg Ser Ala Asp Ala Pro Ala Tyr Lys Gln
385                 390                 395                 400
Gly Gln Asn Gln Leu Tyr Asn Glu Leu Asn Leu Gly Arg Arg Glu Glu
                405                 410                 415
Tyr Asp Val Leu Asp Lys Arg Arg Gly Arg Asp Pro Glu Met Gly Gly
            420                 425                 430
Lys Pro Arg Arg Lys Asn Pro Gln Glu Gly Leu Tyr Asn Glu Leu Gln
            435                 440                 445
Lys Asp Lys Met Ala Glu Ala Tyr Ser Glu Ile Gly Met Lys Gly Glu
            450                 455                 460
Arg Arg Arg Gly Lys Gly His Asp Gly Leu Tyr Gln Gly Leu Ser Thr
465                 470                 475                 480
Ala Thr Lys Asp Thr Tyr Asp Ala Leu His Met Gln Ala Leu Pro Pro
                485                 490                 495
Arg

<210> SEQ ID NO 85
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Met Ala Leu Pro Val Thr Ala Leu Leu Leu Pro Leu Ala Leu Leu Leu
1               5                   10                  15
His Ala Ala Arg Pro Gln Val Gln Leu Gln Gln Ser Gly Ala Glu Val
            20                  25                  30
Lys Lys Pro Gly Ala Ser Val Lys Val Ser Cys Lys Ala Ser Gly Tyr
        35                  40                  45
Thr Phe Thr Asn Tyr Tyr Met His Trp Val Arg Gln Ala Pro Gly Gln
    50                  55                  60
Gly Leu Glu Trp Met Gly Ile Ile Asn Pro Ser Gly Gly Tyr Thr Thr
65                  70                  75                  80
Tyr Ala Gln Lys Phe Gln Gly Arg Leu Thr Met Thr Arg Asp Thr Ser
                85                  90                  95
Thr Ser Thr Val Tyr Met Glu Leu Ser Ser Leu Arg Ser Glu Asp Thr
            100                 105                 110
Ala Val Tyr Tyr Cys Ala Arg Ile Arg Ser Cys Gly Gly Asp Cys Tyr
        115                 120                 125
Tyr Phe Asp Asn Trp Gly Gln Gly Thr Leu Val Thr Val Ser Ser Gly
    130                 135                 140
Gly Gly Gly Ser Gly Gly Gly Gly Ser Gly Gly Gly Gly Ser Gly Gly
145                 150                 155                 160
Gly Gly Ser Asp Ile Gln Leu Thr Gln Ser Pro Ser Thr Leu Ser Ala
                165                 170                 175
Ser Val Gly Asp Arg Val Thr Ile Thr Cys Arg Ala Ser Glu Asn Val
            180                 185                 190
Asn Ile Trp Leu Ala Trp Tyr Gln Gln Lys Pro Gly Lys Ala Pro Lys
        195                 200                 205
Leu Leu Ile Tyr Lys Ser Ser Ser Leu Ala Ser Gly Val Pro Ser Arg
```

```
            210                 215                 220
Phe Ser Gly Ser Gly Ser Gly Ala Glu Phe Thr Leu Thr Ile Ser Ser
225                 230                 235                 240

Leu Gln Pro Asp Asp Phe Ala Thr Tyr Tyr Cys Gln Gln Tyr Gln Ser
                245                 250                 255

Tyr Pro Leu Thr Phe Gly Gly Gly Thr Lys Val Asp Ile Lys Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Lys Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490

<210> SEQ ID NO 86
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Met Ala Leu Pro Val Thr Ala Leu Leu Leu Pro Leu Ala Leu Leu Leu
1               5                   10                  15

His Ala Ala Arg Pro Gln Ile Thr Leu Lys Glu Ser Gly Pro Ala Leu
            20                  25                  30

Val Lys Pro Thr Gln Thr Leu Thr Leu Thr Cys Thr Phe Ser Gly Phe
        35                  40                  45

Ser Leu Ser Thr Ala Gly Val His Val Gly Trp Ile Arg Gln Pro Pro
    50                  55                  60

Gly Lys Ala Leu Glu Trp Leu Ala Leu Ile Ser Trp Ala Asp Asp Lys
65                  70                  75                  80
```

```
Arg Tyr Arg Pro Ser Leu Arg Ser Arg Leu Asp Ile Thr Arg Val Thr
                85                  90                  95
Ser Lys Asp Gln Val Val Leu Ser Met Thr Asn Met Gln Pro Glu Asp
            100                 105                 110
Thr Ala Thr Tyr Tyr Cys Ala Leu Gln Gly Phe Asp Gly Tyr Glu Ala
        115                 120                 125
Asn Trp Gly Pro Gly Thr Leu Val Thr Val Ser Ser Gly Gly Gly Gly
    130                 135                 140
Ser Gly Gly Gly Gly Ser Gly Gly Gly Ser Gly Gly Gly Gly Ser
145                 150                 155                 160
Asp Ile Val Met Thr Gln Ser Pro Ser Ser Leu Ser Ala Ser Ala Gly
            165                 170                 175
Asp Arg Val Thr Ile Thr Cys Arg Ala Ser Arg Gly Ile Ser Ser Ala
        180                 185                 190
Leu Ala Trp Tyr Gln Gln Lys Pro Gly Lys Pro Pro Lys Leu Leu Ile
    195                 200                 205
Tyr Asp Ala Ser Ser Leu Glu Ser Gly Val Pro Ser Arg Phe Ser Gly
210                 215                 220
Ser Gly Ser Gly Thr Asp Phe Thr Leu Thr Ile Asp Ser Leu Glu Pro
225                 230                 235                 240
Glu Asp Phe Ala Thr Tyr Tyr Cys Gln Gln Ser Tyr Ser Thr Pro Trp
                245                 250                 255
Thr Phe Gly Gln Gly Thr Lys Val Asp Ile Lys Thr Thr Thr Pro Ala
            260                 265                 270
Pro Arg Pro Pro Thr Pro Ala Pro Thr Ile Ala Ser Gln Pro Leu Ser
        275                 280                 285
Leu Arg Pro Glu Ala Cys Arg Pro Ala Ala Gly Gly Ala Val His Thr
    290                 295                 300
Arg Gly Leu Asp Phe Ala Cys Asp Ile Tyr Ile Trp Ala Pro Leu Ala
305                 310                 315                 320
Gly Thr Cys Gly Val Leu Leu Leu Ser Leu Val Ile Thr Leu Tyr Cys
                325                 330                 335
Lys Arg Gly Arg Lys Lys Leu Leu Tyr Ile Phe Lys Gln Pro Phe Met
            340                 345                 350
Arg Pro Val Gln Thr Thr Gln Glu Glu Asp Gly Cys Ser Cys Arg Phe
        355                 360                 365
Pro Glu Glu Glu Glu Gly Gly Cys Glu Leu Arg Val Lys Phe Ser Arg
    370                 375                 380
Ser Ala Asp Ala Pro Ala Tyr Lys Gln Gly Gln Asn Gln Leu Tyr Asn
385                 390                 395                 400
Glu Leu Asn Leu Gly Arg Arg Glu Glu Tyr Asp Val Leu Asp Lys Arg
                405                 410                 415
Arg Gly Arg Asp Pro Glu Met Gly Gly Lys Pro Arg Arg Lys Asn Pro
            420                 425                 430
Gln Glu Gly Leu Tyr Asn Glu Leu Gln Lys Asp Lys Met Ala Glu Ala
        435                 440                 445
Tyr Ser Glu Ile Gly Met Lys Gly Glu Arg Arg Arg Gly Lys Gly His
    450                 455                 460
Asp Gly Leu Tyr Gln Gly Leu Ser Thr Ala Thr Lys Asp Thr Tyr Asp
465                 470                 475                 480
Ala Leu His Met Gln Ala Leu Pro Pro Arg
                485                 490
```

```
<210> SEQ ID NO 87
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87
caagtccaac tgcagcagtc aggagcggaa gtgaagaaac caggagcgtc agtcaaagtg    60
tcgtgcaagg ctagcggcta caccttcacc ggctactaca tgcactgggt tcgacaggct   120
ccagggcagg gtctggagtg gatgggccgc atcaacccga attccggtgg gactaactac   180
gcccagaagt tccaggaag agtgaccatg actagggaca cgtcgatcag cactgcgtac   240
atggaactga gccgcctgcg gtccgaggat actgccgtct actactgcgc acgcggaagg   300
tactatggaa tggacgtgtg gggccaaggg actatggtga ctgtgagctc gggagggga   360 ggctccggtg gcggggatc aggaggagga ggatcagggg gaggaggttc cgaaattgtc   420
ctcacccaga gcccggcaac cctctcactt tccccgggag agcgcgcaac catctcttgc   480
cgggctagcc aatccgtgtc gtccaattc gcctggtacc agcaacggcc gggacaagcc   540
cctagactcc tgatctacga cgccagcaac agagcgactg gaattcctcc acgcttttcg   600
ggatcaggct ccggtaccga cttcacccctg actatctcgt cgctcgaacc cgaggatttc   660
gccgcctact actgtcatca gcggtcgaac tggttgtata cgtttggcca gggcaccaag   720
gtggatatca ag                                                      732

<210> SEQ ID NO 88
<211> LENGTH: 759
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88
caagtccaac tcgtccagtc aggagcagaa gtcaagaaac caggtgctag cgtgaaagtg    60
tcgtgcaagg cgtcgggata cactttcacc ggatactaca tgcactgggt ccgccaggcc   120
cccggacaag gactggaatg gatgggctgg atcaacccga atagcggggg aactaattac   180
gcccagaagt ttcagggacg agtgaccatg acccgcgata cctctatctc gaccgcctac   240
atggagctct ccagactgcg ctccgacgat actgcagtgt actactgcgc ccgggacctg   300
aggcggactg tggttactcc tcgcgcctat tatggcatgg acgtgtgggg ccaaggaact   360
actgtgactg tgagctcggg aggcggtggg tcaggcggag gaggtcgggg cggtggtggc   420
tcgggagggg gaggaagcga cattcaactt acgcagagcc cgtcaaccct gtcagcgtca   480
gtgggagatc gggtgaccat cacgtgtcag gccagccagg atatctccaa ctcgctcaac   540
tggtaccagc aaaaggcggg taaagctccg aagctgctga tctacgacgc ttccaccctc   600
gagactggag tcccatccag atttttcggg tcaggaagcg gcaccgattt ctccttcacc   660
atttcgtcct gcaaccgga ggacatcgca acctactact gccagcagca tgacaacttg   720
cctctgacgt tcgggcaggg caccaaggtg gaaatcaag                          759

<210> SEQ ID NO 89
<211> LENGTH: 738
<212> TYPE: DNA
<213> ORGANISM: Artificial Sequence
<220> FEATURE:
```

<223> OTHER INFORMATION: Description of Artificial Sequence: Synthetic
polynucleotide

<400> SEQUENCE: 89

| caagtccaac tcgtccaatc aggagcggaa gtcaaaaagc ccggagctcc agtgaaagtg | 60 |
| tcatgcaagg cctccggcta caccttcacc ggttactata tgcactgggt gcggcaggcc | 120 |
| ccgggccagg ggttggaatg gatgggatgg atcaatccaa actcgggtgg gactaactac | 180 |
| gcccagaagt tccaaggacg ggtgaccatg actaggacac cctcgatctc caccgcatac | 240 |
| atggagctta gcagactccg ctccgacgat accgcagtct actattgcgc gcggggagag | 300 |
| tgggacggat cgtactacta cgattactgg ggccagggaa ctctggtgac tgtttcctcg | 360 |
| ggtggaggag gttcaggcgg aggcggctcg ggcggggggag gatctggagg aggagggtcc | 420 |
| gacattgtgc tgacccaaac tccttcgtcc ctgtcggcca gcgtgggcga ccgcgtgacg | 480 |
| attacgtgca gagctagcca atccatcaat acttacctca actggtacca gcataagccg | 540 |
| gggaaagcac caaagctgct gatctacgcc gcctcatcct tgcagagcgg tgtgccttca | 600 |
| cgctttagcg gatcgggatc gggaacggat ttcaccctga ctatcagctc cctccagccg | 660 |
| gaggattttg cgacctacta ctgtcagcag agcttctcac cgctgacttt cggcggcggg | 720 |
| accaagctgg aaatcaag | 738 |

<210> SEQ ID NO 90
<211> LENGTH: 726
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 90

| caagtgcaac tcgttgaatc aggtggaggt ttggtgcaac ccggaggatc tctcagactg | 60 |
| tcgtgtgcgg cgtccgggtt caccttttcg tcctactgga tgcactgggt gcgccaggtg | 120 |
| ccgggaaaag gactggtgtg ggtgtccaga atcaacaccg acgggtcaac gactacctac | 180 |
| gcagatagcg tggaaggtcg gttcaccatt tcgcgggaca acgctaaaaa cactctgtac | 240 |
| cttcagatga attcactgcg cgatgacgac accgcagtct actactgcgt cggtggacac | 300 |
| tgggcggtct ggggacaggg aactacggtg actgtgtcca gcggcggggg aggaagcggc | 360 |
| ggagggggga gcggaggcgg aggatcagga ggaggcggct ccgatatcca gatgacccag | 420 |
| tcgccatcga ccctctccgc tagcgtgggg gatagggtca ctatcacttg ccgagccagc | 480 |
| caatccatta gcgaccggct tgcctggtac aacagaaaac ctggaaaggc cccgaagctg | 540 |
| ctcatctaca aggcctcgtc actggagtcg ggagtcccgt cccgcttttc cggctcgggc | 600 |
| tcaggcaccg agttcactct gaccatctcg agcctgcagc cggacgattt cgccgtgtat | 660 |
| tactgccagc aatacggaca tctcccaatg tacacgttcg gtcagggcac caaggtcgaa | 720 |
| atcaag | 726 |

<210> SEQ ID NO 91
<211> LENGTH: 723
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 91

| | |
|---|---:|
| caagtccaac tcgttcaatc aggcgcagaa gtcgaaaagc ccggagcatc agtcaaagtc | 60 |
| tcttgcaagg cttccggcta caccttcacg gactactaca tgcactgggt gcgccaggct | 120 |
| ccaggccagg gactggagtg gatgggatgg atcaacccga attccggggg aactaactac | 180 |
| gcccagaagt tcagggccgg ggtgactatg actcgcgata cctcgatctc gactgcgtac | 240 |
| atggagctca gccgcctccg gtcggacgat accgccgtgt actattgtgc gtcgggatgg | 300 |
| gacttcgact actgggggca gggcactctg gtcactgtgt caagcggagg aggtggatca | 360 |
| ggtggaggtg gaagcggggg aggaggttcc ggcggcggag gatcagatat cgtgatgacg | 420 |
| caatcgcctt cctcgttgtc cgcatccgtg ggagacaggg tgaccattac ttgcagagcg | 480 |
| tcccagtcca ttcggtacta cctgtcgtgg taccagcaga agccggggaa agccccaaaa | 540 |
| ctgcttatct atactgcctc gatcctccaa aacggcgtgc catcaagatt cagcggttcg | 600 |
| ggcagcggga ccgactttac cctgactatc agcagcctgc agccggaaga tttcgccacg | 660 |
| tactactgcc tgcaaaccta caccaccccg gacttcggac ctggaaccaa ggtggagatc | 720 |
| aag | 723 |

<210> SEQ ID NO 92
<211> LENGTH: 759
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92

| | |
|---|---:|
| caagtgcaac tcgtccagtc aggtgcagaa gtgaagaaac ccggagcgtc agtcaaagtg | 60 |
| tcatgcaagg cgtcaggcta caccttcacc agctactaca tgcactgggt gcggcaggcc | 120 |
| ccaggccaag gcttggagtg gatgggaatc attaacccgt caggaggctc cacctcctac | 180 |
| gcccagaagt tcagggaag agtgacgatg actcgggata cgtcgacctc gaccgtgtac | 240 |
| atggaactga gctcgctgcg ctccgaggac actgctgtgt actactgcgc acggtacaga | 300 |
| ctcattgccg tggcaggaga ctactactac tatggcatgg acgtctgggg gcagggcact | 360 |
| atggtcactg tgtcgtccgg cggaggaggc tcgggtggag gaggtagcgg aggaggggga | 420 |
| agcggagggg ggggctccga tatccagatg actcagtcgc cttcctccgt gtcggcctcg | 480 |
| gttgagatc gcgtcaccat cacttgtcga gcttcccaag gagtcggtag gtggctggcg | 540 |
| tggtaccagc aaaagccggg aactgccccg aagctcctga tctacgcggc tagcaccctg | 600 |
| cagtcgggag tgccatcccg cttcagcgga tctgggtcag gtaccgactt caccccttacg | 660 |
| atcaacaatc tccagccgga ggactttgcc acctattact gccaacaggc caacagcttc | 720 |
| cctctgactt tcggagggggg cactcgcctg gaaatcaag | 759 |

<210> SEQ ID NO 93
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93

| | |
|---|---:|
| caagtgcaat tggttcaatc aggaggagga gtggtgcaac ctggaagatc tctcagactg | 60 |
| tcgtgtgcgg catcgggatt cactttctca tcatacgcaa tgcactgggt ccgccaggcc | 120 |
| ccgggcaaag gcttggaatg ggtggcggtc atttcatacg acggctcgaa caagtactac | 180 |

-continued

```
gctgacagcg tgaagggacg ctttactatt tcccgggaca attcgaagaa cactctgtac      240
ctccagatga actcccttag ggctgaggac accgccgtct actactgcgc acgctggaaa      300
gtgtcgtcca gctccccagc ttttgactac tggggacagg gaaccccttgt gaccgtgtcg     360 tccggtggag ggggaagcgg cggagggggga tcaggtggcg gcggatcggg aggcggggga    420
tcagaaatcg tgctgactca gtccccggcc acgctgtctc tcagcccggg agagagagcg      480
atcctgtcct gccgcgcctc gcagagcgtg tacactaagt acctgggggtg gtaccagcag    540 aaaccgggtc aagcgcctcg gctgctgatc tacgatgcct ccacccgggc caccggaatc     600
cccgatcggt tctccggcag cggctcggga actgatttca cgctgaccat caatcgcctg     660
gagccggaag atttcgccgt ctattactgc cagcattacg gcgggagccc actcatcacc     720
ttcggtcaag aacccgact cgaaatcaag                                        750
```

<210> SEQ ID NO 94
<211> LENGTH: 738
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 94

```
caagtccaac tccagcagtc aggtgcagaa gtcaaaaagc caggagcatc cgtgaaggtt      60
tcgtgcaaga cttccggcta ccctttacc gggtactccc tccattgggt gagacaagca      120
ccgggccagg gactggagtg gatgggatgg atcaacccaa attcggcgg caccaactat      180 gcgcagaagt tccagggacg ggtgaccatg actcgcgaca cttcgatctc cactgcctac     240
atggagctgt cccgcttgag atctgacgac acggccgtct actactgcgc ccgggatcac     300
tacggaggta attcgctgtt ctactggggg cagggaaccc ttgtgactgt gtcctcgggt    360
ggtggagggt caggaggcgg aggctcaggg ggaggaggta gcggaggagg cggatcagac    420
atccaactga cccagtcacc atcctccatc tcggctagcg tcggagacac cgtgtcgatt      480
acttgtaggg cctcccaaga ctcagggacg tggctggcgt ggtatcagca aaaaccgggc     540
aaagctccga acctgttgat gtacgacgcc agcaccctcg aagatggagt gcctagccgc     600
ttcagcggaa gcgcctcggg cactgaattc acgctgactg tgaatcggct ccagccggag    660
gattcggcga cctactactg ccagcagtac aacagctacc ccctgaccttt tggaggcggg    720 accaaggtgg atatcaag                                                    738
```

<210> SEQ ID NO 95
<211> LENGTH: 744
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 95

```
caagtgcaac tcgtccagtc aggtgcagaa gtgaagaaac caggagcgtc cgtcgaagtg     60
tcgtgtaagg cgtccggcta cactttcacc tcgtactaca tgcactgggt gcggcaggcc     120
ccgggacaag gcctcgaatg gatgggaatc atcaacccga gcggaggctc gactggttac    180
gcccagaagt tccagggaag ggtgacgatg acccgcgata cctcgacttc gaccgttcat    240
atggagctct cgtccctgcg gagcgaggac actgctgtct actattgcgc gcggggagga     300
```

```
tactctagct cctccgatgc atttgacatt tggggccagg gaactatggt gaccgtgtca    360
tcaggcggag gtggatcagg aggaggaggg tcgggagggg gaggcagcgg cggggctggg    420
tcggacattc agatgacgca gtcccctcct agcctgagcg cctcggtggg tgacagagtg    480
accatcactt gcagagcctc gcaagacatc tcctccgcat tggcttggta ccagcaaaag    540
ccgggcactc cgccgaaact gctcatctac gatgcctcct cactggagtc aggagtccca    600
tctcgcttct cggggtcagg aagcggcacc gattttaccc ttaccatctc cagcctgcag    660
cccgaggact cgccacgtac tactgccaa cagttcagct cctacccact gaccttcggg    720
ggcggaactc gcctggaaat caag    744
```

<210> SEQ ID NO 96  
<211> LENGTH: 765  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 96

```
caagtgcaac tcgtccagag cggagcagaa gtcaagaagc caggagcgtc agtgaaagtg    60
tcatgcaagg ccagcggcta tacctttact tcgtatggga tctcctgggt gcggcaggca    120
ccgggccaag gactggagtg gatgggatgg atctcagcct acaacggtaa caccaactac    180
gcccagaagc tgcaaggacg cgtgaccatg actactgata cgagcacctc cactgcctac    240
atggaattgc ggtcccttcg gtcggacgat actgctgtgt actactgcgc aagagtcgcc    300
ggagggatct actactacta cggcatggac gtctgggac agggaaccac cattacggtg    360
tcgagcggag gggaggctc gggggagga ggaagcggag gtggcggctc cggggcggc    420 ggatcggaca ttgtgatgac ccagactcct gactccctgg ctgtttcgtt gggagagcgc    480
gcgactatct cgtgtaagtc cagccactca gtcctgtaca tcgcaataa caagaactac    540 ctcgcgtggt accagcaaaa accgggtcag ccgcctaaac tcctgttcta ctgggcctcc    600
accagaaaga gcggggtgcc agatcgattc tctggatcag gatcaggtac cgactttacg    660
ctgaccatct cgtccctgca gccggaggat ttcgcgactt acttctgcca gcagactcag    720
actttccccc tcaccttcgg tcaaggcacc aggctggaaa tcaat    765
```

<210> SEQ ID NO 97  
<211> LENGTH: 723  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 97

```
caagtccaat tgcagcagag cggagcagaa gtgaagaagc caggagcgtc agtcaaagtg    60
tcgtgtaagg cgtcaggata caccttcacg ggatactaca tgcactgggt gcgccaggcc    120
ccgggccaag gactcgagtg gatgggctgg atcaaccta actctggagg caccaactac    180
gcccagaatt tccaaggcag agtgaccatg acccgggaca cctccatctc gactgcctat    240
atggaactgc ggcggctgcg ctcggacgat actgctgtgt attactgcgc cagcggctgg    300
gactttgact actggggaca gggtactctg gtgactgttt cctcggggag aggcggatcg    360
ggtggaggag gtagcggggg aggggggtcg ggaggcggag gcagcgatat tcgcatgact    420
caatcgccgt cctccctgag cgctagcgtg ggagatcgag tcaccatcac ttgcagagcg    480
```

```
tcacagtcga ttcgctacta cctgtcctgg taccagcaga aaccgggaaa ggcaccaaag      540
cttctgatct acacggcctc catcctgcaa aatggtgtcc catcaaggtt ctccgggtca      600
gggagcggca ctgacttcac tctcaccatc tcctcactcc agcccgagga ctttgcaacc      660
tactactgcc tccagacgta caccaccccg gatttcggtc ctggaaccaa ggtggaaatc      720
aaa                                                                    723

<210> SEQ ID NO 98
<211> LENGTH: 738
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98
caagtccaac tcgtccaaag cggagcagaa gtcaaaaagc caggagcgtc ggtgaaagtg       60
tcttgcaaag ccagcggcta caccttcacg ggttactaca tgcactgggt gcgccaggcg      120
ccgggccagg ggctggagtg gatgggccgg attaaccctaa cagcggggg aactaattac      180 gctcagaagt tccagggtag agtcaccatg actacggaca cttccacttc caccgcctat      240
atggaactgc gctccctccg ctcagatgat actgccgtgt attactgcgc gcggactacc      300
acgtcatacg catttgacat ctgggggccag ggaactatgg tgaccgtgag ctcgggcgga      360
ggcggttcag ggggaggagg aagcggagga ggaggatcgg gaggaggtgg ctccgatatc      420
cagctgactc agtccccgag caccctgtcg gcgtcggtgg gggacagggt taccatcacc      480
tgtagagctt cccaatccat ttcgacttgg ctggcctggt accagcaaaa gccgggaaag      540
gcccctaatt tgcttatcta caaggcatcg accctcgaaa gcgtgtgcc ctcccggttt      600 tcgggatcag gatcagggac cgagttcacc ctgaccatct catcctcca gccggacgac      660 ttcgccactt actactgcca gcagtacaac acctactcgc catacacttt cggccaaggc      720
accaagctgg agatcaag                                                   738

<210> SEQ ID NO 99
<211> LENGTH: 747
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99
caagttcaac tcgtgcaatc aggtggagga ctcgtcaaac ccggaggatc attgagactg       60
tcatgcgaag cgagcggttt tatcttctcc gattactata tgggatggat tcggcaggcc      120
ccgggaaagg gactcgaatg ggtgtcatac atcggaaggt caggctcgtc catgtactac      180
gcagactcgg tgaaaggcag attcaccttt agccgggaca acgccaagaa ttccctctac      240
ttgcagatga acagcctgcg agccgaggat actgctgtct actactgtgc gcgtcgccg      300 gtggtggcag ctactgaaga tttccagcac tggggacagg gaactctggt cacggtgtcg      360
agcggtgggg gcgaagcgg aggcggagga tcggcggcg gaggttcggg gggggaggg      420 tctgacatcg tgatgaccca aacccccagcc accctgagcc tctcccctgg agagcgcgcg      480
actctttcgt gccgcgcttc ccagtcagtg accagcaatt acttggcttg gtaccaacag      540
aagccgggac aggcgccacg gctgctgctt tttggtgcca gcactcgcgc caccggaatc      600
```
ccggatcgct tctcgggctc agggtccggg acggacttca ccctgactat caaccggctg    660
gaacctgagg acttcgcgat gtactactgc cagcagtacg gctccgcacc agtcactttc    720
ggacaaggca ccaagctgga gatcaag                                        747

<210> SEQ ID NO 100
<211> LENGTH: 747
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100
caagtccaac tcgtccagtc gggagcagaa gttagagcac caggagcgtc agtgaaaatc     60
tcatgcaagg cctcgggctt cacgttccgc ggatactaca tccactgggt gcgccaagcc    120
ccgggtcagg gattggagtg gatgggaatc attaacccat caggagggag ccgggcttac    180
gcgcagaagt tccagggacg cgtcactatg acccgagata cttccacctc gactgtgtac    240
atggaactct cgtccctgag gtccgacgac actgcgatgt attactgtgc tcggactgcc    300
agctgcggtg gggactgtta ctacctcgat tactggggcc agggaactct ggtgaccgtg    360
tccagcggag gtggcgggtc aggggggtggc ggaagcggag gcggcggttc aggcggagga    420
ggctcggaca tccaaatgac gcaatcgccg cctacccctga gcgcttccgt gggagatcgg    480
gtgaccatta cttgcagagc atccgagaac gtcaatatct ggctggcctg gtaccaacag    540
aagccgggga aggcccctaa actgctgatc tacaagtcga gcagccttgc ctctggagtg    600
ccctcccgct tctcgggctc gggatcagga gcggaattca ccctcaccat ctcctccctg    660
cagccagatg actttgccac ctactactgc cagcagtacc agagctatcc gttgaccttt    720
gggggaggca ctaaagtgga catcaag                                        747

<210> SEQ ID NO 101
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101
caagttcaac tcgttcaatc aggtggagga ctcgtgcaac caggaagatc actcagactc     60
agctgcgccg cgtcgggatt cactttcgat gactacgcaa tgcactgggt gcggcaggcc    120
ccgggcaaag gactggaatg ggtgagcgga attagctgga ctcggggtc atcgggtac    180 gccgactcgg tgaagggacg ctttacgatc tcccgggaca tgccaagaa ctccctgtat    240 ttgcagatga actccttgag ggctgaggac accgccgtgt actactgcgc taaagatgga    300
tcatcgtcct ggtcctgggg atacttcgat tactggggcc agggcactct ggtgaccgtg    360
tcgtcaggcg gtggagggtc gggcggagga ggtagcggag gcgagggag cagctctgaa    420 ctgacccaag accggcggt gtcggtcgcc cttggtcaga ctgtgcggac tacctgtcag    480
ggggacgcgc tgcgctcgta ctacgcttca tggtaccagc agaagcccgg acaggcacct    540
atgctggtca tctacggaaa gaataaccgc ccatccggca tcccggatcg cttctcgggt    600
tcggacagcg gcgacaccgc atccctgacg atcactggag cgcaggccga ggatgaagcc    660
gactactact gcaattcccg agattcaagc ggctaccctg tgtttgggac cggaactaag    720
gtcaccgtcc tg                                                        732

<210> SEQ ID NO 102
<211> LENGTH: 738
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 102

```
gaagtgcaac tcgtggaatc tggtggagga cttgtgcaac ctggaagatc gttgagactc    60
tcatgtgctg cctccgggtt cacctttgac gactacgcca tgcactgggt gcgccaggca   120
ccaggaaagg gtctggagtg ggtttcgggt atctcgtgga actccgggag cactggctac   180
gctgattcgg tgaaaggccg gtttaccatc tcccgagaca tgcgaagaa ttccctctat   240 ctgcagatga acagcctccg ggccgaggat actgccctgt actactgcgc caaggatagc   300
tcatcatggt acggaggtgg atcggctttc gatatctggg gccagggcac gatggtcacc   360
gtgtcctcgg ggggcggagg ctccggggga ggaggtagcg gaggaggagg atcgagctca   420
gagttgactc aagaacccgc agtgtccgtg gcactgggcc aaaccgtcag gatcacttgc   480
cagggagaca gcctgaggtc gtactacgcg tcctggtacc agcagaagcc gggacaggcc   540
ccggtcctgg tcattttcgg acgctcaaga cgcccatcgg gcatcccgga ccggttcagc   600
ggaagctcct cgggaaacac cgcgtcactt atcattaccg gcgcacaggc tgaggacgaa   660
gcggattact actgcaactc ccgcgacaat actgccaacc attacgtgtt cgggaccgga   720
acgaaactga ctgtcctg                                                 738
```

<210> SEQ ID NO 103
<211> LENGTH: 738
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 103

```
gaagttcaat tggtggaatc tggaggagga cttgtgcaac ccggtagatc tctgagactg    60
tcctgtgcgg catcgggatt caccttcgac gactacgcta tgcactgggt gagacaagcc   120
cctggaaaag gactggagtg ggtgtcaggc atctcctgga atagcgggtc cactggatac   180
gccgattcgg tcaagggtcg cttcaccatt tcccgggaca tgccaagaa ctccctgtac   240 cttcaaatga actccctccg ggccgaggat accgccctct actactgcgc caaagacagc   300
tcgtcatggt atggcggagg gtcggcattt gacatctggg gacagggaac tatggtgact   360
gtgtcatcag gaggcggcgg aagcggcggc ggcgggtccg gcggaggagg gtcgtccagc   420
gaactcaccc aagatccagc agtgagcgtc gcgctgggcc agaccgtcag gatcacgtgc   480
cagggagatt cactgcgctc atactacgcg tcctggtacc agcagaagcc ggggcaggcc   540
ccggtcctcg tgatctacgg aaagaacaac cgcccgtcgg gtatcccaga ccgcttttcg   600
ggtagctcca gcggaaatac ggctagcctg accatcactg agcacaggc tgaggatgaa   660 gcggactact actgcaattc gcggggctca tcgggaacc attacgtgtt cggaactggt   720
accaaggtga ctgtcctg                                                 738
```

<210> SEQ ID NO 104
<211> LENGTH: 753
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 104

```
caagtgcagc tcgttcaatc aggcggagga ctcgttcaac caggaggatc attgcgactc      60
tcatgtgcgg cctctggatt cacgtttagc tcatattgga tgcactgggt gcggcaggcg     120
ccggggaaag gtctggtgtg ggtcagccgc atcaactcag acggctcctc gacttcgtac     180
gccgactccg tgaagggacg ctttaccatt tcccgcgaca cgccaagaa taccctttac      240
cttcagatga actccctccg cgctgaggat accgccgtgt actactgcgt gaggactggc     300
tgggtcggca gctactacta ctacatggac gtgtgggca aaggaactac tgtcaccgtg      360
tcaagcggcg gtggaggttc cggcggggga ggatcggggg gggcggatc gggtggcgga      420
ggatcggaga tcgtgttgac ccagtcgccg gaaccctgt cgctgtcgcc tggggagaga      480
gcaactctgt cctgccgggc ttcccagtcg gtgtcgagca attacctggc atggtaccaa     540
cagaagccgg acagccgcc acgcctgctg atctatgacg tgtcaactcg gcaactgga      600
atccctgcgc ggttcagcgg cggagggagc ggtaccgatt tcaccctgac tatttcctcc     660
ctcgaaccag aagatttcgc cgtctactac tgccagcaga aagcaactg ccgcccctgg      720
acgttcggac aaggaaccaa ggtcgaaatc aag                                  753
```

<210> SEQ ID NO 105
<211> LENGTH: 750
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 105

```
caagtgcaat tggttcaatc aggaggagga gtcgtgcagc ccggaagatc gttgagactg      60
tcatgtgccg cgagcggctt tactttctca agctacggaa tgcattgggt gcgacaggct     120
ccgggaaaag gactggaatg ggtcgcagtg atctcatacg acggctcgaa caagtactac     180
gccgactccg tcaagggtcg gttcacgatt tcgcgcgata attccaagaa cactctgtac     240
ctccaaatga cagcctccg ggcagaggac accgccgtct actactgcgc taagggatac     300
tcgcgctact actactatgg aatggatgtg tggggccagg gaactaccgt gacggtgtcg     360
tccggcggcg gtgggtcggg cggaggcgga tcaggtggag gtggaagcgg aggaggaggg     420
agcgaaatcg tcatgactca gtcccctgct acccttctc tgtcgccggg agaaagagcc      480
atcctgagct gccgggcctc ccagagcgtg tacaccaaat acctgggatg gtaccagcag     540
aagccggggc aggcaccaag gctcctgatc tacgatgcgt ccacccgcgc gactggtatc     600
ccagaccgct tttccggctc ggggtcaggg actgacttca cccttactat caatcggctc     660
gagcctgagg atttcgccgt gtattactgc cagcactacg agggtccccc gctgattacc     720
ttcggccaag gcaccaaagt ggacatcaag                                      750
```

<210> SEQ ID NO 106
<211> LENGTH: 747
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 106

```
caagtgcaac ttgttcaatc aggaggagga ctcgttcaac ccggaggatc actgcgactc    60
tcatgtgcag cgtcggggtt caccttctcc agctacgcaa tgtcctgggt gcgccaagcc   120
cctggaaaag gcctggagtg ggtgtcggcc atctctggga gcggggatc aacttactac    180
gctgactccg tcaagggccg ctttaccatc tcccgggaca acagcaagaa cactctctat   240
ctccagatga actcgctgag agccgaagat accgctgtct actactgcgc gaagagagaa   300
gctgccgcag ggcacgattg gtacttcgac ttgtggggca ggggcaccct tgtgaccgtg   360
tcctccggtg gaggcggatc aggaggtggg ggatcgggtg gaggaggaag cggaggcggc   420
ggttcggaca ttcgcgtcac ccagtcaccg agctccctca gcgcatcggt gggcgaccgg   480
gtcactatca cttgccgggc gtcccagtcg atctcatcgt atctgaattg gtaccagcag   540
aaaccgggaa aggcgccgaa gctgttgatc tacgctgcca gctccctgca gtcgggtgtg   600
ccatcacgct tttccggctc gggatcggga accgatttca ctctgacgat ctctagcctg   660
cagccagaag atttcgccac ttactactgc cagcagtcct acagcatccc tctgactttc   720
ggacaaggga cgaaagtgga gattaag                                       747
```

<210> SEQ ID NO 107
<211> LENGTH: 741
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 107

```
caagtccaac tcgttcagtc atgggcagaa gtcaagaaac ccggtgcaag cgtcaaagtg    60
tcgtgtaagg cctccggcta cactttcact tcctactaca tgcactgggt gcgccaagcc   120
ccgggacagg gccttgaatg gatgggcatc atcaacccat caggaggttc cacgagctac   180
gcgcagaagt tccaggggag agtgacgatg actagagata cctccacgag caccgtctac   240
atggagctgt cgaatctgcg gtcagaggac actgctgtgt attactgcgc gcgctccccg   300
cgggtgacca ctggctactt tgactactgg ggacaaggga ccctggtgac cgtcagctcg   360
ggaggcggag gatcgggagg tggagggtcc ggtggaggcg gctctggagg aggcgggtcg   420
gacattcaat tgacccagag cccatccacc ctctcagcct cggtggggga tagggtgact   480
atcacttgcc gggcctccca gtcaatttcc agctggctgg cttggtacca gcaaaagcct   540
ggaaaggcac cgaagctcct gatctacaag gcctcatctc tggaatcagg agtgccttcg   600
cgcttcagcg gaagcggctc gggaactgag tttaccctga ccatctcgag cctgcagcca   660
gatgacttcg cgacctatta ctgccagcag tactcgtcct acccgttgac tttcggagga   720
ggtacccgcc tcgaaatcaa a                                             741
```

<210> SEQ ID NO 108
<211> LENGTH: 759
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 108

```
caagtccaac tcgtccagtc cggtgcagaa gtcagaaggc caggagcaag cgtgaagatc    60
tcgtgtagag cgtcaggaga caccagcact cgccattaca tccactggct gcgccaggct   120
```

```
ccgggccaag ggccggagtg gatgggtgtg atcaacccga ctacgggacc ggctaccgga      180
agccctgcgt acgcacagat gctgcaggga cgggtgacta tgacccgcga tactagcact      240
aggaccgtgt acatggaact ccgctcgttg cggttcgaag ataccgccgt ctactactgc      300
gcccggtccg tggtgggccg aagcgcccct tactacttcg attactgggg acagggcact      360
ctggtgaccg ttagctccgg tggggaggc tcgggtggag gcggatcggg aggaggaggc       420
agcggtggag ggggatcgga cattcagatg acccagtcac cctcctccct ctcagcctcg      480 gtcgggacc gggtgaccat tacgtgcaga gcctcacaag ggatctcgga ctactccgcc       540
tggtaccagc agaaaccggg aaaagcgcca agctcctga tctacgccgc gagcaccctg       600
caatcaggag tgccatcgcg ctttctgga tcgggctcag ggactgactt cacgctgact       660
atctcctacc ttcagtccga ggatttcgct acctactact gccaacagta ttactcctat      720
cccctgacct ttggcggagg cactaaggtg gacatcaag                              759
```

<210> SEQ ID NO 109
<211> LENGTH: 747
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 109

```
caagtccaac tccagcaatc gggagcagaa gtcaagaaac caggcgcatc ggtgaaagtg       60
tcgtgtaagg cgtcagggta caccttcacc aactactata tgcactgggt gcgccaggct      120
ccaggccagg ggttggagtg gatggggatc atcaatccgt caggtggcta caccacttac      180
gctcagaagt tccagggacg cctcactatg actcgcgata ctagcacctc cacggtgtac      240
atggaactgt catcgctgag gtccgaagat accgccgtct actactgcgc acggatcaga      300
tcctgcggag gagattgtta ctactttgac aactggggac agggcaccct tgttactgtg      360
tcatcgggag aggggaag cggaggaggt ggatcaggcg gcggtggcag cggggcgga        420 ggatcggaca ttcagctgac tcagtccccc tccactttgt cggccagcgt gggagacaga      480
gtgaccatca cttgccgggc gtccgagaac gtcaatatct ggctggcctg gtaccagcaa      540
aagcctggaa aagccccgaa gctgctcatc tataagtcat ccagcctggc gtctggtgtg      600
ccgtcgcggt tctccggcag cgggagcgga gccgagttca ctctcaccat ttcgagcctt      660
caaccggacg atttcgccac ctactactgc cagcagtacc aatcctaccc tctgacgttt      720
ggaggtggaa ccaaggtgga catcaag                                           747
```

<210> SEQ ID NO 110
<211> LENGTH: 738
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 110

```
caaatcactc tgaaagaatc tggaccggcc ctggttaagc cgactcaaac gctcacccct       60
acttgcacct tcagcggatt ctcactcagc actgctggtg tgcacgtcgg atggattaga      120
cagccgcctg gaaaggccct ggaatggctc gccctcatct cctgggccga tgacaagaga      180
tacaggccct cgcttcgatc ccggttggac attacccggg tgacctcgaa agatcaggtg      240
```

```
gtgctctcaa tgaccaatat gcagccggag acaccgcta cgtactactg cgcactgcaa    300
ggatttgacg gctacgaggc taactgggga ccaggtactc tggtcaccgt gagctccggc    360
gggggaggat caggcggggg ggggtcagga ggcggaggct ccggtggagg aggatcggat    420
atcgtcatga cccagtcccc aagctcgctg agcgcgtcag cgggcgaccg cgtgactatc    480
acttgccggg ccagccgcgg catctcctcc gcactggcgt ggtaccagca gaagcctgga    540
aaaccgccaa agctcctgat ctatgatgcc tccagcctgg agtcaggtgt ccccagccgc    600
ttctcgggtt cgggctcggg aaccgacttc actttgacca tcgactcgct ggaaccggaa    660
gatttcgcaa cctactactg tcagcagtcc tactcgaccc cttggacttt tggacaaggg    720
acgaaggtgg acatcaag                                                  738

<210> SEQ ID NO 111
<211> LENGTH: 1464
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111
atggccctcc ctgtcaccgc cctgctgctt ccgctggctc ttctgctcca cgccgctcgg     60
ccccaagtcc aactgcagca gtcaggagcg gaagtgaaga accaggagc gtcagtcaaa    120 gtgtcgtgca aggctagcgg ctacaccttc accggctact acatgcactg ggttcgacag    180
gctccagggc agggtctgga gtggatgggc cgcatcaacc cgaattccgg tgggactaac    240
tacgcccaga agttccaggg aagagtgacc atgactaggg acacgtcgat cagcactgcg    300
tacatggaac tgagccgcct gcggtccgag gatactgccg tctactactg cgcacgcgga    360
aggtactatg gaatggacgt gtggggccaa gggactatgg tgactgtgag ctcggaggg    420 ggaggctccg gtggcggggg atcaggagga ggaggatcag ggggaggagg ttccgaaatt    480
gtcctcaccc agagcccggc aaccctctca ctttccccgg gagagcgcgc aaccatctct    540
tgccgggcta gccaatccgt gtcgtccaat ttcgcctggt accagcaacg gccgggacaa    600
gcccctagac tcctgatcta cgacgccagc aacagagcga ctggaattcc tccacgctt    660 tcgggatcag gctccggtac cgacttcacc ctgactatct cgtcgctcga acccgaggat    720
ttcgccgcct actactgtca tcagcggtcg aactggttgt atacgtttgg ccagggcacc    780
aaggtggata tcaagaccac taccccagca ccgaggccac ccaccccggc tcctaccatc    840
gcctcccagc tctgtccct gcgtccgag gcatgtagac ccgcagctgg tggggccgtg    900
catacccggg gtcttgactt cgcctgcgat atctacattt gggcccctct ggctggtact    960 tgcgggggtcc tgctgctttc actcgtgatc actctttact gtaagcgcgg tcggaagaag    1020
ctgctgtaca tctttaagca acccttcatg aggcctgtgc agactactca agaggaggac    1080
ggctgttcat gccggttccc agaggaggag gaagggcggct cgaactgcg cgtgaaattc    1140 agccgcagcg cagatgctcc agcctacaag cagggcagaa accagctcta caacgaactc    1200
aatcttggtc ggagagagga gtacgacgtg ctggacaagc ggagaggacg ggacccagaa    1260
atgggcggga agccgcgcag aaagaatccc caagagggcc tgtacaacga gctccaaaag    1320
gataagatgg cagaagccta tagcgagatt ggtatgaaag ggaacgcag aagaggcaaa    1380 ggccacgacg gactgtacca gggactcagc accgccacca aggacaccta tgacgctctt    1440
cacatgcagg ccctgccgcc tcgg                                           1464
```

<210> SEQ ID NO 112
<211> LENGTH: 1491
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 112

| | | |
|---|---|---|
| atggccctcc ctgtcaccgc cctgctgctt ccgctggctc ttctgctcca cgccgctcgg | 60 |
| ccccaagtcc aactcgtcca gtcaggagca gaagtcaaga accaggtgc tagcgtgaaa | 120 |
| gtgtcgtgca aggcgtcggg atacactttc accggatact acatgcactg ggtccgccag | 180 |
| gcccccggac aaggactgga atggatgggc tggatcaacc cgaatagcgg gggaactaat | 240 |
| tacgcccaga gtttcaggg acgagtgacc atgacccgcg atacctctat ctcgaccgcc | 300 |
| tacatggagc tctccagact gcgctccgac gatactgcag tgtactactg cgcccgggac | 360 |
| ctgaggcgga ctgtggttac tcctcgcgcc tattatggca tggacgtgtg gggccaagga | 420 |
| actactgtga ctgtgagctc gggaggcggt gggtcaggcg gaggagggtc gggcggtggt | 480 |
| ggctcgggag gggaggaag cgacattcaa cttacgcaga gcccgtcaac cctgtcagcg | 540 |
| tcagtgggag atcgggtgac catcacgtgt caggccagcc aggatatctc caactcgctc | 600 |
| aactggtacc agcaaaaggc gggtaaagct ccgaagctgc tgatctacga cgcttccacc | 660 |
| ctcgagactg gagtcccatc cagatttttcc gggtcaggaa gcggcaccga tttctccttc | 720 |
| accatttcgt ccttgcaacc ggaggacatc gcaacctact actgcagca gcatgacaac | 780 |
| ttgcctctga cgttcgggca gggcaccaag gtggaaatca gaccactac cccagcaccg | 840 |
| aggccaccca ccccggctcc taccatcgcc tcccagcctc tgtccctgcg tccggaggca | 900 |
| tgtagacccg cagctggtgg ggccgtgcat accgggtc ttgacttcgc ctgcgatatc | 960 |
| tacatttggg cccctctggc tggtacttgc ggggtcctgc tgctttcact cgtgatcact | 1020 |
| ctttactgta gcgcggtcg gaagaagctg ctgtacatct ttaagcaacc cttcatgagg | 1080 |
| cctgtgcaga ctactcaaga ggaggacggc tgttcatgcc ggttcccaga ggaggaggaa | 1140 |
| ggcggctgcg aactgcgcgt gaaattcagc cgcagcgcag atgctccagc ctacaagcag | 1200 |
| gggcagaacc agctctacaa cgaactcaat cttggtcgga gagaggagta cgacgtgctg | 1260 |
| gacaagcgga gggacggga cccagaaatg ggcgggaagc cgcgcagaaa gaatccccaa | 1320 |
| gagggcctgt acaacgagct ccaaaaggat aagatggcag aagcctatag cgagattggt | 1380 |
| atgaaagggg aacgcagaag aggcaaaggc cacgacggac tgtaccaggg actcagcacc | 1440 |
| gccaccaagg acacctatga cgctcttcac atgcaggccc tgccgcctcg g | 1491 |

<210> SEQ ID NO 113
<211> LENGTH: 1470
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 113

| | | |
|---|---|---|
| atggccctcc ctgtcaccgc cctgctgctt ccgctggctc ttctgctcca cgccgctcgg | 60 |
| ccccaagtcc aactcgtcca atcaggagcg gaagtcaaaa agcccggagc tccagtgaaa | 120 |
| gtgtcatgca aggcctccgg ctacaccttc accggttact atatgcactg ggtgcggcag | 180 |
| gccccggcc aggggttgga atggatggga tggatcaatc caaactcggg tggactaac | 240 |

```
tacgcccaga agttccaagg acgggtgacc atgactaggg acacctcgat ctccaccgca      300
tacatggagc ttagcagact ccgctccgac gataccgcag tctactattg cgcgcgggga      360
gagtgggacg gatcgtacta ctacgattac tggggccagg gaactctggt gactgtttcc      420
tcgggtggag gaggttcagg cggaggcggc tcgggcgggg aggatctgg aggaggaggg       480 tccgacattg tgctgaccca aactccttcg tccctgtcgg ccagcgtggg cgaccgcgtg      540
acgattacgt gcagagctag ccaatccatc aatacttacc tcaactggta ccagcataag      600
ccggggaaag caccaaagct gctgatctac gccgcctcat ccttgcagag cggtgtgcct      660
tcacgcttta gcggatcggg atcgggaacg gatttcaccc tgactatcag ctccctccag      720
ccggaggatt ttgcgaccta ctactgtcag cagagcttct caccgctgac tttcggcggc      780
gggaccaagc tggaaatcaa gaccactacc ccagcaccga ggccacccac cccggctcct      840
accatcgcct cccagcctct gtccctgcgt ccggaggcat gtagacccgc agctggtggg      900
gccgtgcata cccggggtct tgacttcgcc tgcgatatct catttgggc ccctctggct       960 ggtacttgcg gggtcctgct gctttcactc gtgatcactc tttactgtaa gcgcggtcgg     1020
aagaagctgc tgtacatctt taagcaaccc ttcatgaggc ctgtgcagac tactcaagag     1080
gaggacggct gttcatgccg gttcccagag gaggaggaag gcggctgcga actgcgcgtg     1140
aaattcagcc gcagcgcaga tgctccagcc tacaagcagg ggcagaacca gctctacaac     1200
gaactcaatc ttggtcggag agaggagtac gacgtgctgg acaagcggag aggacgggac     1260
ccagaaatgg gcgggaagcc gcgcagaaag aatccccaag agggcctgta caacgagctc     1320
caaaaggata agatggcaga agcctatagc gagattggta tgaaggggga acgcagaaga     1380
ggcaaaggcc acgacggact gtaccaggga ctcagcaccg ccaccaagga cacctatgac     1440
gctcttcaca tgcaggccct gccgcctcgg                                       1470

<210> SEQ ID NO 114
<211> LENGTH: 1458
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114
atggccctcc ctgtcaccgc cctgctgctt ccgctggctc ttctgctcca cgccgctcgg       60
ccccaagtgc aactcgttga atcaggtgga ggtttggtgc aacccggagg atctctcaga      120
ctgtcgtgtg cggcgtccgg gttcaccttt tcgtcctact ggatgcactg ggtgcgccag      180
gtgccgggaa aggactggt gtgggtgtcc agaatcaaca ccgacgggtc aacgactacc       240
tacgcagata gcgtggaagg tcggttcacc atttcgcggg acaacgctaa aaacactctg      300
taccttcaga tgaattcact gcgcgatgac gacaccgcag tctactactg cgtcggtgga      360
cactgggcgg tctggggaca gggaactacg gtgactgtgt ccagcggcgg gggaggaagc      420
ggcggagggg ggagcggagg cggaggatca ggaggaggcg gctccgatat ccagatgacc      480
cagtcgccat cgaccctctc cgctagcgtg ggggataggg tcactatcac ttgccgagcc      540
agccaatcca ttagcgaccg gcttgcctgg taccaacaga aacctggaaa ggccccgaag      600
ctgctcatct acaaggcctc gtcactggag tcgggagtcc cgtcccgctt tccggctcg       660 ggctcaggca ccgagttcac tctgaccatc tcgagcctgc agccgacga tttcgccgtg       720 tattactgcc agcaatacgg acatctccca atgtacacgt tcggtcaggg caccaaggtc      780
```

```
gaaatcaaga ccactacccc agcaccgagg ccacccaccc cggctcctac catcgcctcc      840
cagcctctgt ccctgcgtcc ggaggcatgt agacccgcag ctggtggggc cgtgcatacc      900
cggggtcttg acttcgcctg cgatatctac atttgggccc ctctggctgg tacttgcggg      960
gtcctgctgc tttcactcgt gatcactctt tactgtaagc gcggtcggaa gaagctgctg     1020
tacatcttta agcaacccct catgaggcct gtgcagacta ctcaagagga ggacggctgt     1080
tcatgccggt tcccagagga ggaggaaggc ggctgcgaac tgcgcgtgaa attcagccgc     1140
agcgcagatg ctccagccta aagcagggg cagaaccagc tctacaacga actcaatctt     1200
ggtcggagag aggagtacga cgtgctggac aagcggagag acgggaccc agaaatgggc      1260 gggaagccgc gcagaaagaa tccccaagag ggcctgtaca cgagctcca aaaggataag      1320 atggcagaag cctatagcga gattggtatg aaagggaac gcagaagagg caaaggccac      1380
gacggactgt accagggact cagcaccgcc accaaggaca cctatgacgc tcttcacatg     1440
caggccctgc cgcctcgg                                                   1458
```

<210> SEQ ID NO 115
<211> LENGTH: 1455
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115

```
atggccctcc ctgtcaccgc cctgctgctt ccgctggctc ttctgctcca cgccgctcgg       60
ccccaagtcc aactcgttca atcaggcgca gaagtcgaaa agcccggagc atcagtcaaa      120
gtctcttgca aggcttccgg ctacaccttc acggactact acatgcactg ggtgcgccag      180
gctccaggcc agggactgga gtggatggga tggatcaacc cgaattccgg gggaactaac      240
tacgcccaga gtttcagggg ccgggtgact atgactcgcg atacctcgat ctcgactgcg      300
tacatggagc tcagccgcct ccggtcggac gataccgccg tgtactattg cgtcgggga      360 tgggacttcg actactgggg gcagggcact ctggtcactg tgtcaagcgg aggaggtgga     420
tcaggtggag gtggaagcgg gggaggaggt tccggcggcg gaggatcaga tatcgtgatg      480
acgcaatcgc cttcctcgtt gtccgcatcc gtgggagaca gggtgaccat tacttgcaga      540
gcgtcccagt ccattcggta ctacctgtcg tggtaccagc agaagccggg gaaagcccca      600
aaactgctta tctatactgc ctcgatcctc caaaacggcg tgccatcaag attcagcggt      660
tcgggcagcg ggaccgactt tacccctgact atcagcagcc tgcagccgga agatttcgcc     720
acgtactact gcctgcaaac ctacaccacc ccggacttcg gacctggaac caaggtggag     780
atcaagacca ctacccccagc accgaggcca cccacccgg ctcctaccat cgcctcccag      840
cctctgtccc tgcgtccgga ggcatgtaga cccgcagctg gtgggcgt gcatacccgg       900 ggtcttgact tcgcctgcga tatctacatt tgggcccctc tggctggtac ttgcggggtc      960
ctgctgcttt cactcgtgat cactctttac tgtaagcgcg gtcggaagaa gctgctgtac     1020
atctttaagc aacccttcat gaggcctgtg cagactacte aagaggagga cggctgttca     1080
tgccggttcc cagaggagga ggaaggcggc tgcgaactgc gcgtgaaatt cagccgcagc     1140
gcagatgctc cagcctacaa gcaggggcag aaccagctct acaacgaact caatcttggt     1200
cggagagagg agtacgacgt gctggacaag cggagaggac gggacccaga aatgggcggg     1260
aagccgcgca gaaagaatcc ccaagagggc ctgtacaacg agctccaaaa ggataagatg     1320
```

```
gcagaagcct atagcgagat tggtatgaaa ggggaacgca gaagaggcaa aggccacgac   1380
ggactgtacc agggactcag caccgccacc aaggacacct atgacgctct tcacatgcag   1440
gccctgccgc ctcgg                                                    1455
```

<210> SEQ ID NO 116
<211> LENGTH: 1491
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 116

```
atggccctcc ctgtcaccgc cctgctgctt ccgctggctc ttctgctcca cgccgctcgg     60
ccccaagtgc aactcgtcca gtcaggtgca gaagtgaaga acccggagc gtcagtcaaa    120 gtgtcatgca aggcgtcagg ctacaccttc accagctact acatgcactg ggtgcggcag    180
gccccaggcc aaggcttgga gtggatggga atcattaacc cgtcaggagg ctccacctcc    240
tacgcccaga gtttcagggg aagagtgacg atgactcggg atacgtcgac ctcgaccgtg    300
tacatggaac tgagctcgct gcgctccgag gacactgctg tgtactactg cgcacggtac    360
agactcattg ccgtggcagg agactactac tactatggca tggacgtctg ggggcagggc    420
actatggtca ctgtgtcgtc cggcggagga ggctcgggtg aggaggtag cggaggaggg    480 ggaagcggag ggggggctc cgatatccag atgactcagt cgccttcctc cgtgtcggcc    540
tcggttggag atcgcgtcac catcacttgt cgagcttccc aaggagtcgg taggtggctg    600
gcgtggtacc agcaaaagcc gggaactgcc ccgaagctcc tgatctacgc ggctagcacc    660
ctgcagtcgg gagtgccatc ccgcttcagc ggatctgggt caggtaccga cttcaccctt    720
acgatcaaca atctccagcc ggaggacttt gccacctatt actgccaaca ggccaacagc    780
ttccctctga ctttcggagg gggcactcgc ctggaaatca agaccactac cccagcaccg    840
aggccaccca ccccggctcc taccatcgcc tcccagcctc tgtccctgcg tccggaggca    900
tgtagacccg cagctggtgg ggccgtgcat cccggggtc ttgacttcgc ctgcgatatc    960
tacatttggg cccctctggc tggtacttgc ggggtcctgc tgctttcact cgtgatcact   1020
ctttactgta gcgcggtcg gaagaagctg ctgtacatct ttaagcaacc cttcatgagg   1080
cctgtgcaga ctactcaaga ggaggacggc tgttcatgcc ggttcccaga ggaggaggaa   1140
ggcggctgcg aactgcgcgt gaaattcagc cgcagcgcag atgctccagc ctacaagcag   1200
gggcagaacc agctctacaa cgaactcaat cttggtcgga gagaggagta cgacgtgctg   1260
gacaagcgga gaggacggga cccagaaatg ggcgggaagc cgcgcagaaa gaatccccaa   1320
gagggcctgt acaacgagct ccaaaaggat aagatggcag aagcctatag cgagattggt   1380
atgaaagggg aacgcagaag aggcaaaggc cacgacggac tgtaccaggg actcagcacc   1440
gccaccaagg acacctatga cgctcttcac atgcaggccc tgccgcctcg g             1491
```

<210> SEQ ID NO 117
<211> LENGTH: 1482
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 117

```
atggccctcc ctgtcaccgc cctgctgctt ccgctggctc ttctgctcca cgccgctcgg      60
ccccaagtgc aattggttca atcaggagga ggagtggtgc aacctggaag atctctcaga     120
ctgtcgtgtg cggcatcggg attcactttc tcatcatacg caatgcactg ggtccgccag     180
gccccgggca aaggcttgga atgggtggcg gtcatttcat acgacggctc gaacaagtac     240
tacgctgaca gcgtgaaggg acgctttact atttcccggg acaattcgaa gaacactctg     300
tacctccaga tgaactccct tagggctgag gacaccgccg tctactactg cgcacgctgg     360
aaagtgtcgt ccagctcccc agcttttgac tactggggac agggaaccct tgtgaccgtg     420
tcgtccggtg gagggggaag cggcggaggg ggatcaggtg gcggcggatc gggaggcggg     480
ggatcagaaa tcgtgctgac tcagtccccg gccacgctgt ctctcagccc gggagagaga     540
gcgatcctgt cctgccgcgc ctcgcagagc gtgtacacta agtacctggg gtggtaccag     600
cagaaaccgg gtcaagcgcc tcggctgctg atctacgatg cctccacccg ggccaccgga     660
atccccgatc ggttctccgg cagcggctcg ggaactgatt tcacgctgac catcaatcgc     720
ctggagccgg aagatttcgc cgtctattac tgccagcatt acggcgggag cccactcatc     780
accttcggtc aaggaacccg actcgaaatc aagaccacta ccccagcacc gaggccaccc     840
accccggctc ctaccatcgc ctcccagcct ctgtccctgc gtccggaggc atgtagaccc     900
gcagctggtg gggccgtgca tacccggggt cttgacttcg cctgcgatat ctacatttgg     960
gcccctctgg ctggtacttg cggggtcctg ctgctttcac tcgtgatcac tctttactgt    1020
aagcgcggtc ggaagaagct gctgtacatc tttaagcaac ccttcatgag gcctgtgcag    1080
actactcaag aggaggacgg ctgttcatgc cggttcccag aggaggagga aggcggctgc    1140
gaactgcgcg tgaaattcag ccgcagcgca gatgctccag cctacaagca ggggcagaac    1200
cagctctaca acgaactcaa tcttggtcgg agagaggagt acgacgtgct ggacaagcgg    1260
agaggacggg acccagaaat gggcgggaag ccgcgcagaa agaatcccca gagggcctg     1320 tacaacgagc tccaaaagga taagatggca gaagcctata gcgagattgg tatgaaaggg    1380
gaacgcagaa gaggcaaagg ccacgacgga ctgtaccagg gactcagcac cgccaccaag    1440
gacacctatg acgctcttca catgcaggcc ctgccgcctc gg                       1482
```

<210> SEQ ID NO 118
<211> LENGTH: 1470
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 118

```
atggccctcc ctgtcaccgc cctgctgctt ccgctggctc ttctgctcca cgccgctcgg      60
ccccaagtcc aactccagca gtcaggtgca gaagtcaaaa agccaggagc atccgtgaag     120
gtttcgtgca agacttccgg ctacccttt accgggtact ccctccattg ggtgagacaa      180
gcaccgggcc agggactgga gtggatggga tggatcaacc caattcgggg cggcaccaac     240
tatgcgcaga agttccaggg acgggtgacc atgactcgcg acacttcgat ctccactgcc     300
tacatggagc tgtcccgctt gagatctgac gacacggccg tctactactg cgccccggat     360
cactacggag gtaattcgct gttctactgg gggcagggaa cccttgtgac tgtgtcctcg     420
ggtggtggag gtcaggagg cggaggctca ggggaggag gtagcggagg aggcggatca      480
gacatccaac tgacccagtc accatcctcc atctcggcta gcgtcggaga caccgtgtcg    540
```

```
attacttgta gggcctccca agactcaggg acgtggctgg cgtggtatca gcaaaaaccg    600
ggcaaagctc cgaacctgtt gatgtacgac gccagcaccc tcgaagatgg agtgcctagc    660
cgcttcagcg gaagcgcctc gggcactgaa ttcacgctga ctgtgaatcg gctccagccg    720
gaggattcgg cgacctacta ctgccagcag tacaacagct accccctgac ctttggaggc    780
gggaccaagg tggatatcaa gaccactacc ccagcaccga ggccacccac cccggctcct    840
accatcgcct cccagcctct gtccctgcgt ccggaggcat gtagacccgc agctggtggg    900
gccgtgcata cccggggtct tgacttcgcc tgcgatatct acatttgggc ccctctggct    960
ggtacttgcg gggtcctgct gctttcactc gtgatcactc tttactgtaa gcgcggtcgg    1020
aagaagctgc tgtacatctt taagcaaccc ttcatgaggc ctgtgcagac tactcaagag    1080
gaggacggct gttcatgccg gttcccagag gaggaggaag gcggctgcga actgcgcgtg    1140
aaattcagcc gcagcgcaga tgctccagcc tacaagcagg ggcagaacca gctctacaac    1200
gaactcaatc ttggtcggag agaggagtac gacgtgctgg acaagcggag aggacgggac    1260
ccagaaatgg gcgggaagcc gcgcagaaag aatccccaag agggcctgta caacgagctc    1320
caaaaggata gatggcaga agcctatagc gagattggta tgaaagggga acgcagaaga    1380
ggcaaaggcc acgacggact gtaccaggga ctcagcaccg ccaccaagga cacctatgac    1440
gctcttcaca tgcaggccct gccgcctcgg                                    1470
```

<210> SEQ ID NO 119
<211> LENGTH: 1476
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 119

```
atggccctcc ctgtcaccgc cctgctgctt ccgctggctc ttctgctcca cgccgctcgg    60 cccccaagtgc aactcgtcca gtcaggtgca gaagtgaaga accaggagc gtccgtcgaa    120 gtgtcgtgta aggcgtccgg ctacactttc acctcgtact acatgcactg ggtgcggcag    180
gccccgggac aaggcctcga atggatggga atcatcaacc cgagcggagg ctcgactggt    240
tacgcccaga gttccagggg aagggtgacg atgacccgcg ataccctcgac ttcgaccgtt    300 catatggagc tctcgtccct gcggagcgag gacactgctg tctactattg cgcgcgggga    360
ggatactcta gctcctccga tgcatttgac atttggggcc agggaactat ggtgaccgtg    420
tcatcaggcg gaggtggatc aggaggagga gggtcgggag ggggaggcag cggcgggggt    480
gggtcggaca ttcagatgac gcagtccccct cctagcctga gcgcctcggt gggtgacaga    540
gtgaccatca cttgcagagc ctcgcaagac atctcctccg cattggcttg gtaccagcaa    600
aagccgggca ctccgccgaa actgctcatc tacgatgcct cctcactgga gtcaggagtc    660
ccatctcgct tctcggggtc aggaagcggg accgatttta cccttaccat ctccagcctg    720
cagcccgagg acttcgccac gtactactgc caacagttca gctcctaccc actgaccttc    780
gggggcggaa ctcgcctgga aatcaagacc actaccccag caccgaggcc acccaccccg    840
gctcctacca tcgcctccca gcctctgtcc ctgcgtccgg aggcatgtag acccgcagct    900
ggtggggccg tgcatacccg gggtcttgac ttcgcctgcg atatctacat ttgggcccct    960
ctggctggta cttgcggggt cctgctgctt tcactcgtga tcactcttta ctgtaagcgc    1020
ggtcggaaga agctgctgta catctttaag caaccttca tgaggcctgt gcagactact    1080
```

-continued

| | |
|---|---|
| caagaggagg acggctgttc atgccggttc ccagaggagg aggaaggcgg ctgcgaactg | 1140 |
| cgcgtgaaat tcagccgcag cgcagatgct ccagcctaca agcaggggca gaaccagctc | 1200 |
| tacaacgaac tcaatcttgg tcggagagag gagtacgacg tgctggacaa gcggagagga | 1260 |
| cgggacccag aaatgggcgg gaagccgcgc agaaagaatc cccaagaggg cctgtacaac | 1320 |
| gagctccaaa aggataagat ggcagaagcc tatagcgaga ttggtatgaa aggggaacgc | 1380 |
| agaagaggca aggccacga cggactgtac cagggactca gcaccgccac caaggacacc | 1440 |
| tatgacgctc ttcacatgca ggccctgccg cctcgg | 1476 |

<210> SEQ ID NO 120
<211> LENGTH: 1497
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120

| | |
|---|---|
| atggccctcc ctgtcaccgc cctgctgctt ccgctggctc ttctgctcca cgccgctcgg | 60 |
| ccccaagtgc aactcgtcca gagcggagca gaagtcaaga agccaggagc gtcagtgaaa | 120 |
| gtgtcatgca aggccagcgg ctataccttt acttcgtatg ggatctcctg ggtgcggcag | 180 |
| gcaccgggcc aaggactgga gtggatggga tggatctcag cctacaacgg taacaccaac | 240 |
| tacgcccaga agctgcaagg acgcgtgacc atgactactg atacgagcac ctccactgcc | 300 |
| tacatggaat gcggtccct tcggtcggac gatactgctg tgtactactg cgcaagagtc | 360 |
| gccggaggga tctactacta ctacggcatg gacgtctggg gacagggaac caccattacg | 420 |
| gtgtcgagcg gaggggggagg ctcgggggga ggaggaagcg gaggtggcgg ctccgggggc | 480 |
| ggcggatcgg acattgtgat gacccagact cctgactccc tggctgtttc gttgggagag | 540 |
| cgcgcgacta tctcgtgtaa gtccagccac tcagtcctgt acaatcgcaa taacaagaac | 600 |
| tacctcgcgt ggtaccagca aaaaccgggt cagccgccta aactcctgtt ctactgggcc | 660 |
| tccaccagaa agagcggggt gccagatcga ttctctggat caggatcagg taccgacttt | 720 |
| acgctgacca tctcgtccct gcagccggag gatttcgcga cttacttctg ccagcagact | 780 |
| cagactttcc ccctcacctt cggtcaaggc accaggctgg aaatcaatac cactacccca | 840 |
| gcaccgagc cacccacccc ggctcctacc atcgcctccc agcctctgtc cctgcgtccg | 900 |
| gaggcatgta acccgcagc tggtgggcc gtgcataccc ggggtcttga cttcgcctgc | 960 |
| gatatctaca tttgggcccc tctggctggt acttgcgggg tcctgctgct ttcactcgtg | 1020 |
| atcactcttt actgtaagcg cggtcggaag aagctgctgt acatctttaa gcaacccttc | 1080 |
| atgaggcctg tgcagactac tcaagaggag gacggctgtt catgccggtt cccagaggag | 1140 |
| gaggaaggcg gctgcgaact gcgcgtgaaa ttcagccgca cgcagatgc tccagcctac | 1200 |
| aagcaggggc agaaccagct ctacaacgaa ctcaatcttg gtcggagaga ggagtacgac | 1260 |
| gtgctggaca gcggagagg acgggaccca gaaatgggcg ggaagccgcg cagaaagaat | 1320 |
| ccccaagagg gcctgtacaa cgagctccaa aaggataaga tggcagaagc ctatagcgag | 1380 |
| attggtatga aggggaacg cagaagaggc aaggccacg acggactgta ccaggactc | 1440 |
| agcaccgcca ccaaggacac ctatgacgct cttcacatgc aggccctgcc gcctcgg | 1497 |

<210> SEQ ID NO 121
<211> LENGTH: 1455
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 121

```
atggccctcc ctgtcaccgc cctgctgctt ccgctggctc ttctgctcca cgccgctcgg      60
ccccaagtcc aattgcagca gagcggagca gaagtgaaga agccaggagc gtcagtcaaa     120
gtgtcgtgta aggcgtcagg atacaccttc acgggatact acatgcactg ggtgcgccag     180
gccccgggcc aaggactcga gtggatgggc tggatcaacc ctaactctgg aggcaccaac     240
tacgcccaga atttccaagg cagagtgacc atgacccggg acacctccat ctcgactgcc     300
tatatggaac tgcggcggct cgcgctcgga cgatactgctg tgtattactg cgccagcggc     360
tgggactttg actactgggg acagggtact ctggtgactg tttcctcggg aggaggcgga     420
tcgggtggag gaggtagcgg gggaggggg tcgggaggcg gaggcagcga tattcgcatg     480
actcaatcgc cgtcctccct gagcgctagc gtggagatc gagtcaccat cacttgcaga     540
gcgtcacagt cgattcgcta ctacctgtcc tggtaccagc agaaaccggg aaaggcacca     600
aagcttctga tctacacggc ctccatcctg caaaatggtg tcccatcaag gttctccggg     660
tcagggagcg gcactgactt cactctcacc atctcctcac tccagcccga ggactttgca     720
acctactact gcctccagac gtacaccacc ccggatttcg gtcctggaac caaggtggaa     780
atcaaaacca ctaccccagc accgaggcca cccacccggg ctcctaccat cgcctcccag     840
cctctgtccc tgcgtccgga ggcatgtaga cccgcagctg gtggggccgt gcatacccgg     900
ggtcttgact cgcctgcga tatctacatt tgggcccctc tggctggtac ttgcggggtc     960
ctgctgcttt cactcgtgat cactctttac tgtaagcgcg gtcggaagaa gctgctgtac    1020
atctttaagc aacccttcat gaggcctgtg cagactactc aagaggagga cggctgttca    1080
tgccggttcc cagaggagga ggaaggcggc tgcgaactgc gcgtgaaatt cagccgcagc    1140
gcagatgctc cagcctacaa gcagggcag aaccagctct acaacgaact caatcttggt    1200
cggagagagg agtacgacgt gctggacaag cggagaggac gggacccaga aatgggcggg    1260
aagccgcgca gaaagaatcc ccaagagggc ctgtacaacg agctcaaaa ggataagatg    1320
gcagaagcct atagcgagat tggtatgaaa ggggaacgca aagaggcaa aggccacgac    1380
ggactgtacc agggactcag caccgccacc aaggacacct atgacgctct tcacatgcag    1440
gccctgccgc ctcgg                                                      1455
```

<210> SEQ ID NO 122
<211> LENGTH: 1470
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 122

```
atggccctcc ctgtcaccgc cctgctgctt ccgctggctc ttctgctcca cgccgctcgg      60
ccccaagtcc aactcgtcca aagcggagca gaagtcaaaa agccaggagc gtcggtgaaa     120
gtgtcttgca aagccagcgg ctacaccttc acgggttact acatgcactg ggtgcgccag     180
gcgccgggcc aggggctgga gtggatgggc cggattaacc ctaacagcgg gggaactaat     240
tacgctcaga agttccaggg tagagtcacc atgactacac acttccac ttccaccgcc       300
tatatggaac tgcgctccct ccgctcagat gatactgccg tgtattactg cgcgcggact     360
```

```
accacgtcat acgcatttga catctggggc cagggaacta tggtgaccgt gagctcgggc    420
ggaggcggtt caggggagg aggaagcgga ggaggaggat cggaggagg tggctccgat    480 atccagctga ctcagtcccc gagcaccctg tcggcgtcgg tggggacag ggttaccatc    540 acctgtagag cttcccaatc catttcgact tggctggcct ggtaccagca aaagccggga    600
aaggccccta atttgcttat ctacaaggca tcgaccctcg aaagcggtgt gccctcccgg    660
ttttcgggat caggatcagg gaccgagttc accctgacca tctcatccct ccagccggac    720
gacttcgcca cttactactg ccagcagtac aacacctact cgccatacac tttcggccaa    780
ggcaccaagc tggagatcaa gaccactacc ccagcaccga ggccacccac cccggctcct    840
accatcgcct cccagcctct gtccctgcgt ccggaggcat gtagacccgc agctggtggg    900
gccgtgcata cccggggtct tgacttcgcc tgcgatatct acatttgggc ccctctggct    960
ggtacttgcg gggtcctgct gctttcactc gtgatcactc tttactgtaa gcgcggtcgg   1020
aagaagctgc tgtacatctt taagcaaccc ttcatgaggc ctgtgcagac tactcaagag   1080
gaggacggct gttcatgccg gttcccagag gaggaggaag gcggctgcga actgcgcgtg   1140
aaattcagcc gcagcgcaga tgctccagcc tacaagcagg gcagaaacca gctctacaac   1200
gaactcaatc ttggtcggag agaggagtac gacgtgctgg acaagcggag aggacgggac   1260
ccagaaatgg gcgggaagcc gcgcagaaag aatccccaag agggcctgta caacgagctc   1320
caaaaggata agatggcaga agcctatagc gagattggta tgaaagggga acgcagaaga   1380
ggcaaaggcc acgacggact gtaccaggga ctcagcaccg ccaccaagga cacctatgac   1440
gctcttcaca tgcaggccct gccgcctcgg                                    1470
```

<210> SEQ ID NO 123
<211> LENGTH: 1479
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123

```
atggccctcc ctgtcaccgc cctgctgctt ccgctggctc ttctgctcca cgccgctcgg     60
ccccaagttc aactcgtgca atcaggtgga ggactcgtca aacccggagg atcattgaga    120
ctgtcatgcg aagcgagcgg ttttatcttc tccgattact atatgggatg gattcggcag    180
gccccgggaa agggactcga atgggtgtca tacatcggaa ggtcaggctc gtccatgtac    240
tacgcagact cggtgaaagg cagattcacc tttagccggg acaacgccaa gaattccctc    300
tacttgcaga tgaacagcct gcgagccgag gatactgctg tctactactg tgccgcgtcg    360
ccggtggtgg cagctactga agatttccag cactggggac agggaactct ggtcacggtg    420
tcgagcggtg gggcggaag cggaggcgga ggatcgggcg gcggaggttc ggggggggga    480
gggtctgaca tcgtgatgac ccaaaccccca gccaccctga cctctccccc tggagagcgc    540
gcgactcttt cgtgccgcgc ttcccagtca gtgaccagca attacttggc ttggtaccaa    600
cagaagccgg gacaggcgcc acggctgctg cttttttggtg ccagcactcg cgccaccgga    660
atcccggatc gcttctcggg ctcagggtcc gggacggact caccctgac tatcaaccgg    720 ctggaacctg aggacttcgc gatgtactac tgccagcagt acggctccgc accagtcact    780
ttcggacaag gcaccaagct ggagatcaag accactaccc cagcaccgag gccacccacc    840
ccggctccta ccatcgcctc ccagcctctg tccctgcgtc cggaggcatg tagacccgca    900
```

```
gctggtgggg ccgtgcatac ccggggtctt gacttcgcct gcgatatcta catttgggcc      960
cctctggctg gtacttgcgg ggtcctgctg ctttcactcg tgatcactct ttactgtaag     1020
cgcggtcgga agaagctgct gtacatcttt aagcaaccct tcatgaggcc tgtgcagact     1080
actcaagagg aggacggctg ttcatgccgg ttcccagagg aggaggaagg cggctgcgaa     1140
ctgcgcgtga aattcagccg cagcgcagat gctccagcct acaagcaggg gcagaaccag     1200
ctctacaacg aactcaatct tggtcggaga gaggagtacg acgtgctgga caagcggaga     1260
ggacgggacc cagaaatggg cgggaagccg cgcagaaaga atccccaaga gggcctgtac     1320
aacgagctcc aaaaggataa gatggcagaa gcctatagcg agattggtat gaaagggaaa     1380
cgcagaagag gcaaaggcca cgacggactg taccagggac tcagcaccgc caccaaggac     1440
acctatgacg ctcttcacat gcaggccctg ccgcctcgg                            1479

<210> SEQ ID NO 124
<211> LENGTH: 1479
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124
atggccctcc ctgtcaccgc cctgctgctt ccgctggctc ttctgctcca cgccgctcgg       60
ccccaagtcc aactcgtcca gtcgggagca gaagttagag caccaggagc gtcagtgaaa      120
atctcatgca aggcctcggg cttcacgttc gcgggatact acatccactg ggtgcgccaa      180
gccccgggtc agggattgga gtggatggga atcattaacc catcaggagg agccgggct       240 tacgcgcaga agttccaggg acgcgtcact atgacccgag atacttccac ctcgactgtg      300
tacatggaac tctcgtccct gaggtccgac gacactgcga tgtattactg cgctcggact      360
gccagctgcg gtggggactg ttactacctc gattactggg gccagggaac tctggtgacc      420
gtgtccagcg gaggtggcgg gtcagggggt ggcggaagcg gaggcggcgg ttcaggcgga      480
ggaggctcgg acatccaaat gacgcaatcg ccgcctaccc tgagcgcttc cgtgggagat      540
cgggtgacca ttacttgcag agcatccgag aacgtcaata tctggctggc ctggtaccaa      600
cagaagccgg ggaaggcccc taaactgctg atctacaagt cgagcagcct tgcctctgga      660
gtgccctccc gcttctcggg ctcgggatca ggagcggaat tcaccctcac catctcctcc      720
ctgcagccag atgactttgc cacctactac tgccagcagt accagagcta tccgttgacc      780
tttgggggag gcactaaagt ggacatcaag accactaccc cagcaccgag gccacccacc      840
ccggctccta ccatcgcctc ccagcctctg tccctgcgtc cggaggcatg tagacccgca      900
gctggtgggg ccgtgcatac ccggggtctt gacttcgcct gcgatatcta catttgggcc      960
cctctggctg gtacttgcgg ggtcctgctg ctttcactcg tgatcactct ttactgtaag     1020
cgcggtcgga agaagctgct gtacatcttt aagcaaccct tcatgaggcc tgtgcagact     1080
actcaagagg aggacggctg ttcatgccgg ttcccagagg aggaggaagg cggctgcgaa     1140
ctgcgcgtga aattcagccg cagcgcagat gctccagcct acaagcaggg gcagaaccag     1200
ctctacaacg aactcaatct tggtcggaga gaggagtacg acgtgctgga caagcggaga     1260
ggacgggacc cagaaatggg cgggaagccg cgcagaaaga atccccaaga gggcctgtac     1320
aacgagctcc aaaaggataa gatggcagaa gcctatagcg agattggtat gaaagggaaa     1380
cgcagaagag gcaaaggcca cgacggactg taccagggac tcagcaccgc caccaaggac     1440
```

```
acctatgacg ctcttcacat gcaggccctg ccgcctcgg                              1479
```

<210> SEQ ID NO 125
<211> LENGTH: 1464
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125

```
atggccctcc ctgtcaccgc cctgctgctt ccgctggctc ttctgctcca cgccgctcgg       60
cccccaagttc aactcgttca atcaggtgga ggactcgtgc aaccaggaag atcactcaga    120
ctcagctgcg ccgcgtcggg attcactttc gatgactacg caatgcactg ggtgcggcag     180
gccccgggca aaggactgga atgggtgagc ggaattagct ggaactcggg gtccatcggg     240
tacgccgact cggtgaaggg acgctttacg atctcccggg acaatgccaa gaactccctg     300
tatttgcaga tgaactcctt gagggctgag gacaccgccg tgtactactg cgctaaagat     360
ggatcatcgt cctggtcctg gggatacttc gattactggg ccagggcac tctggtgacc      420
gtgtcgtcag gcggtggagg gtcggccgga ggaggtagcg gaggcggagg gagcagctct    480
gaactgaccc aagacccggc ggtgtcggtc gcccttggtc agactgtgcg gactacctgt     540
caggggacg cgctgcgctc gtactacgct tcatggtacc agcagaagcc cggacaggca     600
cctatgctgg tcatctacgg aaagaataac cgcccatccg gcatcccgga tcgcttctcg     660
ggttcggaca gcggcgacac cgcatccctg acgatcactg gagcgcaggc cgaggatgaa      720
gccgactact actgcaattc ccgagattca agcggctacc ctgtgtttgg gaccggaact     780
aaggtcaccg tcctgaccac taccccagca ccgaggccac ccaccccggc tcctaccatc     840
gcctcccagc ctctgtccct gcgtccggag gcatgtagac ccgcagctgg tggggccgtg    900
catacccggg gtcttgactt cgcctgcgat atctacattt gggcccctct ggctggtact     960
tgcggggtcc tgctgctttc actcgtgatc actctttact gtaagcgcgg tcggaagaag    1020
ctgctgtaca tctttaagca acccttcatg aggcctgtgc agactactca agaggaggac    1080
ggctgttcat gccggttccc agaggaggag gaaggcggct gcgaactgcg cgtgaaattc    1140
agccgcagcg cagatgctcc agcctacaag caggggcaga accagctcta caacgaactc    1200
aatcttggtc ggagagagga gtacgacgtg ctggacaagc ggagaggacg ggacccagaa    1260
atgggcggga agccgcgcag aaagaatccc caagagggcc tgtacaacga gctccaaaag    1320
gataagatgg cagaagccta tagcgagatt ggtatgaaag gggaacgcag aagaggcaaa    1380
ggccacgacg gactgtacca gggactcagc accgccacca aggacaccta tgacgctctt    1440
cacatgcagg ccctgccgcc tcgg                                            1464
```

<210> SEQ ID NO 126
<211> LENGTH: 1470
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126

```
atggccctcc ctgtcaccgc cctgctgctt ccgctggctc ttctgctcca cgccgctcgg       60
cccgaagtgc aactcgtgga atctggtgga ggacttgtgc aacctggaag atcgttgaga    120
```

| | |
|---|---|
| ctctcatgtg ctgcctccgg gttcaccttt gacgactacg ccatgcactg ggtgcgccag | 180 |
| gcaccaggaa agggtctgga gtgggtttcg ggtatctcgt ggaactccgg gagcactggc | 240 |
| tacgctgatt cggtgaaagg ccggtttacc atctcccgag acaatgcgaa gaattccctc | 300 |
| tatctgcaga tgaacagcct ccgggccgag atactgccc tgtactactg cgccaaggat | 360 |
| agctcatcat ggtacggagg tggatcggct ttcgatatct ggggccaggg cacgatggtc | 420 |
| accgtgtcct cggggggcgg aggctccggg ggaggaggta gcggaggagg aggatcgagc | 480 |
| tcagagttga ctcaagaacc cgcagtgtcc gtggcactgg gccaaaccgt caggatcact | 540 |
| tgccagggag acagcctgag gtcgtactac gcgtcctggt accagcagaa gccgggacag | 600 |
| gccccggtcc tggtcatttt cggacgctca agacgcccat cgggcatccc ggaccggttc | 660 |
| agcggaagct cctcgggaaa caccgcgtca cttatcatta ccggcgcaca ggctgaggac | 720 |
| gaagcggatt actactgcaa ctcccgcgac aatactgcca accattacgt gttcgggacc | 780 |
| ggaacgaaac tgactgtcct gaccactacc ccagcaccga ggccacccac cccggctcct | 840 |
| accatcgcct cccagcctct gtccctgcgt ccggaggcat gtagacccgc agctggtggg | 900 |
| gccgtgcata cccggggtct tgacttcgcc tgcgatatct acatttgggc ccctctggct | 960 |
| ggtacttgcg gggtcctgct gctttcactc gtgatcactc tttactgtaa gcgcggtcgg | 1020 |
| aagaagctgc tgtacatctt taagcaaccc ttcatgaggc ctgtgcagac tactcaagag | 1080 |
| gaggacggct gttcatgccg gttcccagag gaggaggaag cggctgcga actgcgcgtg | 1140 |
| aaattcagcc gcagcgcaga tgctccagcc tacaagcagg gcagaaccag gctctacaac | 1200 |
| gaactcaatc ttggtcggag agaggagtac gacgtgctgg acaagcggag aggacgggac | 1260 |
| ccagaaatgg gcgggaagcc gcgcagaaag aatccccaag agggcctgta caacgagctc | 1320 |
| caaaaggata gatggcaga agcctatagc gagattggta tgaaagggga acgcagaaga | 1380 |
| ggcaaaggcc acgacggact gtaccaggga ctcagcaccg ccaccaagga cacctatgac | 1440 |
| gctcttcaca tgcaggccct gccgcctcgg | 1470 |

<210> SEQ ID NO 127
<211> LENGTH: 1470
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 127

| | |
|---|---|
| atggccctcc ctgtcaccgc cctgctgctt ccgctggctc ttctgctcca cgccgctcgg | 60 |
| cccgaagttc aattggtgga atctggagga ggacttgtgc aacccggtag atctctgaga | 120 |
| ctgtcctgtg cggcatcggg attcaccttc gacgactacg ctatgcactg ggtgagacaa | 180 |
| gccccctgga aaggactgga gtgggtgtca ggcatctcct ggaatagcgg gtccactgga | 240 |
| tacgccgatt cggtcaaggg tcgcttcacc atttcccggg acaatgccaa gaactccctg | 300 |
| taccttcaaa tgaactccct ccgggccgag ataccgccc tctactactg cgccaaagac | 360 |
| agctcgtcat ggtatggcgg agggtcggca tttgacatct ggggacaggg aactatggtg | 420 |
| actgtgtcat caggaggcgg cggaagcggc ggcggcgggt ccggcggagg aggtcgtcc | 480 |
| agcgaactca cccaagatcc agcagtgagc gtcgcgctgg ccagaccgt caggatcacg | 540 |
| tgccagggag attcactgcg ctcatactac gcgtcctggt accagcagaa gccggggcag | 600 |
| gccccggtcc tcgtgatcta cggaaagaac aaccgcccgt cgggtatccc agaccgcttt | 660 |

| | |
|---|---|
| tcgggtagct ccagcggaaa tacggctagc ctgaccatca ctggagcaca ggctgaggat | 720 |
| gaagcggact actactgcaa ttcgcggggc tcatcgggga accattacgt gttcggaact | 780 |
| ggtaccaagg tgactgtcct gaccactacc ccagcaccga ggccacccac cccggctcct | 840 |
| accatcgcct cccagcctct gtccctgcgt ccggaggcat gtagacccgc agctggtggg | 900 |
| gccgtgcata cccggggtct tgacttcgcc tgcgatatct acatttgggc ccctctggct | 960 |
| ggtacttgcg gggtcctgct gctttcactc gtgatcactc tttactgtaa gcgcggtcgg | 1020 |
| aagaagctgc tgtacatctt taagcaaccc ttcatgaggc ctgtgcagac tactcaagag | 1080 |
| gaggacggct gttcatgccg gttcccagag gaggaggaag gcggctgcga actgcgcgtg | 1140 |
| aaattcagcc gcagcgcaga tgctccagcc tacaagcagg ggcagaacca gctctacaac | 1200 |
| gaactcaatc ttggtcggag agaggagtac gacgtgctgg acaagcggag aggacgggac | 1260 |
| ccagaaatgg gcgggaagcc gcgcagaaag aatccccaag agggcctgta caacgagctc | 1320 |
| caaaaggata gatggcaga agcctatagc gagattggta tgaaggggga acgcagaaga | 1380 |
| ggcaaaggcc acgacggact gtaccaggga ctcagcaccg ccaccaagga cacctatgac | 1440 |
| gctcttcaca tgcaggccct gccgcctcgg | 1470 |

<210> SEQ ID NO 128
<211> LENGTH: 1485
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 128

| | |
|---|---|
| atggccctcc ctgtcaccgc cctgctgctt ccgctggctc ttctgctcca cgccgctcgg | 60 |
| cccccaagtgc agctcgttca atcaggcgga ggactcgttc aaccaggagg atcattgcga | 120 |
| ctctcatgtg cggcctctgg attcacgttt agctcatatt ggatgcactg ggtgcggcag | 180 |
| gcgccgggga aaggtctggt gtgggtcagc cgcatcaact cagacggctc ctcgacttcg | 240 |
| tacgccgact ccgtgaaggg acgctttacc atttcccgcg acaacgccaa gaatacccttt | 300 |
| taccttcaga tgaactccct ccgcgctgag gataccgccg tgtactactg cgtgaggact | 360 |
| ggctgggtcg gcagctacta ctactacatg gacgtgtggg gcaaaggaac tactgtcacc | 420 |
| gtgtcaagcg gcggtggagg ttccggcggg ggaggatcgg ggggggcgg atcgggtggc | 480 |
| ggaggatcgg agatcgtgtt gacccagtcg ccgggaaccc tgtcgctgtc gcctggggag | 540 |
| agagcaactc tgtcctgccg ggcttccaag tcggtgtcga gcaattacct ggcatggtac | 600 |
| caacagaagc cgggacagcc gccacgcctg ctgatctatg acgtgtcaac tcgggcaact | 660 |
| ggaatccctg cgcggttcag cggcggaggg agcgtaccgg atttcaccct gactatttcc | 720 |
| tccctcgaac cagaagattt cgccgtctac tactgccagc agagaagcaa ctggccgccc | 780 |
| tggacgttcg gacaaggaac caaggtcgaa atcaagacca ctaccccagc accgaggcca | 840 |
| cccaccccgg ctcctaccat cgcctcccag cctctgtccc tgcgtccgga ggcatgtaga | 900 |
| cccgcagctg gtggggccgt gcataccccgg ggtcttgact cgcctgcgca tatctacatt | 960 |
| tgggcccctc tggctggtac ttgcggggtc ctgctgcttt cactcgtgat cactctttac | 1020 |
| tgtaagcgcg gtcggaagaa gctgctgtac atctttaagc aacccttcat gaggcctgtg | 1080 |
| cagactactc aagaggagga cggctgttca tgccggttcc cagaggagga ggaaggcggc | 1140 |
| tgcgaactgc gcgtgaaatt cagccgcagc gcagatgctc cagcctacaa gcaggggcag | 1200 |

| | |
|---|---|
| aaccagctct acaacgaact caatcttggt cggagagagg agtacgacgt gctggacaag | 1260 |
| cggagaggac gggacccaga aatgggcggg aagccgcgca gaaagaatcc ccaagagggc | 1320 |
| ctgtacaacg agctccaaaa ggataagatg gcagaagcct atagcgagat tggtatgaaa | 1380 |
| ggggaacgca gaagaggcaa aggccacgac ggactgtacc agggactcag caccgccacc | 1440 |
| aaggacaccct atgacgctct tcacatgcag gccctgccgc ctcgg | 1485 |

<210> SEQ ID NO 129
<211> LENGTH: 1482
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 129

| | |
|---|---|
| atggccctcc ctgtcaccgc cctgctgctt ccgctggctc ttctgctcca cgccgctcgg | 60 |
| ccccaagtgc aattggttca atcaggagga ggagtcgtgc agcccggaag atcgttgaga | 120 |
| ctgtcatgtg ccgcgagcgg ctttactttc tcaagctacg aatgcattg ggtgcgacag | 180 |
| gctccgggaa aaggactgga atgggtcgca gtgatctcat acgacggctc gaacaagtac | 240 |
| tacgccgact ccgtcaaggg tcggttcacg atttcgcgcg ataattccaa gaacactctg | 300 |
| tacctccaaa tgaacagcct ccgggcagag gacaccgccg tctactactg cgctaaggga | 360 |
| tactcgcgct actactacta tggaatggat gtgtggggcc agggaactac cgtgacggtg | 420 |
| tcgtccggcg gcggtgggtc gggcggaggc ggatcaggtg gaggtggaag cggaggagga | 480 |
| gggagcgaaa tcgtcatgac tcagtcccct gctacccttt ctctgtcgcc gggagaaaga | 540 |
| gccatcctga gctgccgggc ctcccagagc gtgtacacca aatacctggg atggtaccag | 600 |
| cagaagccgg ggcaggcacc aaggctcctg atctacgatg cgtccacccg cgcgactggt | 660 |
| atcccagacc gcttttccgg ctcggggtca gggactgact tcaccccttac tatcaatcgg | 720 |
| ctcgagcctg aggatttcgc cgtgtattac tgccagcact acggagggtc cccgctgatt | 780 |
| accttcggcc aaggcaccaa agtggacatc aagaccacta ccccagcacc gaggccaccc | 840 |
| accccggctc ctaccatcgc ctcccagcct ctgtccctgc gtccggaggc atgtagaccc | 900 |
| gcagctggtg gggccgtgca tacccggggt cttgacttcg cctgcgatat ctacatttgg | 960 |
| gcccctctgg ctggtacttg cggggtcctg ctgctttcac tcgtgatcac tctttactgt | 1020 |
| aagcgcggtc ggaagaagct gctgtacatc tttaagcaac ccttcatgag gcctgtgcag | 1080 |
| actactcaag aggaggacgg ctgttcatgc cggttcccag aggaggagga aggcggctgc | 1140 |
| gaactgcgcg tgaaattcag ccgcagcgca gatgctccag cctacaagca ggggcagaac | 1200 |
| cagctctaca cgaactcaa tcttggtcgg agagaggagt acgacgtgct ggacaagcgg | 1260 |
| agaggacggg acccagaaat gggcgggaag ccgcgcagaa gaatcccca agagggcctg | 1320 |
| tacaacgagc tccaaaagga taagatggca gaagcctata gcgagattgg tatgaaaggg | 1380 |
| gaacgcagaa gaggcaaagg ccacgacgga ctgtaccagg gactcagcac cgccaccaag | 1440 |
| gacacctatg acgctcttca catgcaggcc ctgccgcctc gg | 1482 |

<210> SEQ ID NO 130
<211> LENGTH: 1479
<212> TYPE: DNA
<213> ORGANISM: Artificial Sequence
<220> FEATURE:
<223> OTHER INFORMATION: Description of Artificial Sequence: Synthetic polynucleotide

```
<400> SEQUENCE: 130
atggccctcc ctgtcaccgc cctgctgctt ccgctggctc ttctgctcca cgccgctcgg      60 cccccaagtgc aacttgttca atcaggagga ggactcgttc aacccggagg atcactgcga    120
ctctcatgtg cagcgtcggg gttcaccttc tccagctacg caatgtcctg ggtgcgccaa    180 gccccctggaa aaggcctgga gtgggtgtcg gccatctctg ggagcggggg atcaacttac    240
tacgctgact ccgtcaaggg ccgctttacc atctcccggg acaacagcaa gaacactctc    300
tatctccaga tgaactcgct gagagccgaa gataccgctg tctactactg cgcgaagaga    360
gaagctgccg cagggcacga ttggtacttc gacttgtggg gcaggggcac ccttgtgacc    420
gtgtcctccg gtggaggcgg atcaggaggt gggggatcgg gtggaggagg aagcggaggc    480
ggcggttcgg acattcgcgt cacccagtca ccgagctccc tcagcgcatc ggtgggcgac    540
cgggtcacta tcacttgccg ggcgtcccag tcgatctcat cgtatctgaa ttggtaccag    600
cagaaaccgg gaaaggcgcc gaagctgttg atctacgctg ccagctccct gcagtcgggt    660
gtgccatcac gcttttccgg ctcgggatcg ggaaccgatt tcactctgac gatctctagc    720
ctgcagccaa agatttcgc cacttactac tgccagcagt cctacagcat ccctctgact    780
ttcggacaag ggacgaaagt ggagattaag accactaccc cagcaccgag gccacccacc    840
ccggctccta ccatcgcctc ccagcctctg tccctgcgtc cggaggcatg tagacccgca    900
gctggtgggg ccgtgcatac ccgggtgctt gacttcgcct gcgatatcta catttgggcc    960
cctctggctg gtacttgcgg ggtcctgctg ctttcactcg tgatcactct ttactgtaag   1020
cgcggtcgga agaagctgct gtacatctt aagcaaccct tcatgaggcc tgtgcagact   1080
actcaagagg aggacggctg ttcatgccgg ttcccagagg aggaggaagg cggctgcgaa   1140
ctgcgcgtga aattcagccg cagcgcagat gctccagcct acaagcaggg gcagaaccag   1200
ctctacaacg aactcaatct tggtcggaga gaggagtacg acgtgctgga caagcggaga   1260
ggacgggacc cagaaatggg cgggaagccg cgcagaaaga tccccaaga gggcctgtac   1320 aacgagctcc aaaaggataa gatggcagaa gcctatagcg agattggtat gaaaggggaa   1380
cgcagaagag gcaaaggcca cgacggactg taccagggac tcagcaccgc caccaaggac   1440
acctatgacg ctcttcacat gcaggccctg ccgcctcgg                          1479
```

<210> SEQ ID NO 131
<211> LENGTH: 1473
<212> TYPE: DNA
<213> ORGANISM: Artificial Sequence
<220> FEATURE:
<223> OTHER INFORMATION: Description of Artificial Sequence: Synthetic polynucleotide

```
<400> SEQUENCE: 131
atggccctcc ctgtcaccgc cctgctgctt ccgctggctc ttctgctcca cgccgctcgg      60 cccccaagtcc aactcgttca gtcatgggca gaagtcaaga aacccggtgc aagcgtcaaa    120
gtgtcgtgta aggcctccgg ctacactttc acttcctact acatgcactg ggtgcgccaa    180
gccccgggac agggccttga atggatgggc atcatcaacc catcaggagg ttccacgagc    240
tacgcgcaga agttccaggg gagagtgacg atgactagag ataccttcac gagcaccgtc    300
tacatggagc tgtcgaatct gcggtcagag gacactgctg tgtattactg cgcgcgctcc    360 ccgcggtga ccactggcta ctttgactac tggggacaag ggaccctggt gaccgtcagc    420 tcggggaggcg gaggatcggg aggtggaggg tccggtggag gcggctctgg aggaggcggg    480
```

```
tcggacattc aattgaccca gagcccatcc accctctcag cctcggtggg ggatagggtg        540
actatcactt gccgggcctc ccagtcaatt tccagctggc tggcttggta ccagcaaaag        600
cctggaaagg caccgaagct cctgatctac aaggcctcat ctctggaatc aggagtgcct        660
tcgcgcttca gcggaagcgg ctcgggaact gagtttaccc tgaccatctc gagcctgcag        720
ccagatgact tcgcgaccta ttactgccag cagtactcgt cctacccgtt gactttcgga        780
ggaggtaccc gcctcgaaat caaaaccact accccagcac cgaggccacc caccccggct        840
cctaccatcg cctcccagcc tctgtccctg cgtccggagg catgtagacc cgcagctggt        900
ggggccgtgc atacccgggg tcttgacttc gcctgcgata tctacatttg gccccctctg        960
gctggtactt gcggggtcct gctgctttca ctcgtgatca ctctttactg taagcgcggt       1020
cggaagaagc tgctgtacat ctttaagcaa cccttcatga ggcctgtgca gactactcaa       1080
gaggaggacg gctgttcatg ccggttccca gaggaggagg aaggcggctg cgaactgcgc       1140
gtgaaattca gccgcagcgc agatgctcca gcctacaagc aggggcagaa ccagctctac       1200
aacgaactca atcttggtcg gagagaggag tacgacgtgc tggacaagcg gagaggacgg       1260
gacccagaaa tgggcgggaa gccgcgcaga aagaatcccc aagagggcct gtacaacgag       1320
ctccaaaagg ataagatggc agaagcctat agcgagattg gtatgaaagg ggaacgcaga       1380
agaggcaaag gccacgacgg actgtaccag ggactcagca ccgccaccaa ggacacctat       1440
gacgctcttc acatgcaggc cctgccgcct cgg                                    1473

<210> SEQ ID NO 132
<211> LENGTH: 1491
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 132
atggccctcc ctgtcaccgc cctgctgctt ccgctggctc ttctgctcca cgccgctcgg         60
ccccaagtcc aactcgtcca gtccggtgca gaagtcagaa ggccaggagc aagcgtgaag        120
atctcgtgta gagcgtcagg agacaccagc actcgccatt acatccactg gctgcgccag        180
gctccgggcc aagggccgga gtggatgggt gtgatcaacc cgactacggg accggctacc        240
ggaagccctg cgtacgcaca gatgctgcag ggacgggtga ctatgacccg cgatactagc        300
actaggaccg tgtacatgga actccgctcg ttgcggttcg aagataccgc cgtctactac        360
tgcgcccggt ccgtggtggg ccgaagcgcc ccttactact tcgattactg gggacagggc        420
actctggtga ccgttagctc cggtggggga ggctcgggtg gaggcggatc gggaggagga        480
ggcagcggtg aggggggatc ggacattcag atgacccagt caccctcctc cctctcagcc        540
tcggtcgggg accgggtgac cattacgtgc agagcctcac aagggatctc ggactactcc        600
gcctggtacc agcagaaacc gggaaaagcg ccaaagctcc tgatctacgc cgcgagcacc        660
ctgcaatcag gagtgccatc gcgctttctt ggatcgggct cagggactga cttcacgctg        720
actatctcct accttcagtc cgaggatttc gctacctact actgccaaca gtattactcc        780
tatcccctga cctttggcgg aggcactaag gtggacatca gaccactac cccagcaccg        840 aggccaccca cccgggctcc taccatcgcc tcccagcctc tgtccctgcg tccggaggca        900
tgtagacccg cagctggtgg ggccgtgcat acccggggtc ttgacttcgc ctgcgatatc        960
tacatttggg cccctctggc tggtacttgc ggggtcctgc tgctttcact cgtgatcact       1020
```

```
ctttactgta agcgcggtcg gaagaagctg ctgtacatct taagcaaccc cttcatgagg    1080
cctgtgcaga ctactcaaga ggaggacggc tgttcatgcc ggttcccaga ggaggaggaa    1140
ggcggctgcg aactgcgcgt gaaattcagc cgcagcgcag atgctccagc ctacaagcag    1200
gggcagaacc agctctacaa cgaactcaat cttggtcgga gagaggagta cgacgtgctg    1260
gacaagcgga gaggacggga cccagaaatg ggcgggaagc cgcgcagaaa gaatccccaa    1320
gagggcctgt acaacgagct ccaaaaggat aagatggcag aagcctatag cgagattggt    1380
atgaaagggg aacgcagaag aggcaaaggc cacgacggac tgtaccaggg actcagcacc    1440
gccaccaagg acacctatga cgctcttcac atgcaggccc tgccgcctcg g             1491
```

<210> SEQ ID NO 133
<211> LENGTH: 1479
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 133

```
atggccctcc ctgtcaccgc cctgctgctt ccgctggctc ttctgctcca cgccgctcgg      60 cccccaagtcc aactccagca atcgggagca gaagtcaaga aaccaggcgc atcggtgaaa    120
gtgtcgtgta aggcgtcagg gtacaccttc accaactact atatgcactg ggtgcgccag    180
gctccaggcc aggggttgga gtggatgggg atcatcaatc cgtcaggtgg ctacaccact    240
tacgctcaga agttccaggg acgcctcact atgactcgcg atactagcac ctccacggtg    300
tacatggaac tgtcatcgct gaggtccgaa gataccgccg tctactactg cgcacggatc    360
agatcctgcg gaggagattg ttactacttt gacaactggg gacagggcac ccttgttact    420
gtgtcatcgg gaggagggg aagcggagga ggtggatcag gcggcggtgg cagcggggc     480 ggaggatcgg acattcagct gactcagtcc ccctccactt tgtcggccag cgtgggagac    540
agagtgacca tcacttgccg ggcgtccgag aacgtcaata tctggctggc ctggtaccag    600
caaaagcctg gaaaagcccc gaagctgctc atctataagt catccagcct ggcgtctggt    660
gtgccgtcgc ggttctccgg cagcgggagc ggagccgagt tcactctcac catttcgagc    720
cttcaaccgg acgatttcgc cacctactac tgccagcagt accaatccta ccctctgacg    780
tttggaggtg gaaccaaggt ggacatcaag accactaccc cagcaccgag gccacccacc    840
ccggctccta ccatcgcctc ccagcctctg tccctgcgtc cggaggcatg tagacccgca    900
gctggtgggg ccgtgcatac ccggggtctt gacttcgcct gcgatatcta catttgggcc    960
cctctggctg gtacttgcgg ggtcctgctg ctttcactcg tgatcactct ttactgtaag   1020
cgcggtcgga agaagctgct gtacatcttt aagcaaccct tcatgaggcc tgtgcagact   1080
actcaagagg aggacggctg ttcatgccgg ttcccagagg aggaaggg cggctgcgaa    1140 ctgcgcgtga aattcagccg cagcgcagat gctccagcct acaagcaggg gcagaaccag   1200
ctctacaacg aactcaatct tggtcggaga gaggagtacg acgtgctgga caagcggaga   1260
ggacgggacc cagaaatggg cgggaagccg cgcagaaaga atccccaaga gggcctgtac   1320
aacgagctcc aaaaggataa gatggcagaa gcctatagcg agattggtat gaaaggggaa   1380
cgcagaagag gcaaaggcca cgacggactg taccagggac tcagcaccgc caccaaggac   1440
acctatgacg ctcttcacat gcaggccctg ccgcctcgg                          1479
```

<210> SEQ ID NO 134
<211> LENGTH: 1470
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 134

```
atggccctcc ctgtcaccgc cctgctgctt ccgctggctc ttctgctcca cgccgctcgg      60
ccccaaatca ctctgaaaga atctggaccg gccctggtta agccgactca aacgctcacc     120
cttacttgca ccttcagcgg attctcactc agcactgctg gtgtgcacgt cggatggatt     180
agacagccgc tggaaaggc cctggaatgg ctcgccctca tctcctgggc cgatgacaag     240
agatacaggc cctcgcttcg atcccggttg gacattaccc gggtgacctc gaaagatcag     300
gtggtgctct caatgaccaa tatgcagccg gaggacaccg ctacgtacta ctgcgcactg     360
caaggatttg acggctacga ggctaactgg ggaccaggta ctctggtcac cgtgagctcc     420
ggcggggag atcaggcgg ggggggtca ggaggcggag gctccggtgg aggaggatcg     480
gatatcgtca tgacccagtc cccaagctcg ctgagcgcgt cagcgggcga ccgcgtgact     540
atcacttgcc gggccagccg cggcatctcc tccgcactgg cgtggtacca gcagaagcct     600
ggaaaaccgc caaagctcct gatctatgat gcctccagcc tggagtcagg tgtccccagc     660
cgcttctcgg gttcgggctc gggaaccgac ttcactttga ccatcgactc gctggaaccg     720
gaagatttcg caacctacta ctgtcagcag tcctactcga cccccttggac ttttggacaa     780
gggacgaagg tggacatcaa gaccactacc ccagcaccga ggccaccacc ccggctcct     840
accatcgcct cccagcctct gtccctgcgt ccggaggcat gtagaccgc agctggtggg     900
gccgtgcata cccggggtct tgacttcgcc tgcgatatct acatttgggc ccctctggct     960
ggtacttgcg gggtcctgct gctttcactc gtgatcactc tttactgtaa gcgcggtcgg    1020
aagaagctgc tgtacatctt taagcaaccc ttcatgaggc ctgtgcagac tactcaagag    1080
gaggacggct gttcatgccg gttcccagag gaggaggaag gcggctgcga actgcgcgtg    1140
aaattcagcc gcagcgcaga tgctccagcc tacaagcagg gcagaaccc gctctacaac    1200
gaactcaatc ttggtcggag agaggagtac gacgtgctgg acaagcggag aggacgggac    1260
ccagaaatgg gcgggaagcc gcgcagaaag aatccccaag agggcctgta caacgagctc    1320
caaaaggata gatggcaga agcctatagc gagattggta tgaaggggga acgcagaaga    1380
ggcaaaggcc acgacggact gtaccaggga ctcagcaccg ccaccaagga cacctatgac    1440
gctcttcaca tgcaggccct gccgcctcgg                                    1470
```

<210> SEQ ID NO 135
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gly Gly Gly Gly Ser
1               5

<210> SEQ ID NO 136
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 136

Gly Tyr Thr Phe Thr Gly Tyr Tyr Met His
1               5                   10

<210> SEQ ID NO 137
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gly Phe Thr Phe Ser Ser Tyr Trp Met His
1               5                   10

<210> SEQ ID NO 138
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gly Tyr Thr Phe Thr Asp Tyr Tyr Met His
1               5                   10

<210> SEQ ID NO 139
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Gly Tyr Thr Phe Thr Ser Tyr Tyr Met His
1               5                   10

<210> SEQ ID NO 140
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Gly Phe Thr Phe Ser Ser Tyr Ala Met His
1               5                   10

<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gly Tyr Pro Phe Thr Gly Tyr Ser Leu His
1               5                   10
```

```
<210> SEQ ID NO 142
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gly Tyr Thr Phe Thr Ser Tyr Tyr Met His
1               5                   10

<210> SEQ ID NO 143
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gly Tyr Thr Phe Thr Ser Tyr Gly Ile Ser
1               5                   10

<210> SEQ ID NO 144
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gly Tyr Thr Phe Thr Gly Tyr Tyr Met His
1               5                   10

<210> SEQ ID NO 145
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gly Phe Ile Phe Ser Asp Tyr Tyr Met Gly
1               5                   10

<210> SEQ ID NO 146
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gly Phe Thr Phe Arg Gly Tyr Tyr Ile His
1               5                   10

<210> SEQ ID NO 147
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 147

Gly Phe Thr Phe Asp Asp Tyr Ala Met His
1               5                   10

<210> SEQ ID NO 148
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Phe Thr Phe Ser Ser Tyr Trp Met His
1               5                   10

<210> SEQ ID NO 149
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gly Phe Thr Phe Ser Ser Tyr Gly Met His
1               5                   10

<210> SEQ ID NO 150
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gly Phe Thr Phe Ser Ser Tyr Ala Met Ser
1               5                   10

<210> SEQ ID NO 151
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gly Tyr Thr Phe Thr Ser Tyr Tyr Met His
1               5                   10

<210> SEQ ID NO 152
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gly Asp Thr Ser Thr Arg His Tyr Ile His
1               5                   10

<210> SEQ ID NO 153
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 153

Gly Tyr Thr Phe Thr Asn Tyr Tyr Met His
1               5                   10

<210> SEQ ID NO 154
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Gly Phe Ser Leu Ser Thr Ala Gly Val His Val Gly
1               5                   10

<210> SEQ ID NO 155
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Arg Ile Asn Pro Asn Ser Gly Gly Thr Asn Tyr Ala Gln Lys Phe Gln
1               5                   10                  15

Gly

<210> SEQ ID NO 156
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Trp Ile Asn Pro Asn Ser Gly Gly Thr Asn Tyr Ala Gln Lys Phe Gln
1               5                   10                  15

Gly

<210> SEQ ID NO 157
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Arg Ile Asn Thr Asp Gly Ser Thr Thr Thr Tyr Ala Asp Ser Val Glu
1               5                   10                  15

Gly

<210> SEQ ID NO 158
<211> LENGTH: 16
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 158

Ile Ile Asn Pro Ser Gly Gly Ser Thr Ser Tyr Ala Gln Lys Phe Gln
1               5                   10                  15

<210> SEQ ID NO 159
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Trp Ile Asn Pro Asn Ser Gly Gly Thr Asn Tyr Ala Gln Lys Phe Gln
1               5                   10                  15
Gly

<210> SEQ ID NO 160
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ile Ile Asn Pro Ser Gly Gly Ser Thr Gly Tyr Ala Gln Lys Phe Gln
1               5                   10                  15
Gly

<210> SEQ ID NO 161
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Trp Ile Ser Ala Tyr Asn Gly Asn Thr Asn Tyr Ala Gln Lys Leu Gln
1               5                   10                  15

<210> SEQ ID NO 162
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Trp Ile Asn Pro Asn Ser Gly Gly Thr Asn Tyr Ala Gln Asn Phe Gln
1               5                   10                  15
Gly

<210> SEQ ID NO 163
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

```
Arg Ile Asn Pro Asn Ser Gly Gly Thr Asn Tyr Ala Gln Lys Phe Gln
1               5                   10                  15

Gly

<210> SEQ ID NO 164
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Tyr Ile Gly Arg Ser Gly Ser Ser Met Tyr Tyr Ala Asp Ser Val Lys
1               5                   10                  15

Gly

<210> SEQ ID NO 165
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Ile Ile Asn Pro Ser Gly Gly Ser Arg Ala Tyr Ala Gln Lys Phe Gln
1               5                   10                  15

Gly

<210> SEQ ID NO 166
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Gly Ile Ser Trp Asn Ser Gly Ser Ile Gly Tyr Ala Asp Ser Val Lys
1               5                   10                  15

<210> SEQ ID NO 167
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Gly Ile Ser Trp Asn Ser Gly Ser Thr Gly Tyr Ala Asp Ser Val Lys
1               5                   10                  15

Gly

<210> SEQ ID NO 168
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168
```

Arg Ile Asn Ser Asp Gly Ser Ser Thr Ser Tyr Ala Asp Ser Val Lys
1               5                   10                  15

Gly

<210> SEQ ID NO 169
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Val Ile Ser Tyr Asp Gly Ser Asn Lys Tyr Ala Asp Ser Val Lys
1               5                   10                  15

Gly

<210> SEQ ID NO 170
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Ala Ile Ser Gly Ser Gly Gly Ser Thr Tyr Tyr Ala Asp Ser Val Lys
1               5                   10                  15

Gly

<210> SEQ ID NO 171
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Ile Ile Asn Pro Ser Gly Gly Ser Thr Ser Tyr Ala Gln Lys Phe Gln
1               5                   10                  15

Gly

<210> SEQ ID NO 172
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Val Ile Asn Pro Thr Thr Gly Pro Ala Thr Gly Ser Pro Ala Tyr Ala
1               5                   10                  15

Gln Met Leu Gln Gly
            20

<210> SEQ ID NO 173
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 173

Ile Ile Asn Pro Ser Gly Gly Tyr Thr Thr Tyr Ala Gln Lys Phe Gln
1               5                   10                  15
Gly

<210> SEQ ID NO 174
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Leu Ile Ser Trp Ala Asp Asp Lys Arg Tyr Arg Pro Ser Leu Arg Ser
1               5                   10                  15

<210> SEQ ID NO 175
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Gly Arg Tyr Tyr Gly Met Asp Val
1               5

<210> SEQ ID NO 176
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Asp Leu Arg Arg Thr Val Val Thr Pro Arg Ala Tyr Tyr Gly Met Asp
1               5                   10                  15
Val

<210> SEQ ID NO 177
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Gly Glu Trp Asp Gly Ser Tyr Tyr Tyr Asp Tyr
1               5                   10

<210> SEQ ID NO 178
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Gly His Trp Ala Val
1               5
```

```
<210> SEQ ID NO 179
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Gly Trp Asp Phe Asp Tyr
1               5

<210> SEQ ID NO 180
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Tyr Arg Leu Ile Ala Val Ala Gly Asp Tyr Tyr Tyr Tyr Gly Met Asp
1               5                   10                  15

Val

<210> SEQ ID NO 181
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Trp Lys Val Ser Ser Ser Ser Pro Ala Phe Asp Tyr
1               5                   10

<210> SEQ ID NO 182
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Asp His Tyr Gly Gly Asn Ser Leu Phe Tyr
1               5                   10

<210> SEQ ID NO 183
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Gly Gly Tyr Ser Ser Ser Ser Asp Ala Phe Asp Ile
1               5                   10

<210> SEQ ID NO 184
<211> LENGTH: 13
<212> TYPE: PRT
<213> ORGANISM: Artificial Sequence
<220> FEATURE:
<223> OTHER INFORMATION: Description of Artificial Sequence: Synthetic
```

```
                          peptide

<400> SEQUENCE: 184

Val Ala Gly Gly Ile Tyr Tyr Tyr Tyr Gly Met Asp Val
1               5                   10

<210> SEQ ID NO 185
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Gly Trp Asp Phe Asp Tyr
1               5

<210> SEQ ID NO 186
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Thr Thr Thr Ser Tyr Ala Phe Asp Ile
1               5

<210> SEQ ID NO 187
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ser Pro Val Val Ala Ala Thr Glu Asp Phe Gln His
1               5                   10

<210> SEQ ID NO 188
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Thr Ala Ser Cys Gly Gly Asp Cys Tyr Tyr Leu Asp Tyr
1               5                   10

<210> SEQ ID NO 189
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Asp Gly Ser Ser Ser Trp Ser Trp Gly Tyr Phe Asp Tyr
1               5                   10

<210> SEQ ID NO 190
```

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Asp Ser Ser Ser Trp Tyr Gly Gly Gly Ser Ala Phe Asp Ile
1               5                   10

<210> SEQ ID NO 191
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Asp Ser Ser Ser Trp Tyr Gly Gly Gly Ser Ala Phe Asp Ile
1               5                   10

<210> SEQ ID NO 192
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Thr Gly Trp Val Gly Ser Tyr Tyr Tyr Tyr Met Asp Val
1               5                   10

<210> SEQ ID NO 193
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Gly Tyr Ser Arg Tyr Tyr Tyr Tyr Gly Met Asp Val
1               5                   10

<210> SEQ ID NO 194
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Arg Glu Ala Ala Ala Gly His Asp Trp Tyr Phe Asp Leu
1               5                   10

<210> SEQ ID NO 195
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195
```

```
Ser Pro Arg Val Thr Thr Gly Tyr Phe Asp Tyr
1               5                   10
```

<210> SEQ ID NO 196
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

```
Ser Val Val Gly Arg Ser Ala Pro Tyr Tyr Phe Asp Tyr
1               5                   10
```

<210> SEQ ID NO 197
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

```
Ile Arg Ser Cys Gly Gly Asp Cys Tyr Tyr Phe Asp Asn
1               5                   10
```

<210> SEQ ID NO 198
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

```
Gln Gly Phe Asp Gly Tyr Glu Ala Asn
1               5
```

<210> SEQ ID NO 199
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

```
Arg Ala Ser Gln Ser Val Ser Ser Asn Phe Ala
1               5                   10
```

<210> SEQ ID NO 200
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

```
Gln Ala Ser Gln Asp Ile Ser Asn Ser Leu Asn
1               5                   10
```

<210> SEQ ID NO 201
<211> LENGTH: 11
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 201

Arg Ala Ser Gln Ser Ile Asn Thr Tyr Leu Asn
1               5                   10

<210> SEQ ID NO 202
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Arg Ala Ser Gln Ser Ile Ser Asp Arg Leu Ala
1               5                   10

<210> SEQ ID NO 203
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Arg Ala Ser Gln Ser Ile Arg Tyr Tyr Leu Ser
1               5                   10

<210> SEQ ID NO 204
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Arg Ala Ser Gln Gly Val Gly Arg Trp Leu Ala
1               5                   10

<210> SEQ ID NO 205
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Arg Ala Ser Gln Ser Val Tyr Thr Lys Tyr Leu Gly
1               5                   10

<210> SEQ ID NO 206
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Arg Ala Ser Gln Asp Ser Gly Thr Trp Leu Ala
1               5                   10

```
<210> SEQ ID NO 207
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Arg Ala Ser Gln Asp Ile Ser Ser Ala Leu Ala
1               5                   10

<210> SEQ ID NO 208
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Lys Ser Ser His Ser Val Leu Tyr Asn Arg Asn Asn Lys Asn Tyr Leu
1               5                   10                  15

Ala

<210> SEQ ID NO 209
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Arg Ala Ser Gln Ser Ile Arg Tyr Tyr Leu Ser
1               5                   10

<210> SEQ ID NO 210
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Arg Ala Ser Gln Ser Ile Ser Thr Trp Leu Ala
1               5                   10

<210> SEQ ID NO 211
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Arg Ala Ser Gln Ser Val Thr Ser Asn Tyr Leu Ala
1               5                   10

<210> SEQ ID NO 212
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 212

Arg Ala Ser Glu Asn Val Asn Ile Trp Leu Ala
1               5                   10

<210> SEQ ID NO 213
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Gln Gly Asp Ala Leu Arg Ser Tyr Tyr Ala Ser
1               5                   10

<210> SEQ ID NO 214
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Gln Gly Asp Ser Leu Arg Ser Tyr Tyr Ala Ser
1               5                   10

<210> SEQ ID NO 215
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Gln Gly Asp Ser Leu Arg Ser Tyr Tyr Ala Ser
1               5                   10

<210> SEQ ID NO 216
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Arg Ala Ser Gln Ser Val Ser Ser Asn Tyr Leu Ala
1               5                   10

<210> SEQ ID NO 217
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Arg Ala Ser Gln Ser Val Tyr Thr Lys Tyr Leu Gly
1               5                   10

<210> SEQ ID NO 218
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Arg Ala Ser Gln Ser Ile Ser Ser Tyr Leu Asn
1               5                   10

<210> SEQ ID NO 219
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Arg Ala Ser Gln Ser Ile Ser Ser Trp Leu Ala
1               5                   10

<210> SEQ ID NO 220
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Arg Ala Ser Gln Gly Ile Ser Asp Tyr Ser
1               5                   10

<210> SEQ ID NO 221
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Arg Ala Ser Glu Asn Val Asn Ile Trp Leu Ala
1               5                   10

<210> SEQ ID NO 222
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Arg Ala Ser Arg Gly Ile Ser Ser Ala Leu Ala
1               5                   10

<210> SEQ ID NO 223
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Asp Ala Ser Asn Arg Ala Thr
```

```
1               5

<210> SEQ ID NO 224
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Asp Ala Ser Thr Leu Glu Thr
1               5

<210> SEQ ID NO 225
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Ala Ala Ser Ser Leu Gln Ser
1               5

<210> SEQ ID NO 226
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Lys Ala Ser Ser Leu Glu
1               5

<210> SEQ ID NO 227
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Thr Ala Ser Ile Leu Gln Asn
1               5

<210> SEQ ID NO 228
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Ala Ala Ser Thr Leu Gln Ser
1               5

<210> SEQ ID NO 229
<211> LENGTH: 7
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 229

Asp Ala Ser Thr Arg Ala Thr
1               5

<210> SEQ ID NO 230
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Asp Ala Ser Thr Leu Glu Asp
1               5

<210> SEQ ID NO 231
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Asp Ala Ser Ser Leu Glu Ser
1               5

<210> SEQ ID NO 232
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Trp Ala Ser Thr Arg Lys Ser
1               5

<210> SEQ ID NO 233
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Thr Ala Ser Ile Leu Gln Asn
1               5

<210> SEQ ID NO 234
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Lys Ala Ser Thr Leu Glu Ser
1               5

<210> SEQ ID NO 235

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Gly Ala Ser Thr Arg Ala Thr
1               5

<210> SEQ ID NO 236
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Lys Ser Ser Ser Leu Ala Ser
1               5

<210> SEQ ID NO 237
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Gly Lys Asn Asn Arg Pro Ser
1               5

<210> SEQ ID NO 238
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Gly Arg Ser Arg Arg Pro Ser
1               5

<210> SEQ ID NO 239
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Gly Lys Asn Asn Arg Pro Ser
1               5

<210> SEQ ID NO 240
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240
```

Asp Val Ser Thr Arg Ala Thr
1               5

<210> SEQ ID NO 241
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Asp Ala Ser Thr Arg Ala Thr
1               5

<210> SEQ ID NO 242
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Ala Ala Ser Ser Leu Gln Ser
1               5

<210> SEQ ID NO 243
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Lys Ala Ser Ser Leu Glu Ser
1               5

<210> SEQ ID NO 244
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Ala Ala Ser Thr Leu Gln Ser
1               5

<210> SEQ ID NO 245
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Lys Ser Ser Ser Leu Ala Ser
1               5

<210> SEQ ID NO 246
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 246

Asp Ala Ser Ser Leu Glu Ser
1               5

<210> SEQ ID NO 247
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

His Gln Arg Ser Asn Trp Leu Tyr Thr
1               5

<210> SEQ ID NO 248
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Gln Gln His Asp Asn Leu Pro Leu Thr
1               5

<210> SEQ ID NO 249
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Gln Gln Ser Phe Ser Pro Leu Thr
1               5

<210> SEQ ID NO 250
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Gln Gln Tyr Gly His Leu Pro Met Tyr Thr
1               5                   10

<210> SEQ ID NO 251
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Leu Gln Thr Tyr Thr Thr Pro Asp
1               5
```

```
<210> SEQ ID NO 252
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Gln Gln Ala Asn Ser Phe Pro Leu Thr
1               5

<210> SEQ ID NO 253
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Gln His Tyr Gly Gly Ser Pro Leu Ile Thr
1               5                   10

<210> SEQ ID NO 254
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Gln Gln Tyr Asn Ser Tyr Pro Leu Thr
1               5

<210> SEQ ID NO 255
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Gln Gln Phe Ser Ser Tyr Pro Leu Thr
1               5

<210> SEQ ID NO 256
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Gln Gln Thr Gln Thr Phe Pro Leu Thr
1               5

<210> SEQ ID NO 257
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257
```

```
Leu Gln Thr Tyr Thr Thr Pro Asp
1               5

<210> SEQ ID NO 258
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Gln Gln Tyr Asn Thr Tyr Ser Pro Tyr Thr
1               5                   10

<210> SEQ ID NO 259
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Gln Gln Tyr Gly Ser Ala Pro Val Thr
1               5

<210> SEQ ID NO 260
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Gln Gln Tyr Gln Ser Tyr Pro Leu Thr
1               5

<210> SEQ ID NO 261
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Asn Ser Arg Asp Ser Ser Gly Tyr Pro Val
1               5                   10

<210> SEQ ID NO 262
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Asn Ser Arg Asp Asn Thr Ala Asn His Tyr Val
1               5                   10

<210> SEQ ID NO 263
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 263

Asn Ser Arg Gly Ser Ser Gly Asn His Tyr Val
1               5                   10

<210> SEQ ID NO 264
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Gln Gln Arg Ser Asn Trp Pro Pro Trp Thr
1               5                   10

<210> SEQ ID NO 265
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Gln His Tyr Gly Gly Ser Pro Leu Ile Thr
1               5                   10

<210> SEQ ID NO 266
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Gln Gln Ser Tyr Ser Ile Pro Leu Thr
1               5

<210> SEQ ID NO 267
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Gln Gln Tyr Ser Ser Tyr Pro Leu Thr
1               5

<210> SEQ ID NO 268
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Gln Gln Tyr Tyr Ser Tyr Pro Leu Thr
1               5
```

<210> SEQ ID NO 269
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Gln Gln Tyr Gln Ser Tyr Pro Leu Thr
1               5

<210> SEQ ID NO 270
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Gln Gln Ser Tyr Ser Thr Pro Trp Thr
1               5

<210> SEQ ID NO 271
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 271
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa                                      150

<210> SEQ ID NO 272
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Arg Gly Asp Ser
1

<210> SEQ ID NO 273
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
aaaaaaaaaa aaaaaaaaaa aaaaaaaaaa aaaaaaaaaa aaaaaaaaaa aaaaaaaaaa      60
aaaa                                                                   64

<210> SEQ ID NO 274
<211> LENGTH: 17
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 274

Val Ile Ser Tyr Asp Gly Ser Asn Lys Tyr Tyr Ala Asp Ser Val Lys
1               5                   10                  15

Gly

<210> SEQ ID NO 275
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
                20                  25                  30

Thr Met Asn Trp Val Lys Gln Ser His Gly Lys Ser Leu Glu Trp Ile
            35                  40                  45

Gly Leu Ile Thr Pro Tyr Asn Gly Ala Ser Ser Tyr Asn Gln Lys Phe
    50                  55                  60

Arg Gly Lys Ala Thr Leu Thr Val Asp Lys Ser Ser Ser Thr Ala Tyr
65                  70                  75                  80

Met Asp Leu Leu Ser Leu Thr Ser Glu Asp Ser Ala Val Tyr Phe Cys
                85                  90                  95

Ala Arg Gly Gly Tyr Asp Gly Arg Gly Phe Asp Tyr Trp Gly Gln Gly
                100                 105                 110

Thr Thr Val Thr Val Ser Ser Gly Gly Gly Ser Gly Gly Gly Gly
            115                 120                 125

Ser Gly Gly Gly Gly Ser Asp Ile Glu Leu Thr Gln Ser Pro Ala Ile
    130                 135                 140

Met Ser Ala Ser Pro Gly Glu Lys Val Thr Met Thr Cys Ser Ala Ser
145                 150                 155                 160

Ser Ser Val Ser Tyr Met His Trp Tyr Gln Gln Lys Ser Gly Thr Ser
                165                 170                 175

Pro Lys Arg Trp Ile Tyr Asp Thr Ser Lys Leu Ala Ser Gly Val Pro
            180                 185                 190

Gly Arg Phe Ser Gly Ser Gly Ser Gly Asn Ser Tyr Ser Leu Thr Ile
        195                 200                 205

Ser Ser Val Glu Ala Glu Asp Asp Ala Thr Tyr Tyr Cys Gln Gln Trp
    210                 215                 220

Ser Gly Tyr Pro Leu Thr Phe Gly Ala Gly Thr Lys Leu Glu Ile
225                 230                 235

<210> SEQ ID NO 276
<211> LENGTH: 324
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Asp Ala Ala Gln Pro Ala Ala Ser Glu Val Glu Lys Thr Ala Cys Pro
```

-continued

```
             1               5              10              15
           Ser Gly Lys Lys Ala Arg Glu Ile Asp Glu Ser Leu Ile Phe Tyr Lys
                          20              25              30

Lys Trp Glu Leu Glu Ala Cys Val Asp Ala Ala Leu Leu Ala Thr Gln
                          35              40              45

Met Asp Arg Val Asn Ala Ile Pro Phe Thr Tyr Glu Gln Leu Asp Val
                          50              55              60

Leu Lys His Lys Leu Asp Glu Leu Tyr Pro Gln Gly Tyr Pro Glu Ser
            65              70              75              80

Val Ile Gln His Leu Gly Tyr Leu Phe Leu Lys Met Ser Pro Glu Asp
                          85              90              95

Ile Arg Lys Trp Asn Val Thr Ser Leu Glu Thr Leu Lys Ala Leu Leu
                         100             105             110

Glu Val Asn Lys Gly His Glu Met Ser Pro Gln Val Ala Thr Leu Ile
                         115             120             125

Asp Arg Phe Val Lys Gly Arg Gly Gln Leu Asp Lys Asp Thr Leu Asp
                         130             135             140

Thr Leu Thr Ala Phe Tyr Pro Gly Tyr Leu Cys Ser Leu Ser Pro Glu
           145             150             155             160

Glu Leu Ser Ser Val Pro Pro Ser Ser Ile Trp Ala Val Arg Pro Gln
                         165             170             175

Asp Leu Asp Thr Cys Asp Pro Arg Gln Leu Asp Val Leu Tyr Pro Lys
                         180             185             190

Ala Arg Leu Ala Phe Gln Asn Met Asn Gly Ser Glu Tyr Phe Val Lys
                         195             200             205

Ile Gln Ser Phe Leu Gly Gly Ala Pro Thr Glu Asp Leu Lys Ala Leu
                         210             215             220

Ser Gln Gln Asn Val Ser Met Asp Leu Ala Thr Phe Met Lys Leu Arg
           225             230             235             240

Thr Asp Ala Val Leu Pro Leu Thr Val Ala Glu Val Gln Lys Leu Leu
                         245             250             255

Gly Pro His Val Glu Gly Leu Lys Ala Glu Glu Arg His Arg Pro Val
                         260             265             270

Arg Asp Trp Ile Leu Arg Gln Arg Gln Asp Leu Asp Thr Leu Gly
                         275             280             285

Leu Gly Leu Gln Gly Thr Arg Gly Ser His His His His His His Glu
                         290             295             300

Phe Arg His Asp Ser Gly Leu Asn Asp Ile Phe Glu Ala Gln Lys Ile
           305             310             315             320

Glu Trp His Glu

<210> SEQ ID NO 277
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Gly Ser His His His His His His
1               5              10

<210> SEQ ID NO 278
<211> LENGTH: 293
<212> TYPE: PRT
```

<213> ORGANISM: Homo sapiens

<400> SEQUENCE: 278

```
Glu Val Glu Lys Thr Ala Cys Pro Ser Gly Lys Lys Ala Arg Glu Ile
1               5                   10                  15
Asp Glu Ser Leu Ile Phe Tyr Lys Lys Trp Glu Leu Glu Ala Cys Val
            20                  25                  30
Asp Ala Ala Leu Leu Ala Thr Gln Met Asp Arg Val Asn Ala Ile Pro
        35                  40                  45
Phe Thr Tyr Glu Gln Leu Asp Val Leu Lys His Lys Leu Asp Glu Leu
50                  55                  60
Tyr Pro Gln Gly Tyr Pro Glu Ser Val Ile Gln His Leu Gly Tyr Leu
65                  70                  75                  80
Phe Leu Lys Met Ser Pro Glu Asp Ile Arg Lys Trp Asn Val Thr Ser
                85                  90                  95
Leu Glu Thr Leu Lys Ala Leu Leu Glu Val Asn Lys Gly His Glu Met
            100                 105                 110
Ser Pro Gln Ala Pro Arg Arg Pro Leu Pro Gln Val Ala Thr Leu Ile
        115                 120                 125
Asp Arg Phe Val Lys Gly Arg Gly Gln Leu Asp Lys Asp Thr Leu Asp
130                 135                 140
Thr Leu Thr Ala Phe Tyr Pro Gly Tyr Leu Cys Ser Leu Ser Pro Glu
145                 150                 155                 160
Glu Leu Ser Ser Val Pro Pro Ser Ser Ile Trp Ala Val Arg Pro Gln
                165                 170                 175
Asp Leu Asp Thr Cys Asp Pro Arg Gln Leu Asp Val Leu Tyr Pro Lys
            180                 185                 190
Ala Arg Leu Ala Phe Gln Asn Met Asn Gly Ser Glu Tyr Phe Val Lys
        195                 200                 205
Ile Gln Ser Phe Leu Gly Gly Ala Pro Thr Glu Asp Leu Lys Ala Leu
210                 215                 220
Ser Gln Gln Asn Val Ser Met Asp Leu Ala Thr Phe Met Lys Leu Arg
225                 230                 235                 240
Thr Asp Ala Val Leu Pro Leu Thr Val Ala Glu Val Gln Lys Leu Leu
                245                 250                 255
Gly Pro His Val Glu Gly Leu Lys Ala Glu Glu Arg His Arg Pro Val
            260                 265                 270
Arg Asp Trp Ile Leu Arg Gln Arg Gln Asp Asp Leu Asp Thr Leu Gly
        275                 280                 285
Leu Gly Leu Gln Gly
    290
```

<210> SEQ ID NO 279
<211> LENGTH: 239
<212> TYPE: PRT
<213> ORGANISM: Mus musculus

<400> SEQUENCE: 279

```
Gln Val Gln Leu Gln Gln Ser Gly Pro Glu Leu Glu Lys Pro Gly Ala
1               5                   10                  15
Ser Val Lys Ile Ser Cys Lys Ala Ser Gly Tyr Ser Phe Thr Gly Tyr
            20                  25                  30
Thr Met Asn Trp Val Lys Gln Ser His Gly Lys Ser Leu Glu Trp Ile
        35                  40                  45
Gly Leu Ile Thr Pro Tyr Asn Gly Ala Ser Ser Tyr Asn Gln Lys Phe
```

```
                 50                  55                  60
Arg Gly Lys Ala Thr Leu Thr Val Asp Lys Ser Ser Thr Ala Tyr
 65                  70                  75                  80

Met Asp Leu Leu Ser Leu Thr Ser Glu Asp Ser Ala Val Tyr Phe Cys
                 85                  90                  95

Ala Arg Gly Gly Tyr Asp Gly Arg Gly Phe Asp Tyr Trp Gly Gln Gly
                100                 105                 110

Thr Thr Val Thr Val Ser Ser Gly Gly Gly Ser Gly Gly Gly
                115                 120                 125

Ser Gly Gly Gly Gly Ser Asp Ile Glu Leu Thr Gln Ser Pro Ala Ile
        130                 135                 140

Met Ser Ala Ser Pro Gly Glu Lys Val Thr Met Thr Cys Ser Ala Ser
145                 150                 155                 160

Ser Ser Val Ser Tyr Met His Trp Tyr Gln Gln Lys Ser Gly Thr Ser
                165                 170                 175

Pro Lys Arg Trp Ile Tyr Asp Thr Ser Lys Leu Ala Ser Gly Val Pro
                180                 185                 190

Gly Arg Phe Ser Gly Ser Gly Ser Asn Ser Tyr Ser Leu Thr Ile
            195                 200                 205

Ser Ser Val Glu Ala Glu Asp Asp Ala Thr Tyr Tyr Cys Gln Gln Trp
        210                 215                 220

Ser Gly Tyr Pro Leu Thr Phe Gly Ala Gly Thr Lys Leu Glu Ile
225                 230                 235

<210> SEQ ID NO 280
<211> LENGTH: 19
<212> TYPE: DNA
<213> ORGANISM: Mus musculus

<400> SEQUENCE: 280
ggaggtccct caccttcta                                                   19

<210> SEQ ID NO 281
<211> LENGTH: 19
<212> TYPE: DNA
<213> ORGANISM: Mus musculus

<400> SEQUENCE: 281
cggaggatct tatgctgaa                                                   19

<210> SEQ ID NO 282
<211> LENGTH: 19
<212> TYPE: DNA
<213> ORGANISM: Mus musculus

<400> SEQUENCE: 282
cccgcttcca gatcataca                                                   19

<210> SEQ ID NO 283
<211> LENGTH: 19
<212> TYPE: DNA
<213> ORGANISM: Mus musculus

<400> SEQUENCE: 283
ggagacctca acaagatat                                                   19

<210> SEQ ID NO 284
<211> LENGTH: 19
<212> TYPE: DNA
```

<213> ORGANISM: Mus musculus

<400> SEQUENCE: 284
aaggcatggt cattggtat				19

<210> SEQ ID NO 285
<211> LENGTH: 19
<212> TYPE: DNA
<213> ORGANISM: Mus musculus

<400> SEQUENCE: 285
gcatggtcat tggtatcat				19

<210> SEQ ID NO 286
<211> LENGTH: 19
<212> TYPE: DNA
<213> ORGANISM: Mus musculus

<400> SEQUENCE: 286
ggtcattggt atcatgagt				19

<210> SEQ ID NO 287
<211> LENGTH: 19
<212> TYPE: DNA
<213> ORGANISM: Mus musculus

<400> SEQUENCE: 287
cctagtgggt atccctgta				19

<210> SEQ ID NO 288
<211> LENGTH: 19
<212> TYPE: DNA
<213> ORGANISM: Mus musculus

<400> SEQUENCE: 288
gaggatggac attgttctt				19

<210> SEQ ID NO 289
<211> LENGTH: 19
<212> TYPE: DNA
<213> ORGANISM: Mus musculus

<400> SEQUENCE: 289
gcatgcaggc tacagttca				19

<210> SEQ ID NO 290
<211> LENGTH: 19
<212> TYPE: DNA
<213> ORGANISM: Mus musculus

<400> SEQUENCE: 290
ccagcacatg cactgttga				19

<210> SEQ ID NO 291
<211> LENGTH: 19
<212> TYPE: DNA
<213> ORGANISM: Mus musculus

<400> SEQUENCE: 291
cacatgcact gttgagtga				19

<210> SEQ ID NO 292
<211> LENGTH: 21

```
<212> TYPE: DNA
<213> ORGANISM: Mus musculus

<400> SEQUENCE: 292
ctggaggtcc ctcaccttct a                                              21

<210> SEQ ID NO 293
<211> LENGTH: 21
<212> TYPE: DNA
<213> ORGANISM: Mus musculus

<400> SEQUENCE: 293
gtcggaggat cttatgctga a                                              21

<210> SEQ ID NO 294
<211> LENGTH: 21
<212> TYPE: DNA
<213> ORGANISM: Mus musculus

<400> SEQUENCE: 294
tgcccgcttc cagatcatac a                                              21

<210> SEQ ID NO 295
<211> LENGTH: 21
<212> TYPE: DNA
<213> ORGANISM: Mus musculus

<400> SEQUENCE: 295
ctggagacct caacaagata t                                              21

<210> SEQ ID NO 296
<211> LENGTH: 21
<212> TYPE: DNA
<213> ORGANISM: Mus musculus

<400> SEQUENCE: 296
tcaaggcatg gtcattggta t                                              21

<210> SEQ ID NO 297
<211> LENGTH: 21
<212> TYPE: DNA
<213> ORGANISM: Mus musculus

<400> SEQUENCE: 297
aggcatggtc attggtatca t                                              21

<210> SEQ ID NO 298
<211> LENGTH: 21
<212> TYPE: DNA
<213> ORGANISM: Mus musculus

<400> SEQUENCE: 298
atggtcattg gtatcatgag t                                              21

<210> SEQ ID NO 299
<211> LENGTH: 21
<212> TYPE: DNA
<213> ORGANISM: Mus musculus

<400> SEQUENCE: 299
gccctagtgg gtatccctgt a                                              21

<210> SEQ ID NO 300
```

```
<211> LENGTH: 21
<212> TYPE: DNA
<213> ORGANISM: Mus musculus

<400> SEQUENCE: 300
atgaggatgg acattgttct t                                              21

<210> SEQ ID NO 301
<211> LENGTH: 21
<212> TYPE: DNA
<213> ORGANISM: Mus musculus

<400> SEQUENCE: 301
gagcatgcag gctacagttc a                                              21

<210> SEQ ID NO 302
<211> LENGTH: 21
<212> TYPE: DNA
<213> ORGANISM: Mus musculus

<400> SEQUENCE: 302
ttccagcaca tgcactgttg a                                              21

<210> SEQ ID NO 303
<211> LENGTH: 21
<212> TYPE: DNA
<213> ORGANISM: Mus musculus

<400> SEQUENCE: 303
agcacatgca ctgttgagtg a                                              21

<210> SEQ ID NO 304
<211> LENGTH: 21
<212> TYPE: DNA
<213> ORGANISM: Mus musculus

<400> SEQUENCE: 304
tagaaggtga gggacctcca g                                              21

<210> SEQ ID NO 305
<211> LENGTH: 21
<212> TYPE: DNA
<213> ORGANISM: Mus musculus

<400> SEQUENCE: 305
ttcagcataa gatcctccga c                                              21

<210> SEQ ID NO 306
<211> LENGTH: 21
<212> TYPE: DNA
<213> ORGANISM: Mus musculus

<400> SEQUENCE: 306
tgtatgatct ggaagcgggc a                                              21

<210> SEQ ID NO 307
<211> LENGTH: 21
<212> TYPE: DNA
<213> ORGANISM: Mus musculus

<400> SEQUENCE: 307
atatcttgtt gaggtctcca g                                              21
```

```
<210> SEQ ID NO 308
<211> LENGTH: 21
<212> TYPE: DNA
<213> ORGANISM: Mus musculus

<400> SEQUENCE: 308
ataccaatga ccatgccttg a                                              21

<210> SEQ ID NO 309
<211> LENGTH: 21
<212> TYPE: DNA
<213> ORGANISM: Mus musculus

<400> SEQUENCE: 309
atgataccaa tgaccatgcc t                                              21

<210> SEQ ID NO 310
<211> LENGTH: 21
<212> TYPE: DNA
<213> ORGANISM: Mus musculus

<400> SEQUENCE: 310
atggtcattg gtatcatgag t                                              21

<210> SEQ ID NO 311
<211> LENGTH: 21
<212> TYPE: DNA
<213> ORGANISM: Mus musculus

<400> SEQUENCE: 311
gccctagtgg gtatccctgt a                                              21

<210> SEQ ID NO 312
<211> LENGTH: 21
<212> TYPE: DNA
<213> ORGANISM: Mus musculus

<400> SEQUENCE: 312
atgaggatgg acattgttct t                                              21

<210> SEQ ID NO 313
<211> LENGTH: 21
<212> TYPE: DNA
<213> ORGANISM: Mus musculus

<400> SEQUENCE: 313
gagcatgcag gctacagttc a                                              21

<210> SEQ ID NO 314
<211> LENGTH: 21
<212> TYPE: DNA
<213> ORGANISM: Mus musculus

<400> SEQUENCE: 314
ttccagcaca tgcactgttg a                                              21

<210> SEQ ID NO 315
<211> LENGTH: 21
<212> TYPE: DNA
<213> ORGANISM: Mus musculus

<400> SEQUENCE: 315
agcacatgca ctgtttgagtg a                                             21
```

```
<210> SEQ ID NO 316
<211> LENGTH: 19
<212> TYPE: DNA
<213> ORGANISM: Mus musculus

<400> SEQUENCE: 316
tagaaggtga gggacctcc                                                19

<210> SEQ ID NO 317
<211> LENGTH: 19
<212> TYPE: DNA
<213> ORGANISM: Mus musculus

<400> SEQUENCE: 317
ttcagcataa gatcctccg                                                19

<210> SEQ ID NO 318
<211> LENGTH: 19
<212> TYPE: DNA
<213> ORGANISM: Mus musculus

<400> SEQUENCE: 318
tgtatgatct ggaagcggg                                                19

<210> SEQ ID NO 319
<211> LENGTH: 19
<212> TYPE: DNA
<213> ORGANISM: Mus musculus

<400> SEQUENCE: 319
atatcttgtt gaggtctcc                                                19

<210> SEQ ID NO 320
<211> LENGTH: 19
<212> TYPE: DNA
<213> ORGANISM: Mus musculus

<400> SEQUENCE: 320
ataccaatga ccatgcctt                                                19

<210> SEQ ID NO 321
<211> LENGTH: 19
<212> TYPE: DNA
<213> ORGANISM: Mus musculus

<400> SEQUENCE: 321
atgataccaa tgaccatgc                                                19

<210> SEQ ID NO 322
<211> LENGTH: 19
<212> TYPE: DNA
<213> ORGANISM: Mus musculus

<400> SEQUENCE: 322
atggtcattg gtatcatga                                                19

<210> SEQ ID NO 323
<211> LENGTH: 19
<212> TYPE: DNA
<213> ORGANISM: Mus musculus

<400> SEQUENCE: 323
gccctagtgg gtatccctg                                                19
```

```
<210> SEQ ID NO 324
<211> LENGTH: 19
<212> TYPE: DNA
<213> ORGANISM: Mus musculus

<400> SEQUENCE: 324
atgaggatgg acattgttc                                              19

<210> SEQ ID NO 325
<211> LENGTH: 19
<212> TYPE: DNA
<213> ORGANISM: Mus musculus

<400> SEQUENCE: 325
gagcatgcag gctacagtt                                              19

<210> SEQ ID NO 326
<211> LENGTH: 19
<212> TYPE: DNA
<213> ORGANISM: Mus musculus

<400> SEQUENCE: 326
ttccagcaca tgcactgtt                                              19

<210> SEQ ID NO 327
<211> LENGTH: 19
<212> TYPE: DNA
<213> ORGANISM: Mus musculus

<400> SEQUENCE: 327
agcacatgca ctgttgagt                                              19

<210> SEQ ID NO 328
<211> LENGTH: 19
<212> TYPE: DNA
<213> ORGANISM: Homo sapiens

<400> SEQUENCE: 328
ggccaggatg gttcttaga                                              19

<210> SEQ ID NO 329
<211> LENGTH: 19
<212> TYPE: DNA
<213> ORGANISM: Homo sapiens

<400> SEQUENCE: 329
gcttcgtgct aaactggta                                              19

<210> SEQ ID NO 330
<211> LENGTH: 19
<212> TYPE: DNA
<213> ORGANISM: Homo sapiens

<400> SEQUENCE: 330
gggcgtgact tccacatga                                              19

<210> SEQ ID NO 331
<211> LENGTH: 19
<212> TYPE: DNA
<213> ORGANISM: Homo sapiens

<400> SEQUENCE: 331
```
caggcctaga gaagtttca                                                    19

<210> SEQ ID NO 332
<211> LENGTH: 19
<212> TYPE: DNA
<213> ORGANISM: Homo sapiens

<400> SEQUENCE: 332
cttggaaccc attcctgaa                                                    19

<210> SEQ ID NO 333
<211> LENGTH: 19
<212> TYPE: DNA
<213> ORGANISM: Homo sapiens

<400> SEQUENCE: 333
ggaacccatt cctgaaatt                                                    19

<210> SEQ ID NO 334
<211> LENGTH: 19
<212> TYPE: DNA
<213> ORGANISM: Homo sapiens

<400> SEQUENCE: 334
gaacccattc ctgaaatta                                                    19

<210> SEQ ID NO 335
<211> LENGTH: 19
<212> TYPE: DNA
<213> ORGANISM: Homo sapiens

<400> SEQUENCE: 335
aacccattcc tgaaattat                                                    19

<210> SEQ ID NO 336
<211> LENGTH: 19
<212> TYPE: DNA
<213> ORGANISM: Homo sapiens

<400> SEQUENCE: 336
acccattcct gaaattatt                                                    19

<210> SEQ ID NO 337
<211> LENGTH: 19
<212> TYPE: DNA
<213> ORGANISM: Homo sapiens

<400> SEQUENCE: 337
cccattcctg aaattattt                                                    19

<210> SEQ ID NO 338
<211> LENGTH: 19
<212> TYPE: DNA
<213> ORGANISM: Homo sapiens

<400> SEQUENCE: 338
ctgtggttct attatatta                                                    19

<210> SEQ ID NO 339
<211> LENGTH: 19
<212> TYPE: DNA
<213> ORGANISM: Homo sapiens

<400> SEQUENCE: 339
aaatatgaga gcatgctaa 19

<210> SEQ ID NO 340
<211> LENGTH: 19
<212> TYPE: DNA
<213> ORGANISM: Homo sapiens

<400> SEQUENCE: 340
tctaagaacc atcctggcc 19

<210> SEQ ID NO 341
<211> LENGTH: 19
<212> TYPE: DNA
<213> ORGANISM: Homo sapiens

<400> SEQUENCE: 341
taccagttta gcacgaagc 19

<210> SEQ ID NO 342
<211> LENGTH: 19
<212> TYPE: DNA
<213> ORGANISM: Homo sapiens

<400> SEQUENCE: 342
tcatgtggaa gtcacgccc 19

<210> SEQ ID NO 343
<211> LENGTH: 19
<212> TYPE: DNA
<213> ORGANISM: Homo sapiens

<400> SEQUENCE: 343
tgaaacttct ctaggcctg 19

<210> SEQ ID NO 344
<211> LENGTH: 19
<212> TYPE: DNA
<213> ORGANISM: Homo sapiens

<400> SEQUENCE: 344
ttcaggaatg ggttccaag 19

<210> SEQ ID NO 345
<211> LENGTH: 19
<212> TYPE: DNA
<213> ORGANISM: Homo sapiens

<400> SEQUENCE: 345
aatttcagga atgggttcc 19

<210> SEQ ID NO 346
<211> LENGTH: 19
<212> TYPE: DNA
<213> ORGANISM: Homo sapiens

<400> SEQUENCE: 346
taatttcagg aatgggttc 19

<210> SEQ ID NO 347
<211> LENGTH: 19
<212> TYPE: DNA
<213> ORGANISM: Homo sapiens

```
<400> SEQUENCE: 347
ataatttcag gaatgggtt                                                      19

<210> SEQ ID NO 348
<211> LENGTH: 19
<212> TYPE: DNA
<213> ORGANISM: Homo sapiens

<400> SEQUENCE: 348
aataatttca ggaatgggt                                                      19

<210> SEQ ID NO 349
<211> LENGTH: 19
<212> TYPE: DNA
<213> ORGANISM: Homo sapiens

<400> SEQUENCE: 349
aaataatttc aggaatggg                                                      19

<210> SEQ ID NO 350
<211> LENGTH: 19
<212> TYPE: DNA
<213> ORGANISM: Homo sapiens

<400> SEQUENCE: 350
taatataata gaaccacag                                                      19

<210> SEQ ID NO 351
<211> LENGTH: 19
<212> TYPE: DNA
<213> ORGANISM: Homo sapiens

<400> SEQUENCE: 351
ttagcatgct ctcatattt                                                      19

<210> SEQ ID NO 352
<211> LENGTH: 21
<212> TYPE: DNA
<213> ORGANISM: Homo sapiens

<400> SEQUENCE: 352
gcggccagga tggttcttag a                                                   21

<210> SEQ ID NO 353
<211> LENGTH: 21
<212> TYPE: DNA
<213> ORGANISM: Homo sapiens

<400> SEQUENCE: 353
gagcttcgtg ctaaactggt a                                                   21

<210> SEQ ID NO 354
<211> LENGTH: 21
<212> TYPE: DNA
<213> ORGANISM: Homo sapiens

<400> SEQUENCE: 354
acgggcgtga cttccacatg a                                                   21

<210> SEQ ID NO 355
<211> LENGTH: 21
<212> TYPE: DNA
<213> ORGANISM: Homo sapiens
```

```
<400> SEQUENCE: 355
tgcaggccta gagaagtttc a                                              21

<210> SEQ ID NO 356
<211> LENGTH: 21
<212> TYPE: DNA
<213> ORGANISM: Homo sapiens

<400> SEQUENCE: 356
tccttggaac ccattcctga a                                              21

<210> SEQ ID NO 357
<211> LENGTH: 21
<212> TYPE: DNA
<213> ORGANISM: Homo sapiens

<400> SEQUENCE: 357
ttggaaccca ttcctgaaat t                                              21

<210> SEQ ID NO 358
<211> LENGTH: 21
<212> TYPE: DNA
<213> ORGANISM: Homo sapiens

<400> SEQUENCE: 358
tggaacccat tcctgaaatt a                                              21

<210> SEQ ID NO 359
<211> LENGTH: 21
<212> TYPE: DNA
<213> ORGANISM: Homo sapiens

<400> SEQUENCE: 359
ggaacccatt cctgaaatta t                                              21

<210> SEQ ID NO 360
<211> LENGTH: 21
<212> TYPE: DNA
<213> ORGANISM: Homo sapiens

<400> SEQUENCE: 360
gaacccattc ctgaaattat t                                              21

<210> SEQ ID NO 361
<211> LENGTH: 21
<212> TYPE: DNA
<213> ORGANISM: Homo sapiens

<400> SEQUENCE: 361
aacccattcc tgaaattatt t                                              21

<210> SEQ ID NO 362
<211> LENGTH: 21
<212> TYPE: DNA
<213> ORGANISM: Homo sapiens

<400> SEQUENCE: 362
ccctgtggtt ctattatatt a                                              21

<210> SEQ ID NO 363
<211> LENGTH: 21
<212> TYPE: DNA
```

```
<213> ORGANISM: Homo sapiens

<400> SEQUENCE: 363
ttaaatatga gcatgctaa                                                    21

<210> SEQ ID NO 364
<211> LENGTH: 21
<212> TYPE: DNA
<213> ORGANISM: Homo sapiens

<400> SEQUENCE: 364
tctaagaacc atcctggccg c                                                 21

<210> SEQ ID NO 365
<211> LENGTH: 21
<212> TYPE: DNA
<213> ORGANISM: Homo sapiens

<400> SEQUENCE: 365
taccagttta gcacgaagct c                                                 21

<210> SEQ ID NO 366
<211> LENGTH: 21
<212> TYPE: DNA
<213> ORGANISM: Homo sapiens

<400> SEQUENCE: 366
tcatgtggaa gtcacgcccg t                                                 21

<210> SEQ ID NO 367
<211> LENGTH: 21
<212> TYPE: DNA
<213> ORGANISM: Homo sapiens

<400> SEQUENCE: 367
tgaaacttct ctaggcctgc a                                                 21

<210> SEQ ID NO 368
<211> LENGTH: 21
<212> TYPE: DNA
<213> ORGANISM: Homo sapiens

<400> SEQUENCE: 368
ttcaggaatg ggttccaagg a                                                 21

<210> SEQ ID NO 369
<211> LENGTH: 21
<212> TYPE: DNA
<213> ORGANISM: Homo sapiens

<400> SEQUENCE: 369
aatttcagga atgggttcca a                                                 21

<210> SEQ ID NO 370
<211> LENGTH: 21
<212> TYPE: DNA
<213> ORGANISM: Homo sapiens

<400> SEQUENCE: 370
taatttcagg aatgggttcc a                                                 21

<210> SEQ ID NO 371
<211> LENGTH: 21
```

<212> TYPE: DNA
<213> ORGANISM: Homo sapiens

<400> SEQUENCE: 371
ataatttcag gaatgggttc c                                              21

<210> SEQ ID NO 372
<211> LENGTH: 21
<212> TYPE: DNA
<213> ORGANISM: Homo sapiens

<400> SEQUENCE: 372
aataatttca ggaatgggtt c                                              21

<210> SEQ ID NO 373
<211> LENGTH: 21
<212> TYPE: DNA
<213> ORGANISM: Homo sapiens

<400> SEQUENCE: 373
aaataatttc aggaatgggt t                                              21

<210> SEQ ID NO 374
<211> LENGTH: 21
<212> TYPE: DNA
<213> ORGANISM: Homo sapiens

<400> SEQUENCE: 374
taatataata gaaccacagg g                                              21

<210> SEQ ID NO 375
<211> LENGTH: 21
<212> TYPE: DNA
<213> ORGANISM: Homo sapiens

<400> SEQUENCE: 375
ttagcatgct ctcatattta a                                              21

<210> SEQ ID NO 376
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Met Glu Thr Asp Thr Leu Leu Leu Trp Val Leu Leu Leu Trp Val Pro
1               5                   10                  15

Gly Ser Thr Gly Asp Ala Ala Gln Pro Ala Ala Ser Glu
            20                  25

<210> SEQ ID NO 377
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 377

Thr Arg Gly Ser Gly Lys Pro Ile Pro Asn Pro Leu Leu Gly Leu Asp
1               5                   10                  15

Ser Thr Arg Thr Gly His His His His His His His His His His

His

<210> SEQ ID NO 378
<211> LENGTH: 346
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 378

```
Met Glu Thr Asp Thr Leu Leu Leu Trp Val Leu Leu Leu Trp Val Pro
1               5                   10                  15

Gly Ser Thr Gly Asp Ala Ala Gln Pro Ala Ser Glu Val Glu Lys
            20                  25                  30

Thr Ala Cys Pro Ser Gly Lys Lys Ala Arg Glu Ile Asp Glu Ser Leu
        35                  40                  45

Ile Phe Tyr Lys Lys Trp Glu Leu Glu Ala Cys Val Asp Ala Ala Leu
    50                  55                  60

Leu Ala Thr Gln Met Asp Arg Val Asn Ala Ile Pro Phe Thr Tyr Glu
65                  70                  75                  80

Gln Leu Asp Val Leu Lys His Lys Leu Asp Glu Leu Tyr Pro Gln Gly
                85                  90                  95

Tyr Pro Glu Ser Val Ile Gln His Leu Gly Tyr Leu Phe Leu Lys Met
            100                 105                 110

Ser Pro Glu Asp Ile Arg Lys Trp Gln Val Thr Ser Leu Glu Thr Leu
        115                 120                 125

Lys Ala Leu Leu Glu Val Asn Lys Gly His Glu Met Ser Pro Gln Val
130                 135                 140

Ala Thr Leu Ile Asp Arg Phe Val Lys Gly Arg Gly Gln Leu Asp Lys
145                 150                 155                 160

Asp Thr Leu Asp Thr Leu Thr Ala Phe Tyr Pro Gly Tyr Leu Cys Ser
                165                 170                 175

Leu Ser Pro Glu Glu Leu Ser Ser Val Pro Pro Ser Ser Ile Trp Ala
            180                 185                 190

Val Arg Pro Gln Asp Leu Asp Thr Cys Asp Pro Arg Gln Leu Asp Val
        195                 200                 205

Leu Tyr Pro Lys Ala Arg Leu Ala Phe Gln Asn Met Gln Gly Ser Glu
    210                 215                 220

Tyr Phe Val Lys Ile Gln Ser Phe Leu Gly Gly Ala Pro Thr Glu Asp
225                 230                 235                 240

Leu Lys Ala Leu Ser Gln Gln Gln Val Ser Met Asp Leu Ala Thr Phe
                245                 250                 255

Met Lys Leu Arg Thr Asp Ala Val Leu Pro Leu Thr Val Ala Glu Val
            260                 265                 270

Gln Lys Leu Leu Gly Pro His Val Glu Gly Leu Lys Ala Glu Glu Arg
        275                 280                 285

His Arg Pro Val Arg Asp Trp Ile Leu Arg Gln Arg Gln Asp Asp Leu
    290                 295                 300

Asp Thr Leu Gly Leu Gly Leu Gln Gly Thr Arg Gly Ser Gly Lys Pro
305                 310                 315                 320

Ile Pro Asn Pro Leu Leu Gly Leu Asp Ser Thr Arg Thr Gly His His
                325                 330                 335

His His His His His His His His
```

-continued

```
                340                 345

<210> SEQ ID NO 379
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Met Ala Leu Pro Val Thr Ala Leu Leu Leu Pro Leu Ala Leu Leu Leu
1               5                   10                  15

His Ala Ala Arg Pro
            20

<210> SEQ ID NO 380
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Gly Ser His His His His His His His His
1               5                   10

<210> SEQ ID NO 381
<211> LENGTH: 272
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 381

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Glu Lys Pro Gly Ala Ser Val Lys Val Ser Cys Lys Ala Ser Gly Tyr
        35                  40                  45

Thr Phe Thr Asp Tyr Tyr Met His Trp Val Arg Gln Ala Pro Gly Gln
    50                  55                  60

Gly Leu Glu Trp Met Gly Trp Ile Asn Pro Asn Ser Gly Gly Thr Asn
65                  70                  75                  80

Tyr Ala Gln Lys Phe Gln Gly Arg Val Thr Met Thr Arg Asp Thr Ser
                85                  90                  95

Ile Ser Thr Ala Tyr Met Glu Leu Ser Arg Leu Arg Ser Asp Asp Thr
            100                 105                 110

Ala Val Tyr Tyr Cys Ala Ser Gly Trp Asp Phe Asp Tyr Trp Gly Gln
        115                 120                 125

Gly Thr Leu Val Thr Val Ser Ser Gly Gly Gly Ser Gly Gly Gly
    130                 135                 140

Gly Ser Gly Gly Gly Gly Ser Gly Gly Gly Gly Ser Asp Ile Val Met
145                 150                 155                 160

Thr Gln Ser Pro Ser Ser Leu Ser Ala Ser Val Gly Asp Arg Val Thr
                165                 170                 175

Ile Thr Cys Arg Ala Ser Gln Ser Ile Arg Tyr Tyr Leu Ser Trp Tyr
            180                 185                 190
```

```
Gln Gln Lys Pro Gly Lys Ala Pro Lys Leu Leu Ile Tyr Thr Ala Ser
        195                 200                 205

Ile Leu Gln Asn Gly Val Pro Ser Arg Phe Ser Gly Ser Gly Ser Gly
        210                 215                 220

Thr Asp Phe Thr Leu Thr Ile Ser Ser Leu Gln Pro Glu Asp Phe Ala
225                 230                 235                 240

Thr Tyr Tyr Cys Leu Gln Thr Tyr Thr Thr Pro Asp Phe Gly Pro Gly
                245                 250                 255

Thr Lys Val Glu Ile Lys Gly Ser His His His His His His
            260                 265                 270

<210> SEQ ID NO 382
<211> LENGTH: 132
<212> TYPE: PRT
<213> ORGANISM: Homo sapiens

<400> SEQUENCE: 382

Asp Val Pro Asp Tyr Ala Ser Leu Gly Gly Pro Ser Ser Pro Lys Lys
1               5                   10                  15

Lys Arg Lys Val Ser Arg Gly Val Gln Val Glu Thr Ile Ser Pro Gly
            20                  25                  30

Asp Gly Arg Thr Phe Pro Lys Arg Gly Gln Thr Cys Val Val His Tyr
        35                  40                  45

Thr Gly Met Leu Glu Asp Gly Lys Lys Phe Asp Ser Ser Arg Asp Arg
    50                  55                  60

Asn Lys Pro Phe Lys Phe Met Leu Gly Lys Gln Glu Val Ile Arg Gly
65                  70                  75                  80

Trp Glu Glu Gly Val Ala Gln Met Ser Val Gly Gln Arg Ala Lys Leu
                85                  90                  95

Thr Ile Ser Pro Asp Tyr Ala Tyr Gly Ala Thr Gly His Pro Gly Ile
            100                 105                 110

Ile Pro Pro His Ala Thr Leu Val Phe Asp Val Glu Leu Leu Lys Leu
        115                 120                 125

Glu Thr Ser Tyr
    130

<210> SEQ ID NO 383
<211> LENGTH: 108
<212> TYPE: PRT
<213> ORGANISM: Homo sapiens

<400> SEQUENCE: 383

Val Gln Val Glu Thr Ile Ser Pro Gly Asp Gly Arg Thr Phe Pro Lys
1               5                   10                  15

Arg Gly Gln Thr Cys Val Val His Tyr Thr Gly Met Leu Glu Asp Gly
            20                  25                  30

Lys Lys Phe Asp Ser Ser Arg Asp Arg Asn Lys Pro Phe Lys Phe Met
        35                  40                  45

Leu Gly Lys Gln Glu Val Ile Arg Gly Trp Glu Glu Gly Val Ala Gln
    50                  55                  60

Met Ser Val Gly Gln Arg Ala Lys Leu Thr Ile Ser Pro Asp Tyr Ala
65                  70                  75                  80

Tyr Gly Ala Thr Gly His Pro Gly Ile Ile Pro Pro His Ala Thr Leu
                85                  90                  95

Val Phe Asp Val Glu Leu Leu Lys Leu Glu Thr Ser
            100                 105
```

<210> SEQ ID NO 384
<211> LENGTH: 93
<212> TYPE: PRT
<213> ORGANISM: Homo sapiens

<400> SEQUENCE: 384

Ile Leu Trp His Glu Met Trp His Glu Gly Leu Glu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys
                85                  90

<210> SEQ ID NO 385
<211> LENGTH: 95
<212> TYPE: PRT
<213> ORGANISM: Homo sapiens

<400> SEQUENCE: 385

Ile Leu Trp His Glu Met Trp His Glu Gly Leu Ile Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys Thr Ser
                85                  90                  95

<210> SEQ ID NO 386
<211> LENGTH: 95
<212> TYPE: PRT
<213> ORGANISM: Homo sapiens

<400> SEQUENCE: 386

Ile Leu Trp His Glu Met Trp His Glu Gly Leu Leu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys Thr Ser
                85                  90                  95

```
<210> SEQ ID NO 387
<211> LENGTH: 95
<212> TYPE: PRT
<213> ORGANISM: Homo sapiens

<400> SEQUENCE: 387

Ile Leu Trp His Glu Met Trp His Glu Gly Leu Glu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Leu Gln Ala
65                  70                  75                  80

Trp Asp Leu Tyr Tyr His Val Phe Arg Arg Ile Ser Lys Thr Ser
                85                  90                  95

<210> SEQ ID NO 388
<211> LENGTH: 95
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (78)..(78)
<223> OTHER INFORMATION: Any amino acid

<400> SEQUENCE: 388

Ile Leu Trp His Glu Met Trp His Glu Gly Leu Xaa Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Xaa Gln Ala
65                  70                  75                  80

Trp Asp Leu Tyr Tyr His Val Phe Arg Arg Ile Ser Lys Thr Ser
                85                  90                  95

<210> SEQ ID NO 389
<211> LENGTH: 95
<212> TYPE: PRT
<213> ORGANISM: Homo sapiens

<400> SEQUENCE: 389

Ile Leu Trp His Glu Met Trp His Glu Gly Leu Ile Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60
```

```
Cys Arg Lys Tyr Met Lys Ser Gly Asn Val Lys Asp Leu Leu Gln Ala
 65                  70                  75                  80

Trp Asp Leu Tyr Tyr His Val Phe Arg Arg Ile Ser Lys Thr Ser
                 85                  90                  95

<210> SEQ ID NO 390
<211> LENGTH: 95
<212> TYPE: PRT
<213> ORGANISM: Homo sapiens

<400> SEQUENCE: 390

Ile Leu Trp His Glu Met Trp His Gly Leu Leu Glu Ala Ser Arg
 1               5                  10                  15

Leu Tyr Phe Gly Glu Arg Asn Val Lys Gly Met Phe Glu Val Leu Glu
                 20                  25                  30

Pro Leu His Ala Met Met Glu Arg Gly Pro Gln Thr Leu Lys Glu Thr
                 35                  40                  45

Ser Phe Asn Gln Ala Tyr Gly Arg Asp Leu Met Glu Ala Gln Glu Trp
 50                  55                  60

Cys Arg Lys Tyr Met Lys Ser Gly Asn Val Lys Asp Leu Leu Gln Ala
 65                  70                  75                  80

Trp Asp Leu Tyr Tyr His Val Phe Arg Arg Ile Ser Lys Thr Ser
                 85                  90                  95

<210> SEQ ID NO 391
<211> LENGTH: 383
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 391

Met Ala Leu Pro Val Thr Ala Leu Leu Leu Pro Leu Ala Leu Leu Leu
 1               5                  10                  15

His Ala Ala Arg Pro Gln Val Gln Leu Gln Gln Ser Gly Pro Glu Leu
                 20                  25                  30

Glu Lys Pro Gly Ala Ser Val Lys Ile Ser Cys Lys Ala Ser Gly Tyr
                 35                  40                  45

Ser Phe Thr Gly Tyr Thr Met Asn Trp Val Lys Gln Ser His Gly Lys
 50                  55                  60

Ser Leu Glu Trp Ile Gly Leu Ile Thr Pro Tyr Asn Gly Ala Ser Ser
 65                  70                  75                  80

Tyr Asn Gln Lys Phe Arg Gly Lys Ala Thr Leu Thr Val Asp Lys Ser
                 85                  90                  95

Ser Ser Thr Ala Tyr Met Asp Leu Leu Ser Leu Thr Ser Glu Asp Ser
                100                 105                 110

Ala Val Tyr Phe Cys Ala Arg Gly Gly Tyr Asp Gly Arg Gly Phe Asp
                115                 120                 125

Tyr Trp Gly Gln Gly Thr Thr Val Thr Val Ser Ser Gly Gly Gly Gly
                130                 135                 140

Ser Gly Gly Gly Gly Ser Gly Gly Gly Gly Ser Asp Ile Glu Leu Thr
145                 150                 155                 160

Gln Ser Pro Ala Ile Met Ser Ala Ser Pro Gly Glu Lys Val Thr Met
                165                 170                 175

Thr Cys Ser Ala Ser Ser Ser Val Ser Tyr Met His Trp Tyr Gln Gln
                180                 185                 190
```

```
Lys Ser Gly Thr Ser Pro Lys Arg Trp Ile Tyr Asp Thr Ser Lys Leu
            195                 200                 205

Ala Ser Gly Val Pro Gly Arg Phe Ser Gly Ser Gly Ser Gly Asn Ser
        210                 215                 220

Tyr Ser Leu Thr Ile Ser Ser Val Glu Ala Glu Asp Ala Thr Tyr
225                 230                 235                 240

Tyr Cys Gln Gln Trp Ser Gly Tyr Pro Leu Thr Phe Gly Ala Gly Thr
                245                 250                 255

Lys Leu Glu Ile Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
            275                 280                 285

Pro Ala Ala Gly Gly Ala Val His Thr Arg Gly Leu Asp Phe Ala Cys
        290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Lys Arg Gly Arg Lys Lys Leu
                325                 330                 335

Leu Tyr Ile Phe Lys Gln Pro Phe Met Arg Pro Val Gln Thr Thr Gln
            340                 345                 350

Glu Glu Asp Gly Cys Ser Cys Arg Phe Pro Glu Glu Glu Glu Gly Gly
            355                 360                 365

Cys Glu Leu Arg Val Lys Phe Ser Arg Ser Ala Asp Ala Pro Ala
        370                 375                 380

<210> SEQ ID NO 392
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 392
caagtccagc tccagcagtc gggcccagag ttggagaagc ctggggcgag cgtgaagatc      60
tcatgcaaag cctcaggcta ctcctttact ggatacacga tgaattgggt gaaacagtcg     120
catggaaagt cactggaatg gatcggtctg attacgccct acaacggcgc ctccagctac     180
aaccagaagt tcaggggaaa ggcgaccctt actgtcgaca gtcgtcaag caccgcctac     240 atggacctcc tgtccctgac ctccgaagat agcgcggtct acttttgtgc acgcggaggt     300
tacgatggac ggggattcga ctactggggc cagggaacca ctgtcaccgt gtcgagcgga     360
ggcggaggga gcggaggagg aggcagcgga ggtggagggt cggatatcga actcactcag     420
tccccagcaa tcatgtccgc ttcaccggga gaaaaggtga ccatgacttg ctcggcctcc     480
tcgtccgtgt catacatgca ctggtaccaa caaaaatcgg gacctcccc taagagatgg     540 atctacgata ccagcaaact ggcttcaggc gtgccgggac gcttctcggg ttcggggagc     600
ggaaattcgt attcgttgac catttcgtcc gtggaagccg aggacgacgc aacttattac     660
tgccaacagt ggtcaggcta cccgctcact ttcggagccg gcactaagct ggagatc       717

<210> SEQ ID NO 393
<211> LENGTH: 1149
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 393

```
atggccctcc ctgtcaccgc cctgctgctt ccgctggctc ttctgctcca cgccgctcgg     60
ccccaagtcc agctccagca gtcgggccca gagttggaga agcctggggc gagcgtgaag    120
atctcatgca aagcctcagg ctactccttt actggataca cgatgaattg ggtgaaacag    180
tcgcatggaa agtcactgga atggatcggt ctgattacgc cctacaacgg cgcctccagc    240
tacaaccaga gttcaggggg aaaggcgacc cttactgtcg acaagtcgtc aagcaccgcc    300
tacatggacc tcctgtccct gacctccgaa gatagcgcgg tctacttttg tgcacgcgga    360
ggttacgatg gacggggatt cgactactgg ggccagggaa ccactgtcac cgtgtcgagc    420
ggaggcggag ggagcggagg aggaggcagc ggaggtggag ggtcggatat cgaactcact    480
cagtccccag caatcatgtc cgcttcaccg ggagaaaagg tgaccatgac ttgctcggcc    540
tcctcgtccg tgtcatacat gcactggtac aacaaaaat cggggaccct ccctaagaga    600
tggatctacg ataccagcaa actggcttca ggcgtgccgg acgcttctc gggttcgggg    660
agcggaaatt cgtattcgtt gaccatttcg tccgtggaag ccgaggacga cgcaacttat    720
tactgccaac agtggtcagg ctacccgctc actttcggag ccggcactaa gctggagatc    780
accactaccc cagcaccgag gccacccacc ccggctccta ccatcgcctc ccagcctctg    840
tccctgcgtc cggaggcatg tagacccgca gctggtgggg ccgtgcatac ccggggtctt    900
gacttcgcct gcgatatcta catttgggcc cctctggctg gtacttgcgg ggtcctgctg    960
cttttcactcg tgatcactct ttactgtaag cgcggtcgga agaagctgct gtacatcttt   1020
aagcaaccct tcatgaggcc tgtgcagact actcaagagg aggacggctg ttcatgccgg   1080
ttccagagg aggaggaagg cggctgcgaa ctgcgcgtga aattcagccg cagcgcagat   1140
gctccagcc                                                           1149
```

<210> SEQ ID NO 394
<211> LENGTH: 10
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 394

Gly Tyr Ser Phe Thr Gly Tyr Thr Met Asn
1               5                   10

<210> SEQ ID NO 395
<211> LENGTH: 17
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 395

Leu Ile Thr Pro Tyr Asn Gly Ala Ser Ser Tyr Asn Gln Lys Phe Arg
1               5                   10                  15

Gly

<210> SEQ ID NO 396
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 396

Gly Gly Tyr Asp Gly Arg Gly Phe Asp Tyr
1               5                   10

<210> SEQ ID NO 397
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

Ser Ala Ser Ser Ser Val Ser Tyr Met His
1               5                   10

<210> SEQ ID NO 398
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Asp Thr Ser Lys Leu Ala Ser
1               5

<210> SEQ ID NO 399
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Gln Gln Trp Ser Gly Tyr Pro Leu Thr
1               5

<210> SEQ ID NO 400
<211> LENGTH: 7
<212> TYPE: PRT
<213> ORGANISM: Artificial Sequence
<220> FEATURE:
<223> OTHER INFORMATION: Description of Artificial Sequence: Synthetic
      7xHis tag

<400> SEQUENCE: 400

His His His His His His His
1               5

<210> SEQ ID NO 401
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 401

His His His His His His His His
1               5
```

```
<210> SEQ ID NO 402
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-arginyl
<220> FEATURE:
<221> NAME/KEY: MOD_RES
<222> LOCATION: (2)..(2)
<223> OTHER INFORMATION: Glycyl
<220> FEATURE:
<221> NAME/KEY: MOD_RES
<222> LOCATION: (3)..(3)
<223> OTHER INFORMATION: L-beta-aspartyl

<400> SEQUENCE: 402

Arg Gly Asp Ser
1
```

What is claimed is:

1. An isolated nucleic acid molecule encoding a chimeric antigen receptor (CAR), wherein the CAR comprises: i) a human anti-mesothelin binding domain, ii) a transmembrane domain, and iii) an intracellular signaling domain, and wherein said anti-mesothelin binding domain comprises:
   (a) a light chain variable region comprising: a light chain complementary determining region 1 (LC CDR1) comprising the amino acid sequence of SEQ ID NO: 203; a light chain complementary determining region 2 (LC CDR2) comprising the amino acid sequence of SEQ ID NO: 227; and a light chain complementary determining region 3 (LC CDR3) comprising the amino acid sequence of SEQ ID NO: 251; and
   (b) a heavy chain variable region comprising: a heavy chain complementary determining region 1 (HC CDR1) comprising the amino acid sequence of SEQ ID NO:138; a heavy chain complementary determining region 2 (HC CDR2) comprising the amino acid sequence of SEQ ID NO: 156; and a heavy chain complementary determining region 3 (HC CDR3) comprising the amino acid sequence of SEQ ID NO: 179, wherein the CAR is not a regulatable CAR.

2. The isolated nucleic acid molecule of claim 1, wherein the anti-mesothelin binding domain comprises
   the amino acid sequence of the light chain variable region of SEQ ID NO: 43; or
   an amino acid sequence with 95-99% identity to the amino acid sequence of the light chain variable region of SEQ ID NO: 43.

3. The isolated nucleic acid molecule of claim 1, wherein the anti-mesothelin binding domain comprises
   the amino acid sequence of the heavy chain variable region of SEQ ID NO: 43; or
   an amino acid sequence with 95-99% identity to the amino acid sequence of the heavy chain variable region of SEQ ID NO: 43.

4. The isolated nucleic acid molecule of claim 1, wherein the anti-mesothelin binding domain comprises the amino acid sequence of the light chain variable region of SEQ ID NO: 43; and the heavy chain variable region of SEQ ID NO: 43.

5. The isolated nucleic acid molecule of claim 1, wherein the anti-mesothelin binding domain is a scFv.

6. The isolated nucleic acid molecule of claim 1, wherein
   a) the encoded anti-mesothelin binding domain comprises the sequence SEQ ID NO: 43, or a sequence with 95-99% identify to the amino acid sequence SEQ ID NO: 43; or
   b) the isolated nucleic acid sequence encoding the anti-mesothelin binding domain comprises the sequence of SEQ ID NO: 91, or a sequence with 95-99% identify to the nucleic acid sequence of SEQ ID NO: 91.

7. The isolated nucleic acid molecule of claim 1, wherein the encoded CAR includes a transmembrane domain that comprises a transmembrane domain of a protein selected from the group consisting of the alpha, beta or zeta chain of the T-cell receptor, CD28, CD3 epsilon, CD45, CD4, CD5, CD9, CD16, CD22, CD33, CD37, CD64, CD80, CD86, CD134, CD137 and CD154.

8. The isolated nucleic acid molecule of claim 1, wherein the encoded anti-mesothelin binding domain is connected to the transmembrane domain by a hinge region, wherein
   a) the encoded hinge region comprises the amino acid sequence of SEQ ID NO:2, or the encoded hinge region comprises a sequence with 95-99% identity to the amino acid sequence of SEQ ID NO:2, or
   b) the encoded hinge region comprises the amino acid sequence encoded by the nucleic acid sequence of SEQ ID NO:13, or the encoded hinge region comprises an amino acid sequence encoded by a sequence with 95-99% identity to the nucleic acid sequence of SEQ ID NO:13;
   c) the encoded hinge region comprises the amino acid sequence of SEQ ID NO: 36, or the encoded hinge region comprises a sequence with 95-99% identity to the amino acid sequence of SEQ ID NO:36; or
   d) the encoded hinge region comprises the amino acid sequence encoded by the nucleic acid sequence of SEQ ID NO: 37, or the encoded hinge region comprises an amino acid sequence encoded by a sequence with 95-99% identity to the nucleic acid sequence of SEQ ID NO: 37.

9. The isolated nucleic acid molecule of claim 1, wherein the encoded intracellular signaling domain comprises a costimulatory domain, wherein the encoded costimulatory domain comprises a functional signaling domain derived from a protein selected from the group consisting of OX40, CD2, CD27, CD28, CD5, ICAM-1, LFA-1 (CD11a/CD18), ICOS (CD278), and 4-1BB (CD137).

10. The isolated nucleic acid molecule of claim 1, wherein the encoded intracellular signaling domain comprises a functional signaling domain of 4-1BB and/or a functional signaling domain of CD3 zeta.

11. The isolated nucleic acid molecule of claim 1, wherein the encoded intracellular signaling domain comprises
   (i) the amino acid sequence of SEQ ID NO: 7 and the amino acid sequence of SEQ ID NO:9 or SEQ ID NO:10;
   (ii) the amino acid sequence of SEQ ID NO:7, and an amino acid sequence with 95-99% identity to the amino acid sequence of SEQ ID NO:9 or SEQ ID NO:10, or
   (iii) an amino acid sequence with 95-99% identity to the amino acid sequence of SEQ ID NO:7, and the amino acid sequence of SEQ ID NO:9 or SEQ ID NO:10.

12. The isolated nucleic acid molecule of claim 1, wherein the encoded intracellular signaling domain comprises the amino acid sequence of SEQ ID NO:7 and the amino acid sequence of SEQ ID NO: 9 or SEQ ID NO: 10, wherein the sequences comprising the intracellular signaling domain are expressed in the same frame and as a single polypeptide chain.

13. The isolated nucleic acid molecule of claim 1, wherein the nucleic acid sequence encoding the intracellular signaling domain comprises the nucleic acid sequence of SEQ ID NO: 18, or a sequence with 95-99% identity thereof, and the nucleic acid sequence of SEQ ID NO:20 or SEQ ID NO:21, or a sequence with 95-99% identity thereof.

14. The isolated nucleic acid molecule of claim 1, further comprising a leader sequence, wherein the leader sequence comprises the amino acid sequence of SEQ ID NO: 1.

15. An isolated chimeric antigen receptor (CAR) molecule encoded by the nucleic acid molecule of claim 1.

16. An isolated chimeric antigen receptor (CAR) molecule comprising: i) a human anti-mesothelin binding domain, ii) a transmembrane domain, and iii) an intracellular signaling domain, wherein the human anti-mesothelin binding domain comprises:
   (a) a light chain variable region comprising: a light chain complementary determining region 1 (LC CDR1) comprising the amino acid sequence of SEQ ID NO: 203; a light chain complementary determining region 2 (LC CDR2) comprising the amino acid sequence of SEQ ID NO: 227; and a light chain complementary determining region 3 (LC CDR3) comprising the amino acid sequence of SEQ ID NO: 251; and
   (b) a heavy chain variable region comprising: a heavy chain complementary determining region 1 (HC CDR1) comprising the amino acid sequence of SEQ ID NO:138; a heavy chain complementary determining region 2 (HC CDR2) comprising the amino acid sequence of SEQ ID NO: 156; and a heavy chain complementary determining region 3 (HC CDR3) comprising the amino acid sequence of SEQ ID NO: 179, wherein the CAR is not a regulatable CAR.

17. The isolated CAR molecule of claim 16, wherein the anti-mesothelin binding domain is a scFv.

18. The isolated CAR molecule of claim 16, wherein the anti-mesothelin binding domain comprises:
   (i) the light chain variable region of the amino acid sequence of SEQ ID NO:43, and the heavy chain variable region of the amino acid sequence of SEQ ID NO: 43; or
   (ii) a light chain variable region comprising an amino acid sequence with 95-99% identity with the amino acid sequence of SEQ ID NO: 43; and
   a heavy chain variable region comprising an amino acid sequence with 95-99% identity to the amino acid sequence of SEQ ID NO: 43.

19. The isolated CAR molecule of claim 16, wherein the anti-mesothelin binding domain comprises the sequence of SEQ ID NO: 43, or a sequence with 95-99% identity thereof.

20. The isolated CAR molecule of claim 16, wherein the transmembrane domain comprises
   a transmembrane domain of a protein selected from the group consisting of the alpha, beta or zeta chain of the T-cell receptor, CD28, CD3 epsilon, CD45, CD4, CD5, CD9, CD16, CD22, CD33, CD37, CD64, CD80, CD86, CD134, CD137 and CD154.

21. The isolated CAR molecule of claim 16, wherein the human anti-mesothelin binding domain is connected to the transmembrane domain by a hinge region, wherein the hinge region comprises the amino acid sequence of SEQ ID NO:2 or SEQ ID NO:36, or a sequence with 95-99% identity thereof.

22. The isolated CAR molecule of claim 16, wherein the intracellular signaling domain comprises a costimulatory domain, wherein the costimulatory domain comprises a functional signaling domain of a protein selected from the group consisting of OX40, CD2, CD27, CD28, CD5, ICAM-1, LFA-1 (CD11a/CD18), CD278 (ICOS) and 4-1BB (CD137).

23. The isolated CAR molecule of claim 16, wherein the costimulatory domain comprises the amino acid sequence of SEQ ID NO: 7; or an amino acid sequence with 95-99% identity to the amino acid sequence of SEQ ID NO: 7.

24. The isolated CAR molecule of claim 16, wherein the intracellular signaling domain comprises a functional signaling domain of 4-1BB and a functional signaling domain of CD3 zeta.

25. The isolated CAR molecule of claim 24, wherein the intracellular signaling domain comprises:
   (i) the amino acid sequence of SEQ ID NO: 7 and the amino acid sequence of SEQ ID NO:9;
   (ii) the amino acid sequence of SEQ ID NO:7 and the amino acid sequence of SEQ ID NO: 10;
   (iii) the amino acid sequence of SEQ ID NO:7 and an amino acid sequence with 95-99% identity to the amino acid sequence of SEQ ID NO:9 or SEQ ID NO: 10; or
   (iv) an amino acid sequence with 95-99% identity to the amino acid sequence of SEQ ID NO:7 and the amino acid sequence of SEQ ID NO:9 or SEQ ID NO:10.

26. The isolated CAR molecule of claim 25, wherein the intracellular signaling domain comprises the amino acid sequence of SEQ ID NO: 7 and the amino acid sequence of SEQ ID NO: 9 or SEQ ID NO: 10, wherein the sequences comprising the intracellular signaling domain are expressed in the same frame and as a single polypeptide chain.

27. The isolated CAR molecule of claim 16, further comprising a leader sequence, wherein the leader sequence comprises the amino acid sequence of SEQ ID NO: 1, or a sequence with 95-99% identity to the amino acid sequence of SEQ ID NO: 1.

28. A human anti-mesothelin binding domain comprising a light chain variable region comprising a light chain complementary determining region 1 (LC CDR1), a light chain complementary determining region 2 (LC CDR2), and a light chain complementary determining region 3 (LC CDR3) of the anti-mesothelin binding domain sequence of SEQ ID NO: 43, and a heavy chain variable region comprising a heavy chain complementary determining region 1 (HC CDR1), a heavy chain complementary determining region 2 (HC CDR2), and a heavy chain complementary determining region 3 (HC CDR3) of the human anti-mesothelin binding domain sequence of SEQ ID NO: 43, wherein the anti-mesothelin binding domain is not part of a regulatable CAR.

29. The human anti-mesothelin binding domain of claim 28, wherein the human anti-mesothelin binding domain:
    (a) is a scFv comprising the light chain and the heavy chain of the amino acid sequence of SEQ ID NO: 43; or
    (b) the human anti-mesothelin binding domain comprises:
    (b)(i) a light chain variable region comprising an amino acid sequence having a sequence with 95-99% identity with the amino acid sequence of SEQ ID NO: 43; and
    (b)(ii) a heavy chain variable region comprising an amino acid sequence having a sequence with 95-99% identity to the amino acid sequence of SEQ ID NO: 43.

30. A vector comprising the nucleic acid molecule of claim 1, wherein the vector is selected from the group consisting of a DNA, a RNA, a plasmid, a lentivirus vector, adenoviral vector, or a retrovirus vector.

31. An immune effector cell comprising the nucleic acid molecule of claim 1.

32. A method of making an immune effector cell comprising transducing an immune effector cell with a vector of claim 30.

33. A method of generating a population of RNA-engineered cells comprising introducing an in vitro transcribed RNA or synthetic RNA into a cell, wherein the RNA comprises the nucleic acid molecule of claim 1.

34. A method of providing an anti-cancer immunity in a mammal comprising administering to the mammal an effective amount of a cell comprising a CAR nucleic acid molecule of claim 1.

35. A method of treating a mammal having a disease or condition associated with cells that express mesothelin comprising administering to the mammal an effective amount of a cell comprising a CAR nucleic acid molecule of claim 1.

36. The method of claim 35, wherein the disease is a cancer selected from the group consisting of mesothelioma, malignant pleural mesothelioma, non-small cell lung cancer, small cell lung cancer, squamous cell lung cancer, or large cell lung cancer, pancreatic cancer, pancreatic ductal adenocarcinoma, pancreatic metastatic cancer, ovarian cancer, colorectal cancer and bladder cancer, or any combination thereof.

37. The cell of claim 31, further expressing a polypeptide that comprises an extracellular portion of any of PD1, PD-L1, CEACAM, LAGS, CTLA4, VISTA, CD160, BTLA, LAIR1, TIM3, 2B4 or TIGIT, associated with a second polypeptide that comprises a costimulatory domain and/or a primary signaling domain.

38. The method of claim 35, wherein:
    the nucleic acid comprises an in vitro transcribed nucleic acid, and is introduced into the cell, and
    the subject receives an initial administration of the cells comprising the nucleic acid, and one or more subsequent administrations of cells comprising the nucleic acid, wherein the one or more subsequent administrations are administered less than 15 days, after the previous administration.

39. An isolated chimeric antigen receptor (CAR) molecule comprising i) a human anti-mesothelin binding domain, ii) a transmembrane domain, and iii) an intracellular signaling domain, wherein the human anti-mesothelin binding domain comprises:
    a light chain complementary determining region 1 (LC CDR1) comprising the amino acid sequence of SEQ ID NO: 203, a light chain complementary determining region 2 (LC CDR2) comprising the amino acid sequence of SEQ ID NO: 227, and a light chain complementary determining region 3 (LC CDR3) comprising the amino acid sequence of SEQ ID NO: 251, and
    a heavy chain complementary determining region 1 (HC CDR1) comprising the amino acid sequence of SEQ ID NO:138, a heavy chain complementary determining region 2 (HC CDR2) comprising the amino acid sequence of SEQ ID NO: 156, and a heavy chain complementary determining region 3 (HC CDR3) comprising the amino acid sequence of SEQ ID NO: 179, and
    wherein the CAR molecule comprises the amino acid sequence of SEQ ID NO: 67, or a sequence with 95-99% identity thereof, wherein the CAR is not a regulatable CAR.

40. An isolated nucleic acid molecule encoding a chimeric antigen receptor (CAR), wherein the CAR comprises: i) a human anti-mesothelin binding domain, ii) a transmembrane domain, and iii) an intracellular signaling domain, and wherein said anti-mesothelin binding domain comprises:
    (a) a light chain variable region comprising: a light chain complementary determining region 1 (LC CDR1) comprising the amino acid sequence of SEQ ID NO: 203; a light chain complementary determining region 2 (LC CDR2) comprising the amino acid sequence of SEQ ID NO: 227; and a light chain complementary determining region 3 (LC CDR3) comprising the amino acid sequence of SEQ ID NO: 251; and
    (b) a heavy chain variable region comprising: a heavy chain complementary determining region 1(HC CDR1) comprising the amino acid sequence of SEQ ID NO:138; a heavy chain complementary determining region 2 (HC CDR2) comprising the amino acid sequence of SEQ ID NO: 156; and a heavy chain complementary determining region 3 (HC CDR3) comprising the amino acid sequence of SEQ ID NO: 179; and
    wherein the nucleic acid encoding the CAR comprises the nucleic acid sequence of SEQ ID NO: 115, or a sequence with 95-99% identity thereof, wherein the CAR is not a regulatable CAR.

41. The isolated nucleic acid molecule of claim 40, wherein the nucleic acid encoding the CAR comprises the nucleic acid sequence of SEQ ID NO: 115.

42. The isolated nucleic acid molecule of claim 40, which encodes a CAR comprising the amino acid sequence of SEQ ID NO: 67, or a sequence with 95-99% identity thereof.

43. The isolated nucleic acid molecule of claim 40, which encodes a CAR comprising the amino acid sequence of SEQ ID NO: 67.

44. The isolated nucleic acid molecule of claim 1, wherein the encoded CAR comprises a transmembrane domain that comprises the amino acid sequence of SEQ ID NO: 6, or a transmembrane domain that comprises an amino acid sequence with 95-99% identity to the amino acid sequence of SEQ ID NO:6.

45. The isolated nucleic acid molecule of claim 1, wherein the sequence encoding the transmembrane domain comprises the nucleic acid sequence of SEQ ID NO: 17; or a sequence with 95-99% identify to the nucleic acid sequence of SEQ ID NO:17.

46. The isolated nucleic acid molecule of claim 1, wherein the encoded costimulatory domain comprises the amino acid sequence of SEQ ID NO: 7, or a sequence with 95-99% identity to the amino acid sequence of SEQ ID NO: 7.

47. The isolated nucleic acid molecule of claim 1, wherein the sequence encoding the costimulatory domain comprises the nucleic acid sequence of SEQ ID NO: 18, or a sequence with 95-99% identity to the nucleic acid sequence of SEQ ID NO: 18.

48. The isolated CAR molecule of claim 16, wherein the transmembrane domain comprises the amino acid sequence of SEQ ID NO: 6, or a sequence with 95-99% identity to the amino acid sequence of SEQ ID NO: 6.

49. The method of claim 38, wherein the cell is a T cell or NK cell.

* * * * *